(12) United States Patent
Hishiya

(10) Patent No.: US 11,390,899 B2
(45) Date of Patent: Jul. 19, 2022

(54) CELL-ASSOCIATED SECRETION-ENHANCING FUSION PROTEINS

(71) Applicant: SOLA Biosciences, LLC, Natick, MA (US)

(72) Inventor: Akinori Hishiya, Belmont, MA (US)

(73) Assignee: SOLA BIOSCIENCES, LLC, Natick, MA (US)

( * ) Notice: Subject to any disclaimer, the term of this patent is extended or adjusted under 35 U.S.C. 154(b) by 480 days.

(21) Appl. No.: 16/336,417

(22) PCT Filed: Sep. 26, 2017

(86) PCT No.: PCT/US2017/053383
§ 371 (c)(1),
(2) Date: Mar. 25, 2019

(87) PCT Pub. No.: WO2018/058088
PCT Pub. Date: Mar. 29, 2018

(65) Prior Publication Data
US 2019/0241925 A1    Aug. 8, 2019

Related U.S. Application Data

(60) Provisional application No. 62/399,955, filed on Sep. 26, 2016.

(51) Int. Cl.
| C07K 14/00 | (2006.01) |
| C12P 21/02 | (2006.01) |
| C07K 14/715 | (2006.01) |
| C07K 14/755 | (2006.01) |
| C07K 16/22 | (2006.01) |
| C07K 16/24 | (2006.01) |
| C12N 9/64 | (2006.01) |
| C07K 16/00 | (2006.01) |
| C07K 14/745 | (2006.01) |
| C07K 14/705 | (2006.01) |
| A61K 48/00 | (2006.01) |

(52) U.S. Cl.
CPC ............ *C12P 21/02* (2013.01); *C07K 14/705* (2013.01); *C07K 14/70575* (2013.01); *C07K 14/7151* (2013.01); *C07K 14/7155* (2013.01); *C07K 14/745* (2013.01); *C07K 14/755* (2013.01); *C07K 16/00* (2013.01); *C07K 16/22* (2013.01); *C07K 16/241* (2013.01); *C07K 16/244* (2013.01); *C12N 9/644* (2013.01); *C12N 9/6437* (2013.01); *A61K 48/00* (2013.01); *C07K 2317/14* (2013.01); *C07K 2317/52* (2013.01); *C07K 2319/03* (2013.01); *C07K 2319/30* (2013.01); *C07K 2319/35* (2013.01); *C07K 2319/43* (2013.01); *C07K 2319/70* (2013.01); *C12N 2710/16622* (2013.01)

(58) Field of Classification Search
None
See application file for complete search history.

(56) References Cited

U.S. PATENT DOCUMENTS

2012/0237975 A1* 9/2012 Schrum .................. C07K 16/00
435/69.6
2015/0299756 A1* 10/2015 Hishiya .................. C07K 14/47
514/44 R

FOREIGN PATENT DOCUMENTS

WO    2012087835 A2    6/2012
WO    2015117229 A1    8/2015

OTHER PUBLICATIONS

Arai et al., Design of the linkers which effectively separate domains of a bifunctional fusion protein. Protein Eng., 14(8):529-532 (2001).
Baucke et al., Membrane Proteins Specified by Herpes Simplex Viruses V. Identification of an Fc-Binding Glycoprotein. J. Virol., 32(3): 779-789 (1979).
Chan et al., Therapeutic antibodies for autoimmunity and inflammation. Nat. Rev, 10: 301-316 (2010).
Chapman et al., Characterization of the Interaction between the Herpes Simplex Virus Type I Fc Receptor and Immunoglobulin G*. J. Biol. Chem., 274:6911-19 (1999).
Crasto et al., LINKER: a program to generate linker sequences for fusion proteins. Protein Eng., 13(5):309-314 (2000).
DeLano et al., Convergent Solutions to Binding at a Protein-Protein Interface. Science, 287:1279-1283 (2000).

(Continued)

*Primary Examiner* — Jeanette M Lieb
(74) *Attorney, Agent, or Firm* — Honigman LLP; Kelly T. Murphy

(57) ABSTRACT

Cell-associated secretion-enhancing fusion proteins are disclosed that comprise a target protein binding domain and a transmembrane retention domain. Co-expression in a host cell of a fusion protein and a target protein of interest that is temporarily bound by the fusion protein leads to an increased level of target protein secreted from the host cell. The fusion proteins are engineered to be retained with the producing host cell, thus eliminating a non-natural component from the extracellular media of the host cell and simplifying purification of the target protein. Nucleic acid molecules encoding such fusion proteins are also disclosed for use in expressing the fusion proteins in host cells, for use in restoring lost or diminished cell functions, and for use in treating diseases characterized by a lost or diminished cell function. Methods and compositions comprising fusion proteins of the invention are disclosed for use in enhancing the level of co-expressed target proteins secreted from host cells.

64 Claims, 35 Drawing Sheets
Specification includes a Sequence Listing.

(56) References Cited

OTHER PUBLICATIONS

Demaurex, pH Homeostasis of Cellular Organelles. News Physiol. Sci., 17:1-5 (2002).
George et al., An analysis of protein domain linkers: their classification and role in protein folding. Protein Eng., 15(11):871-879 (2002).
Hanke al., Herpes simplex virus IgG Fc receptors induced using recombinant adenovirus vectors expressing glycoproteins E and I. Virology, 177(2):437-444 (1990).
Hedner, Mechanism of Action of Recombinant Activated Factor VII: An Update. Semin. Hematol., 43(suppl 1):S105S107 (2006).
Hennessy et al., Not all J domains are created equal: Implications for the specificity of Hsp40-Hsp70 interactions. Protein Science, 14:1697-1709 (2005).
Jackson et al., Identification of a consensus motif for retention of transmembrane proteins in the endoplasmic reticulum. EMBO J., 9(10): 3153-3162 (1990).
Kampinga et al.,The HSP70 chaperone machinery: J proteins as drivers of functional specificity. Nat. Rev. Biol., 11:579-592 (2010).
Kontermann, Recombinant bispecific antibodies for cancer therapy. Acta Pharmacol. Sin., 26(1): 1-9 (2005).
Kufer et al., A revival of bispecific antibodies. Trends Biotechnol., 22(5): 238-244 (2004).
Lee et al., Improving the Expression of a Soluble Receptor:Fc fusion Protein in CHO Cells by Coexpression with the Receptor Ligand. Cell Technol. for Cell Products, 29-39 (2007).
Marvin et al., Recombinant approaches to IgG-like bispecific antibodies. Acta Pharmacol. Sin., 26(6): 649-658 (2005).
Muyldermans et al., Sequence and structure of VH domain from naturally occurring camel heavy chain immunoglubulins lacking light chains. Protein Eng., 7: 1129-1135 (1994).
Muyldermans et al., Recognition of antigens by single-domain antibody fragments: the superfluous luxury of paired domains. Trends Biochem. Sci., 26: 230-235 (2001).
Nguyen et al., Heavy-chain antibodies in Camelidae; a case of evolutionary innovation. Immunogenetics, 54: 39-47 (2002).
Para et al., Immunoglobulin G(Fc)-binding receptors on virions of herpes simplex virus type 1 and transfer of these receptors to the cell surface by infection. J. Virol., 34(3): 512-520 (1980).
Powell et al., Safety and prolonged activity of recombinant factor VIII Fc fusion protein in hemophilia A patients. Blood, 119(13): 3031-3037 (2012).
Robinson et al., Optimizing the stability of single-chain proteins by linker length and composition mutagenesis. Proc. Natl. Acad. Sci. USA, 95: 5929-5934 (1998).
Strauch et al., Computational design of a pH-sensitive IgG binding protein. Proc. Natl. Acad. Sci. USA, 111(2): 675-680 (2014).
Takayama et al., Molecular chaperone targeting and regulation by BAG family proteins. Nat. Cell Biol., 3: E237-E241 (2001).
Vu et al., Comparison of llama VH sequences from conventional and heavy chain antibodies. Mol. Immunol., 34: 1121-1131 (1997).
Ward et al., Binding activities of a repertoire of single immunoglobulin variable domains secreted from *Escherichia coli*. Nature, 341: 544-546 (1989).
Watanabe et al., Optimizing pH response of affinity between protein G and IgG Fc. How electrostatic modulations affect protein-protein interactions. J. Biol. Chem., 284 (18): 12373-12383 (2009).
Yang et al., Hexamer peptide affinity resins that bind the Fc region of human immunoglobulin G. J. Peptide Res., 66 (Suppl. 1): 120-137 (2006).
Cheng, et al. Membrane-tethered proteins for basic research, imaging, and therapy. Med Res Rev Nov. 2008, vol. 28 No. 6 pp. 885-928.
Feb. 13, 2018 International Search Report of PCT/US17/53383.

* cited by examiner

TPB(gE)-TMR(VSVG)

Target Protein Binding Domain | Flag Tag | Transmembrane Retention Domain gE

DDESLFFGDTGLSKNPIELVEGWFSSWKSSIASFFFIIGLI
IGLFLVLRVGIHLCIKLKHTKKRQIYTDIEMNRLGK (SEQ ID NO:193)

Fig. 10A

TPB(gE)-TMR(VSVG) with KK motif

Target Protein Binding Domain | Flag Tag | Transmembrane Retention Domain gE

DDESLFFGDTGLSKNPIELVEGWFSSWKSSIASFFFIIGLI
IGLFLVLRVGIHLCIKLKHTKKRQIYTDIEMNRLGKKTC (SEQ ID NO:194)

|               | 1 | 2 | 3 | 4 |
|---|---|---|---|---|
| Anti-VEGF Mab | − | + | + | + |
| CMP-TPB(gE)-TMR(VSVG) | − | − | + | − |
| CMP-TPB(gE)-TMR(p23) | − | − | − | + |

CMP-TPB(gE)-TMR(KDELR) (Invention)

CMP-TPB(gE')-TMR(KDELR) (Invention)

CMP-TPB-TMR (KDELR) (Invention)

1: mock culture
2: IL13Rα2TF-Fc (target protein)
3: IL13Rα2TF-Fc + CMP-TPB-TMR(CD4)
4: IL13Rα2TF-Fc + CMP-TPB-TMR(Integrin)
5: IL13Rα2TF-Fc + CMP-TPB-TMR(UGT1)
6: IL13Rα2TF-Fc + CMP-TPB-TMR(KDELR truncated TMR)
7: IL13Rα2TF-Fc + CMP-TPB-TMR(p23)
8: IL13Rα2TF-Fc + CMP-TPB-TMR(p24)
9: IL13Rα2TF-Fc + CMP-TPB-TMR(LAMP2)
10: IL13Rα2TF-Fc + CMP-TPB-TMR(LIMP2 C-terminal TM region)
11: IL13Rα2TF-Fc + CMP-TPB-TMR(CDM6PR)
12: IL13Rα2TF-Fc + CMP-TPB-TMR(VSVG)
13: IL13Rα2TF-Fc + CMP-TPB-TMR(CNX)
14: IL13Rα2TF-Fc + CMP-TPB-TMR(CNX truncated TMR)
15: IL13Rα2TF-Fc + CMP-TPB-TMR(gE)
16: IL13Rα2TF-Fc + CMP-TPB-TMR(ERGIC53)
17: IL13Rα2TF-Fc + CMP-TPB-TMR(gp84)
18: IL13Rα2TF-Fc + TMR(gp73)-CMP-TPB
19: IL13Rα2TF-Fc + TMR(LIMP2 N-terminal TM region)-CMP-TPB
20: IL13Rα2TF-Fc + CMP-TPB-TMR(KDELR)
21: IL13Rα2TF-Fc + TMR(LIMP2 N-terminal TM region)-CMP-TPB-TMR(LIMP2 C-terminal TM region)

Fig. 22E

CMP-TPB(gE)-TMR(VSVG)

CMP Domain — Target Protein Binding Domain — Flag Tag — Transmembrane Retention Domain Signal Sequence — [CMP] — Linker — gE — [Flag] — TMR DDESLFFGDTGLSKNPIELVEGWFSSWKSSIASFFFIIGLI
IGLFLVLRVGIHLCIKLKHTKKRQIYTDIEMNRLGK (SEQ ID NO:193)

Fig. 23A

CMP-TPB(gE)-TMR(VSVG) with KK motif

CMP Domain — Target Protein Binding Domain — Flag Tag — Transmembrane Retention Domain Signal Sequence — [CMP] — Linker — gE — [Flag] — TMR with KK DDESLFFGDTGLSKNPIELVEGWFSSWKSSIASFFFIIGLI
IGLFLVLRVGIHLCIKLKHTKKRQIYTDIEMNRLGKKTC (SEQ ID NO:194)

Fig. 23B

CELL-ASSOCIATED SECRETION-ENHANCING FUSION PROTEINS

CROSS-REFERENCE TO RELATED APPLICATIONS

This application is a United States national stage filing under 35 U.S.C. § 371 of international application No. PCT/US2017/053383, filed Sep. 26, 2017, designating the U.S., which claims priority to U.S. Provisional Application No. 62/399,955, filed Sep. 26, 2016.

FIELD OF THE INVENTION

This invention is in the field of engineered proteins and protein expression. In particular, the invention is directed to a family of cell-associated secretion-enhancing fusion proteins useful for enhancing the level of a target protein of interest that is secreted from a host cell. Such fusion proteins of the invention advantageously remain associated with the host cell rather than being co-secreted from the host cell in the same manner as the target protein of interest.

BACKGROUND OF THE INVENTION

Expressing a protein of interest in a culture of genetically engineered cells at levels that permit isolation in quantities sufficient for research, development, or commercial use typically can employ a variety of recombinant techniques and cell culture methodologies. Such techniques include in vitro methods of isolating and recombining a nucleic acid molecule that encodes a protein of interest, operably linking the nucleic acid molecule to appropriate transcriptional and translational elements, inserting the engineered genetic material into an appropriate expression vector, introducing the resulting recombinant expression vector into compatible host cells, culturing the host cells containing the recombinant expression vector under conditions that permit expression of the protein of interest, and purifying the expressed protein of interest from the host cells and/or the media of cultures of the host cells. Maximizing expression of a protein of interest is a multifactorial challenge requiring keen attention to each component of a production campaign. The discovery of means or methods to improve yield or purity may be critical for a particular protein of interest to be adequately studied, formulated, clinically tested, and ultimately brought to market.

Particularly desirable is an expression system in which a protein of interest is not only expressed but is also secreted from a recombinant host cell, thereby providing a substantial degree of purification from many of the other proteins expressed within the host cell. To more readily comply with regulatory concerns, an expression system that promotes secretion of a protein of interest should also minimize or prevent secretion of any other protein species that is not already known to be a component of an end-stage or harvest-ready cell culture medium.

Although many advances in target protein expression have been made in recent years, there remains a need to develop protein expression systems that will increase the level of a target protein expressed and secreted by an engineered host cell. Furthermore, an improved expression system will ideally increase the level of target protein secreted into the extracellular culture media without also increasing or adding additional components to the extracellular media that would make subsequent purification and processing of the target protein into a usable product more difficult.

SUMMARY OF THE INVENTION

The invention described herein solves the above problems by providing compositions and methods for enhancing the level of a target protein of interest that is secreted from a host cell. The enhanced level of secretion of a target protein of interest from a host cell is accomplished according to this invention by expressing the target protein of interest in the presence of a cell-associated secretion-enhancing (CASE) fusion protein as disclosed herein. A CASE fusion protein of the invention is designed to specifically bind to a target protein of interest and also to associate with the intracellular membrane of the secretory pathway of a host cell. The CASE fusion protein can release the target protein of interest within the protein secretory pathway for secretion from the cell, while the CASE fusion protein itself maintains association with the intracellular membrane. In this way, a CASE fusion protein is retained within the host cell while the target protein of interest is secreted from the host cell, where the target protein can be detected, purified, or permitted to function without interference or contamination by intracellular host cell components.

In an embodiment, a cell-associated secretion-enhancing (CASE) fusion protein disclosed herein comprises:
 (a) a target protein binding (TPB) domain,
 (b) a transmembrane retention (TMR) domain, and
 (c) optionally, a chaperone machinery polypeptide (CMP) domain.

Each domain of a CASE fusion protein of the invention may be linked to an adjacent domain directly or indirectly via a linker of one or more amino acids. Each domain of a CASE fusion protein of the invention may be obtained from a different "parent" (or "donor") polypeptide or protein that itself is known to possess a region or domain that has a functional activity required for a particular domain of a CASE fusion protein. A domain of a CASE fusion protein of the invention may also be a derivative, mutated, or otherwise altered form of a particular region or domain of parent or donor polypeptide or protein. Further, a domain of a CASE fusion protein of the invention may also be a synthetic polypeptide that is not known to be part of any naturally occurring or previously described polypeptide or protein but that has been shown to possess a functional activity required for a particular domain of a CASE fusion protein of the invention. Accordingly, a CASE fusion protein of the invention is a recombinant, non-naturally occurring, fusion protein that is capable of binding a target protein of interest and enhances the level of the target protein secreted from a host cell that co-expresses the target protein and the CASE fusion protein, as compared to the level of target protein secreted from a host cell that expresses the target protein in the absence of the CASE fusion protein.

According to the invention, a target protein binding (TPB) domain of a CASE fusion protein described herein binds a target protein of interest that is expressed in the endoplasmic reticulum (ER) of a host cell and releases or does not bind the target protein of interest within the Golgi apparatus or a secretory vesicle of the host cell in which the target protein of interest and the CASE fusion protein are co-expressed. In an aspect of the invention, a TPB domain of a CASE fusion protein of the invention binds a target protein of interest at a pH of the ER of a host cell in which the target protein of interest and the CASE fusion protein are co-expressed. More preferably, a TPB domain of a CASE fusion protein of the invention binds a target protein of interest in the ER and releases or does not bind the target protein at a pH of the Golgi apparatus or secretory vesicle of a host cell in which the target protein of interest and the CASE fusion protein are co-expressed.

Any of a variety of polypeptides that bind a target protein of interest may be used as a target protein binding (TPB) domain of a cell-associated secretion-enhancing (CASE) fusion protein of the invention. Examples of polypeptides that may be used as a target protein binding (TPB) domain in a CASE fusion protein of the invention include, but are not limited to, an antibody binding polypeptide, e.g., an Fc-binding polypeptide (e.g., when a target protein comprises an antibody Fc region), a ligand binding domain of a receptor protein (e.g., when a target protein is a ligand of the receptor), a protein ligand of a target protein (e.g., when a target protein is a receptor or ligand binding fragment of a receptor), a PDZ domain of a PDZ domain-containing protein that binds to a PDZ-binding domain of a target protein, and the like.

In an embodiment, when a target protein of interest comprises an antibody Fc region, for example, as in the case of an antibody, an Fc-fusion protein, or a single domain antibody, a TPB domain of a CASE fusion protein of the invention may comprise an Fc-binding domain of any of a number of Fc-binding polypeptides and proteins including, but not limited to, herpes simplex virus glycoprotein E (gE), FcB6, Protein A, Protein G, GB919, and the Fc-binding region of the hcFR protein. In a preferred embodiment, when a target protein of interest comprises an antibody Fc region, a TPB domain of a CASE fusion protein of the invention comprises an Fc-binding portion of the herpes simplex virus glycoprotein E (gE).

In another embodiment, a TPB domain of a CASE fusion protein of the invention may also comprise a region of Protein L that binds immunoglobulin light chains. Such a TPB domain may be used in a CASE fusion protein that is employed to enhance the level of a target protein secreted from a host cell when the target protein comprises one or more antibody light chains, such as, but not limited to, an antibody, a Fab fragment, F(ab')2, a single chain antibody (scFv), and the like.

In a particular embodiment of the invention, when a target protein of interest is a cytokine, the TPB domain of a CASE fusion protein of the invention is a ligand-binding domain of a corresponding cytokine receptor that binds the cytokine target protein.

In another particular embodiment, a target protein of interest is a receptor protein or ligand-binding portion of a receptor, and the TPB domain of a CASE fusion protein of the invention is a protein ligand or portion thereof that is bound by the receptor target protein or a ligand-binding portion of the receptor. For example, when the target protein of interest is a cytokine receptor protein or comprises a cytokine binding portion thereof, the TPB domain of a fusion protein of the invention may be the cytokine or a portion of the cytokine that is bound by the cytokine receptor protein or a cytokine-binding portion of the receptor.

In a particular embodiment wherein the target protein, such as the cystic fibrosis transmembrane conductance regulator (CFTR) protein, possesses a PDZ-binding domain, then the TPB domain of a CASE fusion protein of the invention may comprise a PDZ domain from any of a variety of proteins that possess a PDZ domain. In a preferred embodiment, when a target protein possesses a PDZ-binding domain, a TPB domain of a CASE fusion protein of the invention comprises a PDZ domain from any of the members of the NHERF family of PDZ adapter proteins including, but not limited to, NHERF1 (also known as NHERF, EBP50, or SLC9A3R1), NHERF2 (also known as E3KARP or SLC9A3R2), and PDZK1 (also known as CAP70 or NHERF3).

In particular embodiments of the invention, a TPB domain of a CASE fusion protein of the invention binds or remains bound to a target protein at pH 7.2 (±0.2) or the conditions of the host cell endoplasmic reticulum (ER), and then releases or does not bind the target protein at a pH below 7 or under conditions as found in the subsequent secretory pathway. In another embodiment, a TPB domain of a CASE fusion protein of the invention is a polypeptide that binds a target protein at pH 7 or the conditions of the host cell ER and releases or does not bind a target protein at pH 6.7 or the conditions as found in the cis Golgi of a host cell. In another embodiment, a TPB domain of a CASE fusion protein of the invention is a polypeptide that binds a target protein at pH 7 or the conditions as found in the host cell ER and releases or does not bind a target protein at pH 6.3 or the conditions as found in the medial Golgi of a host cell. In another embodiment, a TPB domain of a fusion protein of the invention is a polypeptide that binds a target protein at pH 7 or the conditions found in the host cell ER and releases or does not bind a target protein at pH 6.0 or the conditions as found in the trans Golgi of a host cell. In still another embodiment, a TPB domain of a CASE fusion protein of the invention is a polypeptide that binds a target protein at pH 7 or the conditions as found in the host cell ER and releases or does not bind a target protein at pH of 5.5 or the conditions as found in secretory vesicles of a host cell.

In addition to a TPB domain, a cell-associated secretion-enhancing (CASE) fusion protein of the invention also comprises at least one transmembrane retention (TMR) domain that functions to retain the fusion protein with the host cell in which the fusion protein is expressed. Preferably, a TMR domain comprises at least a portion of a transmembrane region of a membrane-associated protein, although synthetic membrane-spanning polypeptides may also be used as a TMR domain. A preferred TMR domain of a fusion protein of the invention comprises or is derived from the membrane-spanning region (transmembrane region) of a membrane-associated protein that normally traverses the membrane of a cell at least once. Preferably, the region of a transmembrane protein employed as a TMR domain in a CASE fusion protein of the present invention comprises a sufficient portion of the transmembrane region so that when the fusion protein is co-expressed with a target protein interest, the fusion protein is retained with the host cell or is not otherwise co-secreted with the target protein from the host cell.

In an aspect of the invention, a transmembrane retention (TMR) domain of a CASE fusion protein described herein comprises at least the membrane-spanning region or derivative thereof from a membrane-associated protein that associates with the membrane of the secretory pathway without trapping the fusion protein in the endoplasmic reticulum (ER) of a host cell. More preferably, a TMR domain of a CASE fusion protein described herein prevents the fusion protein from being trapped in the ER and also prevents the fusion protein from being co-secreted with a target protein of interest that is co-expressed with the fusion protein in a host cell. Even more preferably, a TMR domain of a CASE fusion protein described herein does not include a tandem lysine (dilysine) motif that retains the fusion protein in the ER.

In a preferred embodiment, a CASE fusion protein of the invention comprises a TMR domain that comprises a membrane-spanning region of a transmembrane protein selected from the group consisting of: human CD4, human p23, human p24 p, human LAMP2, human LIMP2, cation dependent mannose-6-phosphate receptor, vesicular stomatitis virus glycoprotein (VSV-G), herpesvirus 1 envelope glycoprotein I, Borna disease virus gp84, and human KDEL receptor 1 protein (KDELR).

A particularly preferred CASE fusion protein of the invention comprises a TMR domain that comprises a transmembrane region of the VSV-G protein or the transmembrane region of the KDEL receptor 1 protein (KDELR).

A TMR domain of a CASE fusion protein described herein may include all or an operative fragment of a transmembrane region of a transmembrane protein that is normally known to be associated with or embedded in the cell membrane. An "operative fragment" of a transmembrane region of a transmembrane protein is a portion of the transmembrane region such that, when incorporated into a fusion protein of the invention, causes the fusion protein, on co-expression with the target protein, to be retained with (i.e., in or on) the host cell or a membrane of the host cell, or otherwise retards the migration of the fusion protein with the target protein expressed in the host cell such that any portion of the fusion protein secreted to the extracellular culture media is not significant. By "not significant" in this context is meant that the level of fusion protein in the culture media is not detectable or is at a level that is tolerable so as to not require steps specifically aimed at removal of the fusion protein from a host cell culture medium in the further processing of the target protein. For example, the United States Food and Drug Administration (FDA) has found that most biological products (biologics) contain ELISA-based host cell (non-product) protein levels between 1 and 100 ppm. See, *The Handbook of Process Chromatography, Second Edition*, Hagel et al., eds. (Academic Press, London, 2008), Chapter 5, page 131. Such a range of non-drug proteins of host cell origin serves as guidance for the production and regulatory approval of biologics. Accordingly, although a fusion protein of the invention is most preferably not secreted into a host cell culture medium, and therefore not detectable by ELISA, an insignificant and tolerable level of a fusion protein of the invention that is secreted into a host cell culture medium may be, but is not limited to, in order of increasing preference, less than 100 ppm, less than 80 ppm, less than 70 ppm, less than 60 ppm, less than 50 ppm, less than 40 ppm, less than 30 ppm, less than 20 ppm, less than 10 ppm, less than 5 ppm, less than 3 ppm, less than 2 ppm, less than 1 ppm, less than 0.3 ppm, less than 0.15 ppm, less than 0.10 ppm, less than 0.05 ppm, less than 0.02 ppm, less than 0.01 ppm, and less than 0.005 ppm.

The portion of a transmembrane protein useful as a TMR domain in a CASE fusion protein of the invention is not limited to only the membrane-spanning region of the transmembrane protein but may also comprise additional amino acids of the transmembrane protein that are located upstream (N-terminal) and/or downstream (C-terminal) to the membrane-spanning region. In particular embodiments, the entire transmembrane region of a transmembrane protein will be used. In additional embodiments, the entire transmembrane region and all or part of any upstream or downstream region of the transmembrane protein may be used as the TMR domain of a CASE fusion protein according to the invention. Additional amino acids located upstream (N-proximal) from the membrane-embedded portion of a transmembrane protein that may be part of a TMR domain of a fusion protein of the invention may have a range of sizes including, but not limited to, 1 to 70 amino acids, 1 to 75 amino acids, or 1 to 80 amino acids. Additional amino acids located downstream (C-proximal) from the membrane-embedded portion of a transmembrane protein that may be part of a TMR domain of a fusion protein of the invention may have a range of sizes including, but not limited to, 1 to 10 amino acids, 1 to 15 amino acids, 1 to 20 amino acids, 1 to 30 amino acids, 1 to 40 amino acids, 1 to 50 amino acids, 1 to 60 amino acids, 1 to 70 amino acids, 1 to 80 amino acids, 1 to 90 amino acids, 1 to 100 amino acids, 1 to 110 amino acids, 1 to 120 amino acids, 1 to 130 amino acids, 1 to 140 amino acids, 1 to 150 amino acids, 1 to 160 amino acids, 1 to 170 amino acids, and 1 to 200 amino acids.

The TMR domain of a fusion protein described herein may also comprise the entire cytoplasmic region attached to a transmembrane region of a transmembrane protein. Alternatively, the TMR domain may comprise a truncation of the cytoplasmic region by one or more amino acids, for example, to eliminate an undesired signaling function of the cytoplasmic tail. For example, the presence of tandem lysine residues (dilysine) in the C-terminal portion of a cytoplasmic region of a transmembrane protein can serve as a signal to retain the transmembrane protein in the endoplasmic reticulum (ER) and blocking further progression of the protein to the membranes of the Golgi apparatus and secretory vesicles. Accordingly, if the transmembrane region and adjacent C-terminal cytoplasmic region of such an ER-associated transmembrane protein is to be used as a TMR domain of a fusion protein of the invention, any known functional dilysine signal for ER retention should be eliminated or disrupted so that a fusion protein comprising the transmembrane region and any additional cytoplasmic region is not prevented from progressing out of the ER to the Golgi apparatus and/or secretory vesicles.

A preferred TMR domain useful in a CASE fusion protein of the invention may comprise a polypeptide isolated from a transmembrane protein that is associated with any of a variety of membranes of a cell including, but not limited to, a cell membrane, a Golgi complex membrane, a secretory vesicle membrane, a nuclear membrane, a lysosomal membrane, and a mitochondrial membrane.

In an embodiment, a TMR domain of a CASE fusion protein of the invention may comprise a membrane-spanning region of a transmembrane protein selected from the group consisting of: a Type I transmembrane protein, a Type II transmembrane protein, a Type III transmembrane protein, and a Type IV transmembrane protein.

In a particularly preferred embodiment, a TMR domain is derived from a transmembrane region of a Type I transmembrane protein.

In another embodiment, a CASE fusion protein of the invention comprises a TMR domain that comprises a polypeptide in Table 1 (below) or a portion thereof comprising at least one membrane-spanning region.

In another embodiment, the TMR domain polypeptide of such a CASE fusion protein comprises a C-terminal portion of the p23 protein, KDEL receptor 1 protein ("KDELR"), or VSV-G protein ("VSVG"), which C-terminal portion includes the membrane-spanning region.

In another embodiment, a CASE fusion protein of the invention comprises a TMR domain that is selected from the group of polypeptides consisting of: a transmembrane region of CD4 consisting of residues 457-520 of SEQ ID NO:156 (see, also, SEQ ID NO:67 in Table 1), a transmembrane region of p23 consisting of residues 457-492 of SEQ ID NO:160, a transmembrane region of LAMP2 consisting of residues 457-493 of SEQ ID NO:162, a transmembrane region of VSVG consisting of residues 457-533 of SEQ ID NO:165, another transmembrane region of VSVG consisting of SEQ ID NO:193, and truncations of such polypeptides that retain the property of retaining the CASE fusion protein within the intracellular compartment.

In another aspect of the invention, a cell-associated secretion-enhancing (CASE) fusion protein described herein further comprises a "chaperone machinery polypeptide" or "chaperone machinery peptide" ("CMP") domain. A CASE fusion protein comprising all three domains further enhances the amount of target protein that is secreted from a host cell as compared to the level of target protein secreted from the host cell in the absence of the fusion protein or as compared to the level secreted in the presence of a CASE fusion protein that lacks a CMP domain. Accordingly, in a preferred embodiment of the invention, a CASE fusion protein described herein comprises:
  (a) a target protein binding (TPB) domain,
  (b) a transmembrane retention (TMR) domain, and
  (c) a chaperone machinery polypeptide (CMP) domain.

Again, each domain may be fused to an adjacent domain directly or via a linker of one or more amino acids. As described above, the TPB domain comprises a polypeptide that is selected for its ability to bind to a particular target protein of interest, and the TMR domain comprises a polypeptide that is selected mainly to result in the CASE fusion protein being essentially completely retained within the expressing host cell, wherein that combination of TPB and TMR domains results in a fusion protein capable of enhancing the secretion of a co-expressed target protein of interest (the target protein corresponding to the target protein that the TPB domain is capable of binding). The CMP domain when present in a CASE fusion protein, is selected mainly for its ability to improve target protein secretion, presumably by acting as a type of chaperone to a target protein bound by the CASE fusion protein to engage in some manner the cellular chaperone mechanisms involved with processing, folding, membrane-translocation, and/or secretion of proteins expressed in the host cell.

In another aspect of the invention, a CASE fusion protein of the present invention comprises a CMP domain comprising a polypeptide selected from any one or more of the following:

(a) an isolated J domain of a J protein or an active fragment of a J domain; or (b) an isolated polypeptide analog of a J domain, wherein said J domain analog polypeptide comprises the amino acid sequence of formula I:

```
(I)
                                   (SEQ ID NO: 1)
X1-X2-X3-X4-X5-X6-X7-X8-X9,
``` wherein:

X1 is isoleucine (I), leucine (L), valine (V), alanine (A), or methionine (M);

X2 and X3 are each independently any amino acid with the proviso that one or both are K or R;

X4 is any amino acid or X4 may be absent when X1 through X3 are present and X5 through X9 are present;

X5 is tyrosine (Y), tryptophan (W), or phenylalanine (F);

X6 and X7 are each independently any amino acid with the proviso that one or both are lysine (K) or arginine (R); or either one of X6 and X7 may be absent when the other is K or R and when X1 through X5 are present and X8 and X9 are present; and X8 and X9 are any amino acid with the proviso that one or both are leucine (L) or alanine (A); or one of X8 and X9 may be absent when the other is L or A and when X1 through X7 are present;

wherein co-expression of the CASE fusion protein and a target protein in a host cell enhances the level of target protein secreted from the host cell, compared to the level of target protein secreted from a host cell in the absence of a CASE protein.

In preferred embodiments, co-expression of a target protein with a CASE fusion protein that includes a CMP domain in a host cell exhibits increased secretion of the target protein in comparison to a host cell co-expressing a target protein and a CASE protein that does not include a CMP domain.

In a preferred embodiment, a CASE fusion protein described herein comprises a CMP domain comprising a J domain polypeptide fragment selected from the group consisting of:

```
                    (SEQ ID NO: 2)
IKKAYKLALQ,
                    (SEQ ID NO: 3)
IKKAYRLALQ,
                    (SEQ ID NO: 4)
IKKAYRKALQ,
                    (SEQ ID NO: 5)
IKKAYRKLLQ,
                    (SEQ ID NO: 6)
IKKAYRKLA,
                    (SEQ ID NO: 7)
IRKAYRKLSLTL,
                    (SEQ ID NO: 8)
IKKQYRLLSLKY,
                    (SEQ ID NO: 9)
IKKAFHKLAMKY,
                   (SEQ ID NO: 10)
IRQAFKKLALKL,
                   (SEQ ID NO: 11)
IIKAYRKLALQW,
                   (SEQ ID NO: 12)
IARAYRQLARRY,
                   (SEQ ID NO: 13)
IKRAYRRQALRY,
                   (SEQ ID NO: 14)
IKKSYRKLALKY,
and
                   (SEQ ID NO: 15)
IKKAYKRLAMKY.
```

In a preferred embodiment, a cell-associated secretion enhancing (CASE) fusion protein described herein comprises a CMP domain that comprises an isolated polypeptide from a J domain of a J protein comprising the amino acid sequence IKKAFHKLAMKY (SEQ ID NO:9). or IKKAYRKLA (SEQ ID NO:6).

In another embodiment, a CASE fusion protein described herein comprises a CMP domain comprising a polypeptide selected from the group consisting of:

| Sequence Identifier | Amino Acid Sequence 123456789012345 |
|---|---|
| SEQ ID NO: 6 | IKKAYRKLA |
| SEQ ID NO: 2 | IKKAYKLALQ |
| SEQ ID NO: 3 | IKKAYRLALQ |
| SEQ ID NO: 4 | IKKAYRKALQ |
| SEQ ID NO: 5 | IKKAYRKLLQ |
| SEQ ID NO: 203 | IKKYRKLA |
| SEQ ID NO: 204 | IKKAYKLA |
| SEQ ID NO: 205 | IKKAYRLA |
| SEQ ID NO: 206 | IKKAYRKA |
| SEQ ID NO: 207 | LKKAYRKLA |
| SEQ ID NO: 208 | VKKAYRKLA |
| SEQ ID NO: 209 | MKKAYRKLA |
| SEQ ID NO: 210 | AKKAYRKLA |
| SEQ ID NO: 211 | IAKAYRKLA |
| SEQ ID NO: 212 | IKAAYRKLA |
| SEQ ID NO: 213 | IKKRYRKLA |
| SEQ ID NO: 214 | IKKSYRKLA |
| SEQ ID NO: 215 | IKKQYRKLA |
| SEQ ID NO: 216 | IKKEYRKLA |
| SEQ ID NO: 217 | IKKFYRKLA |
| SEQ ID NO: 218 | IKKCYRKLA |
| SEQ ID NO: 219 | IKKAFRKLA |
| SEQ ID NO: 220 | IKKAWRKLA |
| SEQ ID NO: 221 | IKKAYRKQA |
| SEQ ID NO: 222 | IKKAYRKMA |
| SEQ ID NO: 223 | IKKAYRKIA |
| SEQ ID NO: 224 | IKKAYRKAA |
| SEQ ID NO: 225 | IKKAYRKVA |
| SEQ ID NO: 226 | IKKAYRKRA |
| SEQ ID NO: 227 | IKKAYRKLM |
| SEQ ID NO: 228 | IKKAYRKLI |
| SEQ ID NO: 229 | IKKAYRKLV |
| SEQ ID NO: 230 | IKKAYRKLC |
| SEQ ID NO: 231 | IKKAYRKLS |
| SEQ ID NO: 232 | IKKAYRKLY |
| SEQ ID NO: 7 | IRKAYRKLSLTL |
| SEQ ID NO: 8 | IKKQYRLLSLKY |
| SEQ ID NO: 9 | IKKAFHKLAMKY |
| SEQ ID NO: 10 | IRQAFKKLALKL |
| SEQ ID NO: 11 | IIKAYRKLALQW |
| SEQ ID NO: 12 | IARAYRQLARRY |
| SEQ ID NO: 13 | IKRAYRRQALRY |
| SEQ ID NO: 14 | IKKSYRKLALKY |
| SEQ ID NO: 15 | IKKAYKRLAMKY |

In another embodiment, a CASE fusion protein described herein comprises a CMP domain comprising an amino acid sequence selected from the group consisting of:

| | | |
|---|---|---|
| SEQ ID NO: 2 | SEQ ID NO: 3 | SEQ ID NO: 4 |
| SEQ ID NO: 5 | SEQ ID NO: 6 | SEQ ID NO: 7 |
| SEQ ID NO: 8 | SEQ ID NO: 9 | SEQ ID NO: 10 |
| SEQ ID NO: 11 | SEQ ID NO: 12 | SEQ ID NO: 13 |
| SEQ ID NO: 14 | SEQ ID NO: 15 | SEQ ID NO: 16 |
| SEQ ID NO: 17 | SEQ ID NO: 18 | SEQ ID NO: 19 |
| SEQ ID NO: 20 | SEQ ID NO: 21 | SEQ ID NO: 22 |
| SEQ ID NO: 23 | SEQ ID NO: 24 | SEQ ID NO: 25 |
| SEQ ID NO: 26 | SEQ ID NO: 27 | SEQ ID NO: 28 |
| SEQ ID NO: 29 | SEQ ID NO: 30 | SEQ ID NO: 31 |
| SEQ ID NO: 32 | SEQ ID NO: 33 | SEQ ID NO: 34 |
| SEQ ID NO: 35 | SEQ ID NO: 36 | SEQ ID NO: 37 |
| SEQ ID NO: 38 | SEQ ID NO: 39 | SEQ ID NO: 40 |
| SEQ ID NO: 41 | SEQ ID NO: 42 | SEQ ID NO: 43 |
| SEQ ID NO: 44 | SEQ ID NO: 45 | SEQ ID NO: 46 |
| SEQ ID NO: 47 | SEQ ID NO: 48 | SEQ ID NO: 49 |
| SEQ ID NO: 50 | SEQ ID NO: 51 | SEQ ID NO: 52 |
| SEQ ID NO: 53 | SEQ ID NO: 54 | SEQ ID NO: 55 |
| SEQ ID NO: 56 | SEQ ID NO: 57 | SEQ ID NO: 58 |
| SEQ ID NO: 59 | SEQ ID NO: 60 and | SEQ ID NO: 61. |

In another embodiment, a CASE fusion protein described herein comprises a CMP domain, wherein the CMP domain comprises a fragment of a J domain of a J protein or a fragment of a Hsp70 protein; wherein co-expression in a host cell of the CASE fusion protein comprising the CMP domain and a target protein bound by the CASE fusion protein enhances the level of target protein secreted from the host cell compared to the level of target protein secreted from a host cell co-expressing the target protein and a CASE fusion protein without the CMP domain.

In an embodiment, a CASE fusion protein of the invention has a structure, N-terminal to C-terminal, as follows:
(TPB domain)-L-(TMR domain), or
(CMP-domain)-L-(TPB domain)-L-(TMR domain),
wherein each L is, independently, a direct peptide bond or a linker of one or more amino acids. Preferably, the TMR domain comprises a membrane-spanning region of a Type I, a Type III, or a Type IV transmembrane protein. More preferably, the TMR domain comprises a membrane-spanning region of a Type I transmembrane protein.

In an aspect of the invention, a CASE fusion protein described herein comprises a TMR domain comprising an amino acid sequence selected from the group consisting of:

| | | |
|---|---|---|
| SEQ ID NO: 62 | SEQ ID NO: 63 | SEQ ID NO: 64 |
| SEQ ID NO: 65 | SEQ ID NO: 66 | SEQ ID NO: 67 |
| SEQ ID NO: 71 | SEQ ID NO: 73 | SEQ ID NO: 74 |
| SEQ ID NO: 75 | SEQ ID NO: 76 | SEQ ID NO: 77 |
| SEQ ID NO: 80 and | SEQ ID NO: 82. | |

In another embodiment, a CASE fusion protein of the invention has a structure, N-terminal to C-terminal, as follows:
(TMR domain)-L-(TPB domain),
(TMR domain)-L-(CMP domain)-L-(TPB domain), or
(TMR domain)-L-(TPB domain)-L-(CMP domain),
wherein each L is, independently, a direct peptide bond or a linker of one or more amino acids. Preferably, the TMR domain comprises a membrane-spanning region of a Type II or a Type III transmembrane protein.

In another embodiment, a CASE fusion protein of the invention has a structure, N-terminal to
C-terminal, as follows:
(TMR domain)-L-(TPB domain)-L-(TMR domain), or
(TMR domain)-L-(CMP domain)-L-(TPB domain)-L-(TMR domain),
wherein said TMR domains are the same or different, and wherein each L is, independently, a direct peptide bond or a linker of one or more amino acids. Preferably, the N-terminal TMR domain comprises a membrane-spanning region of a Type II or a Type III transmembrane protein, and the C-terminal TMR domain comprises a membrane-spanning region of a Type I, a Type III, or a Type IV transmembrane protein.

In a further embodiment, the CASE fusion protein described above comprises TMR domains that may be the same or different and each TMR domain comprises a membrane-spanning region of a Type III protein. More preferably, each of the TMR domains comprises one or more membrane-spanning regions of KDEL receptor 1 or LIMP2.

In another embodiment, the CASE fusion protein described above comprises TMR domains that may be the same or different and each comprises a membrane-spanning region taken from the KDEL receptor 1 C-terminal fragment shown in SEQ ID NO:71.

The domains of a CASE fusion protein described above may be linked directly to one another or by a linker of one or more amino acids. When a linker peptide (i.e., a linker consisting of two or more amino acids) is used to link one domain with another domain in a CASE fusion protein of the invention, the linker may be one or more amino acids, including 1 to 10 amino acids, 1 to 20 amino acids, and even 1 to 50 amino acids. Typically, a linker will not be more than 20 amino acids and will be selected or designed so that the linker peptide does not interfere with the function of either or both domains it links Preferably, a linker, if present, optimizes the contribution of either or both domains it links in a CASE fusion protein of the invention and thereby increases the level of a target protein of interest that is secreted from a host cell. The linker may be omitted if direct attachment of one domain to another (for example, CMP domain to TPB domain, TPB domain to TRM domain) does not unacceptably diminish the function of either domain or does not unacceptably diminish the desired enhancement in the level of secretion of the target protein or the retention of the fusion protein with the host cell.

In preferred embodiments, each linker, "L", if present in a CASE fusion, is independently an amino acid or is selected from the group consisting of: LE, SR, LEG, GSR, GTGSEFDIAAALE (SEQ ID NO:175); GTGSGEF (SEQ ID NO:176); DIAAA (SEQ ID NO:83); DIAAALE (SEQ ID NO:84); GTGSEF (SEQ ID NO:85); AS; TVA; ASTK (SEQ ID NO:86); GGGSGGSGGSGG (SEQ ID NO:87); DIGGGSGGSGGSGGAAA (SEQ ID NO:88); DIGGGSGGGGSGGGGSAAA (SEQ ID NO:178); AKTTPKLEEGEFSEAR (SEQ ID NO:89); AKTTPKLEEGEFSEARV (SEQ ID NO:90); AKTTPKLGG (SEQ ID NO:91); SAKTTPKLGG (SEQ ID NO:92); SAKTTP (SEQ ID NO:93); RADAAP (SEQ ID NO:94); RADAAPTVS (SEQ ID NO:95); RADAAAAGGPGS (SEQ ID NO:96); RADAAAA(G$_4$S)$_4$ (SEQ ID NO:97); SAKTTPKLEEGEFSEARV (SEQ ID NO:98); ADAAP (SEQ ID NO:99); ADAAPTVSIFPP (SEQ ID NO:100); TVAAP (SEQ ID NO:101); TVAAPSVFIFPP (SEQ ID NO:102); QPKAAP (SEQ ID NO:103); QPKAAPSVTLFPP (SEQ ID NO:104); AKTTPP (SEQ ID NO:105); AKTTPPSVTPLAP (SEQ ID NO:106); AKTTAP (SEQ ID NO:107); AKTTAPSVYPLAP (SEQ ID NO:108); ASTKGP (SEQ ID NO:109); ASTKGPSVFPLAP (SEQ ID NO:110); GGGGS (SEQ ID NO:181); GGGGSGGGGS (SEQ ID NO:180); GGGGSGGGGSGGGGS (SEQ ID NO:111); GGGGSGGGGSGGGGSGGGGS (SEQ ID NO:179); GENKVEYAPALMALS (SEQ ID NO:112); GPAKELTPLKEAKVS (SEQ ID NO:113); GHEAAAVMQVQYPAS (SEQ ID NO:114); GGGGGGGGP (SEQ ID NO:115); GGGGGGGGP (SEQ ID NO:116); PAPNLLGGP (SEQ ID NO:117); PNLLGGP (SEQ ID NO:118); GGGGGGP (SEQ ID NO:119); PAPELLGGP (SEQ ID NO:120); PTISPAPNLLGGP (SEQ ID NO:121); TVAADDDDKSVFIVPP (SEQ ID NO:122); TVDDDDKAAP (SEQ ID NO:123); LVPRGSAAP (SEQ ID NO:124); ASTKGPSV (SEQ ID NO:125); ASTKGPSVFP (SEQ ID NO:126); TVAAPSV (SEQ ID NO:127); and TVAAPSVFI (SEQ ID NO:128).

In another embodiment, a cell-associated secretion-enhancing (CASE) fusion protein described herein may comprise an arrangement of domains wherein, in an N-terminal to C-terminal direction, a CMP domain is the N-terminal domain, which in turn is fused (directly or via a linker of one or more amino acids) to a target protein binding (TPB) domain, which in turn is fused (directly or via a linker of one or more amino acids) to a transmembrane retention (TMR) domain.

In another embodiment, the relative positions of the CMP domain and the TPB domain are switched so that the fusion protein comprises an arrangement of domains wherein, in an N-terminal to C-terminal direction, a TPB domain is fused (directly or via a linker of one or more amino acids) to a CMP domain, which in turn is fused (directly or via a linker of one or more amino acids) a TMR domain. Arrangements of the three domains that position the TMR domain as the most C-terminal domain relative to the other two domains (CMP domain and TPB domain) is particularly preferred when the TMR domain is derived from a Type I transmembrane protein.

In another embodiment, a cell-associated secretion-enhancing (CASE) fusion protein of the invention comprises an arrangement of domains wherein a transmembrane retention (TMR) domain is the most N-terminal domain relative to the CMP domain and the target protein binding (TPB) domain. For example, in a preferred embodiment, a CASE fusion protein of the invention comprises an arrangement of domains wherein, in an N-terminal to C-terminal direction, a TMR domain is fused to a CMP domain, which in turn is fused to a TPB domain. In another embodiment, the relative positions of the CMP domain and the TPB domain are switched so that the fusion protein comprises an arrangement of domains wherein, in an N-terminal to C-terminal direction, a TMR domain is fused to a TPB domain, which in turn is fused to a CMP domain. In both arrangements, each domain may be linked to an adjacent domain directly or indirectly via a linker Arrangements of the three domains that position the TMR domain as the most N-terminal domain relative to other two domains (i.e., CMP and TPB domains) is particularly preferred when the TMR domain is derived from a Type II transmembrane protein.

A cell-associated secretion-enhancing (CASE) fusion protein of the invention may further comprise one or more epitope tags to assist in detecting or isolating the fusion protein. An epitope tag useful in the invention includes, but is not limited to, a V5 epitope tag, a Flag epitope tag, a polyhistidine tag (such as a hexaHis epitope tag; SEQ ID NO:177), a Myc epitope tag, and an HA (human influenza hemagglutinin) epitope tag. An epitope tag may be located at the C-terminus of the fusion protein, at the N-terminus of the fusion protein, or between any two domains, for example, between any two of a TPB domain, a TMR domain, and, if present, a CMP domain. An epitope tag may be linked directly to another domain of the fusion protein or indirectly via a linker of one or more amino acids. Particularly preferred for use in a CASE fusion protein described herein is an epitope tag selected from the group consisting of: a V5 epitope tag consisting of GKPIPNPLLGLDST (SEQ ID NO:131), a Flag epitope tag consisting of DYKDDDDK (SEQ ID NO:132), and a "hexaHis" polyhistidine epitope tag consisting of HHHHHH (SEQ ID NO:177).

A cell-associated secretion-enhancing (CASE) fusion protein of the present invention is demonstrated to significantly enhance the level of a co-expressed target protein of interest secreted from a cell compared to the level of target protein secreted from the cell in the absence of the fusion protein. The level of secreted target protein of interest is regarded as being "significantly enhanced" where the amount of target protein secreted is at least 1.5-fold or more of the amount of target protein secreted without co-expression of a fusion protein of the invention. Increases in amount of secreted target protein of more than 2-fold, more than 3-fold, more than 4-fold, more than 6-fold, more than 8-fold, more than 10-fold, and more than 25-fold or more have been obtained following the methods described herein.

The invention also provides isolated nucleic acid molecules encoding a cell-associated secretion-enhancing (CASE) fusion protein of the invention.

The invention also provides recombinant vectors comprising an isolated nucleic acid encoding a cell-associated secretion-enhancing (CASE) fusion protein of the invention. Such recombinant vectors include cloning vectors to replicate the inserted isolated nucleic acid in a transfected host cell.

The invention also provides expression vectors, wherein an isolated nucleic acid encoding a cell-associated secretion-enhancing (CASE) fusion protein of the invention is operably linked to transcriptional and translational sequences within the vector that are necessary for expression of the fusion protein in a compatible transfected host cell. Any of a variety of expression vectors available in the art may be used to produce a CASE fusion protein of the invention. Examples of expression vectors useful for expressing a fusion protein of the invention include, but are not limited to, plasmid pcDNA, pcDNA3.3 TOPO (Life Technologies, New York), plasmid pTT3, plasmid pEF-BOS, and the like. Particularly preferred is the pcDNA' expression vector, which is a derivative of a pcDNA3 expression vector containing multiple cloning sites as described in Example 1, below.

In another embodiment, an expression vector comprises a nucleic acid encoding a CASE fusion protein of the invention and also a nucleic acid encoding a target protein of interest so that the proteins are co-expressed in a compatible host cell transfected with the expression vector.

An aspect of the invention is an isolated host cell (for example, an isolated transfected host cell, also referred to as an isolated recombinant host cell) that comprises a nucleic acid encoding a cell-associated secretion-enhancing (CASE) fusion protein described herein.

Another aspect of the invention is an isolated host cell (for example, an isolated transfected host cell, also referred to as an isolated recombinant host cell) that comprises a vector comprising a nucleic acid encoding a cell-associated secretion-enhancing (CASE) fusion protein described herein.

Expression vectors of the invention also include gene therapy vectors for expressing a cell-associated secretion-enhancing (CASE) fusion protein of the invention in vivo in a gene therapy to enhance production and secretion from a cell of a lost or deficient target protein function in a plant or animal (including mammals, such as humans, non-human primates, rodents, or livestock).

In another embodiment, the invention provides an isolated host cell (for example, an isolated transfected host cell, also referred to as an isolated recombinant host cell) comprising an expression vector for expressing a cell-associated secretion-enhancing (CASE) fusion protein described herein. A host cell of the invention may be a prokaryotic host cell, such as *Escherichia coli*, or a eukaryotic host cell. Preferably, a host cell is a eukaryotic host cell. Particularly preferred eukaryotic host cells include, without limitation, a mammalian host cell, an insect host cell, a plant host cell, a fungal host cell, a eukaryotic algal host cell, a nematode host cell, a protozoan host cell, and a fish host cell. A preferred mammalian host cell is a human embryonic kidney (HEK293) cell, a Chinese Hamster Ovary (CHO) cell, a COS cell, a Vero cell, an SP2/0 cell, an NS/0 myeloma cell, a baby hamster kidney (BHK) cell, a HeLa cell, a human B cell, a CV-1/EBNA cell, an L cell, a 3T3 cell, an HEPG2 cell, a PerC6 cell, or an MDCK cell. Preferred fungal host cells include *Aspergillus, Neurospora, Saccharomyces, Pichia, Hansenula, Schizosaccharomyces, Kluyveromyces, Yarrowia,* and *Candida*. More preferably, a *Saccharomyces* host cell is a *Saccharomyces cerevisiae* cell.

The invention provides a method of expressing a cell-associated secretion-enhancing (CASE) fusion protein described herein comprising culturing an isolated host cell comprising a vector molecule comprising an isolated nucleic acid molecule encoding the cell-associated secretion-enhancing (CASE) fusion protein under conditions sufficient to produce the fusion protein.

In an aspect of the invention, the invention provides a method of enhancing the level of a target protein of interest that is secreted from an isolated host cell comprising (a) transfecting a host cell with an expression vector comprising a nucleic acid encoding a cell-associated secretion-enhancing (CASE) fusion protein, wherein the fusion protein comprises a target protein binding (TPB) domain, and a transmembrane retention (TMR) domain and wherein the host cell also comprises an expressible gene encoding the target protein of interest (to which the TPB domain of the CASE fusion protein is capable of binding), and (b) culturing said transfected host cell under conditions causing co-expression of the target protein of interest and the CASE fusion protein. In another embodiment of the above-described method, the expression vector comprises a nucleic acid encoding a CASE fusion protein, wherein the fusion comprises a TPB domain, a TMR domain, and a chaperone machinery peptide (CMP) domain.

In another embodiment, a method for enhancing the level of a secreted target protein of interest from a host cell may advantageously be carried out by following the steps:

(1) constructing a recombinant gene sequence encoding a cell-associated secretion-enhancing (CASE) fusion protein comprising a target protein binding (TPB) domain that is capable of binding the target protein of interest and a transmembrane retention (TMR) domain;
(2) inserting the recombinant gene sequence into an expression vector to form a recombinant expression vector wherein said recombinant gene sequence encoding the CASE fusion protein is operably linked to a transcriptional promoter sequence;
(3) transfecting a suitable host cell, wherein the host cell is compatible with the promoter sequence and the recombinant expression vector and wherein the host cell also comprises an expressible gene encoding the target protein of interest; and
(4) culturing said transfected host cell under conditions that lead to co-expression of the CASE fusion protein and the target protein of interest.

In another embodiment of the above method, the encoded cell-associated secretion-enhancing (CASE) fusion protein comprises a target protein binding (TPB) domain, a transmembrane retention (TMR) domain, and further comprises a chaperone machinery polypeptide (CMP) as described herein.

In an embodiment of the invention, a nucleic acid encoding a cell-associated secretion-enhancing (CASE) fusion protein of the invention is inserted into the cells of a plant or non-human animal to express the fusion protein and to enhance the level of secretion of a target protein of interest that is also expressed by the cells of the plant or non-human animal and that the CASE fusion protein is capable of binding. Such methods include producing transgenic plants and transgenic non-human animals in which a nucleic acid encoding a CASE fusion protein of the invention is permanently incorporated into the genome as a functional gene (transgene) such that the plant or non-human animal not only expresses the fusion protein but also passes a copy of the expressible transgene on to progeny.

In another embodiment, the invention provides a method for restoring a protein function in cells of a mammalian subject to treat the mammalian subject that has a disease associated with the deficient secretion of a native secreted target protein in the subject. Such a method comprises introducing an expression vector into cells of the mammalian subject, wherein the expression vector encodes a cell-associated secretion-enhancing (CASE) fusion protein described herein that is expressed in the cells to promote expression and secretion from the cells of the native secreted target protein. Such diseases include, but are not limited to, a prion-associated disease, Alzheimer's disease, Parkinson's disease, Huntington's disease, cystic fibrosis (CF), and α1-antitrypsin (AAT) deficiency. In a particularly preferred embodiment, a method for restoring a protein function is used to treat a human subject deficient in the secretion of cystic fibrosis transmembrane conductance regulator protein (CFTR) and the disease is cystic fibrosis. In this embodiment, an exogenous nucleic acid molecule that is inserted into cells of the human subject encodes a cell-associated secretion-enhancing (CASE) fusion protein, wherein the target protein binding (TPB) domain of the fusion protein specifically binds a CFTR expressed by the cells of the subject. Expression of the fusion protein in the cells of the human subject restores the deficiency of CFTR function by promoting enhanced secretion of the CFTR while advantageously not also secreting the fusion protein, which reduces the possibility of an undesired immune response to the fusion protein.

BRIEF DESCRIPTION OF THE DRAWINGS

FIG. 3A is a diagram depicting a nucleic acid construct encoding a TMR domain polypeptide, i.e., in this example comprising a transmembrane region and C-terminal region of the VSV-G protein or a transmembrane region of the KDELR protein, augmented with a 5' segment encoding a Flag epitope tag, as described in Example 3.

FIG. 3B depicts a nucleic acid construct encoding a cell-associated secretion-enhancing (CASE) fusion protein as described in Example 3 comprising a segment encoding a target protein binding (TPB) domain (in this example, an Fc-binding portion of herpes simplex virus type-1 glycoprotein E, "gE") augmented at its 3' end with a segment encoding a Flag epitope tag, which in turn was linked to a segment encoding a transmembrane retention (TMR) domain comprising either a transmembrane and C-terminal region of the VSV-G protein or a transmembrane region of the KDELR protein as a transmembrane retention (TMR) domain. See Example 3 for additional details.

FIG. 3C shows bar graphs of the fold increase in the amount of IL13Rα2TF-Fc target protein detected by ELISA in the media of cultures of transfected HEK293 host cells expressing the IL13Rα2TF-Fc target protein alone (bar graph 2), co-expressing the IL13Rα2TF-Fc target protein and a TMR(VSVG) polypeptide ("TMR only", bar graph 3), co-expressing the IL13Rα2TF-Fc target protein and a cell-associated secretion-enhancing (CASE) fusion protein comprising a TMR domain comprising a transmembrane region derived from the VSV-G protein and a TPB domain comprising an Fc-binding region of gE ("TPB(gE)-TMR", bar graph 4), co-expressing the IL13Rα2TF-Fc target protein and a TMR(KDELR) polypeptide ("TMR only", bar graph 5), or co-expressing the IL13Rα2TF-Fc target protein and a cell-associated secretion-enhancing (CASE) fusion protein comprising a TMR domain comprising a transmembrane region derived from the KDELR protein and a TPB domain comprising an Fc-binding region of gE ("TPB(gE)-TMR", bar graph 6). The presence ("+") or absence ("−") of expression vectors encoding IL13Rα2TF-Fc target protein, cell-associated secretion-enhancing fusion protein, or TMR polypeptide in the transfected host cells of each culture is indicated below each bar graph. Mock cultures contained cells transfected with expression vector lacking a structural gene for expressing any protein and were used as a negative control (bar graph 1). The data in the bar graphs have been normalized by subtracting non-specific background signal in media from mock cultures and setting the amount of target protein secreted into culture media when expressed in the absence of either fusion protein or either TMR polypeptide at a relative value of 1 (bar graph 2). The results show that co-expression of the IL13Rα2TF-Fc target protein with either the TPB(gE)-TMR(VSVG) fusion protein (bar graph 4) or the TPB(gE)-TMR(KDELR) fusion protein (bar graph 6) significantly enhanced the level of target protein secreted into the culture media as compared to the level of target protein secreted into the culture media when the target protein was expressed in the absence of either fusion protein (bar graph 2) or expressed in the presence of either TMR polypeptide ("TMR only", bar graphs 3 and 5). See Example 3 for additional details.

FIG. 4A shows results of an experiment described in Example 4 that demonstrate improvement in the level of expression of a TNFR1TF-Fc target protein secreted into the media of cultures of transfected cells expressing the TNFR1TF-Fc target protein alone (bar graph 2 from the left) and of transfected cells co-expressing the TNFR1TF-Fc target protein with a cell-associated secretion-enhancing fusion protein of the invention comprising a target protein binding ("TPB") domain comprising an Fc-binding region of herpes simplex virus type-1 glycoprotein E (gE) linked to a transmembrane retention ("TMR") domain comprising a transmembrane region of the VSV-G protein ("TPB(gE)-TMR(VSVG)", bar graph 3). The presence ("+") or absence ("−") of expression vectors encoding target protein or cell-associated secretion-enhancing fusion protein in the transfected host cells of each culture is indicated below each bar graph. Mock cultures contained cells transfected with expression vector lacking a structural gene for expressing any protein and were used as a negative control (bar graph 1).

FIGS. 4B and 4C show aspects and results of further experiments described in Example 4 that demonstrate significant enhancement in the level of secreted TNFR1TF-Fc target protein when co-expressed in a host cell with a cell-associated secretion-enhancing (CASE) fusion protein of the invention comprising various combinations of target protein binding (TPB) domains and transmembrane retention (TMR) domains as compared to the level of TNFR1TF-Fc target protein expressed alone in a host cell.

FIG. 4B shows a general diagram of a nucleic acid construct encoding the structure of a TPB-TMR fusion protein used in the additional experiments of Example 4 comprising a segment encoding a target protein binding (TPB) domain linked at its 3' end to a segment encoding a Flag epitope tag, which in turn was linked at its 3' end to a segment encoding a transmembrane retention (TMR) domain. The 5' end of the nucleic acid construct was also augmented with a signal sequence to direct the TPB-TMR fusion protein into the intracellular membrane of the endoplasmic reticulum. In this study, the encoded fusion proteins comprised a TMR domain that comprised either a transmembrane region of the vesicular stomatitis virus transmembrane glycoprotein (VSVG) or a transmembrane region of the KDEL receptor 1 protein (KDELR), which is an endoplasmic reticulum (ER) receptor protein that binds to resident ER proteins comprising the ER localization amino acid motif K-D-E-L (SEQ ID NO:152). The TPB domain of the fusion proteins employed in these experiments were an Fc-binding portin of the herpes simplex virus type-1 glycoprotein E ("gE"), an Fc-binding protein of Protein A ("A"), an Fc-binding portion of Protein G ("G"), or an Fc-binding portion of GB919, a mutant form of Protein G that exhibits an Fc-binding affinity that is more pH sensitive than wild-type Protein G while increasing the affinity for IgG. See Example 4 for additional details.

FIG. 4C shows bar graphs that indicate the level of TNFR1TF-Fc target protein secreted into culture media of transfected HEK 293 cells in Example 4. The level of TNFR1TF-Fc target protein secreted into culture media of transfected cells expressing the target protein alone was set as a relative value of 1 (bar graph 1). Bar graph 2 shows the relative level of TNFR1TF-Fc target protein secreted into culture media of cells that co-expressed the target protein and a TPB(gE)-TMR(VSVG) fusion protein. Bar graph 3 shows the relative level of TNFR1TF-Fc target protein secreted into culture media of cells that co-expressed the target protein and a TPB(Prot A)-TMR(VSVG) fusion protein. Bar graph 4 shows the relative level of TNFR1TF-Fc target protein secreted into culture media of cells that co-expressed the target protein and a TPB(Prot G)-TMR (VSVG) fusion protein. Bar graph 5 shows the relative level of TNFR1TF-Fc target protein secreted into culture media of cells that co-expressed the target protein and a TPB (GB919)-TMR(VSVG) fusion protein. Bar graph 6 shows the relative level of TNFR1TF-Fc target protein secreted into culture media of cells that co-expressed the target protein and a TPB(gE)-TMR(KDELR) fusion protein. Bar graph 7 shows the relative level of TNFR1TF-Fc target protein secreted into culture media of cells that co-expressed the target protein and a TPB(Prot A)-TMR(KDELR) fusion protein. Bar graph 8 shows the relative level of TNFR1TF-Fc target protein secreted into culture media of cells that co-expressed the target protein and a TPB(Prot G)-TMR (KDELR) fusion protein. Bar graph 9 shows the relative level of TNFR1TF-Fc target protein secreted into culture media of cells that co-expressed the target protein and a TPB(GB919)-TMR(KDELR) fusion protein. The results show that a significantly enhanced level of the TNFR1TF-Fc target protein was secreted into the culture media of cells that co-expressed the target protein with each of the fusion proteins as compared to the level of TNFR1TF-Fc target protein secreted into culture media of cells that expressed the target protein alone (bar graph 1). See Example 4 for additional details.

FIG. 6 shows bar graphs of the fold increase in the amount of a humanized anti-VEGF-A IgG1 monoclonal antibody ("Anti-VEGF Mab") target protein detected by ELISA in the media of cultures of transfected HEK293 host cells expressing the antibody target protein alone (bar graph 2), or co-expressing the antibody target protein and a cell-associated secretion-enhancing fusion protein comprising an Fc-binding region of gE linked to a transmembrane retention (TMR) domain comprising a transmembrane region of a VSV-G protein ("TPB(gE)-TMR(VSVG)", bar graph 3) as described in Example 6. The presence ("+") or absence ("−") of expression vectors encoding target protein or cell-associated secretion-enhancing fusion protein in the transfected host cells of each culture is indicated below each bar graph. Mock cultures contained cells transfected with expression vector lacking a structural gene for expressing any protein and were used as a negative control (bar graph 1). Culture media were assayed for anti-VEGF Mab target protein by detecting binding to VEGF-A in an ELISA as described in Example 6. The data in the bar graphs have been normalized by subtracting non-specific background signal in media from mock cultures and setting the amount of anti-VEGF-A Mab target protein secreted into culture media when expressed in the absence of the cell-associated secretion-enhancing fusion protein at a relative value of 1 ("Anti-VEGF Mab" alone, bar graph 2). The results show that co-expression of the antibody target protein with the cell-associated secretion-enhancing TPB(gE)-TMR(VSVG) fusion protein (bar graph 3) significantly enhanced the level of antibody target protein secreted into culture media as compared to the level of target protein secreted into culture media when expressed in the absence of the cell-associated secretion-enhancing fusion protein (bar graph 2). The results also indicate that the anti-VEGF-A antibody target protein that was secreted into the culture media was functional as it retained VEGF-A binding activity in the ELISA. See Example 6 for additional details.

FIG. 7 shows bar graphs of the fold increase in the amount of a Factor VII-Fc target protein (FVII-Fc) detected by ELISA in the media of cultures of transfected HEK293 host cells expressing the target protein alone (bar graph 2) or co-expressing the FVII-Fc target protein and a cell-associated secretion-enhancing fusion protein comprising an Fc-binding region of gE linked to a transmembrane retention (TMR) domain comprising a transmembrane region of a VSV-G protein ("TPB(gE)-TMR(VSVG)", bar graph 3) as described in Example 7. The presence ("+") or absence ("−") of expression vectors encoding target protein or cell-associated secretion-enhancing fusion protein in the transfected host cells of each culture is indicated below each bar graph. Mock cultures contained cells transfected with expression vector lacking a structural gene for expressing any protein and were used as a negative control (bar graph 1). The data in the bar graphs have been normalized by subtracting non-specific background signal in media from mock cultures and setting the amount of target protein secreted into culture media when expressed in the absence of the cell-associated secretion-enhancing fusion protein at a relative value of 1 (bar graph 2). The results show that co-expression of the FVII-Fc target protein with the cell-associated secretion-enhancing TPB(gE)-TMR(VSVG) fusion protein (bar graph 3) significantly enhanced the level of target protein secreted into the culture media as compared to the level of target protein secreted into the culture media when the target protein was expressed in the absence of the cell-associated secretion-enhancing fusion protein (bar graph 2). See Example 7 for additional details.

FIG. 14C shows a Western blot analysis of the location of the CMP-TPB(gE)-TMR(VSVG) fusion protein of the invention in cells ("Cell Lysate", lanes 1-3) and in culture media ("Culture Media", lanes 4-6) as described in Example 14. The presence ("+") or absence ("−") of an expression vector encoding the fusion protein in the transfected host cells of each culture is indicated above each lane. Mock cultures contained cells transfected with expression vector lacking a structural gene for expressing any protein and were used as a negative control ("mock", lanes 1 and 4). The results show that the cell-associated secretion-enhancing CMP-TPB(gE)-TMR(VSVG) fusion of the invention was detected only in cell lysates (lane 3) and not detectable in cell culture media (lane 6), showing that the CMP-TPB(gE)-TMR(VSVG) fusion protein was retained with the host cell and not secreted. All host cells were co-transfected with a reporter plasmid expressing the non-secreted green fluorescent protein ("GFP") to show successful transfection and operability of the transfected host cells (lanes 1-3 in lower panel of FIG. 14C). See Example 14 for additional details.

FIG. 15 shows bar graphs of the fold increase in the amount of a humanized anti-IL8 IgG1 monoclonal antibody ("Anti-IL8 Mab") target protein detected by ELISA in the media of cultures of transfected HEK293 host cells expressing the antibody target protein alone (bar graph 2), co-expressing the antibody target protein and a CMP-TPB(gE)-TMR(VSVG) fusion protein of the invention (bar graph 3), wherein TMR(VSVG) comprises a transmembrane region of the VSVG protein (see, Table 1, SEQ ID NO:62), or co-expressing the antibody target protein and a CMP-TPB (gE)-TMR(p23) fusion protein of the invention (bar graph 4), wherein TMR(p23) comprises a transmembrane region of the p23 protein (see, Table 1, SEQ ID NO:65), as described in Example 15. The presence ("+") or absence ("−") of expression vectors encoding target protein or fusion protein in the transfected host cells of each culture is indicated below each bar graph. Mock cultures contained cells transfected with expression vector lacking a structural gene for expressing any protein and were used as a negative control (bar graph 1). Culture media were assayed for anti-IL8 Mab target protein by detecting binding to IL-8 in an ELISA as described in Example 15. The data in the bar graphs have been normalized by subtracting non-specific background signal in media from mock cultures and setting the amount of anti-IL8 Mab target protein secreted into culture media when expressed alone (i.e., in the absence of either fusion protein) at a relative value of 1 (bar graph 2). The results show that co-expression of the anti-IL8 Mab target protein with either the CMP-TPB(gE)-TMR(VSVG) fusion protein (bar graph 3) or the CMP-TPB(gE)-TMR (p23) fusion protein (bar graph 4) significantly enhanced the level of anti-IL8 Mab target protein secreted into culture media as compared to the level of anti-IL8 Mab target protein secreted into culture media when expressed in the absence of either fusion protein (bar graph 2). The results also indicate that the anti-IL8 monoclonal antibody target protein that was secreted into the culture media was functional, since it retained IL8 binding activity in the ELISA. The results also show that varying the particular TMR domain used in a cell-associated secretion-enhancing fusion protein of the invention can significantly impact the degree of enhancement of the level of target protein secreted from a cell as the two fusion proteins differed only in the particular TMR domain used (i.e., TMR(VSVG) domain or TMR(p23) domain). See Example 15 for additional details.

FIG. 16 shows bar graphs of the fold increase in the amount of a humanized anti-VEGF-A IgG1 monoclonal antibody ("Anti-VEGF Mab") target protein detected by ELISA in the media of cultures of transfected HEK293 host cells expressing the antibody target protein alone (bar graph 2), co-expressing the antibody target protein and a cell-associated secretion enhancing CMP-TPB(gE)-TMR (VSVG) fusion protein of the invention (bar graph 3), or co-expressing the antibody target protein and cell-associated secretion-enhancing a CMP-TPB(gE)-TMR(p23) fusion protein of the invention (bar graph 4), as described in Example 16. The presence ("+") or absence ("−") of expression vectors encoding target protein or fusion protein in the transfected host cells of each culture is indicated below each bar graph. Mock cultures contained cells transfected with expression vector lacking a structural gene for expressing any protein and were used as a negative control (bar graph 1). Culture media were assayed for anti-VEGF Mab target protein by detecting binding to VEGF-A in an ELISA as described in Example 16. The data in the bar graphs have been normalized by subtracting non-specific background signal in media from mock cultures and setting the amount of anti-VEGF-A Mab target protein secreted into culture media when expressed in the absence of either fusion protein at a relative value of 1 ("Anti-VEGF Mab" alone, bar graph 2). The results show that co-expression of the antibody target protein with either the CMP-TPB(gE)-TMR(VSVG) fusion protein (bar graph 3) or the CMP-TPB(gE)-TMR(p23) fusion protein (bar graph 4) significantly enhanced the level of antibody target protein secreted into culture media as compared to the level of target protein secreted into culture media when expressed in the absence of either fusion protein (bar graph 2). As in the results shown in FIG. 15C, above, the results in FIG. 16 also show that varying the particular TMR domain used in the design of a cell-associated secretion-enhancing fusion protein can have a marked impact on the degree of enhanced secretion that results from co-expression of the target protein and the fusion protein, as the two fusion proteins differed only in the particular TMR domain used (i.e., TMR(VSVG) domain or TMR(p23) domain). The results also indicate that the anti-VEGF-A antibody target protein that was secreted into the culture media was functional as it retained VEGF-A binding activity in the ELISA. See Example 16 for additional details.

FIG. 17 shows bar graphs of the fold increase in the amount of a humanized anti-TNFα IgG1 monoclonal antibody ("Anti-TNFα Mab") target protein detected by ELISA in the media of cultures of transfected HEK293 host cells expressing the antibody target protein alone (bar graph 2), co-expressing the antibody target protein and a CMP-TPB (gE)-TMR(VSVG) fusion protein of the invention (bar graph 3), or co-expressing the antibody target protein and a CMP-TPB(gE)-TMR(p23) fusion protein of the invention (bar graph 4) as described in Example 17. The presence ("+") or absence ("−") of expression vectors encoding target protein or fusion protein in the transfected host cells of each culture is indicated below each bar graph. Mock cultures contained cells transfected with expression vector lacking a structural gene for expressing any protein and were used as a negative control (bar graph 1). Culture media were assayed for anti-TNFα Mab target protein by detecting binding to TNFα in an ELISA as described in Example 17. The data in the bar graphs have been normalized by subtracting non-specific background signal in media from mock cultures and setting the amount of anti-TNFα Mab target protein secreted into culture media when expressed in the absence of either fusion protein at a relative value of 1 (bar graph 2). The results show that co-expression of the anti-TNFα Mab target protein with either the CMP-TPB(gE)-TMR(VSVG) fusion protein (bar graph 3) or the CMP-TPB(gE)-TMR(p23) fusion protein (bar graph 4) significantly enhanced the level of anti-TNFα Mab target protein secreted into culture media as compared to the level of anti-TNFα Mab target protein secreted into culture media when expressed in the absence of either fusion protein (bar graph 2). As in the results shown in FIGS. 15 and 16, above, the results also show that varying the particular TMR domain used in the design of a cell-associated secretion-enhancing fusion protein can have an impact on the degree of enhanced secretion that results from co-expression of the target protein and the fusion protein, as the two fusion proteins differed only in the particular TMR domain used (i.e., TMR(VSVG) or TMR(p23) domain). Note also that the results in FIG. 17 show that a greater enhancement in the level of secretion of the target protein was obtained when the target protein was co-expressed with the CMP-TPB(gE)-TMR(VSVG) fusion protein than with the CMP-TPB(gE)-TMR(p23) fusion protein in contrast to the results shown in FIGS. 15 and 16 in which co-expression of the respective target proteins with the CMP-TPB(gE)-TMR(p23) fusion protein provided a greater enhancement in the level of target protein secretion than that obtained with the CMP-TPB(gE)-TMR(VSVG) fusion protein. Thus, a preliminary comparison of the levels of secretion obtained by co-expressing a given target protein with fusion proteins that differ only in TMR domains may reveal an optimal enhancement in the level of secretion of the target protein. The results also indicate that the anti-TNFα antibody target protein that was secreted into the culture media was functional, as it retained TNFα binding activity in the ELISA. See Example 17 for additional details.

Referring to FIG. 19C, the presence ("+") or the absence ("−") of expression vectors encoding target protein or fusion protein in the transfected host cells of each culture is indicated above each lane of the Western blot. It can be seen that the level of secretion of the IL13Rα2TF-Fc fusion target protein co-expressed with the CMP-TPB(Prot A) fusion protein (lane 3), the CMP-TPB (gE)-TMR(VSVG) fusion protein (lane 5), both the CMP-TPB(gE)-TMR(VSVG) and CMP-TPB(gI)-TMR(VSVG) fusion proteins (lane 6), or the CMP-TPB(IL13)-TMR (VSVG) fusion (lane 7) resulted in a significantly greater level of IL13Rα2TF-Fc target protein being secreted into culture media, as compared to the level of target protein secreted into the media from cultures of transfected cells expressing the IL13Rα2TF-Fc target protein alone (lane 2). See Example 18 for additional details.

FIGS. 22A-22E include diagrams and descriptions for various fusion proteins and comparative test results from co-expression of individual fusion protein variants with an IL13Rα2TF-Fc target protein. FIGS. 22A-22C show diagrams for nucleic acid constructs for expression of fusion proteins in three different formats, differing with respect to the location of the TMR domain in the fusion protein relative to the positions of the CMP and TPB domains. FIG. 22D is a series of bar graphs showing the results of co-expression of the target protein with the various fusion protein analogues, in comparison with expression of the target protein alone and with mock cultures expressing no recombinant protein. FIG. 22E is the key for the numbered bar graphs comprising FIG. 22D.

FIG. 22A depicts a nucleic acid construct for a series of fusion proteins as described in Example 21 in which a segment encoding a "chaperone machinery polypeptide" ("CMP") domain comprising a 12 amino acid peptide (IKKAFHKLAMKY, SEQ ID NO:9) from the J domain of the Erdj4 protein was linked to a segment encoding a target protein binding (TPB) domain comprising an Fc-binding portion of gE, augmented at its 3' end with a segment encoding a Flag epitope tag, which in turn was linked to a transmembrane retention (TMR) domain, wherein the TMR domain comprises one of 16 different transmembrane regions derived from 14 different transmembrane proteins. The segment of the construct encoding the CMP domain was augmented at its 5' end with a segment encoding an N-terminal signal sequence for the fusion protein. The construct was designated "CMP-TPB(gE)-TMR". This arrangement of domains is seen in constructs nos. 3-17 and 20 in FIG. 22E. See Example 21 for additional details.

FIG. 22B depicts a nucleic acid construct for fusion proteins as described in Example 21 in which a segment encoding a transmembrane retention (TMR) domain comprising a transmembrane region from a Gp73 protein (Type II protein) or from a LIMP2 protein (Type III protein) was linked to a segment encoding a CMP domain comprising a 12 amino acid peptide (IKKAFHKLAMKY, SEQ ID NO:9) from the J domain of the Erdj4 protein, which in turn was linked to a segment encoding a target protein binding (TPB) domain comprising an Fc-binding portion of gE which was augmented at its 3' end with a segment encoding a Flag epitope tag. The construct was designated "TMR-CMP-TPB (gE)". This arrangement of domains is seen in constructs nos. 18 and 19 in FIG. 22E. See Example 21 for additional details.

FIG. 22C depicts a nucleic acid construct for a fusion protein as described in Example 21 in which a segment encoding a transmembrane retention (TMR) domain comprising an N-proximal transmembrane region from a LIMP2 protein was linked to a segment encoding a "chaperone machinery polypeptide" ("CMP") domain comprising a 12 amino acid peptide (IKKAFHKLAMKY, SEQ ID NO:9) from the J domain of the Erdj4 protein, which in turn was linked to a segment encoding a target protein binding (TPB) domain comprising an Fc-binding portion of gE which was augmented at its 3' end with a segment encoding a Flag epitope tag which in turn was linked to a segment encoding another TMR domain comprising a C-proximal transmembrane region from a LIMP2 protein. The construct was designated "TMR-CMP-TPB(gE)-TMR" and its arrangement of domains is illustrated in construct no. 21 in FIG. 22E. See Example 21 of additional details.

FIG. 22D is a series of bar graphs showing the fold increase in the amount of a IL13Rα2TF-Fc target protein detected by ELISA in the media of cultures of transfected HEK293 host cells expressing the target protein alone (bar graph 2), co-expressing the target protein and each of 16 examples of a CMP-TPB(gE)-TMR fusion protein (bar graphs 3-17 and 20), co-expressing the target protein and each of two examples of a TMR-CMP-TPB(gE) fusion protein (bar graphs 18 and 19), or co-expressing the target protein and an example of a TMR-CMP-TPB(gE)-TMR fusion protein (bar graph 21), as described in Example 21. The presence ("+") or absence ("−") of expression vectors encoding target protein or a fusion protein in the transfected host cells of each culture is indicated below each bar graph. Mock cultures contained cells transfected with "empty" expression vector lacking a structural gene for expressing any protein and were used as a negative control (bar graph 1).

FIG. 22E shows the designations for each of the relevant protein species expressed in the transfected hosts cells of each culture corresponding to bar graphs 1-21 of FIG. 22D. Each designation includes in parentheses an identification of the transmembrane protein that served as the source of the transmembrane retention domain selected for each of the expressed fusion proteins. See Example 21 for additional details.

FIG. 23A is a diagram of a nucleic acid construct coding for a fusion protein as described in Example 22, in which a segment encoding a "chaperone machinery polypeptide" ("CMP") domain comprising a 12 amino acid peptide (IK-KAFHKLAMKY, SEQ ID NO:9) from the J domain of the Erdj4 protein was linked to a segment encoding a target protein binding (TPB) domain comprising an Fc-binding portion of herpes simplex virus type-1 glycoprotein E (gE) augmented at its 3' end with a segment encoding a Flag epitope tag, which in turn was linked to a segment encoding a transmembrane retention (TMR) domain comprising the transmembrane region of VSV-g (SEQ ID NO:193). The segment of the construct encoding the CMP domain was augmented at its 5' end with a segment encoding an N-terminal signal sequence for the fusion protein. The construct was designated "CMP-TPB(gE)-TMR(VSVG)". See Example 22 for additional details.

FIG. 23B is a diagram of a nucleic acid construct coding for a fusion protein as described in Example 22, in which a segment encoding a "chaperone machinery polypeptide" ("CMP") domain comprising a 12 amino acid peptide (IK-KAFHKLAMKY, SEQ ID NO:9) from the J domain of the Erdj4 protein was linked to a segment encoding a target protein binding (TPB) domain comprising an Fc-binding portion of gE protein augmented at its 3' end with a segment encoding a Flag epitope tag, which in turn was linked to a segment encoding a transmembrane retention (TMR) domain comprising a mutated version of the transmembrane region of VSV-G in which the C-terminus of the VSV-G transmembrane region was engineered to include three additional amino acids (K-T-C) to create a tandem lysine or "dilysine" (K-K) motif at positions −4 and −3 from the C-terminus ("TMR with KK motif", SEQ ID NO:194). This amino acid motif at the C-terminus of the cytoplasmic region of a transmembrane protein is known to localize proteins in the endoplasmic reticulum (ER). The segment of the construct encoding the CMP domain was augmented at its 5' end with a segment encoding an N-terminal signal sequence for the fusion protein. The construct was designated "CMP-TPB(gE)-TMR(VSVG) with KK motif". See Example 22 for additional details.

DETAILED DESCRIPTION OF THE INVENTION

Figure 1:
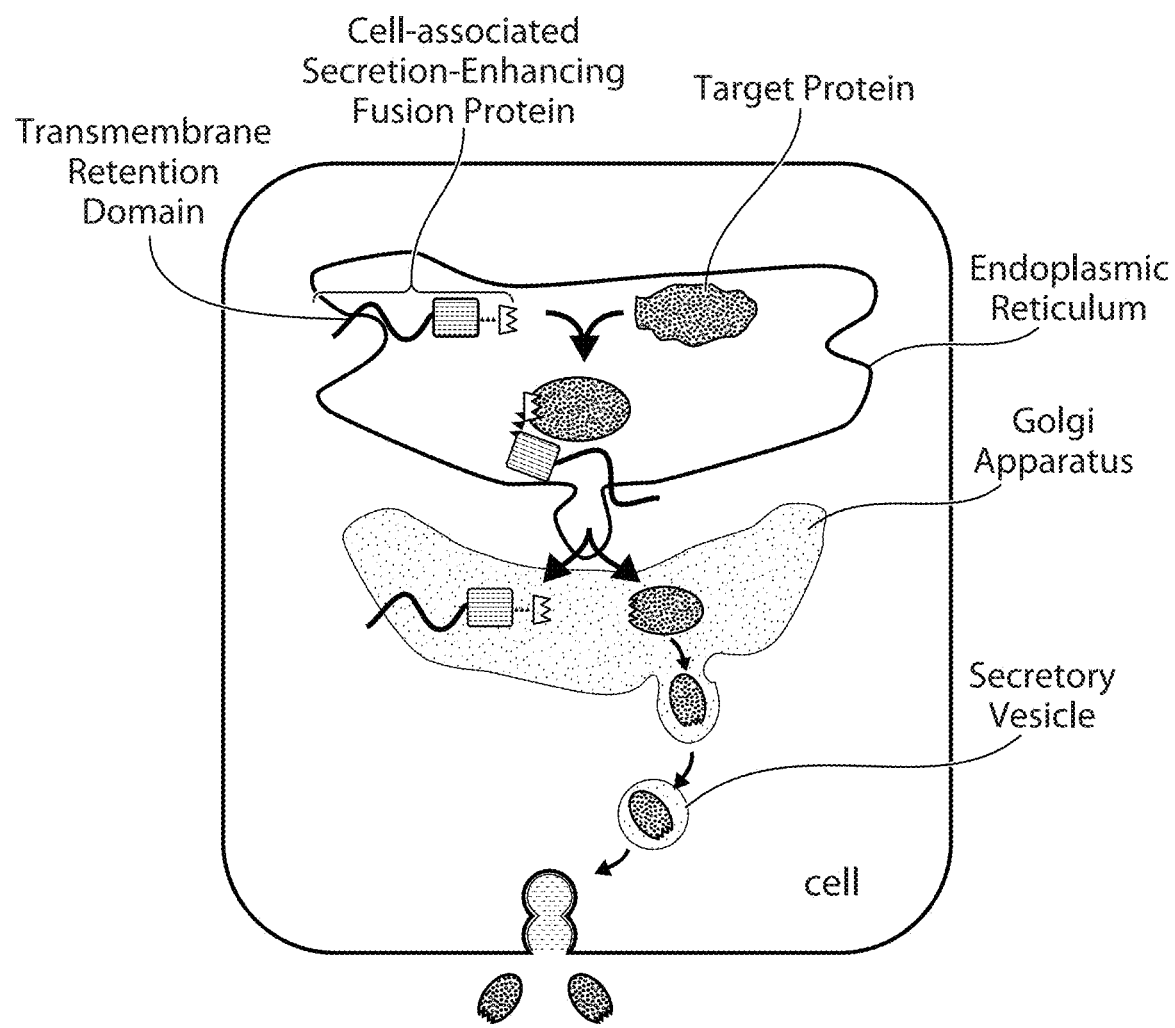
FIG. 1 is a diagrammatic illustration of how the process of the present invention is believed to operate in a recombinant eukaryotic host cell, showing the general location and association of a cell-associated secretion-enhancing (CASE) fusion protein of the invention with a target protein of interest co-expressed in the eukaryotic host cell. As depicted in the illustration, a CASE fusion protein of the invention comprises a target protein binding (TPB) domain and a transmembrane retention (TMR) domain. The TMR domain anchors the fusion protein to the intracellular membrane system extending along the secretory pathway from the endoplasmic reticulum (ER) to the Golgi apparatus prior to the formation of secretory vesicles. In the illustration, a CASE fusion protein associated with the ER membrane is envisaged as binding to a nascent target protein via its TPB domain in the lumen of the ER where the fusion protein protects the target protein from being retro-translocated to the cytoplasm for degradation. The binding complex of the CASE fusion protein and the target protein is further envisaged as entering the Golgi apparatus where the fusion protein dissociates from the target protein, presumably coincident with the progressive lowering of pH along the secretory pathway. The fusion protein remains associated with the membrane of the Golgi apparatus while the dissociated target protein is enveloped within a secretory vesicle, which then fuses to the cell membrane to release the target protein from the host cell.

A major advantage of secreting a protein of interest from cells in a production culture is that the purification of the protein species from the medium of a culture of largely intact cells is typically far more economical than if the protein species remained in the cells and required purification away from all of the other cellular components that are released upon disrupting the cells. Moreover, regulatory approval of a protein of interest as well as a production protocol for the protein of interest is generally more expedient when components of a production run are known and do not include new contaminating species that have not previously existed in previous production protocols. Accordingly, any effort to improve production yields of proteins that have recognized medical and commercial value preferably will comprise such features as described.

This invention provides a new family of engineered fusion proteins, wherein the fusion protein binds to a target protein of interest that is co-expressed within a host cell and wherein the fusion protein also enhances the amount of target protein that is secreted from the host cell while also remaining associated with the host cell so as not to be co-secreted with the target protein of interest. Thus, a fusion protein of the invention provides a means of elevating the yield of a target protein of interest that can be secreted from a host cell into a culture medium, without also becoming a new contaminating component of the host cell culture medium. Accordingly, fusion proteins of the invention are referred to as cell-associated secretion-enhancing ("CASE") fusion proteins. A CASE fusion protein described herein comprises:

(a) a target protein binding ("TPB") domain,
(b) a transmembrane retention ("TMR") domain, and
(c) optionally, a chaperone machinery polypeptide ("CMP") domain.

The domains of a CASE fusion protein according to the invention are typically selected from different proteins, are derivatives of portions of different proteins, or may be polypeptides not previously known to exist in nature. The TPB domain comprises a polypeptide that is selected for its ability to bind to a particular target protein of interest, and the TMR domain comprises a polypeptide that is selected mainly to result in the CASE fusion protein being essentially completely retained within the expressing host cell. The CMP domain ("chaperone machinery polypeptide", "chaperone machinery peptide"), when present in a CASE fusion protein, is selected mainly for its ability to improve target protein secretion, presumably by acting as a type of chaperone to a target protein bound by the CASE fusion protein to engage in some manner the cellular chaperone mechanisms involved with processing, folding, membrane-translocation, and/or secretion. Where two domains of a CASE fusion protein are selected from the same natural protein, they are not in the same orientation with respect to each other as found in the native protein from which they were derived. Thus, it will be understood that CASE fusion proteins of the invention are formed as the result of a deliberate recombination and engineering of polypeptide domains yielding artificial, synthesized fusion proteins that do not occur in nature and that possess at least one desirable functional activity or property for each required domain, i.e., the TPB domain provides a target protein binding function, the TMR domain provides a membrane-association function, and the combination of the TPB and TMR domains results in a fusion protein providing increased secretion of a co-expressed target protein. The CMP domain, when present, provides a significant enhancement in the level of secreted target protein compared to that obtained when the target protein is co-expressed with a CASE fusion protein comprising the TPB and TMR domains but lacking the CMP domain.

According to the invention, co-expression in a host cell of a CASE fusion protein described herein with a target protein of interest enhances the level of target protein secreted from the host cell as compared to the level that is secreted when the target protein is expressed in the absence of the fusion protein, and the enhancement in the level of secretion of the target protein occurs wherein the CASE fusion protein remains associated with the host cell such that no significant amount of the fusion protein is secreted into the host cell extracellular culture media where it may otherwise be considered a new contaminant within the culture media containing the secreted target protein. By "no significant amount" in this context is meant that the level of CASE fusion protein in the culture media is not detectable or is at a level that is tolerable so as to not require steps specifically aimed at removal of the fusion protein from the culture media in the further purification or processing of the target protein. The United States Food and Drug Administration (FDA) has found that most biological products (biologics) contain ELISA-based host cell (non-product) protein levels between 1 and 100 ppm. See, *The Handbook of Process Chromatography, Second Edition*, Hagel et al., eds. (Academic Press, London, 2008), Chapter 5, page 131. Such a range of non-drug proteins of host cell origin serves as guidance for the production and regulatory approval of biologics. Accordingly, although a fusion protein of the invention is most preferably not secreted into a host cell culture medium, and therefore not detectable by ELISA, an insignificant and tolerable level of a fusion protein of the invention that is secreted into a host cell culture medium may be, but is not limited to, in order of increasing preference, less than 100 ppm, less than 80 ppm, less than 70 ppm, less than 60 ppm, less than 50 ppm, less than 40 ppm, less than 30 ppm, less than 20 ppm, less than 10 ppm, less than 5 ppm, less than 3 ppm, less than 2 ppm, less than 1 ppm, less than 0.3 ppm, less than 0.15 ppm, less than 0.10 ppm, less than 0.05 ppm, less than 0.02 ppm, less than 0.01 ppm, and less than 0.005 ppm.

The domains of a CASE fusion protein described herein are chosen so that the fusion protein provides the desired activity of enhancing the level of a target protein of interest that is secreted from a host cell when the fusion protein is co-expressed with the target protein and to provide such enhancement in the level of secreted target protein without also being co-secreted with the target protein. While not intending to be bound by any particular scientific theory to explain the expression enhancement mechanism, it appears that the target protein binding (TPB) domain of a CASE fusion protein described herein binds a target protein that is expressed in the endoplasmic reticulum (ER) of a host cell and subsequently releases the target protein within the Golgi apparatus or at the formation of a secretory vesicle that envelopes the target protein for secretion from the cell, while the TMR domain of the fusion protein anchors the fusion protein to the cellular membrane of the secretory pathway without permanently retaining the fusion protein in the ER or without interfering with the formation of a secretory vesicle required for secretion of the target protein from the cell. The CASE fusion protein co-expressed with the target protein in a host cell appears to have a chaperone-like effect that improves or for reasons not known assists the intracellular processing of the target protein for secretion from the host cell.

In addition to enhancing yields of target proteins secreted from cells into the media of production cultures, a CASE fusion protein of the invention also provides a technical solution when there is a failure to secrete desired or adequate quantities of an endogenous (i.e., component of the cell's proteome) or heterologous (i.e., recombinant) target protein of interest in cells of a eukaryotic organism, such as a plant, a non-human animal, or even a human subject. The present invention provides compositions and methods for treating non-human or human individuals for a disease or disorder in which there is a failure to secrete sufficient levels of a functional protein in vivo, where inadequate secretion of a protein or a functional version of a secreted protein leads to a pathological state. Examples of diseases in which such deficiency in adequate levels of secretion of a protein species has been demonstrated or implicated include, but are not limited to, cystic fibrosis (CF), Alzheimer's disease; Parkinson's disease; Huntington's disease; and prion-associated disease (transmissible spongiform encephalopathy).

In order to more clearly describe the invention, the following comments and definitions of terms apply.

Unless otherwise defined herein, scientific and technical terms used in connection with the present invention shall have the meanings that are commonly understood by those of ordinary skill in the art. The meaning and scope of the terms should be clear; however, in the event of any latent ambiguity, definitions provided herein take precedent over any dictionary or extrinsic definition. Further, unless otherwise required by context, singular terms shall include pluralities and plural terms shall include the singular. In this application, the use of the term "or" means "and/or," unless stated otherwise. Furthermore, the use of the term "including", as well as other forms, such as "includes" and "included", is not limiting as is also the case for the terms "comprising," "comprises," and "comprised."

Generally, nomenclatures used in connection with and techniques of protein and nucleic acid chemistry (including methods of recombinant nucleic acid and polymerase chain reaction (PCR)), cell and tissue culture, molecular biology, genetics, microbiology, biochemistry, proteomics, pharmacology, and pharmaceutical science described herein are those well-known and commonly used in the art. The methods and techniques of the present invention are generally performed according to conventional methods in the art and as described in various general and more specific references available in the art. Assays and purification techniques are performed according to protocols available in the art, including in manuals of laboratory techniques and manufacturer's specifications, as commonly accomplished in the art or as described herein.

Unless indicated otherwise, when the terms "about" and "approximately" are used in combination with an amount, number, or value, then that combination describes the recited amount, number, or value alone as well as the amount, number, or value plus or minus 10% of that amount, number, or value. By way of example, the phrases "about 40%" and "approximately 40%" disclose both "40%" and "from 36% to 44%, inclusive".

The terms "protein of interest", "target protein of interest", or "target protein" are synonymous and refer to any protein, polypeptide, or peptide for which there is a need or desire to enhance the level of secretion from a host cell that expresses the protein, polypeptide, or peptide.

The term "isolated" as in an "isolated molecule" (e.g., "isolated protein" or "isolated nucleic acid") is a molecule that by virtue of its origin or source of derivation: is not associated with naturally associated components that accompany it in its native state; is substantially free of other kinds of molecules from the same species; is expressed by a cell from a different species; or does not occur in nature. Thus, a protein (including, a polypeptide or a peptide) or nucleic acid molecule that is chemically synthesized or synthesized in a cellular system different from the cell from which it naturally originates will be "isolated" from its naturally associated components. Typically, a protein or nucleic acid molecule may also be rendered substantially free of naturally associated components by isolation, using respectively protein or nucleic acid purification techniques well known in the art.

The term "vector", as used herein, is intended to refer to a nucleic acid molecule capable of transporting another nucleic acid to which it has been linked. One type of vector is a "plasmid", which refers to a circular double stranded nucleic acid (typically, DNA) loop into which additional nucleic acid segments may be inserted. Another type of vector is a viral (i.e., virus-based) vector wherein additional nucleic acid segments may be inserted into an engineered viral genome for transport into a cell and, in some cases, then into a chromosome of the cell. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into a chromosome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include other forms of expression vectors, such as viral vectors (e.g., replication defective retroviruses, lentivirus-derived vectors, and adenovirus-derived vectors), which serve equivalent or comparable functions.

The term "operably linked" refers to a juxtaposition of described components wherein the components are in a relationship permitting them to function in their intended manner. A control sequence "operably linked" to a coding sequence is ligated in such a way that expression of the coding sequence is achieved under conditions compatible with the control sequences. "Operably linked" sequences may include both expression control sequences that are contiguous with the gene of interest and expression control sequences that act in trans or at a distance to control the gene of interest. The term "expression control sequence" refers to polynucleotide sequences that are necessary to effect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (such as, a Kozak consensus sequence); sequences that enhance protein stability; and when desired, sequences that enhance protein secretion. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include components whose presence is essential for expression and processing, and can also include additional components whose presence is advantageous, for example, leader sequences and fusion partner sequences. Unless stated otherwise, a description or statement herein of inserting a nucleic acid molecule encoding a fusion protein of the invention into an expression vector means that the inserted nucleic acid has also been operably linked within the vector to a functional promoter and other transcriptional and translational control elements required for expression of the encoded fusion protein when the expression vector containing the inserted nucleic acid molecule is introduced into compatible host cells or compatible cells of an organism.

The term "target protein binding domain" and its abbreviation "TPB domain" refer to any polypeptide that has a binding affinity for a target protein and bestows that binding affinity on a CASE fusion protein in which it is present. Preferably, a TPB domain will also show a high degree of specificity, namely, that its binding will be specific for one target protein, and the domain will not exhibit affinity for different, structurally unrelated proteins that may be present in the proteome of a host cell that is co-expressing the target protein and the CASE fusion protein. A TPB domain may be a naturally occurring domain that binds to a target protein. A TPB domain may also be a synthetic, non-naturally occurring polypeptide domain found to have the desired affinity for a target protein. Preferably (as noted above), a TPB domain of a CASE fusion protein described herein binds a target protein that is co-expressed with the fusion protein in the endoplasmic reticulum (ER) of a host cell and subsequently releases the target protein within the Golgi apparatus or at the formation of a secretory vesicle that envelopes the target protein for secretion from the cell. Polypeptides that can serve as TPB domains of CASE fusion protein of the invention may be discovered by screening for target protein binding affinity for a particular target protein.

Known methods for such screening include, but are not limited to, phage display library screening, yeast two hybrid screening, far-western screening, high-throughput ELISA, and the like.

The term "transmembrane retention domain," its abbreviation "TMR domain", and "transmembrane retention signal" as used herein refer to a polypeptide domain included in a CASE fusion protein of the invention that causes the fusion protein to remain associated with the host cell in which the fusion protein is co-expressed with a target protein of interest. The TMR domain comprises at least a portion of a transmembrane (TM) region of a transmembrane protein that normally traverses the membrane of a cell. The region of a transmembrane protein employed as a TMR domain in the fusion proteins of the present invention will comprise a sufficient fragment of the membrane-spanning region of a transmembrane protein so that, when incorporated into a CASE fusion protein of the invention, the fusion protein remains associated with the cell and is not secreted from the cell. The TMR domain used in the fusion proteins described herein may include all or an operative fragment of the transmembrane region of a transmembrane protein that is normally known to be embedded in the membrane. The portion of a transmembrane protein useful as a TMR domain is not limited to only the membrane-spanning region of the transmembrane protein but may also comprise additional flanking amino acids of the transmembrane protein that are located upstream (N-terminal) and/or downstream (C-terminal) to the membrane-spanning region. As discussed below, a particularly preferred TMR domain for use in fusion proteins according to the invention is derived from a type I transmembrane protein. Preferably, a TMR domain of a CASE fusion protein of the invention anchors the fusion protein to the cellular membrane of the secretory pathway without permanently retaining the fusion protein in the ER or without interfering with the formation of a secretory vesicle required for secreting the target protein from the cell. Accordingly, a transmembrane region of a protein that is known to reside in the endoplasmic reticulum (ER) or a transmembrane region that is otherwise known to localize a protein exclusively to the ER is not preferred for use as a TMR domain of a CASE fusion protein of the invention unless the ER-retaining function has been deleted or otherwise inactivated. For example, as shown herein, a transmembrane region of the KDEL 1 receptor (KDELR) protein, which is present in the ER membrane, is a preferred transmembrane region for use as a TMR domain of a CASE fusion protein of the invention. While not intending to be bound by any particular scientific theory of a mechanism, it is assumed that a transmembrane region that anchors a protein to the ER also blocks a fusion protein comprising such a transmembrane region from progressing to the Golgi apparatus of the secretory pathway and therefore would inhibit and not enhance secretion of a target protein bound by the fusion protein. The success shown in the examples below of using a transmembrane region from the KDELR protein, which is found in the ER, as a TMR domain in a CASE fusion protein of the invention may be due to the fact that the KDELR protein is not permanently anchored in the ER but must move back and forth between the ER and Golgi apparatus.

The term "chaperone machinery polypeptide", "chaperone machinery peptide", and its abbreviation "CMP" refer to a polypeptide whose presence in a cell-associated secretion-enhancing (CASE) fusion protein described herein enhances the level of secretion of a co-expressed target protein above that observed when the target protein is co-expressed with the same or substantially the same CASE fusion protein lacking the CMP. As explained and exemplified in more detail below, a CMP domain useful in the invention may comprise one or more of the following:

a known polypeptide domain of a known component of the ubiquitous Hsp70 chaperone system (or corresponding chaperone system), such as, but not limited to, a J domain of a J protein;

an isolated polypeptide of a known domain of a known component protein of a chaperone system, such as, but not limited to, a defined peptide of a J domain of J protein; or a synthetic, non-naturally-occurring peptide analog of a naturally-occurring peptide of a known component protein of a chaperone system.

While not wishing to be bound by any particular scientific theory as to the possible mechanism of expression enhancement provided by inclusion of a CMP domain, a CMP domain of a CASE fusion protein of the invention is presumed to engage or recruit some aspect of a host cell Hsp70 chaperone system (or equivalent system in other host cells) that provides a further enhancement in the level of secretion of a co-expressed target protein bound by the CASE fusion protein (as compared to the level observed when the target protein is co-expressed with the same or substantially the same CASE fusion protein lacking the CMP domain) perhaps by increasing the numbers of target proteins that are properly folded within the ER and that enter the secretory pathway.

According to the nomenclature used herein, the source of a polypeptide employed as a TPB, TMR, or CMP domain in any fusion protein described herein may be referred to by an abbreviation of the name of the source protein or polypeptide set in parentheses to the right of the particular domain. For example, "TPB(gE)" indicates that the target protein binding (TPB) domain comprises all or a polypeptide fragment of the herpes simplex virus type-1 envelope (viral membrane) glycoprotein E ("gE"). The shorthand designation "TPB(gE)" does not, however, disclose whether TPB domain comprises all or a portion of the gE protein. The particular binding function and amino acid sequence of the particular polypeptide of gE used in the TPB domain of the fusion protein will be obtained from other information given in the disclosure. For example, as explained herein, the gE protein is known to bind the immunoglobulin Fc region and is employed in several examples of the disclosure for that property. Accordingly, a TPB domain may employ a portion of gE that binds a target protein of interest that comprises an Fc region. The particular amino acid sequence of the gE protein employed in such a TPB domain of a fusion protein is given in the description of particular embodiments in the text including, for example, in tables setting forth the amino acid sequences of the domains of particular fusion proteins. Similarly, the use of parenthetical abbreviations to the right of the terms "TMR" and "CMP" indicate the source protein or polypeptide used in selecting those domains. The actual amino acid sequence of the TMR or CMP domain must be obtained from descriptions in the text, including for example, the tables of the amino acid sequences of the domains of the particular fusion proteins included in the Examples section herein. The term "operative fragment" when used in conjunction with a transmembrane region means a polypeptide corresponding to some but not all amino acids of a membrane-spanning region of a transmembrane protein, which polypeptide is effective, when incorporated as the TMR domain of a CASE fusion protein of the invention, to cause the fusion protein to be retained with the cell.

As used herein, "significantly enhanced" signifies an increase, e.g., in the yield or level of a target protein of interest secreted from a host cell, of at least 1.5-fold over a comparative standard amount (e.g., the amount of target protein secreted from cells in the absence of co-expression with a fusion protein of the invention). For a secreted target protein of interest that is also a therapeutically and commercially important protein, an enhancement of 1.5-fold or more would be recognized by persons in the pharmaceutical industry as providing a significant reduction in production costs and also a significant increase in the availability of the therapeutically and commercially important protein.

When used to describe a negative threshold, e.g., as in "without significant secretion into the culture medium", the term "significant" refers to an amount of a protein at the level of detection of the assay used to detect the presence of such protein. For example, a statement that expression of a fusion protein resulted in "no significant secretion" of the fusion protein from a host cell means that according to the technique used to assay for the presence of secreted fusion protein, no protein or only a negligible amount of the protein was detected in such assay. A "negligible" amount in this context would be an amount that is sufficiently low so as to be tolerable in preparations of the target protein, and "tolerable" may refer to causing no adverse effects that need to be neutralized or to requiring no further steps to eliminate the negligible amount of the substance from preparations. In a context of pharmaceutical preparations, specific limits for negligible or tolerable amounts of an impurity or contaminant may be set by a reviewing authority such as the FDA. Another way of expressing the result of no significant amount of CASE fusion protein being secreted to the culture media of a host cell for the purposes of the present invention will be that the extracellular culture media of the host cell expressing the CASE fusion protein is "essentially free" of the CASE fusion protein, wherein it will be understood that any amount of CASE fusion protein reaching the culture medium will be undetectable by standard assays (for example, ELISA) or will be an amount that is insufficient to affect the target protein biological activity in a preparation of the target protein made from the culture media.

The terms "heterologous" and "exogenous" are synonymous and are used broadly as adjectives to describe any molecule (e.g., protein, polypeptide, nucleic acid) that is not native to a host cell containing or expressing the molecule. Accordingly, "heterologous" and "exogenous" encompass the term "recombinant" as defined below.

As used herein, the term "recombinant" when used as an adjective describes non-naturally altered or manipulated nucleic acids, host cells transfected with exogenous (non-endogenous) nucleic acids, or polypeptides expressed non-naturally, through manipulation of isolated nucleic acid (typically DNA) and transfection of host cells or through manipulation of endogenous nucleic acid to alternative expression by introduction of non-endogenous nucleic acid. "Recombinant" is a term that specifically encompasses DNA molecules that have been constructed in vitro using genetic engineering techniques, and use of the term "recombinant" as an adjective to describe a molecule, construct, vector, cell, protein, polypeptide, peptide, or polynucleotide specifically excludes naturally occurring ("endogenous") such molecules, constructs, vectors, cells, proteins, polypeptides, peptides, and polynucleotides in their respective, un-isolated, native locations (for example, intracellular, tissue, or organ locations).

The term "recombinant host cell" (or simply, in context, "host cell"), as used herein, is intended to refer to a cell into which exogenous nucleic acid has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein. Host cells useful in various aspects of the invention may be prokaryotic and eukaryotic cells. Preferred prokaryotic host cells include various bacterial cells, including *Escherichia coli*. While some manipulations, constructions, expressions, or replications of nucleic acids or encoded polypeptides related to the invention may be conducted using prokaryotic or eukaryotic host cells, the preferred host cells for producing enhanced levels of a secreted target protein of interest according to the invention, are eukaryotic host cells. Preferred eukaryotic host cells include, without limitation, a mammalian host cell, an insect host cell, a plant host cell, a fungal host cell, a eukaryotic algal host cell, a nematode host cell, a protozoan host cell, and a fish host cell. Preferably, a mammalian host cell is a Chinese Hamster Ovary (CHO) cell, a COS cell, a Vero cell, an SP2/0 cell, an NS/0 myeloma cell, a human embryonic kidney (HEK293) cell, a baby hamster kidney (BHK) cell, a HeLa cell, a human B cell, a CV-1/EBNA cell, an L cell, a 3T3 cell, an HEPG2 cell, a PerC6 cell, or an MDCK cell. Preferred fungal host cells include *Aspergillus, Neurospora, Saccharomyces, Pichia, Hansenula, Schizosaccharomyces, Kluyveromyces, Yarrowia*, and *Candida*. A particularly preferred *Saccharomyces* host cell is a *Saccharomyces cerevisiae* cell. A particularly preferred insect host cell is an Sf9 cell.

"Transgenic organism", as known in the art and as used herein, refers to an organism having cells that contain a transgene, wherein the transgene introduced into the organism (or an ancestor of the organism) expresses a polypeptide not naturally expressed in the organism or not naturally expressed at the normal or proper level to provide the intended function of the polypeptide to the organism. A "transgene" is a nucleic acid construct, which is stably and operably integrated into the genome of a cell from which a transgenic organism develops, directing the expression of an encoded gene product in one or more cell types or tissues of the transgenic organism. In transgenic plants and non-human animals, a nucleic acid encoding a particular protein (e.g., a fusion protein of the invention) is permanently incorporated into the genome as a functional gene (transgene) such that the plant or non-human animal not only expresses the fusion protein, but also passes a copy of the expressible transgene on to progeny.

The terms "disease" and "disorder" are used interchangeably to indicate a pathological state identified according to accepted medical standards and practices in the art.

As used herein, the term "effective amount" refers to the amount of a therapy that is sufficient to reduce or ameliorate the severity and/or duration of a disease or one or more symptoms thereof; to prevent the advancement of a detrimental or pathological state; to cause regression of a pathological state; to prevent recurrence, development, onset, or progression of one or more symptoms associated with a pathological state; to detect a disorder; or to enhance or improve the prophylactic or therapeutic effect(s) of a therapy (e.g., the administration of another prophylactic or therapeutic agent).

A "biological sample," as used herein, includes, but is not limited to, any quantity of a substance from a living organism or formerly living organism. Such organisms include, but are not limited to, humans, non-human primates, mice, rats, monkeys, dogs, rabbits, ruminants, and other animals. Such substances of a biological sample may include, but are not limited to, blood, serum, plasma, lymph, urine, saliva, sputum, mucus, synovial fluid, milk, amniotic fluid, spinal fluid, semen, cells, organs (for example, heart, spleen, lung, kidney, breast, brain, eye, tongue, stomach, pancreas, intestines, gall bladder, reproductive organs, appendix), tissues (for example, bone, cartilage, muscle, skin), bone marrow, and lymph nodes.

A composition or method described herein as "comprising" (or which "comprises") one or more named elements or steps is open-ended, meaning that the named elements or steps are essential, but other elements or steps may be added within the scope of the composition or method. To avoid prolixity, it is also understood that any composition or method described as "comprising" (or which "comprises") one or more named elements or steps also describes the corresponding, more limited, composition or method "consisting essentially of" (or which "consists essentially of") the same named elements or steps, meaning that the composition or method includes the named essential elements or steps and may also include additional elements or steps that do not materially affect the basic and novel characteristic(s) of the composition or method. It is also understood that any composition or method described herein as "comprising" (or which "comprises") or "consisting essentially of" (or which "consists of") one or more named elements or steps also describes the corresponding, more limited, and close-ended composition or method "consisting of" (or which "consists of") the named elements or steps to the exclusion of any other unnamed element or step.

In any composition or method disclosed herein, known or disclosed equivalents of any named essential element or step may be substituted for that element or step.

Unless specifically indicated, a composition or method is not limited by any particular order of the listed elements or steps, unless a particular method step requires the prior performance of another step.

It is also understood that an element or step "selected from the group consisting of" or "any of" (or equivalent phrase) refers to one or more of the elements or steps in the list that follows, including combinations of any two or more of the listed elements or steps.

Unless otherwise indicated, reference to a range of values is understood to include both boundary values of the recited range, as well as all values in between. Thus, in a disclosure of a pH range, e.g., pH 6.8 to pH 7.2 (or the equivalent notation, pH 7.0±0.2), the disclosure will be understood to include any pH value from and including pH 6.8 and above, up to pH 7.2, inclusive.

Cell-Associated Secretion-Enhancing (CASE) Fusion Proteins

According to the invention, the level of a target protein of interest secreted from a host cell is significantly higher (i.e., at least 1.5-fold higher) when the target protein is co-expressed in the host cell with a cell-associated secretion-enhancing (CASE) fusion protein described herein as compared to the level of target protein secreted from the host cell when the target protein is expressed in the absence of the fusion protein.

A cell-associated secretion-enhancing (CASE) fusion protein of the invention comprises two domains:
(a) a target protein binding (TPB) domain, which specifically binds a target protein of interest co-expressed in a host cell, and
(b) a transmembrane retention (TMR) domain, which is required for the fusion protein to be retained with the host cell while the co-expressed target protein is secreted from the host cell.

The TPB and TMR domains may be contiguous or linked together by an amino acid or peptide linker (containing two or more peptide bonded amino acids) to form a linear fusion protein. Additional domains for detection or to aid purification of the fusion protein are also contemplated. A non-limiting example of such an addition domain is a Flag epitope tag or a V5 epitope tag or a hexahistidine affinity tag. Selection of the domains for construction of a CASE fusion protein according to the invention are discussed in detail below.

In a preferred embodiment, a CASE fusion protein of the invention comprises three domains:
(a) a target protein binding (TPB) domain, which specifically binds a target protein of interest co-expressed in a host cell,
(b) a transmembrane retention (TMR) domain, which is required for the fusion protein to be retained with the host cell while the co-expressed target protein is secreted from the host cell, and
(c) a chaperone machinery peptide (CMP) domain, which enhances expression and secretion of a co-expressed target protein of interest.

Target Protein Binding (TPB) Domains Useful in the Invention

A cell-associated secretion-enhancing (CASE) fusion protein of the invention comprises a target protein binding (TPB) domain that binds a target protein of interest for which an elevated level of secretion from a host cell is desired. The more specific the binding affinity of a TPB domain is for a target protein, the less likely other proteins may potentially interfere with the enhancement in the level of expression and secretion of the target protein of interest when practicing the present invention.

A CASE fusion protein according to the invention and a target protein of interest (for which the TPB domain has an affinity) will be co-expressed in the same host cell. To obtain the maximum benefit of the present invention the target protein will be a protein that is secreted to the extracellular media when expressed by the host cell, and the target protein binding domain will be selected primarily for its ability to bind with the target protein. A TPB domain of a fusion protein of the invention may be any protein, polypeptide, or binding domain that is capable of binding to a particular target protein of interest and permits the target protein to be secreted from the cell at significantly higher levels than in the absence of the fusion protein.

The TPB domain must not only bind to a target protein but must also release the target protein into the cellular secretion pathway under conditions encountered inside the expressing host cell. A CASE fusion protein that incorporates a TPB domain that binds with too great an affinity or that cannot be induced to release the target protein at an appropriate stage of secretion will fail to enhance secretion of the target. This will often be marked by an accumulation of the fusion protein/target protein complex in a particular compartment of the producing host cell, such as the endoplasmic reticulum (ER). Among the intracellular conditions that influence the release of the target protein from a fusion protein/target protein complex is the local pH of specific organelles and vesicles of the cell. The pH of various eukaryotic organelles involved with expression and secretion of proteins has been measured. During the process of expression and secretion, a protein in a eukaryotic cell experiences a relatively rapid acidification as it passes through the ER to the Golgi complex (Golgi apparatus, Golgi) and into a secretory vesicle. In particular, a protein to be secreted will pass through the ER, which is typically maintained at around neutral pH 7.2 (±0.2), on to the Golgi complex, where the protein experiences a successive lowering of pH from pH 6.7 (±0.2) in the cis Golgi, to pH 6.3 (±0.2) in the medial Golgi, and down to pH 6.0 (±0.2) in the trans Golgi network, and thereafter the protein will be sequestered in a secretory vesicle in which the pH is 5.5 (±0.4) in preparation for secretion from the cell. See, for example, the review by Demaurex, *News Physiol. Sci.,* 17: 1-5 (February 2002). Other intracellular conditions may also play a role in target protein dissociation from the fusion proteins of the invention and subsequent secretion from the host cell. As regards the influence of pH, however, particular embodiments of a fusion protein of the invention will advantageously bind the target protein in the ER at a pH of 7.2 (±0.2), but release the target protein at a pH that is below pH 7.2 (±0.2), as found in the Golgi apparatus and secretory vesicles. Accordingly, a preferred TPB domain of a fusion protein of the invention binds or remains bound to a target protein at pH 7.2 (±0.2) or the conditions of the host cell ER, and then releases or does not bind the target protein at a pH below 7 or under conditions as found in the subsequent secretory pathway. In another embodiment, a TPB domain of a fusion protein of the invention is a polypeptide that binds a target protein at pH 7 or the conditions of the host cell ER and releases or does not bind a target protein at pH 6.7 or the conditions as found in the cis Golgi of a host cell. In another embodiment, a TPB domain of a fusion protein of the invention is a polypeptide that binds a target protein at pH 7 or the conditions as found in the ER and releases or does not bind a target protein at pH 6.3 or the conditions as found in the medial Golgi of a host cell. In another embodiment, a TPB domain of a fusion protein of the invention is a polypeptide that binds a target protein at pH 7 or the conditions found in the ER and releases or does not bind a target protein at pH 6.0 or the conditions (pH or otherwise) as found in the trans Golgi of a host cell. In still another embodiment, a TPB domain of a fusion protein of the invention is a polypeptide that binds a target protein at pH 7 or the conditions as found in the ER and releases or does not bind a target protein at pH of 5.5 or the conditions (pH or otherwise) as found in secretory vesicles of a host cell. The foregoing having been stated, working examples presented infra demonstrate that target protein binding domains derived from polypeptides known to have dissociation thresholds at lower pH (e.g., ~pH 4.5) have been shown to work, and work well, in the secretion-enhancing fusion proteins of the present invention—such results indicating that factors in addition to pH influence the optimized enhancement results achieved according to the teachings herein.

Keeping in mind the requirement for a CASE fusion protein of the invention to bind and release a target protein passing from the ER to secretory vesicles, examples of polypeptides that may be used as a TPB domain in a fusion protein of the invention include, but are not limited to, an antibody or antigen binding fragment thereof that specifically binds a target protein, an immunoglobulin-specific binding protein that binds a target protein that is an immunoglobulin or fragment thereof, an Fc-binding protein (when a target protein comprises an antibody Fc region), a ligand binding domain of a receptor protein that binds a target protein that is a ligand of the receptor (e.g., a binding portion of an IL13 receptor, where the target protein is IL13), a protein ligand when the target protein is a receptor or ligand binding fragment of a receptor (for example a cytokine, where the target protein is a cytokine receptor, or cytokine-binding fragment thereof), a PDZ domain when the target protein comprises a PDZ-binding domain, and the like. Binding proteins or polypeptide fragments binding to a target protein may be discovered by any known method, such as by screening a phage display library, yeast 2 hybrid system screening, far-western screening, high-throughput ELISA screening, and other methods.

In an embodiment of the invention, a TPB domain of a CASE fusion protein of the invention may advantageously be any of a variety of non-immunoglobulin proteins and polypeptides, or portions thereof, which are known to specifically bind Fc domains under intracellular conditions but to dissociate from the Fc domain at some point along the secretory pathway. For example, a TPB domain that binds to an Fc region at pH 7 and dissociates from the Fc-containing target protein at a pH below 7, for instance at pH 6.7, pH 6.5, pH 6.3, pH 5.7, or pH 5.5 is expected to release the target protein at pH conditions that can be found in cellular secretory vesicles. The typical pH range encountered in the secretion system of mammalian cells is from about pH 7 to pH 5.5, and therefore the most preferred TPB domains utilized in the present invention will have dissociation conditions from the target in this range. TPB domains that dissociate from the target protein at pH lower than 5.5 may have limited utility in the methods of the present invention unless a host cell having a secretory pathway exhibiting more acidic condition is used, or the host cell culture is treated (e.g., by altering culture conditions) in a manner to effect the dissociation of the target protein from any co-expressed fusion protein according to the invention.

A variety of standard ligand binding assays are available in the field for use in determining whether a particular protein or polypeptide is able to bind a particular ligand at one or more pH values. Such assays may include binding assays in which a target protein is labeled (for example, using a radiolabel, fluorescent label, or other signaling system) so that target protein can be detected whether bound or unbound by a protein comprising a TPB domain. Other binding assays include, without limitation, an immunoblot or an enzyme-linked immunosorbent assay (ELISA) that employs a detection antibody directed to the target protein for use in determining whether or not the target protein is bound to a protein comprising a TPB domain. Binding can also be measured in real time using surface plasmon resonance (SPR) binding assays.

In some embodiments, a TPB domain will be selected on the basis of affinity for the target protein, e.g., in terms of a relatively rapid on rate constant ($k_{on}$) or a relatively slow off rate constant ($k_{off}$), as measured, for example, by surface plasmon resonance. A dissociation constant ($K_D$) can be calculated according to the formula $K_D=k_{off}/k_{on}$. In particular embodiments of the invention, a CASE fusion protein will have a dissociation constant ($K_D$) to the target protein of $10^{-6}$ M or less.

Examples of polypeptides that may be used as or in a TPB domain of a CASE fusion protein of the invention include, but are not limited to, an antigen binding site isolated from natural and genetically engineered antibodies and antigen-binding fragments thereof, wherein the antigen binding site of an antibody or antigen-binding fragment binds a target protein for which an enhanced level of secretion from a host cell is desired. In this context, antibodies can easily be raised that bind a target protein using standard methods available in the art, and antigen-binding fragments can be produced from such antibodies by well-known techniques, such as papain or pepsin digestion or using recombinant DNA methods, PCR methods, or other standard methods of manipulating and recombining DNA. A variety of genetically engineered antibody formats are known in the art that may be used for a TPB domain of a CASE fusion protein of the invention. Such formats include, but are not limited to, Fab fragments, F(ab')$_2$ fragments, single chain Fv (scFv) antibodies, and single domain antibodies (dAb). See, for example, a review of the variety of functional genetically engineered antibody binding formats available in the art in Marvin et al., *Acta Pharmacol. Sin.*, 26(6): 649-658 (2005); Kufer et al, *Trends Biotechnol.*, 22(5): 238-244 (2004); Kontermann, *Acta Pharmacol. Sin.*, 26(1): 1-9 (2005), and Chan et al., *Nat. Rev,* 10: 301-316 (2010). Particularly useful in the invention are antibody molecules or fragments in which an antigen binding site directed to a target protein is provided in a single polypeptide because such polypeptides can be easily linked to another domain or transmembrane retention domain to form a fusion protein of the invention using standard in vitro methods for recombining nucleic acids. For example, a single chain Fv antibody (scFv) comprises both VH and VL domains of an antigen binding site linked in a single polypeptide. Another source of a single chain antigen binding site is a single domain antibody (dAb) in which the entire antigen binding site is present in a single heavy chain variable domain. See, for example, Ward et al., *Nature,* 341: 544-546 (1989); Muyldermans et al., *Protein Eng.,* 7: 1129-1135 (1994); Vu et al., *Mol. Immunol.,* 34: 1121-1131 (1997); Muyldermans et al., *Trends Biochem. Sci.,* 26: 230-235 (2001); Nguyen et al., *Immunogenetics,* 54: 39-47 (2002).

By way of non-limiting example, in the case in which a target protein is a receptor or functional ligand-binding portion thereof, the protein ligand, or a receptor-binding portion thereof, may be used as a TPB domain in a CASE fusion protein of the invention. Functional portions of receptors include, but are not limited to, the extracellular domain of a membrane-associated receptor that includes a functional ligand-binding site. Typically, such extracellular portions comprising a functional ligand binding site are referred to as "truncated receptors" because the transmembrane and cytoplasmic domains of the receptor molecule have been removed. Using standard nucleic acid recombinant methods, a truncated receptor may be fused to an Fc region (such as a hinge-CH2-CH3 region) to form a truncated receptor-Fc fusion protein that dimerizes to form a homodimeric "trap" molecule that can bind two ligand molecules (by analogy to a naturally-occurring IgG molecule). An example of a truncated receptor fragment ("TF") employed in the Examples below is an extracellular fragment of the IL-13Rα2 receptor, and a trap molecule derived from the truncated fragment of the IL-13Rα2 receptor is designated "IL13Rα2TF-Fc". According to the invention, the level of a truncated receptor-Fc trap molecule secreted from a host cell may be elevated by co-expression with a cell-associated secretion-enhancing (CASE) fusion protein of the invention comprising the corresponding protein ligand of the receptor, or receptor-binding portion of the ligand, as its TPB domain, wherein the protein ligand is a single polypeptide chain, such as certain cytokine polypeptides (for example, IL13, IL8, and the like). Depending on the particular receptor protein species, other protein ligands that may be used in a CASE fusion protein as a TPB domain to bind a target receptor protein or ligand-binding portion thereof include, without limitation, a polypeptide co-receptor, a polypeptide co-repressor, and a polypeptide co-factor.

For use in enhancing secretion of a target immunoglobulin protein or a synthetic construct comprising an Fc region (including trap molecules discussed above), a CASE fusion protein of the invention may comprise a polypeptide or portion thereof that possess an Fc binding domain. Proteins that can serve as a source of an Fc-binding domain for use in a TPB domain of a CASE fusion protein of the invention include, but are not limited to, a glycoprotein E (gE) or Fc-binding portion thereof from herpes simplex virus type 1 (HSV-1), a staphylococcal Protein A, a streptococcal Protein G, an FcBP protein, and the like. A gE/gI complex also has affinity for Fc regions. A number of synthetic peptides also have been identified that bind Fc domains. See, for example, DeLano et al., *Science,* 287:1279-1283 (2000); Yang et al., *J. Peptide Res.,* 66(Suppl. 1): 120-137 (2006). As shown in the Examples below, such Fc-binding proteins and peptides may be particularly useful as TPB domains in CASE fusion proteins of the invention to provide enhanced levels of target proteins comprising an Fc region that are secreted from a host cell.

In another non-limiting example, when a target protein of interest is a protein ligand (for example, a cytokine) that is bound by a known receptor molecule, a TPB domain of a fusion protein of the invention may comprise the cognate receptor, or ligand-binding portion thereof, that binds the target ligand protein.

In an embodiment wherein the target protein, such as the cystic fibrosis transmembrane conductance regulator (CFTR) protein, possesses a PDZ-binding domain, then the TPB domain of a CASE fusion protein of the invention preferably comprises a PDZ domain from any of a variety of proteins that possess a PDZ domain. In a preferred embodiment, when a target protein possesses a PDZ-binding domain, a TPB domain of a CASE fusion protein of the invention comprises a PDZ domain from any of the members of the NHERF family of PDZ adapter proteins including, but not limited to, NHERF1 (also known as NHERF, EBP50, or SLC9A3R1), NHERF2 (also known as E3KARP or SLC9A3R2), and PDZK1 (also known as CAP70 or NHERF3).

Transmembrane Retention (TMR) Domains Useful in the Invention

Transmembrane proteins are membrane-bound proteins that comprise one or more transmembrane regions that are embedded in and traverse at least once a cellular membrane. Such a transmembrane region or a functional fragment thereof may be used as a transmembrane retention (TMR) domain of a cell-associated secretion-enhancing (CASE) fusion protein of the invention. According to the invention, a TMR domain prevents the fusion protein from being secreted from a host cell without interfering with the enhancement of the level of secretion of the target protein from the host cell.

A TMR domain useful in a fusion protein of the invention may be isolated from a transmembrane protein that is associated with any of a variety of membranes of a cell including, but not limited to, a cell membrane, an endoplasmic reticulum membrane, a Golgi complex membrane, a lysosomal membrane, a nuclear membrane, and a mitochondrial membrane.

Figure 8:
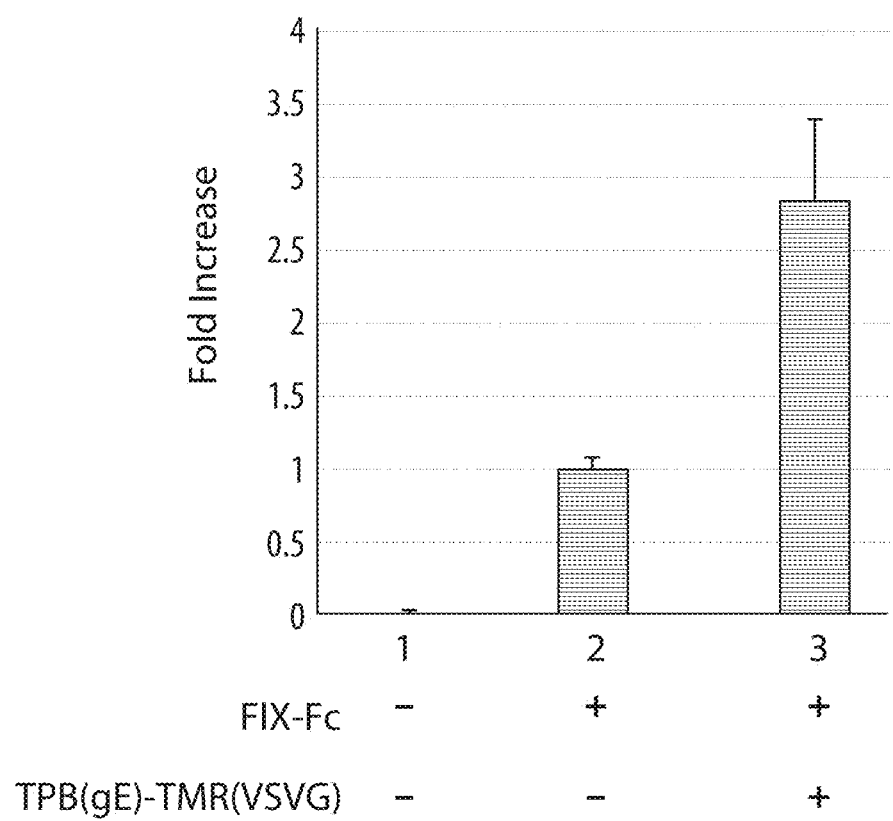
FIG. 8 shows bar graphs of the fold increase in the amount of a Factor IX-Fc target protein (FIX-Fc) detected by ELISA in the media of cultures of transfected HEK293 host cells expressing the target protein alone (bar graph 2) or co-expressing the target protein and a cell-associated secretion-enhancing fusion protein comprising an Fc-binding region of gE linked to a transmembrane retention (TMR) domain comprising a transmembrane region of a VSV-G protein ("TPB(gE)-TMR(VSVG)", bar graphs 3), as described in Example 8. The presence ("+") or absence ("−") of expression vectors encoding target protein or a fusion protein in the transfected host cells of each culture is indicated below each bar graph. Mock cultures contained cells transfected with "empty" expression vector lacking a structural gene for expressing any protein and were used as a negative control (bar graph 1). The data in the bar graphs have been normalized by subtracting non-specific background signal in media from mock cultures and setting the amount of target protein secreted into culture media when expressed in the absence of the cell-associated secretion-enhancing fusion protein at a relative value of 1 (bar graph 2). The results show that co-expression of the FIX-Fc target protein with the cell-associated secretion-enhancing TPB(gE)-TMR(VSVG) fusion protein (bar graph 3) significantly enhanced the level of target protein secreted into the culture media as compared to the level of target protein secreted into the culture media when the target protein was expressed in the absence of the cell-associated secretion-enhancing fusion protein (bar graph 2). See Example 8 for additional details.

There are four general classes or types of transmembrane proteins (Types I-IV). See, Nelson and Cox, *Principles of Biochemistry* (2008), FIG. 8-22. A schematic diagram of the general relevant features of the four types of transmembrane proteins is shown in FIG. 8. In FIG. 8, the transmembrane regions of each type of transmembrane protein are indicated schematically by loops within the lipid bilayer and are not meant to indicate any particular primary, secondary, tertiary, or quaternary structure of any particular protein species.

A Type I transmembrane protein has its N-terminal region targeted to the endoplasmic reticulum (ER) lumen and its C-terminal region directed to the cytoplasm. A type II transmembrane protein has its N-terminal region targeted to the cytoplasmic domain and its C-terminal region directed to the ER lumen. A Type III transmembrane protein is a "multi-pass" transmembrane protein that has more than one segment of the translated protein that spans the cellular membrane. A Type IV transmembrane protein is also a multi-pass transmembrane protein, where multiple membrane-spanning regions orient to form an aqueous channel through the cellular membrane.

A TMR domain of a cell-associated secretion-enhancing (CASE) fusion protein of the invention comprises all or part of a transmembrane region of a transmembrane protein that normally traverses the membrane of a cell with which the transmembrane protein is normally associated. A TMR domain of a CASE fusion protein of the invention may comprise not only a membrane-spanning region of a transmembrane protein but also additional amino acids of the transmembrane protein that are located in flanking regions, either upstream (N-terminal) and/or downstream (C-terminal) to the membrane-spanning or membrane-embedded region of the transmembrane protein. For example, in particular embodiments, the entire transmembrane region of a transmembrane protein will be used. In additional embodiments, the entire transmembrane region and all or part of any upstream or downstream region of the membrane-embedded portion of a transmembrane protein may be used as the TMR domain of a fusion protein according to the invention. Additional amino acids located upstream (N-proximal) from the membrane-embedded portion of a transmembrane protein that may be part of a TMR domain of a fusion protein of the invention may have a range of sizes including, but not limited to, 1 to 70 amino acids, 1 to 75 amino acids, or 1 to 80 amino acids. In some embodiments, a region of 1 to 75 amino acids of the upstream region may be used along with all or part of the membrane-embedded region as the TMR domain of a CASE fusion protein of the invention.

In some embodiments, a TMR domains of a CASE fusion protein of the invention may comprise a membrane-embedded portion of a transmembrane protein as well as all or a portion of the C-terminal (downstream) portion of the membrane-embedded region of the transmembrane protein. Additional amino acids located downstream (C-proximal) from the membrane-embedded portion of a transmembrane protein that may be part of a TMR domain of a fusion protein of the invention may have a range of sizes including, but not limited to, 1 to 10 amino acids, 1 to 15 amino acids, 1 to 20 amino acids, 1 to 30 amino acids, 1 to 40 amino acids, 1 to 50 amino acids, 1 to 60 amino acids, 1 to 70 amino acids, 1 to 80 amino acids, 1 to 90 amino acids, 1 to 100 amino acids, 1 to 110 amino acids, 1 to 120 amino acids, 1 to 130 amino acids, 1 to 140 amino acids, 1 to 150 amino acids, 1 to 160 amino acids, 1 to 170 amino acids, and 1 to 200 amino acids.

A TMR domain of a fusion protein described herein may also comprise the entire cytoplasmic region attached to a transmembrane region of a transmembrane protein or a truncation of the cytoplasmic region by one or more amino acids, for example, to eliminate an undesired signaling function of the cytoplasmic tail. For example, the presence of tandem lysine residues (dilysine) in the C-terminal portion of a cytoplasmic region of a transmembrane protein can serve as a signal to retain the transmembrane protein in the ER. Accordingly, if the membrane-embedded (transmembrane) region and all or part of the adjacent cytoplasmic C-terminal region of an ER-associated transmembrane protein is to be used as a TMR domain of a fusion protein of the invention, any known functional dilysine signal for ER retention should be eliminated or disrupted so that a fusion protein comprising the transmembrane region and any adjacent cytoplasmic region is not prevented by a dilysine ER retention motif from progressing out of the ER to the Golgi apparatus and/or secretory vesicles.

Table 1, below, provides a list of several examples of transmembrane proteins along with the amino acid sequences of a portion of the protein that contains the transmembrane (TM) region (underlined). A TMR domain that may be used in a cell-associated secretion-enhancing (CASE) fusion proteins of the invention, will use a part of the transmembrane region sequence sufficient to cause the fusion protein to be retained with the cell (preferably, within the cellular membrane of the secretory pathway) when expressed in a host cell. Other portions of the transmembrane protein, including segments of the flanking regions upstream or downstream of the TM region may be used to construct a TMR domain, so long as their inclusion enhances, or at least does not significantly diminish the transmembrane retention functionality of the TMR domain. Within each of the fragmentary amino acid sequences for selected transmembrane proteins presented in Table 1, all of the sequences given in the table may potentially be used as a TMR domain, although not all transmembrane regions are as efficient as others in functioning as a TMR domain in CASE fusion proteins of the invention. Alternatively, internal segments including at least a portion of the underlined membrane-spanning region may be used to make up a TMR domain for a CASE fusion protein of the invention, so long as the selected segments provide the function of causing the expressed fusion protein to be retained in the host cell while the co-expressed target protein is secreted from the host cell.

TABLE 1

Amino Acid Sequences of Representative Transmembrane Retention (TMR) Domains

| Name and Type of Transmembrane Protein | SEQ ID NO. | Amino Acid Sequence of isolated Transmembrane Retention Domain 12345678901234567890123456789 0 |
|---|---|---|
| VSV-G (NP_955548; Vesicular stomatitis Indiana virus glycoprotein) Type I | SEQ ID NO: 62 | DDESLFFGDTGLSKNPIELVEGWFSSWK<u>SS</u> <u>IASFFIIGLIIGLFLVLR</u>VGIHLCIKLKH TKKRQIYTDIEMNRLGK |

TABLE 1-continued

Amino Acid Sequences of Representative
Transmembrane Retention (TMR) Domains

| Name and Type of Transmembrane Protein | SEQ ID NO. | Amino Acid Sequence of isolated Transmembrane Retention Domain 12345678901234567890123456 7890 |
|---|---|---|
| Human herpesvirus 1 Envelope glycoprotein E (NP_044670.1) Type I | SEQ ID NO: 63 | PTHPHVGAPPHAPPTHGA<u>LRLGAVMGAALL LSALGLSVWAC</u>MTCWRRRAWRAVKSRASGK GPTYIRVADSELYADWSSDSEGERDQVPWL APPERPDSPSTNGSGFEILSPTAPSVYPRS DGHQSRRQLTTFGSGRPDRRYSQASDSSVF W |
| Human herpesvirus 1 Envelope glycoprotein I (NP_044669.1) Type I | SEQ ID NO: 64 | PHGVNHEPPSNATRATRDSRSALTVTQIIQ <u>IAIPASIIALVFLGSCICF</u>IHRCQRRYRRS RRPIYMPQIPTGISCAVNEAAMARLGAELK SHPSTPPKSRRRSSRTPMPSLTAIAEESEP AGAAGLPTPPVDPTTSTPTPPLLV |
| human p23 (NP_006818.3; Transmembrane emp24 domain-containing protein 10) Type I | SEQ ID NO: 65 | TR<u>VLYFSIFSMFCLIGLATWQVF</u>YLRRFFK AKKLIE |
| human p24 (NP_006806.1; Transmembrane emp24 domain-containing protein 2) Type I | SEQ ID NO: 66 | SR<u>VVLWSFFEALVLVAMTLGQIYY</u>LKRFFE VRRW |
| human CD4 (NP_000607.1; T-cell surface glycoprotein CD4) Type I | SEQ ID NO: 67 | QP<u>MALIVLGGVAGLLLFIGLGIFF</u>CVRCRH RRRQAERMSQIKRLLSEKKTCQCPHRFQKT CSPI |
| human Integrin αV (NP_001138471.1; Integrin alpha-V) Type I | SEQ ID NO: 68 | PV<u>PVWVIILAVLAGLLLLAVLVFV</u>MYRMGF FKRVRPPQEEQEREQLQPHENGEGNSET |
| human UGT1 NP_000454.1; UDP-glucuronosyltransferase 1-1) Type I | SEQ ID NO: 69 | LD<u>VIGFLLAVVLTVAFITF</u>KCCAYGYRKCL GKKGRVKKAHKSKTH |
| human Calnexin (NP_001019820.1; Calnexin) Type I | SEQ ID NO: 70 | PFRMTPFSAIGLELWSMTSDIFFDNFIICA DRRIVDDWANDGWGLKKAADGAAEPGVVGQ MIEAAEERP<u>WLWVVYILTVALPVFLVILFC</u> CSGKKQTSGMEYKKTDAPQPDVKEEEEEKE EEKDKGDEEEEGEEKLEEKQKSDAEEDGGT VSQEEEDRKPKAEEDEILNRSPRNRKPRRE |
| human KDEL receptor 1 (NP_006792.1; ER lumen protein retaining receptor 1) Type III | SEQ ID NO: 71 | <u>NLFRFLGDLSHLLAIILLLLK</u>IWKSRSCAG ISGK<u>SQVLFAVVFTARYLDLFTN</u>YISLYNT <u>CMKVVYIACSFTTVWLIYS</u>KFKATYDGNHD TFRVEFLVVPTAILAFLVNHDFTPLEILWT FSIYLESVAILPQLFMVSKTGEAETITS<u>HY LFALGVYRTLYLFNWIWRYHFEGFFDLIAI VAGLVQTVLYCDFFYLYIT</u>KVLKGKKLSLP A |
| Gp73 (NP_057632.2; Golgi membrane protein 1) Type II | SEQ ID NO: 72 | MMGLGNGRRSMK<u>SPPLVLAALVACIIVLGF NYWIA</u> |
| human LAMP2 (NP_001116078.1; Lysosome-associated membrane glycoprotein 2) Type I | SEQ ID NO: 73 | T<u>ILIPIIVGAGLSGLIIVIVIAYVIG</u>RRKS YAGYQTL |

TABLE 1-continued

Amino Acid Sequences of Representative Transmembrane Retention (TMR) Domains

| Name and Type of Transmembrane Protein | SEQ ID NO. | Amino Acid Sequence of isolated Transmembrane Retention Domain<br>123456789012345678901234567890 |
|---|---|---|
| human LIMP2 (NP_001191184.1; Lysosome membrane protein 2) fragment of TM domain Type III | SEQ ID NO: 74 | MGRCCFYTAGTLSLLLLVTSVTLLVARVF |
| human LIMP2 fragment of TM domain Type III | SEQ ID NO: 75 | TLIITNIPYIIMALGVFFGLVFTWLACKGQ GSMDEGTADERAPLIRT |
| human CD Man-6-P receptor (NP_002346.1; Cation-dependent mannose-6-phosphate receptor) Type I | SEQ ID NO: 76 | SHLSVGSILLVTFASLVAVYWGGFLYQRL VVGAKGMEQFPHLAFWQDLGNLVADGCDFV CRSKPRNVPAAYRGVGDDQLGEESEERDDH LLPM |
| human CI Man-6-P receptor (NP_000867.2; Cation-independent mannose-6-phosphate receptor) Type I | SEQ ID NO: 77 | SQAVGAVLSLLLVALTCCLLALLLYKKERR ETVISKLTTCCRRSSNVSYKYSKVNKEEET DENETEWLMEEIQLPPPRQGKEGQENGHIT TKSVKALSSLHGDDQDSEDEVLTIPEVKVH SGRGAGAESSHPVRNAQSNALQEREDDRVG LVRGEKARKGKSSSAQQKTVSSTKLVSFHD DSDEDLLHI |
| VSV-G (Vesicular stomatitis Indiana virus glycoprotein) truncated TMR domain Type I | SEQ ID NO: 78 | SSWKSSIASFFFIIGLIIGLFLVLRVGIHL CIKLKHTKKRQIYTDIEMMRLGK |
| human Calnexin Truncated TMR (NP_001019820.1; Calnexin) Type I | SEQ ID NO: 79 | PFRMTPFSAIGLELWSMTSDIFFDNFIICA DRRIVDDWANDGWGLKKAADGAAEPGVVGQ MIEAAEERPWLWVVYILTVALPVFLVILFC CSG |
| human KDEL receptor1 truncated TMR domain (NP_006792.1; ER lumen protein retaining receptor 1) Type III | SEQ ID NO: 80 | DLIAIVAGLVQTVLYCDFFYLYITKVLKGK KLSLPA |
| Human ERGIC-53 (NP_005561; ER-Golgi intermediate compartment 53 kDa protein) Type I | SEQ ID NO: 81 | LSTVHFIIFVVVQTVLFIGYIMYRSQQEAA AKKFF |
| gp84 Borna disease virus glycoprotein (NP_042023.1) Type I | SEQ ID NO: 82 | LGGVLYLISLCVSLPASFARRRRLGRWQE |

Selecting a TMR Domain

Data provided in the Examples below indicate that several factors should be considered in selecting a transmembrane region for use as TMR domain in a CASE fusion protein of the invention. Among these factors are a recognition of what is the particular transmembrane protein type (Type I, II, III, or IV) being considered for use as the source of the TMR domain, a recognition of the natural subcellular location of the transmembrane protein, and a recognition that the target protein binding (TPB) domain and the TMR domain and, when present, the chaperone machinery polypeptide (CMP) domain, in a fusion protein according to the invention may affect each other's function in the overall process described herein for enhancing expression and secretion of a target protein of interest.

As noted above and diagrammed in FIG. 18, the four types of transmembrane proteins can be distinguished from one another by the relative orientation of the N- and C-termini with respect to the cytoplasm and the endoplasmic reticulum (ER) lumen and whether the transmembrane region of the protein traverses a membrane (such as the ER membrane as indicated in FIG. 18) only once ("single pass" transmembrane region) or comprises two or more membrane-spanning regions so that the protein as a whole passes through a membrane more than once (multi-pass transmembrane region).

Knowing that a transmembrane region is derived from a particular type of transmembrane protein suggests a preferred orientation and location for the TMR domain relative to the CMP and TPB domains in a CASE fusion protein of the invention. This is particularly important with respect to Type I and Type II transmembrane proteins, which have fixed orientations and locations for their N- and C-termini with respect to the cytoplasm and ER lumen on either side of the transmembrane region. For example, when a transmembrane region from a Type I transmembrane protein is used as the TMR domain of a CASE fusion protein of the invention, the Type I-derived TMR is preferably located as the most C-terminal domain relative to the CMP and TPB domains. Thus, the most common configurations of a CASE fusion protein of the present invention that have a Type I-derived TMR domain will comprise an N-terminal to C-terminal linear structure illustrated as follows:

(1) (TPB domain)-L-(TMR domain),
(2) (CMP domain)-L-(TPB domain)-L-(TMR domain), or
(3) (TPB domain)-L-(CMP domain)-L-(TMR domain), where each L in the formulae represents a direct peptide bond linking two domains or a linker of one or more amino acid residues.

A preferred transmembrane region for use in a TMR domain of a CASE fusion protein of the invention is derived from the Type I vesicular stomatitis virus glycoprotein (VSV-G) as shown in Table 1 and in several of the examples below. In contrast, see Examples 10 and 22, in which the localization of a fusion protein utilizing the VSVG TMR domain is altered by introducing a dilysine motif near the end of the cytoplasmic tail that localizes the fusion protein in the ER, abolishing target protein secretion.

In addition, a CASE fusion protein comprising a Type I-derived TMR domain preferably comprises an N-terminal signal sequence, which is characteristic of Type I transmembrane proteins to direct the N-terminus of the fusion protein through the ER membrane and into the ER lumen.

When a transmembrane region of a Type II transmembrane protein is employed as a TMR domain, a CASE fusion protein of the invention preferably should comprise an arrangement of domains wherein the Type II-derived TMR domain is the most N-terminal domain relative to the CMP domain and the TPB domain. For example, a CASE fusion protein may comprise an arrangement of domains wherein, in an N-terminal to C-terminal direction, a Type II-derived TMR domain is linked to a CMP domain, which in turn is linked to a TPB domain. See, for example, the description of a Flag-tagged TMR(gp73)-CMP-TPB(gE) fusion protein in Table 49 of Example 21, below. In another example, the relative positions of the CMP domain and the TPB domain may be switched so that the fusion protein comprises an arrangement of domains wherein, in an N-terminal to C-terminal direction, a Type II-derived TMR domain is fused to a TPB domain, which in turn is fused to a CMP domain. In both arrangements, each domain may be linked to an adjacent domain directly (direct peptide bond) or via a linker of one or more amino acid residues. Thus, the most common configurations of a CASE fusion protein of the present invention that have a Type II-derived TMR domain will comprise an N-terminal to C-terminal linear structure illustrated as follows:

(1) (TMR domain)-L-(TPB domain),
(2) (TMR domain)-L-(CMP domain)-L-(TPB domain), or
(3) (TMR domain)-L-(TPB domain)-L-(CMP domain), where each L in the formulae represents a direct peptide bond linking two domains or a linker of one or more amino acid residues.

When a transmembrane region from a Type III transmembrane protein is used as the TMR domain of a CASE fusion protein of the invention, the location of the TMR domain in the linear structure of the fusion protein will vary according to how many membrane-spanning regions of the transmembrane region are selected and what is the orientation of the membrane-spanning region(s) selected, N-terminal to C-terminal, relative to the cytoplasmic and ER sides of the cellular membrane. Use of more than one TMR domain is also contemplated, especially when Type III-derived TMR domains are used, with the CMP domain and TPB domain preferably forming a loop oriented in the ER lumen between two membrane-anchoring TMR domains. See, FIG. 18.

Accordingly, possible linear configurations for a fusion protein of the invention utilizing TMR domains derived from Type III transmembrane proteins may be illustrated as follows and may include the use of plural TMR domains:

(1) (TMR domain)-L-(TPB domain)
(2) (TMR domain)-L-(CMP domain)-L-(TPB domain),
(3) (TMR domain)-L-(TPB domain)-L-(CMP domain),
(4) (TMR domain 1)-L-(TPB domain)-L-(TMR domain 2),
(5) (TMR domain 1)-L-(CMP domain)-L-(TPB domain)-L-(TMR domain 2),
(6) (TMR domain 1)-L-(TPB domain)-L-(CMP domain)-L-(TMR domain 2),
(7) (TPB domain)-L-(TMR domain),
(8) (CMP domain)-L-(TPB domain)-L-(TMR domain), or
(9) (TPB domain)-L-(CMP domain)-L-(TMR domain), where each L in the formulae represents a direct peptide bond linking two domains or a linker of one or more amino acid residues and wherein "TMR domain 1" may be the same as or different from "TMR domain 2".

In preferred embodiments a TMR domain derived from all or a portion of a Type III protein transmembrane region is located as the most C-terminal domain relative to the CMP and TPB domains, similar to the preferred arrangement for using a Type I-derived TMR domain. Unlike Type I transmembrane proteins, Type III transmembrane proteins do not require an N-terminal signal sequence to direct the N-terminus of the transmembrane protein into the ER membrane and through to the ER lumen. In a CASE fusion protein comprising a Type III-derived TMR domain, however, an N-terminal signal sequence may still be required to achieve the desired position of the CMP and TPB domains in the ER lumen.

In the same manner as TMR domains may be selected from the transmembrane region of a Type III protein, a suitable TMR domain may be selected from all or a portion of a Type IV protein. It will be recognized, however, that for the purposes of the present invention, the channel-forming function of a Type IV transmembrane region will typically be an unwanted property; consequently, the TMR domain selected will have that channel-forming function disrupted and only a transmembrane retention function will be retained.

Least preferred as a source of a transmembrane region for a TMR domain in a CASE fusion protein of the invention is any protein that naturally and permanently resides in the membrane of the endoplasmic reticulum (ER). The transmembrane regions of such ER-associated proteins, such as calnexin, appear to be particularly well-anchored to the ER membrane and prevent the protein from passing into the Golgi apparatus. Fusion proteins comprising a TMR domain comprising the transmembrane region of ER-associated proteins, such as calnexin, are greatly diminished in the ability to promote secretion of target proteins of interest relative to fusion proteins in which the TMR domain comprises the transmembrane region of a protein that does not naturally reside in the ER.

Moreover, the presence of tandem lysine residues (dilysine) in the C-terminal portion of a cytoplasmic region of a transmembrane protein can serve as a signal to retain the transmembrane protein in the ER. Jackson et al., *EMBO J.*, 9(10): 3153-3162 (1990). This tandem lysine ER-retention motif typically occurs as the most C-terminal set of tandem lysine residues, such as at −4 and −3 positions from the C-terminus of a protein. Accordingly, if the transmembrane region of such an ER-associated transmembrane protein is to be used as a TMR domain of a fusion protein of the invention, the functional dilysine signal for ER retention should be eliminated or disrupted so that a fusion protein comprising the transmembrane region and any additional cytoplasmic region does not prevent the fusion protein from progressing out of the ER to the Golgi apparatus.

A preferred transmembrane region for use in a TMR domain of a CASE fusion protein of the invention is derived from the Type III KDEL receptor 1 (KDELR) protein as shown in Table 1 and in the examples below, such as Examples 19 and 21. Unlike proteins known to reside exclusively in the ER, the KDELR protein is known to move between the ER and Golgi and therefore, it is presumed, the transmembrane region does not function to permanently anchor the protein in the ER.

Standard Assays for Polypeptides Useful as Transmembrane Retention (TMR) Domains In addition to the particular features of the invention elucidated in the examples below, it is evident that proteins comprising an Fc region, such as the IL13Rα2TF-Fc and TNFR1TF-Fc fusion proteins, are also useful as representative target proteins of interest in assays to determine whether or not a particular polypeptide is useful as a transmembrane retention (TMR) domain in a cell-associated secretion-enhancing (CASE) fusion protein according to the invention. In such a TMR assay, a recombinant nucleic acid molecule is produced by standard methods (for example, nucleic acid synthesis, recombinant DNA techniques, and/or polymerase change reaction (PCR) methods) that encodes the amino acid sequence of a fusion protein comprising a target protein binding (TPB) domain comprising a polypeptide that binds the Fc region fused in frame with a candidate TMR domain. The candidate TMR domain comprises a portion of a membrane protein that normally resides in or traverses a cellular or intracellular membrane in accordance with the features of a TMR domain described herein.

Non-limiting, illustrative, examples of pairs of fusion proteins differing in TMR domains include the TPB(gE)-TMR(VSVG) fusion protein in Table 5 and the TPB(gE)-TMR(KDELR) fusion protein in Table 8, the TPB(gE)-TMR (VSGV) fusion protein in Table 10 and the TPB(gE)-TMR (KDELR) fusion protein in Table 8, the TPB(Prot A)-TMR (VSVG) fusion protein in Table 11 and the TPB(Prot A)-TMR(KDELR) fusion protein in Table 14, the TPB(Prot G)-TMR(VSVG) fusion protein in Table 12 and the TPB (Prot G)-TMR(KDELR) fusion protein in Table 15, and the TPB(GB919)-TMR(VSVG) fusion protein in Table 13 and the TPB(GB919)-TMR(KDELR) fusion protein in Table 16. Thus, by way of non-limiting example, in order to test or assess any candidate polypeptide as a TMR domain, a nucleic acid encoding the candidate TMR domain is linked in frame to a nucleic acid encoding the common portion of any of the above pairs of fusion proteins. The resulting recombinant nucleic acid encoding the test fusion protein is then inserted into an expression vector, such as the pcDNA' expression vector used in the examples. A separate recombinant vector is made to express the target protein, such as the IL13Rα2TF-Fc or TNFR1TF-Fc target protein. Cells of a mammalian cell line, such as HEK 293 cells used in the examples below, are co-transfected with the two expression vectors. Control cells are transfected only with the expression vector encoding the target protein. The transfected cells are then isolated and grown in culture under conditions that permit expression of the proteins encoded on the expression vectors. Control cells are transfected only with the recombinant expression vector encoding the target protein. Samples of the culture media are assayed for the level of secreted target protein, for example using enzyme linked immunosorbent assay (ELISA) as described herein. An enhancement in the level of secreted target protein as compared to the level of target protein in the media of control cells indicates that the fusion protein, and therefore the candidate polypeptide was useful as TMR domain in accordance with the invention. Preferably, the level of enhancement in the level of target protein secreted into the media of cultures of cells co-expressing the fusion protein and the target protein is at least 1.5-fold higher than that of the control cells expressing the target protein alone. Enhancing the level of secreted target protein that is also a therapeutically and commercially important protein by 1.5-fold or more can provide a significant reduction in production costs and also a significant increase in the availability of the therapeutically and commercially important protein.

Chaperone Machinery Polypeptide (CMP) Domains Useful in the Invention

The ability of a cell-associated secretion-enhancing (CASE) fusion protein of the invention comprising a target protein binding (TPB) domain and a transmembrane retention (TMR) domain to enhance the level of secretion of a co-expressed target protein may be still further enhanced by incorporating into the fusion a chaperone machinery peptide (CMP) domain. Whereas the interactions of the TMR and TPB domains with cell components are relatively well defined, i.e., the secretory membrane system and the intended co-expressed target protein, respectively, the precise interaction of a CMP domain with the cell is not. However, as explained and demonstrated herein, in view of the fact that a significant enhancement of the level of target protein secreted from a host cell ion is observed using portions of known components of a cell's chaperone system, it is presumed that a CMP, whether a portion of a known chaperone protein or a synthetic derivative thereof, in some way recruits some aspect of chaperone system to increase the yield of target protein secreted from a host cell. Especially preferred for use as a CMP domain of a CASE fusion protein according to the invention are isolated J domains of J proteins, polypeptides from within the a helix II region of J domains, and analogs of such polypeptides from within the a helix H region of J domains defined by structural formula I as described below.

Chaperone and Co-Chaperone Proteins as CMP Domains

To deal with the continual risk of not attaining or maintaining proper functional protein conformations, cells possess a system of proteins that serve as molecular chaperones to assist in the folding and refolding of nascent and mature proteins into their proper conformations. The heat shock 70 kilodalton (kDa) proteins (also referred to "Hsp70s") constitute one of the most ubiquitous classes of chaperone proteins in the cells of a wide variety of eukaryotic and prokaryotic cells. The "Hsp70 machinery" comprises chaperone proteins, co-chaperone proteins, such as J proteins, and nucleotide exchange factors (NEFs). A protein of the Hsp70 machinery of a cell may be used as a CMP domain of a fusion protein of the invention. Perhaps reflecting the fact that such chaperone proteins are ubiquitous in both eukaryotic and prokaryotic cells, eukaryotic chaperone proteins, such as BipATPase, as well as prokaryotic chaperone proteins, such as DnaK, may be used as a CMP domain in fusion proteins of the invention for promoting secretion of a target protein of interest from a eukaryotic host cell. A CMP domain of a fusion protein of the invention may also be a fragment of a functional chaperone or co-chaperone protein. A preferred co-chaperone protein for use as a CMP domain of a fusion protein of the invention is a co-chaperone protein such as a J protein. A CMP domain of a fusion protein of the invention may also comprise a J domain of a J protein, a polypeptide from a J domain, or a J domain analog that comprises amino acid sequences that may not be known to be present in any J domain.

J Domains as CMP Domains

Members of the family of J proteins, including so-called Hsp40-like proteins, are classically defined by the presence of a J domain, which is a region typically between 45-75 amino acids in length with structural and sequence features similar to the prototypical 73-amino acid DnaJ protein of *Escherichia coli*. The J domains of a variety of co-chaperone J proteins have been determined. See, for example, Kampinga et al., *Nat. Rev.*, 11: 579-592 (2010); Hennessy et al., *Protein Science*, 14:1697-1709 (2005). A J domain useful as a CMP domain of a cell-associated secretion-enhancing (CASE) fusion protein of the invention has the key defining features of a J domain of members of the J protein family, namely, a polypeptide domain from a J protein characterized by four α-helices (I, II, III, IV) and typically having the highly conserved tripeptide sequence of histidine, proline, and aspartic acid (referred to as the "HPD motif") located at the amino terminal end of a "loop" region between helices II and III. Only a few J domains have been identified that lack the HPD motif. The site of interaction (binding) of a J domain with an Hsp70-ATP chaperone protein complex is believed to be a region extending from within helix II and including the HPD motif. Representative J domains include, but are not limited to, a J domain of the bacterial DnaJ protein, a J domain of an ERdj protein (for example, a J domain of ERdj3 or ERdj5), a J domain of a large T antigen of SV40, and a J domain of a mammalian cysteine string protein (CSP-α). The amino acid sequences for these and other, non-limiting representative J domains that may be used as CMP domains in fusion proteins of the invention are provided in Table 2 below.

It is noted that computer programs used to identify J domains are typically in agreement with respect to identifying the above-mentioned essential regions and motifs that define a J domain within a J protein. However, there can be some variability between programs with respect to which amino acids of a J protein are identified as the amino and carboxy residues of the J domain with the J domain. Such variability is typically with respect to the inclusion or exclusion of from one to several amino acid residues at the amino and carboxy termini of the output sequence of the entire J domain. In the construction and use of various CASE fusion proteins according to the invention, such as in the Examples below, no evidence has been obtained that would implicate such minor variations in the boundary residues of a J domain within a J protein as causing any significant difference in the results.

TABLE 2

Amino acid Sequences of Representative Isolated J Domains

| J Protein Source of J Domain | SEQ ID NO: | J Domain Amino Acid Sequence 12345678901234567890123456 7890 |
|---|---|---|
| human Hsp40 (NP_006136; Heat Shock Protein 40) | 16 | KDYYQTLGLARGASDEEIKRAYRRQALRYH PDKNKEPGAEEKFKEIAEAYDVLSDPRK |
| human ErdJ1 (NM_022365; DnaJC1, HTJ1, MTJ1, DnaJ homolog subfamily C member 1 protein, DNAJL1) | 17 | LNFYQFLGVQQDASSADIRKAYRKLSLTLH PDKNKDENAETQFRQLVAIYEVLKDDER |
| human ErdJ2 (NM_001017975; HFM1, SEC63 domain containing 1 protein, MER3, hHFM1) | 18 | YNPYEVLNLDPGATVAEIKKQYRLLSLKYH PDKGGDEVMFMRIAKAYAALTDEES |
| human ErdJ3 (NM_016306; DNAJB11, DnaJ (Hsp40) homolog, subfamily B, member 11, ERj3p, HEDJ, ERj3, ABBP2, ER-associated DNAJ protein 3) | 19 | RDFYKILGVPRSASIKDIKKAYRKLALQLH PDRNPDDPQAQEKFQDLGAAYEVLSDSEK |
| human ErdJ4 (NM_012328; DNAJB9, microvascular differentiation gene 1 protein, MDG1, endothelial Mdg1) | 20 | KSYYDILGVPKSASERQIKKAFHKLAMKYH PDKNKSPDAEAKFREIAEAYETLSDANR |

TABLE 2-continued

Amino acid Sequences of Representative Isolated J Domains

| J Protein Source of J Domain | SEQ ID NO: | J Domain Amino Acid Sequence 12345678901234567890123456789 0 |
|---|---|---|
| human ErdJ5 (NM_018981; DNAJC10, ER-resident protein ERdj5, JPD1, J-domain-containing protein disulfide isomerase-like protein, DnaJ (Hsp40) homolog, subfamily C, member 10, hMTHr protein) | 21 | QDFYSLLGVSKTASSREIRQAFKKLALKLH PDKNPNNPNAHGDFLKINRAYEVLKDEDL |
| human ErdJ6 (NM_006260; DNAJC3, DnaJ (Hsp40) homolog, subfamily C, member 3 protein, protein-kinase, interferon-inducible double stranded RNA dependent inhibitor protein, P58IPK protein, PRKRI, 58 kDa cellular inhibitor protein, p58 inhibitor of protein kinase) | 22 | RDYYKILGVKRNAKKQEIIKAYRKLALQWH PDNFQNEEEKKKAEKKFIDIAAAKEVLSDP EM |
| human CSP (NP_079495; cysteine string protein alpha, CSPalpha protein, DNAJC5 protein, cysteine string protein, DnaJ (Hsp40) homolog, subfamily C, member 5 protein, CSP protein) | 23 | ESLYHVLGLDKNATSDDIKKSYRKLALKYH PDKNPDNPEAADKFKEINNAHAILTDATK |
| SV40 large T antigen (YP_003708382; large tumor antigen T-ag [Simian virus 40]) | 24 | LQLMDLLGLERSAWGNIPLMRKAYLKKCKE FHPDKGGDEEKMKKMNTLYKKMEDGVK |
| DnaJ | 25 | QDYYEILGVSKTAEEREIKKAYKRLAMKYH PDRNQGDKEAEAKFKEIKEAYEVLTDSQK |
| human dnaJ homolog subfamily C, member 8 | 26 | NPFEVLQIDPEVTDEEIKKRFRQLSILVHP DKNQDDADRAQKAFEAVDKAYKLLLDQEQK KRALDVIQ |
| human dnaJ homolog subfamily C, member 5B | 27 | EALYEILGLHKGASNEEIKKTYRKLALKHH PDKNPDDPAATEKFKEINNAHATLTDISK |
| human dnaJ homolog subfamily C, member 14 | 28 | LNPFHVLGVEATASDVELKKAYRQLAVMVH PDKNHHPPAEEEAFKVLRAAWDIVSNAEK |
| human dnaJ homolog subfamily C, member 25 precursor | 29 | RDCYEVLGVSRSAGKAEIARAYRQLARRYH PDRYRPQPGDEGPGRTPQSAEEAFLLVATA YETLKDEET |
| human dnaJ homolog subfamily B, member 2, isoform a | 30 | ASYYEILDVPRSASADDIKKAYRRKALQWH PDKNPDNKEFAEKKFKEVAEAYEVLSDKHK |
| human dnaJ homolog subfamily B, member 2, isoform b | 31 | ASYYEILDVPRSASADDIKKAYRRKALQWH PDKNPDNKEFAEKKFKEVAEAYEVLSDKHK |
| Chain A, nmr structure of Bc008182 protein, a human Dnaj-like domain | 32 | TTYYDVLGVKPNATQEELKKAYRKLALKYH PDKNPNEGSKFKQISQAYEVLSDAKK |
| Chain A, solution structure of J Domain of Hsj1a | 33 | ASYYEILDVPRSASADDIKKAYRRKALQWH PDKNPDNKEFAEKKFKEVAEAYEVLSDKHK |
| Chain A, solution structure of a Dnaj-like domain from human ras-associated protein Rap1 | 34 | KDSWDMLGVKPGASRDEVNKAYRKLAVLLH PDKCVAPGSEDAFKAVVNARTALLKNIK |
| Chain A, solution structure of Dnaj domain of human protein Hcg3, a hypothetical protein Tmp_locus_21 | 35 | VDYYEVLDVPRQASSEAIKKAYRKLALKWH PDKNPENKEEAERRFKQVAEAYEVLSDAKK |

TABLE 2-continued

Amino acid Sequences of Representative Isolated J Domains

| J Protein Source of J Domain | SEQ ID NO: | J Domain Amino Acid Sequence |
|---|---|---|
| Chain A, solution structure of J domain from Dnaj homolog, human Tid1 protein | 36 | GDYYQILGVPRNASQKEIKKAYYQLAKKYH PDTNKDDPKAKEKFSQLAEAYEVLSDEVK |
| Chain A, solution structure of J domain from human Dnaj subfamily B, member 9 | 37 | GSYYDILGVPKSASERQIKKAFHKLAMKYH PDKNKSPDAEAKFREIAEAYETLSDANR |
| Chain A, solution structure of J domain from human Dnaj subfamily B, member 12 | 38 | GDYYEILGVSRGASDEDLKKAYRRLALKFH PDKNHAPGATEAFKAIGTAYAVLSNPEK |
| Chain A, human Hsp40 (HDJ-1), nmr | 39 | KDYYQTLGLARGASDEEIKRAYRRQALRYH PDKNKEPGAEEKFKEIAEAYDVLSDPRK |
| Chain A, solution structure of Dnaj domain from human Williams-Beuren syndrome chromosome region 18 protein | 40 | TALYDLLGVPSTATQAQIKAAYYRQCFLYH PDRNSGSAEAAERFTRISQAYVVLGSATL |
| Chain A, solution structure of J domain of Dnaj homolog subfamily B, member 8 | 41 | ANYYEVLGVQASASPEDIKKAYRKLALRWH PDKNPDNKEEAEKKFKLVSEAYEVLSDSKK |
| Chain A, solution structure of J domain of Dnaj homolog subfamily C, member 12 | 42 | EDYYTLLGCDELSSVEQILAEFKVRALECH PDKHPENPKAVETFQKLQKAKEILTNEES |
| Chain A, Dnaj domain of human Kiaa0730 protein | 43 | SILKEVTSWEQAWKLPESERKKIIRRLYL KWHPDKNPENHDIANEVFKHLQNEINR |
| human dnaJ homolog, subfamily B, member 6, isoform a | 44 | VDYYEVLGVQRHASPEDIKKAYRKLALKWH PDKNPENKEEAERKFKQVAEAYEVLSDAKK |
| human dnaJ homolog, subfamily B, member 6, isoform b | 45 | VDYYEVLGVQRHASPEDIKKAYRKLALKWH PDKNPENKEEAERKFKQVAEAYEVLSDAKK |
| human dnaJ homolog, subfamily B, member 9 precursor | 46 | KSYYDILGVPKSASERQIKKAFHKLAMKYH PDKNKSPDAEAKFREIAEAYETLSDANR |
| human DnaJ (Hsp40) homolog, subfamily C, member 8, isoform CRA_c | 47 | LNPFEVLQIDPEVTDEEIKKRFRQLSILVH PDKNQDDADRAQKAFEAVDKAYKLLLDQEQ |
| human DnaJ (Hsp40) homolog, subfamily C, member 13, isoform CRA_b | 48 | DDAYEVLNLPQGQGPHDESKIRKAYFRLAQ KYHPDKNPEGRDMFEKVNKAYEFLCTKSA |
| human DnaJ (Hsp40) homolog, subfamily C, member 19, isoform CRA_e | 49 | REAALILGVSPTANKGKIRDAHRRIMLLNH PDKGK |
| human DnaJ (Hsp40) homolog, subfamily C, member 5, isoform CRA_b | 50 | ESLYHVLGLDKNATSDDIKKSYRKLALKYH PDKNPDNPEAADKFKEINNAHAILTDATK |
| human DnaJ (Hsp40) homolog, subfamily C, member 4, isoform CRA_f | 51 | STYYELLGVHPGASTEEVKRAFFSKSKELH PDRDPGNPSLHSRFVELSEAYRVLSREQS |
| human zinc finger, CSL-type containing 3, isoform CRA_c | 52 | KDWYSILGADPSANISDLKQKYQKLILMYH PDKQSTDVPAGTVEECVQKFIEIDQAWKIL GNEET |
| human DnaJ (Hsp40) homolog, subfamily C, member 17, isoform CRA_a | 53 | MDLYALLGIEEKAADKEVKKAYRQKALSCH PDKNPDNPRAAELFHQLSQALEVLTDAAA |
| human DnaJ (Hsp40) homolog, subfamily B, member 9, isoform CRA_a | 54 | KSYYDILGVPKSASERQIKKAFHKLAMKYH PDKNKSPDAEAKFREIAEGASVPAASSF |

TABLE 2-continued

Amino acid Sequences of Representative Isolated J Domains

| J Protein Source of J Domain | SEQ ID NO: | J Domain Amino Acid Sequence 123456789012345678901234567890 |
|---|---|---|
| human DnaJ (Hsp40) homolog, subfamily C, member 4, isoform CRA_g | 55 | STYYELLGVHPGASTEEVKRAFFSKSKELH PDRDPGNPSLHSRFVELSEAYRVLSREQS |
| human DnaJ (Hsp40) homolog, subfamily C, member 4, isoform CRA_a | 56 | STYYELLGVHPGASTEEVKRAFFSKSKELH PDRDPGNPSLHSRFVELSEAYRVLSREQS |
| human DnaJ (Hsp40) homolog, subfamily C, member 11, isoform CRA_c | 57 | EDYYSLLNVRREASSEELKAAYRRLCMLYH PDKHRDPELKSQAERLFNLVKQAYEVLSDP QT |
| human zinc finger, CSL-type containing 3, isoform CRA_b | 58 | KDWYSILGADPSANISDLKQKYQKLILMYH PDKQSTDVPAGTVEECVQKFIEIDQAWKIL G-NEET |
| human J-type co-chaperone HSC20, isoform CRA_c | 59 | RDYFSLMDCNRSFRVDTAKLQHRYQQLQRL VHPDFFSQRSQTEKDFSEKHSTLVNDAYKT LLAPLS |
| human hCG1994888, isoform CRA_d | 60 | RDCYEVLGVSRSAGKAEIARAYRQLARRYH PDRYRPQPGDEGPGRTPQSAEEAFLLVATA YETLKDEET |
| human DnaJ (Hsp40) homolog, subfamily A, member 1, isoform CRA_a | 61 | TTYYDVLGVKPNATQEELKKAYRKLALKYH PDKNPNEGEKVKMLYISSQ |

J Domain Active Fragments and J Domain Analogs as CMP Domains

The terms "J domain active fragment" or "active fragment of a J domain" refer to a fragment of a J domain of a co-chaperone J protein that retains the ability to increase the level of secreted target protein when present as a CMP domain in a cell-associated secretion-enhancing (CASE) fusion protein described herein. J domain active fragments useful in the invention will commonly retain the region of a J domain at the C-terminal extremity of a helix II. Larger portions of a J domain may be active as well, but excision of all or part of the C-terminal nine amino acids of a helix II invariably leads to loss of protein secretion enhancement activity.

Only a relatively small portion of a J domain is required for use as a CMP domain of a CASE fusion to provide an enhancement in the level of target protein secreted from a host cell. Such enhancement in the level of target protein secreted from a cell may be provided by a polypeptide fragment isolated from within a J domain and that consists of as little as 9 or 10 amino acids. Individual J domain polypeptide fragments useful in the invention are not all identical in amino acid sequence, but may share some sequence homology and structural features in addition to providing an enhanced activity required for use as a CMP domain of a CASE fusion protein of the invention. J domain active fragments and J domain analog polypeptides useful in the invention include those previously described for enhancing expression of a target protein expressed in transfected host cells in International Publication No. WO 2014/089375. In particular, a J domain analog that may be used as a CMP domain in a CASE fusion protein of the invention may be a polypeptide that comprises the amino acid sequence of formula I:

(I)
$$X1\text{-}X2\text{-}X3\text{-}X4\text{-}X5\text{-}X6\text{-}X7\text{-}X8\text{-}X9,$$
(SEQ ID NO: 1)

X1 is isoleucine (I), leucine (L), valine (V), alanine (A), or methionine (M);

X2 and X3 are each independently any amino acid with the proviso that one or both are K or R;

X4 is any amino acid or X4 may be absent when X1 through X3 are present and X5 through X9 are present;

X5 is tyrosine (Y), tryptophan (W), or phenylalanine (F);

X6 and X7 are each independently any amino acid with the proviso that one or both are lysine (K) or arginine (R); or either one of X6 and X7 may be absent when the other is K or R and when X1 through X5 are present and X8 and X9 are present; and X8 and X9 are any amino acid with the proviso that one or both are leucine (L) or alanine (A); or one of X8 and X9 may be absent when the other is L or A and when X1 through X7 are present.

Examples of J domain analog polypeptides that may be used as CMP domain in CASE fusion protein of the invention include, but are not limited to:

| Sequence Identifier | Amino Acid Sequence 123456789012345 |
|---|---|
| SEQ ID NO: 6 | IKKAYRKLA |
| SEQ ID NO: 2 | IKKAYKLALQ |
| SEQ ID NO: 3 | IKKAYRLALQ |
| SEQ ID NO: 4 | IKKAYRKALQ |
| SEQ ID NO: 5 | IKKAYRKLLQ |

| Sequence Identifier | Amino Acid Sequence 123456789012345 |
|---|---|
| SEQ ID NO: 203 | IKKYRKLA |
| SEQ ID NO: 204 | IKKAYKLA |
| SEQ ID NO: 205 | IKKAYRLA |
| SEQ ID NO: 206 | IKKAYRKA |
| SEQ ID NO: 207 | LKKAYRKLA |
| SEQ ID NO: 208 | VKKAYRKLA |
| SEQ ID NO: 209 | MKKAYRKLA |
| SEQ ID NO: 210 | AKKAYRKLA |
| SEQ ID NO: 211 | IAKAYRKLA |
| SEQ ID NO: 212 | IKAAYRKLA |
| SEQ ID NO: 213 | IKKRYRKLA |
| SEQ ID NO: 214 | IKKSYRKLA |
| SEQ ID NO: 215 | IKKQYRKLA |
| SEQ ID NO: 216 | IKKEYRKLA |
| SEQ ID NO: 217 | IKKFYRKLA |
| SEQ ID NO: 218 | IKKCYRKLA |
| SEQ ID NO: 219 | IKKAFRKLA |
| SEQ ID NO: 220 | IKKAWRKLA |
| SEQ ID NO: 221 | IKKAYRKQA |
| SEQ ID NO: 222 | IKKAYRKMA |
| SEQ ID NO: 223 | IKKAYRKIA |
| SEQ ID NO: 224 | IKKAYRKAA |
| SEQ ID NO: 225 | IKKAYRKVA |
| SEQ ID NO: 226 | IKKAYRKRA |
| SEQ ID NO: 227 | IKKAYRKLM |
| SEQ ID NO: 228 | IKKAYRKLI |
| SEQ ID NO: 229 | IKKAYRKLV |
| SEQ ID NO: 230 | IKKAYRKLC |
| SEQ ID NO: 231 | IKKAYRKLS |
| SEQ ID NO: 232 | IKKAYRKLY |
| SEQ ID NO: 7 | IRKAYRKLSLTL |
| SEQ ID NO: 8 | IKKQYRLLSLKY |
| SEQ ID NO: 9 | IKKAFHKLAMKY |
| SEQ ID NO: 10 | IRQAFKKLALKL |
| SEQ ID NO: 11 | IIKAYRKLALQW |
| SEQ ID NO: 12 | IARAYRQLARRY |
| SEQ ID NO: 13 | IKRAYRRQALRY |
| SEQ ID NO: 14 | IKKSYRKLALKY |
| SEQ ID NO: 15 | IKKAYKRLAMKY |

A preferred polypeptide of the foregoing formula I for use as a CMP domain in a CASE fusion of protein of the invention is an isolated peptide having or comprising the amino acid sequence I-K-K-A-Y-R-K-L-A (SEQ ID NO:6), which also corresponds to a region within the J domain of the Erdj3 protein.

In addition to a J domain active fragment or a J domain analog polypeptide of formula I described herein, another polypeptide that may be used as a CMP domain in a cell-associated secretion-enhancing (CASE) fusion protein of the invention is a decapeptide selected from the group consisting of:

```
                                        (SEQ ID NO: 2)
            IKKAYKLALQ,
                                        (SEQ ID NO: 3)
            IKKAYRLALQ,
                                        (SEQ ID NO: 4)
            IKKAYRKALQ,
and
                                        (SEQ ID NO: 5)
            IKKAYRKLLQ.
```

Another polypeptide that may be used as a CMP domain in a CASE fusion protein of the invention is an isolated polypeptide from a J domain of a J protein comprising an amino acid sequence selected from the group consisting of:

```
                                        (SEQ ID NO: 6)
            IKKAYRKLA,
                                        (SEQ ID NO: 7)
            IRKAYRKLSLTL,
                                        (SEQ ID NO: 8)
            IKKQYRLLSLKY,
                                        (SEQ ID NO: 9)
            IKKAFHKLAMKY,
                                        (SEQ ID NO: 10)
            IRQAFKKLALKL,
                                        (SEQ ID NO: 11)
            IIKAYRKLALQW,
                                        (SEQ ID NO: 12)
            IARAYRQLARRY,
                                        (SEQ ID NO: 13)
            IKRAYRRQALRY,
                                        (SEQ ID NO: 14)
            IKKSYRKLALKY,
and
                                        (SEQ ID NO: 15)
            IKKAYKRLAMKY.
```

Particularly preferred for use as a CMP domain in a CASE fusion protein of the invention is an isolated polypeptide having or comprising the amino acid sequence IKKAFHKLAMKY (SEQ ID NO:9), which is the sequence of an isolated polypeptide of the Erdj4 protein.

The smaller size of J domain polypeptide fragments and of J domain analog polypeptides compared to complete (full-length) J domains reduces the size of the fusion protein that is constructed and co-expressed with a target protein in a host cell. Thus, the size of recombinant nucleic acid molecules encoding such fusion proteins can be correspondingly smaller than nucleic acid molecules that encode fusion proteins comprising a complete J domain as a CMP domain.

BAG Domains as CMP Domains

Members of the BAG family of proteins found in eukaryotes are a type of co-factor of the chaperone system referred to as a nucleotide exchange factor (NEF). NEF possess diverse N-terminal domains and a conserved C-terminal Hsp70-binding domain (the BAG domain) that can interact with the ATPase domain of Hsp70. See, for example, Kampinga et al., *Nat. Rev. Biol.*, 11:579-592 (2010). BAG proteins have a topology, binding domains, and binding specificities that are consistent with a protein designed to participate in recruiting the Hsp70 chaperone machinery. Although a BAG protein might participate as a NEF in the Hsp70 machinery, many studies suggest that BAG proteins may predominantly be involved in regulatory mechanisms to control a variety of activities, including promoting cell growth, quiescence, or apoptosis; regulating transcription complex formation; and modulating signal transduction. See, for example, the review by Takayama et al., *Nat. Cell Biol.*, 3: E237-E241 (2001). Recently, it has been reported that when recombinant proteins of interest are linked to a BAG domain, the resulting fusion proteins are expressed at levels that are greater than those of the protein alone. See, International Publication No. WO 2012/087835 A2.

A cell-associated secretion-enhancing (CASE) fusion protein of the invention clearly has a structure and function unlike any of the previously described BAG fusion proteins. A BAG domain may serve as a CMP domain in a CASE fusion protein described herein provided the co-expression of the fusion protein with a target protein of interest in a host cell significantly enhances the level of target protein secreted from the host cell as compared to the level in the absence of the fusion protein and provided the fusion protein remains associated with the host cell.

In addition to those mentioned above, suitable CMP domains may be derived from other molecular chaperones of cellular chaperone machinery known to those skilled in the art. Additional CMP domains may be found, for example, in molecular chaperones such as Bip (Binding immunoglobulin protein), molecular co-chaperones such as a nucleotide exchange factor, or a protein molecule involved in protein folding/cellular quality control systems. Table 3, below, lists several proteins involved in cellular chaperone machinery that may be used as sources of polypeptides for use in a CMP domain of a CASE fusion protein of the invention.

TABLE 3

| Proteins of Cellular Chaperone Machinery Providing CMP Domains | | |
|---|---|---|
| Source of CMP sequence | ER resident member | Function/Activity |
| Hsp70 family | Bip/Grp78/HSPA5 | Protein folding |
| Hsp40 family | Erdj1/Mtj1/DnaJC1 | Protein folding |
| | Erdj2/hSec63/DnaJC2 | Protein folding |
| | Erdj3/HEDJ/Erj3/ABBP-2/DnaJB11 | Protein folding |
| | Erdj4/Mdg1/DnaJB9 | Protein folding |
| | Erdj5/JPDI/DnaJC10 | Protein folding |
| | Erdj6/P58IPK/PRKRI/DnaJC3 | Protein folding |
| | Erdj7/Erj7/DnaJC25 | Protein folding |
| Hsp90 family | Grp94/Hsp90b1/Tra1 | Protein folding |
| Hsp60 family | N/A | Protein folding |
| Small heat shock proteins | N/A | Protein folding |
| Lectin | Calnexin | Protein folding/ recognition of protein misfolding |
| | Calreticulin | Protein folding/ recognition of protein misfolding |
| | OS9 | Protein degradation/ recognition of protein misfolding |
| | XTPB-3/XTP3 | Protein degradation/ recognition of protein misfolding |
| Lectin/EDEM family | EDEM1 | Protein degradation/ recognition of protein misfolding |
| | EDEM2 | Protein degradation/ recognition of protein misfolding |
| | EDEM3 | Protein degradation/ recognition of protein misfolding |
| Cyclophilin | Cyclophilin B | Peptidyl-prolyl isomerase |
| FKBP | FKBP2 | Peptidyl-prolyl isomerase |
| | FKBP7 | Peptidyl-prolyl isomerase |

TABLE 3-continued

Proteins of Cellular Chaperone Machinery Providing CMP Domains

| Source of CMP sequence | ER resident member | Function/Activity |
|---|---|---|
| | FKBP9 | Peptidyl-prolyl isomerase |
| | FKBP10 | Peptidyl-prolyl isomerase |
| | FKBP11 | Peptidyl-prolyl isomerase |
| | FKBP13 | Peptidyl-prolyl isomerase |
| | FKBP14 | Peptidyl-prolyl isomerase |
| | FKBP23 | Peptidyl-prolyl isomerase |
| | FKBP52 | Peptidyl-prolyl isomerase |
| | FKBP60 | Peptidyl-prolyl isomerase |
| | FKBP65 | Peptidyl-prolyl isomerase |
| Other Peptidyl-prolyl isomerases | Peptidyl-prolyl cis-trans isomerase D/Cyp40 | Peptidyl-prolyl isomerase |
| | CNPY3/Protein canopy homolog 3 | Protein folding |
| Ero1 | Ero1 alpha | Sulfydryl oxidase |
| | Ero1 beta | Sulfydryl oxidase |
| Oxidereductase | PDI | Protein disulfide-isomerase |
| | PDIR | Protein disulfide-isomerase |
| | Erp5/P5/Protein disulfide-isomerase A6 | Protein disulfide-isomerase |
| | ERp18/Thioredoxin domain-containing protein 12 | Protein disulfide-isomerase |
| | ERp19/Thioredoxin domain-containing protein 12 | Protein disulfide-isomerase |
| | ERp27 | Protein disulfide-isomerase |
| | ERp29 | Protein disulfide-isomerase |
| | ERp46/Thioredoxin domain-containing protein 5 | Protein disulfide-isomerase |
| | ERp72/Protein disulfide-isomerase A4 | Protein disulfide-isomerase |
| | ERp57/Grp58/Protein disulfide-isomerase A3 | Protein disulfide-isomerase |
| | SEP15 | Protein disulfide-isomerase |
| PDI-Erv | QSOX1 | Thiol oxidase |
| | QSOX2 | Thiol oxidase |
| Hsp110/HSP105 | N/A | Nucleotide Exchange Factor |
| BAG family | N/A | Nucleotide Exchange Factor |
| Nucleotide Exchange Factor for Bip | GRP170/HYOU1/ORP150 | Protein folding |
| Nucleotide Exchange Factor for Bip | BAP/SIL1 | Protein folding |
| | Sel1 | Protein degradation/recognition of protein misfolding |
| Glycosyl transferase | UGGT/UDP-glucose:glycoprotein glucosyltransferase 1 | recognition of protein misfolding/Glycosylation |

The efficacy of an isolated CMP domain to enhance the level of secretion of a target protein may be determined experimentally by comparing the level of target protein secreted from a host cell that co-expresses the target protein and a fusion protein comprising a TPB domain that binds the target protein, a TMR domain, and the CMP domain with the level of target protein that is secreted from a host cell that co-expresses the target protein and the same or essentially the same fusion protein, but lacking the CMP domain. Such experimental methods are illustrated in the working examples below.

Linkers

Within a cell-associated secretion-enhancing (CASE) fusion protein of the invention, any domain may be linked to an adjacent domain by methods known in the art. By way of non-limiting example, a chaperone machinery peptide (CMP) domain may be linked directly to a target protein binding (TPB) domain or linked indirectly via a linker of one or more amino acid residues. Or, in another non-limiting example, a TPB domain may be linked directly to a transmembrane retention (TMR) domain or linked indirectly via a linker of one or more amino acid residues. Other domains, such as an epitope tag, may also be linked directly to an adjacent domain or linked indirectly via a linker in a CASE fusion protein of the invention. A CASE fusion protein of the invention may use one or more linkers to link one or more adjacent domains, and the linkers may be the same or different in amino acid composition and in length of amino acid residues.

At the amino acid level, a linker may be one or more amino acids, including 1 to 10 amino acids, 1 to 20 amino acids, and even 1 to 50 amino acids. Typically, for CASE fusion proteins comprising TPB, TMR, and CMP domains, with respect to linking a CMP domain to a TPB domain or to a TMR domain, it is not necessary to use a linker that is more than 20 amino acids because linking a CMP domain via a short linker of 20 or fewer amino acids to a TPB domain does not significantly diminish the necessary biochemical and functional properties of the TPB domain (data not shown).

Selecting one or more polypeptide linkers to produce a CASE fusion protein according to the invention is within the knowledge and skill of practitioners in the art. See, for example, Arai et al., *Protein Eng.*, 14(8): 529-532 (2001); Crasto et al., *Protein Eng.*, 13(5): 309-314 (2000); George et al., *Protein Eng.*, 15(11): 871-879 (2003); Robinson et al., *Proc. Natl. Acad. Sci. USA*, 95: 5929-5934 (1998). General considerations for using a particular linker to link one domain with another domain in a CASE fusion protein may include those in making other fusion proteins in which one functional domain is linked to another functional domain, for example, as may be considered in linking immunoglobulin variable and/or constant domains in a wide variety of formats for producing engineered functional binding proteins. Clearly, a linker preferably does not interfere with the respective functions of the domains in a CASE fusion protein according to the invention. A linker, if present in a fusion protein of the invention, is selected to optimize the yield of the target protein secreted from a cell, and it may be omitted if direct attachment of a one domain to another domain of the fusion protein achieves a desired enhanced level of secretion of a co-expressed target protein. Linkers present in a CASE fusion protein of the invention may comprise one or more amino acids encoded by a nucleotide sequence present on a segment of nucleic acid in or around a cloning site of an expression vector into which is inserted in frame a nucleic acid segment encoding one or more protein domains (e.g., TPB, TMR, and/or CMP domain) or an entire fusion protein as described herein.

Linkers, especially those that are four amino acids and longer, preferably possess a flexibility that permits the component domains of the fusion protein to fold into its proper, functional conformation. A variety of relatively flexible linkers are known in the field for linking functional domains. A linker may also be used to link one or more additional domains, such as an epitope tag, to a domain of a CASE fusion protein of the invention. Examples of linkers of two or more amino acids that may be used in preparing a fusion protein according to the invention include, but are not limited to, LE, SR, LEG, GSR, GTGSEFDIAAALE (SEQ ID NO:175); GTGSEF (SEQ ID NO:176); DIAAA (SEQ ID NO:83); DIAAALE (SEQ ID NO:84); GTGSEF (SEQ ID NO:85); AS; TVA; ASTK (SEQ ID NO:86); GGGSGGSGGSGG (SEQ ID NO:87); DIGGGSGGSGGSGGAAA (SEQ ID NO:88); DIGGGGSGGGGSGGGGSAAA (SEQ ID NO:178); AKTTPKLEEGEFSEAR (SEQ ID NO:89); AKTTPKLEEGEFSEARV (SEQ ID NO:90); AKTTPKLGG (SEQ ID NO:91); SAKTTPKLGG (SEQ ID NO:92); SAKTTP (SEQ ID NO:93); RADAAP (SEQ ID NO:94); RADAAPTVS (SEQ ID NO:95); RADAAAAGGPGS (SEQ ID NO:96); RADAAAA($G_4S$)$_4$ (SEQ ID NO:97); SAKTTPKLEEGEFSEARV (SEQ ID NO:98); ADAAP (SEQ ID NO:99); ADAAPTVSIFPP (SEQ ID NO:100); TVAAP (SEQ ID NO:101); TVAAPSVFIFPP (SEQ ID NO:102); QPKAAP (SEQ ID NO:103); QPKAAPSVTLFPP (SEQ ID NO:104); AKTTPP (SEQ ID NO:105); AKTTPPSVTPLAP (SEQ ID NO:106); AKTTAP (SEQ ID NO:107); AKTTAPSVYPLAP (SEQ ID NO:108); ASTKGP (SEQ ID NO:109); ASTKGPSVFPLAP (SEQ ID NO:110); GGGGS (SEQ ID NO:181); GGGGSGGGGS (SEQ ID NO:180); GGGGSGGGGSGGGGS (SEQ ID NO:111); GGGGSGGGGSGGGGSGGGGS (SEQ ID NO:179); GENKVEYAPALMALS (SEQ ID NO:112); GPAKELTPLKEAKVS (SEQ ID NO:113); GHEAAAVMQVQYPAS (SEQ ID NO:114); GGGGGGGP (SEQ ID NO:115); GGGGGGGGP (SEQ ID NO:116); PAPNLLGGP (SEQ ID NO:117); PNLLGGP (SEQ ID NO:118); GGGGGGP (SEQ ID NO:119); PAPELLGGP (SEQ ID NO:120); PTISPAPNLLGGP (SEQ ID NO:121); TVAADDDDKSVFIVPP (SEQ ID NO:122); TVDDDDKAAP (SEQ ID NO:123); LVPRGSAAP (SEQ ID NO:124); ASTKGPSV (SEQ ID NO:125); ASTKGPSVFP (SEQ ID NO:126); TVAAPSV (SEQ ID NO:127); TVAAPSVFI (SEQ ID NO:128); and the like. Particular mention is made of the series of linkers based on polymers of GGGGS (SEQ ID NO:181), having the shorthand formula "$(G_4S)_x$," wherein x is an integer, preferably 1, 2, 3, or 4.

As will be apparent from studying diagrams and the amino acid sequences of fusion protein constructs described in detail below, only linker sequences of 8 amino acid residues or more are depicted schematically in the diagrams of fusion proteins appearing in the drawings. Examples of polypeptide linkers of 8 or more amino acids are depicted in FIGS. 11B, 12C, 13C, 19B, 20A, 20B, 22A, and 23A with a zigzag line connecting two domains. Short peptide linkers of 2-7 amino acid residues between domains are not illustrated in any of the diagrams of the drawings, although from the amino acid sequence information given below, the length and sequence of such linkers is disclosed.

Fusion Protein Constructs

A cell-associated secretion-enhancing (CASE) fusion protein of the invention comprises at least two main domains: a target protein binding (TPB) domain and a transmembrane retention (TMR) domain. A CASE fusion protein of the invention may further comprise a chaperone machinery peptide (CMP) domain. Although not wishing to be bound by any particular scientific theory of how a fusion protein of the invention operates, a rational approach for constructing a fusion protein of the invention is to consider the orientation of the Type (I-IV) of transmembrane protein from which the TMR domain is derived and then arrange the TPB domain and, if present, the CMP domain, relative to that TMR domain so that the TPB domain and, if present, the CMP domain, will be present in the lumen of the endoplasmic reticulum (ER) where the target protein of interest is also located, as explained below. The CASE fusion protein is believed to act as a sort of synthetic chaperone protein, assisting in the transmission of the target protein to which it binds along the secretory pathway.

In addition to a TPB domain, a TMR domain, and, if present, a CMP domain, a CASE fusion protein according to the invention may also comprise an appropriate signal sequence to direct the TPB domain and, if present, a CMP domain of the fusion protein on expression into the lumen of the endoplasmic reticulum (ER). In particular embodiments, the signal sequence will be fused at the N-terminus of the fusion protein, in particular where the TMR domain is derived from a Type I transmembrane protein and is located at the C-terminal end of the fusion protein. The signal sequence may conveniently correspond to the signal sequence of the protein from which the N-terminal domain of the fusion protein is derived. For example, where the most N-terminal domain is a J domain of a J protein (or a fragment or analog thereof), it is preferred to use a signal sequence from the same J protein that supplied the J domain. Alternatively, the signal sequence of a soluble secreted protein may be used, as in the constructs disclosed below that utilize the signal sequence from human insulin. However, any suitable signal sequence that operates to translocate the TPB and/or CMP domains of the CASE fusion protein to the ER may be utilized.

Figure 18:
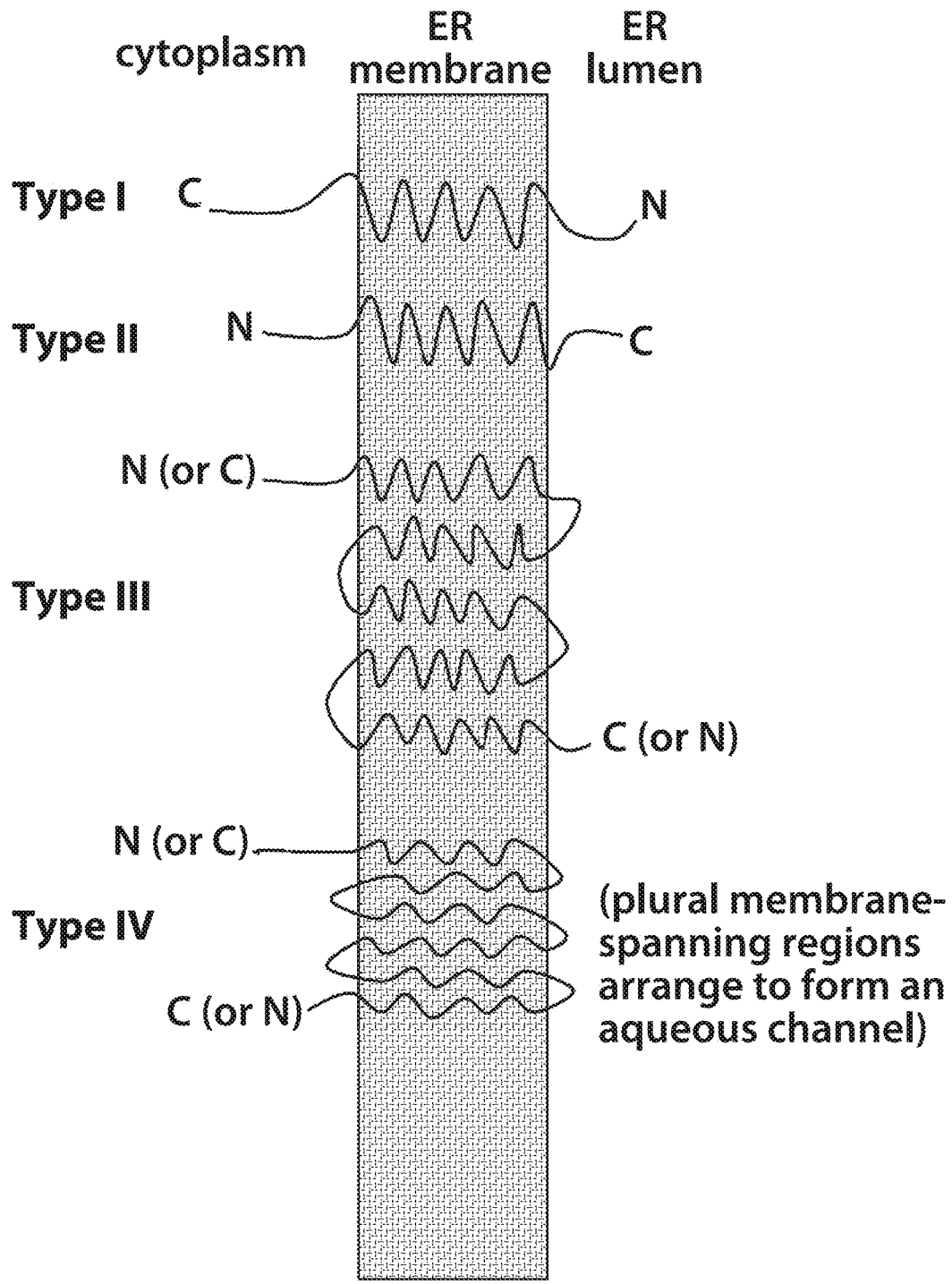
FIG. 18 illustrates certain characteristic features of Type I, II, III, and IV transmembrane proteins and the expected orientation of the proteins when inserted into the endoplasmic reticulum (ER) membrane relative to the cytoplasmic and ER lumen sides of the membrane. See, Nelson and Cox, *Principles of Biochemistry* (2008), FIG. 8-22. The transmembrane region of each type of protein within the ER membrane is arbitrarily represented as a series of loops traversing the breadth of the membrane but is not meant to indicate any particular structure; the actual structure will vary depending on the amino acid sequence of the particular protein species. Type III transmembrane proteins are distinguished from Types I and II as having more than one membrane-spanning region, but the exact number of transmembrane regions, the structure of each transmembrane region, and the distance between each transmembrane region varies depending on the particular species of Type III protein. A Type IV transmembrane protein has multiple membrane-spanning regions which form an aqueous channel through the cell membrane. The diagram of a Type III transmembrane protein in FIG. 18 has been illustrated as having five transmembrane regions with a relatively small intervening portion of the protein between adjacent transmembrane regions either in the cytoplasm or ER lumen, however proteins of this class may have as few as two membrane-spanning regions up to eight or more membrane-spanning regions. Likewise, the channel-forming multi-pass transmembrane regions of Type IV proteins is depicted in this drawing as having 6 membrane-spanning regions, but particular Type IV proteins may exhibit fewer or more membrane-spanning regions. "N" indicates an amino terminus and "C" indicates a carboxyl terminus of each type of transmembrane protein when inserted into the ER membrane. The locations of the N- and C-termini for the Type III and Type IV transmembrane proteins are indicated alternatively because the orientation with respect to N- and C-termini when inserted into the ER membrane varies among Type III and IV transmembrane proteins from one protein to the next.

The orientations of the transmembrane regions of the four types (Types I-IV) of transmembrane proteins with respect to cytoplasm and ER lumen are diagrammed in FIG. 18. For example, during synthesis (translation) of a Type I transmembrane protein, the protein traverses the ER membrane so that its N-terminus containing a signal sequence is inserted into the ER lumen, the protein's traverse through the membrane stops when the transmembrane region is embedded in the membrane, and any region of the protein C-terminal to the membrane-spanning region is then located in the cytoplasm. See, FIG. 18. Accordingly, in the case of using a TMR domain derived from a Type I transmembrane protein, a TPB domain and, if present, a CMP domain of a CASE fusion protein are preferably located in the N-proximal region and upstream from the Type I TMR domain in order to be located in the ER lumen with the co-expressed target protein of interest. Such an arrangement of domains for a fusion protein of the invention using a Type I TMR domain is exemplified by an order of domains in which (N-terminal to C-terminal) a CMP domain, if present, is fused to a TPB domain, which in turn is fused to a TMR domain comprising the transmembrane region of a Type I transmembrane protein. In another arrangement, the relative positions of the CMP domain and the TPB domain are switched so that the fusion protein comprises an arrangement of domains where, in an N-terminal to C-terminal direction, a TPB domain is fused to a CMP domain, which in turn is fused to a Type I TMR domain. In both arrangements, each domain may be linked to an adjacent domain directly or indirectly via a linker molecule. Thus, non-limiting exemplary arrangements of three domains that position the TMR domain as the most C-proximal domain relative to the other domains (i.e., TPB domain and CMP domain) are particularly preferred when the TMR domain is derived from a Type I transmembrane protein.

In contrast to the Type I transmembrane protein, in a Type II transmembrane protein, the TM region is in the N-terminal region of the protein so that the N-terminus of the protein is in the cytoplasm and the C-terminal region of the protein is in the ER lumen. See, FIG. 18. Accordingly, in the case of using a TMR domain derived from a Type II transmembrane protein, a TPB domain and, if present, a CMP domain should be located downstream, i.e., C-proximal, from the Type II TMR domain in order to be located in the ER lumen with the co-expressed target protein of interest. Such an arrangement of domains for a fusion protein of the invention using a Type II TMR domain is exemplified by an order of domains (N-terminal to C-terminal) in which a Type II TMR domain is fused to a CMP domain, which in turn is fused to a TPB domain. In another non-limiting exemplary arrangement, the relative positions of a CMP domain and the TPB domain are switched so that the fusion protein comprises an arrangement of domains where, in an N-terminal to C-terminal direction, a Type II TMR domain is fused to a TPB domain, which in turn is fused to a CMP domain. In both arrangements, each domain may be linked to an adjacent domain directly or indirectly via a linker. Thus, arrangements of the three domains that position the TMR domain as the most N-proximal domain relative to the other two domains (TPB and CMP domains) are particularly preferred when the TMR domain is derived from a Type II transmembrane protein.

For the construction of a CASE fusion protein with a TMR domain derived from a multi-pass transmembrane protein (having more than one traversal of the cellular membrane), such as a Type III transmembrane protein, the location of a TPB domain and, when present, a CMP domain in a CASE fusion protein of the invention, will depend on the known configuration of the multi-pass transmembrane protein. See, FIG. 18. Preferably, in order to more accurately determine the configurations of the multiple membrane-spanning segments of a multi-pass transmembrane protein, a hydropathy plot for the particular multi-pass transmembrane protein may be considered. A hydropathy plot takes into account the hydrophobicity and hydrophilicity of short segments (around 20 amino acids) of the amino acid sequence of a particular protein. The hydropathy plot would permit the practitioner to decide how much of the transmembrane region to use in constructing a TMR domain, and how to orient the TMR domain in relation to the other functional domains of a CASE fusion protein according to the invention.

Nucleic Acids Encoding CASE Fusion Proteins

Standard techniques may be used for constructing recombinant nucleic acid molecules, transfecting cells (for example, without limitation, electroporation, liposome-mediated transfection, transformation methods) with vector molecules, and culturing host cells to express a cell-associated secretion-enhancing (CASE) fusion protein of the invention alone or to co-express the fusion protein with a target protein of interest. Enzymatic reactions and purification techniques may be performed as commonly accomplished in the art, as described in a manufacturer's specifications, or as described herein. The foregoing techniques and procedures may be generally performed according to conventional methods well known in the art and as described in various general references that are cited and discussed throughout the present specification. See e.g., Sambrook et al., eds., *Molecular Cloning: A Laboratory Manual, Second Edition* (Cold Spring Harbor Laboratory Press, Cold Spring Harbor, N.Y., 1989) and Ausubel et al. (eds.), *Current Protocols in Molecular Biology* (John Wiley & Sons, New York, 2012), which are incorporated herein by reference.

Using standard methods available in the art as mentioned above, a nucleic acid molecule (typically DNA) is constructed that encodes a CASE fusion protein that promotes secretion of a co-expressed target protein of interest from a host cell at a significantly enhanced level as compared to the level of target protein secreted in the absence of the CASE fusion protein. A nucleic acid molecule encoding a desired CASE fusion protein can be inserted into any of a variety cloning vectors available in the art for the purpose of replicating the recombinant structural gene for the CASE fusion protein. For expressing a CASE fusion protein, a nucleic acid molecule encoding the CASE fusion protein can be inserted into any of a variety of expression vectors available in the art, wherein the inserted nucleic acid is operably linked to transcriptional and translational signals required for expression in a compatible host cell. An expression vector with the inserted nucleic acid encoding the CASE fusion protein is then introduced into a compatible host cell that permits expression of the fusion protein from the expression vector. In one embodiment, the vector may also contain a copy of a functional structural gene encoding the target protein of interest if the host cell does not already possess a functional gene for the target protein of interest, for example, in the chromosome of the host cell or in another expression vector present in the host cell.

While a description herein for assembling a nucleic acid construct encoding a CASE fusion protein of the invention may suggest a particular stepwise order to the linking of various nucleic acid molecules followed by insertion of the fully assembled nucleic acid construct into an expression vector, it will be understood and appreciated that the exact order of linking segments of nucleic acid molecules to produce a nucleic acid construct encoding a desired CASE fusion protein is at the discretion of the practitioner in this art. Moreover, although it is possible to first link all segments together to form a nucleic acid molecule encoding a CASE fusion protein prior to insertion into an expression vector, in some cases, a nucleic acid segment encoding one or more domains may already properly reside within an expression vector so that it is practical to insert one or more nucleic acid segments adjacent to the segment(s) already residing in the expression vector and thereby assemble within the expression vector an operably linked structural gene for a desired fusion protein of the invention.

Expression vectors encoding a CASE fusion protein of the invention may be transfected into any of a variety of host cells that are compatible for expressing the fusion protein from the particular expression vector. Although some steps in the process of constructing a recombinant structural gene encoding a CASE fusion protein of the invention may be conducted in either prokaryotic or eukaryotic cells, the preferred host cell for expressing and using CASE fusion protein to enhance the level of secretion of a co-expressed target protein of interest is a eukaryotic host cell, more preferably a cell of an isolated animal cell line, and even more preferably a cell of an isolated mammalian cell line. Examples of eukaryotic host cells that are useful in the invention include, but are not limited to, a mammalian host cell, an insect host cell, a plant host cell, a fungal host cell, a eukaryotic algal host cell, a nematode host cell, a protozoan host cell, and a fish host cell. Mammalian host cells useful for co-expressing a fusion protein of the invention and a target protein of interest include, but are not limited to, a Chinese Hamster Ovary (CHO) cell, a COS cell, a Vero cell, an SP2/0 cell, an NS/0 myeloma cell, a human embryonic kidney (HEK293) cell, a baby hamster kidney (BHK) cell, a HeLa cell, a human B cell, a CV-1/EBNA cell, an L cell, a 3T3 cell, an HEPG2 cell, a PerC6 cell, and an MDCK cell. Fungal host cells useful for expressing a fusion protein of the invention include, but are not limited to, *Aspergillus, Neurospora, Saccharomyces, Pichia, Hansenula, Schizosaccharomyces, Kluyveromyces, Yarrowia*, and *Candida*. A particularly useful *Saccharomyces* host cell is a *Saccharomyces cerevisiae* cell.

By following the methods and examples described herein, significantly enhanced levels of a target protein of interest secreted from a recombinant host cell may be achieved. For the purposes of the invention, a significantly enhanced level of a target protein secreted from a host cell is achieved where at least a 1.5-fold increase in the level of secreted target protein is obtained, when compared with the level of the same target protein secreted from a host cell not utilizing a co-expressed CASE fusion protein according to the invention. As noted above, for a secreted target protein of interest that is also a therapeutically and commercially important protein, an enhancement of 1.5-fold or more would be recognized by persons in the pharmaceutical industry as providing a significant reduction in production costs and also a significant increase in the availability of the therapeutically and commercially important protein. As demonstrated in the examples that follow, increases in the level of target protein secreted from a host cell of greater than 1.5-fold, 2-fold, 2.5-fold, 3-fold, 4-fold, 4.5-fold, 6-fold, 7-fold, 8-fold, 10-fold, and 15-fold have been achieved. In preferred embodiments, an enhanced level of target protein secreted from a host cell of at least 2-fold the level of target protein secreted from a host cell in the absence of a CASE fusion protein is achieved. More preferably, use of a CASE fusion protein of the invention results in an increase in the level of a co-expressed target protein secreted from a host cell of 2.5-fold or higher. Most preferably, the enhanced level of target protein secreted from a host cell is achieved without a significant amount of the CASE fusion protein being co-secreted with the target protein into the extracellular media.

EXAMPLES

Example 1

Compositions and Methods for Enhancing Levels of Secretion of Target Proteins Using a Co-Expressed Cell-Associated Secretion-Enhancing (CASE) Fusion Protein Retained in the Host Cell Expression vector plasmids were constructed for expressing fusion proteins for enhancing the level of secretion of specific proteins (target proteins). As described below, fusion proteins were usually linked to a standard epitope tag for easy identification or isolation using a corresponding anti-tag antibody and standard immunoblot (such as dot blot, Western blot) assays.

A DNA linker molecule having a nucleotide sequence containing various restriction enzyme sites for cloning heterologous DNA molecules was produced by annealing two single-stranded DNA molecules having the sequences shown below (5' to 3'):

```
                                          (SEQ ID NO: 129)
AGCTTGGTACCGGATCCGAATTCGATATCGCGGCCGCTCTCGAGTCTAGA
GGGCC
and
                                          (SEQ ID NO: 130)
CTCTAGACTCGAGAGCGGCCGCGATATCGAATTCGGATCCGGTACCA.
```

The annealed linker molecule was then inserted into plasmid pcDNA3 (catalogue no. V790-20, Invitrogen) digested with HindIII and ApaI downstream of a CMV promoter to yield the expression vector plasmid pcDNA' for use in mammalian host cells. The pcDNA' expression vector was used in the studies described in the examples below that show an enhancement in the level of a target protein of interest secreted from transfected cells co-expressing the target protein and a fusion protein according to the invention.

DNA molecules encoding the V5 epitope tag (GKPIPNPLLGLDST; SEQ ID NO:131) or the Flag epitope tag (DYKDDDDK; SEQ ID NO:132) were synthesized and inserted into plasmid pcDNA' digested with XhoI and XbaI, to yield plasmids V5-pcDNA' and Flag-pcDNA', respectively.

A DNA molecule having the coding sequence for the Flag epitope tag, i.e., GATTACAAGGATGACGATGACAAG (SEQ ID NO:133), was inserted into plasmid pcDNA' digested with XhoI and XbaI to yield plasmid Flag-pcDNA'.

To express Factor VII protein (FVII), a DNA molecule encoding FVII protein was inserted into plasmid V5-pcDNA' digested with HindIII and KpnI.

A DNA molecule encoding an Fc region polypeptide of a human IgG1 molecule was synthesized and inserted into V5-pcDNA' digested with XbaI and ApaI.

Unless indicated otherwise, each DNA molecule encoding a target protein binding (TPB) domain for a corresponding target protein of interest in the examples below was inserted into plasmid Flag-pcDNA' digested with NotI and XhoI to yield the corresponding (TPB domain)-pcDNA' vector.

Unless indicated otherwise, a DNA molecule encoding a C-terminal transmembrane retention (TMR) domain was cloned into a (TPB domain)-Flag-pcDNA' vector digested with XbaI and ApaI to yield the corresponding (TPB domain)-Flag-(TMR domain)-pcDNA' plasmid vector.

Unless indicated otherwise, a DNA molecule encoding an N-terminal transmembrane retention (TMR) domain was cloned into plasmid Flag-pcDNA' digested with HindIII and KpnI to yield the corresponding (TMR domain)-(TPB domain)-Flag-pcDNA' vector.

Unless indicated otherwise, a DNA molecule encoding a chaperone machinery peptide (CMP) was inserted into Flag-pcDNA' vectors digested with EcoRI and EcoRV to yield the corresponding (CMP)-Flag-pcDNA' vector.

Expression and Detection of Target Proteins in HEK293 Cells and Culture Media

A host cell was transfected with a separate expression vector for each protein (target protein, fusion protein, green fluorescent protein) that was intended to be expressed in the host cell. Expression vector plasmids encoding various protein constructs were transfected into human embryonic kidney (HEK293) cells with X-tremeGENE™ HP transfection reagent (catalogue no. 06365752001, Roche Applied Science, Penzberg, Germany) or with FUGENE® HD transfection reagent (catalogue no. E2311, Promega, Madison, Wis., USA), which yielded comparable transfection efficiencies.

Unless otherwise indicated, every transfection included a plasmid expressing a green fluorescent protein (GFP) as an internal control for monitoring transfection efficiency.

Cultures of transfected cells were incubated for two days, and cells were lysed in lysis buffer (10 mM Tris-HCl, pH 8.0, 150 mM NaCl, 10 mM EDTA, 2% SDS) containing 2 mM phenylmethylsulfonyl fluoride (PMSF) protease inhibitor. After brief sonication, cells were analyzed for expressed proteins using dot blot or Western immunoblot (Western blot) assays. For Western blot analysis, culture samples (for example, cells, cell-free culture medium, or cells and medium) were boiled in SDS-sample buffer (reducing and denaturing conditions) and run on polyacrylamide electrophoresis gel, followed by transfer of separated protein bands to polyvinylidene difluoride membrane (PVDF membrane). The expression of GFP as an internal transfection control was detected using an anti-GFP antibody.

Expressed proteins in dot and Western blots were detected using a chemiluminescent signal. Briefly, blots were reacted with a primary antibody that binds the particular epitope tag (e.g., V5 or Flag) carried by the proteins. After rinsing away unreacted primary antibody, a secondary, enzyme-linked antibody (e.g., horseradish peroxidase-linked anti-IgG antibody) was allowed to react with primary antibody molecules bound to the blots. After rinsing, manufacturer's chemiluminescent reagent was added. Chemiluminescent signals in blots were captured on X-ray film. Where indicated, the images of the chemiluminescent signals were scanned with a densitometer and analyzed using the NIH ImageJ image processing program.

Plasmid for humanized anti-IL-8 antibody, p6G425V11N35A.choSD (catalog No. 209552) was purchased from the American Type Culture Collection (Manassas, Va.).

Fc Fusion Proteins

One strategy that has been employed to generate more stable forms of therapeutically relevant proteins, and especially receptor proteins, is to prepare a fusion protein version of a protein of interest in which all or a functional portion of the protein of interest is linked to an immunoglobulin "Fc region" comprising the "CH2-CH3" or "hinge-CH2-CH3" regions of an immunoglobulin heavy chain using, for example, recombinant DNA methods, including polymerase chain reaction (PCR). Upon expression, the Fc regions of each of two fusion proteins can associate to form a homodimer in a manner similar to what occurs when two immunoglobulin heavy chains dimerize via their respective Fc regions, while preserving the functional portion of the protein of interest fused to each Fc region so that the homodimer comprises two functional portions of the protein of interest. Such an Fc target protein format has been used to design families of potentially useful drugs that provide a desired therapeutically relevant activity and, owing to the presence of the dimerized Fc regions, also exhibits an increased in vivo serum half-life, which in turn should reduce dosing frequencies. Several such Fc target proteins have been constructed to illustrate the operation of the present invention in the following examples. Fc target proteins include those in which a truncated form (TF) of a cell surface receptor protein comprises the extracellular ligand-binding portion of the cell surface receptor protein that is fused to an Fc region to yield a soluble version of the receptor referred to as a "trap" molecule. Such Fc trap molecules include the IL13Rα2TF-Fc fusion protein and the TNFR1TF-Fc fusion protein used in the studies described in the Examples below. Such Fc trap molecules may comprise a standard epitope tag, such as a Flag or V5 epitope tag, which permits the Fc trap molecule to be detected using a corresponding standard anti-tag antibody (for example, anti-Flag or anti-V5 epitope tag antibody). Such epitope tags may be located at the N-terminus or C-terminus of the Fc fusion protein or even within the Fc fusion protein, for example, between the amino acid sequence of the truncated receptor (IL13Rα2TF or TNFR1TF) and the amino acid sequence for the Fc region, as shown in the examples described below.

Example 2

Enhanced Level of Secreted IL13Rα2-Fc Target Protein

In this experiment, an IL13Rα2-Fc target protein (trap molecule) was used as a representative example of an Fc target protein. The IL13 receptor, IL13Rα2, is a membrane protein that binds to interleukin-13 (IL13) and mediates allergic inflammation. The IL13Rα2 receptor protein is known to be an unstable protein in a mammalian cell due to the difficulties of protein folding (*Genetic Engineering &*

Biotechnology News, 28(5) (2008)). Part of the expressed IL13Rα2 protein is digested on the cell surface and shed into the extracellular space. The truncated form that is shed from the cell surface is approximately the N-terminal 320 amino acids of mature IL13Rα2. This truncated form of IL13Rα2 still possesses the ability to bind IL13, but cannot transmit a signal to the cell owing to the absence of transmembrane and cytoplasmic regions of the full-length IL13Rα2 protein. Therefore, the truncated form of IL13Rα2 has been used as a type of decoy receptor to treat asthma by binding IL13 molecules without transducing a signal to the cell to set off an inflammatory response (Zhang, et al., *J. Biol. Chem.*, 272(14): 9474-80 (1997)). A genetically engineered, truncated form of IL13Rα2 has been expressed in bacteria, however the protein aggregates into inclusion bodies. It is known that one limitation to the expression of the truncated IL13Rα2 protein by transfected cells has been ascribed to inefficient folding into its proper functional conformation. When proteins cannot fold into their proper conformation they are ushered to the proteasome for degradation and scavenging of amino acids. Accordingly, production of truncated IL13Rα2 molecules in transfected cells has been recognized as a technical problem by industry and there is a persistent desire to overcome the natural limitations of expression and secretion for this protein (Lee et al., *Cell Technol. for Cell Products*, 29-39 (2007)).

The truncated form of IL13Rα2 used herein is referred to as "IL13Rα2TF". In this experiment, the IL13Rα2TF was fused to an Fc region (hinge-CH2-CH3) to form an IL13Rα2TF-Fc trap molecule, which was employed as a target protein of interest. Upon expression, the IL13Rα2TF-Fc trap molecule forms a homodimer by pairing of CH3 domains of two monomers. This experiment examined the effect of co-expression of the IL13Rα2TF-Fc target protein and a cell-associated secretion-enhancing (CASE) fusion protein on the level of secretion of the IL13Rα2TF-Fc target protein from a transfected HEK293 host cell.

Figure 2A:
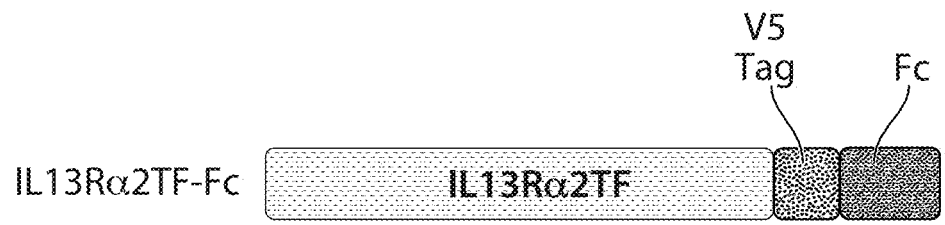
FIG. 2A is a diagram depicting a nucleic acid construct encoding a target protein described in Example 2 and comprising a segment encoding a truncated form of the IL13Rα2 receptor protein ("IL13Rα2TF") augmented at its 3' end with a segment encoding a V5 epitope tag, which in turn was linked to a segment encoding an immunoglobulin Fc region comprising the hinge-CH2-CH3 region of an IgG heavy chain (designated "Fc") to promote formation of homodimers. The encoded target protein was designated "IL13Rα2TF-Fc". See Example 2 for additional details.

FIG. 2A shows a diagram of a nucleic acid construct that was prepared comprising a polynucleotide segment encoding an IL13Rα2TF-Fc target protein that was augmented in its 3' region and upstream from a segment encoding the Fc region with a segment encoding a V5 epitope tag for easy identification of the expressed protein using a standard anti-V5 antibody. The amino acid sequence for the V5-tagged IL13Rα2TF-Fc monomer of the target protein used in this experiment is shown in Table 4 below.

TABLE 4

Amino Acid Sequence of a V5-Tagged
IL13Rα2TF-Fc Target Protein Monomer

| Encoded Protein or Region (N- to C-terminal) | Sequence Identifier | Amino Acid Sequence 12345678901234567890123456780 |
|---|---|---|
| V5-tagged IL13Rα2TF-Fc target protein | SEQ ID NO: 137 | MAFVCLAIGCLYTFLISTTFGCTSSSDTEI KVNPPQDFEIVDPGYLGYLYLQWQPPLSLD HFKECTVEYELKYRNIGSETWKTIITKNLH YKDGFDLNKGIEAKIHTLLPWQCTNGSEVQ SSWAETTYWISPQGIPETKVQDMDCVYYNW QYLLCSWKPGIGVLLDTNYNLFYWYEGLDH ALQCVDYIKADGQNIGCRFPYLEASDYKDF YICVNGSSENKPIRSSYFTFQLQNIVKPLP PVYLTFTRESSCEIKLKWSIPLGPIPARCF DYEIEIREDDTTLVTATVENETYTLKTTNE TRQLCFVVRSKVNIYCSDDGIWSEWSDKQC WEGEDLSKKGTGSEFDIAAALEGKPIPNPL LGLDSTSRPKSCDKTHTCPPCPAPELLGGP SVFLFPPKPKDTLMISRTPEVTCVVVDVSH EDPEVKFNWYVDGVEVHNAKTKPREEQYNS TYRVVSVLTVLHQDWLNGKEYKCKVSNKAL PAPIEKTISKAKGQPREPQVYTLPPSRDEL TKNQVSLTCLVKGFYPSDIAVEWESNGQPE NNYKTTPPVLDSDGSFFLYSKLTVDKSRWQ QGNVFSCSVMHEALHNHYTQKSLSLSPGK |
| IL13Rα2 signal sequence | Residues 1-26 of SEQ ID NO: 137 | MAFVCLAIGCLYTFLISTTFGCTSSS |
| IL13Rα2TF | residues 27-339 of SEQ ID NO: 137 | DTEIKVNPPQDFEIVDPGYLGYLYLQWQPP LSLDHFKECTVEYELKYRNIGSETWKTIIT KNLHYKDGFDLNKGIEAKIHTLLPWQCTNG SEVQSSWAETTYWISPQGIPETKVQDMDCV YYNWQYLLCSWKPGIGVLLDTNYNLFYWYE GLDHALQCVDYIKADGQNIGCRFPYLEASD YKDFYICVNGSSENKPIRSSYFTFQLQNIV KPLPPVYLTFTRESSCEIKLKWSIPLGPIP ARCFDYEIEIREDDTTLVTATVENETYTLK TTNETRQLCFVVRSKVNIYCSDDGIWSEWS DKQCWEGEDLSKK |
| Linker | residues 340-352 of SEQ ID NO: 137 | GTGSEFDIAAALE |

TABLE 4-continued

Amino Acid Sequence of a V5-Tagged
IL13Rα2TF-Fc Target Protein Monomer

| Encoded Protein or Region (N- to C-terminal) | Sequence Identifier | Amino Acid Sequence 123456789012345678901234567890 |
|---|---|---|
| V5 epitope domain | residues 353-366 of SEQ ID NO: 137 | GKPIPNPLLGLDST |
| Linker | residues 367-368 of SEQ ID NO: 137 | SR |
| Fc domain | residues 369-599 of SEQ ID NO: 137 | PKSCDKTHTCPPCPAPELLGGPSVFLFPPK PKDTLMISRTPEVTCVVVDVSHEDPEVKFN WYVDGVEVHNAKTKPREEQYNSTYRVVSVL TVLHQDWLNGKEYKCKVSNKALPAPIEKTI SKAKGQPREPQVYTLPPSRDELTKNQVSLT CLVKGFYPSDIAVEWESNGQPENNYKTTPP VLDSDGSFFLYSKLTVDKSRWQQGNVFSCS VMHEALHNHYTQKSLSLSPGK |

Figure 2B:
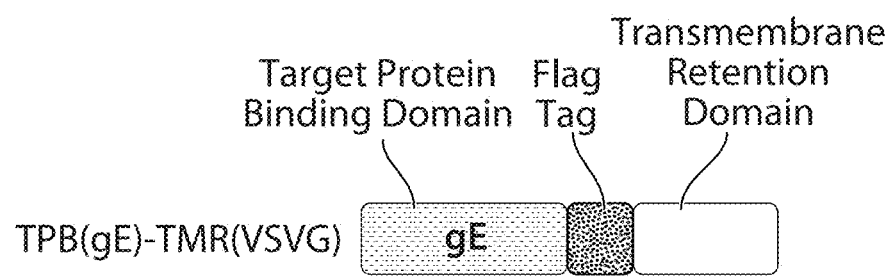
FIG. 2B is a diagram depicting a nucleic acid construct encoding a cell-associated secretion-enhancing fusion protein of the invention comprising a segment encoding an Fc-binding region of a herpes simplex virus type-1 glycoprotein E (gE) as a target protein binding (TPB) domain augmented at its 3' end with a segment encoding a Flag epitope tag for easy identification with a standard anti-Flag antibody, which in turn was linked to a segment encoding the transmembrane region of the type I transmembrane VSV-G protein as a transmembrane retention (TMR) domain ("TPB(gE)-TMR (VSVG)"). See Example 2 for additional details.

FIG. 2B shows a diagram of a nucleic acid construct that was prepared comprising a segment encoding a TPB-TMR (VSGS) fusion protein that was augmented with a segment encoding a Flag epitope tag (for easy identification of the fusion protein using a standard anti-Flag antibody) between a 5' segment encoding the gE Fc-binding protein (TPB domain) and a 3' segment encoding a transmembrane region from the vesicular stomatitis virus transmembrane glycoprotein (VSV-G protein) for use as a TMR domain, i.e., "TMR(VSVG)". The amino acid sequence for the TPB(gE)-TMR(VSVG) fusion protein used in this experiment is shown in Table 5 below.

TABLE 5

Amino Acid Sequence of a Flag-Tagged
TPB(gE)-TMR(VSVG) Fusion Protein

| Encoded Protein or Region (N- to C-terminal) | Sequence Identifier | Amino Acid Sequence 123456789012345678901234567890 |
|---|---|---|
| Flag-tagged TPB(gE)-TMR(VSVG) fusion protein | SEQ ID NO: 182 | MALWMRLLPLLALLALWGPDPAAAGTGSGE FDIAAAGTPKTSWRRVSVGEDVSLLPAPGP TGRGPTQKLLWAVEPLDGCGPLHPSWVSLM PPKQVPETVVDAACMRAPVPLAMAYAPPAP SATGGLRTDFVWQERAAVVNRSLVIHGVRE TDSGLYTLSVGDIKDPARQVASVVLVVQPA PVPTPPPTPADYDEDDNDEGEDESLAGTPA SGTPRLPPPPAPPRSWPSAPEVSHVRGVTV RMETPEAILFSPGETFSTNVSIHAIAHDDQ TYSMDVVWLRFDVPTSCAEMRIYESCLYHP QLPECLSPADAPCAASTWTSRLAVRSYAGC SRTNPPPRCSAEAHMEPVPGLAWQAASVNL EFRDASPQHSGLYLCVVYVNDHIHAWGHIT ISTAAQYRNAVVEQPLPQRGADLAELEGDY KDDDDKGSRSSWKSSIASFFFIIGLIIGLF LVLRVGIHLCIKLKHTKKRQIYTDIEMNRL GK |
| Human insulin signal sequence | residues 1-24 of SEQ ID NO: 182 | MALWMRLLPLLALLALWGPDPAAA |
| Linker | residues 25-36 of SEQ ID NO: 182 | GTGSGEFDIAAA |
| TPB(gE) Domain | residues 37-415 of SEQ ID NO: 182 | GTPKTSWRRVSVGEDVSLLPAPGPTGRGPT QKLLWAVEPLDGCGPLHPSWVSLMPPKQVP ETVVDAACMRAPVPLAMAYAPPAPSATGGL RTDFVWQERAAVVNRSLVIHGVRETDSGLY TLSVGDIKDPARQVASVVLVVQPAPVPTPP PTPADYDEDDNDEGEDESLAGTPASGTPRL PPPPAPPRSWPSAPEVSHVRGVTVRMETPE |

TABLE 5-continued

Amino Acid Sequence of a Flag-Tagged
TPB(gE)-TMR(VSVG) Fusion Protein

| Encoded Protein or Region (N- to C-terminal) | Sequence Identifier | Amino Acid Sequence 123456789012345678901234567890 |
|---|---|---|
| | | AILFSPGETFSTNVSIHAIAHDDQTYSMDV VWLRFDVPTSCAEMRIYESCLYHPQLPECL SPADAPCAASTWTSRLAVRSYAGCSRTNPP PRCSAEAHMEPVPGLAWQAASVNLEFRDAS PQHSGLYLCVVYVNDHIHAWGHITISTAAQ YRNAVVEQPLPQRGADLAE |
| Linker | residues 416-418 of SEQ ID NO: 182 | LEG |
| Flag epitope domain | residues 419-426 of SEQ ID NO: 182 | DYKDDDDK |
| Linker | residues 427-429 of SEQ ID NO: 182 | GSR |
| TMR(VSVG) Domain | residues 430-482 of SEQ ID NO: 182 | SSWKSSIASFFFIIGLIIGLFLVLRVGIHL CIKLKHTKKRQIYTDIEMNRLGK |

Figure 2C:
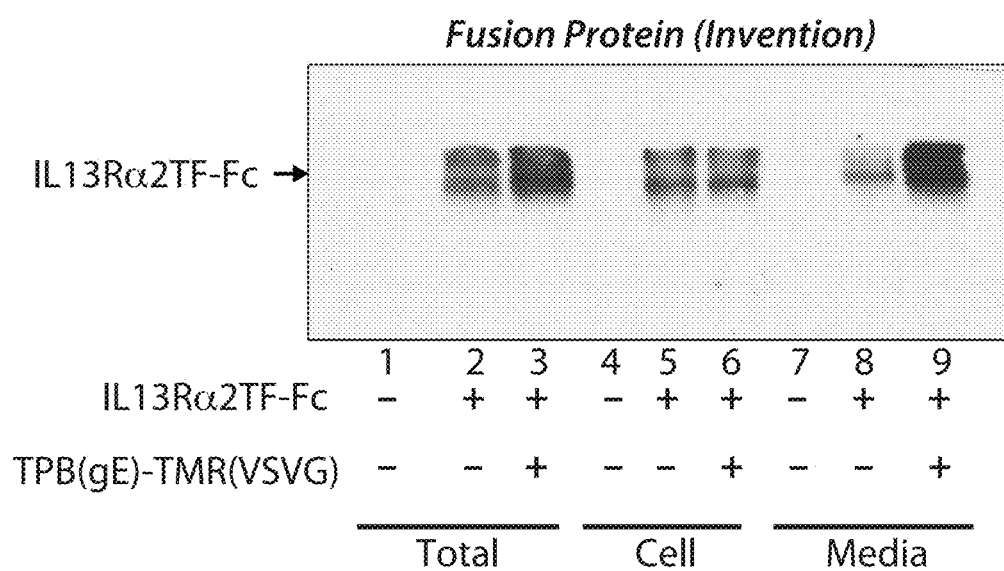
FIG. 2C shows X-ray film images of chemiluminescent signals of a Western blot analysis of samples of total culture, i.e., cells and media ("Total", lanes 1-3), of cell lysates ("Cell", lanes 4-6), and of culture media ("Media", lanes 7-9) of transfected cells expressing the IL13Rα2TF-Fc target protein alone (lanes 2, 5, and 8), and when co-expressed with a synthetic secretion enhancer CASE fusion protein (lanes 3, 6, and 9), as described in Example 2. The presence ("+") or absence ("−") of expression vectors encoding the target protein or a cell-associated secretion-enhancing fusion protein in the transfected host cells of each culture is indicated below each lane of the Western blot. Mock cultures contained cells transfected with expression vector lacking a structural gene for expressing any protein (lanes 1, 4, and 7). It can be seen that co-expression of the IL13Rα2TF-Fc target protein with the TPB(gE)-TMR (VSVG) fusion protein of the invention significantly enhanced the level of secreted IL13Rα2TF-Fc target protein (lanes 3 and 9), whereas in the absence of the fusion protein, a barely detectable amount of the IL13Rα2TF-Fc target protein was secreted into the culture media (lane 8). See Example 2 for additional details.

HEK293 cells were transfected with expression vector plasmids to compare levels of IL13Rα2TF-Fc target protein secreted into culture media when the IL13Rα2TF-Fc target protein was expressed alone or co-expressed with the TPB (gE)-TMR(VSVG) fusion protein. Transfected cells were cultured for two days, and samples of cell cultures were harvested and analyzed by Western blot (immunoblot) assay using a horseradish peroxidase-conjugated goat anti-human IgG (heavy and light chains) polyclonal F(ab')₂ antibody (Code No. 109-036-088, Jackson ImmunoResearch Laboratories, Inc., West Grove, Pa.) to detect the IL13Rα2TF-Fc target protein in Western blots. Mock cultures containing cells transfected with "empty vector", i.e., an expression vector lacking a structural gene for expressing any protein, were included as negative controls. The results of culturing the transfectant host cells and detecting IL13Rα2TF-Fc target protein expression by Western blot are shown in FIG. 2C for samples of cells and media ("Total", lanes 1-3), cell lysates ("Cell", lanes 4-6), and cell free culture media alone ("Media", lanes 7-9). As shown in the FIG. 2C, the level of expression of the IL13Rα2TF-Fc target protein secreted into the culture media was significantly greater in a culture of transfected cells co-expressing the IL13Rα2TF-Fc target protein and the TPB(gE)-TMR(VSGV) fusion protein (lane 9) than in a culture of cells expressing the IL13Rα2TF-Fc target protein alone (lane 8).

Example 3

Comparison of Enhanced Levels of Secreted IL13Rα2TF-Fc Target Protein Using Fusion Proteins with Different Transmembrane Retention (TMR) Domains This experiment compared the level of IL13Rα2-Fc target protein secreted from a host cell when co-expressed with either of two fusion proteins that differ in their transmembrane retention (TMR) domains or when co-expressed with either of the component TMR domains of the fusion proteins.

The V5-tagged IL13Rα2TF-Fc target protein used in this experiment was the same as described in Example 2 and Table 4 above.

Figure 3A:
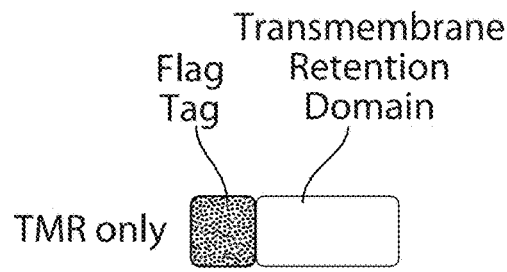
FIGS. 3A-3C show aspects and results of an experiment described in Example 3 that demonstrates significant enhancement in the secretion of an IL13Rα2TF-Fc target protein of interest when co-expressed with a cell-associated secretion-enhancing (CASE) fusion protein but not when the target protein is co-expressed with a peptide comprising the TMR alone.

FIG. 3A shows a general diagram of a nucleic acid construct comprising a segment encoding a transmembrane retention (TMR) domain that was augmented at its 5' end with a segment encoding a Flag epitope tag for easy identification of the expressed protein using a standard anti-Flag antibody.

Two different Flag-tagged TMR polypeptides were used in this study as "TMR only" polypeptides. One of the Flag-tagged TMR polypeptides comprised a transmembrane region of the VSVG protein. The amino acid sequence for this Flag-tagged TMR(VSVG) polypeptide is shown in Table 6 below.

TABLE 6

| Encoded Protein or Region (N- to C-terminal) | Sequence Identifier | Amino Acid Sequence 123456789012345678901234567890 |
|---|---|---|
| Flag-tagged TMR(VSVG) fusion protein | SEQ ID NO: 183 | MALWMRLLPLLALLALWGPDPAAAGTGSGE FDIAAALEGDYKDDDDKGSRSSWKSSIASF FFIIGLIIGLFLVLRVGIHLCIKLKHTKKR QIYTDIEMNRLGK |

TABLE 6-continued

Amino Acid Sequence for Flag-Tagged TMR(VSVG) Polypeptide

| Encoded Protein or Region (N- to C-terminal) | Sequence Identifier | Amino Acid Sequence 123456789012345678901234567890 |
|---|---|---|
| Human insulin signal sequence | residues 1-24 of SEQ ID NO: 183 | MALWMRLLPLLALLALWGPDPAAA |
| Linker | residues 25-39 of SEQ ID NO: 183 | GTGSGEFDIAAALEG |
| Flag epitope domain | residues 40-47 of SEQ ID NO: 183 | DYKDDDDK |
| Linker | residues 48-50 of SEQ ID NO: 183 | GSR |
| TMR(VSVG) Domain | residues 51-103 of SEQ ID NO: 183 | SSWKSSIASFFFIIGLIIGLFLVLRVGIHL CIKLKHTKKRQIYTDIEMNRLGK |

The other Flag-tagged TMR polypeptide used in this experiment comprised a transmembrane region of the KDEL receptor 1 protein. The amino acid sequence for this Flag-tagged TMR(KDELR) polypeptide is shown in Table 7 below.

TABLE 7

Amino Acid Sequence of a Flag-Tagged TMR(KDELR) Polypeptide

| Encoded Protein or Region (N- to C-terminal) | Sequence Identifier | Amino Acid Sequence 123456789012345678901234567890 |
|---|---|---|
| Flag-tagged TMR(KDELR) fusion protein | SEQ ID NO: 184 | MALWMRLLPLLALLALWGPDPAAAGTGSGE FDIAAALEGDYKDDDDKGSRNLFRFLGDLS HLLAIILLLLKIWKSRSCAGISGKSQVLFA VVFTARYLDLFTNYISLYNTCMKVVYIACS FTTVWLIYSKFKATYDGNHDTFRVEFLVVP TAILAFLVNHDFTPLEILWTFSIYLESVAI LPQLFMVSKTGEAETITSHYLFALGVYRTL YLFNWIWRYHFEGFFDLIAIVAGLVQTVLY CDFFYLYITKVLKGKKLSLPA |
| Human insulin signal sequence | residues 1-24 of SEQ ID NO: 184 | MALWMRLLPLLALLALWGPDPAAA |
| Linker | residues 25-39 of SEQ ID NO: 184 | GTGSGEFDIAAALEG |
| Flag epitope domain | residues 40-47 of SEQ ID NO: 184 | DYKDDDDK |
| Linker | residues 48-50 of SEQ ID NO: 184 | GSR |

TABLE 7-continued

Amino Acid Sequence of a Flag-Tagged TMR(KDELR) Polypeptide

| Encoded Protein or Region (N- to C-terminal) | Sequence Identifier | Amino Acid Sequence 123456789012345678901234567890 |
|---|---|---|
| TMR(KDELR) Domain | residues 51-261 of SEQ ID NO: 184 | NLFRFLGDLSHLLAIILLLLKIWKSRSCAG ISGKSQVLFAVVFTARYLDLFTNYISLYNT CMKVVYIACSFTTVWLIYSKFKATYDGNHD TFRVEFLVVPTAILAFLVNHDFTPLEILWT FSIYLESVAILPQLFMVSKTGEAETITSHY LFALGVYRTLYLFNWIWRYHFEGFFDLIAI VAGLVQTVLYCDFFYLYITKVLKGKKLSLP A |

Figure 3B:
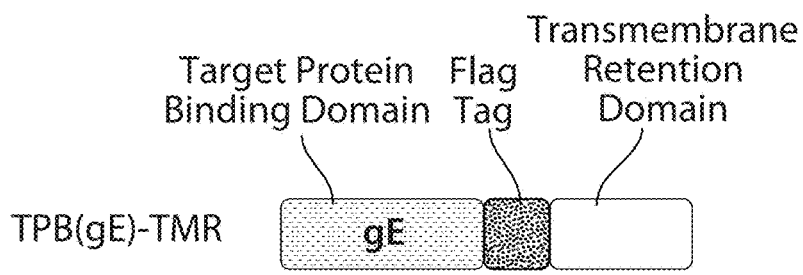

FIG. 3B shows a general diagram of a nucleic acid construct encoding a TPB-TMR fusion protein that was augmented with a segment encoding a Flag epitope tag (for easy identification of the fusion protein using a standard anti-Flag antibody) between a 5' segment encoding the Fc-binding region of the gE protein (TPB domain) and a 3' segment encoding a transmembrane region of the KDELR protein. Two fusion proteins were used in this experiment: One of the fusion proteins was the Flag-tagged TPB(gE)-TMR(VSV TABLE 8-continued Amino Acid Sequence of a Flag-Tagged
TPB(gE)-TMR(KDELR) Fusion Protein

| Encoded Protein or Region (N- to C-terminal) | Sequence Identifier | Amino Acid Sequence 12345678901234567890123456 7890 |
|---|---|---|
| | | SPADAPCAASTWTSRLAVRSYAGCSRTNPP PRCSAEAHMEPVPGLAWQAASVNLEFRDAS PQHSGLYLCVVYVNDHIHAWGHITISTAAQ YRNAVVEQPLPQRGADLAE |
| Linker | residues 416-418 of SEQ ID NO: 185 | LEG |
| Flag epitope domain | residues 419-426 of SEQ ID NO: 185 | DYKDDDDK |
| Linker | residues 427-429 of SEQ ID NO: 185 | GSR |
| TMR(KDELR) Domain | residues 430-640 of SEQ ID NO: 185 | NLFRFLGDLSHLLAIILLLLKIWKSRSCAG ISGKSQVLFAVVFTARYLDLFTNYISLYNT CMKVVYIACSFTTVWLIYSKFKATYDGNHD TFRVEFLVVPTAILAFLVNHDFTPLEILWT FSIYLESVAILPQLFMVSKTGEAETITSHY LFALGVYRTLYLFNWIWRYHFEGFFDLIAI VAGLVQTVLYCDFFYLYITKVLKGKKLSLP A |

HEK293 cells were transfected with expression vector plasmids to compare levels of IL13Rα2TF-Fc target protein secreted into culture media when the IL13Rα2TF-Fc target protein was expressed alone, when co-expressed with a Flag-tagged TPB-TMR(VSVG) fusion protein described in Example 2, when co-expressed with the Flag-tagged TMR (VSVG) polypeptide, when co-expressed with the Flag-tagged TPB(gE)-TMR(KDELR) fusion protein, or when co-expressed with the Flag-tagged TMR(KDELR) polypeptide. Mock cultures containing cells transfected with "empty vector", i.e., an expression vector lacking a structural gene for expressing any protein, were included as a negative control. IL13Rα2TF-Fc target protein in culture samples was determined by ELISA.

Figure 3C:
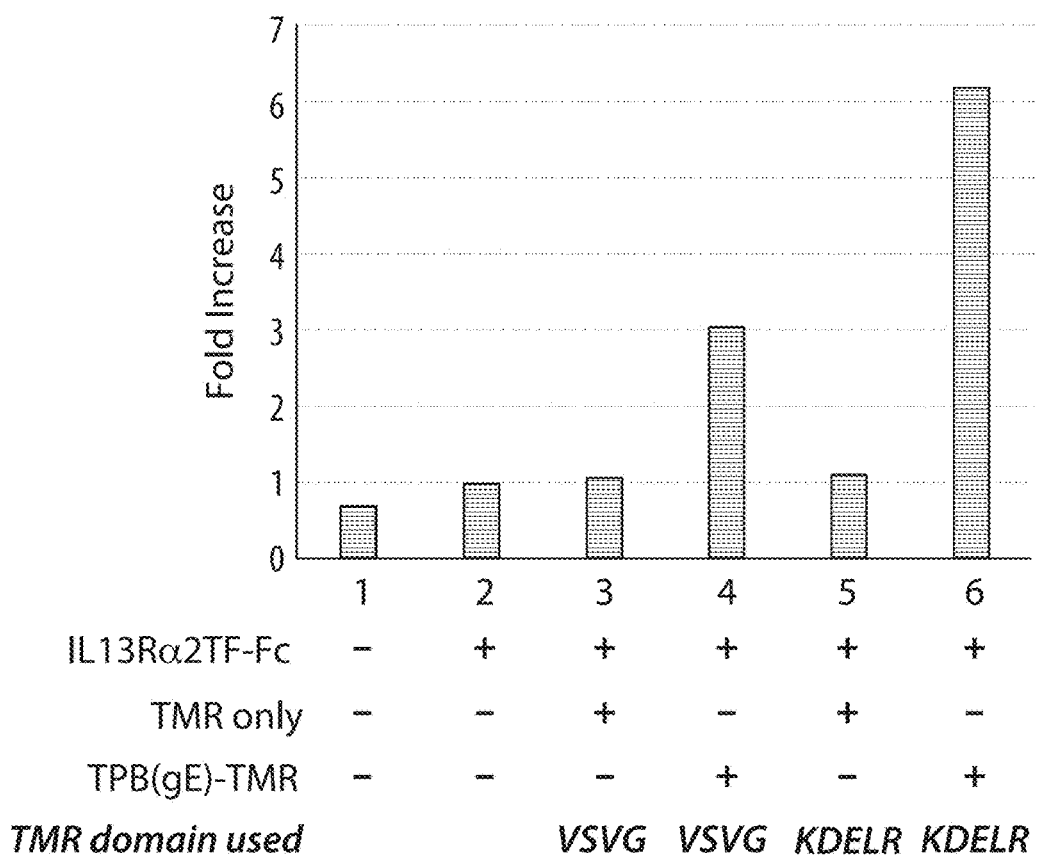

The relative levels of IL13Rα2TF-Fc target protein secreted into the media of the various transfectant cell cultures are shown in the bar graphs in FIG. 3C. The level of IL13Rα2TF-Fc target protein secreted into the medium of cells expressing the target protein alone was set at a relative value of "1" fold increase as shown in bar graph 2 of FIG. 3C. Co-expression of the IL13Rα2TF-Fc target protein and either the TMR(VSVG) polypeptide (bar graph 3) or the TMR(KDELR) polypeptide (bar graph 5) resulted in approximately the same level of target protein secreted into the medium of cultures of cells expressing the target protein alone (bar graph 2). In contrast, as shown in bar graph 4 of FIG. 3C, co-expression of the IL13Rα2TF-Fc target protein and the TPB(gE)-TMR(VSVG) fusion protein yielded a 3-fold increase in the level of target protein secreted into the culture medium compared to cells expressing the IL13Rα2TF-Fc target protein alone (bar graph 2). Surprisingly, as shown in bar graph 6 of FIG. 3C, the level of target protein secreted into the culture medium in cultures of cells that co-expressed the IL13Rα2TF-Fc target protein and the TPB(gE)-TMR(KDELR) fusion protein was more than double the level of target protein secreted into medium of cultures of cells co-expressing the IL13Rα2TF-Fc target protein and the TPB(gE)-TMR(VSVG) fusion protein (bar graph 3) and was more than a 6-fold increase in the level of target protein secreted from control cultures expressing the IL13Rα2TF-Fc target protein alone (bar graph 2). The results indicate that judicious selection of a TMR domain can significantly affect the level of target protein secreted into the culture medium.

Example 4

Enhanced Level of Secreted TNFR1TF-Fc Target Protein

This experiment examined the enhancement in the level of a TNFα receptor 1 trap molecule when co-expressed with the TPB(gE)-TMR(VSVG) fusion protein.

The TPB(gE)-TMR(VSVG) fusion protein used in this experiment was the same as described in Example 2 and Table 5 above.

The target protein comprised a truncated form (TF) of the TNFα receptor 1 protein fused to an Fc region (hinge-CH2-CH3). The amino acid sequence of the "TNFR1TF-Fc" target protein monomer is shown in the Table 9, below. On expression, the monitor will homodimerize through the Fc region, resulting in a bivalent target protein.

TABLE 9

Amino Acid Sequence of a V5-Tagged TNFR1TF-Fc Target Protein Monomer

| Protein Region (N- to C-terminal) | Sequence Identifier | Amino Acid Sequence 123456789012345678901234567890 |
|---|---|---|
| TNFR1TF Fc fusion protein | SEQ ID NO: 186 | MGLSTVPDLLLPLVLLELLVGIYPSGVIGL VPHLGDREKRDSVCPQGKYIHPQNNSICCT KCHKGTYLYNDCPGPGQDTDCRECESGSFT ASENHLRHCLSCSKCRKEMGQVEISSCTVD RDTVCGCRKNQYRHYWSENLFQCFNCSLCL NGTVHLSCQEKQNTVCTCHAGFFLRENECV SCSNCKKSLECTKLCLPQIENVKGTEDSGT TGTGSEFDIAAALEGKPIPNPLLGLDSTSR PKSCDKTHTCPPCPAPELLGGPSVFLFPPK PKDTLMISRTPEVTCVVVDVSHEDPEVKFN WYVDGVEVHNAKTKPREEQYNSTYRVVSVL TVLHQDWLNGKEYKCKVSNKALPAPIEKTI SKAKGQPREPQVYTLPPSRDELTKNQVSLT CLVKGFYPSDIAVEWESNGQPENNYKTTPP VLDSDGSFFLYSKLTVDKSRWQQGNVFSCS VMHEALHNHYTQKSLSLSPGK |
| TNFR1TF | residues 1-211 of SEQ ID NO: 186 | MGLSTVPDLLLPLVLLELLVGIYPSGVIGL VPHLGDREKRDSVCPQGKYIHPQNNSICCT KCHKGTYLYNDCPGPGQDTDCRECESGSFT ASENHLRHCLSCSKCRKEMGQVEISSCTVD RDTVCGCRKNQYRHYWSENLFQCFNCSLCL NGTVHLSCQEKQNTVCTCHAGFFLRENECV SCSNCKKSLECTKLCLPQIENVKGTEDSGT T |
| Linker | residues 212-224 of SEQ ID NO: 186 | GTGSEFDIAAALE |
| V5 epitope domain | residues 225-238 of SEQ ID NO: 186 | GKPIPNPLLGLDST |
| Linker | residues 239-240 of SEQ ID NO: 186 | SR |
| Fc domain | residues 241-471 of SEQ ID NO: 186 | PKSCDKTHTCPPCPAPELLGGPSVFLFPPK PKDTLMISRTPEVTCVVVDVSHEDPEVKFN WYVDGVEVHNAKTKPREEQYNSTYRVVSVL TVLHQDWLNGKEYKCKVSNKALPAPIEKTI SKAKGQPREPQVYTLPPSRDELTKNQVSLT CLVKGFYPSDIAVEWESNGQPENNYKTTPP VLDSDGSFFLYSKLTVDKSRWQQGNVFSCS VMHEALHNHYTQKSLSLSPGK |

HEK293 cells were transfected with expression vector plasmids for co-expression of the TNFR1TF-Fc target protein and the TPB(gE)-TMR(VSVG) fusion protein. Mock cultures containing cells transfected with "empty vector", i.e., an expression vector lacking a structural gene for expressing any protein, were included as a negative control. TNFR1TF-Fc target protein in culture samples was determined by ELISA.

The relative levels of TNFR1TF-Fc target protein secreted into culture medium are shown in FIG. 4. The level of TNFR1TF-Fc target protein secreted into the medium of cells expressing the target protein alone was set at a relative value of "1" fold increase as shown in bar graph 2 of FIG. 4. The level of expression of the TNFR1TF-Fc target protein secreted into the culture medium was increased by 5.5-fold in a culture of transfected cells co-expressing the TNFR1TF-Fc target protein and the TPB(gE)-TMR(VSGV) fusion protein (bar graph 3) compared to the level in the medium of a culture of cells expressing the IL13Rα2TF-Fc target protein alone (bar graph 2).

Additional Experiments: Comparison of Enhanced Levels of Secreted TNFR1TF-Fc Target Protein Using Fusion Proteins with Different Target Protein Binding (TPB) and Transmembrane Retention (TMR) Domains.

This example examined the effectiveness of various fusion proteins comprising alternative target protein binding (TPB) and transmembrane retention (TMR) domains for enhancing the level of secretion of a V5 epitope-tagged TNFR1TF-Fc target protein into the media of cultures of transfected host cells.

FIG. 4B shows a general diagram of a nucleic acid construct encoding a TPB-TMR fusion protein comprising a segment encoding a target protein binding (TPB) domain linked at its 3' end to a segment encoding a Flag epitope tag, which in turn was linked at its 3' end to a segment encoding a transmembrane retention (TMR) domain. The 5' end of the nucleic acid construct was also augmented with a signal sequence to direct the TPB-TMR fusion protein into the intracellular membrane of the endoplasmic reticulum. In this study, the encoded fusion proteins comprised a TMR domain that comprised either a transmembrane region of the vesicular stomatitis virus transmembrane glycoprotein (VSVG) or a transmembrane region of the KDEL receptor 1 protein (KDELR), which is an endoplasmic reticulum (ER) receptor protein that binds to resident ER proteins comprising the ER localization amino acid motif K-D-E-L (SEQ ID NO:152). The TPB domain of the fusion proteins employed in this study were an Fc-binding portin of the herpes simplex virus type-1 glycoprotein E ("gE"), an Fc-binding protein of Protein A ("A"), or an Fc-binding portion of Protein G ("G").

The V5-tagged TNFR1TF-Fc target protein used in this study was the same as that described in Table 9 above.

The Flag-tagged TPB(gE)-TMR(VSVG) fusion protein (SEQ ID NO:190) used in this study is shown in Table 10 below.

TABLE 10

Amino Acid Sequence for a Flag-tagged TPB(gE)-TMR(VSVG) Fusion Protein

| Encoded Protein or Region (N- to C-terminal) | Sequence Identifier | Amino Acid Sequence 12345678901234567890123456789 0 |
|---|---|---|
| Flag-tagged TPB(gE)-TMR(VSVG) fusion protein | SEQ ID NO: 190 | MALWMRLLPLLALLALWGPDPAAAGTGSGE FDIAAAGTPKTSWRRVSVGEDVSLLPAPGP TGRGPTQKLLWAVEPLDGCGPLHPSWVSLM PPKQVPETVVDAACMRAPVPLAMAYAPPAP SATGGLRTDFVWQERAAVVNRSLVIHGVRE TDSGLYTLSVGDIKDPARQVASVVLVVQPA PVPTPPPTPADYDEDDNDEGEDESLAGTPA SGTPRLPPPPAPPRSWPSAPEVSHVRGVTV RMETPEAILFSPGETFSTNVSIHAIAHDDQ TYSMDVVWLRFDVPTSCAEMRIYESCLYHP QLPECLSPADAPCAASTWTSRLAVRSYAGC SRTNPPPRCSAEAHMEPVPGLAWQAASVNL EFRDASPQHSGLYLCVVYVNDHIHAWGHIT ISTAAQYRNAVVEQPLPQRGADLAELEGDY KDDDDKGSRDDESLFFGDTGLSKNPIELVE GWFSSWKSSIASFFFIIGLIIGLFLVLRVG IHLCIKLKHTKKRQIYTDIEMNRLGK |
| Human insulin signal sequence | residues 1-24 of SEQ ID NO: 190 | MALWMRLLPLLALLALWGPDPAAA |
| Linker | residues 25-36 of SEQ ID NO: 190 | GTGSGEFDIAAA |
| TPB(gE) Domain | residues 37-415 of SEQ ID NO: 190 | GTPKTSWRRVSVGEDVSLLPAPGPTGRGPT QKLLWAVEPLDGCGPLHPSWVSLMPPKQVP ETVVDAACMRAPVPLAMAYAPPAPSATGGL RTDFVWQERAAVVNRSLVIHGVRETDSGLY TLSVGDIKDPARQVASVVLVVQPAPVPTPP PTPADYDEDDNDEGEDESLAGTPASGTPRL PPPPAPPRSWPSAPEVSHVRGVTVRMETPE AILFSPGETFSTNVSIHAIAHDDQTYSMDV VWLRFDVPTSCAEMRIYESCLYHPQLPECL SPADAPCAASTWTSRLAVRSYAGCSRTNPP PRCSAEAHMEPVPGLAWQAASVNLEFRDAS PQHSGLYLCVVYVNDHIHAWGHITISTAAQ YRNAVVEQPLPQRGADLAE |
| Linker | residues 416-418 of SEQ ID NO: 190 | LEG |
| Flag epitope domain | residues 419-426 of SEQ ID NO: 190 | DYKDDDDK |
| Linker | residues 427-429 of SEQ ID NO: 190 | GSR |
| TMR Domain (VSVG) | residues 430-506 of SEQ ID NO: 190 | DDESLFFGDTGLSKNPIELVEGWFSSWKSS IASFFFIIGLIIGLFLVLRVGIHLCIKLKH TKKRQIYTDIEMNRLGK |

The amino acid sequence for a Flag-tagged TPB(Prot A)-TMR(VSVG) fusion is shown in Table 11 below.

TABLE 11

Amino Acid Sequence of a Flag-Tagged TPB(Prot A)-TMR(VSVG) Fusion Protein.

| Encoded Protein or Region (N- to C-terminal) | Sequence Identifier | Amino Acid Sequence 12345678901234567890123456789 0 |
|---|---|---|
| Flag-tagged TPB(Prot A)-TMR(VSVG) fusion protein | SEQ ID NO: 195 | MALWMRLLPLLALLALWGPDPAAAGTGSGE FDIAAAADNKFNKEQQNAFYEILNMPNLNE EQRNGFIQSLKDDPSQSANVLGEAKKLNDS QAPKLEGDYKDDDDKGSRDDESLFFGDTGL SKNPIELVEGWFSSWKSSIASFFFIIGLII GLFLVLRVGIHLCIKLKHTKKRQIYTDIEM NRLGK |
| Human insulin signal sequence | residues 1-24 of SEQ ID NO: 195 | MALWMRLLPLLALLALWGPDPAAA |
| Linker | residues 25-36 of SEQ ID NO: 195 | GTGSGEFDIAAA |
| TPB(Prot A) Domain (from Protein A) | residues 37-94 of SEQ ID NO: 195 | ADNKFNKEQQNAFYEILNMPNLNEEQRNGF IQSLKDDPSQSANVLGEAKKLNDSQAPK |
| Linker | residues 95-97 of SEQ ID NO: 195 | LEG |
| Flag epitope domain | residues 98-105 of SEQ ID NO: 195 | DYKDDDDK |
| Linker | residues 106-108 of SEQ ID NO: 195 | GSR |
| TMR(VSVG)Domain | residues 109-185 of SEQ ID NO: 195 | DDESLFFGDTGLSKNPIELVEGWFSSWKSS IASFFFIIGLIIGLFLVLRVGIHLCIKLKH TKKRQIYTDIEMNRLGK |

The amino acid sequence for a Flag-tagged TPB(Prot G)-TMR(VSVG) fusion is shown in Table 12 below.

TABLE 12

Amino Acid Sequence of a Flag-Tagged TPB(Prot G)-TMR(VSVG) Fusion Protein.

| Encoded Protein or Region (N- to C-terminal) | Sequence Identifier | Amino Acid Sequence 12345678901234567890123456789 0 |
|---|---|---|
| Flag-tagged TPB(Prot G)-TMR(VSVG) fusion protein | SEQ ID NO: 196 | MALWMRLLPLLALLALWGPDPAAAGTGSGE FDIAAATYKLVINGKTLKGETTTEAVDAAT AEKVFKQYANDNGVDGEWTYDDATKTFTVT EKPEVIDASELTPAVTLEGDYKDDDDKGSR DDESLFFGDTGLSKNPIELVEGWFSSWKSS IASFFFIIGLIIGLFLVLRVGIHLCIKLKH TKKRQIYTDIEMNRLGK |
| Human insulin signal sequence | residues 1-24 of SEQ ID NO: 196 | MALWMRLLPLLALLALWGPDPAAA |
| Linker | residues 25-36 of SEQ ID NO: 196 | GTGSGEFDIAAA |

TABLE 12-continued

Amino Acid Sequence of a Flag-Tagged TPB(Prot G)-TMR(VSVG) Fusion Protein.

| Encoded Protein or Region (N- to C-terminal) | Sequence Identifier | Amino Acid Sequence 12345678901234567890123456 7890 |
|---|---|---|
| TPB(Prot G) Domain (from Protein G) | residues 37-106 of SEQ ID NO: 196 | TYKLVINGKTLKGETTTEAVDAATAEKVFK QYANDNGVDGEWTYDDATKTFTVTEKPEVI DASELTPAVT |
| Linker | residues 107-109 of SEQ ID NO: 196 | LEG |
| Flag epitope domain | residues 110-117 of SEQ ID NO: 196 | DYKDDDDK |
| Linker | residues 118-120 of SEQ ID NO: 196 | GSR |
| TMR(VSVG) Domain | residues 121-197 of SEQ ID NO: 196 | DDESLFFGDTGLSKNPIELVEGWFSSWKSS IASFFFIIGLIIGLFLVLRVGIHLCIKLKH TKKRQIYTDIEMNRLGK |

Another fusion protein comprised a TPB domain comprising an Fc-binding region of the GB919 protein. The GB919 is a histidine-substituted Fc-binding mutant Protein G that was engineered to make the dissociation from bound IgG more pH sensitive in order to reduce the harsh acidic conditions (e.g., pH 3) that are normally required to elute Fc-containing proteins bound to Protein G. The mutant GB919 exhibited an Fc-binding that was more pH sensitive than that of wildtype Protein G and also an increased affinity for IgG by a factor of 11 as compared with wildtype Protein G (Watanabe et al., *J. Biol. Chem.*, 284 (10):12373-12383 (2009)). In particular, the IgG bound to the GB919 mutant protein could be eluted at conditions more typical of using Protein A, such as pH 4.2, instead of much harsher pH, such as pH 3-3.1, required for elution from wildtype Protein G (Watanabe et al., 2009, supra).

The amino acid sequence for a Flag-tagged TPB(GB919)-TMR(VSVG) fusion is shown in Table 13 below.

TABLE 13

Amino Acid Sequence of a Flag-Tagged TPB(GB919)-TMR(VSVG) Fusion Protein.

| Encoded Protein or Region (N- to C-terminal) | Sequence Identifier | Amino Acid Sequence 12345678901234567890123456 7890 |
|---|---|---|
| Flag-tagged TPB(GB919)-TMR(VSVG) fusion protein | SEQ ID NO: 197 | MALWMRLLPLLALLALWGPDPAAAGTSGE FDIAAADTYKLILNGKTLKGETTTEAVDAA TELEGDYKDDDDKGSRDDESLFFGDTGLSK TAEKVFKHYANEHGVHGHWTYDPETKTFTV NPIELVEGWFSSWKSSIASFFFIIGLIIGL FLVLRVGIHLCIKLKHTKKRQIYTDIEMNR LGK |
| Human insulin signal sequence | residues 1-24 of SEQ ID NO: 197 | MALWMRLLPLLALLALWGPDPAAA |
| Linker | residues 25-36 of SEQ ID NO: 197 | GTSGEFDIAAA |
| TPB(GB919) Domain | residues 37-92 of SEQ ID NO: 197 | DTYKLILNGKTLKGETTTEAVDAATAEKVF KHYANEHGVHGHWTYDPETKTFTVTE |
| Linker | residues 93-95 of SEQ ID NO: 197 | LEG |
| Flag epitope domain | residues 96-103 of SEQ ID NO: 197 | DYKDDDDK |

TABLE 13-continued

Amino Acid Sequence of a Flag-Tagged TPB(GB919)-TMR(VSVG) Fusion Protein.

| Encoded Protein or Region (N- to C-terminal) | Sequence Identifier | Amino Acid Sequence 12345678901234567890123456789 0 |
|---|---|---|
| Linker | residues 104-106 of SEQ ID NO: 197 | GSR |
| TMR(VSVG)Domain | residues 107-183 of SEQ ID NO: 197 | DDESLFFGDTGLSKNPIELVEGWFSSWKSS IASFFFIIGLIIGLFLVLRVGIHLCIKLKH TKKRQIYTDIEMNRLGK |

The Flag-tagged TPB(gE)-TMR(KDELR) fusion protein (SEQ ID NO:185) used in this experiment is the same as that described in Table 8 of Example 3 above.

The amino acid sequence of a Flag-tagged TPB(Prot A)-TMR(KDELR) fusion protein used in this experiment is shown in Table 14 below.

TABLE 14

Amino Acid Sequence of a Flag-Tagged TPB(Prot A)-TMR(I(DELR) Fusion Protein.

| Encoded Protein or Region (N- to C-terminal) | Sequence Identifier | Amino Acid Sequence 12345678901234567890123456789 0 |
|---|---|---|
| Flag-tagged TPB(Prot A)-TMR(KDELR) fusion protein | SEQ ID NO: 198 | MALWMRLLPLLALLALWGPDPAAAGTGSGE FDIAAAADNKFNKEQQNAFYEILNMPNLNE EQRNGFIQSLKDDPSQSANVLGEAKKLNDS QAPKLEGDYKDDDDKGSRNLFRFLGDLSHL LAIILLLLKIWKSRSCAGISGKSQVLFAVV FTARYLDLFTNYISLYNTCMKVVYIACSFT TVWLIYSKFKATYDGNHDTFRVEFLVVPTA ILAFLVNHDFTPLEILWTFSIYLESVAILP QLFMVSKTGEAETITSHYLFALGVYRTLYL FNWIWRYHFEGFFDLIAIVAGLVQTVLYCD FFYLYITKVLKGKKLSLPA |
| Human insulin signal sequence | residues 1-24 of SEQ ID NO: 198 | MALWMRLLPLLALLALWGPDPAAA |
| Linker | residues 25-36 of SEQ ID NO: 198 | GTGSGEFDIAAA |
| TPB(Prot A) Domain (from Protein A) | residues 37-94 of SEQ ID NO: 198 | ADNKFNKEQQNAFYEILNMPNLNEEQRNGF IQSLKDDPSQSANVLGEAKKLNDSQAPK |
| Linker | residues 95-97 of SEQ ID NO: 198 | LEG |
| Flag epitope domain | residues 98-105 of SEQ ID NO: 198 | DYKDDDDK |
| Linker | residues 106-108 of SEQ ID NO: 198 | GSR |
| TMR(KDELR) Domain | residues 109-319 of SEQ ID NO: 198 | NLFRFLGDLSHLLAIILLLLKIWKSRSCAG ISGKSQVLFAVVFTARYLDLFTNYISLYNT CMKVVYIACSFTTVWLIYSKFKATYDGNHD TFRVEFLVVPTAILAFLVNHDFTPLEILWT FSIYLESVAILPQLFMVSKTGEAETITSHY LFALGVYRTLYLFNWIWRYHFEGFFDLIAI VAGLVQTVLYCDFFYLYITKVLKGKKLSLP A |

The amino acid sequence of a Flag-tagged TPB(Prot G)-TMR(KDELR) fusion protein comprising an Fc-binding region of Protein G as a target protein binding domain and a Flag epitope tag is shown in the Table 15 below.

TABLE 15

Amino Acid Sequence of a Flag-Tagged TPB(Prot G)-TMR(KDELR) Fusion Protein.

| Encoded Protein or Region (N- to C- terminal) | Sequence Identifier | Amino Acid Sequence 12345678901234567890123456789 0 |
|---|---|---|
| Flag-tagged TPB(Prot G)-TMR(KDELR) fusion protein | SEQ ID NO: 199 | MALWMRLLPLLALLALWGPDPAAAGTGSGE FDIAAAATYKLVINGKTLKGETTTEAVDAA TAEKVFKQYANDNGVDGEWTYDDATKTFTV TEKPEVIDASELTPAVTLEGDYKDDDDKGS RNLFRFLGDLSHLLAIILLLLKIWKSRSCA GISGKSQVLFAVVFTARYLDLFTNYISLYN TCMKVVYIACSFTTVWLIYSKFKATYDGNH DTFRVEFLVVPTAILAFLVNHDFTPLEILW TFSIYLESVAILPQLFMVSKTGEAETITSH YLFALGVYRTLYLFNWIWRYHFEGFFDLIA IVAGLVQTVLYCDFFYLYITKVLKGKKLSL PA |
| Human insulin signal sequence | residues 1-24 of SEQ ID NO: 199 | MALWMRLLPLLALLALWGPDPAAA |
| Linker | residues 25-36 of SEQ ID NO: 199 | GTGSGEFDIAAA |
| TPB(Prot G) Domain (from Protein G) | residues 37-107 of SEQ ID NO: 199 | TYKLVINGKTLKGETTTEAVDAATAEKVFK QYANDNGVDGEWTYDDATKTFTVTEKPEVI DASELTPAVT |
| Linker | residues 108-110 of SEQ ID NO: 199 | LEG |
| Flag epitope domain | residues 111-118 of SEQ ID NO: 199 | DYKDDDDK |
| Linker | residues 119-121 of SEQ ID NO: 199 | GSR |
| TMR(KDELR) Domain | residues 122-332 of SEQ ID NO: 199 | NLFRFLGDLSHLLAIILLLLKIWKSRSCAG ISGKSQVLFAVVFTARYLDLFTNYISLYNT CMKVVYIACSFTTVWLIYSKFKATYDGNHD TFRVEFLVVPTAILAFLVNHDFTPLEILWT FSIYLESVAILPQLFMVSKTGEAETITSHY LFALGVYRTLYLFNWIWRYHFEGFFDLIAI VAGLVQTVLYCDFFYLYITKVLKGKKLSLP A |

The amino acid sequence for a TPB(GB919)-TMR (KDELR) fusion is shown in Table 16 below.

TABLE 16

Amino Acid Sequence of a Flag-Tagged TPB(GB919) - TMR(KDELR) Fusion Protein.

| Encoded Protein or Region (N- to C- terminal) | Sequence Identifier | Amino Acid Sequence 12345678901234567890123456789 0 |
|---|---|---|
| Flag-tagged TPB(GB919)-TMR(KDELR) fusion protein | SEQ ID NO: 200 | MALWMRLLPLLALLALWGPDPAAAGTGSGE FDIAAADTYKLILNGKTLKGETTTEAVDAA TAEKVFKHYANEHGVHGHWTYDPETKTFTV TELEGDYKDDDDKGSRNLFRFLGDLSHLLA IILLLLKIWKSRSCAGISGKSQVLFAVVFT |

TABLE 16-continued

Amino Acid Sequence of a Flag-Tagged TPB(GB919) - TMR(KDELR) Fusion Protein.

| Encoded Protein or Region (N- to C- terminal) | Sequence Identifier | Amino Acid Sequence 123456789012345678901234567890 |
|---|---|---|
| | | ARYLDLFTNYISLYNTCMKVVYIACSFTTV WLIYSKFKATYDGNHDTFRVEFLVVPTAIL AFLVNHDFTPLEILWTFSIYLESVAILPQL FMVSKTGEAETITSHYLFALGVYRTLYLFN WIWRYHFEGFFDLIAIVAGLVQTVLYCDFF YLYITKVLKGKKLSLPA |
| Human insulin signal sequence | residues 1-24 of SEQ ID NO: 200 | MALWMRLLPLLALLALWGPDPAAA |
| Linker | residues 25-36 of SEQ ID NO: 200 | GTGSGEFDIAAA |
| TPB(GB919) Domain | residues 37-92 of SEQ ID NO: 200 | DTYKLILNGKTLKGETTTEAVDAATAEKVF KHYANEHGVHGHWTYDPETKTFTVTE |
| Linker | residues 93-95 of SEQ ID NO: 200 | LEG |
| Flag epitope domain | residues 96-103 of SEQ ID NO: 200 | DYKDDDDK |
| Linker | residues 104-106 of SEQ ID NO: 200 | GSR |
| TMR(KDELR) Domain | residues 107-317 of SEQ ID NO: 200 | NLFRFLGDLSHLLAIILLLLKIWKSRSCAG ISGKSQVLFAVVFTARYLDLFTNYISLYNT CMKVVYIACSFTTVWLIYSKFKATYDGNHD TFRVEFLVVPTAILAFLVNHDFTPLEILWT FSIYLESVAILPQLFMVSKTGEAETITSHY LFALGVYRTLYLFNWIWRYHFEGFFDLIAI VAGLVQTVLYCDFFYLYITKVLKGKKLSLP A |

HEK293 cells were transfected with expression vector plasmids to compare levels of expression in culture media of cells expressing the TNFR1TF-Fc target protein alone or co-expressing the target protein and each of the fusion proteins, i.e., TPB(gE)-TMR(VSVG), TPB(Prot A)-TMR(VSVG), TPB(Prot G)-TMR(VSVG), TPB(GB919)-TMR(VSVG), TPB(gE)-TMR(KDELR), TPB(Prot A)-TMR(KDELR), TPB(Prot G)-TMR(KDELR), or TPB(GB919)-TMR(KDELR). Transfected cells were cultured for two days, and samples of the culture media were harvested and analyzed by ELISA. The ELISA used a recombinant purified Protein A immobilized in the wells of 96-well microtiter plates as a binding protein for the TNFR1TF-Fc target protein and a peroxidase-conjugated goat anti-human IgG F(ab')$_2$ antibody fragment (Jackson ImmunoResearch Laboratories, Product No. 109-036-098) as a detection reagent for TNFR1TF-Fc target protein bound to the immobilized Protein A. Wells coated with the recombinant purified Protein A were incubated with media of transfected cells that expressed the TNFR1TF-Fc target protein alone or that co-expressed the TNR1TF-Fc target protein and each of the fusion proteins.

Figure 4A:
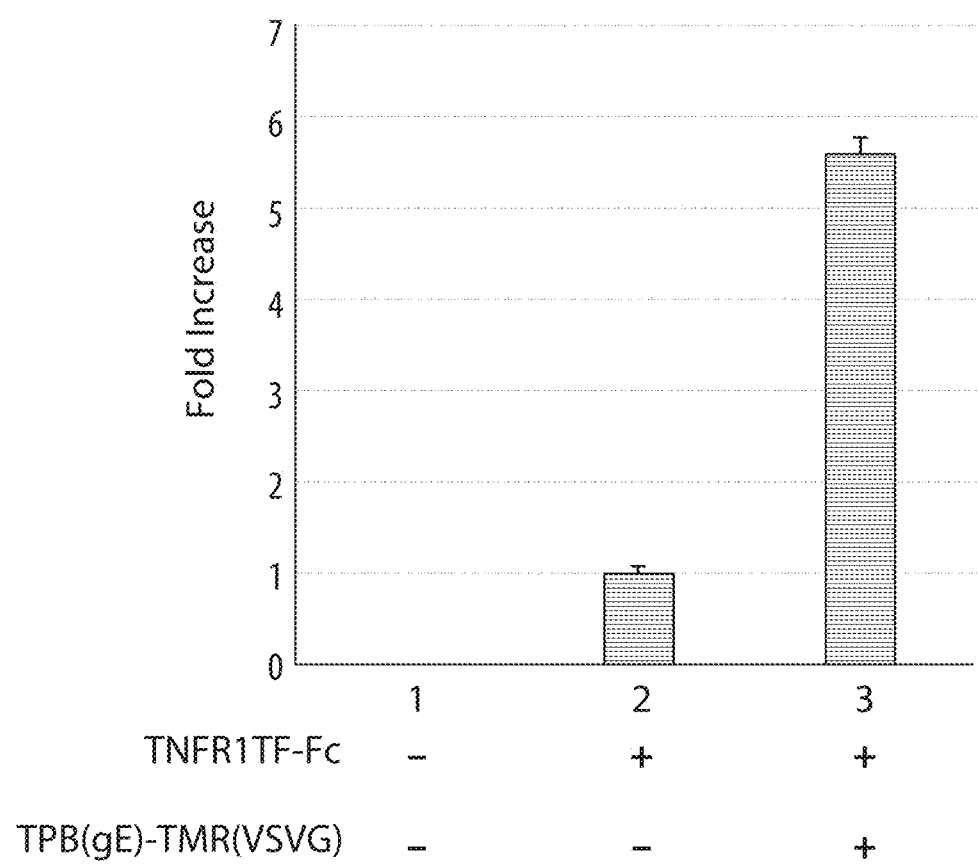
Figure 4B:
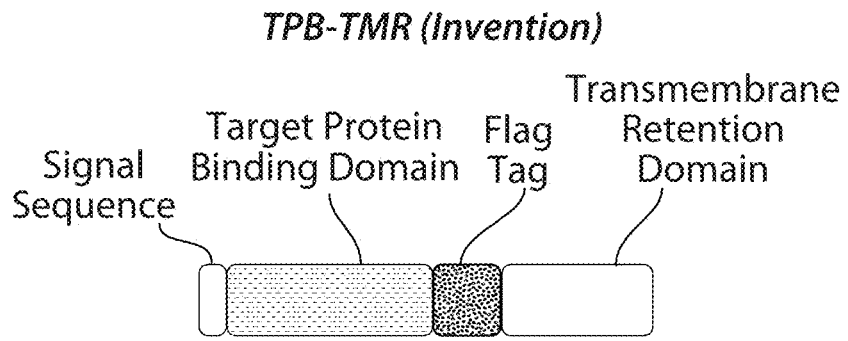
Figure 4C:
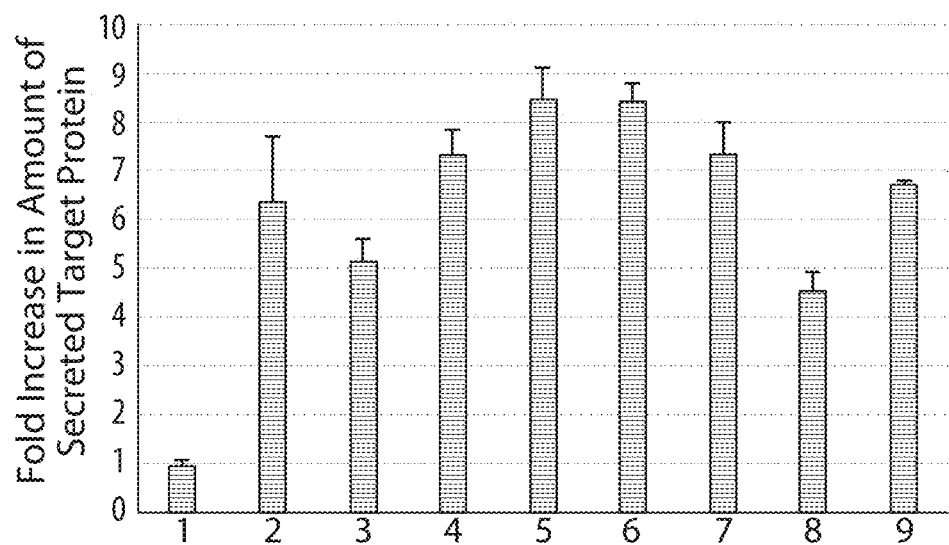

The results are shown in the bar graphs in FIG. 4C. The data in the bar graphs have been normalized by setting the amount of TNFR1TF-Fc target protein secreted into culture medium of cells that expressed the TNFR1TF-Fc target protein alone at a relative value of 1 (bar graph 1). Accordingly, bar graphs 2-9 of FIG. 4C show the relative level of secreted TNFR1TF-Fc target protein when co-expressed with each of the fusion proteins: TPB(gE)-TMR(VSVG) fusion protein (bar graph 2), TPB(Prot A)-TMR(VSVG) fusion protein (bar graph 3), TPB(Prot G)-TMR(VSVG) fusion protein (bar graph 4), TPB(GB919)-TMR(VSVG) fusion protein (bar graph 5), TPB(gE)-TMR(KDELR) fusion protein (bar graph 6), TPB(Prot A)-TMR(KDELR) fusion protein (bar graph 7), TPB(Prot G)-TMR(KDELR) fusion protein (bar graph 8), and TPB(GB919)-TMR(KDELR) fusion protein (bar graph 9). The results show that a significantly enhanced level of the TNFR1TF-Fc target protein was secreted into the culture media of cells that co-expressed the target protein with each of the fusion proteins as compared to the level of TNFR1TF-Fc target protein secreted into culture media of cells that expressed the target protein alone (bar graph 1).

Taken together, the results shown in FIG. 4C indicate that any of a variety of polypeptides that are known to bind a particular target protein of interest may be used as a TPB domain in combination with any of a variety of transmembrane regions to make a TPB-TMR fusion according to the invention that significantly enhances the level of the target protein secreted from a host cell that co-expresses the target protein and the fusion protein. Furthermore, the results also indicate that when there are multiple polypeptides known to bind a target protein of interest, it is likely that one can easily optimize the enhancement in the level of secreted target protein by adjusting the particular combination of polypeptides used as TPB and TMR domains in a fusion protein.

Example 5

Enhanced Level of Secreted Anti-TNFα Monoclonal Antibody

Adalimumab (Humira®, AbbVie Inc.) is a fully human monoclonal antibody that binds and inhibits TNFα. The antibody is useful in the treatment of inflammatory and autoimmune disorders. This experiment examined the enhancement in the level of an anti-TNFα fully human monoclonal antibody (Mab) target protein when co-expressed with the TPB(gE)-TMR(VSVG) fusion protein.

The TPB(gE)-TMR(VSVG) fusion protein used in this experiment was the same as described in Example 2 and Table 5 above.

The amino acid sequences for the light and heavy chains of the anti-TNFα Mab target protein (adalimumab) employed in this experiment are shown in Table 17, below.

HEK293 cells were transfected with expression vector plasmids for co-expression of the anti-TNFα Mab target protein and the TPB(gE)-TMR(VSVG) fusion protein. Mock cultures containing cells transfected with "empty vector", i.e., an expression vector lacking a structural gene for expressing any protein, were included as a negative control. Anti-TNFα Mab target protein in culture samples was determined by ELISA.

Figure 5:
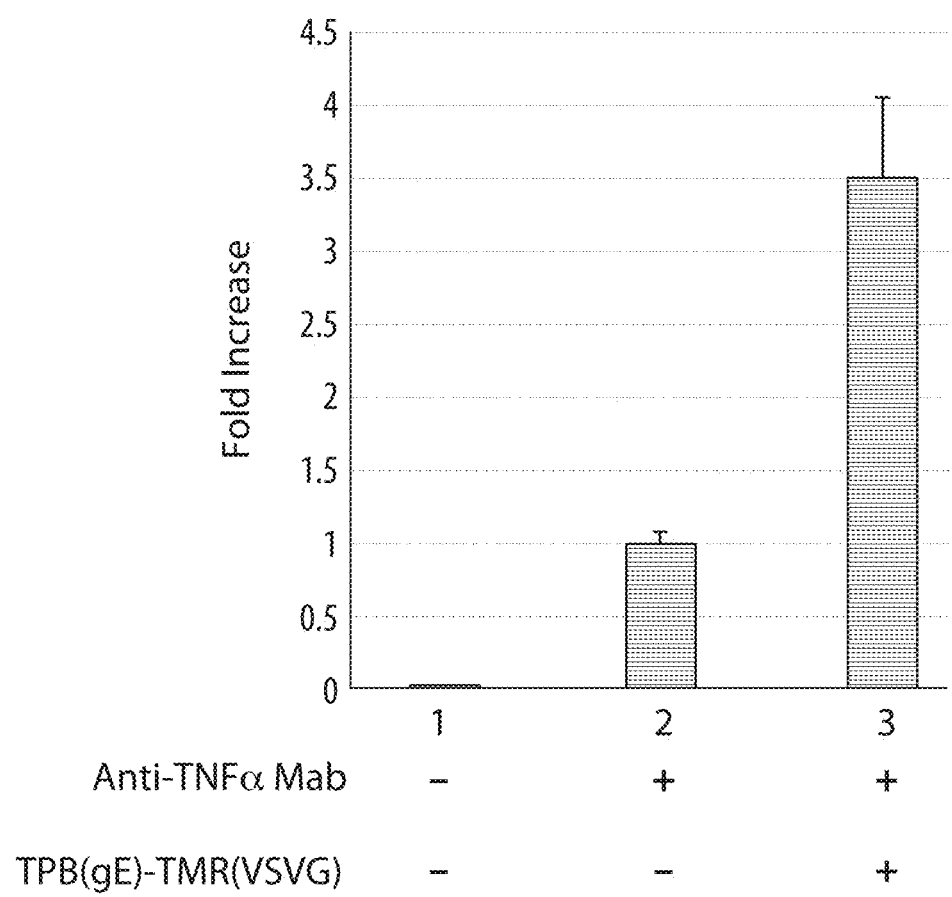
FIG. 5 shows bar graphs of the fold increase in the amount of a humanized anti-TNFα IgG1 monoclonal antibody ("Anti-TNFα Mab") target protein detected by ELISA in the media of cultures of transfected HEK293 host cells expressing the antibody target protein alone (bar graph 2) or co-expressing the antibody target protein and a cell-associated secretion-enhancing fusion protein of the invention comprising target protein binding ("TPB") domain comprising an Fc-binding region of herpes simplex virus type-1 glycoprotein E (gE) linked to a transmembrane retention (TMR) domain comprising a transmembrane region of a VSV-G protein ("TPB(gE)-TMR(VSVG)", bar graph 3) as described in Example 5. The presence ("+") or absence ("−") of expression vectors encoding target protein or cell-associated secretion-enhancing fusion protein in the transfected host cells of each culture is indicated below each bar graph. Mock cultures contained cells transfected with expression vector lacking a structural gene for expressing any protein and were used as a negative control (bar graph 1). Culture media were assayed for anti-TNFα Mab target protein by detecting binding to TNFα in an ELISA as described in Example 5. The data in the bar graphs have been normalized by subtracting non-specific background signal in media from mock cultures and setting the amount of anti-TNFα Mab target protein secreted into culture media when expressed in the absence of the cell-associated secretion-enhancing fusion protein at a relative value of 1 (bar graph 2). The results show that co-expression of the anti-TNFα Mab target protein with the cell-associated secretion-enhancing TPB (gE)-TMR(VSVG) fusion protein (bar graph 3) significantly enhanced the level of anti-TNFα Mab target protein secreted into culture media as compared to the level of anti-TNFα Mab target protein secreted into culture media when expressed in the absence of the fusion protein (bar graph 2). The results also indicate that the anti-TNFα antibody target protein that was secreted into the culture media was functional, as it retained TNFα binding activity in the ELISA. See Example 5 for additional details.

The relative levels of anti-TNFα Mab target protein secreted into culture medium are shown in FIG. 5. The level of anti-TNFα Mab target protein secreted into the medium of cells expressing the target protein alone was set at a relative value of "1" fold increase as shown in bar graph 2 of FIG. 5. The level of expression of the anti-TNFα Mab target protein secreted into the culture medium was increased by 3.5-fold in a culture of transfected cells co-expressing the anti-TNFα Mab target protein and the TPB (gE)-TMR(VSGV) fusion protein (bar graph 3) compared to the level in the medium of a culture of cells expressing the anti-TNFα Mab target protein alone (bar graph 2).

Example 6

Enhanced Level of Secreted Anti-VEGF Monoclonal Antibody

This experiment examined the enhancement in the level of an anti-VEGF-A humanized monoclonal antibody (bevacizumab) target protein when co-expressed with the TPB (gE)-TMR(VSVG) fusion protein.

The TPB(gE)-TMR(VSVG) fusion protein used in this experiment was the same as described above in Example 2 and Table 5.

The amino acid sequences for the light and heavy chains of the anti-VEGF Mab target protein (anti-VEGF Mab) employed in this experiment are shown in Table 18 below.

TABLE 17

Amino Acid Sequences of Light and Heavy Chains of Anti-TNFα Mab Target Protein

| Encoded Protein or Region (N- to C- terminal) | Sequence Identifier | Amino Acid Sequence 123456789012345678901234567890 |
|---|---|---|
| Light chain | SEQ ID NO: 144 | MGWSCIILFLVATATGVHSDIQMTQSPSSL SASVGDRVTITCRSSQGIRNYLHWYQQKPG KAPKLLIYAASTLQSGVPSRFSGSGSGTDF TLTISSLQPEDVATYYCQRYNRAPYTFGQG TKVEIKRTVAAPSVFIFPPSDEQLKSGTAS VVCLLNNFYPREAKVQWKVDNALQSGNSQE SVTEQDSKDSTYSLSSTLTLSKADYEKHKV YACEVTHQGLSSPVTKSFNRGEC |
| Heavy chain | SEQ ID NO: 145 | MGWSLIILFLVATATGVHSEVQLVESGGGL VQPGRSLRLSCAASGFTFDDYAMHWVRQAP GKGLEWVSAITWNSGHIDYADSVEGRFTIS RDNAKNSLYLQMNSLRAEDTAVYYCAKVSY LSTASSLDVWGQGTLVTVSSASTKGPSVFP LAPSSKSTSGGTAALGCLVKDYFPEPVTVS WNSGALTSGVHTFPAVLQSSGLYSLSSVVT VPSSSLGTQTYICNVNHKPSNTKVDKKVEP KSCDKTHTCPPCPAPELLGGPSVFLFPPKP KDTLMISRTPEVTCVVVDVSHEDPEVKFNW YVDGVEVHNAKTKPREEQYNSTYRVVSVLT VLHQDWLNGKEYKCKVSNKALPAPIEKTIS KAKGQPREPQVYTLPPSRDELTKNQVSLTC LVKGFYPSDIAVEWESNGQPENNYKTTPPV LDSDGSFFLYSKLTVDKSRWQQGNVFSCSV MHEALHNHYTQKSLSLSPGK |

TABLE 18

Amino Acid Sequences of Light and Heavy Chains of
Anti-VEGF Mab Target Protein.

| Encoded Protein or Region (N- to C-terminal) | Sequence Identifier | Amino Acid Sequence 12345678901234567890123456789 0 |
|---|---|---|
| Light chain | SEQ ID NO: 142 | MGWSCIILFLVATATGVHSDIQMTQSPSSL<br>SASVGDRVTITCSASQDISNYLNWYQQKPG<br>KAPKVLIYFTSSLHSGVPSRFSGSGSGTDF<br>TLTISSLQPEDFATYYCQQYSTVPWTFGQG<br>TKVEIKRTVAAPSVFIFPPSDEQLKSGTAS<br>VVCLLNNFYPREAKVQWKVDNALQSGNSQE<br>SVTEQDSKDSTYSLSSTLTLSKADYEKHKV<br>YACEVTHQGLSSPVTKSFNRGEC |
| Heavy chain | SEQ ID NO: 143 | MGWSLIILFLVATATGVHSEVQLVESGGGL<br>VQPGGSLRLSCAASGYTFTNYGMNWVRQAP<br>GKGLEWVGWINTYTGEPTYAADFKRRFTFS<br>LDTSKSTAYLQMNSLRAEDTAVYYCAKYPH<br>YYGSSHWYFDVWGQGTLVTVSSASTKGPSV<br>FPLAPSSKSTSGGTAALGCLVKDYFPEPVT<br>VSWNSGALTSGVHTFPAVLQSSGLYSLSSV<br>VTVPSSSLGTQTYICNVNHKPSNTKVDKKV<br>EPKSCDKTHTCPPCPAPELLGGPSVFLFPP<br>KPKDTLMISRTPEVTCVVVDVSHEDPEVKF<br>NWYVDGVEVHNAKTKPREEQYNSTYRVVSV<br>LTVLHQDWLNGKEYKCKVSNKALPAPIEKT<br>ISKAKGQPREPQVYTLPPSRDELTKNQVSL<br>TCLVKGFYPSDIAVEWESNGQPENNYKTTP<br>PVLDSDGSFFLYSKLTVDKSRWQQGNVFSC<br>SVMHEALHNHYTQKSLSLSPGK |

HEK293 cells were transfected with expression vector plasmids for co-expression of the anti-VEGF Mab target protein and the TPB(gE)-TMR(VSVG) fusion protein. Mock cultures containing cells transfected with "empty vector", i.e., an expression vector lacking a structural gene for expressing any protein, were included as a negative control. Anti-VEGF Mab target protein in culture samples was determined by ELISA.

The relative levels of anti-VEGF Mab target protein secreted into culture medium are shown in FIG. 6. The level of anti-TNFα Mab target protein secreted into the medium of cells expressing the target protein alone was set at a relative value of "1" fold increase as shown in bar graph 2 of FIG. 6. The level of expression of the anti-VEGF mAb target protein secreted into the culture medium was increased by more than 3-fold in a culture of transfected cells co-expressing the anti-VEGF mAb target protein and the TPB(gE)-TMR(VSGV) fusion protein (bar graph 3) compared to the level in the medium of a culture of cells expressing the anti-VEGF Mab target protein alone (bar graph 2).

Example 7

Enhanced Level of Secreted FVII-Fc Target Protein

Factor VII (FVII) is the serine esterase of the extrinsic coagulation pathway and is widely used to treat a variety of bleeding complications. See, Hedner, *Semin. Hematol.*, 43(suppl 1): S105S107 (2006). A complex of FVII and tissue factor (TF) in the presence of phospholipids and calcium activates Factor X to Factor Xa. However, the production of FVII is also inefficient owing to difficulties in expression and secretion of the protein. In this experiment, a FVII-Fc target protein was used as a representative example of an Fc drug comprising a protein of interest, i.e., FVII, fused to an immunoglobulin Fc region (hinge-CH2-CH3). The expressed FVII-Fc fusion polypeptide is expected to homodimerize via the Fc regions. This experiment examined the enhancement in the level of a FVII-Fc molecule secreted into culture medium when co-expressed with TPB(gE)-TMR(VSVG) fusion protein in transfectant host cells.

The Flag-tagged TPB(gE)-TMR(VSVG) fusion protein used in this experiment is the same as described in Example 2 and Table 5 above.

The amino acid sequence of the monomer chain of a V5-tagged FVII-Fc target protein is shown in the Table 19 below.

TABLE 19

Amino Acid Sequence of a V5-Tagged FVII-Fc Target Protein Monomer

| Encoded Protein or Region (N- to C- terminal) | Sequence Identifier | Amino Acid Sequence<br>1234567890123456789012345678 90 |
|---|---|---|
| V5-tagged FVII-Fc target protein | SEQ ID NO: 187 | MVSQALRLLCLLLGLQGCLAAGGVAKASGG<br>ETRDMPWKPGPHRVFVTQEEAHGVLHRRRR<br>ANAFLEELRPGSLERECKEEQCSFEEAREI<br>FKDAERTKLFWISYSDGDQCASSPCQNGGS<br>CKDQLQSYICFCLPAFEGRNCETHKDDQLI<br>CVNENGGCEQYCSDHTGTKRSCRCHEGYSL<br>LADGVSCTPTVEYPCGKIPILEKRNASKPQ<br>GRIVGGKVCPKGECPWQVLLLVNGAQLCGG<br>TLINTIWVVSAAHCFDKIKNWRNLIAVLGE<br>HDLSEHDGDEQSRRVAQVIIPSTYVPGTTN<br>HDIALLRLHQPVVLTDHVVPLCLPERTFSE<br>RTLAFVRFSLVSGWGQLLDRGATALELMVL<br>NVPRLMTQDCLQQSRKVGDSPNITEYMFCA<br>GYSDGSKDSCKGDSGGPHATHYRGTWYLTG<br>IVSWGQGCATVGHFGVYTRVSQYIEWLQKL<br>MRSEPRPGVLLRAPFPLEGKPIPNPLLGLD<br>STSRPKSCDKTHTCPPCPAPELLGGPSVFL<br>FPPKPKDTLMISRTPEVTCVVVDVSHEDPE<br>VKFNWYVDGVEVHNAKTKPREEQYNSTYRV<br>VSVLTVLHQDWLNGKEYKCKVSNKALPAPI<br>EKTISKAKGQPREPQVYTLPPSRDELTKNQ<br>VSLTCLVKGFYPSDIAVEWESNGQPENNYK<br>TTPPVLDSDGSFFLYSKLTVDKSRWQQGNV<br>FSCSVMHEALHNHYTQKSLSLSPGK |
| FVII | residues 1-466 of SEQ ID NO: 187 | MVSQALRLLCLLLGLQGCLAAGGVAKASGG<br>ETRDMPWKPGPHRVFVTQEEAHGVLHRRRR<br>ANAFLEELRPGSLERECKEEQCSFEEAREI<br>FKDAERTKLFWISYSDGDQCASSPCQNGGS<br>CKDQLQSYICFCLPAFEGRNCETHKDDQLI<br>CVNENGGCEQYCSDHTGTKRSCRCHEGYSL<br>LADGVSCTPTVEYPCGKIPILEKRNASKPQ<br>GRIVGGKVCPKGECPWQVLLLVNGAQLCGG<br>TLINTIWVVSAAHCFDKIKNWRNLIAVLGE<br>HDLSEHDGDEQSRRVAQVIIPSTYVPGTTN<br>HDIALLRLHQPVVLTDHVVPLCLPERTFSE<br>RTLAFVRFSLVSGWGQLLDRGATALELMVL<br>NVPRLMTQDCLQQSRKVGDSPNITEYMFCA<br>GYSDGSKDSCKGDSGGPHATHYRGTWYLTG<br>IVSWGQGCATVGHFGVYTRVSQYIEWLQKL<br>MRSEPRPGVLLRAPFP |
| Linker | residues 467-468 of SEQ ID NO: 187 | LE |
| V5 epitope domain | residues 469-482 of SEQ ID NO: 187 | GKPIPNPLLGLDST |
| Linker | residues 483-484 of SEQ ID NO: 187 | SR |
| Fc domain | residues 485-715 of SEQ ID NO: 187 | PKSCDKTHTCPPCPAPELLGGPSVFLFPPK<br>PKDTLMISRTPEVTCVVVDVSHEDPEVKFN<br>WYVDGVEVHNAKTKPREEQYNSTYRVVSVL<br>TVLHQDWLNGKEYKCKVSNKALPAPIEKTI<br>SKAKGQPREPQVYTLPPSRDELTKNQVSLT<br>CLVKGFYPSDIAVEWESNGQPENNYKTTPP<br>VLDSDGSFFLYSKLTVDKSRWQQGNVFSCS<br>VMHEALHNHYTQKSLSLSPGK |

HEK293 cells were transfected with expression vector plasmids for co-expression of the FVII-Fc target protein and the TPB(gE)-TMR(VSVG) fusion protein. Mock cultures containing cells transfected with "empty vector", i.e., an expression vector lacking a structural gene for expressing any protein, were included as a negative control. FVII-Fc target protein in culture samples was determined by ELISA.

The relative levels of FVII-Fc target protein secreted into culture medium are shown in FIG. 7. The level of FVII-Fc target protein secreted into the medium of cells expressing the target protein alone was set at a relative value of "1" fold increase as shown in bar graph 2 of FIG. 7. The level of expression of the FVII-Fc target protein secreted into the culture medium was increased by nine-fold in a culture of transfected cells co-expressing the FVII-Fc target protein and the TPB(gE)-TMR(VSGV) fusion protein (bar graph 3) compared to the level in the medium of a culture of cells expressing the FVII-Fc target protein alone (bar graph 2).

Example 8

Enhanced Level of Secreted FIX-Fc Target Protein

This experiment examined the enhancement in the level of a FIX-Fc molecule secreted into culture medium when co-expressed with TPB(gE)-TMR(VSVG) fusion protein in transfectant host cells.

The TPB(gE)-TMR(VSVG) fusion protein used in this experiment was the same as described in Example 2 and Table 5 above.

The amino acid sequence of the monomer chain of a V5-tagged FIX-Fc target protein is shown in the Table 20 below.

TABLE 20

Amino Acid Sequence of a V5-Tagged FIX-Fc Target Protein Monomer

| Encoded Protein or Region (N- to C-terminal) | Sequence Identifier | Amino Acid Sequence 12345678901234567890123456789 0 |
|---|---|---|
| V5-tagged FIX-Fc target protein | SEQ ID NO: 188 | MQRVNMIMAESPGLITICLLGYLLSAECTV FLDHENANKILNRPKRYNSGKLEEFVQGNL ERECMEEKCSFEEAREVFENTERTTEFWKQ YVDGDQCESNPCLNGGSCKDDINSYECWCP FGFEGKNCELDVTCNIKNGRCEQFCKNSAD NKVVCSCTEGYRLAENQKSCEPAVPFPCGR VSVSQTSKLTRAETVFPDVDYVNSTEAETI LDNITQSTQSFNDFTRVVGGEDAKPGQFPW QVVLNGKVDAFCGGSIVNEKWIVTAAHCVE TGVKITVVAGEHNIEETEHTEQKRNVIRII PHHNYNAAINKYNHDIALLELDEPLVLNSY VTPICIADKEYTNIFLKFGSGYVSGWGRVF HKGRSALVLQYLRVPLVDRATCLRSTKFTI YNNMFCAGFHEGGRDSCQGDSGGPHVTEVE GTSFLTGIISWGEECAMKGKYGIYTKVSRY VNWIKEKTKLTLEGKPIPNPLLGLDSTSRP KSCDKTHTCPPCPAPELLGGPSVFLFPPKP KDTLMISRTPEVTCVVVDVSHEDPEVKFNW YVDGVEVHNAKTKPREEQYNSTYRVVSVLT VLHQDWLNGKEYKCKVSNKALPAPIEKTIS KAKGQPREPQVYTLPPSRDELTKNQVSLTC LVKGFYPSDIAVEWESNGQPENNYKTTPPV LDSDGSFFLYSKLTVDKSRWQQGNVFSCSV MHEALHNHYTQKSLSLSPGK |
| FIX | residues 1-461 of SEQ ID NO: 188 | MQRVNMIMAESPGLITICLLGYLLSAECTV FLDHENANKILNRPKRYNSGKLEEFVQGNL ERECMEEKCSFEEAREVFENTERTTEFWKQ YVDGDQCESNPCLNGGSCKDDINSYECWCP FGFEGKNCELDVTCNIKNGRCEQFCKNSAD NKVVCSCTEGYRLAENQKSCEPAVPFPCGR VSVSQTSKLTRAETVFPDVDYVNSTEAETI LDNITQSTQSFNDFTRVVGGEDAKPGQFPW QVVLNGKVDAFCGGSIVNEKWIVTAAHCVE TGVKITVVAGEHNIEETEHTEQKRNVIRII PHHNYNAAINKYNHDIALLELDEPLVLNSY VTPICIADKEYTNIFLKFGSGYVSGWGRVF HKGRSALVLQYLRVPLVDRATCLRSTKFTI YNNMFCAGFHEGGRDSCQGDSGGPHVTEVE GTSFLTGIISWGEECAMKGKYGIYTKVSRY VNWIKEKTKLT |
| Linker | residues 462-463 of SEQ ID NO: 188 | LE |
| V5 epitope domain | residues 464-477 of SEQ ID NO: 188 | GKPIPNPLLGLDST |
| Linker | residues 478-479 of SEQ ID NO: 188 | SR |

TABLE 20-continued

Amino Acid Sequence of a V5-Tagged FIX-Fc Target Protein Monomer

| Encoded Protein or Region (N- to C-terminal) | Sequence Identifier | Amino Acid Sequence 12345678901234567890123456789 0 |
|---|---|---|
| Fc domain | residues 480-710 of SEQ ID NO: 188 | PKSCDKTHTCPPCPAPELLGGPSVFLFPPK PKDTLMISRTPEVTCVVVDVSHEDPEVKFN WYVDGVEVHNAKTKPREEQYNSTYRVVSVL TVLHQDWLNGKEYKCKVSNKALPAPIEKTI SKAKGQPREPQVYTLPPSRDELTKNQVSLT CLVKGFYPSDIAVEWESNGQPENNYKTTPP VLDSDGSFFLYSKLTVDKSRWQQGNVFSCS VMHEALHNHYTQKSLSLSPGK |

HEK293 cells were transfected with expression vector plasmids for co-expression of the FIX-Fc target protein and the TPB(gE)-TMR(VSVG) fusion protein. Mock cultures containing cells transfected with "empty vector", i.e., an expression vector lacking a structural gene for expressing any protein, were included as a negative control. FIX-Fc target protein in culture samples was determined by ELISA.

The relative levels of FIX-Fc target protein secreted into culture medium are shown in FIG. 8. The level of FIX-Fc target protein secreted into the medium of cells expressing the target protein alone was set at a relative value of "1" fold increase as shown in bar graph 2 of FIG. 8. The level of expression of the FIX-Fc target protein secreted into the culture medium was increased by three-fold in a culture of transfected cells co-expressing the FVII-Fc target protein and the TPV(gE)-TMR(VSGV) fusion protein (bar graph 3) compared to the level in the medium of a culture of cells expressing the FVII-Fc target protein alone (bar graph 2).

Example 9

Enhanced Level of Secreted FVIII-Fc Target Protein

The biological importance of Factor VIII (FVIII) is demonstrated in hemophilia A, a congenital bleeding disorder occurring primarily in males that results from an X-chromosome-linked deficiency of FVIII. Standard treatment is replacement therapy that involves supply of functional exogenous FVIII to the patient, which enables natural clotting to stop the bleeding. A FVIII-Fc protein (providing a Factor VIII dimer) was developed to provide a prolonged half-life of FVIII activity in hemophilia A patients (Powell et al., *Blood,* 119(13): 3031-3037 (2012)). A B-domain deleted FVIII-Fc protein was approved by the United States Food and Drug Administration in 2013 (ELOCTATE®; Biogen Idec). This experiment examined the enhancement in the level of a FVIII-Fc molecule secreted into culture medium when co-expressed with a TPB(gE)-TMR(KDELR) fusion protein in transfectant host cells.

The amino acid sequence for a Flag-tagged TPB(gE)-TMR(KDELR) fusion protein used in this experiment is the same as that shown in Table 8 of Example 3 above.

The amino acid sequence of a V5-tagged FVIII-Fc target protein monomer used in this experiment is shown in Table 21, below.

TABLE 21

Amino Acid Sequence of a V5-Tagged FVIII-Fc Target Protein Monomer

| Encoded Protein or Region (N- to C-terminal) | Sequence Identifier | Amino Acid Sequence 12345678901234567890123456789 0 |
|---|---|---|
| V5-tagged FVIII-Fc target protein | SEQ ID NO: 189 | MQIELSTCFFLCLLRFCFSATRRYYLGAVE LSWDYMQSDLGELPVDARFPPRVPKSFPFN TSVVYKKTLFVEFTDHLFNIAKPRPPWMGL LGPTIQAEVYDTVVITLKNMASHPVSLHAV GVSYWKASEGAEYDDQTSQREKEDDKVFPG GSHTYVWQVLKENGPMASDPLCLTYSYLSH VDLVKDLNSGLIGALLVCREGSLAKEKTQT LHKFILLFAVFDEGKSWHSETKNSLMQDRD AASARAWPKMHTVNGYVNRSLPGLIGCHRK SVYWHVIGMGTTPEVHSIFLEGHTFLVRNH RQASLEISPITFLTAQTLLMDLGQFLLFCH ISSHQHDGMEAYVKVDSCPEEPQLRMKNNE EAEDYDDDLTDSEMDVVRFDDDNSPSFIQI RSVAKKHPKTWVHYIAAEEEDWDYAPLVLA PDDRSYKSQYLNNGPQRIGRKYKKVRFMAY TDETFKTREAIQHESGILGPLLYGEVGDTL LIIFKNQASRPYNIYPHGITDVRPLYSRRL |

TABLE 21-continued

Amino Acid Sequence of a V5-Tagged FVIII-Fc
Target Protein Monomer

| Encoded Protein or Region (N- to C-terminal) | Sequence Identifier | Amino Acid Sequence 12345678901234567890123456 7890 |
|---|---|---|
| | | PKGVKHLKDFPILPGEIFKYKWTVTVEDGP
TKSDPRCLTRYYSSFVNMERDLASGLIGPL
LICYKESVDQRGNQIMSDKRNVILFSVFDE
NRSWYLTENIQRFLPNPAGVQLEDPEFQAS
NIMHSINGYVFDSLQLSVCLHEVAYWYILS
IGAQTDFLSVFFSGYTFKHKMVYEDTLTLF
PFSGETVFMSMENPGLWILGCHNSDFRNRG
MTALLKVSSCDKNTGDYYEDSYEDISAYLL
SKNNAIEPRSFSQNSRHPSTRQKQFNATTI
PENDIEKTDPWFAHRTPMPKIQNVSSSDLL
MLLRQSPTPHGLSLSDLQEAKYETFSDDPS
PGAIDSNNSLSEMTHFRPQLHHSGDMVFTP
ESGLQLRLNEKLGTTAATELKKLDFKVSST
SNNLISTIPSDNLAAGTDNTSSLGPPSMPV
HYDSQLDTTLFGKKSSPLTESGGPLSLSEE
NNDSKLLESGLMNSQESSWGKNVSSTESGR
LFKGKRAHGPALLTKDNALFKVSISLLKTN
KTSNNSATNRKTHIDGPSLLIENSPSVWQN
ILESDTEFKKVTPLIHDRMLMDKNATALRL
NHMSNKTTSSKNMEMVQQKKEGPIPPDAQN
PDMSFFKMLFLPESARWIQRTHGKNSLNSG
QGPSPKQLVSLGPEKSVEGQNFLSEKNKVV
VGKGEFTKDVGLKEMVFPSSRNLFLTNLDN
LHENNTHNQEKKIQEEIEKKETLIQENVVL
PQIHTVTGTKNFMKNLFLLSTRQNVEGSYD
GAYAPVLQDFRSLNDSTNRTKKHTAHFSKK
GEEENLEGLGNQTKQIVEKYACTTRISPNT
SQQNFVTQRSKRALKQFRLPLEETELEKRI
IVDDTSTQWSKNMKHLTPSTLTQIDYNEKE
KGAITQSPLSDCLTRSHSIPQANRSPLPIA
KVSSFPSIRPIYLTRVLFQDNSSHLPAASY
RKKDSGVQESSHFLQGAKKNNLSLAILTLE
MTGDQREVGSLGTSATNSVTYKKVENTVLP
KPDLPKTSGKVELLPKVHIYQKDLFPTETS
NGSPGHLDLVEGSLLQGTEGAIKWNEANRP
GKVPFLRVATESSAKTPSKLLDPLAWDNHY
GTQIPKEEWKSQEKSPEKTAFKKKDTILSL
NACESNHAIAAINEGQNKPEIEVTWAKQGR
TERLCSQNPPVLKRHQREITRTTLQSDQEE
IDYDDTISVEMKKEDFDIYDEDENQSPRSF
QKKTRHYFIAAVERLWDYGMSSSPHVLRNR
AQSGSVPQFKKVVFQEFTDGSFTQPLYRGE
LNEHLGLLGPYIRAEVEDNIMVTFRNQASR
PYSFYSSLISYEEDQRQGAEPRKNFVKPNE
TKTYFWKVQHHMAPTKDEFDCKAWAYFSDV
DLEKDVHSGLIGPLLVCHTNTLNPAHGRQV
TVQEFALFFTIFDETKSWYFTENMERNCRA
PCNIQMEDPTFKENYRFHAINGYIMDTLPG
LVMAQDQRIRWYLLSMGSNENIHSIHFSGH
VFTVRKKEEYKMALYNLYPGVFETVEMLPS
KAGIWRVECLIGEHLHAGMSTLFLVYSNKC
QTPLGMASGHIRDFQITASGQYGQWAPKLA
RLHYSGSINAWSTKEPFSWIKVDLLAPMII
HGIKTQGARQKFSSLYISQFIIMYSLDGKK
WQTYRGNSTGTLMVFFGNVDSSGIKHNIFN
PPIIARYIRLHPTHYSIRSTLRMELMGCDL
NSCSMPLGMESKAISDAQITASSYFTNMFA
TWSPSKARLHLQGRSNAWRPQVNNPKEWLQ
VDFQKTMKVTGVTTQGVKSLLTSMYVKEFL
ISSSQDGHQWTLFFQNGKVKVFQGNQDSFT
PVVNSLDPPLLTRYLRIHPQSWVHQIALRM
EVLGCEAQDLYLEGKPIPNPLLGLDSTSRP
KSCDKTHTCPPCPAPELLGGPSVFLFPPKP
KDTLMISRTPEVTCVVVDVSHEDPEVKFNW
YVDGVEVHNAKTKPREEQYNSTYRVVSVLT
VLHQDWLNGKEYKCKVSNKALPAPIEKTIS
KAKGQPREPQVYTLPPSRDELTKNQVSLTC
LVKGFYPSDIAVEWESNGQPENNYKTTPPV
LDSDGSFFLYSKLTVDKSRWQQGNVFSCSV
MHEALHNHYTQKSLSLSPGK |

TABLE 21-continued

Amino Acid Sequence of a V5-Tagged FVIII-Fc
Target Protein Monomer

| Encoded Protein or Region (N- to C-terminal) | Sequence Identifier | Amino Acid Sequence 1234567890123456789012345 67890 |
|---|---|---|
| FVIII signal sequence | Residues 1-19 of SEQ ID NO: 189 | MQIELSTCFFLCLLRFCFS |
| FVIII | residues 20-2351 of SEQ ID NO: 189 | ATRRYYLGAVELSWDYMQSDLGELPVDARF PPRVPKSFPFNTSVVYKKTLFVEFTDHLFN IAKPRPPWMGLLGPTIQAEVYDTVVITLKN MASHPVSLHAVGVSYWKASEGAEYDDQTSQ REKEDDKVFPGGSHTYVWQVLKENGPMASD PLCLTYSYLSHVDLVKDLNSGLIGALLVCR EGSLAKEKTQTLHKFILLFAVFDEGKSWHS ETKNSLMQDRDAASARAWPKMHTVNGYVNR SLPGLIGCHRKSVYWHVIGMGTTPEVHSIF LEGHTFLVRNHRQASLEISPITFLTAQTLL MDLGQFLLFCHISSHQHDGMEAYVKVDSCP EEPQLRMKNNEEAEDYDDDLTDSEMDVVRF DDDNSPSFIQIRSVAKKHPKTWVHYIAAEE EDWDYAPLVLAPDDRSYKSQYLNNGPQRIG RKYKKVRFMAYTDETFKTREAIQHESGILG PLLYGEVGDTLLIIFKNQASRPYNIYPHGI TDVRPLYSRRLPKGVKHLKDFPILPGEIFK YKWTVTVEDGPTKSDPRCLTRYYSSFVNME RDLASGLIGPLLICYKESVDQRGNQIMSDK RNVILFSVFDENRSWYLTENIQRFLPNPAG VQLEDPEFQASNIMHSINGYVFDSLQLSVC LHEVAYWYILSIGAQTDFLSVFFSGYTFKH KMVYEDTLTLFPFSGETVFMSMENPGLWIL GCHNSDFRNRGMTALLKVSSCDKNTGDYYE DSYEDISAYLLSKNNAIEPRSFSQNSRHPS TRQKQFNATTIPENDIEKTDPWFAHRTPMP KIQNVSSSDLLMLLRQSPTPHGLSLSDLQE AKYETFSDDPSPGAIDSNNSLSEMTHFRPQ LHHSGDMVFTPESGLQLRLNEKLGTTAATE LKKLDFKVSSTSNNLISTIPSDNLAAGTDN TSSLGPPSMPVHYDSQLDTTLFGKKSSPLT ESGGPLSLSEENNDSKLLESGLMNSQESSW GKNVSSTESGRLFKGKRAHGPALLTKDNAL FKVSISLLKTNKTSNNSATNRKTHIDGPSL LIENSPSVWQNILESDTEFKKVTPLIHDRM LMDKNATALRLNHMSNKTTSSKNMEMVQQK KEGPIPPDAQNPDMSFFKMLFLPESARWIQ RTHGKNSLNSGQGPSPKQLVSLGPEKSVEG QNFLSEKNKVVVGKGEFTKDVGLKEMVFPS SRNLFLTNLDNLHENNTHNQEKKIQEEIEK KETLIQENVVLPQIHTVTGTKNFMKNLFLL STRQNVEGSYDGAYAPVLQDFRSLNDSTNR TKKHTAHFSKKGEEENLEGLGNQTKQIVEK YACTTRISPNTSQQNFVTQRSKRALKQFRL PLEETELEKRIIVDDTSTQWSKNMKHLTPS TLTQIDYNEKEKGAITQSPLSDCLTRSHSI PQANRSPLPIAKVSSFPSIRPIYLTRVLFQ DNSSHLPAASYRKKDSGVQESSHFLQGAKK NNLSLAILTLEMTGDQREVGSLGTSATNSV TYKKVENTVLPKPDLPKTSGKVELLPKVHI YQKDLFPTETSNGSPGHLDLVEGSLLQGTE GAIKWNEANRPGKVPFLRVATESSAKTPSK LLDPLAWDNHYGTQIPKEEWKSQEKSPEKT AFKKKDTILSLNACESNHAIAAINEGQNKP EIEVTWAKQGRTERLCSQNPPVLKRHQREI TRTTLQSDQEEIDYDDTISVEMKKEDFDIY DEDENQSPRSFQKKTRHYFIAAVERLWDYG MSSSPHVLRNRAQSGSVPQFKKVVFQEFTD GSFTQPLYRGELNEHLGLLGPYIRAEVEDN IMVTFRNQASRPYSFYSSLISYEEDQRQGA EPRKNFVKPNETKTYFWKVQHHMAPTKDEF DCKAWAYFSDVDLEKDVHSGLIGPLLVCHT NTLNPAHGRQVTVQEFALFFTIFDETKSWY FTENMERNCRAPCNIQMEDPTFKENYRFHA INGYIMDTLPGLVMAQDQRIRWYLLSMGSN ENIHSIHFSGHVFTVRKKEEYKMALYNLYP GVFETVEMLPSKAGIWRVECLIGEHLHAGM |

TABLE 21-continued

Amino Acid Sequence of a V5-Tagged FVIII-Fc
Target Protein Monomer

| Encoded Protein or Region (N- to C-terminal) | Sequence Identifier | Amino Acid Sequence<br>12345678901234567890123 4567890 |
|---|---|---|
| | | STLFLVYSNKCQTPLGMASGHIRDFQITAS<br>GQYGQWAPKLARLHYSGSINAWSTKEPFSW<br>IKVDLLAPMIIHGIKTQGARQKFSSLYISQ<br>FIIMYSLDGKKWQTYRGNSTGTLMVFFGNV<br>DSSGIKHNIFNPPIIARYIRLHPTHYSIRS<br>TLRMELMGCDLNSCSMPLGMESKAISDAQI<br>TASSYFTNMFATWSPSKARLHLQGRSNAWR<br>PQVNNPKEWLQVDFQKTMKVTGVTTQGVKS<br>LLTSMYVKEFLISSSQDGHQWTLFFQNGKV<br>KVFQGNQDSFTPVVNSLDPPLLTRYLRIHP<br>QSWVHQIALRMEVLGCEAQDLY |
| Linker | residues 2352-2353 of SEQ ID NO: 189 | LE |
| V5 epitope domain | residues 2354-2367 of SEQ ID NO: 189 | GKPIPNPLLGLDST |
| Linker | residues 2368-2369 of SEQ ID NO: 189 | SR |
| Fc domain | residues 2370-2600 of SEQ ID NO: 189 | PKSCDKTHTCPPCPAPELLGGPSVFLFPPK<br>PKDTLMISRTPEVTCVVVDVSHEDPEVKFN<br>WYVDGVEVHNAKTKPREEQYNSTYRVVSVL<br>TVLHQDWLNGKEYKCKVSNKALPAPIEKTI<br>SKAKGQPREPQVYTLPPSRDELTKNQVSLT<br>CLVKGFYPSDIAVEWESNGQPENNYKTTPP<br>VLDSDGSFFLYSKLTVDKSRWQQGNVFSCS<br>VMHEALHNHYTQKSLSLSPGK |

HEK293 cells were transfected with expression vector plasmids for co-expression of the FVIII-Fc target protein and the TPV(gE)-TMR(KDELR) fusion protein. Mock cultures containing cells transfected with "empty vector", i.e., an expression vector lacking a structural gene for expressing any protein, were included as a negative control. FVIII-Fc target protein in culture samples was determined by ELISA.

Figure 9:
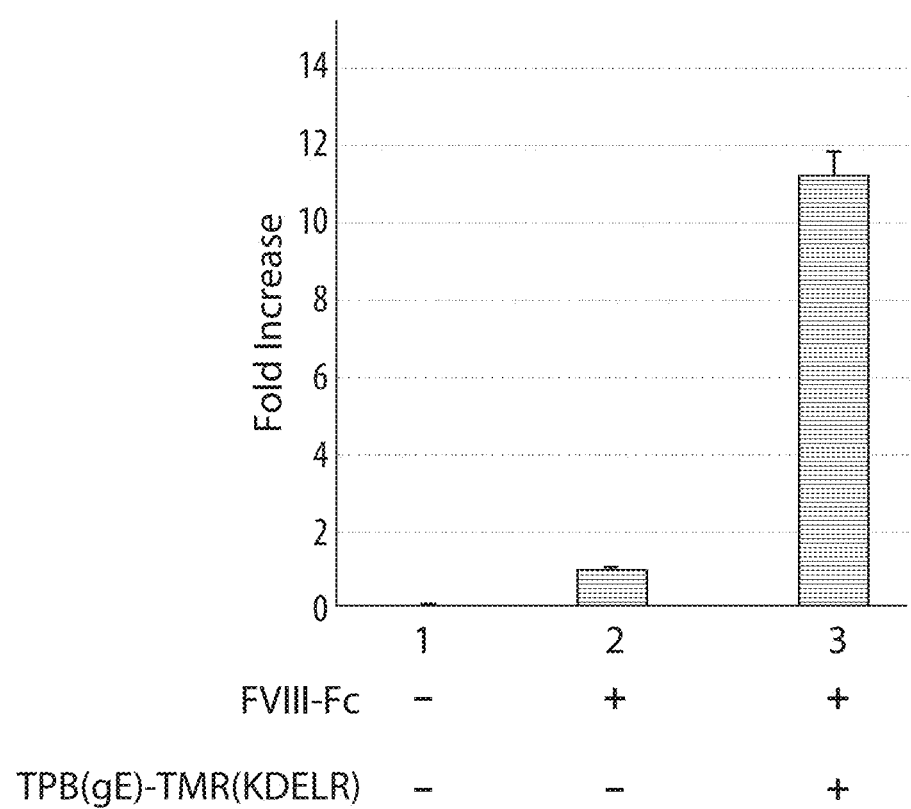
FIG. 9 shows bar graphs of the fold increase in the amount of a Factor VIII-Fc target protein detected by ELISA in the media of cultures of transfected HEK293 host cells expressing the target protein alone (bar graph 2) or co-expressing the FVIII-Fc target protein and a cell-associated secretion-enhancing fusion protein comprising an Fc-binding region of gE linked to a transmembrane retention (TMR) domain comprising a transmembrane region of a KDELR protein ("TPB(gE)-TMR(KDELR)", bar graph 3) as described in Example 9. The presence ("+") or absence ("−") of expression vectors encoding target protein or cell-associated secretion-enhancing fusion protein in the transfected host cells of each culture is indicated below each bar graph. Mock cultures contained cells transfected with expression vector lacking a structural gene for expressing any protein and were used as a negative control (bar graph 1). The data in the bar graphs have been normalized by subtracting non-specific background signal in media from mock cultures and setting the amount of target protein secreted into culture media when expressed in the absence of either fusion protein at a relative value of 1 (bar graph 2). The results show that co-expression of the FVIII-Fc target protein with the cell-associated secretion-enhancing TPB(gE)-TMR(KDELR) fusion protein (bar graph 3) significantly enhanced the level of target protein secreted into the culture media as compared to the level of target protein secreted into the culture media when the target protein was expressed in the absence of the cell-associated secretion-enhancing fusion protein (bar graph 2). See Example 9 for additional details.

The relative levels of FVIII-Fc target protein secreted into culture medium are shown in FIG. 9. The level of FVIII-Fc target protein secreted into the medium of cells expressing the target protein alone was set at a relative value of "1" fold increase as shown in bar graph 2 of FIG. 9. The level of expression of the FVIII-Fc target protein secreted into the culture medium was increased by eleven-fold in a culture of transfected cells co-expressing the FVIII-Fc target protein and the TPV(gE)-TMR(KDELR) fusion protein (bar graph 3) compared to the level in the medium of a culture of cells expressing the FVII-Fc target protein alone (bar graph 2).

Example 10

Effect of Retaining Fusion Protein in Endoplasmic Reticulum on Secretion of Target Protein This experiment compared the level of secretion of a target protein when co-expressed with a TPB(gE)-TMR (VSVG) fusion protein, comprising the Fc binding region of gE and the transmembrane region of the VSV-G protein, and when co-expressed with essentially the same fusion protein but wherein TMR domain was engineered to include a known endoplasmic reticulum (ER) retention sequence (dilysine motif) at its C-terminus.

The target protein was the V5-tagged IL13Rα2TF-Fc target protein described above in Example 2 and Table 4.

FIG. 10A shows a diagram of a nucleic acid construct encoding a TPB-TMR(VSVG) fusion protein that was augmented with a segment encoding a Flag epitope tag between a 5' segment encoding the Fc-binding region of the gE protein (TPB domain) and a 3' segment encoding a TMR domain encoding an amino acid sequence (SEQ ID NO:193) of a wildtype transmembrane region of the VSVG protein. The entire amino acid sequence of the Flag-tagged TPB (gE)-TMR(VSVG) fusion protein (SEQ ID NO:190) used in this experiment is shown in Table 10 (see Example 4, above).

FIG. 10B shows a diagram of a nucleic acid construct encoding the other TPB-TMR (VSVG) fusion protein used in this experiment designated "TPB(gE)-TMR(VSVG) with KK motif" that was augmented with a segment encoding a Flag epitope tag between a 5' segment encoding the Fc-binding region of the gE protein (TPB domain) and a 3' segment encoding a mutated transmembrane region of the VSVG protein that was engineered to contain an amino acid sequence (SEQ ID NO:194) with tandem lysine residues (dilysine motif) inserted at positions −3 and −4 of the C-terminal cytoplasmic region of the fusion protein. The entire amino acid sequence of this "Flag-tagged TPB(gE)-TMR(VSVG) with KK" fusion protein is shown in Table 22 below.

TABLE 22

Amino Acid Sequence for a Flag-Tagged TPB(gE)-TMR(VSVG) with KK Motif Fusion Protein

| Encoded Protein or Region (N- to C- terminal) | Sequence Identifier | Amino Acid Sequence 12345678901234567890123456 7890 |
|---|---|---|
| Flag-tagged TPB(gE)-TMR(VSVG) with KK motif fusion protein | SEQ ID NO: 191 | MALWMRLLPLLALLALWGPDPAAAGTGSGE FDIAAAGTPKTSWRRVSVGEDVSLLPAPGP TGRGPTQKLLWAVEPLDGCGPLHPSWVSLM PPKQVPETVVDAACMRAPVPLAMAYAPPAP SATGGLRTDFVWQERAAVVNRSLVIHGVRE TDSGLYTLSVGDIKDPARQVASVVLVVQPA PVPTPPPTPADYDEDDNDEGEDESLAGTPA SGTPRLPPPPAPPRSWPSAPEVSHVRGVTV RMETPEAILFSPGETFSTNVSIHAIAHDDQ TYSMDVVWLRFDVPTSCAEMRIYESCLYHP QLPECLSPADAPCAASTWTSRLAVRSYAGC SRTNPPPRCSAEAHMEPVPGLAWQAASVNL EFRDASPQHSGLYLCVVYVNDHIHAWGHIT ISTAAQYRNAVVEQPLPQRGADLAELEGDY KDDDDKGSRDDESLFFGDTGLSKNPIELVE GWFSSWKSSIASFFFIIGLIIGLFLVLRVG IHLCIKLKHTKKRQIYTDIEMNRLGKKTC |
| Human insulin signal sequence | residues 1-24 of SEQ ID NO: 191 | MALWMRLLPLLALLALWGPDPAAA |
| Linker | residues 25-36 of SEQ ID NO: 191 | GTGSGEFDIAAA |
| TPB(gE) Domain | residues 37-415 of SEQ ID NO: 191 | GTPKTSWRRVSVGEDVSLLPAPGPTGRGPT QKLLWAVEPLDGCGPLHPSWVSLMPPKQVP ETVVDAACMRAPVPLAMAYAPPAPSATGGL RTDFVWQERAAVVNRSLVIHGVRETDSGLY TLSVGDIKDPARQVASVVLVVQPAPVPTPP PTPADYDEDDNDEGEDESLAGTPASGTPRL PPPPAPPRSWPSAPEVSHVRGVTVRMETPE AILFSPGETFSTNVSIHAIAHDDQTYSMDV VWLRFDVPTSCAEMRIYESCLYHPQLPECL SPADAPCAASTWTSRLAVRSYAGCSRTNPP PRCSAEAHMEPVPGLAWQAASVNLEFRDAS PQHSGLYLCVVYVNDHIHAWGHITISTAAQ YRNAVVEQPLPQRGADLAE |
| Linker | residues 416-418 of SEQ ID NO: 191 | LEG |
| Flag epitope domain | residues 419-426 of SEQ ID NO: 191 | DYKDDDDK |
| Linker | residues 427-429 of SEQ ID NO: 191 | GSR |
| TMR(VSVG) Domain with KK motif | residues 430-509 of SEQ ID NO: 191 | DDESLFFGDTGLSKNPIELVEGWFSSWKSS IASFFFIIGLIIGLFLVLRVGIHLCIKLKH TKKRQIYTDIEMNRLGKKTC |

HEK293 cells were transfected with expression vector plasmids to compare levels of IL13Rα2TF-Fc target protein secreted into culture media when the IL13Rα2TF-Fc target protein was expressed alone, when co-expressed with a Flag-tagged TPB(gE)-TMR (VSVG) fusion protein, or when co-expressed with the Flag-tagged TPB(gE)-TMR (VSVG) with KK motif fusion protein. Mock cultures containing cells transfected with "empty vector", i.e., an expression vector lacking a structural gene for expressing any protein, were included as a negative control. IL13Rα2TF-Fc target protein in samples of culture media was determined by ELISA.

Figure 10C:
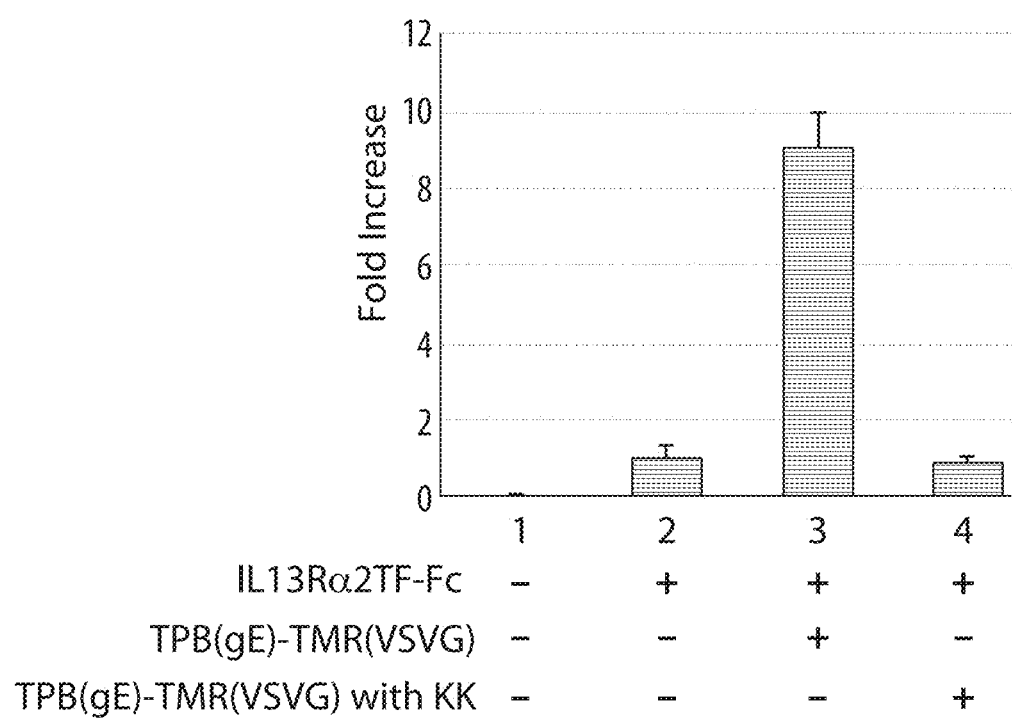
FIG. 10C shows bar graphs of the fold increase in the amount of IL13Rα2TF-Fc target protein detected by ELISA in the media of cultures of transfected HEK293 host cells expressing the IL13Rα2TF-Fc target protein alone (bar graph 2), co-expressing the target protein and a cell-associated secretion-enhancing TPB-TMR(VSVG) fusion protein corresponding to the construct of diagram FIG. 10A (bar graph 3), or co-expressing the target protein and a "TPB-TMR(VSVG) with KK motif" fusion protein corresponding to the construct of diagram FIG. 10B (bar graph 4). The presence ("+") or absence ("−") of expression vectors encoding target protein or fusion protein in the transfected host cells of each culture is indicated below each bar graph. Mock cultures contained cells transfected with expression vector lacking a structural gene for expressing any protein and were used as a negative control (bar graph 1). The results show that co-expression of the IL13Rα2TF-Fc target protein with the cell-associated secretion-enhancing TPB (gE)-TMR(VSVG) fusion protein (bar graph 3) significantly enhanced the level of target protein secreted into the culture media as compared to the level of target protein secreted into the culture media when the target protein was expressed in the absence of either fusion protein (bar graph 2). In contrast, co-expression of the IL13Rα2TF-Fc target protein with the ER-bound "TPB(gE)-TMR(VSVG) with KK motif" did not enhance and in fact reduced the level of target protein secreted into the culture media (bar graph 4) compared to the level of target protein secreted into culture media when the target protein was expressed in the absence of either fusion protein (bar graph 2). The results shown in bar graph 4 indicate that localization of the fusion protein (and presumably bound to the IL13Rα2TF-Fc target protein) to the ER inhibits orderly progression of the target protein into the secretory pathway. See Example 10 for additional details.

The relative levels of IL13Rα2TF-Fc target protein secreted into the media of the various transfectant cell cultures are shown in the bar graphs in FIG. 10C. The level of IL13Rα2TF-Fc target protein secreted into the medium of cells expressing the target protein alone was set at a relative value of "1" fold increase as shown in bar graph 2 of FIG. 10C. Co-expression of the IL13Rα2TF-Fc target protein and the TPB(gE)-TMR(VSVG) resulted in a nine-fold increase in the level of target protein secreted into the culture medium (bar graph 3) as compared to the level in media of cultures of cells expressing the target protein alone (bar graph 2). In contrast, as shown in bar graph 4 of FIG. 10C, co-expression of the IL13Rα2TF-Fc target protein and the TPB(gE)-TMR (VSVG) with KK motif fusion protein yielded a level of target protein secreted into the culture medium that appeared to be even lower than the level in cultures of cells expressing the target protein alone (bar graph 2). The results indicate that a transmembrane region useful as a TMR domain in a cell-associated secretion-enhancing (CASE) fusion protein of the invention should not comprise a C-terminal KK motif or any other signal known to localize a transmembrane protein exclusively in the ER. Thus, for a CASE fusion protein of the invention to enhance secretion of a co-expressed target protein, the TMR domain of the fusion protein must be able to function and associate with the membranes of the intracellular secretory pathway, i.e., ER, Golgi, and secretory vesicles, without being retained exclusively in the ER.

Additional Experiments: Further Examples of the Effect of Retaining Fusion Protein in Endoplasmic Reticulum on Secretion of Target Protein.

The following study was conducted to further examine the effect of ER retention of fusion proteins on the level of a target protein of interest secreted from host cells. In this study, the target protein was the TNFR1TF-Fc described above in Table 9 of Example 4. The fusion proteins used in this study comprised one of three different TPB domains that bind the Fc region of the target protein in combination with either the wildtype or mutant (dilysine motif) versions of the TMR(VSVG) domains employed in Example 10 above.

Figure 10D:
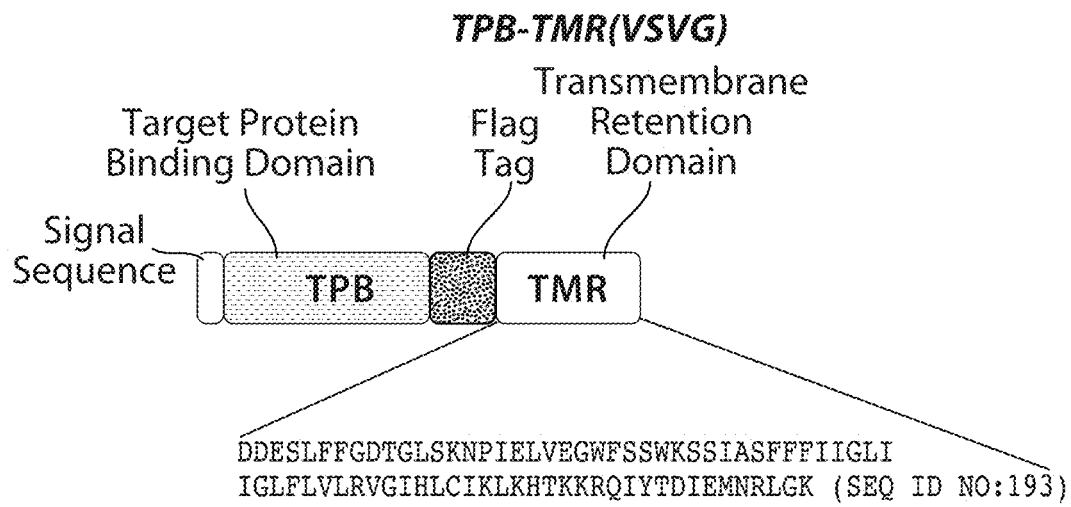
FIG. 10D shows a general diagram of a nucleic acid construct encoding the structure of TPB-TMR fusion proteins used in additional experiments of Example 10, comprising a segment encoding a target protein binding (TPB) domain linked at its 3' end to a segment encoding a Flag epitope tag, which in turn was linked at its 3' end to a segment encoding a transmembrane retention (TMR) domain comprising a wildtype amino acid sequence (SEQ ID NO:193) of a transmembrane region of the VSVG protein. The the hinge-CH2-CH3 region of an IgG heavy chain. On expression, the Fc regions are expected to promote formation of FVII-V5-Fc homodimers. The expressed target protein can be detected using a standard antibody to the V5 epitope tag. The encoded protein was designated "FVII-Fc". See Example 12 for additional details.
Figure 10E:
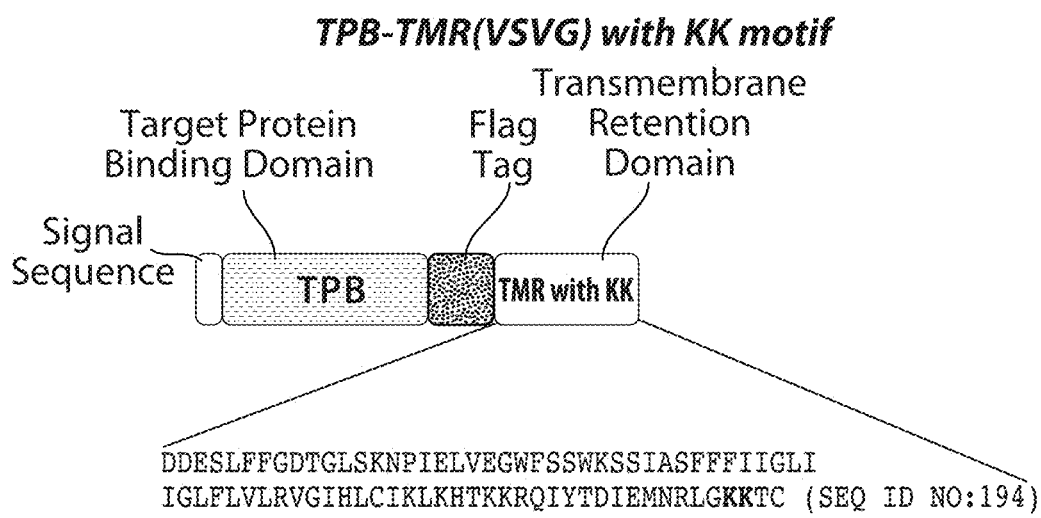
FIG. 10A is a diagram of a nucleic acid construct coding for a cell-associated secretion-enhancing fusion protein of the invention comprising a segment encoding an Fc-binding portion of a gE protein as a target protein binding domain (TPB) augmented at its 3' end with a segment encoding a Flag epitope tag, which in turn was linked to a segment encoding a transmembrane retention domain (TMR) comprising the transmembrane region of VSV-G. The diagram shows the encoded amino acid sequence (SEQ ID NO:193) of the TMR domain of the fusion protein construct. The construct was designated "TPB(gE)-TMR(VSVG)". See Example 10 for additional details.
FIG. 10B is a diagram of a nucleic acid construct coding for a fusion protein in which a segment encoding a target protein binding domain (TPB) comprising an Fc-binding portion of a gE protein is augmented at its 3' end with a segment encoding a Flag epitope tag, which in turn was linked to a segment encoding a transmembrane retention domain (TMR) comprising a mutated version of the transmembrane region of VSV-G in which the C-terminus of the VSV-G transmembrane region was engineered to include three additional amino acids (K-T-C) to create a dilysine (K-K) motif at positions −4 and −3 from the C-terminus ("TPB(gE)-TMR(VSVG) with KK motif"). This tandem lysine amino acid motif at the C-terminus of the cytoplasmic region of transmembrane proteins is known to localize such proteins in the endoplasmic reticulum (ER). The diagram shows the encoded amino acid sequence (SEQ ID NO:194) of the TMR domain of the fusion protein construct showing the tandem lysine residues (K-K) at positions −4 and −3 from the C-terminus and the C-terminal cysteine (C) residue. See Example 10 for additional details.

FIG. 10D shows a general diagram of a nucleic acid construct encoding a TPB-TMR(VSVG) fusion protein in which a 5' segment encoding the TPB domain is augmented at its 3' end with a segment encoding a Flag epitope tag, which in turn was linked in frame at its 3' end to a segment encoding a transmembrane retention (TMR) domain comprising a wildtype amino acid sequence of a transmembrane region of the VSVG protein (SEQ ID NO:193) FIG. 10E shows a general diagram of a nucleic acid construct encoding a TPB-TMR fusion protein similar to that shown in FIG. 10D, except that the segment encoding a TMR domain comprises an engineered amino acid sequence of a transmembrane region of the VSVG protein comprising tandem lysine residues (dilysine motif for ER retention) inserted at positions −3 and −4 of the C-terminal cytoplasmic region of the fusion protein (SEQ ID NO:194).

The Flag-tagged TPB(gE)-TMR(VSVG) fusion protein used in this study comprising a TPB domain comprising an Fc binding portion of the gE protein and a TMR domain comprising a wildtype transmembrane region of VSVG was the same as that described above in Table 10 of Example 4.

The Flag-tagged TPB(gE)-TMR(VSVG) "with KK" fusion protein used in this study comprising a TPB domain comprising an Fc binding portion of gE and a TMR domain comprising a transmembrane region of the VSVG protein engineered to contain tandem lysine residues inserted at positions −3 and −4 of the C-terminal cytoplasmic region of the fusion protein was the same as described above in Table 22, above.

The amino acid sequence for a Flag-tagged TPB(Prot A)-TMR(VSVG) fusion comprising a TPB domain comprising an Fc-binding portion of Protein A and a TMR domain comprising a wildtype transmembrane region of VSVG was the same as shown in Table 11 of Example 4, above.

The amino acid sequence for a Flag-tagged TPB(Prot A)-TMR(VSVG) with KK motif is shown in Table 23 below.

TABLE 23

Amino Acid Sequence of a Flag-Tagged TPB(Prot A)-TMR(VSVG) with KK Motif Fusion Protein.

| Encoded Protein or Region (N- to C-terminal) | Sequence Identifier | Amino Acid Sequence 12345678901234567890123456789 0 |
|---|---|---|
| Flag-tagged TPB(Prot A)-TMR(VSVG) fusion protein | SEQ ID NO: 201 | MALWMRLLPLLALLALWGPDPAAAGTGSGE FDIAAAADNKFNKEQQNAFYEILNMPNLNE EQRNGFIQSLKDDPSQSANVLGEAKKLNDS QAPKLEGDYKDDDDKGSRDDESLFFGDTGL SKNPIELVEGWFSSWKSSIASFFFIIGLII GLFLVLRVGIHLCIKLKHTKKRQIYTDIEM NRLGKKTC |
| Human insulin signal sequence | residues 1-24 of SEQ ID NO: 201 | MALWMRLLPLLALLALWGPDPAAA |
| Linker | residues 25-36 of SEQ ID NO: 201 | GTGSGEFDIAAA |
| TPB(Prot A) Domain (from Protein A) | residues 37-94 of SEQ ID NO: 201 | ADNKFNKEQQNAFYEILNMPNLNEEQRNGF IQSLKDDPSQSANVLGEAKKLNDSQAPK |
| Linker | residues 95-97 of SEQ ID NO: 201 | LEG |
| Flag epitope domain | residues 98-105 of SEQ ID NO: 201 | DYKDDDDK |

TABLE 23-continued

Amino Acid Sequence of a Flag-Tagged TPB(Prot A)-
TMR(VSVG) with KK Motif Fusion Protein.

| Encoded Protein or Region (N- to C- terminal) | Sequence Identifier | Amino Acid Sequence 12345678901234567890123456789 0 |
|---|---|---|
| Linker | residues 106-108 of SEQ ID NO: 201 | GSR |
| TMR(VSVG) Domain with KK motif | residues 109-188 of SEQ ID NO: 201 | DDESLFFGDTGLSKNPIELVEGWFSSWKSS IASFFFIIGLIIGLFLVLRVGIHLCIKLKH TKKRQIYTDIEMNRLGKKTC |

The amino acid sequence for a Flag-tagged TPB(Prot GB919)-TMR(VSVG) fusion protein comprising a TPB domain that comprises an Fc-binding portion of Protein GB919 and a TMR domain comprising a wildtype transmembrane region of VSVG was the same as shown in Table 13 of Example 4, above.

The amino acid sequence for a Flag-tagged TPB(Prot GB919)-TMR(VSVG) with KK motif is shown in Table 24 below.

HEK293 cells were transfected with expression vector plasmids to compare levels of TNFR1TF-Fc target protein secreted into culture media when the TNFR1TF-Fc target protein was expressed alone and when co-expressed with each of the fusion proteins: Flag-tagged TPB(gE)-TMR (VSVG), Flag-tagged TPB(gE)-TMR (VSVG) with KK motif, Flag-tagged TPB(Prot A)-TMR(VSVG), Flag-tagged TPB(Prot A)-TMR(VSVG) with KK motif, Flag-tagged TPB(GB919)-TMR(VSVG), and Flag-tagged TPB (GB919)-TMR(VSVG) with KK motif. Mock cultures con-

TABLE 24

Amino Acid Sequence of a Flag-Tagged TPB(Prot GB919)-
TMR(VSVG) with KK Motif Fusion Protein.

| Encoded Protein or Region (N- to C- terminal) | Sequence Identifier | Amino Acid Sequence 12345678901234567890123456789 0 |
|---|---|---|
| Flag-tagged TPB(GB919)- TMR(VSVG) fusion protein | SEQ ID NO: 202 | MALWMRLLPLLALLALWGPDPAAAGTGSGE FDIAAADTYKLILNGKTLKGETTTEAVDAA TAEKVFKHYANEHGVHGHWTYDPETKTFTV TELEGDYKDDDDKGSRDDESLFFGDTGLSK NPIELVEGWFSSWKSSIASFFFIIGLIIGL FLVLRVGIHLCIKLKHTKKRQIYTDIEMNR LGKKTC |
| Human insulin signal sequence | residues 1-24 of SEQ ID NO: 202 | MALWMRLLPLLALLALWGPDPAAA |
| Linker | residues 25-36 of SEQ ID NO: 202 | GTGSGEFDIAAA |
| TPB(GB919) Domain | residues 37-92 of SEQ ID NO: 202 | DTYKLILNGKTLKGETTTEAVDAATAEKVF KHYANEHGVHGHWTYDPETKTFTVTE |
| Linker | residues 93-95 of SEQ ID NO: 202 | LEG |
| Flag epitope domain | residues 96-103 of SEQ ID NO: 202 | DYKDDDDK |
| Linker | residues 104-106 of SEQ ID NO: 202 | GSR |
| TMR(VSVG) Domain with KK motif | residues 107-186 of SEQ ID NO: 202 | DDESLFFGDTGLSKNPIELVEGWFSSWKSS IASFFFIIGLIIGLFLVLRVGIHLCIKLKH TKKRQIYTDIEMNRLGKKTC | taining cells transfected with "empty vector", i.e., an expression vector lacking a structural gene for expressing any protein, were included as a negative control. TNFR1TF-Fc target protein in samples of culture media was determined by ELISA.

Figure 10F:
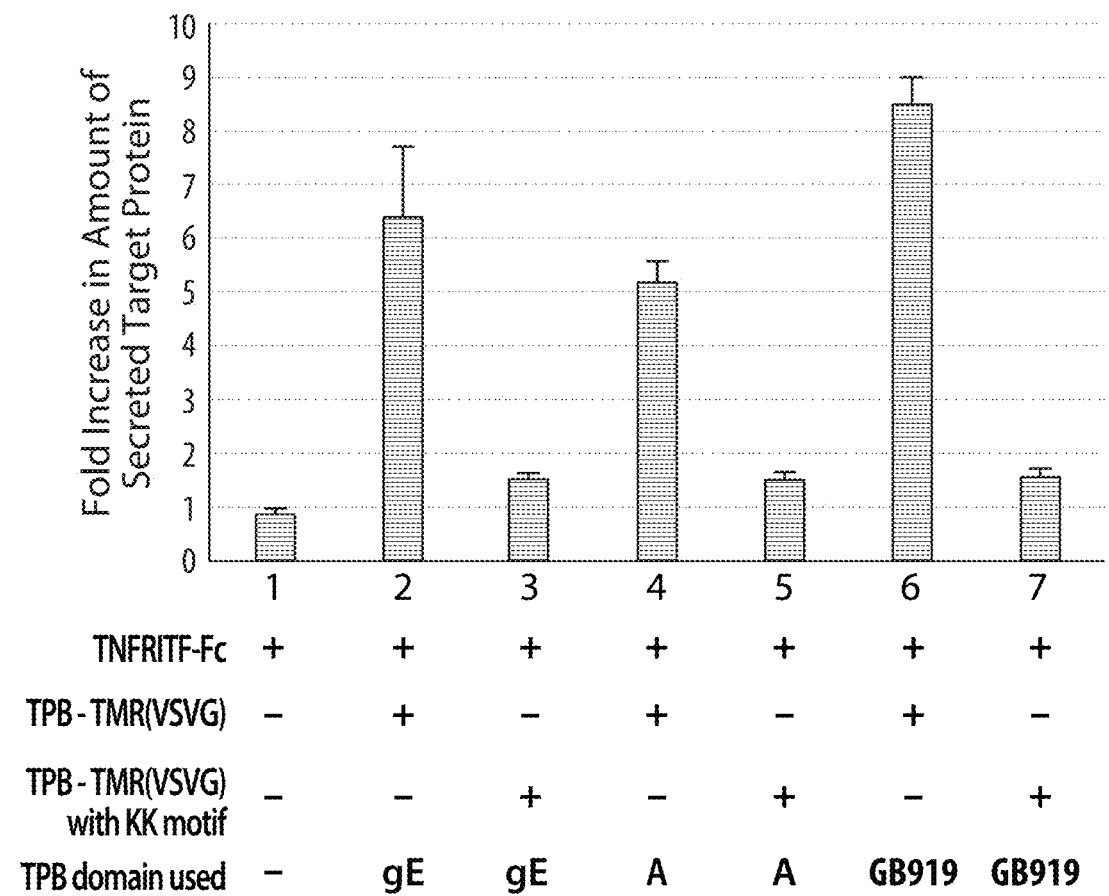

The relative levels of TNFR1TF-Fc target protein secreted into the media of the various transfectant cell cultures are shown in the bar graphs in FIG. 10F. The level of TNFR1TF-Fc target protein secreted into the medium of cells expressing the target protein alone was set at a relative value of "1" fold increase as shown in bar graph 1 of FIG. 10F. Co-expression of the TNFR1TF-Fc target protein with each of the fusion proteins comprising different TPB domains that bind the Fc region of the target protein but having the same wildtype TMR(VSVG) resulted in a significant enhancement in the level of target protein secreted into the culture media of transfected cells (see, bar graphs 2, 4, and 6) as compared to the level from cultures of transfected cells expressing the target protein alone (bar graph 1). However, such enhancement in the level of secreted TNFR1TF-Fc target protein was abolished when the TMR (VSVG) domain of each of the fusion proteins was engineered to contain the KK motif, which is known to restrict proteins to the ER membranes (see, bar graphs 3, 5, and 7). The results are consistent with those discussed above using the IL13Rα2TF-Fc target protein. Taken together, the results in these studies clearly indicate that whereas alternative TPB domains for a particular target protein can be used in a CASE fusion protein of the invention, it is critical that TMR domain not include a C-terminal KK motif or any other signal known to localize a transmembrane protein exclusively in the ER.

Example 11

Further Enhancement of Level of Target Protein Secreted from Cells Co-Expressing a CASE Fusion Protein Comprising a CMP Domain This experiment examined the effect of adding a chaperone machinery peptide ("CMP") as an additional domain in a cell-associated secretion-enhancing (CASE) a fusion protein previously shown to enhance the level of secretion of a co-expressed target protein.

The target protein used in this study was the V5-tagged IL13Rα2TF-Fc target protein described above in Example 2 and Table 4.

The cell-associated secretion-enhancing (CASE) Flag-tagged TPB(gE)-TMR(VSVG) fusion protein used in this experiment was the same as described above in Example 2 and Table 5.

Figure 11A:
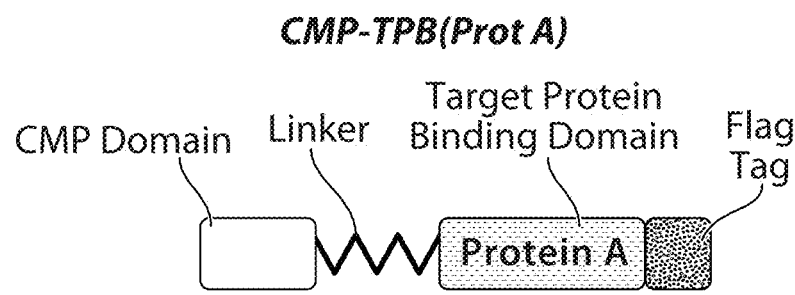

FIG. 11A shows a diagram of a nucleic acid construct encoding a fusion protein comprising a segment encoding a chaperone machinery polypeptide ("CMP") domain comprising a peptide isolated from the J domain of the Erdj4 co-chaperone protein, which was linked to a segment encoding an Fc-binding portion of a staphylococcal Protein A ("A") as a target protein binding ("TPB") domain augmented at its 3' end with a segment encoding a Flag epitope tag for easy identification with a standard anti-Flag antibody. The fusion protein was designated "CMP-TPB(Prot A)". The entire amino acid sequence of this Flag-tagged CMP-Protein A fusion protein used in this experiment is shown in Table 25 below.

TABLE 25

Amino Acid Sequence of a Flag-Tagged CMP-TPB(Prot A) Fusion Protein

| Encoded Protein or Region (N- to C-terminal) | Sequence Identifier | Amino Acid Sequence 123456789012345678901234567890 |
|---|---|---|
| Flag-tagged CMP-TPB(Prot A) fusion protein | SEQ ID NO: 192 | MALWMRLLPLLALLALWGPDPAAAGTGSGE FIKKAFHKLAMKYDIGGGGSGGGGSGGGGS AAAQQNAFYEILNMPNLNEEQRNGFIQSLK DDPSQSANVLGEAKKLNDSLEGDYKDDDDK |
| Human insulin signal sequence | residues 1-24 of SEQ ID NO: 192 | MALWMRLLPLLALLALWGPDPAAA |
| Linker | residues 25-31 of SEQ ID NO: 192 | GTGSGEF |
| CMP Domain (peptide from J domain of Erdj4) | residues 32-43 of SEQ ID NO: 192 | IKKAFHKLAMKY |
| Linker | residues 44-63 of SEQ ID NO: 192 | DIGGGSGGSGGSGGAAA |
| TPB(Prot A) Domain | residues 64-109 of SEQ ID NO: 192 | QQNAFYEILNMPNLNEEQRNGFIQSLK DDPSQSANVLGEAKKLNDS |
| Linker | residues 110-112 of SEQ ID NO: 192 | LEG |

TABLE 25-continued

Amino Acid Sequence of a Flag-Tagged CMP-TPB(Prot A) Fusion Protein

| Encoded Protein or Region (N- to C-terminal) | Sequence Identifier | Amino Acid Sequence 123456789012345678901234567890 |
|---|---|---|
| Flag epitope domain | residues 113-120 of SEQ ID NO: 192 | DYKDDDDK |

Figure 11B:
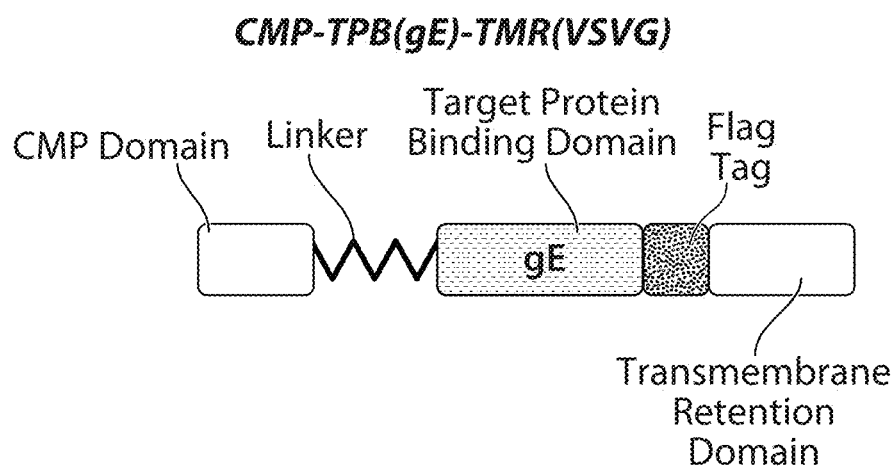

FIG. 11B shows a diagram of a nucleic acid construct encoding a cell-associated secretion-enhancing (CASE) fusion protein of the invention comprising a segment encoding a CMP domain comprising a peptide isolated from the J domain of the Erdj4 protein linked to a segment encoding an Fc-binding portion of a gE protein as a target protein binding (TPB) domain augmented at its 3' end with a segment encoding a Flag epitope tag for easy identification with a standard anti-Flag antibody, which in turn was linked to a segment encoding a transmembrane retention (TMR) domain comprising a transmembrane region of a type I transmembrane VSVG protein. The fusion protein was designated "CMP-TPB(gE)-TMR(VSVG)". The amino acid sequence for this Flag-tagged CMP-TPB(gE)-TMR fusion protein is shown in Table 26 below.

TABLE 26

Amino Acid Sequence of a Flag-Tagged CMP-TPB(gE)-TMR(VSVG) Fusion Protein

| Encoded Protein or Region (N- to C-terminal) | Sequence Identifier | Amino Acid Sequence 123456789012345678901234567890 |
|---|---|---|
| Flag-tagged CMP-TPB-TMR(VSVG) fusion protein | SEQ ID NO: 134 | MALWMRLLPLLALLALWGPDPAAAGTGSGE FIKKAFHKLAMKYDIGGGGSGGGGSGGGGS AAAGTPKTSWRRVSVGEDVSLLPAPGPTGR GPTQKLLWAVEPLDGCGPLHPSWVSLMPPK QVPETVVDAACMRAPVPLAMAYAPPAPSAT GGLRTDFVWQERAAVVNRSLVIHGVRETDS GLYTLSVGDIKDPARQVASVVLVVQPAPVP TPPPTPADYDEDDNDEGEDESLAGTPASGT PRLPPPPAPPRSWPSAPEVSHVRGVTVRME TPEAILFSPGETFSTNVSIHAIAHDDQTYS MDVVWLRFDVPTSCAEMRIYESCLYHPQLP ECLSPADAPCAASTWTSRLAVRSYAGCSRT NPPPRCSAEAHMEPVPGLAWQAASVNLEFR DASPQHSGLYLCVVYVNDHIHAWGHITIST AAQYRNAVVEQPLPQRGADLAELEGDYKDD DDKGSRSSWKSSIASFFFIIGLIIGLFLVL RVGIHLCIKLKHTKKRQIYTDIEMNRLGK |
| Human insulin signal sequence | residues 1-24 of SEQ ID NO: 134 | MALWMRLLPLLALLALWGPDPAAA |
| Linker | residues 25-31 of SEQ ID NO: 134 | GTGSGEF |
| CMP Domain (peptide from J domain of Erdj4 protein) | residues 32-43 of SEQ ID NO: 134 | IKKAFHKLAMKY |
| Linker | residues 44-63 of SEQ ID NO: 134 | DIGGGSGGSGGSGGAAA |
| TPB(gE) Domain | residues 64-442 of SEQ ID NO: 134 | GTPKTSWRRVSVGEDVSLLPAPGPTGRGPT QKLLWAVEPLDGCGPLHPSWVSLMPPKQVP ETVVDAACMRAPVPLAMAYAPPAPSATGGL RTDFVWQERAAVVNRSLVIHGVRETDSGLY TLSVGDIKDPARQVASVVLVVQPAPVPTPP PTPADYDEDDNDEGEDESLAGTPASGTPRL PPPPAPPRSWPSAPEVSHVRGVTVRMETPE AILFSPGETFSTNVSIHAIAHDDQTYSMDV VWLRFDVPTSCAEMRIYESCLYHPQLPECL |

TABLE 26-continued

Amino Acid Sequence of a Flag-Tagged CMP-TPB(gE)-TMR(VSVG) Fusion Protein

| Encoded Protein or Region (N- to C-terminal) | Sequence Identifier | Amino Acid Sequence 12345678901234567890123456789 0 |
|---|---|---|
| | | SPADAPCAASTWTSRLAVRSYAGCSRTNPP PRCSAEAHMEPVPGLAWQAASVNLEFRDAS PQHSGLYLCVVYVNDHIHAWGHITISTAAQ YRNAVVEQPLPQRGADLAE |
| Linker | residues 443-445 of SEQ ID NO: 134 | LEG |
| Flag epitope domain | residues 446-453 of SEQ ID NO: 134 | DYKDDDDK |
| Linker | residues 454-456 of SEQ ID NO: 134 | GSR |
| TMR(VSVG) Domain | residues 457-509 of SEQ ID NO: 134 | SSWKSSIASFFFIIGLIIGLFLVLRVGIHL CIKLKHTKKRQIYTDIEMNRLGK |

HEK293 cells were transfected with expression vector plasmids for co-expression of the IL13Rα2TF-Fc target protein and the CMP-TPB(Prot A) fusion protein, the previously described TPB(gE)-TMR(VSVG) fusion protein, or the CMP-TPB(gE)-TMR(VSVG). Mock cultures containing cells transfected with "empty vector", i.e., an expression vector lacking a structural gene for expressing any protein, were included as a negative control. IL13Rα2TF-Fc target protein in culture samples was determined by ELISA.

Figure 11C:
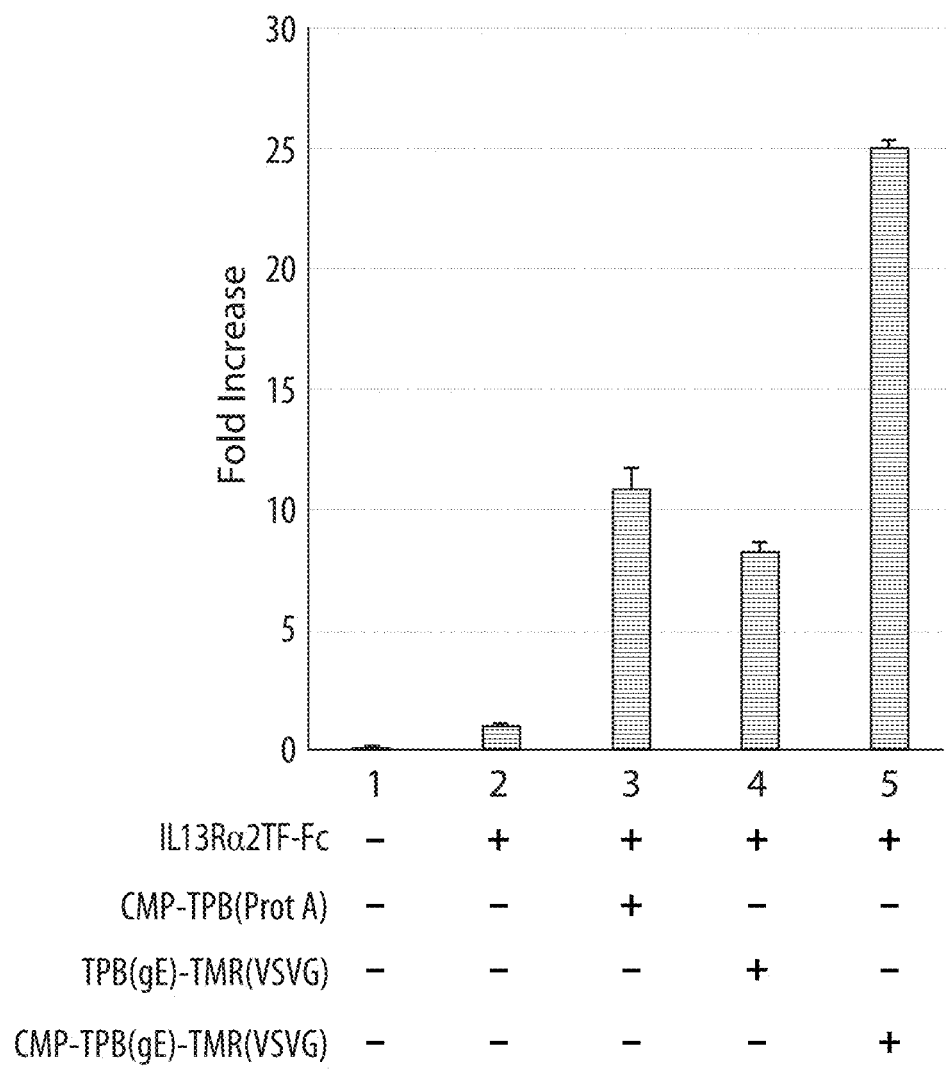

The relative levels of IL13Rα2TF-Fc target protein secreted into culture media are shown in the bar graphs in FIG. 11C. The level of IL13Rα2TF-Fc target protein secreted into the medium of cells expressing the target protein alone was set at a relative value of "1" fold increase as shown in bar graph 2 of FIG. 11C. The results show that co-expression of the IL13Rα2TF-Fc target protein with either the CMP-TPB(Prot A) fusion protein (bar graph 3) or the TPB(gE)-TMR(VSVG) fusion protein (bar graph 4) significantly enhanced the level of target protein secreted into the culture media by, respectively, 11-fold (bar graph 3) and 9-fold (bar graph 4) as compared to the level of target protein secreted into the medium of a culture of cells expressing the target protein alone, i.e., in the absence of any of the fusion proteins (bar graph 2). A somewhat higher level of secreted target protein was observed in cultures of cells co-expressing the target protein and the CMP-TPB(Prot A) fusion protein (i.e., 11-fold, bar graph 3) as compared to that in cultures of cells co-expressing the target protein and the CASE TPB(gE)-TMR(VSVG) fusion protein (i.e., 9-fold, bar graph 4); however, co-expression of a target protein and the CMP-TPB(Prot A) fusion protein lacks the benefit of a TMR domain in the fusion protein to keep it associated with the host cell while releasing the target protein and thereby preventing the fusion protein from being co-secreted with the target protein into the culture medium.

Surprisingly, an unexpected and significant further enhancement in the level of target protein secreted into the culture medium was observed when the IL13Rα2TF-Fc target protein was co-expressed with the CMP-TPB(gE)-TMR(VSVG) fusion protein as shown in bar graph 5 of FIG. 11C, where the level of target protein secreted into culture medium was 25-fold higher than that secreted into the medium of a culture of cells expressing the target protein alone (bar graph 2).

The results show that co-expression of a target protein and a fusion protein comprising a TPB domain, a TMR domain, and a CMP domain may result in a significantly greater enhancement in the level of target protein secreted from a host cells as compared to the level of target protein secreted from cells that co-express the target protein and a CASE fusion protein comprising a TPB domain and a TMR domain, but lacking a CMP domain.

Example 12

Enhanced Level of FVII-Fc Target Protein Secreted from Cells

In this experiment, two fusion proteins were constructed and compared for the ability to enhance the level of FVII-Fc target protein secreted from a host cell co-expressing the target protein and each of the fusion proteins as compared to the level of target protein secreted from a host cell that expressed the target protein alone. Both fusion proteins possessed a J domain of the Erdj3 co-chaperone protein and an Fc-binding region, which was either the Fc-binding region of Protein G (CAA27638.1, GenBank, NCBI) or the Fc-binding domain the gE protein of herpes simplex virus-1 (Baucke et al., *J. Virol.*, 32(3): 779-789 (1979), Para et al., *J. Virol.*, 34(3): 512-520 (1980)). Protein G is the streptococcal Protein G that is well-known for its binding with high affinity to the Fc region of immunoglobulins, such as IgG antibodies. The gE protein is known to bind Fc regions (Chapman et al., *J. Biol. Chem.*, 274:6911-19 (1999)).

Figure 12A:
FIG. 12B is a diagram depicting a nucleic acid construct encoding a fusion protein described in Example 12 and comprising a segment encoding a J domain of the Erdj3 protein as a "chaperone machinery peptide" ("CMP") domain linked to a segment encoding an Fc-binding portion of Protein G as a target protein binding (TPB) domain augmented at its 3' end with a segment encoding a Flag epitope tag for easy identification with a standard anti-Flag antibody. The encoded fusion protein was designated "CMP-TPB(Prot G)". See Example 12 for additional details.
FIG. 12C is a diagram depicting a nucleic acid construct encoding a cell-associated secretion-enhancing (CASE) fusion protein of the invention as described in Example 12 and comprising a segment encoding a J domain of the Erdj3 protein as a "chaperone machinery peptide" ("CMP") domain linked to a segment encoding an Fc-binding portion of a gE protein as a target protein binding (TPB) domain augmented at its 3' end with a segment encoding a Flag epitope tag for easy identification with a standard anti-Flag antibody, which in turn was linked to a segment encoding a transmembrane region of the type I transmembrane VSV-G protein (VSVG) as a transmembrane retention (TMR) domain. The fusion protein was designated "CM-TPB(gE)-TMR(VSVG)". See Example 12 for additional details.
FIG. 12D shows X-ray film images of chemiluminescent signals of a Western blot analysis of samples of total culture, i.e., cells and culture media ("Total", lanes 1-4), of cell lysates ("Cell", lanes 5-8), and of culture media ("Media", lanes 9-12) of transfected host cells expressing the FVII-Fc target protein when expressed alone ("FVII-Fc", lanes 2, 6, and 10), when co-expressed with the CMP TPB(Prot G) fusion protein (lanes 3, 7, and 11), or when co-expressed with the cell-associated secretion-enhancing CMP-TPB (gE)-TMR(VSVG) fusion protein of the invention (lanes 4, 8, and 12), as described in Example 12. The presence ("+") or absence ("−") of expression vectors encoding the target protein or a fusion protein in the transfected host cells of each culture is indicated above each lane of the Western blot. It can be seen that co-expression of the FVII-Fc target protein with the CMP-TPB(Prot G) fusion protein or the cell-associated secretion-enhancing CMP-TPB(gE)-TMR (VSVG) fusion protein of the invention significantly enhanced the level of secreted FVII-Fc target protein (lanes 11 and 12) as compared to expression of FVII-Fc target protein alone (lane 10). In the absence of either fusion protein, a relatively small amount of the FVII-Fc target protein was secreted into the culture media (lane 10). However, a significant amount of the CMP-TPB(Prot G) fusion protein was secreted into the culture media with the co-expressed FVII-Fc target protein (lane 11) and an even greater amount of the CMP-TPB(Prot G) fusion protein appeared to be present in the host cell (lane 7). In contrast, the CMP-TPB(gE)-TMR(VSVG) fusion protein of the invention was not secreted into the media with the co-expressed FVII-Fc target protein (lane 12) but remained associated with the host cell (lane 8). Lanes 1, 5, and 9 show the absence of signal from mock cultures, which were cells transfected with "empty vector", i.e., an expression vector lacking a structural gene for expressing any protein, included as negative controls. See Example 12 for additional details.

As in Example 7 above, in this experiment, the FVII-Fc target protein was used as a representative example of trap molecule ("Fc drug") comprising a protein of interest, i.e., FVII, fused to an immunoglobulin Fc region (hinge-CH2-CH3). FIG. 12A shows a diagram of a nucleic acid construct encoding the FVII-Fc homodimer target protein that is augmented in its 3' region and upstream of the Fc coding region with a segment encoding a V5 epitope tag for easy identification of the expressed protein using a standard anti-V5 antibody. The V5-tagged FVII-Fc target protein monomer was the same as described in Example 7 and Table 19.

Figure 12B:
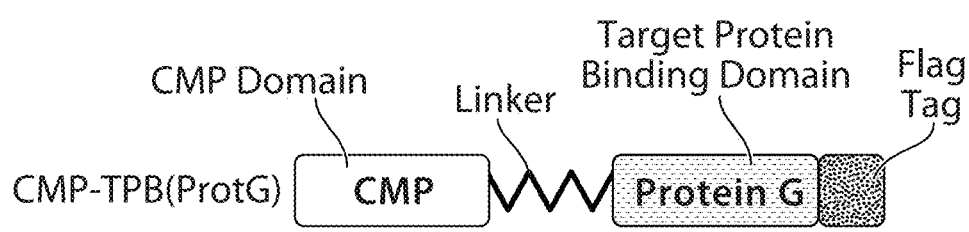

FIG. 12B shows a diagram of a nucleic acid construct encoding a fusion protein comprising a J domain of an Erdj3 co-chaperone protein as a chaperone machinery polypeptide (CMP) linked to a segment encoding an Fc-binding region of Protein G as a target protein binding (TPB) domain, which was augmented at its 3' end with a segment encoding a Flag epitope tag for easy identification with an anti-Flag antibody. The construct was designated "CMP-TPB(Prot G)". The amino acid sequence of the encoded Flag-tagged fusion protein is shown in Table 27 below.

TABLE 27

Amino Acid Sequence of a Flag-Tagged CMP-TPB(Prot G) Fusion Protein.

| Encoded Protein or Region (N- to C-terminal) | Sequence Identifier | Amino Acid Sequence 12345678901234567890123456789 0 |
|---|---|---|
| Flag-tagged CMP-TPB(Prot G) fusion protein | SEQ ID NO: 135 | MAPQNLSTFCLLLLYLIGAVIAGRDFYKIL GVPRSASIKDIKKAYRKLALQLHPDRNPDD PQAQEKFQDLGAAYEVLSDSEKRDIGGGSG GSGGSGGAAATYKLVINGKTLKGETTTEAV DAATAEKVFKQYANDNGVDGEWTYDDATKT FTVTEKPEVIDASELTPAVTLEGDYKDDDD KGSRGPYSIVSPKC |
| Erdj3 signal sequence | residues 1-22 of SEQ ID NO: 135 | MAPQNLSTFCLLLLYLIGAVIA |
| CMP Domain (from Erdj3) | residues 23-83 of SEQ ID NO: 135 | GRDFYKILGVPRSASIKDIKKAYRKLALQL HPDRNPDDPQAQEKFQDLGAAYEVLSDSEK R |
| Linker | residues 84-100 of SEQ ID NO: 135 | DIGGGSGGSGGSGGAAA |
| TPB(Prot G) Domain | residues 101-170 of SEQ ID NO: 135 | TYKLVINGKTLKGETTTEAVDAATAEKVFK QYANDNGVDGEWTYDDATKTFTVTEKPEVI DASELTPAVT |
| Linker | residues 171-173 of SEQ ID NO: 135 | LEG |
| Flag epitope domain | residues 174-181 of SEQ ID NO: 135 | DYKDDDDK |
| C-terminal vector residues | residues 182-194 of SEQ ID NO: 135 | GSRGPYSIVSPKC |

Figure 12C:
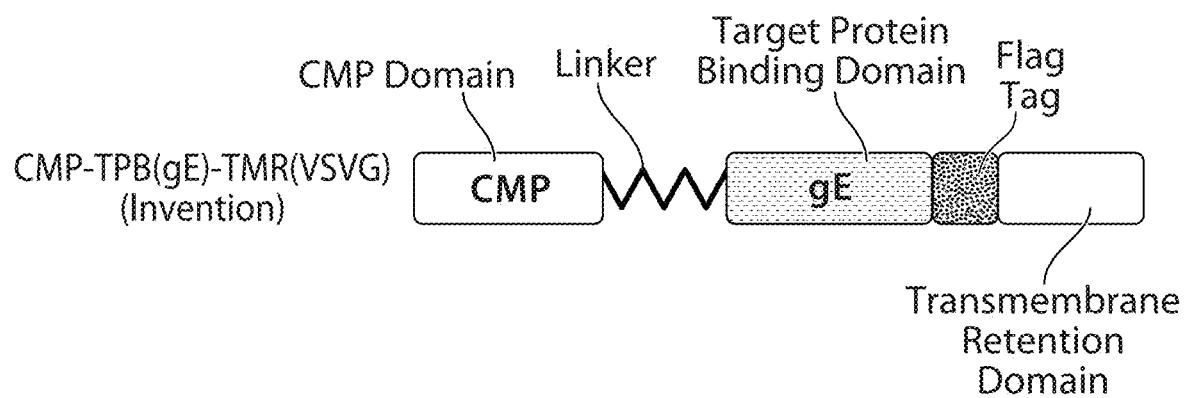

FIG. 12C shows a diagram of a nucleic acid construct encoding a cell-associated secretion-enhancing (CASE) fusion protein of the invention comprising a J domain of an Erdj3 protein as a chaperone machinery polypeptide (CMP) domain linked to a segment encoding an Fc-binding portion of the gE protein as a target protein binding (TPB) domain augmented at its 3' end with a segment encoding a Flag epitope tag, which in turn was linked to a segment encoding a transmembrane retention (TMR) domain comprising a portion of the transmembrane region of a VSV-G Type I transmembrane protein. The construct was also augmented at its 5' end with a segment encoding the Erdj3 signal sequence (not shown in FIG. 12C). The construct was designated "CMP-TPB(gE)-TMR(VSVG)". The amino acid sequence of the encoded Flag-tagged fusion protein is shown in Table 28 below.

TABLE 28

Amino Acid Sequence of a Flag-Tagged CMP-TPB(gE)-TMR(VSVG) Fusion Protein

| Encoded Protein or Region (N- to C-terminal) | Sequence Identifier | Amino Acid Sequence<br>12345678901234567890 1234567890 |
|---|---|---|
| Flag-tagged CMP-TPB(gE)-TMR(VSVG) fusion protein | SEQ ID NO: 136 | MAPQNLSTFCLLLLYLIGAVIAGRDFYKIL<br>GVPRSASIKDIKKAYRKLALQLHPDRNPDD<br>PQAQEKFQDLGAAYEVLSDSEKRDIGGGSG<br>GSGGSGGAAAGTPKTSWRRVSVGEDVSLLP<br>APGPTGRGPTQKLLWAVEPLDGCGPLHPSW<br>VSLMPPKQVPETVVDAACMRAPVPLAMAYA<br>PPAPSATGGLRTDFVWQERAAVVNRSLVIH<br>GVRETDSGLYTLSVGDIKDPARQVASVVLV<br>VQPAPVPTPPPTPADYDEDDNDEGEDESLA<br>GTPASGTPRLPPPPAPPRSWPSAPEVSHVR<br>GVTVRMETPEAILFSPGETFSTNVSIHAIA<br>HDDQTYSMDVVWLRFDVPTSCAEMRIYESC<br>LYHPQLPECLSPADAPCAASTWTSRLAVRS<br>YAGCSRTNPPPRCSAEAHMEPVPGLAWQAA<br>SVNLEFRDASPQHSGLYLCVVYVNDHIHAW<br>GHITISTAAQYRNAVVEQPLPQRGADLAEL<br>EGDYKDDDDKGSRDDESLFFGDTGLSKNPI<br>ELVEGWFSSWKSSIASFFFIIGLIIGLFLV<br>LRVGIHLCIKLKHTKKRQIYTDIEMNRLGK |
| Erdj3 signal sequence | residues 1-22 of SEQ ID NO: 136 | MAPQNLSTFCLLLLYLIGAVIA |
| CMP Domain (from Erdj3) | residues 23-83 of SEQ ID NO: 136 | GRDFYKILGVPRSASIKDIKKAYRKLALQL<br>HPDRNPDDPQAQEKFQDLGAAYEVLSDSEK<br>R |
| Linker | residues 84-100 of SEQ ID NO: 136 | DIGGGSGGSGGSGGAAA |
| TPB(gE) Domain | residues 101-479 of SEQ ID NO: 136 | GTPKTSWRRVSVGEDVSLLPAPGPTGRGPT<br>QKLLWAVEPLDGCGPLHPSWVSLMPPKQVP<br>ETVVDAACMRAPVPLAMAYAPPAPSATGGL<br>RTDFVWQERAAVVNRSLVIHGVRETDSGLY<br>TLSVGDIKDPARQVASVVLVVQPAPVPTPP<br>PTPADYDEDDNDEGEDESLAGTPASGTPRL<br>PPPPAPPRSWPSAPEVSHVRGVTVRMETPE<br>AILFSPGETFSTNVSIHAIAHDDQTYSMDV<br>VWLRFDVPTSCAEMRIYESCLYHPQLPECL<br>SPADAPCAASTWTSRLAVRSYAGCSRTNPP<br>PRCSAEAHMEPVPGLAWQAASVNLEFRDAS<br>PQHSGLYLCVVYVNDHIHAWGHITISTAAQ<br>YRNAVVEQPLPQRGADLAE |
| Linker | residues 480-482 of SEQ ID NO: 136 | LEG |
| Flag epitope domain | residues 483-490 of SEQ ID NO: 136 | DYKDDDDK |
| Linker | residues 491-493 of SEQ ID NO: 136 | GSR |
| TMR(VSVG) Domain | residues 494-570 of SEQ ID NO: 136 | DDESLFFGDTGLSKNPIELVEGWFSSWKSS<br>IASFFFIIGLIIGLFLVLRVGIHLCIKLKH<br>TKKRQIYTDIEMNRLGK |

In addition to determining whether either of the fusion proteins were effective in enhancing the level of FVII-Fc target protein secreted from a host cell, the experiment also examined whether or not the CMP-TPB(Prot G) fusion protein would be co-secreted with the target protein into the culture medium along with the co-expressed FVII-Fc target protein and whether the CMP-TPB(gE)-TMR(VSVG) fusion protein would be retained in the host cell while the co-expressed FVII-Fc target protein was secreted into the culture medium.

Figure 12D:
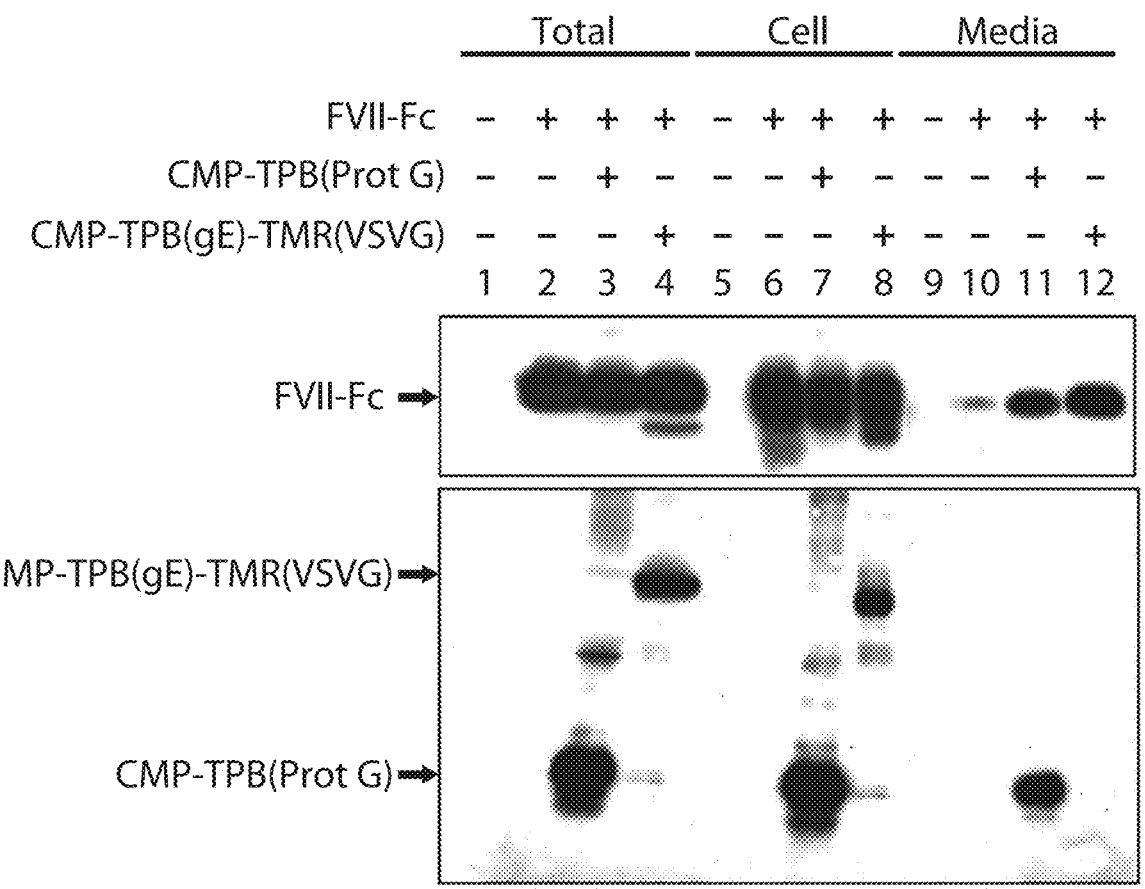

HEK293 cells were transfected with expression vector plasmids to compare levels of FVII-Fc target protein secreted into culture media when the FVII-Fc target protein was expressed alone, co-expressed with the CMP-TPB(Prot G) fusion protein, or co-expressed with the CMP-TPB(gE)-TMR(VSVG) fusion protein. Transfected cells were cultured for two days, and samples of cell cultures were harvested and analyzed by Western blot (immunoblot) assay using an anti-V5 antibody to detect V5-tagged FVII-Fc target protein. The level of expression of the FVII-Fc target protein was determined in both culture media and lysates of transfected host cells expressing the FVII-Fc target protein alone, co-expressing the FVII-Fc target protein and the CMP-TPB(Prot G) fusion protein, and co-expressing the FVII-Fc target protein and the CMP-TPB(gE)-TMR(VSVG) fusion protein. Mock cultures containing cells transfected with "empty vector", i.e., an expression vector lacking a structural gene for expressing any protein, were included as negative controls. The results of culturing transfected host cells and detecting protein expression by Western blot are shown in FIG. 12D for samples of cells and media ("Total", lanes 1-4), cell lysates ("Cell", lanes 5-8), and culture media alone ("Media", lanes 9-12) using an anti-V5 antibody (upper panel) to detect FVII-Fc target protein or an anti-Flag antibody (lower panel) to detect either CMP-TPB(Prot G) or CMP-TPB(gE)-TMR(VSVG) fusion proteins. As shown in the top panel of FIG. 12D, the level of expression of the FVII-Fc target protein secreted into the culture media was significantly greater in a culture of transfected cells co-expressing the FVII-Fc target protein and the CMP-TPB (Prot G) fusion protein (lane 11) than in a culture of cells expressing the FVII-Fc target protein alone (lane 10), but a surprising and significant further enhancement of the level of FVII-Fc target protein secreted into the culture medium was observed when the target protein was co-expressed with the CMP-TPB(gE)-TMR(VSVG) fusion protein of the invention (lane 12). Densitometer scanning of the Western blot confirmed that the relative level of secreted FVII-Fc target protein was greater when co-expressed with the CMP-TPB(gE)-TMR(VSVG) fusion protein of the invention (179.8 for FVII-Fc in lane 12) as compared to the level of secreted FVII-Fc target protein when co-expressed with the CMP-TPB(Prot G) fusion protein (117.9 for FVII-Fc in lane 11).

In addition, the results in FIG. 12D show that in the culture media of transfected cells co-expressing the FVII-Fc target protein and the CMP-TPB(Prot G) protein, a significant amount of the CMP-TPB(Prot G) fusion protein was not only associated with the transfected host cells (lane 7) but also was secreted into the culture media along with the FVII-Fc target protein (lane 11). The data in FIG. 12D do not indicate whether or not a relatively large or small portion of the FVII-Fc target protein remained bound to the CMP-TPB (Prot G) fusion protein in the cells (lane 7) or when secreted into the culture media (lane 11). The binding affinity of Protein G for immunoglobulin Fc regions is known to be relatively high, and dissociation of IgG from Protein G requires an acidic pH, reportedly as low as pH 3.1. See, Watanabe et al., *J. Biol. Chem.*, 284 (10):12373-12383 (2009). Samples for the Western blot analysis were denatured by boiling in standard SDS-sample buffer containing reducing agent to dissociate complexes and multimeric proteins prior to running on the SDS-polyacrylamide gel. Accordingly, it cannot be ruled out that a significant amount of the FVII-Fc target protein may be bound with the CMP-TPB(Prot G) fusion protein inside the cell (lane 7) and in the culture media (lane 11).

In contrast to the localization of the CMP-TPB(Prot G) fusion protein in both cells and culture media (lanes 7 and 11, respectively) and the possible association of the FVII-Fc target protein with the CMP-TPB(Prot G) protein, the CMP-TPB(gE)-TMR(VSVG) fusion protein was only detected within transfected cells (lane 8), and no significant amount of the CMP-TPB(gE)-TMR(VSVG) fusion protein was detected in the culture media of transfected cells that co-expressed the FVII-Fc target protein and the CMP-TPB(gE)-TMR(VSVG) fusion protein of the invention (lane 12). Accordingly, since the CMP-TPB(gE)-TMR(VSVG) fusion protein remained associated with the cells and was not secreted into the culture media, the FVII-Fc target protein secreted into the culture media is expected to be free of any significant CMP-TPB(gE)-TMR(VSVG) fusion protein. Moreover, as noted above, densitometer scanning of the Western blot in FIG. 12D confirmed that the relative level of FVII-Fc target protein secreted into the culture media was actually greater when co-expressed with the CMP-TPB(gE)-TMR(VSVG) fusion protein of the invention (densitometer scan reading of 179.8 for FVII-Fc in lane 12) as compared to the level of secreted FVII-Fc target protein when co-expressed with the CMP-TPB(Prot G) fusion protein (densitometer scan reading of 117.9 for FVII-Fc in lane 11).

The data indicate that: (1) co-expression of CMP-TPB (gE)-TMR(VSVG) fusion protein significantly enhances the level of FVII-Fc target protein secreted into the culture media of transfected host cells (lane 12) as compared to the level secreted into culture media of transfected host cells expressing the FVII-Fc target protein in the absence of any fusion protein (lane 10) and as compared to the level secreted into the culture media of transfected host cells that co-express the target protein and the CMP-TPB(Prot G) fusion (lane 11); (2) the transmembrane retention (TMR) domain in the CMP-TPB(gE)-TMR(VSVG) fusion protein functions to localize the fusion protein with the host cell so that no significant or detectable amount of the fusion protein is released into the culture media (see lanes 8 and 12); and (3) the culture media of transfected host cells co-expressing the FVII-Fc target and the CMP-TPB(gE)-TMR(VSVG) fusion protein does not contain a significant or detectable amount of a recombinant protein species other than the desired FVII-Fc target protein (lane 12), in contrast to the culture media of transfected host cells that co-express the FVII-Fc target protein and the CMP-TPB(Prot G) fusion protein (lane 11), where a significant level of CMP-TPB (Prot G) fusion protein is co-secreted with the target protein.

Example 13

Enhanced Levels of IL13Rα2TF-Fc Target Protein Secreted from Cells

In this experiment, an IL13Rα2TF-Fc target protein was used as a representative example of an "Fc drug". The IL13Rα2TF-Fc target protein used in this experiment was the same V5-tagged IL13Rα2TF-Fc monomer as described in Example 2 and Table 4 above.

Figure 13A:
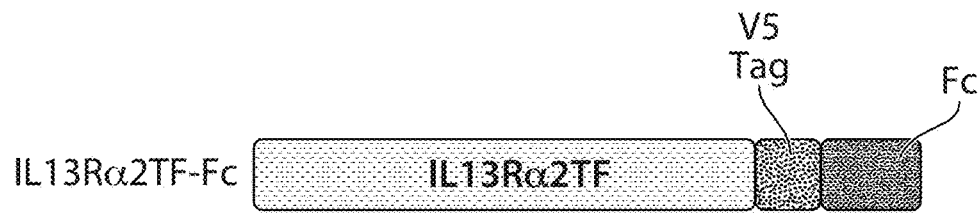
FIG. 13A is a diagram depicting a nucleic acid construct encoding a target protein described in Example 13 (and Example 1) and comprising a segment encoding a truncated form of the IL13Rα2 receptor protein ("IL13Rα2TF") augmented at its 3' end with a segment encoding a V5 epitope tag, which in turn was linked to a segment encoding an immunoglobulin Fc region comprising the hinge-CH2-CH3 region of an IgG heavy chain (designated "Fc") to promote formation of homodimers. The encoded target protein was designated "IL13Rα2TF-Fc". See Example 13 for additional details.

FIG. 13A shows a diagram of a nucleic acid construct that was prepared comprising a segment encoding an IL13Rα2TF-Fc target protein that was augmented in its 3' region and upstream from a segment encoding an Fc coding region with a segment encoding a V5 epitope tag for easy identification of the expressed protein using a standard anti-V5 antibody.

Figure 13B:
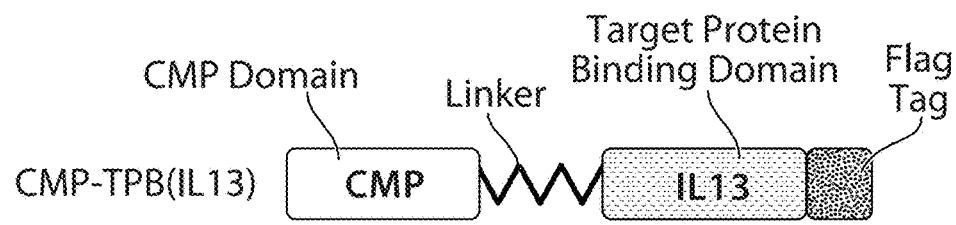
FIG. 13B is a diagram depicting a nucleic acid construct encoding a fusion protein comprising a segment encoding a "chaperone machinery polypeptide" ("CMP") domain consisting of a J domain from Erdj3 linked to a segment encoding a target protein binding (TPB) domain consisting of IL13, which was augmented at its 3' end with a segment encoding a Flag epitope tag for easy identification of the fusion protein. The encoded fusion protein was designated "CMP-TPB(IL13)". See Example 13 for additional details.

FIG. 13B shows a diagram of a nucleic acid construct encoding a CMP-TPB fusion protein comprising a segment encoding a CMP domain comprising a J domain from Erdj3 linked to a segment encoding IL13 as a target protein binding (TPB) domain, which was augmented at its 3' end with a segment encoding a Flag epitope tag for easy identification of the fusion protein. The construct was augmented at its 5' end with a segment encoding the Erdj3 signal sequence (not shown in FIG. 13B). The encoded fusion protein was designated "CMP-TPB(IL13)". The amino acid sequence of the encoded CMP-TPB(IL13) fusion protein is shown in Table 29 below.

TABLE 29

Amino Acid Sequence of a Flag-Tagged CMP-TPB(IL13) Fusion Protein

| Encoded Protein or Region (N- to C-terminal) | Sequence Identifier | Amino Acid Sequence 12345678901234567890123456 7890 |
|---|---|---|
| Flag-tagged CMP-TPB fusion protein | SEQ ID NO: 138 | MAPQNLSTFCLLLLYLIGAVIAGRDFYKIL GVPRSASIKDIKKAYRKLALQLHPDRNPDD PQAQEKFQDLGAAYEVLSDSEKRDIGGGSG GSGGSGGAAALTCLGGFASPGPVPPSTALR ELIEELVNITQNQKAPLCNGSMVWSINLTA GMYCAALESLINVSGCSAIEKTQRMLSGFC PHKVSAGQFSSLHVRDTKIEVAQFVKDLLL HLKKLFREGQFNLEGDYKDDDDK |
| Erdj3 signal sequence | residues 1-22 of SEQ ID NO: 138 | MAPQNLSTFCLLLLYLIGAVIA |
| CMP Domain (from Erdj3) | residues 23-83 of SEQ ID NO: 138 | GRDFYKILGVPRSASIKDIKKAYRKLALQL HPDRNPDDPQAQEKFQDLGAAYEVLSDSEK R |
| Linker | residues 84-100 of SEQ ID NO: 138 | DIGGGSGGSGGSGGAAA |
| TPB(IL13) Domain | residues 101-222 of SEQ ID NO: 138 | LTCLGGFASPGPVPPSTALRELIEELVNIT QNQKAPLCNGSMVWSINLTAGMYCAALESL INVSGCSAIEKTQRMLSGFCPHKVSAGQFS SLHVRDTKIEVAQFVKDLLLHLKKLFREGQ FN |
| Linker | residues 223-225 of SEQ ID NO: 138 | LEG |
| Flag epitope domain | residues 226-233 of SEQ ID NO: 138 | DYKDDDDK |

Figure 13C:
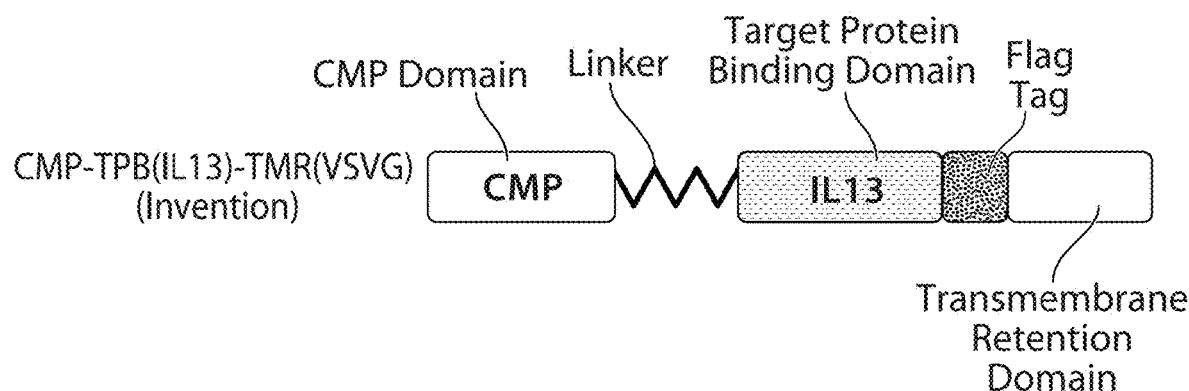
FIG. 13C is a diagram depicting a nucleic acid construct encoding a cell-associated secretion-enhancing (CASE) fusion protein according to the invention comprising a segment encoding a "chaperone machinery polypeptide" ("CMP") domain consisting of the J domain from the Erdj3 protein linked to a segment encoding a target protein binding (TPB) domain consisting of IL13, which was augmented at its 3' end with a segment encoding a Flag epitope tag, which in turn was linked to a segment encoding a transmembrane retention (TMR) domain consisting of the transmembrane and C-terminal region of the VSV-G protein. The encoded fusion protein was designated "CMP-TPB(IL13)-TMR (VSVG)". See Example 13 for additional details.

FIG. 13C shows a diagram depicting a nucleic acid construct that was prepared encoding a fusion protein according to the invention comprising a segment encoding a J domain from the Erdj3 protein as a CMP Domain linked to a segment encoding IL13 as a target protein binding (TPB) domain, which was augmented at its 3' end with a segment encoding a Flag epitope tag, which in turn was linked to a segment encoding a C-terminal region of the VSVG protein as a transmembrane retention (TMR) domain. The construct was augmented at its 5' end with a segment encoding the Erdj3 signal sequence (not shown in FIG. 13C). The encoded fusion protein was designated "CMP-TPB(IL13)-TMR(VSVG)". The amino acid sequence of this fusion protein, which includes a Flag epitope tag, is shown in Table 30 below.

TABLE 30

Amino Acid Sequence of a Flag-Tagged CMP-TPB(IL13)-TMR(VSVG) Fusion Protein.

| Encoded Protein or Region (N- to C-terminal) | Sequence Identifier | Amino Acid Sequence 12345678901234567890123456 7890 |
|---|---|---|
| Flag-tagged CMP-TPB-TMR(VSVG) fusion protein | SEQ ID NO: 139 | MAPQNLSTFCLLLLYLIGAVIAGRDFYKIL GVPRSASIKDIKKAYRKLALQLHPDRNPDD PQAQEKFQDLGAAYEVLSDSEKRDIGGGSG GSGGSGGAAALTCLGGFASPGPVPPSTALR ELIEELVNITQNQKAPLCNGSMVWSINLTA GMYCAALESLINVSGCSAIEKTQRMLSGFC PHKVSAGQFSSLHVRDTKIEVAQFVKDLLL HLKKLFREGQFNLEGDYKDDDDKGSRDDES LFFGDTGLSKNPIELVEGWFSSWKSSIASF FFIIGLIIGLFLVLRVGIHLCIKLKHTKKR QIYTDIEMNRLGK |

TABLE 30-continued

Amino Acid Sequence of a Flag-Tagged CMP-TPB(IL13)-TMR(VSVG) Fusion Protein.

| Encoded Protein or Region (N- to C-terminal) | Sequence Identifier | Amino Acid Sequence 12345678901234567890123456789 0 |
|---|---|---|
| Erdj3 signal sequence | residues 1-22 of SEQ ID NO: 139 | MAPQNLSTFCLLLLYLIGAVIA |
| CMP Domain (from Erdj3) | residues 23-83 of SEQ ID NO: 139 | GRDFYKILGVPRSASIKDIKKAYRKLALQL HPDRNPDDPQAQEKFQDLGAAYEVLSDSEK R |
| Linker | residues 84-100 of SEQ ID NO: 139 | DIGGGSGGSGGSGGAAA |
| TPB(IL13) Domain | residues 101-222 of SEQ ID NO: 139 | LTCLGGFASPGPVPPSTALRELIEELVNIT QNQKAPLCNGSMVWSINLTAGMYCAALESL INVSGCSAIEKTQRMLSGFCPHKVSAGQFS SLHVRDTKIEVAQFVKDLLLHLKKLFREGQ FN |
| Linker | residues 223-225 of SEQ ID NO: 139 | LEG |
| Flag epitope domain | residues 226-233 of SEQ ID NO: 139 | DYKDDDDK |
| Linker | residues 234-236 of SEQ ID NO: 139 | GSR |
| TMR(VSVG) Domain | residues 237-313 of SEQ ID NO: 139 | DDESLFFGDTGLSKNPIELVEGWFSSWKSS IASFFFIIGLIIGLFLVLRVGIHLCIKLKH TKKRQIYTDIEMNRLGK |

Figure 13D:
FIG. 13D shows X-ray film images of chemiluminescent signals of a Western blot analysis of samples of total culture, i.e., cells and media ("Total", lanes 1-4), of cell lysates ("Cell", lanes 5-8), and of culture media ("Media", lanes 9-12) of transfected cells expressing the IL13Rα2TF-Fc target protein alone (lanes 2, 6, and 10), when co-expressed with a CMP-TPB(IL13) fusion protein (lanes 3, 7, and 11), or when co-expressed with a cell-associated secretion-enhancing CMP-TPB(IL13)-TMR(VSVG) fusion protein of the invention (lanes 4, 8, and 12), as described in Example 13. The presence ("+") or absence ("−") of expression vectors encoding the target protein or a fusion protein in the transfected host cells of each culture is indicated above each lane of the Western blot. Mock cultures contained cells transfected with expression vector lacking a structural gene for expressing any protein (lanes 1, 5, and 9). It can be seen that co-expression of the IL13Rα2TF-Fc target protein with the CMP-TPB(IL13) fusion protein or the CMP-TPB(IL13)-TMR(VSVG) fusion protein of the invention significantly enhanced the level of secreted FVII-Fc target protein (lanes 11 and 12), with a greater level of target protein secreted into the culture media of cells co-expressing the target protein and the CMP-TPB(IL13)-TMR(VSVG) fusion protein of the invention (lane 12) than that of cells co-expressing the target protein and the CMP-TPB(IL13) fusion protein (lane 11). In contrast, in the absence of either fusion protein, a barely detectable amount of the IL13Rα2TF-Fc target protein was secreted into the culture media (lane 10). See Example 13 for additional details.

HEK293 cells were transfected with expression vector plasmids to compare levels of expression in culture media of IL13Rα2TF-Fc target protein expressed alone, co-expressed with the CMP-TPB(IL13) fusion protein, or co-expressed with the CMP-TPB(IL13)-TMR(VSVG) fusion protein of this invention. Transfected cells were cultured for two days, and samples of cell cultures were harvested and analyzed by Western blot assay using an anti-V5 antibody to detect secreted V5-tagged IL13Rα2TF-Fc target protein. FIG. 13D shows X-ray film images of chemiluminescent signals of the Western blot analysis of the culture samples. Mock cultures contained cells transfected with expression vector lacking a structural gene for expressing any protein (lanes 1, 5, and 9). As shown in FIG. 13D, when expressed in the absence of either fusion protein, the IL13Rα2TF-Fc target protein was clearly detected in a sample of cells and media ("Total", lane 2) and in cell lysates ("Cell", lane 6), but only barely detected in the culture media ("Media", lane 10). Co-expression of the IL13Rα2TF-Fc target protein with the CMP-TPB(IL13) fusion protein or the CMP-TPB(IL13)-TMR(VSVG) fusion protein of the invention dramatically enhanced the level of secreted IL13Rα2TF-Fc target protein (lanes 11 and 12) compared to the level of target protein secreted into the culture media when expressed in the absence of either fusion protein (lane 10). The Western blot also indicates that using a CMP fusion protein, i.e., either CMP-TPB(IL13) or CMP-TPB(IL13)-TMR(VSVG), led to a reduced level of expressed target protein being left inside the cell (compare lanes 6, 7, and 8).

The results show that the co-expression of the IL13Rα2TF-Fc target protein and either fusion protein significantly enhanced the level of expressed target protein secreted into culture media as compared to the level secreted in the absence of a CMP fusion protein. As noted above, co-expression of a target protein and a CMP-TPB-TMR fusion protein of this invention leads to improved secretion of the target protein, presumably without a significant amount of the fusion protein being co-secreted with the target protein into the culture medium. See, e.g., Example 12, supra.

Example 14

CMP-TPB(gE)-TMR(VSVG) Fusion Protein Enhances the Level of Co-Expressed Factor VIII-V5-Fc Target Protein Secreted from Cells The biological importance of Factor FVIII is demonstrated in hemophilia A, a congenital bleeding disorder occurring primarily in males that results from an X-chromosome-linked deficiency of FVIII. Standard treatment is replacement therapy that involves supply of functional exogenous FVIII to the patient, which enables natural clotting to stop the bleeding. A FVIII-Fc protein (providing a Factor VIII dimer) was developed to provide a prolonged half-life of FVIII activity in hemophilia A patients (Powell et al., *Blood,* 119(13): 3031-3037 (2012)). A B-domain deleted FVIII-Fc protein was approved by the United States Food and Drug Administration in 2013 (ELOCTATE®; Biogen Idec).

This experiment examined the effect of the Flag-tagged CMP-TPB(gE)-TMR(VSVG), described in Example 12 and Table 28 above, on the level of secretion of a V5-tagged FVIII-Fc target protein when the two proteins were co-expressed in the same host cell. The amino acid sequence of one chain of the V5-tagged FVIII-Fc target protein is shown in Table 31 below.

TABLE 31

Amino Acid Sequence of a V5-Tagged FVIII-Fc Target Protein Monomer.

| Encoded Protein or Region (N- to C-terminal) | Sequence Identifier | Amino Acid Sequence 12345678901234567890123456789 |
|---|---|---|
| V5-tagged FVIII-Fc target protein | SEQ ID NO: 140 | MQIELSTCFFLCLLRFCFSATRRYYLGAVE LSWDYMQSDLGELPVDARFPPRVPKSFPFN TSVVYKKTLFVEFTDHLFNIAKPRPPWMGL LGPTIQAEVYDTVVITLKNMASHPVSLHAV GVSYWKASEGAEYDDQTSQREKEDDKVFPG GSHTYVWQVLKENGPMASDPLCLTYSYLSH VDLVKDLNSGLIGALLVCREGSLAKEKTQT LHKFILLFAVFDEGKSWHSETKNSLMQDRD AASARAWPKMHTVNGYVNRSLPGLIGCHRK SVYWHVIGMGTTPEVHSIFLEGHTFLVRNH RQASLEISPITFLTAQTLLMDLGQFLLFCH ISSSHQHDGMEAYVKVDSCPEEPQLRMKNNE EAEDYDDDLTDSEMDVVRFDDDNSPSFIQI RSVAKKHPKTWVHYIAAEEEDWDYAPLVLA PDDRSYKSQYLNNGPQRIGRKYKKVRFMAY TDETFKTREAIQHESGILGPLLYGEVGDTL LIIFKNQASRPYNIYPHGITDVRPLYSRRL PKGVKHLKDFPILPGEIFKYKWTVTVEDGP TKSDPRCLTRYYSSFVNMERDLASGLIGPL LICYKESVDQRGNQIMSDKRNVILFSVFDE NRSWYLTENIQRFLPNPAGVQLEDPEFQAS NIMHSINGYVFDSLQLSVCLHEVAYWYILS IGAQTDFLSVFFSGYTFKHKMVYEDTLTLF PFSGETVFMSMENPGLWILGCHNSDFRNRG MTALLKVSSCDKNTGDYYEDSYEDISAYLL SKNNAIEPRSFSQNSRHPSTRQKQFNATTI PENDIEKTDPWFAHRTPMPKIQNVSSSDLL MLLRQSPTPHGLSLSDLQEAKYETFSDDPS PGAIDSNNSLSEMTHFRPQLHHSGDMVFTP ESGLQLRLNEKLGTTAATELKKLDFKVSST SNNLISTIPSDNLAAGTDNTSSLGPPSMPV HYDSQLDTTLFGKKSSPLTESGGPLSLSEE NNDSKLLESGLMNSQESSWGKNVSSTESGR LFKGKRAHGPALLTKDNALFKVSISLLKTN KTSNNSATNRKTHIDGPSLLIENSPSVWQN ILESDTEFKKVTPLIHDRMLMDKNATALRL NHMSNKTTSSKNMEMVQQKKEGPIPPDAQN PDMSFFKMLFLPESARWIQRTHGKNSLNSG QGPSPKQLVSLGPEKSVEGQNFLSEKNKVV VGKGEFTKDVGLKEMVFPSSRNLFLTNLDN LHENNTHNQEKKIQEEIEKKETLIQENVVL PQIHTVTGTKNFMKNLFLLSTRQNVEGSYD GAYAPVLQDFRSLNDSTNRTKKHTAHFSKK GEEENLEGLGNQTKQIVEKYACTTRISPNT SQQNFVTQRSKRALKQFRLPLEETELEKRI IVDDTSTQWSKNMKHLTPSTLTQIDYNEKE KGAITQSPLSDCLTRSHSIPQANRSPLPIA KVSSFPSIRPIYLTRVLFQDNSSHLPAASY RKKDSGVQESSHFLQGAKKNNLSLAILTLE MTGDQREVGSLGTSATNSVTYKKVENTVLP KPDLPKTSGKVELLPKVHIYQKDLFPTETS NGSPGHLDLVEGSLLQGTEGAIKWNEANRP GKVPFLRVATESSAKTPSKLLDPLAWDNHY GTQIPKEEWKSQEKSPEKTAFKKKDTILSL NACESNHAIAAINEGQNKPEIEVTWAKQGR TERLCSQNPPVLKRHQREITRTTLQSDQEE IDYDDTISVEMKKEDFDIYDEDENQSPRSF QKKTRHYFIAAVERLWDYGMSSSPHVLRNR AQSGSVPQFKKVVFQEFTDGSFTQPLYRGE LNEHLGLLGPYIRAEVEDNIMVTFRNQASR PYSFYSSLISYEEDQRQGAEPRKNFVKPNE TKTYFWKVQHHMAPTKDEFDCKAWAYFSDV DLEKDVHSGLIGPLLVCHTNTLNPAHGRQV TVQEFALFFTIFDETKSWYFTENMERNCRA PCNIQMEDPTFKENYRFHAINGYIMDTLPG |

TABLE 31-continued

Amino Acid Sequence of a V5-Tagged FVIII-Fc Target Protein Monomer.

| Encoded Protein or Region (N- to C-terminal) | Sequence Identifier | Amino Acid Sequence 12345678901234567890123456789 0 |
|---|---|---|
| | | LVMAQDQRIRWYLLSMGSNENIHSIHFSGH VFTVRKKEEYKMALYNLYPGVFETVEMLPS KAGIWRVECLIGEHLHAGMSTLFLVYSNKC QTPLGMASGHIRDFQITASGQYGQWAPKLA RLHYSGSINAWSTKEPFSWIKVDLLAPMII HGIKTQGARQKFSSLYISQFIIMYSLDGKK WQTYRGNSTGTLMVFFGNVDSSGIKHNIFN PPIIARYIRLHPTHYSIRSTLRMELMGCDL NSCSMPLGMESKAISDAQITASSYFTNMFA TWSPSKARLHLQGRSNAWRPQVNNPKEWLQ VDFQKTMKVTGVTTQGVKSLLTSMYVKEFL ISSSQDGHQWTLFFQNGKVKVFQGNQDSFT PVVNSLDPPLLTRYLRIHPQSWVHQIALRM EVLGCEAQDLYLEGKPIPNPLLGLDSTSRP KSCDKTHTCPPCPAPELLGGPSVFLFPPKP KDTLMISRTPEVTCVVVDVSHEDPEVKFNW YVDGVEVHNAKTKPREEQYNSTYRVVSVLT VLHQDWLNGKEYKCKVSNKALPAPIEKTIS KAKGQPREPQVYTLPPSRDELTKNQVSLTC LVKGFYPSDIAVEWESNGQPENNYKTTPPV LDSDGSFFLYSKLTVDKSRWQQGNVFSCSV MHEALHNHYTQKSLSLSPGK |
| FVIII signal sequence | Residues 1-19 of SEQ ID NO: 140 | MQIELSTCFFLCLLRFCFS |
| FVIII | residues 20-2351 of SEQ ID NO: 140 | ATRRYYLGAVELSWDYMQSDLGELPVDARF PPRVPKSFPFNTSVVYKKTLFVEFTDHLFN IAKPRPPWMGLLGPTIQAEVYDTVVITLKN MASHPVSLHAVGVSYWKASEGAEYDDQTSQ REKEDDKVFPGGSHTYVWQVLKENGPMASD PLCLTYSYLSHVDLVKDLNSGLIGALLVCR EGSLAKEKTQTLHKFILLFAVFDEGKSWHS ETKNSLMQDRDAASARAWPKMHTVNGYVNR SLPGLIGCHRKSVYWHVIGMGTTPEVHSIF LEGHTFLVRNHRQASLEISPITFLTAQTLL MDLGQFLLFCHISSHQHDGMEAYVKVDSCP EEPQLRMKNNEEAEDYDDDLTDSEMDVVRF DDDNSPSFIQIRSVAKKHPKTWVHYIAAEE EDWDYAPLVLAPDDRSYKSQYLNNGPQRIG RKYKKVRFMAYTDETFKTREAIQHESGILG PLLYGEVGDTLLIIFKNQASRPYNIYPHGI TDVRPLYSRRLPKGVKHLKDFPILPGEIFK YKWTVTVEDGPTKSDPRCLTRYYSSFVNME RDLASGLIGPLLICYKESVDQRGNQIMSDK RNVILFSVFDENRSWYLTENIQRFLPNPAG VQLEDPEFQASNIMHSINGYVFDSLQLSVC LHEVAYWYILSIGAQTDFLSVFFSGYTFKH KMVYEDTLTLFPFSGETVFMSMENPGLWIL GCHNSDFRNRGMTALLKVSSCDKNTGDYYE DSYEDISAYLLSKNNAIEPRSFSQNSRHPS TRQKQFNATTIPENDIEKTDPWFAHRTPMP KIQNVSSSDLLMLLRQSPTPHGLSLSDLQE AKYETFSDDPSPGAIDSNNSLSEMTHFRPQ LHHSGDMVFTPESGLQLRLNEKLGTTAATE LKKLDFKVSSTSNNLISTIPSDNLAAGTDN TSSLGPPSMPVHYDSQLDTTLFGKKSSPLT ESGGPLSLSEENNDSKLLESGLMNSQESSW GKNVSSTESGRLFKGKRAHGPALLTKDNAL FKVSISLLKTNKTSNNSATNRKTHIDGPSL LIENSPSVWQNILESDTEFKKVTPLIHDRM LMDKNATALRLNHMSNKTTSSKNMEMVQQK KEGPIPPDAQNPDMSFFKMLFLPESARWIQ RTHGKNSLNSGQGPSPKQLVSLGPEKSVEG QNFLSEKNKVVVGKGEFTKDVGLKEMVFPS SRNLFLTNLDNLHENNTHNQEKKIQEEIEK KETLIQENVVLPQIHTVTGTKNFMKNLFLL STRQNVEGSYDGAYAPVLQDFRSLNDSTNR TKKHTAHFSKKGEEENLEGLGNQTKQIVEK YACTTRISPNTSQQNFVTQRSKRALKQFRL PLEETELEKRIIVDDTSTQWSKNMKHLTPS |

TABLE 31-continued

Amino Acid Sequence of a V5-Tagged FVIII-Fc Target Protein Monomer.

| Encoded Protein or Region (N- to C-terminal) | Sequence Identifier | Amino Acid Sequence 12345678901234567890123456789 0 |
|---|---|---|
| | | TLTQIDYNEKEKGAITQSPLSDCLTRSHSI |
| | | PQANRSPLPIAKVSSFPSIRPIYLTRVLFQ |
| | | DNSSHLPAASYRKKDSGVQESSHFLQGAKK |
| | | NNLSLAILTLEMTGDQREVGSLGTSATNSV |
| | | TYKKVENTVLPKPDLPKTSGKVELLPKVHI |
| | | YQKDLFPTETSNGSPGHLDLVEGSLLQGTE |
| | | GAIKWNEANRPGKVPFLRVATESSAKTPSK |
| | | LLDPLAWDNHYGTQIPKEEWKSQEKSPEKT |
| | | AFKKKDTILSLNACESNHAIAAINEGQNKP |
| | | EIEVTWAKQGRTERLCSQNPPVLKRHQREI |
| | | TRTTLQSDQEEIDYDDTISVEMKKEDFDIY |
| | | DEDENQSPRSFQKKTRHYFIAAVERLWDYG |
| | | MSSSPHVLRNRAQSGSVPQFKKVVFQEFTD |
| | | GSFTQPLYRGELNEHLGLLGPYIRAEVEDN |
| | | IMVTFRNQASRPYSFYSSLISYEEDQRQGA |
| | | EPRKNFVKPNETKTYFWKVQHHMAPTKDEF |
| | | DCKAWAYFSDVDLEKDVHSGLIGPLLVCHT |
| | | NTLNPAHGRQVTVQEFALFFTIFDETKSWY |
| | | FTENMERNCRAPCNIQMEDPTFKENYRFHA |
| | | INGYIMDTLPGLVMAQDQRIRWYLLSMGSN |
| | | ENIHSIHFSGHVFTVRKKEEYKMALYNLYP |
| | | GVFETVEMLPSKAGIWRVECLIGEHLHAGM |
| | | STLFLVYSNKCQTPLGMASGHIRDFQITAS |
| | | GQYGQWAPKLARLHYSGSINAWSTKEPFSW |
| | | IKVDLLAPMIIHGIKTQGARQKFSSLYISQ |
| | | FIIMYSLDGKKWQTYRGNSTGTLMVFFGNV |
| | | DSSGIKHNIFNPPIIARYIRLHPTHYSIRS |
| | | TLRMELMGCDLNSCSMPLGMESKAISDAQI |
| | | TASSYFTNMFATWSPSKARLHLQGRSNAWR |
| | | PQVNNPKEWLQVDFQKTMKVTGVTTQGVKS |
| | | LLTSMYVKEFLISSSQDGHQWTLFFQNGKV |
| | | KVFQGNQDSFTPVVNSLDPPLLTRYLRIHP |
| | | QSWVHQIALRMEVLGCEAQDLY |
| Linker | residues 2352-2353 of SEQ ID NO: 140 | LE |
| V5 epitope domain | residues 2354-2367 of SEQ ID NO: 140 | GKPIPNPLLGLDST |
| Linker | residues 2368-2369 of SEQ ID NO: 140 | SR |
| Fc domain | residues 2370-2600 of SEQ ID NO: 140 | PKSCDKTHTCPPCPAPELLGGPSVFLFPPK PKDTLMISRTPEVTCVVVDVSHEDPEVKFN WYVDGVEVHNAKTKPREEQYNSTYRVVSVL TVLHQDWLNGKEYKCKVSNKALPAPIEKTI SKAKGQPREPQVYTLPPSRDELTKNQVSLT CLVKGFYPSDIAVEWESNGQPENNYKTTPP VLDSDGSFFLYSKLTVDKSRWQQGNVFSCS VMHEALHNHYTQKSLSLSPGK |

The host HEK293 cells were transfected with expression plasmids for the FVIII-Fc target protein alone, with expression plasmids for FVIII-Fc and the CMP-TPB(gE)-TMR (VSVG) fusion protein of the invention, or with mock "empty vector" plasmids (control). The levels of target protein secretion were measured by ELISA.

Figure 14A:
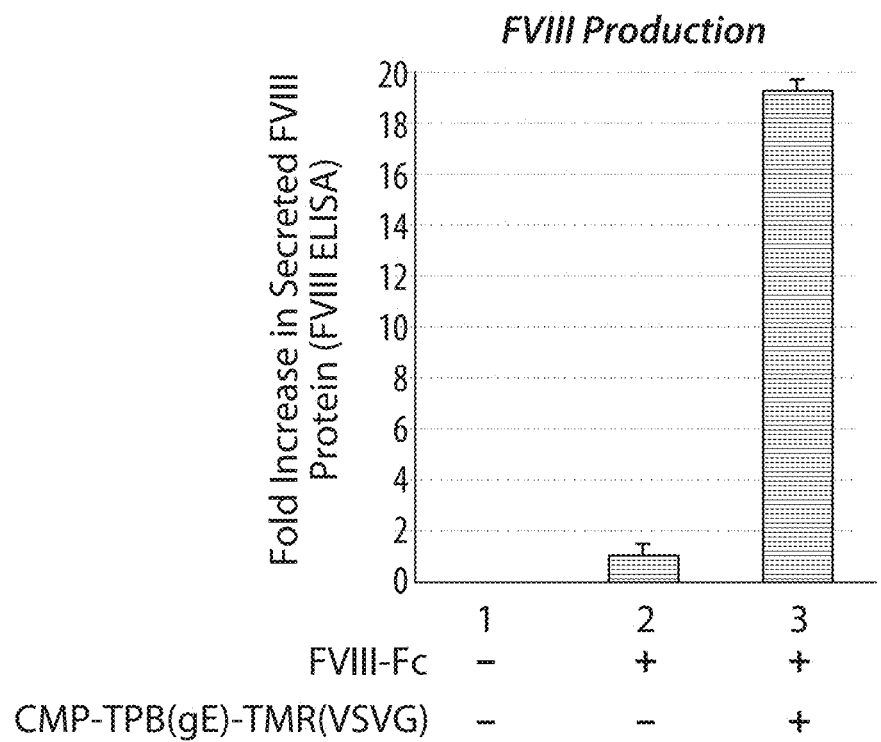
FIG. 14A shows bar graphs of the fold increase in FVIII-Fc target protein detected by ELISA in media of cultures of transfected HEK293 host cells expressing an FVIII-Fc target protein alone (bar graph 2) or co-expressing the FVIII-Fc target protein and a CMP-TPB(gE)-TMR (VSVG) fusion protein of the invention (bar graph 3) as described in Example 14. Culture media were assayed for FVIII protein using an enzyme-linked immunosorbent assay (ELISA). The presence ("+") or absence ("−") of expression vectors encoding target protein or fusion protein in the transfected host cells of each culture is indicated below each bar graph. Mock cultures contained cells transfected with expression vector lacking a structural gene for expressing any protein and were used as a negative control (bar graph 1, absence (−) of both target protein and CMP-TPB(gE)-TMR(VSVG) expression vectors). The data in the bar graphs have been normalized by subtracting non-specific background signal in media from mock cultures and setting the amount of FVIII-Fc target protein secreted into culture media when expressed in the absence of the CMP-TPB(gE)-TMR(VSVG) fusion protein at a relative value of 1 (bar graph 2). The results show that co-expression of the FVIII-Fc target protein and the CMP-TPB(gE)-TMR(VSVG) fusion protein of the invention significantly enhanced the level of FVIII-Fc target protein secreted into culture media (bar graph 3) as compared to the level of target protein secreted into culture media when expressed in the absence of the CMP-TPB(gE)-TMR(VSVG) fusion protein (bar graph 2). See Example 14 for additional details.

Referring to FIG. 14A, the bar graphs show the fold increase in FVIII-Fc target protein detected by ELISA in media of cultures of transfected HEK293 host cells expressing an FVIII-Fc target protein alone or co-expressing the FVIII-Fc target protein and a CMP-TPB(gE)-TMR(VSVG) fusion protein of the invention. Samples of culture media were assayed for FVIII protein using a commercially available enzyme-linked immunosorbent assay (ELISA) (Visu-Lize™ FVIII Antigen Kit, Affinity Biologics Inc.). Mock cultures contained cells transfected with expression vector lacking a structural gene for expressing any protein and were used as a negative control (bar graph 1). The data in the bar graphs have been normalized by subtracting non-specific background signal in media from mock cultures and setting the amount of FVIII-Fc target protein secreted into culture media when expressed in the absence of the CMP-TPB(gE)-TMR(VSVG) fusion protein at a relative value of 1 (bar graph 2). The results show that co-expression of the FVIII-Fc target protein and the CMP-TPB(gE)-TMR(VSVG) CASE fusion protein of the invention significantly enhanced (by 19-fold) the level of FVIII-Fc target protein secreted from transfected host cells into the culture media (bar graph 3) as compared to the level of target protein secreted into culture media when expressed in the absence of the CMP-TPB(gE)-TMR(VSVG) fusion protein (bar graph 2).

Figure 14B:
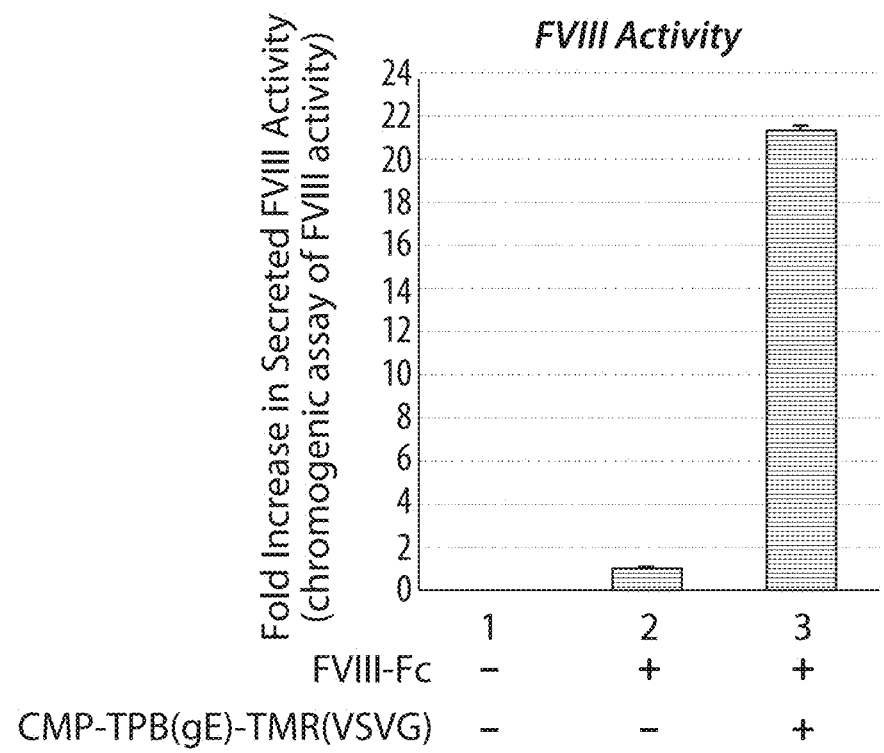
FIG. 14B shows bar graphs of the fold increase in FVIII activity in media of cultures of transfected HEK293 host cells expressing the FVIII-Fc target protein alone (bar graph 2) or co-expressing the FVIII-Fc target protein and the CMP-TPB(gE)-TMR(VSVG) fusion protein of the invention (bar graph 3) as described in Example 14. The media were assayed for FVIII activity using a standard chromogenic assay. The presence ("+") or absence ("−") of expression vectors encoding target protein or fusion protein in the transfected host cells of each culture is indicated below each bar graph. Mock cultures (bar graph 1) contained cells transfected with expression vector lacking a structural gene for expressing any protein and were used as a negative control. The data in the bar graphs have been normalized by subtracting non-specific background signal in media from mock cultures and setting the amount of FVIII activity secreted into culture media when expressed in the absence of the CMP-TPB(gE)-TMR(VSVG) fusion protein at a relative value of 1 (bar graph 2). The results show that co-expression of the FVIII-Fc target protein and the CMP-TPB(gE)-TMR (VSVG) fusion protein of the invention significantly enhanced the level of FVIII activity secreted into culture media (bar graph 3) as compared to the level of FVIII activity secreted into culture media when expressed in the absence of the CMP-TPB(gE)-TMR(VSVG) fusion protein (bar graph 2). See Example 14 for additional details.

FIG. 14B shows bar graphs of the fold increase in FVIII activity in samples of culture media as detected by chromogenic assay (BIOPHEN FVIII:C, HYPHEN BioMed, Paris, France). Mock cultures contained cells transfected with expression vector lacking a structural gene for expressing any protein and were used as a negative control (bar graph 1). The data in the bar graphs have been normalized by subtracting non-specific background signal in media from mock cultures and setting the amount of FVIII activity secreted into culture media when expressed in the absence of the CMP-TPB(gE)-TMR(VSVG) fusion protein at a relative value of 1 (bar graph 2). Similar to the results for secretion of the FVIII-Fc target protein shown in the bar graphs in FIG. 14A, the results in FIG. 14B show that co-expression of the FVIII-Fc target protein and the CMP-TPB(gE)-TMR(VSVG) fusion protein of the invention significantly enhanced (by 21-fold) the level of FVIII activity secreted into culture media (bar graph 3) as compared to the level of FVIII activity secreted into culture media when expressed in the absence of the CMP-TPB(gE)-TMR(VSVG) fusion protein (bar graph 2).

FIG. 14C shows a Western blot analysis of the location of the CMP-TPB(gE)-TMR(VSVG) fusion protein of the invention in the transfected host cells ("Cell Lysate", lanes 1-3) and in culture media ("Culture Media", lanes 4-6). As noted above, mock cultures contained cells transfected with expression vector lacking a structural gene for expressing any protein and were used as a negative control ("mock", lanes 1 and 4). The Western blot analysis shows that the CMP-TPB-TMR(VSVG) fusion protein was detected only in the samples of cell lysates (lane 3) and not in samples of cell culture media (lane 6), indicating that the CMP-TPB (gE)-TMR(VSVG) fusion protein remained associated with the host cell and was not secreted into the culture media with the FVIII-Fc target protein (bar graph 3 in FIG. 14A, bar graph 3 in FIG. 14B). All host cells were also co-transfected with a reporter plasmid expressing green fluorescent protein ("GFP") to show successful transfection and operability of the transfected host cells, as indicated by the expression of GFP in lanes 1-3 in the lower panel of FIG. 14C.

Example 15

Enhancement of Levels of Secreted Anti-IL8 IgG1 Antibody

The above examples showed that expression and secretion of target proteins comprising a protein of interest fused to an immunoglobulin Fc region, as a model of an "Fc drug", were significantly enhanced when co-expressed with a cell-associated secretion-enhancing (CASE) fusion protein of the invention. This study compared secretion enhancement of an anti-IL8 monoclonal antibody target protein (anti-IL8 Mab) when co-expressed with either of two fusion proteins of the invention.

The CMP-TPB(gE)-TMR(VSVG) fusion protein used in this study was the same Flag-tagged CMP-TPB(gE)-TMR (VSVG) described in Example 12 and Table 28 above Another fusion protein was prepared that was similar to the CMP-TPB(gE)-TMR(VSVG) fusion protein but comprising the transmembrane region of the p23 protein, designated "TMR(p23)", as the TMR domain. This fusion protein was designated "CMP-TPB(gE)-TMR(p23)". The amino acid sequence of the CMP-TPB(gE)-TMR(p23) fusion protein, which includes a Flag epitope tag, is shown in Table 32 below.

TABLE 32

Amino Acid Sequence of a Flag-Tagged CMP-TPB(gE)-TMR(p23) Fusion Protein

| Encoded Protein or Region (N- to C-terminal) | Sequence Identifier | Amino Acid Sequence 12345678901234567890123456789 0 |
|---|---|---|
| Flag-tagged CMP-TPB-TMR(p23) fusion protein | SEQ ID NO: 141 | MAPQNLSTFCLLLLYLIGAVIAGRDFYKIL GVPRSASIKDIKKAYRKLALQLHPDRNPDD PQAQEKFQDLGAAYEVLSDSEKRDIGGGSG GSGGSGGAAAGTPKTSWRRVSVGEDVSLLP APGPTGRGPTQKLLWAVEPLDGCGPLHPSW VSLMPPKQVPETVVDAACMRAPVPLAMAYA PPAPSATGGLRTDFVWQERAAVVNRSLVIH GVRETDSGLYTLSVGDIKDPARQVASVVLV VQPAPVPTPPPTPADYDEDDNDEGEDESLA GTPASGTPRLPPPPAPPRSWPSAPEVSHVR GVTVRMETPEAILFSPGETFSTNVSIHAIA HDDQTYSMDVVWLRFDVPTSCAEMRIYESC LYHPQLPECLSPADAPCAASTWTSRLAVRS YAGCSRTNPPPRCSAEAHMEPVPGLAWQAA SVNLEFRDASPQHSGLYLCVVYVNDHIHAW GHITISTAAQYRNAVVEQPLPQRGADLAEL EGDYKDDDDKGSRTRVLYFSIFSMFCLIGL ATWQVFYLRRFFKAKKLIE |
| Erdj3 signal sequence | residues 1-22 of SEQ ID NO: 141 | MAPQNLSTFCLLLLYLIGAVIA |
| CMP Domain (from Erdj3) | residues 23-83 of SEQ ID NO: 141 | GRDFYKILGVPRSASIKDIKKAYRKLALQL HPDRNPDDPQAQEKFQDLGAAYEVLSDSEK R |

TABLE 32-continued

Amino Acid Sequence of a Flag-Tagged CMP-TPB(gE)-TMR(p23) Fusion Protein

| Encoded Protein or Region (N- to C-terminal) | Sequence Identifier | Amino Acid Sequence 12345678901234567890123456789 0 |
|---|---|---|
| Linker | residues 84-100 of SEQ ID NO: 141 | DIGGGSGGSGGSGGAAA |
| TPB(gE) Domain | residues 101-479 of SEQ ID NO: 141 | GTPKTSWRRVSVGEDVSLLPAPGPTGRGPT QKLLWAVEPLDGCGPLHPSWVSLMPPKQVP ETVVDAACMRAPVPLAMAYAPPAPSATGGL RTDFVWQERAAVVNRSLVIHGVRETDSGLY TLSVGDIKDPARQVASVVLVVQPAPVPTPP PTPADYDEDDNDEGEDESLAGTPASGTPRL PPPPAPPRSWPSAPEVSHVRGVTVRMETPE AILFSPGETFSTNVSIHAIAHDDQTYSMDV VWLRFDVPTSCAEMRIYESCLYHPQLPECL SPADAPCAASTWTSRLAVRSYAGCSRTNPP PRCSAEAHMEPVPGLAWQAASVNLEFRDAS PQHSGLYLCVVYVNDHIHAWGHITISTAAQ YRNAVVEQPLPQRGADLAE |
| Linker | residues 480-482 of SEQ ID NO: 141 | LEG |
| Flag epitope domain | residues 483-490 of SEQ ID NO: 141 | DYKDDDDK |
| Linker | residues 491-493 of SEQ ID NO: 141 | GSR |
| TMR(p23) Domain | residues 494-529 of SEQ ID NO: 141 | TR<u>VLYFSIFSMFCLIGLATWQVF</u>YLRRFFK AKKLIE |

HEK293 cells were transfected with expression vector plasmids for expressing the anti-IL8 Mab target protein alone or for co-expressing the target protein and either the CMP-TPB(gE)-TMR(VSVG) fusion protein or the CMP-TPB(gE)-TMR(p23) fusion protein.

Expression of the anti-IL8 Mab target protein in culture media was analyzed by ELISA with IL8 as a substrate and an anti-human IgG antibody (anti-hIgG antibody, catalog no. AP112P, Millipore) as a detecting antibody. A 96-well plate was coated with IL8 and incubated with media from cultures of cells transfected to express the anti-IL8 Mab target protein alone or co-expressing anti-IL8 Mab target protein and either the CMP-TPB(gE)-TMR(VSVG) fusion protein or the CMP-TPB(gE)-TMR(p23). Mock cultures were tested by the same ELISA as negative controls.

The results are shown in the bar graphs in FIG. 15. Mock cultures (bar graph 1) contained cells transfected with expression vector lacking a structural gene for expressing any protein and were used as a negative control. The data in the bar graphs have been normalized by subtracting non-specific background signal in media from mock cultures and setting the amount of anti-IL8 Mab target protein secreted into culture media when expressed in the absence of either fusion protein at a relative value of 1 (bar graph 2). The results show that co-expression of the anti-IL8 Mab target protein with either the CMP-TPB(gE)-TMR(VSVG) fusion protein (bar graph 3) or the CMP-TPB(gE)-TMR(p23) fusion protein (bar graph 4) significantly enhanced the level of anti-IL8 Mab target protein secreted into the culture media as compared to the level of target protein secreted into culture media when expressed in the absence of either fusion protein (bar graph 2). In particular, co-expression of the anti-IL8 Mab target protein and the CMP-TPB(gE)-TMR (VSVG) fusion protein resulted in a 2.5-fold increase in the level of anti-IL8 Mab target protein secreted into culture media as compared to the level of target protein secreted into culture media when expressed in the absence of either fusion protein. Co-expression of the anti-IL8 Mab target protein and the CMP-TPB(gE)-TMR(p23) fusion protein resulted in more than a 4-fold increase in the level of anti-IL8 Mab target protein secreted into culture media as compared to the level of anti-IL8 Mab secreted into culture media when expressed in the absence of either fusion protein. The results also indicate that the anti-IL8 Mab target protein that was secreted into the culture media was functional, as it retained IL8 binding activity in the ELISA. The results further indicate that selection of a particular transmembrane region for use as the TMR domain in a CASE fusion protein of the invention can affect the level of enhancement of target protein secreted from a host cell. As shown here, one transmembrane region used as a TMR domain of a CASE fusion protein may provide a higher level of enhancement of target protein secreted from a cell than that provided by a CASE fusion protein comprising a different TMR domain. More broadly, the results also show that the level of target protein secreted from a host cell can be adjusted (to be higher or lower) as such a need may arise according to the selection of the TMR domain. For example, although in many cases the goal may be to simply maximize the level of target protein that is secreted from a cell, in some cases the maximum level of secreted target protein that may be obtainable, at least theoretically, may lead to some undesirable effect outside the cell, in the medium, in the overall production run, or in a subsequent purification protocol. In such cases, it may be beneficial to opt for an enhanced but not maximal level of target protein secreted from a cell.

Example 16

Enhancement in the Level of Secretion of a Therapeutic Anti-VEGF Antibody Target Protein Using CASE Fusion Proteins with Different TMR Domains This experiment examined the level of anti-VEGF-A monoclonal antibody secreted from a cell when co-expressed with either of two CASE fusion proteins comprising different TMR domains.

The anti-VEGF-A monoclonal antibody (anti-VEGF Mab) used in this experiment was the same as described in Example 6 and Table 18 above.

The anti-VEGF Mab target protein was expressed in HEK293 cells in the presence and absence of either the CMP-TPB(gE)-TMR(VSVG) fusion protein described in Example 12 and Table 28 above or the CMP-TPB(gE)-TMR (p23) fusion protein described in Example 15 and Table 32 above. Samples of the media from cell cultures were assayed for anti-VEGF-A Mab by ELISA using VEGF as a substrate. The wells of a 96-well plate were coated with recombinant purified human VEGF-A and incubated with media from cultures of cells transfected to express the anti-VEGF-A Mab target protein ("Anti-VEGF Mab") alone or co-expressing anti-VEGF Mab target protein and either the CMP-TPB(gE)-TMR(VSVG) CASE fusion protein of the invention or the CMP-TPB(gE)-TMR(p23) CASE fusion protein of the invention.

The results are shown in the bar graphs in FIG. 16. Mock cultures contained cells transfected with an expression vector lacking a structural gene for expressing any protein and were used as a negative control (bar graph 1). The results in the bar graphs have been normalized by subtracting non-specific background signal in media from mock cultures and setting the amount of anti-VEGF Mab target protein secreted into culture media when expressed in the absence of either fusion protein at a relative value of 1 ("Anti-VEGF Mab", bar graph 2). The results show that co-expression of the anti-VEGF-A Mab target protein with either the CMP-TPB (gE)-TMR(VSVG) fusion protein (bar graph 3) or the CMP-TPB(gE)-TMR(p23) fusion protein (bar graph 4) significantly enhanced the level of anti-VEGF-A Mab target protein secreted into culture media as compared to the level of anti-VEGF-A Mab target protein secreted into culture media when expressed in the absence of either fusion protein (bar graph 2). In particular, as shown in bar graph 3 of FIG. 16, co-expression of the anti-VEGF-A Mab target protein and the CMP-TPB(gE)-TMR(VSVG) fusion protein resulted in a 4-fold increase in the level of anti-VEGF-A Mab target protein secreted into the culture media as compared to the level of target protein secreted into culture media when expressed in the absence of the fusion protein (bar graph 2). As shown in bar graph 4 of FIG. 16, co-expression of the anti-VEGF-A Mab target protein and the CMP-TPB(gE)-TMR(p23) fusion protein resulted in a 7-fold increase in the level of anti-VEGF-A Mab target protein secreted into culture media as compared to the level target protein secreted into culture media in the absence the fusion protein (bar graph 2).

As noted regarding the results in Example 15 above, the results here also show that selection of a transmembrane region for use as a TMR domain in a CASE fusion protein of the invention can have a significant effect on the level of enhancement of secreted target protein that is obtained. The results also indicate that the anti-VEGF-A Mab target protein that was secreted into the culture media was functional, as it retained VEGF-binding activity in the ELISA.

Example 17

Enhancement in the Level of Secretion of a Therapeutic Anti-TNFα Antibody Target Protein Using CASE Fusion Proteins with Different TMR Domains This experiment examined the level of anti-TNFα monoclonal antibody (adalimumab) secreted from a cell when co-expressed with either of two CASE fusion proteins comprising different TMR domains.

The anti-TNFα monoclonal antibody (anti-TNFα Mab) was the same as that described in Example 5 and Table 17.

The anti-TNFα Mab target protein was expressed in HEK293 cells in the presence and absence of the CMP-TPB (gE)-TMR(VSVG) fusion protein described in Example 12 and Table 28 or the CMP-TPB(gE)-TMR(p23) fusion protein described in Example 15 and Table 32. Samples of culture media were analyzed for anti-TNFα Mab target protein by assaying for TNFα binding in an ELISA. Wells of a 96-well plate were coated with recombinant purified human TNFα and incubated with culture media of transfected host cells expressing anti-TNFα Mab alone or culture media of transfected cells co-expressing anti-TNFα Mab and either the CMP-TPB-TMR(VSVG) fusion protein or the CMP-TPB-TMR(p23) fusion protein.

Figure 19A:
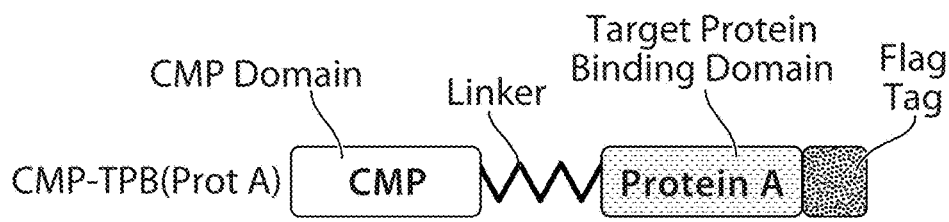
FIG. 19A is a diagram depicting a nucleic acid construct encoding a fusion protein described in Example 18, in which a segment encoding a "chaperone machinery polypeptide" ("CMP") domain comprising a J domain from Erdj3 linked to a segment encoding a target protein binding ("TPB") domain comprising an Fc-binding portion of Protein A ("Protein A"), which construct was augmented at its 3' end with a segment encoding a Flag epitope tag for easy identification with a standard anti-Flag antibody. The encoded fusion protein is designated "CMP-TPB(Prot A)". See Example 18 for additional details.

The results are shown in the bar graphs in FIG. 17. Mock cultures contained host cells transfected with expression vector lacking a structural gene for expressing any protein and were used as a negative control (bar graph 1). The data in the bar graphs have been normalized by subtracting non-specific background signal in media from mock cultures and setting the amount of anti-TNFα Mab target protein secreted into culture media when expressed in the absence of either fusion protein at a relative value of 1 (bar graph 2). The results show that co-expression of the anti-TNFα Mab target protein with either the CMP-TPB(gE)-TMR(VSVG) fusion protein (bar graph 3) or the TPB-TPB(gE)-TMR(p23) fusion protein (bar graph 4) significantly enhanced the level of anti-TNFα Mab target protein secreted into culture media as compared to the level of anti-TNFα Mab target protein secreted into culture media when expressed in the absence of either fusion protein (bar graph 2). In particular, as shown in bar graph 3 of FIG. 17, co-expression of the anti-TNFα Mab target protein and the CMP-TPB(gE)-TMR(VSVG) fusion protein resulted in a 3-fold increase in the level of anti-TNFα Mab target protein secreted into the culture media as compared to the level of target protein secreted into the media when expressed in the absence of either fusion protein (bar graph 2). As shown in bar graph 4 of FIG. 17, co-expression of the anti-TNFα Mab target protein with the CMP-TPB(gE)-TMR(p23) fusion protein resulted in a greater than 2-fold increase in the level of anti-TNFα Mab target protein secreted into culture media as compared to the level of target protein secreted into culture media in the absence of either fusion protein (bar graph 2). The results also indicate that the anti-TNFα Mab target protein that was secreted into the culture media was functional, as it retained TNFα binding activity in the ELISA. As noted with respect to the results in Examples 15 and 16 above, the results here also show that selection of a particular transmembrane region for use as a TMR domain of a CASE fusion protein of the invention can have an effect on the level of optimal enhancement of target protein secreted from a cell.

its 5' end with a segment encoding the Erdj3 signal sequence (not shown in FIG. 19A). The construct was designated "CMP-TPB(Prot A)". The amino acid sequence of the encoded Flag-tagged CMP-TPB(Prot A) fusion protein is shown in Table 33 below.

TABLE 33

Amino Acid Sequence of a Flag-Tagged CMP-TPB(Prot A) Fusion Protein.

| Encoded Protein or Region (N- to C-terminal) | Sequence Identifier | Amino Acid Sequence 123456789012345678901234567890 |
|---|---|---|
| Flag-tagged CMP-TPB(Prot A) fusion protein | SEQ ID NO: 146 | MAPQNLSTFCLLLLYLIGAVIAGRDFYKIL GVPRSASIKDIKKAYRKLALQLHPDRNPDD PQAQEKFQDLGAAYEVLSDSEKRDIGGGSG GSGGSGGAAAADNKFNKEQQNAFYEILNMP NLNEEQRNGFIQSLKDDPSQSANVLGEAKK LNDSQAPKLEGDYKDDDDK |
| Erdj3 signal sequence | residues 1-22 of SEQ ID NO: 146 | MAPQNLSTFCLLLLYLIGAVIA |
| CMP Domain (from Erdj3) | residues 23-83 of SEQ ID NO: 146 | GRDFYKILGVPRSASIKDIKKAYRKLALQL HPDRNPDDPQAQEKFQDLGAAYEVLSDSEK R |
| Linker | residues 84-100 of SEQ ID NO: 146 | DIGGGSGGSGGSGGAAA |
| TPB(Prot A) Domain (from Protein A) | residues 101-158 of SEQ ID NO: 146 | ADNKFNKEQQNAFYEILNMPNLNEEQRNGF IQSLKDDPSQSANVLGEAKKLNDSQAPK |
| Linker | residues 159-161 of SEQ ID NO: 146 | LEG |
| Flag epitope domain | residues 162-169 of SEQ ID NO: 146 | DYKDDDDK |

Example 18

Further Studies of Fusion Proteins Comprising Alternative Target Protein Binding (TPB) Domains for Enhancing Expression of Target Proteins This example examined the effectiveness of various fusion proteins comprising alternative target protein binding (TPB) domains for enhancing the level of secretion of a V5 epitope-tagged IL13Rα2TF-Fc target protein into the media of cultures of transfected host cells.

The V5-tagged IL13Rα2TF-Fc target protein used in this experiment was the same as described in Example 2 and Table 4 above.

Figure 19B:
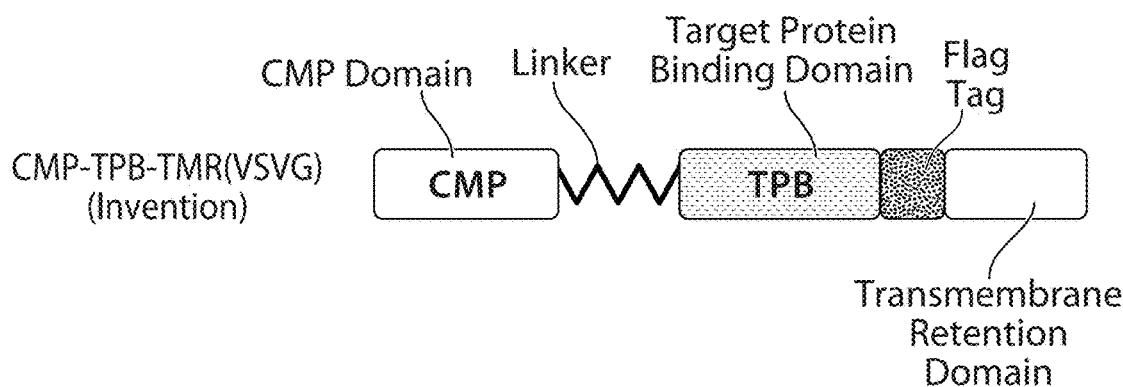
FIG. 19B is a diagram depicting the general structure of a nucleic acid construct coding for a series of fusion proteins described in Example 18, in which a segment encoding a CMP domain comprising a J domain from Erdj3 was linked to a segment encoding a TPB domain, wherein the TPB domain ("TPB") was comprised, alternatively, of a gE-binding portion of the herpes simplex virus type-1 glycoprotein I (designated "gI" in FIG. 19C), an Fc-binding portion of herpes simplex virus type-1 glycoprotein E (designated "gE" in FIG. 19C), interleukin 13 (designated "IL13" in FIG. 19C), or an Fc-binding portion of human Fc receptor I (designated "hFcR" in FIG. 19C), which construct was augmented at its 3' end with a segment encoding a Flag epitope tag, which in turn was linked to a segment encoding a transmembrane retention (TMR) domain comprising a transmembrane and C-terminal region of the VSV-G protein. This construct for the series of fusion proteins that vary with respect to the particular TPB domain is designated "CMP-TPB-TMR(VSVG)". See, Example 18 for additional details. The gI segment used in these experiments, which lacks Fc-binding properties, was not, strictly speaking, a target protein binding domain as that term is used herein; however, gI forms a complex with gE, and it was included in this experiment to investigate whether gI would augment in any way the target binding properties of gE.

FIG. 19A shows a diagram of a nucleic acid construct encoding a fusion protein comprising a J domain of a J protein as a CMP domain linked to a segment encoding an Fc-binding region of Protein A as a target protein binding (TPB) domain, which was augmented at its 3' end with a segment encoding a Flag epitope tag for easy identification with an anti-Flag antibody. The construct was augmented at FIG. 19B depicts the general structure of a nucleic acid construct encoding a series of fusion proteins prepared for this experiment. Each construct comprised a segment encoding a CMP domain comprising a J domain from Erdj3 linked to a segment encoding a target protein binding (TPB) domain, wherein the TPB domain comprised one of several domains of known binding activity: a gE-binding portion of the herpes simplex virus type-1 glycoprotein I ("gI" in FIG. 19C, no Fc binding activity), an Fc-binding portion of herpes simplex virus type-1 glycoprotein E ("gE" in FIG. 19C), interleukin 13 ("IL13" in FIG. 19C), or an Fc-binding portion of human Fc receptor I ("hFcR" in FIG. 19C). Referring again to the general structure diagram FIG. 19B, the segment encoding the TPB domain in each construct was augmented at its 3' end with a segment encoding a Flag epitope tag, which in turn was linked to a segment encoding a TMR domain comprising the transmembrane region from the VSV-G protein. The construct was augmented at its 5' end with a segment encoding the Erdj3 signal sequence (not shown in FIG. 19B). This construct for the series of fusion proteins that vary with respect to the particular TPB domain was designated "CMP-TPB-TMR(VSVG)".

The CMP-TPB(gE)-TMR(VSVG) fusion protein used in this study was that described in Example 12 and Table 28 above, and thus included a Flag epitope tag and an Fc-binding portion of the herpes simplex type-1 glycoprotein E as its TPB domain (designated "TPB(gE)").

It is noted that the herpes simplex virus type-1 glycoprotein I (gI) forms a complex with the herpes simplex virus type-1 glycoprotein E (gE). Therefore, the gI protein or a polypeptide segment thereof is not a target protein binding domain as defined herein. However, a CMP-TPB(gI)-TMR (VSVG) fusion protein, which includes a segment of gI that binds the Fc-binding portion of gE, was constructed and used in this study to investigate whether or not the gI::gE complex formed between co-expressed CMP-TPB(gE)-TMR(VSVG) and CMP-TPB(gI)-TMR(VSVG) fusion proteins would have an effect on the performance of the CMP-TPB(gE)-TMR(VSVG) to enhance the level of secreted IL13Rα2TF-Fc target protein. See FIG. 19C, results in lanes 4-6.

The amino acid sequence of the CMP-TPB(gI)-TMR (VSVG) fusion protein comprising a gE-binding portion of the gI protein and a Flag epitope tag is shown in Table 34 below.

TABLE 34

Amino Acid Sequence of a Flag-Tagged CMP-TPB(gI)-TMR(VSVG) Fusion Protein.

| Encoded Protein or Region (N- to C-terminal) | Sequence Identifier | Amino Acid Sequence 12345678901234567890123456789 |
|---|---|---|
| Flag-tagged CMP-TPB(gI)-TMR(VSVG) fusion protein | SEQ ID NO: 149 | MAPQNLSTFCLLLLYLIGAVIAGRDFYKIL GVPRSASIKDIKKAYRKLALQLHPDRNPDD PQAQEKFQDLGAAYEVLSDSEKRDIGGGSG GSGGSGGAAALVVRGPTVSLVSNSFVDAGA LGPDGVVEEDLLILGELRFVGDQVPHTTYY DGVVELWHYPMGHKCPRVVHVVTVTACPRR PAVAFALCRATDSTHSPAYPTLELNLAQQP LLRVRRATRDYAGVYVLRVWVGDAPNASLF VLGMAIAAEGTLAYNGSAHGSCDPKLLPYS APRLAPASVYQPAPNPASTPSTTTSTPSTT TSTPSTTIPAPQASTTPFPTGDPKPQLEGD YKDDDDKGSRDDESLFFGDTGLSKNPIELV EGWFSSWKSSIASFFFIIGLIIGLFLVLRV GIHLCIKLKHTKKRQIYTDIEMNRLGK |
| Erdj3 signal sequence | residues 1-22 of SEQ ID NO: 149 | MAPQNLSTFCLLLLYLIGAVIA |
| CMP Domain (from Erdj3) | residues 23-83 of SEQ ID NO: 149 | GRDFYKILGVPRSASIKDIKKAYRKLALQL HPDRNPDDPQAQEKFQDLGAAYEVLSDSEK R |
| Linker | residues 84-100 of SEQ ID NO: 149 | DIGGGSGGSGGSGGAAA |
| TPB(gI) Domain (from gI) | residues 101-326 of SEQ ID NO: 149 | LVVRGPTVSLVSNSFVDAGALGPDGVVEED LLILGELRFVGDQVPHTTYYDGVVELWHYP MGHKCPRVVHVVTVTACPRRPAVAFALCRA TDSTHSPAYPTLELNLAQQPLLRVRRATRD YAGVYVLRVWVGDAPNASLFVLGMAIAAEG TLAYNGSAHGSCDPKLLPYSAPRLAPASVY QPAPNPASTPSTTTSTPSTTTSTPSTTIPA PQASTTPFPTGDPKPQ |
| Linker | residues 327-329 of SEQ ID NO: 149 | LEG |
| Flag epitope domain | residues 330-337 of SEQ ID NO: 149 | DYKDDDDK |
| Linker | residues 338-340 of SEQ ID NO: 149 | GSR |
| TMR(VSVG) Domain | residues 341-417 of SEQ ID NO: 149 | DDESLFFGDTGLSKNPIELVEGWFSSWKSS IASFFFIIGLIIGLFLVLRVGIHLCIKLKH TKKRQIYTDIEMNRLGK |

The amino acid sequence of a CMP-TPB(IL13)-TMR (VSVG) fusion protein comprising a Flag epitope tag was that described in Example 13 and Table 30 above.

The amino acid sequence of a CMP-TPB(hFcR)-TMR (VSVG) fusion protein comprising an Fc-binding region of the hFcR protein and including a Flag epitope tag is shown in Table 35 below.

TABLE 35

Amino Acid Sequence of a Flag-Tagged CMP-TPB(hFcR)-TMR(VSVG) Fusion Protein.

| Encoded Protein or Region (N- to C- terminal) | Sequence Identifier | Amino Acid Sequence 12345678901234567890123 4567890 |
|---|---|---|
| Flag-tagged CMP-TPB (hFcR)- TMR (VSVG) fusion protein | SEQ ID NO: 150 | MAPQNLSTFCLLLLYLIGAVIAGRDFYKIL GVPRSASIKDIKKAYRKLALQLHPDRNPDD PQAQEKFQDLGAAYEVLSDSEKRDIGGGSG GSGGGSGGAAAAVITLQPPWVSVFQEETVTL HCEVLHLPGSSSTQWFLNGTATQTSTPSYR ITSASVNDSGEYRCQRGLSGRSDPIQLEIH RGWLLLQVSSRVFTEGEPLALRCHAWKDKL VYNVLYYRNGKAFKFFHWNSNLTILKTNIS HNGTYHCSGMLEGDYKDDDDKGSRDDESLF FGDTGLSKNPIELVEGWFSSWKSSIASFFF IIGLIIGLFLVLRVGIHLCIKLKHTKKRQI YTDIEMNRLGK |
| Erdj3 signal sequence | residues 1-22 of SEQ ID NO: 150 | MAPQNLSTFCLLLLYLIGAVIA |
| CMP Domain (from Erdj3) | residues 23-83 of SEQ ID NO: 150 | GRDFYKILGVPRSASIKDIKKAYRKLALQL HPDRNPDDPQAQEKFQDLGAAYEVLSDSEK R |
| Linker | residues 84-100 of SEQ ID NO: 150 | DIGGGSGGSGGSGGAAA |
| TPB(hFcR) Domain (from hFcR) | residues 101-250 of SEQ ID NO: 150 | AVITLQPPWVSVFQEETVTLHCEVLHLPGS SSTQWFLNGTATQTSTPSYRITSASVNDSG EYRCQRGLSGRSDPIQLEIHRGWLLLQVSS RVFTEGEPLALRCHAWKDKLVYNVLYYRNG KAFKFFHWNSNLTILKTNISHNGTYHCSGM |
| Linker | residues 251-253 of SEQ ID NO: 150 | LEG |
| Flag epitope domain | residues 254-261 of SEQ ID NO: 150 | DYKDDDDK |
| Linker | residues 262-264 of SEQ ID NO: 150 | GSR |
| TMR(VSVG)Domain | residues 265-341 of SEQ ID NO: 150 | DDESLFFGDTGLSKNPIELVEGWFSSWKSS IASFFFIIGLIIGLFLVLRVGIHLCIKLKH TKKRQIYTDIEMNRLGK |

HEK293 cells were transfected with expression vector plasmids to compare levels of expression in culture media of the IL13Rα2TF-Fc target protein expressed alone or co-expressed with each of the following fusion proteins: a CMP-TPB(Prot A) fusion protein, a CMP-TPB(gI)-TMR (VSVG) fusion protein, a CMP-TPB(gE)-TMR(VSVG), both the CMP-TPB(gI)-TMR(VSVG) and the CMP-TPB (gE)-TMR(VSVG) fusion proteins, CMP-TPB(IL13)-TMR (VSVG) fusion protein, and a CMP-TPB(hFcR)-TMR (VSVG) fusion protein. Transfected cells were cultured for two days, and samples of cell culture media were harvested and analyzed by Western blot (immunoblot) assay using an anti-V5 antibody to detect secreted V5-tagged IL13Rα2TF-Fc target protein.

Figure 19C:
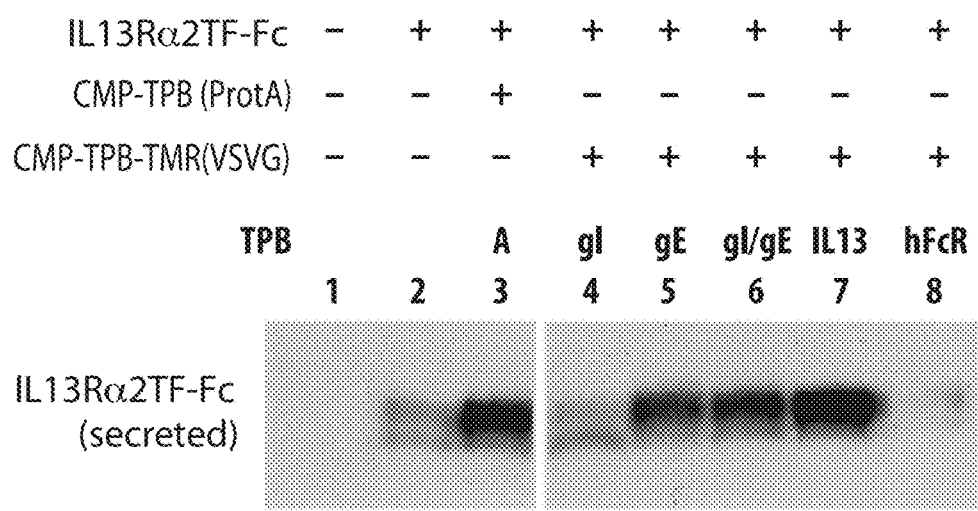
FIG. 19C shows X-ray film images of chemiluminescent signals for IL13Rα2TF-Fc target protein in media from cultures of transfected host cells as described in Example 18. As explained above, for the fusion protein structures designated "CMP-TPB(Prot A)" and "CMP-TPB-TMR(VSVG)", the CMP domain was the same J domain of Erdj3. Lane 1 of FIG. 19C shows Western blot results for media from a mock culture that contained host cells transfected with an expression vector lacking a structural gene for expressing any protein; lane 2 shows results for media from a culture of transfected host cells expressing the IL13Rα2TF-Fc target protein in the absence of any fusion protein; lane 3 shows results for media from a culture of transfected cells co-expressing the IL13Rα2TF-Fc target protein and a CMP-TPB(Prot A) fusion protein, wherein the "TPB(Prot A)" domain is a target protein binding (TPB) domain that is an Fc-binding portion of Protein A (which is designated "A" in the TPB row above lane 3); lane 4 shows results for media from a culture of transfected cells co-expressing the IL13Rα2TF-Fc target protein and a CMP-TPB(gI)-TMR(VSVG) fusion protein wherein the "TPB (gI)" domain is a target protein binding (TPB) domain that is a gE-binding portion of herpes simplex virus type-1 glycoprotein I (designated "gI" in the TPB row above lane 4); lane 5 shows results for media from a culture of transfected cells co-expressing the IL13Rα2TF-Fc target protein and a J-TPB(gE)-TMR(VSVG) fusion protein wherein "TPB(gE)" is a TPB domain that is an Fc-binding portion of herpes simplex virus type-1 glycoprotein E (designated "gE" in the TPB row above lane 5); lane 6 shows results for media from a culture of transfected cells expressing the IL13Rα2TF-Fc target protein and both a CMP-TPB(gI)-TMR(VSVG) fusion protein and a CMP-TPB(gE)-TMR (VSVG) fusion protein (the target protein binding domain (TPB) of the two co-expressed fusion proteins is designated "gI/gE" in the TPB row above lane 6); lane 7 shows results for media from a culture of transfected cells co-expressing the IL13Rα2TF target protein and a CMP-TPB(IL13)-TMR (VSVG) fusion protein wherein "TPB(IL13)" is a TPB domain that is interleukin 13 (designated "IL13" in the TPB row above lane 7); and lane 8 shows results for media from a culture of transfected cells co-expressing the IL13Rα2TF-Fc target protein and a CMP-TPB(hFcR)-TMR(VSVG) fusion protein wherein "TPB(hFcR)" is a TPB domain that is an Fc-binding portion of hFcR (designated "hFcR" in the TPB row above lane 8).

FIG. 19C shows X-ray film images of chemiluminescent signals of the Western blot analysis of culture media from the HEK293 transfectants. Mock cultures contained cells transfected with expression vector lacking a structural gene for expressing any protein (lane 1). As shown in lane 2 of FIG. 19C, when expressed in the absence of any fusion protein, a relatively low, but detectable, amount of the IL13Rα2TF-Fc target protein was secreted into the culture media. In contrast, the amount of IL13Rα2TF-Fc target protein secreted into culture media was significantly enhanced when the target protein was co-expressed with a CMP-TPB(Prot A) fusion protein (lane 3). Significantly enhanced secretion of the target protein also was observed where the target protein was co-expressed with a CMP-TPB (gE)-TMR(VSVG) fusion protein (lane 5), co-expressed with both CMP-TPB(gI)-TMR(VSVG) and CMP-TPB(gE)-TMR(VSVG) fusion proteins (lane 6), and co-expressed with a CMP-TPB(IL13)-TMR(VSVG) ligand (lane 7) as compared to the level of IL13Rα2TF-Fc target protein secreted into the media of cultures of transfected host cells expressing the target protein alone (lane 2).

The data in FIG. 19C also show that no enhancement in the level of IL13Rα2TF-Fc target protein secreted into media was observed for cultures of transfected host cells co-expressing the IL13Rα2TF-Fc target protein and a CMP-TPB(gI)-TMR(VSVG) fusion protein (lane 4 of FIG. 19C), where the level of the target protein secreted into the culture media was comparable to that observed in media from cultures of cells expressing the IL13Rα2TF-Fc target protein alone (lane 2). This observed lack of enhanced secretion would appear to be consistent with the fact that gI does not bind Fc regions (Hanke al., *Virology*, 177(2): 437-444 (1990)). In contrast, the co-expression of the IL13Rα2TF-Fc target protein and the CMP-TPB(gE)-TMR(VSVG) fusion protein resulted in a significant enhancement in the level of secreted IL13Rα2TF-Fc target protein (lane 5), which is consistent with the fact that the gE protein binds Fc regions (Hanke al., *Virology,* 177(2): 437-444 (1990)). That the CMP-TPB(gI)-TMR(VSVG) fusion protein did not otherwise inhibit expression or secretion of the IL13Rα2TF-Fc target protein was indicated by the finding that co-expression of the IL13Rα2TF-Fc target protein and both the CMP-TPB(gI)-TMR(VSVG) and CMP-TPB(gE)-TMR (VSVG) fusion proteins yielded a significant enhancement in the level of secretion of the IL13Rα2TF-Fc target protein (lane 6) similar to that observed in media from cultures co-expressing the IL13Rα2TF-Fc target protein and the CMP-TPB(gE)-TMR(VSVG) fusion protein (lane 5). Moreover, the results in lanes 4, 5, and 6 of FIG. 19C indicate the importance of using a functional TPB domain in a fusion protein of the invention to ensure that the fusion protein is effective in enhancing the secretion of a desired target protein from a host cell.

As shown in lane 8 of FIG. 19C, co-expression of the IL13Rα2TF-Fc protein with a CMP-TPB(FcR)-TMR (VSVG) fusion protein not only failed to enhance expression of secreted IL13Rα2TF-Fc but actually appeared to suppress even the low basal level of secretion observed in transfected host cells expressing the IL13Rα2TF-Fc target protein alone (lane 2). The result in lane 8 of FIG. 19C is similar to the lack of enhanced secretion of the target protein observed in earlier work (not shown) that examined the effect of co-expressing the IL13Rα2TF-Fc target protein with a J domain fusion protein comprising the Fc-binding region of hFcR as a TPB domain but lacking a transmembrane retention (TMR) domain. The result in lane 8 of FIG. 19C shows that the lack of enhanced secretion in the earlier work could not be overcome by the addition of a TMR domain comprising the VSVG transmembrane region to a CMP (J domain) fusion protein comprising an Fc-binding domain of hFcR as a TPB domain. It may be that the Fc-binding region of the hFcR protein when employed as TPB domain in the structural organization of a fusion protein of the invention may have such a high affinity for the Fc region as to prevent release into the secretory pathway.

Taking all of the results into consideration, it appears that the Fc-binding region of the gE protein is particularly useful as the TPB domain of a CASE fusion protein of the invention when the goal is to enhance the level of a target protein secreted from a cell wherein the target protein comprises an Fc region.

Example 19

Improved Activity of Fusion Proteins Incorporating a Truncated Version of gE Target Protein Binding In this experiment, two fusion proteins of the invention comprising different portions of the Fc-binding region of the gE protein as target protein binding (TPB) domains were compared for their ability to enhance the level of secretion of an IL13Rα2TF-Fc target protein.

The IL13Rα2TF-Fc target protein used in this experiment was the V5-tagged IL13Rα2TF-Fc target protein described in Example 2 and Table 4 above.

FIG. 20A depicts a nucleic acid construct encoding a cell-associated secretion-enhancing (CASE) fusion protein of the invention comprising a CMP domain comprising a polypeptide (IKKAFHKLAMKY; SEQ ID NO:9) from the J domain of the Erdj4 protein linked to a segment encoding TPB domain comprising an Fc-binding portion of the gE protein, which in turn was linked to a segment encoding a Flag epitope tag, and followed by a segment encoding a TMR domain comprising a transmembrane region of the Type III protein, KDEL receptor 1 protein (KDELR), which is an ER receptor protein that binds to resident ER proteins comprising the ER localization amino acid motif K-D-E-L (SEQ ID NO:152). The TMR(KDELR) segment used in the construct is shown in Table 1, SEQ ID NO:71 (membrane-spanning domains are underlined). The segment of the construct encoding the CMP domain was also augmented at its 5' end with a segment encoding a signal sequence of human insulin. The construct was designated "CMP-TPB (gE)-TMR(KDELR)". The amino acid sequence of the CMP-TPB(gE)-TMR(KDELR) fusion protein is shown in Table 36 below, where it can be seen that a 379 amino acid portion of the gE protein, which comprises the Fc binding domain, was employed as the TPB domain.

TABLE 36

Amino Acid Sequence of a Flag-Tagged CMP-TPB(gE)-TMR(KDELR) Fusion Protein.

| Encoded Protein or Region (N- to C-terminal) | Sequence Identifier | Amino Acid Sequence 123456789012345678901234567890 |
|---|---|---|
| Flag-tagged CMP-TPB(gE)-TMR(KDELR) fusion protein | SEQ ID NO: 151 | MALWMRLLPLLALLALWGPDPAAAGTGSGE<br>FIKKAFHKLAMKYDIGGGGSGGGGSGGGGS<br>AAAGTPKTSWRRVSVGEDVSLLPAPGPTGR<br>GPTQKLLWAVEPLDGCGPLHPSWVSLMPPK<br>QVPETVVDAACMRAPVPLAMAYAPPAPSAT<br>GGLRTDFVWQERAAVVNRSLVIHGVRETDS |

TABLE 36-continued Amino Acid Sequence of a Flag-Tagged CMP-TPB(gE)-TMR(KDELR) Fusion Protein.

| Encoded Protein or Region (N- to C- terminal) | Sequence Identifier | Amino Acid Sequence 12345678901234567890123456789 0 |
|---|---|---|
| | | GLYTLSVGDIKDPARQVASVVLVVQPAPVP TPPPTPADYDEDDNDEGEDESLAGTPASGT PRLPPPPAPPRSWPSAPEVSHVRGVTVRME TPEAILFSPGETFSTNVSIHAIAHDDQTYS MDVVWLRFDVPTSCAEMRIYESCLYHPQLP ECLSPADAPCAASTWTSRLAVRSYAGCSRT NPPPRCSAEAHMEPVPGLAWQAASVNLEFR DASPQHSGLYLCVVYVNDHIHAWGHITIST AAQYRNAVVEQPLPQRGADLAELEGDYKDD DDKGSRNLFRFLGDLSHLLAIILLLLKIWK SRSCAGISGKSQVLFAVVFTARYLDLFTNY ISLYNTCMKVVYIACSFTTVWLIYSKFKAT YDGNHDTFRVEFLVVPTAILAFLVNHDFTP LEILWTFSIYLESVAILPQLFMVSKTGEAE TITSHYLFALGVYRTLYLFNWIWRYHFEGF FDLIAIVAGLVQTVLYCDFFYLYITKVLKG KKLSLPA |
| Human insulin signal sequence | residues 1-24 of SEQ ID NO: 151 | MALWMRLLPLLALLALWGPDPAAA |
| Linker | residues 25-31 of SEQ ID NO: 151 | GTGSGEF |
| CMP Domain (peptide from J domain of Erdj4) | residues 32-43 of SEQ ID NO: 151 | IKKAFHKLAMKY |
| Linker | residues 44-63 of SEQ ID NO: 151 | DIGGGGSGGGGSGGGGSAAA |
| TPB(gE)Domain (Fc-binding region of gE) | residues 64-442 of SEQ ID NO: 151 | GTPKTSWRRV Erdj4 protein linked to a segment encoding a truncated portion of the Fc-binding region of gE comprising (gE') as the TPB domain, which construct was augmented at its 3' end with a segment encoding a Flag epitope tag, which in turn was linked to a segment encoding a transmembrane region of the KDELR protein as a TMR domain. The segment of the construct encoding the CMP domain was augmented at its 5' end with a segment encoding an N-terminal signal sequence of human insulin. The construct was designated "CMP-TPB(gE')-TMR(KDELR)". The amino acid sequence of the Flag epitope-tagged CMP-TPB(E')-TMR(KDELR) fusion protein is shown in Table 37 below, where it can be seen that a 178 amino acid portion of the gE protein, designated gE', comprising the Fc binding domain, was employed as the TPB domain.

TABLE 37

Amino Acid Sequence of a Flag-Tagged CMP-TPB(gE')-TMR(KDELR) Fusion Protein.

| Encoded Protein or Region (N- to C-terminal) | Sequence Identifier | Amino Acid Sequence 12345678901234567890123456789 0 |
|---|---|---|
| Flag-tagged CMP-TPB(gE')-TMR(KDELR) fusion protein | SEQ ID NO: 153 | MALWMRLLPLLALLALWGPDPAAAGTGSGE FIKKAFHKLAMKYDIGGGGSGGGGSGGGGS AAAAPEVSHVRGVTVRMETPEAILFSPGET FSTNVSIHAIAHDDQTYSMDVVWLRFDVPT SCAEMRIYESCLYHPQLPECLSPADAPCAA STWTSRLAVRSYAGCSRTNPPPRCSAEAHM EPVPGLAWQAASVNLEFRDASPQHSGLYLC VVYVNDHIHAWGHITISTAAQYRNAVVEQP LLEGDYKDDDDKGSRNLFRFLGDLSHLLAI ILLLLKIWKSRSCAGISGKSQVLFAVVFTA RYLDLFTNYISLYNTCMKVVYIACSFTTVW LIYSKFKATYDGNHDTFRVEFLVVPTAILA FLVNHDFTPLEILWTFSIYLESVAILPQLF MVSKTGEAETITSHYLFALGVYRTLYLFNW IWRYHFEGFFDLIAIVAGLVQTVLYCDFFY LYITKVLKGKKLSLPA |
| Human insulin signal sequence | residues 1-24 of SEQ ID NO: 153 | MALWMRLLPLLALLALWGPDPAAA |
| Linker | residues 25-31 of SEQ ID NO: 153 | GTGSGEF |
| CMP Domain (peptide from J domain of Erdj4) | residues 32-43 of SEQ ID NO: 153 | IKKAFHKLAMKY |
| Linker | residues 44-63 of SEQ ID NO: 153 | DIGGGGSGGGGSGGGGSAAA |
| TPB(gE') Domain (gE' Fc binding region) | residues 64-241 of SEQ ID NO: 153 | APEVSHVRGVTVRMETPEAILFSPGETFST NVSIHAIAHDDQTYSMDVVWLRFDVPTSCA EMRIYESCLYHPQLPECLSPADAPCAASTW TSRLAVRSYAGCSRTNPPPRCSAEAHMEPV PGLAWQAASVNLEFRDASPQHSGLYLCVVY VNDHIHAWGHITISTAAQYRNAVVEQPL |
| Linker | residues 242-244 of SEQ ID NO: 153 | LEG |
| Flag epitope domain | residues 245-252 of SEQ ID NO: 153 | DYKDDDDK |
| Linker | residues 253-255 of SEQ ID NO: 153 | GSR |
| TMR(KDELR) Domain | residues 256-466 of SEQ ID NO: 153 | NLFRFLGDLSHLLAIILLLLKIWKSRSCAG ISGKSQVLFAVVFTARYLDLFTNYISLYNT CMKVVYIACSFTTVWLIYSKFKATYDGNHD TFRVEFLVVPTAILAFLVNHDFTPLEILWT FSIYLESVAILPQLFMVSKTGEAETITSHY LFALGVYRTLYLFNWIWRYHFEGFFDLIAI VAGLVQTVLYCDFFYLYITKVLKGKKLSLP A |

HEK293 cells were transfected with expression vector plasmids to compare levels of secretion of target protein in culture media of transfectants that expressed the target protein alone or co-expressed the target protein with the CMP-TPB(gE)-TMR(KDELR) fusion protein or the CMP-TPB(gE')-TMR(KDELR) fusion protein. Transfected host cells were cultured for two days, and samples of transfectant culture media were harvested and analyzed by ELISA. Wells of a 96-well plate were coated with recombinant purified Protein A and incubated with culture media of transfected cells. IL13Rα2TF-Fc target protein bound to Protein A was detected using a peroxidase-conjugated goat anti-human IgG F(ab')$_2$ antibody fragment (Jackson ImmunoResearch Laboratories, Product No. 109-036-098).

Figure 20A:
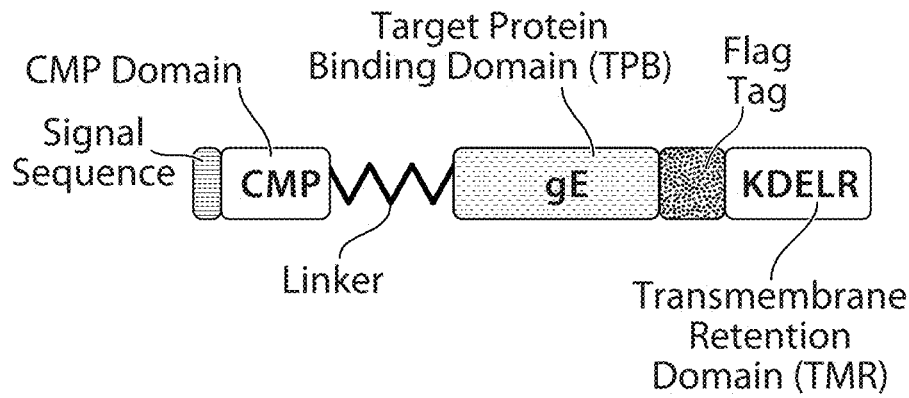
FIG. 20A depicts a nucleic acid construct encoding a fusion protein as described in Example 19 in which a segment encoding a "chaperone machinery polypeptide" ("CMP") domain comprising a polypeptide from a J domain of the Erdj4 protein was linked to a segment encoding an Fc-binding portion of gE ("gE") as the target protein binding (TPB) domain. The construct was augmented at its 3' end with a segment encoding a Flag epitope tag, which in turn was linked to a segment encoding a transmembrane region of the KDELR protein as a transmembrane retention (TMR) domain. The segment of the construct encoding the CMP domain was augmented at its 5' end with a segment encoding an N-terminal signal sequence of human insulin. The construct was designated "CMP-TPB(gE)-TMR(KDELR)". See Example 19 for additional details.
Figure 20B:
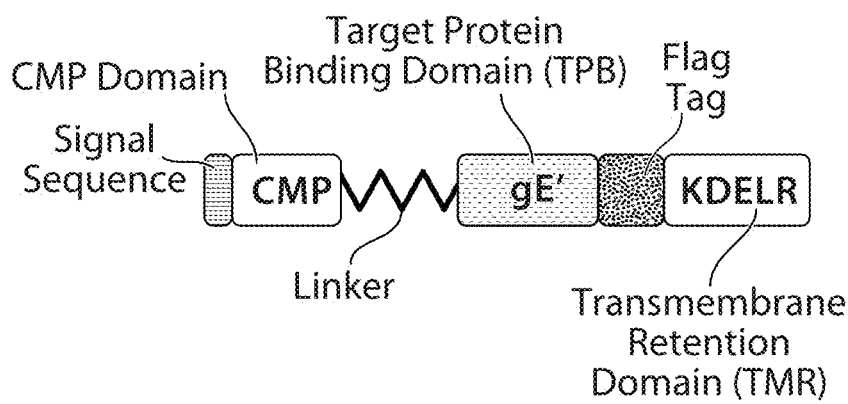
FIG. 20B depicts a nucleic acid construct encoding a fusion protein as described in Example 19 in which a segment encoding a "chaperone machinery polypeptide" ("CMP") domain comprising a J domain from Erdj4 was linked to a segment encoding a truncated portion of gE comprising an Fc-binding domain (gE') as the target protein binding (TPB) domain. The construct was augmented at its 3' end with a segment encoding a Flag epitope tag, which in turn was linked to a segment encoding a transmembrane region of the KDELR protein as a transmembrane retention (TMR) domain. The segment of the construct encoding the CMP domain was augmented at its 5' end with a segment encoding an N-terminal signal sequence for the fusion protein. The construct was designated "CMP-TPB(gE')-TMR(KDELR)" in Example 19. See Example 19 for additional details.
Figure 20C:
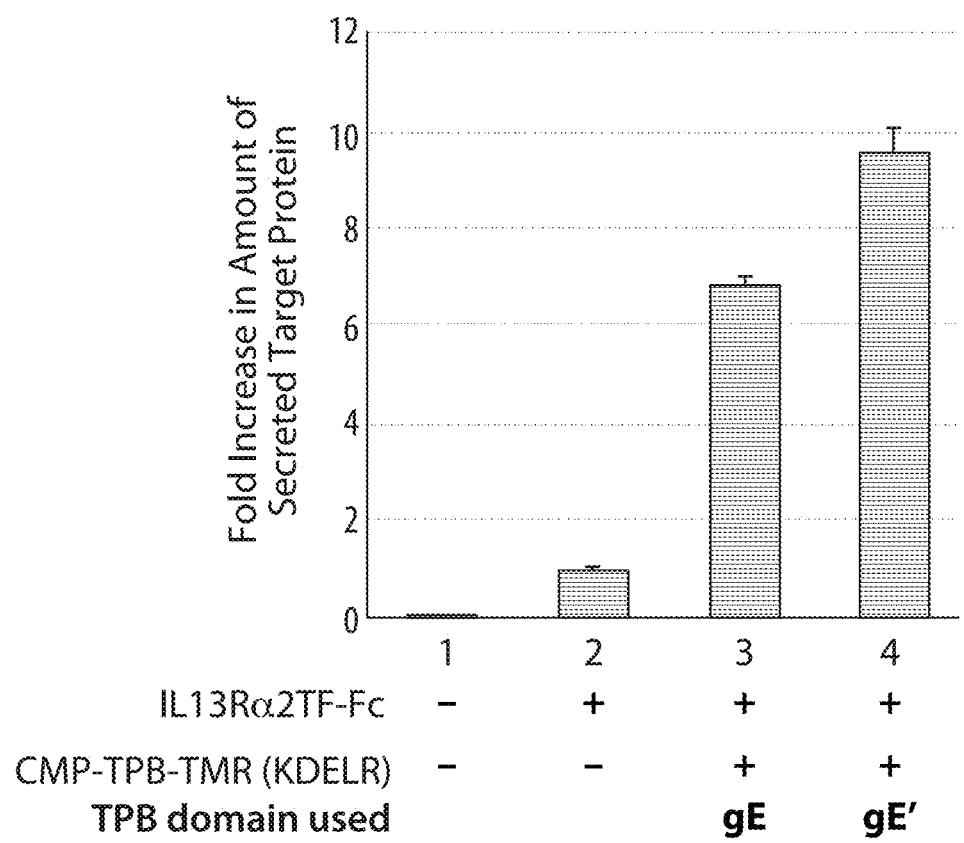
FIG. 20C shows bar graphs of the fold increase in the amount of IL13Rα2TF-Fc target protein detected by ELISA in the media of cultures of transfected HEK293 host cells expressing the target protein alone (bar graph 2), co-expressing the IL13Rα2TF-Fc target protein and a CMP-TPB(gE)-TMR(KDELR) fusion protein wherein the TPB comprises a portion of gE comprising an Fc-binding region (designated "gE", bar graph 3), or co-expressing the IL13Rα2TF-Fc target protein and a CMP-TPB(gE')-TMR(KDELR) fusion protein wherein the TPB domain comprises a truncated portion of the Fc-binding region of gE (designated "gE'"; bar graph 4) as described in Example 19. The presence ("+") or absence ("−") of expression vectors encoding target protein or fusion protein in the transfected host cells of each culture is indicated below each bar graph. Mock cultures contained cells transfected with expression vector lacking a structural gene for expressing any protein and were used as a negative control (bar graph 1). The data in the bar graphs have been normalized by subtracting non-specific background signal in media from mock cultures and setting the amount of target protein secreted into culture media when expressed in the absence of either fusion protein at a relative value of 1 (bar graph 2). The results show that co-expression of the IL13Rα2TF-Fc target protein with either the CMP-TPB (gE)-TMR(KDELR) fusion protein (bar graph 3) or the CMP-TPB(gE')-TMR(KDELR) fusion protein (bar graph 4) significantly enhanced the level of target protein secreted into the culture media as compared to the level of target protein secreted into the culture media when the target protein was expressed in the absence of either fusion protein (bar graph 2). See Example 19 for details.

The results are shown in the bar graphs in FIG. 20C. The results of assaying mock cultures containing cells transfected with expression vector lacking a structural gene for expressing any protein are shown in bar graph 1. The data in the bar graphs have been normalized by subtracting non-specific background signal in media from mock cultures and setting the amount of IL13Rα2TF-Fc target protein secreted into culture media when expressed in the absence of either fusion protein at a relative value of 1 (bar graph 2). These results show that co-expression of the IL13Rα2TF-Fc target protein with either the CMP-TPB(gE)-TMR(KDELR) fusion protein (bar graph 3) or the CMP-TPB(gE') -TMR (KDELR) fusion protein (bar graph 4) significantly enhanced the level of IL13Rα2TF-Fc target protein secreted into the culture media as compared to the level of anti-IL13Rα2TF-Fc target protein secreted into culture media when expressed in the absence of either fusion protein (bar graph 2). Specifically, co-expression of the IL13Rα2TF-Fc target protein and the CMP-TPB(gE)-TMR(KDELR) fusion protein resulted in a 7-fold increase in the level of target protein secreted into culture media (bar graph 3) as compared to the level of target protein secreted into the culture media when expressed in the absence of fusion protein (bar graph 2). Surprisingly, co-expression of the IL13Rα2TF-Fc target protein and the CMP-TPB(gE')-TMR(KDELR) fusion protein resulted in more than a 9-fold increase in the level of target protein secreted into culture media (bar graph 4), as compared to the level of target protein secreted into culture media when expressed in the absence of either fusion protein (bar graph 2). Thus, use of the CMP-TPB(gE')-TMR (KDELR) fusion protein provided an approximately 30 percent greater level of enhancement of target protein secretion than that obtained using CMP-TPB(gE)-TMR(KDELR) fusion protein.

As shown in Table 36, above, the CMP-TPB(gE)-TMR (KDELR) fusion protein employed a 379 amino acid polypeptide of the gE protein as the TPB domain, whereas the CMP-TPB(gE')-TMR(KDELR) fusion protein employed a considerably smaller, 178 amino acid polypeptide (gE') from within the 379 amino acid polypeptide of the gE protein as the TPB domain (see Table 37). Thus, the fusion protein comprising the smaller gE polypeptide (gE') provided a greater enhancement in the level of secretion of the co-expressed IL13Rα2TF-Fc target protein than the fusion protein comprising the larger 379 amino acid portion of gE. (Compare bar graph 4 (CMP-TPB(gE')-TMR(KDELR) fusion protein) with bar graph 3 (CMP-TPB(gE)-TMR (KDELR) fusion protein) of FIG. 20C.) These results indicate that performance of the CASE fusion proteins to enhance target protein expression/secretion may be adjusted by optimization of the size of the component domains, while preserving their main function, in this case target protein binding.

Example 20

Enhanced Expression of Secreted IL13Rα2TF-Fc Target Protein Co-Expressed with Fusion Proteins Comprising Different Target Protein Binding Domains The target protein binding (TPB) domain of a fusion protein of the invention must not only bind a target protein but also release the target protein for secretion via the cellular secretory pathway that follows after the endoplasmic reticulum (ER) to the Golgi apparatus and on to secretory vesicles. After the binding complex comprising the fusion protein and the target protein moves from the ER to the Golgi apparatus, the fusion protein is expected to dissociate from the target protein so that the target protein can be separately secreted from the cell. This dissociation may advantageously occur within the drop from approximately neutral pH from the ER (approximately pH 7-7.4) to pH 6.7 in the cis Golgi, to pH 6.3 in the medial Golgi, to pH 6.0 in the trans Golgi, and then down to pH 5.5 in the secretory vesicles that eventually fuse with the cell membrane and release the target protein. If a fusion proteins does not release the target protein within the conditions (pH or otherwise) of the secretion pathway of the host cell, the target protein will remain associated with the fusion protein and be localized wherever the fusion protein is ultimately localized within the cell via the transmembrane retention (TMR) domain. As shown in this example, however, successful target protein secretion enhancement may be achieved even using TPB domains derived from proteins requiring very harsh pH conditions (~pH 4.2) for dissociation from a binding partner.

This example examined the effect of varying the TPB domain in fusion proteins of the invention constructed using the same CMP and TMR domains, for enhancing secretion of the same target protein. Three different Fc-binding domains of three different Fc-binding proteins were used in constructing fusion proteins for co-expression in HEK293 transformants with the IL13Rα2TF-Fc target protein described previously.

FIG. 21A is a diagram depicting the general structure of a nucleic acid construct for expression of a series of cell-associated secretion-enhancing (CASE) fusion proteins of the invention. Each construct encoded a fusion protein comprising a CMP domain comprising a polypeptide (IKKAFHKLAMKY; SEQ ID NO:9) from the J domain of the Erdj4 protein linked to a TPB domain segment encoding an Fc-binding portion of either the gE protein (Baucke et al., *J. Virol.,* 32(3): 779-789 (1979), Para et al., *J. Virol.,* 34(3): 512-520 (1980), the FcB6.1 protein described by Strauch et al., *Proc. Natl. Acad. Sci. USA,* 111(2): 675-680 (2014), or the Protein GB0919 protein described by Watanabe et al., *J. Biol. Chem.,* 284(18) (2009), described herein as "GB919". The segment encoding the TPB domain was in turn linked to a segment encoding a Flag epitope tag, followed by a segment encoding a transmembrane retention (TMR) domain comprising a transmembrane region of the KDELR protein. The segment of the construct encoding the CMP domain was also augmented at its 5' end with a segment encoding a signal sequence of human insulin. The construct was designated "CMP-TPB(gE/FcB6.1/GB919)-TMR (KDELR)".

The amino acid sequence for the V5-tagged IL13Rα2TF-Fc target protein used in this experiment was described in in Example 2 and Table 4 above.

The amino acid sequence of a CMP-TPB(gE)-TMR (KDELR) fusion protein used in this experiment was described in Example 19 and Table 36 above.

Another fusion protein comprised a TPB domain comprising the Fc-binding region of the FcB6.1 protein. The FcB6.1 protein was engineered with various mutations to optimize the balance between affinity and the pH dependence of Fc-binding (Strauch et al., 2014, supra). In particular, the FcB6.1 protein bound IgG at pH 8.2 and exhibited an approximately 500-fold weaker binding at pH 5.5, where nearly complete elution of IgG was obtained when FcB6.1 was linked to chromatographic resin particles, whereas there was very little difference in Protein A binding to IgG at either pH 8.2 and pH 5.5 (Strauch et al., 2014). Accordingly, the FcB6.1 protein provided an advantageous means to purify Fc-containing proteins by affinity chromatography using much milder conditions for elution that the harsher acidic pH values required for elution from Protein A affinity columns (e.g., pH 3-pH 4), which can cause antibody and Fc-containing proteins to denature and aggregate resulting in reduced yields (Strauch et al., 2014). The amino acid sequence of a CMP-TPB(FcB6.1)-TMR(KDELR) fusion protein used in this experiment is shown in Table 38 below.

TABLE 38

Amino Acid Sequence of a Flag-Tagged CMP-TPB(FcB6.1)-TMR(KDELR) Fusion Protein.

| Encoded Protein or Region (N- to C-terminal) | Sequence Identifier | Amino Acid Sequence 12345678901234567890123456789 |
|---|---|---|
| Flag-tagged CMP-TPB(FcB6.1)-TMR(KDELR) fusion protein | SEQ ID NO: 154 | MALWMRLLPLLALLALWGPDPAAAGTGSGE FIKKAFHKLAMKYDIGGGGSGGGGSGGGGS AAAAPEEALIVVDMQRDFMPGGALPVPEGD KIIPKVNEYIRKFKEKGALIVATRDWHPEN HISFRERGGPWPRHCVQNTPGAEFVVDLPE DAVIISKATEPDKEAYSGFEGTDLAKILRG NGVKRVYICGVATEYCVSRTAVDALKHGFE VYLLRDAVKGIKPTFEQQSFFYMSLKGIKI VQFLEGDYKDDDDKGSRNLFRFLGDLSHLL AIILLLLKIWKSRSCAGISGKSQVLFAVVF TARYLDLFTNYISLYNTCMKVVYIACSFTT VWLIYSKFKATYDGNHDTFRVEFLVVPTAI LAFLVNHDFTPLEILWTFSIYLESVAILPQ LFMVSKTGEAETITSHYLFALGVYRTLYLF NWIWRYHFEGFFDLIAIVAGLVQTVLYCDF FYLYITKVLKGKKLSLPA |
| Human insulin signal sequence | residues 1-24 of SEQ ID NO: 154 | MALWMRLLPLLALLALWGPDPAAA |
| Linker | residues 25-31 of SEQ ID NO: 154 | GTGSGEF |
| CMP sequence (peptide from J domain of Erdj4) | residues 32-43 of SEQ ID NO: 154 | IKKAFHKLAMKY |
| Linker | residues 44-63 of SEQ ID NO: 154 | DIGGGGSGGGGSGGGGSAAA |
| TPB(FcB6.1) Domain | residues 64-243 of SEQ ID NO: 154 | APEEALIVVDMQRDFMPGGALPVPEGDKII PKVNEYIRKFKEKGALIVATRDWHPENHIS FRERGGPWPRHCVQNTPGAEFVVDLPEDAV IISKATEPDKEAYSGFEGTDLAKILRGNGV KRVYICGVATEYCVSRTAVDALKHGFEVYL LRDAVKGIKPTFEQQSFFYMSLKGIKIVQF |
| Linker | residues 244-246 of SEQ ID NO: 154 | LEG |
| Flag epitope domain | residues 247-254 of SEQ ID NO: 154 | DYKDDDDK |
| Linker | residues 255-257 of SEQ ID NO: 154 | GSR |
| TMR(KDELR) Domain | residues 258-468 of SEQ ID NO: 154 | NLFRFLGDLSHLLAIILLLLKIWKSRSCAG ISGKSQVLFAVVFTARYLDLFTNYISLYNT CMKVVYIACSFTTVWLIYSKFKATYDGNHD TFRVEFLVVPTAILAFLVNHDFTPLEILWT |

TABLE 38-continued

Amino Acid Sequence of a Flag-Tagged CMP-TPB(FcB6.1)-TMR(KDELR) Fusion Protein.

| Encoded Protein or Region (N- to C-terminal) | Sequence Identifier | Amino Acid Sequence 123456789012345678901234567890 |
|---|---|---|
| | | FSIYLESVAILPQLFMVSKTGEAETITSHY LFALGVYRTLYLFNWIWRYHFEGFFDLIAI VAGLVQTVLYCDFFYLYITKVLKGKKLSLP A |

Another fusion protein comprised a TPB domain comprising an Fc-binding region of the GB919 protein. The GB919 is a histidine-substituted Fc-binding mutant Protein G that was engineered to make the dissociation from bound IgG more pH sensitive in order to reduce the harsh acidic conditions (e.g., pH 3) that are normally required to elute Fc-containing proteins bound to Protein G. The mutant GB919 exhibited an Fc-binding that was more pH sensitive while increasing the affinity for IgG by a factor of 11 compared with wildtype Protein G (Watanabe et al., *J. Biol. Chem.*, 284 (10):12373-12383 (2009)). In particular, the IgG bound to the GB919 mutant protein could be eluted at conditions more typical of using Protein A, such as pH 4.2, instead of much harsher pH, such as pH 3-3.1, required for elution from wildtype Protein G (Watanabe et al., 2009, supra). The amino acid sequence of a CMP-TPB(GB919)-TMR(KDELR) fusion protein used in this experiment is shown in Table 39 below.

TABLE 39

Amino Acid Sequence of a Flag-Tagged CMP-TPB(GB919)-TMR(KDELR) Fusion Protein.

| Encoded Protein or Region (N- to C-terminal) | Sequence Identifier | Amino Acid Sequence 123456789012345678901234567890 |
|---|---|---|
| Flag-tagged CMP-TPB(GB919)-TMR(KDELR) fusion protein | SEQ ID NO: 155 | MALWMRLLPLLALLALWGPDPAAAGTGSGE FIKKAFHKLAMKYDIGGGGSGGGGSGGGGS AAAADTYKLILNGKTLKGETTTEAVDAATA EKVFKHYANEHGVHGHWTYDPETKTFTVTE LEGDYKDDDDKGSRNLFRFLGDLSHLLAII LLLLKIWKSRSCAGISGKSQVLFAVVFTAR YLDLFTNYISLYNTCMKVVYIACSFTTVWL IYSKFKATYDGNHDTFRVEFLVVPTAILAF LVNHDFTPLEILWTFSIYLESVAILPQLFM VSKTGEAETITSHYLFALGVYRTLYLFNWI WRYHFEGFFDLIAIVAGLVQTVLYCDFFYL YITKVLKGKKLSLPA |
| Human insulin signal sequence | residues 1-24 of SEQ ID NO: 155 | MALWMRLLPLLALLALWGPDPAAA |
| Linker | residues 25-31 of SEQ ID NO: 155 | GTGSGEF |
| CMP Domain (peptide from J domain of Erdj4) | residues 32-43 of SEQ ID NO: 155 | IKKAFHKLAMKY |
| Linker | residues 44-63 of SEQ ID NO: 155 | DIGGGGSGGGGSGGGGSAAA |
| TPB(GB919) Domain | residues 64-120 of SEQ ID NO: 155 | ADTYKLILNGKTLKGETTTEAVDAATAEKV FKHYANEHGVHGHWTYDPETKTFTVTE |
| Linker | residues 121-123 of SEQ ID NO: 155 | LEG |
| Flag epitope domain | residues 124-131 of SEQ ID NO: 155 | DYKDDDDK |

TABLE 39-continued

Amino Acid Sequence of a Flag-Tagged CMP-TPB(GB919)-
TMR(KDELR) Fusion Protein.

| Encoded Protein or Region (N- to C-terminal) | Sequence Identifier | Amino Acid Sequence<br>12345678901234567890123456789 0 |
|---|---|---|
| Linker | residues 132-134 of SEQ ID NO: 155 | GSR |
| TMR(KDELR) Domain | residues 135-345 of SEQ ID NO: 155 | NLFRFLGDLSHLLAIILLLLKIWKSRSCAG ISGKSQVLFAVVFTARYLDLFTNYISLYNT CMKVVYIACSFTTVWLIYSKFKATYDGNHD TFRVEFLVVPTAILAFLVNHDFTPLEILWT FSIYLESVAILPQLFMVSKTGEAETITSHY LFALGVYRTLYLFNWIWRYHFEGFFDLIAI VAGLVQTVLYCDFFYLYITKVLKGKKLSLP A |

HEK293 cells were transfected with expression vector plasmids to compare levels of expression in culture media of cells expressing the IL13Rα2TF-Fc target protein alone or co-expressing the target protein and each of the three fusion proteins, i.e., CMP-TPB(gE)-TMR(KDELR), CMP-TPB (FcB6.1)-TMR(KDELR), or CMP-TPB(GB919)-TMR (KDELR). Transfected cells were cultured for two days, and samples of cell culture media were harvested and analyzed by ELISA with immobilized Protein A as a binding protein for the target protein and a peroxidase-conjugated goat anti-human IgG F(ab')$_2$ antibody fragment (Jackson ImmunoResearch Laboratories, Product No. 109-036-098) as a detection reagent. Wells of a 96-well plate were coated with recombinant purified Protein A and incubated with culture media of transfected cells expressing IL13Rα2TF-Fc target protein alone or culture media of transfected cells co-expressing IL13Rα2TF-Fc target protein and CMP-TPB (gE)-TMR(KDELR), IL13Rα2TF-Fc target protein and CMP-TPB(FcB6.1)-TMR(KDELR), or IL13Rα2TF-Fc target protein and CMP-GB919-TMR(KDELR).

Figure 21A:
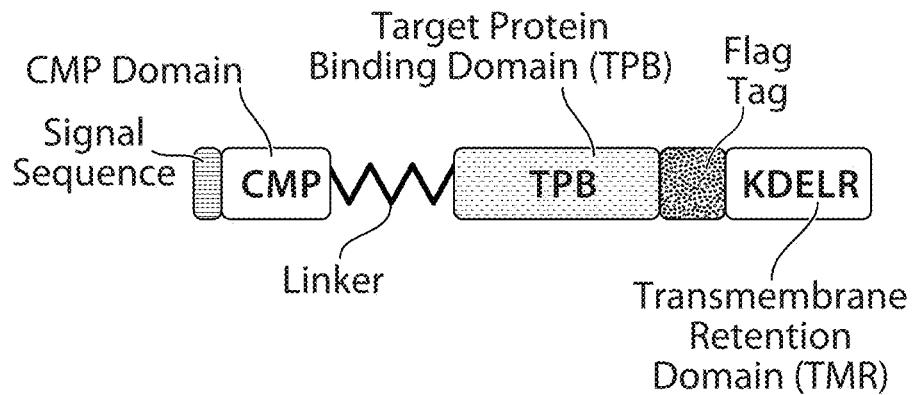
FIG. 21A is a diagram showing the general structure of nucleic acid constructs encoding a series of fusion proteins as described in Example 20, in which a segment encoding a CMP domain comprising a 12 amino acid peptide (IKKAFHKLAMKY, SEQ ID NO:9) from the J domain of the Erdj4 protein is linked to a segment encoding a target protein binding (TPB) domain, wherein the TPB domain comprises an Fc-binding portion of herpes simplex virus type-1 glycoprotein E (gE), of an Fc-binding portion of the engineered FcB6.1 protein (FcB6.1), or of an Fc-binding portion of the GB919 mutant protein. The selected TPB domain in each case was augmented at its 3' end with a segment encoding a Flag epitope tag, which in turn was linked to a segment encoding a transmembrane retention (TMR) domain comprising a transmembrane region of the KDELR protein. The segment of the construct encoding the CMP domain was augmented at its 5' end with a segment encoding an N-terminal signal sequence for the fusion protein. This construct for the series of fusion proteins that varies with respect to the particular TPBD was designated "CMP-TPB-TMR (KDELR)". See, Example 20 for additional details.
Figure 21B:
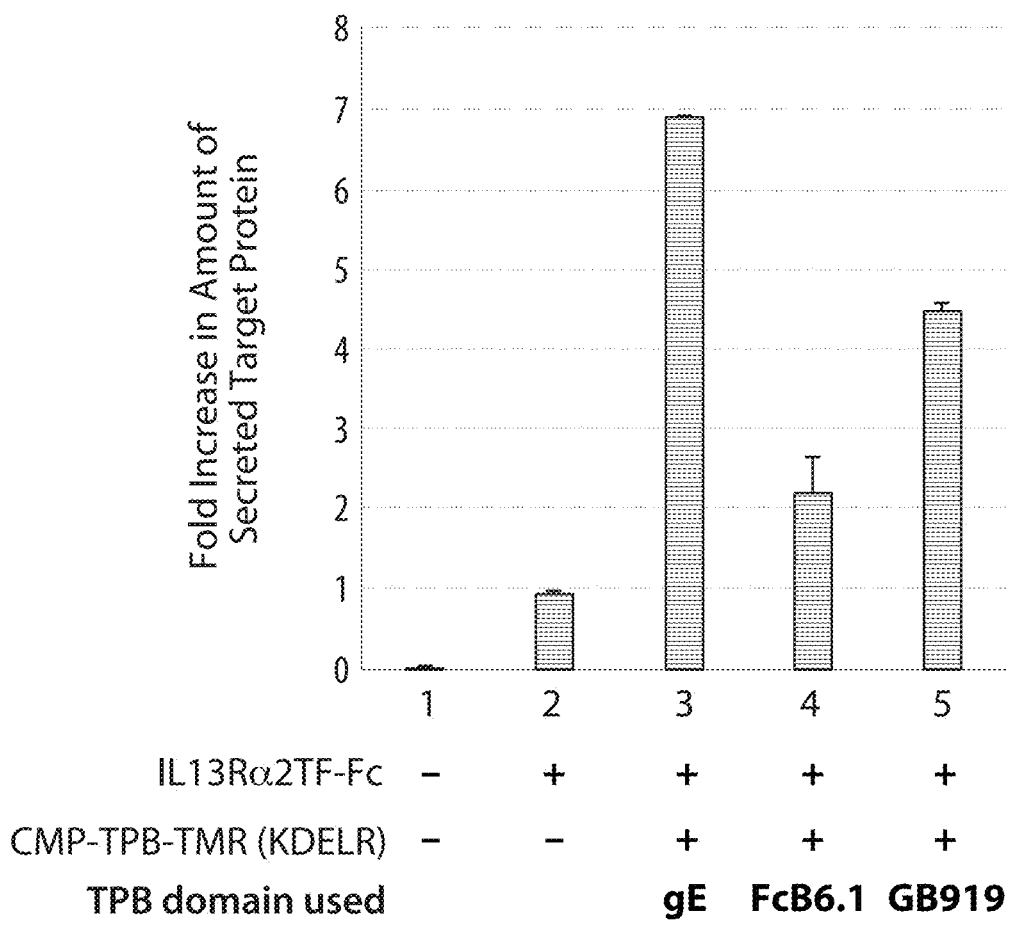
FIG. 21B shows the results of comparative tests of the effects of co-expression of each of the fusion proteins against expression of target protein alone or mock cultures transfected with empty vectors, expressing no protein. Cell culture media from two-day growths of HEK293 transfectants were measured with an ELISA to detect IL13Rα2TF-Fc target protein. The results show relative amounts of secreted target protein in culture media of transfected host cells expressing the target protein alone (bar graph 2), or of host cells co-expressing the IL13Rα2TF-Fc target protein and a CMP-TPB(gE)-TMR(KDELR) fusion protein wherein the TPB domain comprises a portion of gE comprising an Fc-binding region (bar graph 3), or of host cells co-expressing the IL13Rα2TF-Fc target protein and CMP-TPB (FcB6.1)-TMR(KDELR) fusion protein wherein the TPB domain comprises the FcB6.1 Fc-binding polypeptide (bar graph 4), or host cells co-expressing the IL13Rα2TF-Fc target protein and CMP-TPB(GB919.1)-TMR(KDELR) fusion protein wherein the TPB domain comprises the GB919.1 Fc-binding polypeptide (bar graph 5), as described in Example 20. The presence ("+") or absence ("−") of expression vectors encoding target protein or fusion protein in the transfected host cells of each culture is indicated below each bar graph. Mock cultures contained cells transfected with "empty) expression vector lacking a structural gene for expressing any protein and were used as a negative control (bar graph 1). The data in the bar graphs have been normalized by subtracting non-specific background signal in media from mock cultures and setting the amount of target protein secreted into culture media when expressed in the absence of either fusion protein at a relative value of 1 (bar graph 2). See Example 20 for additional details.

The results are shown in the bar graphs in FIG. 21B. ELISA results from mock cultures (bar graph 1) contained cells transfected with expression vector lacking a structural gene for expressing any protein and were used as a negative control. The data in the bar graphs have been normalized by subtracting non-specific background signal in media from mock cultures and setting the amount of IL13Rα2TF-Fc target protein secreted into culture media when expressed in the absence of fusion protein at a relative value of 1 (bar graph 2). The results show that co-expression of the IL13Rα2TF-Fc target protein with the CMP-TPB(gE)-TMR (KDELR) fusion protein (bar graph 3), with the CMP-TPB (FcB6.1)-TMR(KDELR) fusion protein (bar graph 4), or with the CMP-TPB(GB919)-TMR(KDELR) fusion protein (bar graph 5) all significantly enhanced the level of IL13Rα2TF-Fc target protein secreted into the culture media as compared to the level of IL13Rα2TF-Fc target protein secreted into culture media when expressed in the absence of any fusion protein (bar graph 2).

Similar to the results shown in Example 12, above, in which a CMP-TPB(gE)-TMR(VSVG) fusion protein of the invention comprising a 379 amino acid portion of the gE protein as a TPB domain (Table 28) significantly enhanced the level of secretion of a co-expressed FVII-Fc target protein, in this study, a CMP-TPB(gE)-TMR(KDELR) fusion protein of the invention comprising the same TPB (gE) domain also significantly enhanced the level of secretion of a co-expressed IL13Rα2TF-Fc target protein (bar graph 3 of FIG. 21B). Enhanced levels of secretion of the IL13Rα2TF-Fc target protein were also observed when the target protein was co-expressed with a fusion protein comprising a TPB domain comprising an Fc-binding region of the FcB6.1 protein (bar graph 4 of FIG. 21B) and when the target protein was co-expressed with a fusion protein comprising a TPB domain comprising an Fc-binding portion of GB919 protein (bar graph 5 of FIG. 21B).

The results obtained with the CMP-TPB(GB919)-TMR (KDELR) fusion protein, which comprises an Fc-binding region of the GB919 mutant protein, which was engineered to increase the pH sensitivity of Fc binding from pH 3.1 of the wildtype Protein G to pH 4.2, similar to that for the Fc-binding domain of Protein A (Watanabe et al., 2009, supra), provided an enhanced level of secretion of the co-expressed IL13Rα2TF-Fc target protein that was approximately twice the level of enhancement provided by a CMP-TPB(FcB6.1)-TMR(KDELR) fusion (compare bar graph 5 with bar graph 4 of FIG. 21B). The greater enhancement in the level of secreted target protein co-expressed with the CMP-TPB(GB919)-TMR(KDELR) fusion protein as compared to that when co-expressed with CMP-TPB (FcB6.1)-TMR(KDELR) fusion protein was even more surprising in view of the fact that the Fc-binding domain of FcB6.1 protein releases IgG at pH 5.5 (Strauch et al., 2014), which is also the pH of cellular secretory vesicles (Demaurex, News Physiol. Sci., 17: 1-5 (2002)). Accordingly, the results of this example shown in FIG. 21B indicate that a range of Fc-binding polypeptides will be useful as TPB domains in the fusion proteins according to the invention, even where their published dissociation conditions for an Fc region are not likely to be presented in a host cell's normal secretion pathway. As demonstrated in this example, the FcB6.1 and GB919 polypeptides were useful in fusion proteins according to the invention to enhance target protein secretion by HEK293 transfectant cells, even though published reports indicated that very low pH conditions were necessary for eluting Fc-containing proteins from affinity substrates exhibiting them.

Example 21

Variation of TMR Domains for a Cell-Associated Secretion-Enhancing (CASE) Fusion Protein While not intending to be bound by any particular scientific theory regarding its mechanism of action, a cell-associated secretion-enhancing (CASE) fusion protein of the invention comprising a chaperone machinery polypeptide (CMP) domain is envisaged as binding at its target protein binding (TPB) domain to a nascent target protein in the endoplasmic reticulum (ER) to form a binding complex, recruiting the binding complex into the Hsp70 chaperone system of the host cell by means of its CMP domain, and releasing the bound target protein within the Golgi apparatus or secretory vesicles for secretion from the host cell while remaining associated with the host cell by means of its transmembrane retention (TMR) domain.

In this example, 19 different fusion proteins comprising different transmembrane regions derived from various cell-associated proteins were examined and compared for the ability to enhance the level of secretion of the IL13Rα2TF-Fc target protein. The structural formats of the fusion proteins used in this example are diagrammed in FIGS. 22A, 22B, and 22C. The results of co-expression of the target protein with one of the CASE fusion proteins, compared with target protein expression alone and mock cultures, are shown in FIG. 22D, and FIG. 22E provides the key to the numbered bar graphs of FIG. 22D.

FIG. 22A depicts a nucleic acid construct for a series of fusion proteins comprising a segment encoding a CMP domain comprising a polypeptide (IKKAFHKLAMKY; SEQ ID NO:9) from the J domain of the Erdj4 protein linked to a segment encoding an Fc-binding portion of the gE protein (Baucke et al. (1979), Para et al. (1980), supra), which was linked to a segment encoding a Flag epitope tag, which in turn was linked to a segment encoding a TMR domain comprising a transmembrane region selected from one of 16 different transmembrane proteins. The construct was augmented at its 5' end with a segment encoding the signal sequence of human insulin. Each of the fusion proteins was designated in the list below by number. Fusion proteins numbered No. 3 to No. 17, and No. 20 had the format depicted in the diagram of FIG. 22A. The format for this type of fusion protein construct was designated "CMP-TPB(gE)-TMR".

FIG. 22B depicts a nucleic acid construct for fusion proteins comprising a segment encoding a TMR domain comprising a transmembrane region from a Type II protein (fusion protein No. 18) or a Type III protein (fusion protein No. 19). In this format, the N-terminal TMR domain was linked to a segment encoding a CMP domain comprising a 12 amino acid peptide (IKKAFHKLAMKY, SEQ ID NO:9) from the J domain of the Erdj4 protein, which in turn was linked to a segment encoding a TPB domain comprising an Fc-binding portion of gE protein, which was augmented at its 3' end with a segment encoding a Flag epitope tag. The format for this type of construct was designated "TMR-CMP-TPB(gE)".

FIG. 22C depicts a nucleic acid construct for a fusion protein comprising a segment encoding a TMR domain comprising an N-proximal transmembrane region from a LIMP2 protein linked to a segment encoding a CMP domain comprising a 12 amino acid peptide (IKKAFHKLAMKY, SEQ ID NO:9) from the J domain of the Erdj4 protein, which in turn was linked to a segment encoding a TPB domain comprising an Fc-binding portion of gE protein, which in turn was linked to a segment encoding a Flag epitope tag, which in turn was linked to a segment encoding another TMR domain comprising a C-proximal transmembrane region from a LIMP2 protein. The fusion protein in this format, having two TMR domains derived from different membrane-spanning regions of the Type III protein LIMP2 positioned at either end of the fusion protein, was designated in the list below as No. 21 (see, also, FIG. 22E at no. 21). The format for this construct was designated "TMR-CMP-TPB(gE)-TMR".

The amino acid sequence for the V5-tagged IL13Rα2TF-Fc target protein used in this experiment was described in Example 2 and Table 4 above.

The amino acid sequence of the CMP-TPB(gE)-TMR (CD4) fusion protein (No. 3) is shown in Table 40 below.

TABLE 40

Amino Acid Sequence of a Flag-Tagged CMP-TPB(gE)-TMR(CD4) Fusion Protein

| Encoded Protein or Region (N- to C-terminal) | Sequence Identifier | Amino Acid Sequence 123456789012345678901234567890 |
|---|---|---|
| Flag-tagged CMMP-TPB(gE)-TMR(CD4) fusion protein | SEQ ID NO: 156 | MALWMRLLPLLALLALWGPDPAAAGTGSGE<br>FIKKAFHKLAMKYDIGGGGSGGGGSGGGGS<br>AAAGTPKTSWRRVSVGEDVSLLPAPGPTGR<br>GPTQKLLWAVEPLDGCGPLHPSWVSLMPPK<br>QVPETVVDAACMRAPVPLAMAYAPPAPSAT<br>GGLRTDFVWQERAAVVNRSLVIHGVRETDS<br>GLYTLSVGDIKDPARQVASVVLVVQPAPVP<br>TPPPTPADYDEDDNDEGEDESLAGTPASGT<br>PRLPPPPAPPRSWPSAPEVSHVRGVTVRME<br>TPEAILFSPGETFSTNVSIHAIAHDDQTYS<br>MDVVWLRFDVPTSCAEMRIYESCLYHPQLP<br>ECLSPADAPCAASTWTSRLAVRSYAGCSRT<br>NPPPRCSAEAHMEPVPGLAWQAASVNLEFR<br>DASPQHSGLYLCVVYVNDHIHAWGHITIST<br>AAQYRNAVVEQPLPQRGADLAELEGDYKDD<br>DDKGSRQPMALIVLGGVAGLLLFIGLGIFF<br>CVRCRHRRRQAFRMSQIKRLLSEKKTCQCP<br>HRFQKTCSPI |

TABLE 40-continued

Amino Acid Sequence of a Flag-Tagged CMP-TPB(gE)-TMR(CD4) Fusion Protein

| Encoded Protein or Region (N- to C-terminal) | Sequence Identifier | Amino Acid Sequence 12345678901234567890123456789 0 |
|---|---|---|
| Human insulin signal sequence | residues 1-24 of SEQ ID NO: 156 | MALWMRLLPLLALLALWGPDPAAA |
| Linker | residues 25-31 of SEQ ID NO: 156 | GTGSGEF |
| CMP Domain (peptide from J domain of Erdj4) | residues 32-43 of SEQ ID NO: 156 | IKKAFHKLAMKY |
| Linker | residues 44-63 of SEQ ID NO: 156 | DIGGGGSGGGGSGGGGSAAA |
| TPB(gE) Domain | residues 64-442 of SEQ ID NO: 156 | GTPKTSWRRVSVGEDVSLLPAPGPTGRGPT QKLLWAVEPLDGCGPLHPSWVSLMPPKQVP ETVVDAACMRAPVPLAMAYAPPAPSATGGL RTDFVWQERAAVVNRSLVIHGVRETDSGLY TLSVGDIKDPARQVASVVLVVQPAPVPTPP PTPADYDEDDNDEGEDESLAGTPASGTPRL PPPPAPPRSWPSAPEVSHVRGVTVRMETPE AILFSPGETFSTNVSIHAIAHDDQTYSMDV VWLRFDVPTSCAEMRIYESCLYHPQLPECL SPADAPCAASTWTSRLAVRSYAGCSRTNPP PRCSAEAHMEPVPGLAWQAASVNLEFRDAS PQHSGLYLCVVYVNDHIHAWGHITISTAAQ YRNAVVEQPLPQRGADLAE |
| Linker | residues 443-445 of SEQ ID NO: 156 | LEG |
| Flag epitope domain | residues 446-453 of SEQ ID NO: 156 | DYKDDDDK |
| Linker | residues 454-456 of SEQ ID NO: 156 | GSR |
| TMR(CD4) Domain | residues 457-520 of SEQ ID NO: 156 | QPMALIVLGGVAGLLLFIGLGIFFURCRH RRKAERMSQIKRLLSEKKICQCPHBFQKT CSPI |

The amino acid sequence of the CMP-TPB(gE)-TMR (Integrin) fusion protein (No. 4) is shown in Table 41 below.

TABLE 41

Amino Acid Sequence of a Flag-Tagged CMP-TPB(gE)-TMR(Integrin) Fusion Protein

| Encoded Protein or Region (N- to C-terminal) | Sequence Identifier | Amino Acid Sequence 12345678901234567890123456789 0 |
|---|---|---|
| Flag-tagged CMP-TPB(gE)-TMR(Integrin) fusion protein | SEQ ID NO: 157 | MALWMRLLPLLALLALWGPDPAAAGTGSGE FIKKAFHKLAMKYDIGGGGSGGGGSGGGGS AAAGTPKTSWRRVSVGEDVSLLPAPGPTGR GPTQKLLWAVEPLDGCGPLHPSWVSLMPPK QVPETVVDAACMRAPVPLAMAYAPPAPSAT GGLRTDFVWQERAAVVNRSLVIHGVRETDS GLYTLSVGDIKDPARQVASVVLVVQPAPVP TPPPTPADYDEDDNDEGEDESLAGTPASGT PRLPPPPAPPRSWPSAPEVSHVRGVTVRME |

TABLE 41-continued

Amino Acid Sequence of a Flag-Tagged CMP-TPB(gE)-TMR(Integrin) Fusion Protein

| Encoded Protein or Region (N- to C-terminal) | Sequence Identifier | Amino Acid Sequence 12345678901234567890123 4567890 |
|---|---|---|
| | | TPEAILFSPGETFSTNVSIHAIAHDDQTYS MDVVWLRFDVPTSCAEMRIYESCLYHPQLP ECLSPADAPCAASTWTSRLAVRSYAGCSRT NPPPRCSAEAHMEPVPGLAWQAASVNLEFR DASPQHSGLYLCVVYVNDHIHAWGHITIST AAQYRNAVVEQPLPQRGADLAELEGDYKDD DDKGSRPVPVWVIILAVLAGLLLLAVLVFV MYRMGFEKRVRPPQEEQEREQLQPHENGEG NSET |
| Human insulin signal sequence | residues 1-24 of SEQ ID NO: 157 | MALWMRLLPLLALLALWGPDPAAA |
| Linker | residues 25-31 of SEQ ID NO: 157 | GTGSGEF |
| CMP Domain (peptide from J domain of Erdj4) | residues 32-43 of SEQ ID NO: 157 | IKKAFHKLAMKY |
| Linker | residues 44-63 of SEQ ID NO: 157 | DIGGGGSGGGGSGGGGSAAA |
| TPB(gE) Domain | residues 64-442 of SEQ ID NO: 157 | GTPKTSWRRVSVGEDVSLLPAPGPTGRGPT QKLLWAVEPLDGCGPLHPSWVSLMPPKQVP ETVVDAACMRAPVPLAMAYAPPAPSATGGL RTDFVWQERAAVVNRSLVIHGVRETDSGLY TLSVGDIKDPARQVASVVLVVQPAPVPTPP PTPADYDEDDNDEGEDESLAGTPASGTPRL PPPPAPPRSWPSAPEVSHVRGVTVRMETPE AILFSPGETFSTNVSIHAIAHDDQTYSMDV VWLRFDVPTSCAEMRIYESCLYHPQLPECL SPADAPCAASTWTSRLAVRSYAGCSRTNPP PRCSAEAHMEPVPGLAWQAASVNLEFRDAS PQHSGLYLCVVYVNDHIHAWGHITISTAAQ YRNAVVEQPLPQRGADLAE |
| Linker | residues 443-445 of SEQ ID NO: 157 | LEG |
| Flag epitope domain | residues 446-453 of SEQ ID NO: 157 | DYKDDDDK |
| Linker | residues 454-456 of SEQ ID NO: 157 | GSR |
| TMR(Integrin) Domain | residues 457-514 of SEQ ID NO: 157 | PVPVWVIILAVLAGLLLLAVLVFVMYRMGF FKRVRPPQEEQEREQLQPHENGEGNSET |

The amino acid sequence of the CMP-TPB(gE)-TMR (UGT1) fusion protein (No. 5) is shown in Table 42 below.

TABLE 42

Amino Acid Sequence of a Flag-Tagged CMP-TPB(gE)-TMR(UGT1) Fusion Protein

| Encoded Protein or Region (N- to C-terminal) | Sequence Identifier | Amino Acid Sequence |
|---|---|---|
| Flag-tagged CMP-TPB(gE)-TMR(UGT1) fusion protein | SEQ ID NO: 158 | MALWMRLLPLLALLALWGPDPAAAGTGSGE FIKKAFHKLAMKYDIGGGGSGGGGSGGGGS AAAGTPKTSWRRVSVGEDVSLLPAPGPTGR GPTQKLLWAVEPLDGCGPLHPSWVSLMPPK QVPETVVDAACMRAPVPLAMAYAPPAPSAT GGLRTDFVWQERAAVVNRSLVIHGVRETDS GLYTLSVGDIKDPARQVASVVLVVQPAPVP TPPPTPADYDEDDNDEGEDESLAGTPASGT PRLPPPPAPPRSWPSAPEVSHVRGVTVRME TPEAILFSPGETFSTNVSIHAIAHDDQTYS MDVVWLRFDVPTSCAEMRIYESCLYHPQLP ECLSPADAPCAASTWTSRLAVRSYAGCSRT NPPPRCSAEAHMEPVPGLAWQAASVNLEFR DASPQHSGLYLCVVYVNDHIHAWGHITIST AAQYRNAVVEQPLPQRGADLAELEGDYKDD DDKGSRLDVIGFLLAVVLTVAFITFKCCAY GYRKCLGKKGRVKKAHKSKTH |
| Human insulin signal sequence | residues 1-24 of SEQ ID NO: 158 | MALWMRLLPLLALLALWGPDPAAA |
| Linker | residues 25-31 of SEQ ID NO: 158 | GTGSGEF |
| CMP Domain (peptide from J domain of Erdj4) | residues 32-43 of SEQ ID NO: 158 | IKKAFHKLAMKY |
| Linker | residues 44-63 of SEQ ID NO: 158 | DIGGGGSGGGGSGGGGSAAA |
| TPB(gE) Domain | residues 64-442 of SEQ ID NO: 158 | GTPKTSWRRVSVGEDVSLLPAPGPTGRGPT QKLLWAVEPLDGCGPLHPSWVSLMPPKQVP ETVVDAACMRAPVPLAMAYAPPAPSATGGL RTDFVWQERAAVVNRSLVIHGVRETDSGLY TLSVGDIKDPARQVASVVLVVQPAPVPTPP PTPADYDEDDNDEGEDESLAGTPASGTPRL PPPPAPPRSWPSAPEVSHVRGVTVRMETPE AILFSPGETFSTNVSIHAIAHDDQTYSMDV VWLRFDVPTSCAEMRIYESCLYHPQLPECL SPADAPCAASTWTSRLAVRSYAGCSRTNPP PRCSAEAHMEPVPGLAWQAASVNLEFRDAS PQHSGLYLCVVYVNDHIHAWGHITISTAAQ YRNAVVEQPLPQRGADLAE |
| Linker | residues 443-445 of SEQ ID NO: 158 | LEG |
| Flag epitope domain | residues 445-453 of SEQ ID NO: 158 | DYKDDDDK |
| Linker | residues 454-456 of SEQ ID NO: 158 | GSR |
| TRM(UGT1) Domain | residues 457-501 of SEQ ID NO: 158 | LDVIGFLLAVVLTVAFITFKCCAYGYRKCL GKKGRVKKAHKSKTH |

The amino acid sequence of the CMP-TPB(gE)-TMR (truncated KDELR) fusion protein (No. 6) is shown in Table 43 below.

TABLE 43

Amino Acid Sequence of a Flag-Tagged CMP-TPB(gE)-TMR(truncated KDELR) Fusion Protein

| Encoded Protein or Region (N- to C-terminal) | Sequence Identifier | Amino Acid Sequence 12345678901234567890123456789 |
|---|---|---|
| Flag-tagged CMP-TPB(gE)-TMR(truncated KDELR) fusion protein | SEQ ID NO: 159 | MALWMRLLPLLALLALWGPDPAAAGTGSGE FIKKAFHKLAMKYDIGGGGSGGGGSGGGGS AAAGTPKTSWRRVSVGEDVSLLPAPGPTGR GPTQKLLWAVEPLDGCGPLHPSWVSLMPPK QVPETVVDAACMRAPVPLAMAYAPPAPSAT GGLRTDFVWQERAAVVNRSLVIHGVRETDS GLYTLSVGDIKDPARQVASVVLVVQPAPVP TPPPTPADYDEDDNDEGEDESLAGTPASGT PRLPPPPAPPRSWPSAPEVSHVRGVTVRME TPEAILFSPGETFSTNVSIHAIAHDDQTYS MDVVWLRFDVPTSCAEMRIYESCLYHPQLP ECLSPADAPCAASTWTSRLAVRSYAGCSRT NPPPRCSAEAHMEPVPGLAWQAASVNLEFR DASPQHSGLYLCVVYVNDHIHAWGHITIST AAQYRNAVVEQPLPQRGADLAELEGDYKDD DDKGSRDLIAIVAGLVQTVLYCDFFYLYIT KVLKGKKLSLPA |
| Human insulin signal sequence | residues 1-24 of SEQ ID NO: 159 | MALWMRLLPLLALLALWGPDPAAA |
| Linker | residues 25-31 of SEQ ID NO: 159 | GTGSGEF |
| CMP Domain (peptide from J domain of Erdj4) | residues 32-43 of SEQ ID NO: 159 | IKKAFHKLAMKY |
| Linker | residues 44-63 of SEQ ID NO: 159 | DIGGGGSGGGGSGGGGSAAA |
| TPB(gE) Domain | residues 64-442 of SEQ ID NO: 159 | GTPKTSWRRVSVGEDVSLLPAPGPTGRGPT QKLLWAVEPLDGCGPLHPSWVSLMPPKQVP ETVVDAACMRAPVPLAMAYAPPAPSATGGL RTDFVWQERAAVVNRSLVIHGVRETDSGLY TLSVGDIKDPARQVASVVLVVQPAPVPTPP PTPADYDEDDNDEGEDESLAGTPASGTPRL PPPPAPPRSWPSAPEVSHVRGVTVRMETPE AILFSPGETFSTNVSIHAIAHDDQTYSMDV VWLRFDVPTSCAEMRIYESCLYHPQLPECL SPADAPCAASTWTSRLAVRSYAGCSRTNPP PRCSAEAHMEPVPGLAWQAASVNLEFRDAS PQHSGLYLCVVYVNDHIHAWGHITISTAAQ YRNAVVEQPLPQRGADLAE |
| Linker | residues 443-445 of SEQ ID NO: 159 | LEG |
| Flag epitope domain | residues 446-453 of SEQ ID NO: 159 | DYKDDDDK |
| Linker | residues 454-456 of SEQ ID NO: 159 | GSR |
| TMR(truncated KDELR) Domain | residues 457-492 of SEQ ID NO: 159 | DLIAIVAGLVQTVLYCDFFYLYITKVLKGK KLSLPA |

The amino acid sequence of the CMP-TPB(gE)-TMR (p23) fusion protein (No. 7) is shown in Table 44 below.

TABLE 44

Amino Acid Sequence of a Flag-Tagged CMP-TPB(gE)-TMR(p23) Fusion Protein

| Encoded Protein or Region (N- to C-terminal) | Sequence Identifier | Amino Acid Sequence 12345678901234567890123456 7890 |
|---|---|---|
| Flag-tagged CMP-TPB(gE)-TMR(p23) fusion protein | SEQ ID NO: 160 | MALWMRLLPLLALLALWGPDPAAAGTGSGE FIKKAFHKLAMKYDIGGGGSGGGGSGGGGS AAAGTPKTSWRRVSVGEDVSLLPAPGPTGR GPTQKLLWAVEPLDGCGPLHPSWVSLMPPK QVPETVVDAACMRAPVPLAMAYAPPAPSAT GGLRTDFVWQERAAVVNRSLVIHGVRETDS GLYTLSVGDIKDPARQVASVVLVVQPAPVP TPPPTPADYDEDDNDEGEDESLAGTPASGT PRLPPPPAPPRSWPSAPEVSHVRGVTVRME TPEAILFSPGETFSTNVSIHAIAHDDQTYS MDVVWLRFDVPTSCAEMRIYESCLYHPQLP ECLSPADAPCAASTWTSRLAVRSYAGCSRT NPPPRCSAEAHMEPVPGLAWQAASVNLEFR DASPQHSGLYLCVVYVNDHIHAWGHITIST AAQYRNAVVEQPLPQRGADLAELEGDYKDD DDKGSRTRVLYFSIFSMFCLIGLATWQVFY LRRFFKAKKLIE |
| Human insulin signal sequence | residues 1-24 of SEQ ID NO: 160 | MALWMRLLPLLALLALWGPDPAAA |
| Linker | residues 25-31 of SEQ ID NO: 160 | GTGSGEF |
| CMP Domain (peptide from J domain of Erdj4) | residues 32-43 of SEQ ID NO: 160 | IKKAFHKLAMKY |
| Linker | residues 44-63 of SEQ ID NO: 160 | DIGGGGSGGGGSGGGGSAAA |
| TPB(gE) Domain | residues 64-442 of SEQ ID NO: 160 | GTPKTSWRRVSVGEDVSLLPAPGPTGRGPT QKLLWAVEPLDGCGPLHPSWVSLMPPKQVP ETVVDAACMRAPVPLAMAYAPPAPSATGGL RTDFVWQERAAVVNRSLVIHGVRETDSGLY TLSVGDIKDPARQVASVVLVVQPAPVPTPP PTPADYDEDDNDEGEDESLAGTPASGTPRL PPPPAPPRSWPSAPEVSHVRGVTVRMETPE AILFSPGETFSTNVSIHAIAHDDQTYSMDV VWLRFDVPTSCAEMRIYESCLYHPQLPECL SPADAPCAASTWTSRLAVRSYAGCSRTNPP PRCSAEAHMEPVPGLAWQAASVNLEFRDAS PQHSGLYLCVVYVNDHIHAWGHITISTAAQ YRNAVVEQPLPQRGADLAE |
| Linker | residues 443-445 of SEQ ID NO: 160 | LEG |
| Flag epitope domain | residues 446-453 of SEQ ID NO: 160 | DYKDDDDK |
| Linker | residues 454-456 of SEQ ID NO: 160 | GSR |
| TMR(p23) Domain | residues 457-492 of SEQ ID NO: 160 | TRVLYFSIFSMFCLIGLATWQVFYLRRFFK AKKLIE |

The amino acid sequence of the CMP-TPB(gE)-TMR (p24) fusion protein (No. 8) is shown in Table 45 below.

TABLE 45

Amino Acid Sequence of a Flag-Tagged CMP-TPB(gE)-TMR(p24) Fusion Protein

| Encoded Protein or Region (N- to C-terminal) | Sequence Identifier | Amino Acid Sequence<br>12345678901234567890123456789 0 |
|---|---|---|
| Flag-tagged CMP-TPB(gE)-TMR(p24) fusion protein | SEQ ID NO: 161 | MALWMRLLPLLALLALWGPDPAAAGTGSGE FIKKAFHKLAMKYDIGGGGSGGGGSGGGGS AAAGTPKTSWRRVSVGEDVSLLPAPGPTGR GPTQKLLWAVEPLDGCGPLHPSWVSLMPPK QVPETVVDAACMRAPVPLAMAYAPPAPSAT GGLRTDFVWQERAAVVNRSLVIHGVRETDS GLYTLSVGDIKDPARQVASVVLVVQPAPVP TPPPTPADYDEDDNDEGEDESLAGTPASGT PRLPPPPAPPRSWPSAPEVSHVRGVTVRME TPEAILFSPGETFSTNVSIHAIAHDDQTYS MDVVWLRFDVPTSCAEMRIYESCLYHPQLP ECLSPADAPCAASTWTSRLAVRSYAGCSRT NPPPRCSAEAHMEPVPGLAWQAASVNLEFR DASPQHSGLYLCVVYVNDHIHAWGHITIST AAQYRNAVVEQPLPQRGADLAELEGDYKDD DDKGSRSRVVLWSFFEALVLVAMTLGQIYY LKRFFEVRRVV |
| Human insulin signal sequence | residues 1-24 of SEQ ID NO: 161 | MALWMRLLPLLALLALWGPDPAAA |
| Linker | residues 25-31 of SEQ ID NO: 161 | GTGSGEF |
| CMP Domain (peptide from J domain of Erdj4) | residues 32-43 of SEQ ID NO: 161 | IKKAFHKLAMKY |
| Linker | residues 44-63 of SEQ ID NO: 161 | DIGGGGSGGGGSGGGGSAAA |
| TPB(gE) Domain | residues 64-442 of SEQ ID NO: 161 | GTPKTSWRRVSVGEDVSLLPAPGPTGRGPT QKLLWAVEPLDGCGPLHPSWVSLMPPKQVP ETVVDAACMRAPVPLAMAYAPPAPSATGGL RTDFVWQERAAVVNRSLVIHGVRETDSGLY TLSVGDIKDPARQVASVVLVVQPAPVPTPP PTPADYDEDDNDEGEDESLAGTPASGTPRL PPPPAPPRSWPSAPEVSHVRGVTVRMETPE AILFSPGETFSTNVSIHAIAHDDQTYSMDV VWLRFDVPTSCAEMRIYESCLYHPQLPECL SPADAPCAASTWTSRLAVRSYAGCSRTNPP PRCSAEAHMEPVPGLAWQAASVNLEFRDAS PQHSGLYLCVVYVNDHIHAWGHITISTAAQ YRNAVVEQPLPQRGADLAE |
| Linker | residues 443-445 of SEQ ID NO: 161 | LEG |
| Flag epitope domain | residues 446-453 of SEQ ID NO: 161 | DYKDDDDK |
| Linker | residues 454-456 of SEQ ID NO: 161 | GSR |
| TMR(p24) Domain | residues 457-491 of SEQ ID NO: 161 | SRVVLWSFFEALVLVAMTLGQIYYLKRFFE VRRVV |

The amino acid sequence of the CMP-TPB(gE)-TMR (LAMP2) fusion protein (No. 9) is shown in Table 46 below.

TABLE 46

Amino Acid Sequence of a Flag-Tagged CMP-TPB(gE)-TMR(LAMP2) Fusion Protein

| Encoded Protein or Region (N- to C-terminal) | Sequence Identifier | Amino Acid Sequence 12345678901234567890123456789 0 |
|---|---|---|
| Flag-tagged CMP-TPB(gE)-TMR(LAMP2) fusion protein | SEQ ID NO: 162 | MALWMRLLPLLALLALWGPDPAAAGTGSGE FIKKAFHKLAMKYDIGGGGSGGGGSGGGGS AAAGTPKTSWRRVSVGEDVSLLPAPGPTGR GPTQKLLWAVEPLDGCGPLHPSWVSLMPPK QVPETVVDAACMRAPVPLAMAYAPPAPSAT GGLRTDFVWQERAAVVNRSLVIHGVRETDS GLYTLSVGDIKDPARQVASVVLVVQPAPVP TPPPTPADYDEDDNDEGEDESLAGTPASGT PRLPPPPAPPRSWPSAPEVSHVRGVTVRME TPEAILFSPGETFSTNVSIHAIAHDDQTYS MDVVWLRFDVPTSCAEMRIYESCLYHPQLP ECLSPADAPCAASTWTSRLAVRSYAGCSRT NPPPRCSAEAHMEPVPGLAWQAASVNLEFR DASPQHSGLYLCVVYVNDHIHAWGHITIST AAQYRNAVVEQPLPQRGADLAELEGDYKDD DDKGSRTILIPIIVGAGLSGLIIVIVIAYV IGRRKSYAGYQTL |
| Human insulin signal sequence | residues 1-24 of SEQ ID NO: 162 | MALWMRLLPLLALLALWGPDPAAA |
| Linker | residues 25-31 of SEQ ID NO: 162 | GTGSGEF |
| CMP Domain (peptide from J domain of Erdj4) | residues 32-43 of SEQ ID NO: 162 | IKKAFHKLAMKY |
| Linker | residues 44-63 of SEQ ID NO: 162 | DIGGGGSGGGGSGGGGSAAA |
| TPB(gE) Domain | residues 64-442 of SEQ ID NO: 162 | GTPKTSWRRVSVGEDVSLLPAPGPTGRGPT QKLLWAVEPLDGCGPLHPSWVSLMPPKQVP ETVVDAACMRAPVPLAMAYAPPAPSATGGL RTDFVWQERAAVVNRSLVIHGVRETDSGLY TLSVGDIKDPARQVASVVLVVQPAPVPTPP PTPADYDEDDNDEGEDESLAGTPASGTPRL PPPPAPPRSWPSAPEVSHVRGVTVRMETPE AILFSPGETFSTNVSIHAIAHDDQTYSMDV VWLRFDVPTSCAEMRIYESCLYHPQLPECL SPADAPCAASTWTSRLAVRSYAGCSRTNPP PRCSAEAHMEPVPGLAWQAASVNLEFRDAS PQHSGLYLCVVYVNDHIHAWGHITISTAAQ YRNAVVEQPLPQRGADLAE |
| Linker | residues 443-445 of SEQ ID NO: 162 | LEG |
| Flag epitope domain | residues 446-453 of SEQ ID NO: 162 | DYKDDDDK |
| Linker | residues 454-456 of SEQ ID NO: 162 | GSR |
| TMR(LAMP2) Domain | residues 457-493 of SEQ ID NO: 162 | TILIPIIVGAGLSGLIIVIVIAYVIGRRKS YAGYQTL |

The amino acid sequence of the CMP-TPB(gE)-TMR (LIMP2 truncated C-terminal TMR) fusion protein (No. 10) is shown in Table 47 below.

TABLE 47

Amino Acid Sequence of a Flag-Tagged CMP-TPB(gE)-TMR(LIMP2 truncated C-terminal TMR) Fusion Protein

| Encoded Protein or Region (N- to C-terminal) | Sequence Identifier | Amino Acid Sequence 12345678901234567890123456 7890 |
|---|---|---|
| Flag-tagged CMP-TPB(gE)-TMR(LIMP2 truncated C-terminal TMR) fusion protein | SEQ ID NO: 163 | MALWMRLLPLLALLALWGPDPAAAGTGSGE FIKKAFHKLAMKYDIGGGGSGGGGSGGGGS AAAGTPKTSWRRVSVGEDVSLLPAPGPTGR GPTQKLLWAVEPLDGCGPLHPSWVSLMPPK QVPETVVDAACMRAPVPLAMAYAPPAPSAT GGLRTDFVWQERAAVVNRSLVIHGVRETDS GLYTLSVGDIKDPARQVASVVLVVQPAPVP TPPPTPADYDEDDNDEGEDESLAGTPASGT PRLPPPPAPPRSWPSAPEVSHVRGVTVRME TPEAILFSPGETFSTNVSIHAIAHDDQTYS MDVVWLRFDVPTSCAEMRIYESCLYHPQLP ECLSPADAPCAASTWTSRLAVRSYAGCSRT NPPPRCSAEAHMEPVPGLAWQAASVNLEFR DASPQHSGLYLCVVYVNDHIHAWGHITIST AAQYRNAVVEQPLPQRGADLAELEGDYKDD DDKGSRTLIITNIPYIIMALGVFFGLVFTW LACKGQGSMDEGTADERAPLIRT |
| Human insulin signal sequence | residues 1-24 of SEQ ID NO: 163 | MALWMRLLPLLALLALWGPDPAAA |
| Linker | residues 25-31 of SEQ ID NO: 163 | GTGSGEF |
| CMP Domain (peptide from J domain of Erdj4) | residues 32-43 of SEQ ID NO: 163 | IKKAFHKLAMKY |
| Linker | residues 44-63 of SEQ ID NO: 163 | DIGGGGSGGGGSGGGGSAAA |
| TPB(gE) Domain | residues 64-442 of SEQ ID NO: 163 | GTPKTSWRRVSVGEDVSLLPAPGPTGRGPT QKLLWAVEPLDGCGPLHPSWVSLMPPKQVP ETVVDAACMRAPVPLAMAYAPPAPSATGGL RTDFVWQERAAVVNRSLVIHGVRETDSGLY TLSVGDIKDPARQVASVVLVVQPAPVPTPP PTPADYDEDDNDEGEDESLAGTPASGTPRL PPPPAPPRSWPSAPEVSHVRGVTVRMETPE AILFSPGETFSTNVSIHAIAHDDQTYSMDV VWLRFDVPTSCAEMRIYESCLYHPQLPECL SPADAPCAASTWTSRLAVRSYAGCSRTNPP PRCSAEAHMEPVPGLAWQAASVNLEFRDAS PQHSGLYLCVVYVNDHIHAWGHITISTAAQ YRNAVVEQPLPQRGADLAE |
| Linker | residues 443-445 of SEQ ID NO: 163 | LEG |
| Flag epitope domain | residues 446-453 of SEQ ID NO: 163 | DYKDDDDK |
| Linker | residues 454-456 of SEQ ID NO: 163 | GSR |
| TMR(LIMP2 truncated C-terminal TMR) Domain | residues 457-503 of SEQ ID NO: 163 | TLIITNIPYIIMALGVFFGLVFTWLACKGQ GSMDEGTADERAPLIRT |

The amino acid sequence of the CMP-TPB(gE)-TMR (CDM6PR) fusion protein (No. 11) is shown in Table 48 below.

TABLE 48

Amino Acid Sequence of a Flag-Tagged CMP-TPB(gE)-TMR(CDM6PR) Fusion Protein

| Encoded Protein or Region (N- to C-terminal) | Sequence Identifier | Amino Acid Sequence 12345678901234567890 |
|---|---|---|
| Flag-tagged CMP-TPB(gE)-TMR(CDM6PR) fusion protein | SEQ ID NO: 164 | MALWMRLLPLLALLALWGPDPAAAGTGSGE FIKKAFHKLAMKYDIGGGGSGGGGSGGGGS AAAGTPKTSWRRVSVGEDVSLLPAPGPTGR GPTQKLLWAVEPLDGCGPLHPSWVSLMPPK QVPETVVDAACMRAPVPLAMAYAPPAPSAT GGLRTDFVWQERAAVVNRSLVIHGVRETDS GLYTLSVGDIKDPARQVASVVLVVQPAPVP TPPPTPADYDEDDNDEGEDESLAGTPASGT PRLPPPPAPPRSWPSAPEVSHVRGVTVRME TPEAILFSPGETFSTNVSIHAIAHDDQTYS MDVVWLRFDVPTSCAEMRIYESCLYHPQLP ECLSPADAPCAASTWTSRLAVRSYAGCSRT NPPPRCSAEAHMEPVPGLAWQAASVNLEFR DASPQHSGLYLCVVYVNDHIHAWGHITIST AAQYRNAVVEQPLPQRGADLAELEGDYKDD DDKGSRSHLSVGSILLVTFASLVAVYVVGG FLYQRLVVGAKGMEQFPHLAFWQDLGNLVA DGCDFVCRSKPRNVPAAYRGVDDQLGEES EERDDHLLPM |
| Human insulin signal sequence | residues 1-24 of SEQ ID NO: 164 | MALWMRLLPLLALLALWGPDPAAA |
| Linker | residues 25-31 of SEQ ID NO: 164 | GTGSGEF |
| CMP Domain (peptide from J domain of Erdj4) | residues 32-43 of SEQ ID NO: 164 | IKKAFHKLAMKY |
| Linker | residues 44-63 of SEQ ID NO: 164 | DIGGGGSGGGGSGGGGSAAA |
| TPB(gE) Domain | residues 64-442 of SEQ ID NO: 164 | GTPKTSWRRVSVGEDVSLLPAPGPTGRGPT QKLLWAVEPLDGCGPLHPSWVSLMPPKQVP ETVVDAACMRAPVPLAMAYAPPAPSATGGL RTDFVWQERAAVVNRSLVIHGVRETDSGLY TLSVGDIKDPARQVASVVLVVQPAPVPTPP PTPADYDEDDNDEGEDESLAGTPASGTPRL PPPPAPPRSWPSAPEVSHVRGVTVRMETPE AILFSPGETFSTNVSIHAIAHDDQTYSMDV VWLRFDVPTSCAEMRIYESCLYHPQLPECL SPADAPCAASTWTSRLAVRSYAGCSRTNPP PRCSAEAHMEPVPGLAWQAASVNLEFRDAS PQHSGLYLCVVYVNDHIHAWGHITISTAAQ YRNAVVEQPLPQRGADLAE |
| Linker | residues 443-445 of SEQ ID NO: 164 | LEG |
| Flag epitope domain | residues 446-453 of SEQ ID NO: 164 | DYKDDDDK |
| Linker | residues 454-456 of SEQ ID NO: 164 | GSR |
| TMR(CDM6PR) Domain | residues 457-5550 of SEQ ID NO: 164 | SHLSVGSILLVTFASLVAVYVVGGFLYQRL VVGAKGMEQFPHLAFWQDLGNLVADGCDFV CRSKPRNVPAAYRGVDDQLGEESEERDDH LLPM |

The amino acid sequence of the CMP-TPB(gE)-TMR (VSVG) fusion protein (No. 12) is shown in Table 49 below.

TABLE 49

Amino Acid Sequence of a Flag-Tagged CMP-TPB(gE)-TMR(VSVG) Fusion Protein

| Encoded Protein or Region (N- to C- terminal) | Sequence Identifier | Amino Acid Sequence 12345678901234567890123456 7890 |
|---|---|---|
| Flag-tagged CMP-TPB(gE)-TMR(VSVG) fusion protein | SEQ ID NO: 165 | MALWMRLLPLLALLALWGPDPAAAGTGSGE FIKKAFHKLAMKYDIGGGGSGGGGSGGGGS AAAGTPKTSWRRVSVGEDVSLLPAPGPTGR GPTQKLLWAVEPLDGCGPLHPSWVSLMPPK QVPETVVDAACMRAPVPLAMAYAPPAPSAT GGLRTDFVWQERAAVVNRSLVIHGVRETDS GLYTLSVGDIKDPARQVASVVLVVQPAPVP TPPPTPADYDEDDNDEGEDESLAGTPASGT PRLPPPPAPPRSWPSAPEVSHVRGVTVRME TPEAILFSPGETFSTNVSIHAIAHDDQTYS MDVVWLRFDVPTSCAEMRIYESCLYHPQLP ECLSPADAPCAASTWTSRLAVRSYAGCSRT NPPPRCSAEAHMEPVPGLAWQAASVNLEFR DASPQHSGLYLCVVYVNDHIHAWGHITIST AAQYRNAVVEQPLPQRGADLAELEGDYKDD DDKGSRDDESLFFGDTGLSKNPIELVEGWF SSWKSSIASFFFIIGLIIGLFLVLRVGIHL CIKLKHTKKRQIYTDIEMNRLGK |
| Human insulin signal sequence | residues 1-24 of SEQ ID NO: 165 | MALWMRLLPLLALLALWGPDPAAA |
| Linker | residues 25-31 of SEQ ID NO: 165 | GTGSGEF |
| CMP Domain (peptide from J domain of Erdj4) | residues 32-43 of SEQ ID NO: 165 | IKKAFHKLAMKY |
| Linker | residues 44-63 of SEQ ID NO: 165 | DIGGGGSGGGGSGGGGSAAA |
| TPB(gE) Domain | residues 64-442 of SEQ ID NO: 165 | GTPKTSWRRVSVGEDVSLLPAPGPTGRGPT QKLLWAVEPLDGCGPLHPSWVSLMPPKQVP ETVVDAACMRAPVPLAMAYAPPAPSATGGL RTDFVWQERAAVVNRSLVIHGVRETDSGLY TLSVGDIKDPARQVASVVLVVQPAPVPTPP PTPADYDEDDNDEGEDESLAGTPASGTPRL PPPPAPPRSWPSAPEVSHVRGVTVRMETPE AILFSPGETFSTNVSIHAIAHDDQTYSMDV VWLRFDVPTSCAEMRIYESCLYHPQLPECL SPADAPCAASTWTSRLAVRSYAGCSRTNPP PRCSAEAHMEPVPGLAWQAASVNLEFRDAS PQHSGLYLCVVYVNDHIHAWGHITISTAAQ YRNAVVEQPLPQRGADLAE |
| Linker | residues 443-445 of SEQ ID NO: 165 | LEG |
| Flag epitope domain | residues 446-453 of SEQ ID NO: 165 | DYKDDDDK |
| Linker | residues 454-456 of SEQ ID NO: 165 | GSR |
| TMR(VSVG) Domain | residues 457-533 of SEQ ID NO: 165 | DDESLFFGDTGLSKNPIELVEGWFSSWKSS IASFFFIIGLIIGLFLVLRVGIHLCIKLKH TKKRQIYTDIEMNRLGK |

The amino acid sequence of the CMP-TPB(gE)-TMR (CNX) fusion protein (No. 13) is shown in Table 50 below.

TABLE 50

Amino Acid Sequence of a Flag-Tagged CMP-TPB(gE)-TMR(CNX) Fusion Protein

| Encoded Protein or Region (N- to C-terminal) | Sequence Identifier | Amino Acid Sequence<br>12345678901234567890123456 7890 |
|---|---|---|
| Flag-tagged CMP-TPB(gE)-TMR(CNX) fusion protein | SEQ ID NO: 166 | MALWMRLLPLLALLALWGPDPAAAGTGSGE<br>FIKKAFHKLAMKYDIGGGGSGGGGSGGGGS<br>AAAGTPKTSWRRVSVGEDVSLLPAPGPTGR<br>GPTQKLLWAVEPLDGCGPLHPSWVSLMPPK<br>QVPETVVDAACMRAPVPLAMAYAPPAPSAT<br>GGLRTDFVWQERAAVVNRSLVIHGVRETDS<br>GLYTLSVGDIKDPARQVASVVLVVQPAPVP<br>TPPPTPADYDEDDNDEGEDESLAGTPASGT<br>PRLPPPPAPPRSWPSAPEVSHVRGVTVRME<br>TPEAILFSPGETFSTNVSIHAIAHDDQTYS<br>MDVVWLRFDVPTSCAEMRIYESCLYHPQLP<br>ECLSPADAPCAASTWTSRLAVRSYAGCSRT<br>NPPPRCSAEAHMEPVPGLAWQAASVNLEFR<br>DASPQHSGLYLCVVYVNDHIHAWGHITIST<br>AAQYRNAVVEQPLPQRGADLAELEGDYKDD<br>DDKGSRPERMTPFSAIGLELWSMTSDIFFD<br>NFIICADRRIVDDWANDGWGLKKAADGAAE<br>PGVVGQMIEAAEERPWLWVVYILTVALPVF<br>LVILFCCSGKKQTSGMEYKKTDAPQPDVKE<br>EEEEKEEEKDKGDEEEEGEEKLEEKQKSDA<br>EEDGGTVSQEEEDRKPKAEEDEILNRSPRN<br>RKPRRE |
| Human insulin signal sequence | residues 1-24 of SEQ ID NO: 166 | MALWMRLLPLLALLALWGPDPAAA |
| Linker | residues 25-31 of SEQ ID NO: 166 | GTGSGEF |
| CMP Domain (peptide from J domain of Erdj4) | residues 32-43 of SEQ ID NO: 166 | IKKAFHKLAMKY |
| Linker | residues 44-63 of SEQ ID NO: 166 | DIGGGGSGGGGSGGGGSAAA |
| TPB(gE) Domain | residues 64-442 of SEQ ID NO: 166 | GTPKTSWRRVSVGEDVSLLPAPGPTGRGPT<br>QKLLWAVEPLDGCGPLHPSWVSLMPPKQVP<br>ETVVDAACMRAPVPLAMAYAPPAPSATGGL<br>RTDFVWQERAAVVNRSLVIHGVRETDSGLY<br>TLSVGDIKDPARQVASVVLVVQPAPVPTPP<br>PTPADYDEDDNDEGEDESLAGTPASGTPRL<br>PPPPAPPRSWPSAPEVSHVRGVTVRMETPE<br>AILFSPGETFSTNVSIHAIAHDDQTYSMDV<br>VWLRFDVPTSCAEMRIYESCLYHPQLPECL<br>SPADAPCAASTWTSRLAVRSYAGCSRTNPP<br>PRCSAEAHMEPVPGLAWQAASVNLEFRDAS<br>PQHSGLYLCVVYVNDHIHAWGHITISTAAQ<br>YRNAVVEQPLPQRGADLAE |
| Linker | residues 443-445 of SEQ ID NO: 166 | LEG |
| Flag epitope domain | residues 446-453 of SEQ ID NO: 166 | DYKDDDDK |
| Linker | residues 454-456 of SEQ ID NO: 166 | GSR |

TABLE 50-continued

Amino Acid Sequence of a Flag-Tagged
CMP-TPB(gE)-TMR(CNX) Fusion Protein

| Encoded Protein or Region (N- to C-terminal) | Sequence Identifier | Amino Acid Sequence 123456789012345678901234567890 |
|---|---|---|
| TMR(CNX) Domain | residues 457-636 of SEQ ID NO: 166 | PFRMTPFSAIGLELWSMTSDIFFDNFIICA DRRIVDDWANDGWGLKKAADGAAEPGVVGQ MIEAAEERPWLWVVYILTVALPVFLVILFC CSGKKQTSGMFYKKTDAPQPDVKEEEEEKE EEKDKGDEEEEGEEKLEEKQKSDAEEDGGT VSQEEEDRKPKAEEDEILNRSPRNRKPRRE |

The amino acid sequence of the CMP-TPB(gE)-TMR (truncated CNX) fusion protein (No. 14) is shown in the Table 51 below.

TABLE 51

Amino Acid Sequence of a Flag-Tagged CMP-TPB(gE)-TMR(truncated CNX) Fusion Protein.

| Encoded Protein or Region (N- to C-terminal) | Sequence Identifier | Amino Acid Sequence 123456789012345678901234567890 |
|---|---|---|
| Flag-tagged CMP-TPB(gE)-TMR(truncated CNX) fusion protein | SEQ ID NO: 167 | MALWMRLLPLLALLALWGPDPAAAGTGSGE FIKKAFHKLAMKYDIGGGGSGGGGSGGGGS AAAGTPKTSWRRVSVGEDVSLLPAPGPTGR GPTQKLLWAVEPLDGCGPLHPSWVSLMPPK QVPETVVDAACMRAPVPLAMAYAPPAPSAT GGLRTDFVWQERAAVVNRSLVIHGVRETDS GLYTLSVGDIKDPARQVASVVLVVQPAPVP TPPPTPADYDEDDNDEGEDESLAGTPASGT PRLPPPPAPPRSWPSAPEVSHVRGVTVRME TPEAILFSPGETFSTNVSIHAIAHDDQTYS MDVVWLRFDVPTSCAEMRIYESCLYHPQLP ECLSPADAPCAASTWTSRLAVRSYAGCSRT NPPPRCSAEAHMEPVPGLAWQAASVNLEFR DASPQHSGLYLCVVYVNDHIHAWGHITIST AAQYRNAVVEQPLPQRGADLAELEGDYKDD DDKGSRPFRMTPFSAIGLELWSMTSDIFFD NFIICADRRIVDDWANDGWGLKKAADGAAE PGVVGQMIEAAEERPWLWVVYILTVALPVF LVILFCCSG |
| Human insulin signal sequence | residues 1-24 of SEQ ID NO: 167 | MALWMRLLPLLALLALWGPDPAAA |
| Linker | residues 25-31 of SEQ ID NO: 167 | GTGSGEF |
| CMP Domain (peptide from J domain of Erdj4) | residues 32-43 of SEQ ID NO: 167 | IKKAFHKLAMKY |
| Linker | residues 44-63 of SEQ ID NO: 167 | DIGGGGSGGGGSGGGGSAAA |
| TPB(gE) Domain | residues 64-442 of SEQ ID NO: 167 | GTPKTSWRRVSVGEDVSLLPAPGPTGRGPT QKLLWAVEPLDGCGPLHPSWVSLMPPKQVP ETVVDAACMRAPVPLAMAYAPPAPSATGGL RTDFVWQERAAVVNRSLVIHGVRETDSGLY TLSVGDIKDPARQVASVVLVVQPAPVPTPP PTPADYDEDDNDEGEDESLAGTPASGTPRL PPPPAPPRSWPSAPEVSHVRGVTVRMETPE AILFSPGETFSTNVSIHAIAHDDQTYSMDV VWLRFDVPTSCAEMRIYESCLYHPQLPECL |

TABLE 51-continued

Amino Acid Sequence of a Flag-Tagged CMP-TPB(gE)-TMR(truncated CNX) Fusion Protein.

| Encoded Protein or Region (N- to C-terminal) | Sequence Identifier | Amino Acid Sequence<br>12345678901234567890123456 7890 |
|---|---|---|
| | | SPADAPCAASTWTSRLAVRSYAGCSRTNPP<br>PRCSAEAHMEPVPGLAWQAASVNLEFRDAS<br>PQHSGLYLCVVYVNDHIHAWGHITISTAAQ<br>YRNAVVEQPLPQRGADLAE |
| Linker | residues 443-445 of SEQ ID NO: 167 | LEG |
| Flag epitope domain | residues 446-453 of SEQ ID NO: 167 | DYKDDDDK |
| Linker | residues 454-456 of SEQ ID NO: 167 | GSR |
| TMR(truncated CNX) Domain | residues 457-549 of SEQ ID NO: 167 | PFRMTPFSAIGLELWSMTSDIFFDNFIICA<br>DRRIVDDWANDGWGLKKAADGAAEPGVVGQ<br>MIEAAEERPWLWVVYILTVALPVFLVILFC<br>CSG |

The amino acid sequence of the CMP-TPB(gE)-TMR(gE) fusion protein (No. 15) is shown in Table 52 below.

TABLE 52

Amino Acid Sequence of a Flag-Tagged CMP-TPB(gE)-TMR(gE) Fusion Protein.

| Encoded Protein or Region (N- to C-terminal) | Sequence Identifier | Amino Acid Sequence<br>12345678901234567890123456 7890 |
|---|---|---|
| Flag-tagged CMP-TPB(gE)-TMR(gE) fusion protein | SEQ ID NO: 168 | MALWMRLLPLLALLALWGPDPAAAGTGSGE<br>FIKKAFHKLAMKYDIGGGGSGGGGSGGGGS<br>AAAGTPKTSWRRVSVGEDVSLLPAPGPTGR<br>GPTQKLLWAVEPLDGCGPLHPSWVSLMPPK<br>QVPETVVDAACMRAPVPLAMAYAPPAPSAT<br>GGLRTDFVWQERAAVVNRSLVIHGVRETDS<br>GLYTLSVGDIKDPARQVASVVLVVQPAPVP<br>TPPPTPADYDEDDNDEGEDESLAGTPASGT<br>PRLPPPPAPPRSWPSAPEVSHVRGVTVRME<br>TPEAILFSPGETFSTNVSIHAIAHDDQTYS<br>MDVVWLRFDVPTSCAEMRIYESCLYHPQLP<br>ECLSPADAPCAASTWTSRLAVRSYAGCSRT<br>NPPPRCSAEAHMEPVPGLAWQAASVNLEFR<br>DASPQHSGLYLCVVYVNDHIHAWGHITIST<br>AAQYRNAVVEQPLPQRGADLAELEGDYKDD<br>DDKGSRPTHPHVGAPPHAPPTHGALRLGAV<br>MGAALLLSALGLSVWACMTCWRRRAWRAVK<br>SRASGKGPTYIRVADSELYADWSSDSEGER<br>DQVPWLAPPERPDSPSTNGSGFEILSPTAP<br>SVYPRSDGHQSRRQLTTFGSGRPDRRYSQA<br>SDSSVFW |
| Human insulin signal sequence | residues 1-24 of SEQ ID NO: 168 | MALWMRLLPLLALLALWGPDPAAA |
| Linker | residues 25-31 of SEQ ID NO: 168 | GTGSGEF |
| CMP Domain (peptide from J domain of Erdj4) | residues 32-43 of SEQ ID NO: 168 | IKKAFHKLAMKY |

TABLE 52-continued

Amino Acid Sequence of a Flag-Tagged CMP-TPB(gE)-TMR(gE) Fusion Protein.

| Encoded Protein or Region (N- to C-terminal) | Sequence Identifier | Amino Acid Sequence 12345678901234567890123456789 |
|---|---|---|
| Linker | residues 44-63 of SEQ ID NO: 168 | DIGGGGSGGGGSGGGGSAAA |
| TPB(gE) Domain | residues 64-442 of SEQ ID NO: 168 | GTPKTSWRRVSVGEDVSLLPAPGPTGRGPT QKLLWAVEPLDGCGPLHPSWVSLMPPKQVP ETVVDAACMRAPVPLAMAYAPPAPSATGGL RTDFVWQERAAVVNRSLVIHGVRETDSGLY TLSVGDIKDPARQVASVVLVVQPAPVPTPP PTPADYDEDDNDEGEDESLAGTPASGTPRL PPPPAPPRSWPSAPEVSHVRGVTVRMETPE AILFSPGETFSTNVSIHAIAHDDQTYSMDV VWLRFDVPTSCAEMRIYESCLYHPQLPECL SPADAPCAASTWTSRLAVRSYAGCSRTNPP PRCSAEAHMEPVPGLAWQAASVNLEFRDAS PQHSGLYLCVVYVNDHIHAWGHITISTAAQ YRNAVVEQPLPQRGADLAE |
| Linker | residues 443-445 of SEQ ID NO: 168 | LEG |
| Flag epitope domain | residues 446-453 of SEQ ID NO: 168 | DYKDDDDK |
| Linker | residues 454-456 of SEQ ID NO: 168 | GSR |
| TMR(gE) Domain | residues 457-607 of SEQ ID NO: 168 | PTHPHVGAPPHAPPTHGALRLGAVMGAALL LSALGLSVWACMTCWRRRAWRAVKSRASGK GPTYIRVADSELYADWSSDSEGERDQVPWL APPERPDSPSTNGSGFEILSPTAPSVYPRS DGHQSRRQLTTFGSGRPDRRYSQASDSSVF W |

The amino acid sequence of the CMP-TPB(gE)-TMR(ERGIC53) fusion protein (No. 16) is shown in the Table 53 below.

TABLE 53

Amino Acid Sequence of a Flag-Tagged CMP-TPB(gE)-TMR(ERGIC53) Fusion Protein

| Encoded Protein or Region (N- to C-terminal) | Sequence Identifier | Amino Acid Sequence 12345678901234567890123456789 |
|---|---|---|
| Flag-tagged CMP-TPB(gE)-TMR(ERGIC53) fusion protein | SEQ ID NO: 169 | MALWMRLLPLLALLALWGPDPAAAGTGSGE FIKKAFHKLAMKYDIGGGGSGGGGSGGGGS AAAGTPKTSWRRVSVGEDVSLLPAPGPTGR GPTQKLLWAVEPLDGCGPLHPSWVSLMPPK QVPETVVDAACMRAPVPLAMAYAPPAPSAT GGLRTDFVWQERAAVVNRSLVIHGVRETDS GLYTLSVGDIKDPARQVASVVLVVQPAPVP TPPPTPADYDEDDNDEGEDESLAGTPASGT PRLPPPPAPPRSWPSAPEVSHVRGVTVRME TPEAILFSPGETFSTNVSIHAIAHDDQTYS MDVVWLRFDVPTSCAEMRIYESCLYHPQLP ECLSPADAPCAASTWTSRLAVRSYAGCSRT NPPPRCSAEAHMEPVPGLAWQAASVNLEFR DASPQHSGLYLCVVYVNDHIHAWGHITIST AAQYRNAVVEQPLPQRGADLAELEGDYKDD DDKGSRLSTVHFIIFVVVQTVLFIGYIMYR SQQEAAAKKFF |

TABLE 53-continued

Amino Acid Sequence of a Flag-Tagged
CMP-TPB(gE)-TMR(ERGIC53) Fusion Protein

| Encoded Protein or Region (N- to C-terminal) | Sequence Identifier | Amino Acid Sequence 12345678901234567890123456 7890 |
|---|---|---|
| Human insulin signal sequence | residues 1-24 of SEQ ID NO: 169 | MALWMRLLPLLALLALWGPDPAAA |
| Linker | residues 25-31 of SEQ ID NO: 169 | GTGSGEF |
| CMP Domain (peptide from J domain of Erdj4) | residues 32-43 of SEQ ID NO: 169 | IKKAFHKLAMKY |
| Linker | residues 44-63 of SEQ ID NO: 169 | DIGGGGSGGGGSGGGGSAAA |
| TPB(gE) Domain | residues 64-442 of SEQ ID NO: 169 | GTPKTSWRRVSVGEDVSLLPAPGPTGRGPT QKLLWAVEPLDGCGPLHPSWVSLMPPKQVP ETVVDAACMRAPVPLAMAYAPPAPSATGGL RTDFVWQERAAVVNRSLVIHGVRETDSGLY TLSVGDIKDPARQVASVVLVVQPAPVPTPP PTPADYDEDDNDEGEDESLAGTPASGTPRL PPPPAPPRSWPSAPEVSHVRGVTVRMETPE AILFSPGETFSTNVSIHAIAHDDQTYSMDV VWLRFDVPTSCAEMRIYESCLYHPQLPECL SPADAPCAASTWTSRLAVRSYAGCSRTNPP PRCSAEAHMEPVPGLAWQAASVNLEFRDAS PQHSGLYLCVVYVNDHIHAWGHITISTAAQ YRNAVVEQPLPQRGADLAE |
| Linker | residues 443-445 of SEQ ID NO: 169 | LEG |
| Flag epitope domain | residues 446-453 of SEQ ID NO: 169 | DYKDDDDK |
| Linker | residues 454-456 of SEQ ID NO: 169 | GSR |
| TMR(ERGIC53) Domain | residues 457-491 of SEQ ID NO: 169 | LSTVHFIIFVVVQTVLFIGYIMYRSQQEAA AKKFF |

The amino acid sequence of the CMP-TPB(gE)-TMR (gp84) fusion protein (No. 17) is shown in Table 54 below.

TABLE 54

Amino Acid Sequence of a Flag-Tagged
CMP-TPB(gE)-TMR (gp84) Fusion Protein.

| Encoded Protein or Region (N- to C-terminal) | Sequence Identifier | Amino Acid Sequence 12345678901234567890123456 7890 |
|---|---|---|
| Flag-tagged CMP-TPB(gE)-TMR(gp84) fusion protein | SEQ ID NO: 170 | MALWMRLLPLLALLALWGPDPAAAGTGSGE FIKKAFHKLAMKYDIGGGGSGGGGSGGGGS AAAGTPKTSWRRVSVGEDVSLLPAPGPTGR GPTQKLLWAVEPLDGCGPLHPSWVSLMPPK QVPETVVDAACMRAPVPLAMAYAPPAPSAT GGLRTDFVWQERAAVVNRSLVIHGVRETDS GLYTLSVGDIKDPARQVASVVLVVQPAPVP |

TABLE 54-continued

Amino Acid Sequence of a Flag-Tagged
CMP-TPB(gE)-TMR (gp84) Fusion Protein.

| Encoded Protein or Region (N- to C-terminal) | Sequence Identifier | Amino Acid Sequence 12345678901234567890123456 7890 |
|---|---|---|
| | | TPPPTPADYDEDDNDEGEDESLAGTPASGT PRLPPPPAPPRSWPSAPEVSHVRGVTVRME TPEAILFSPGETFSTNVSIHAIAHDDQTYS MDVVWLRFDVPTSCAEMRIYESCLYHPQLP ECLSPADAPCAASTWTSRLAVRSYAGCSRT NPPPRCSAEAHMEPVPGLAWQAASVNLEFR DASPQHSGLYLCVVYVNDHIHAWGHITIST AAQYRNAVVEQPLPQRGADLAELEGDYKDD DDKGSRLGGVLYLISLCVSLPASFARRRRL GRWQE |
| Human insulin signal sequence | residues 1-24 of SEQ ID NO: 170 | MALWMRLLPLLALLALWGPDPAAA |
| Linker | residues 25-31 of SEQ ID NO: 170 | GTGSGEF |
| CMP Domain (peptide from J domain of Erdj4) | residues 32-43 of SEQ ID NO: 170 | IKKAFHKLAMKY |
| Linker | residues 44-63 of SEQ ID NO: 170 | DIGGGGSGGGGSGGGGSAAA |
| TPB(gE) Domain | residues 64-442 of SEQ ID NO 170 | GTPKTSWRRVSVGEDVSLLPAPGPTGRGPT QKLLWAVEPLDGCGPLHPSWVSLMPPKQVP ETVVDAACMRAPVPLAMAYAPPAPSATGGL RTDFVWQERAAVVNRSLVIHGVRETDSGLY TLSVGDIKDPARQVASVVLVVQPAPVPTPP PTPADYDEDDNDEGEDESLAGTPASGTPRL PPPPAPPRSWPSAPEVSHVRGVTVRMETPE AILFSPGETFSTNVSIHAIAHDDQTYSMDV VWLRFDVPTSCAEMRIYESCLYHPQLPECL SPADAPCAASTWTSRLAVRSYAGCSRTNPP PRCSAEAHMEPVPGLAWQAASVNLEFRDAS PQHSGLYLCVVYVNDHIHAWGHITISTAAQ YRNAVVEQPLPQRGADLAE |
| Linker | residues 443-445 of SEQ ID NO: 170 | LEG |
| Flag epitope domain | residues 446-453 of SEQ ID NO: 170 | DYKDDDDK |
| Linker | residues 454-456 of SEQ ID NO: 170 | GSR |
| TMR(gp84) Domain | residues 457-485 of SEQ ID NO: 170 | LGGVLYLISLCVSLPASFARRRRLGRWQE |

The amino acid sequence of the TMR(gp73)-CMP-TPB (gE) fusion protein (No. 18) is shown in Table 55 below.

TABLE 55

Amino Acid Sequence of a Flag-Tagged TMR(gp73)-CMP-TPB(gE) Fusion Protein

| Encoded Protein or Region (N- to C-terminal) | Sequence Identifier | Amino Acid Sequence 123456789012345678901234567890 |
|---|---|---|
| Flag-tagged TMR(gp73)-CMP-TPB(gE) fusion protein | SEQ ID NO: 171 | MMGLGNGRRSMKSPPLVLAALVACIIVLGF NYWIAGTGSGEFIKKAFHKLAMKYDIGGGG SGGGGSGGGGSAAAGTPKTSWRRVSVGEDV SLLPAPGPTGRGPTQKLLWAVEPLDGCGPL HPSWVSLMPPKQVPETVVDAACMRAPVPLA MAYAPPAPSATGGLRTDFVWQERAAVVNRS LVIHGVRETDSGLYTLSVGDIKDPARQVAS VVLVVQPAPVPTPPPTPADYDEDDNDEGED ESLAGTPASGTPRLPPPPAPPRSWPSAPEV SHVRGVTVRMETPEAILFSPGETFSTNVSI HAIAHDDQTYSMDVVWLRFDVPTSCAEMRI YESCLYHPQLPECLSPADAPCAASTWTSRL AVRSYAGCSRTNPPPRCSAEAHMEPVPGLA WQAASVNLEFRDASPQHSGLYLCVVYVNDH IHAWGHITISTAAQYRNAVVEQPLPQRGAD LAELEGDYKDDDDK |
| TMR(Gp73) Domain | residues 1-35 of SEQ ID NO: 171 | MMGLGNGRRSMKSPPLVLAALVACIIVLGF NYWIA |
| Linker | residues 36-42 of SEQ ID NO: 171 | GTGSGEF |
| CMP Domain (peptide from J domain of Erdj4) | residues 43-54 of SEQ ID NO: 171 | IKKAFHKLAMKY |
| Linker | residues 55-74 of SEQ ID NO: 171 | DIGGGGSGGGGSGGGGSAAA |
| TPB(gE) Domain | residues 75-453 of SEQ ID NO: 171 | GTPKTSWRRVSVGEDVSLLPAPGPTGRGPT QKLLWAVEPLDGCGPLHPSWVSLMPPKQVP ETVVDAACMRAPVPLAMAYAPPAPSATGGL RTDFVWQERAAVVNRSLVIHGVRETDSGLY TLSVGDIKDPARQVASVVLVVQPAPVPTPP PTPADYDEDDNDEGEDESLAGTPASGTPRL PPPPAPPRSWPSAPEVSHVRGVTVRMETPE AILFSPGETFSTNVSIHAIAHDDQTYSMDV VWLRFDVPTSCAEMRIYESCLYHPQLPECL SPADAPCAASTWTSRLAVRSYAGCSRTNPP PRCSAEAHMEPVPGLAWQAASVNLEFRDAS PQHSGLYLCVVYVNDHIHAWGHITISTAAQ YRNAVVEQPLPQRGADLAE |
| Linker | residues 454-456 of SEQ ID NO: 171 | LEG |
| Flag epitope domain | residues 457-464 ref SEQ ID NO: 171 | DYKDDDDK |

The amino acid sequence of the TMR(truncated N-terminal LIMP2)-CMP-TPB(gE) fusion protein (No. 19) is shown in Table 56 below.

TABLE 56

Amino Acid Sequence of a Flag-Tagged TMR(truncated N-terminal LIMP2)-CMP-TPB(gE) Fusion Protein.

| Encoded Protein or Region (N- to C-terminal) | Sequence Identifier | Amino Acid Sequence 123456789012345678901234567890 |
|---|---|---|
| Flag-tagged TMR(truncated N-terminal LIMP2)-CMP-TPB(gE) fusion protein | SEQ ID NO: 172 | MGRCCFYTAGTLSLLLLVTSVTLLVARVFG TGSGEFIKKAFHKLAMKYDIGGGGSGGGGS GGGGSAAAGTPKTSWRRVSVGEDVSLLPAP GPTGRGPTQKLLWAVEPLDGCGPLHPSWVS LMPPKQVPETVVDAACMRAPVPLAMAYAPP APSATGGLRTDFVWQERAAVVNRSLVIHGV RETDSGLYTLSVGDIKDPARQVASVVLVVQ PAPVPTPPPTPADYDEDDNDEGEDESLAGT PASGTPRLPPPPAPPRSWPSAPEVSHVRGV TVRMETPEAILFSPGETFSTNVSIHAIAHD DQTYSMDVVWLRFDVPTSCAEMRIYESCLY HPQLPECLSPADAPCAASTWTSRLAVRSYA GCSRTNPPPRCSAEAHMEPVPGLAWQAASV NLEFRDASPQHSGLYLCVVYVNDHIHAWGH ITISTAAQYRNAVVEQPLPQRGADLAELEG DYKDDDDK |
| TMR(truncated N-terminal LIMP2) Domain | residues 1-29 of SEQ ID NO: 172 | MGRCCFYTAGTLSLLLLVTSVTLLVARV |
| Linker | residues 30-36 of SEQ ID NO: 172 | GTGSGEF |
| CMP Domain (peptide from J domain of Erdj4) | residues 37-48 of SEQ ID NO: 172 | IKKAFHKLAMKY |
| Linker | residues 49-68 of SEQ ID NO: 172 | DIGGGGSGGGGSGGGGSAAA |
| TPB(gE) Domain | residues 69-447 of SEQ ID NO: 172 | GTPKTSWRRVSVGEDVSLLPAPGPTGRGPT QKLLWAVEPLDGCGPLHPSWVSLMPPKQVP ETVVDAACMRAPVPLAMAYAPPAPSATGGL RTDFVWQERAAVVNRSLVIHGVRETDSGLY TLSVGDIKDPARQVASVVLVVQPAPVPTPP PTPADYDEDDNDEGEDESLAGTPASGTPRL PPPPAPPRSWPSAPEVSHVRGVTVRMETPE AILFSPGETFSTNVSIHAIAHDDQTYSMDV VWLRFDVPTSCAEMRIYESCLYHPQLPECL SPADAPCAASTWTSRLAVRSYAGCSRTNPP PRCSAEAHMEPVPGLAWQAASVNLEFRDAS PQHSGLYLCVVYVNDHIHAWGHITISTAAQ YRNAVVEQPLPQRGADLAE |
| Linker | residues 448-450 of SEQ ID NO: 172 | LEG |
| Flag epitope domain | residues 451-458 of SEQ ID NO: 172 | DYKDDDDK |

The amino acid sequence of the CMP-TPB(gE)-TMR (KDELR) fusion protein (No. 20) is described in the Table 36 above (Example 19).

The amino acid sequence of TMR(truncated N-terminal LIMP2)-CMP-TPB(gE)-TMR (truncated C-terminal LIMP2) fusion protein (No. 21) is shown in Table 57 below.

TABLE 57

Amino Acid Sequence of a Flag-Tagged TMR(truncated N-terminal LIMP2)-CMP-TPB(gE)-TMR(truncated C-terminal LIMP2) Fusion Protein

| Encoded Protein or Region (N- to C-terminal) | Sequence Identifier | Amino Acid Sequence 12345678901234567890123456 7890 |
|---|---|---|
| Flag-tagged TMR(truncated N-terminal LIMP2)-CMP-TPB(gE)-TMR (truncated C-terminal LIMP2) fusion protein | SEQ ID NO: 173 | MGRCCFYTAGTLSLLLLVTSVTLLVARVFG TGSGEFIKKAFHKLAMKYDIGGGGSGGGGS GGGGSAAAGTPKTSWRRVSVGEDVSLLPAP GPTGRGPTQKLLWAVEPLDGCGPLHPSWVS LMPPKQVPETVVDAACMRAPVPLAMAYAPP APSATGGLRTDFVWQERAAVVNRSLVIHGV RETDSGLYTLSVGDIKDPARQVASVVLVVQ PAPVPTPPPTPADYDEDDNDEGEDESLAGT PASGTPRLPPPPAPPRSWPSAPEVSHVRGV TVRMETPEAILFSPGETFSTNVSIHAIAHD DQTYSMDVVWLRFDVPTSCAEMRIYESCLY HPQLPECLSPADAPCAASTWTSRLAVRSYA GCSRTNPPPRCSAEAHMEPVPGLAWQAASV NLEFRDASPQHSGLYLCVVYVNDHIHAWGH ITISTAAQYRNAVVEQPLPQRGADLAELEG DYKDDDDKGSRTLIITNIPYIIMALGVFFG LVFTWLACKGQGSMDEGTADERAPLIRT |
| TMR(truncated N-terminal LIMP2) Domain | residues 1-29 of SEQ ID NO: 173 | MCBCCFYTAGTLSLLLLVTSVTLLVARVF |
| Linker | residues 30-36 of SEQ ID NO: 173 | GTGSGEF |
| CMP Domain (peptide from J domain of Erdj4) | residues 37-48 of SEQ ID NO: 173 | IKKAFHKLAMKY |
| Linker | residues 49-68 of SEQ ID NO: 173 | DIGGGGSGGGGSGGGGSAAA |
| TPB(gE) Domain | residues 69-447 of SEQ ID NO: 173 | GTPKTSWRRVSVGEDVSLLPAPGPTGRGPT QKLLWAVEPLDGCGPLHPSWVSLMPPKQVP ETVVDAACMRAPVPLAMAYAPPAPSATGGL RTDFVWQERAAVVNRSLVIHGVRETDSGLY TLSVGDIKDPARQVASVVLVVQPAPVPTPP PTPADYDEDDNDEGEDESLAGTPASGTPRL PPPPAPPRSWPSAPEVSHVRGVTVRMETPE AILFSPGETFSTNVSIHAIAHDDQTYSMDV VWLRFDVPTSCAEMRIYESCLYHPQLPECL SPADAPCAASTWTSRLAVRSYAGCSRTNPP PRCSAEAHMEPVPGLAWQAASVNLEFRDAS PQHSGLYLCVVYVNDHIHAWGHITISTAAQ YRNAVVEQPLPQRGADLAE |
| Linker | residues 448-450 of SEQ ID NO: 173 | LEG |
| Flag epitope domain | residues 451-458 of SEQ ID NO: 173 | DYKDDDDK |
| Linker | residues 459-461 of SEQ ID NO: 173 | GSR |
| TMR(truncated C-terminal LIMP2) Domain | residues 462-508 of SEQ ID NO: 173 | TLIITNIPYIIMALGVFFGLVFTWLACKGQ GSMDEGTADERAPLIRT |

HEK293 cells were transfected with expression vector plasmids to compare levels of expression in culture media of IL13Rα2TF-Fc target protein. The relative amounts of secreted target protein expressed alone or co-expressed with one of the 17 different fusion proteins described above were measured by ELISA. Transfected cells were cultured for two days, and samples of cell media were harvested and analyzed by ELISA with Protein A as a binding protein for the target and peroxidase conjugated goat anti-human IgG F(ab')$_2$ Fragment (Jackson ImmunoResearch Laboratories, 109-036-098) as the detecting reagent. 3,3',5,5'-Tetramethylbenzidine (TMB) was used as a substrate for peroxidase and quantified on a microplate reader at 450 nm.

Figure 22A:
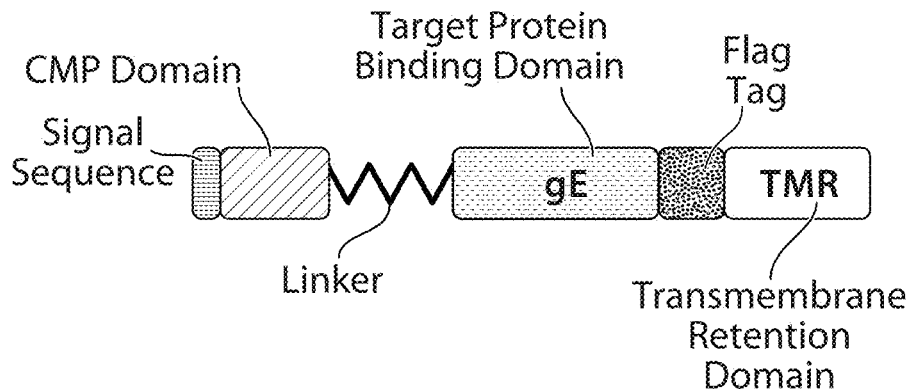
Figure 22B:
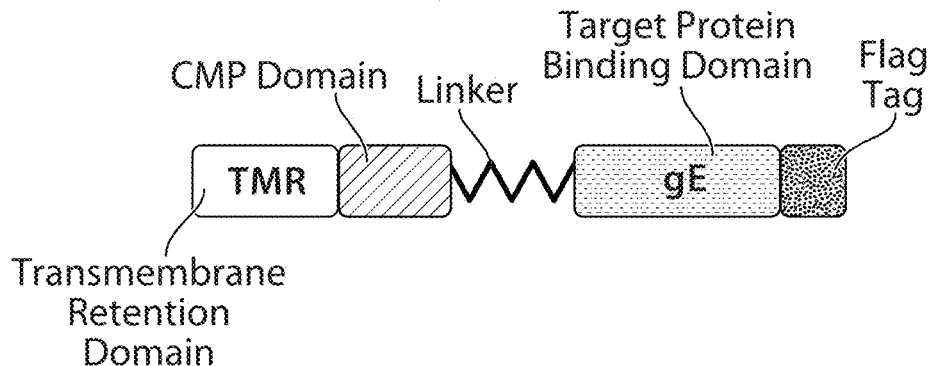
Figure 22C:
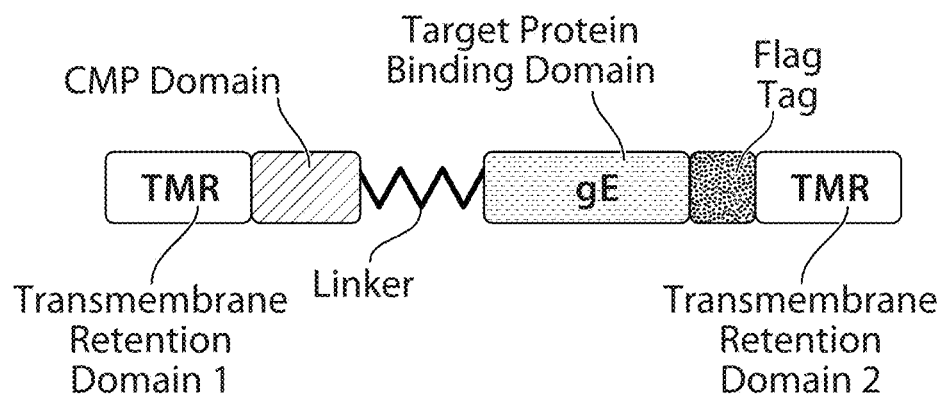
Figure 22D:
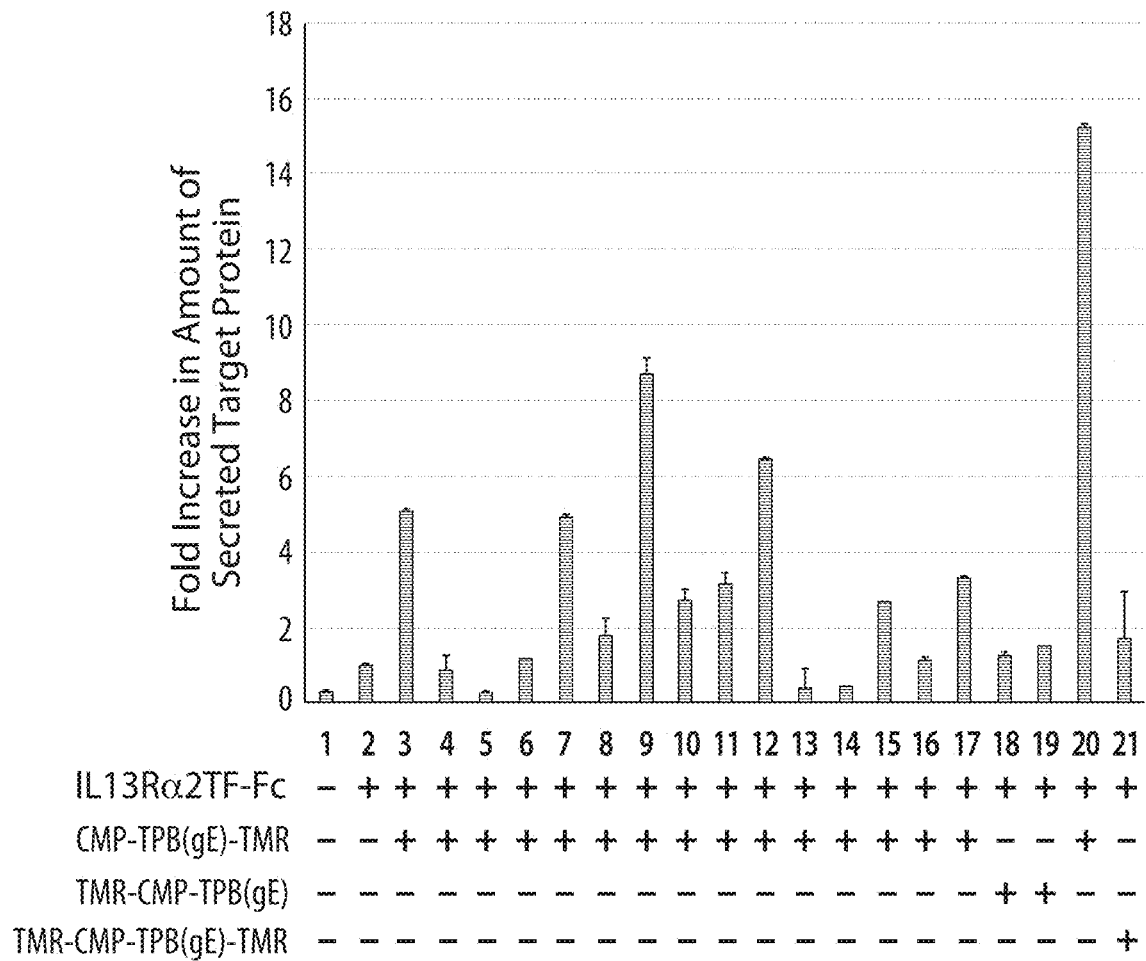

The results are shown in the bar graphs in FIG. 22D. ELISA results for mock cultures containing cells transfected with expression vector lacking a structural gene for expressing any protein are shown in bar graph 1 (negative control). The data in the bar graphs have been normalized by subtracting non-specific background signal in media from mock cultures and setting the amount of IL13Rα2TF-Fc target protein secreted into culture media when expressed in the absence of fusion protein at a relative value of 1 (bar graph 2).

Each of the bar graphs in FIG. 22D provides the results expressed as fold-increase in IL13Rα2TF-Fc target protein secreted into media of each culture compared to that for IL13Rα2TF-Fc target protein expressed alone in the absence of any expression-enhancing fusion protein. The results in the bar graphs of FIG. 22D correspond to the following cultures described in terms of the IL13Rα2TF-Fc target protein and a specific fusion protein:

1: Mock culture. Mock cultures contained cells transfected with expression vector lacking a structural gene for expressing any protein and were used as a negative control 2: IL13Rα2TF-Fc (target protein expressed in the absence of any fusion protein; positive control)

3: IL13Rα2TF-Fc+CMP-TPB(gE)-TMR(CD40)

4: IL13Rα2TF-Fc+CMP-TPB(gE)-TMR(Integrin)

5: IL13Rα2TF-Fc+CMP-TPB(gE)-TMR(UGT1)

6: IL13Rα2TF-Fc+CMP-TPB(gE)-TMR(KDELR truncated TMR)

7: IL13Rα2TF-Fc+CMP-TPB(gE)-TMR(p23)

8: IL13Rα2TF-Fc+CMP-TPB(gE)-TMR(p24)

9: IL13Rα2TF-Fc+CMP-TPB(gE)-TMR(LAMP2)

10: IL13Rα2TF-Fc+CMP-TPB(gE)-TMR(LIMP2 C-terminal TM region)

11: IL13Rα2TF-Fc+CMP-TPB(gE)-TMR(CDM6PR)

12: IL13Rα2TF-Fc+CMP-TPB(gE)-TMR(VSVG)

13: IL13Rα2TF-Fc+CMP-TPB(gE)-TMR(CNX)

14: IL13Rα2TF-Fc+CMP-TPB(gE)-TMR(CNX truncated TMR)

15: IL13Rα2TF-Fc+CMP-TPB(gE)-TMR(gE)

16: IL13Rα2TF-Fc+CMP-TPB(gE)-TMR(ERGIC53)

17: IL13Rα2TF-Fc+CMP-TPB(gE)-TMR(Gp84)

18: IL13Rα2TF-Fc+TMR(Gp73)-CMP-TPB(gE)

19: IL13Rα2TF-Fc+TMR(LIMP2 N-terminal TM region)-CMP-TPB(gE)

20: IL13Rα2TF-Fc+CMP-TPB(gE)-TMR(KDELR)

21: IL13Rα2TF-Fc+TMR(LIMP2 N-terminal TM region)-CMP-TPB(gE)-TMR(LIMP2 C-terminal TM region)

Bar graphs 3, 7, 8, 9, 10, 11, 12, 15, 17, and 20 show a significant enhancement in the level of secreted IL13Rα2TF-Fc target protein when co-expressed in transfected host cells with a fusion protein that comprises an N-proximal CMP domain linked to an Fc-binding target protein binding (TPB) domain, which in turn was linked to a C-terminal transmembrane retention (TMR) domain comprising a transmembrane region of a Type I transmembrane protein compared to the level of secretion of the target protein expressed alone (bar graph 2). The exceptional results indicated in bar graph 20 may be contrasted with the results illustrated in bar graph 6, which correspond to the unexceptional secretion of target protein co-expressed with fusion protein no. 6, which was similar to construct no. 20 but had a drastically truncated KDELR transmembrane retention domain (cf. Table 36, SEQ ID NO:151, and Table 43, SEQ ID NO:159). A general diagram for a construct encoding this set of fusion proteins is shown in FIG. 22A. The positioning of the TMR domain in the C-terminal region of these fusion proteins is consistent with the orientation of the N- and C-terminal regions relative to the transmembrane region of Type I transmembrane proteins. As shown in the diagram in FIG. 18, a Type I transmembrane protein is inserted into the ER membrane such that the N-terminal region resides within the ER lumen and the C-terminal region resides in the cytoplasmic side of the ER membrane. Accordingly, the fusion proteins used to generate the data illustrated by bar graphs 3, 7, 8, 9, 10, 11, 12, 15, 17, and 20 were designed so that the CMP and TPB domains in the N-proximal region of the fusion protein should be localized within the ER lumen to bind nascent target protein via the TPB domain to form a binding complex that presumably can be directed by the CMP domain into the Hsp70 chaperone machinery to enhance the level of expression of target protein destined for secretion upon release in the Golgi apparatus and secretory vesicles. An exception to the positive results observed for such fusion proteins having domains ordered as illustrated in FIG. 22A was the fusion protein used to generate the data for bar graph 4. The fusion protein used to generate the results in bar graph 4 comprised a transmembrane region of the human integrin αV Type I transmembrane protein and did not result in a significant enhancement in the level of secretion of the co-expressed IL13Rα2TF-Fc target protein. In view of the fact that the transmembrane regions of integrins are well known to associate with the transmembrane regions of various other integrins, the negative result in bar graph 4 may reflect possible interference by various associations with host cell integrins within the ER membrane that might interfere with the function of the fusion protein.

Bar graphs 5, 13, 14, and 16 indicate that no significant amount of the IL13Rα2TF-Fc target protein was secreted into culture medium of transfected host cells co-expressing the target protein and a fusion protein that comprised a transmembrane retention (TMR) domain comprising a transmembrane region from proteins known to reside in the endoplasmic reticulum (ER). Bar graph 5 shows the result when the IL13Rα2TF-Fc target protein was co-expressed with a fusion protein in which the TMR domain comprised a transmembrane region of human UDP-glucuronosyltransferase, which is a ubiquitous ER protein (Laakkonen et al., *Mol. Pharmacol.,* 77: 931-939 (2010). For bar graph 13, the TMR domain of the co-expressed fusion protein comprised a transmembrane region of calnexin, which is also known to reside in the ER membrane. As shown in bar graph 14, a fusion protein comprising the amino terminal half of the same calnexin transmembrane region that was used in the fusion protein for bar graph 13 provided no improvement in the secretion of the co-expressed IL13Rα2TF-Fc target protein. Moreover, as shown in bar graph 16 of FIG. 22D, no significant enhancement of secretion of the IL13Rα2TF-Fc target protein was observed when the target protein was co-expressed with a fusion protein comprising a TMR domain that comprised a transmembrane region of the ERGIC53 protein, which resides in the endoplasmic reticulum-Golgi intermediate compartment (ERGIC). The data in bar graphs 5, 13, 14, and 16 of FIG. 22D indicate that fusion proteins comprising TMR domains that comprise transmembrane regions from proteins that reside within the ER (including the ERGIC) are generally not effective in enhancing secretion of target proteins that are co-expressed with such fusion proteins. It would appear that once such a fusion protein binds a target protein the resulting binding complex is retained in the ER and cannot pass into the Golgi apparatus and secretory vesicles where conditions might otherwise facilitate release of the target protein for secretion from the cell.

Bar graph 18 of FIG. 22D shows that a relatively poor result was also obtained when the IL13Rα2TF-Fc target protein was co-expressed with a fusion protein in which the TMR domain comprised a transmembrane region of a Type II transmembrane protein such as the gp73 protein that resides in the membrane of the Golgi apparatus. As indicated in the diagram in FIG. 18, a Type II transmembrane protein is localized in the ER membrane so that the N-terminus of the protein is in the cytoplasm and the C-terminal region is in the ER lumen. Accordingly, it would appear that the configuration of the domains of a fusion protein that comprises a type II transmembrane region as a TMR domain should preferably place the TMR domain at the N-terminal region for insertion into the ER membrane while the CMP domain and TPB domain are positioned downstream (as indicated in the diagram of FIG. 22B) from the TMR domain so that both CMP and TPB domains remain in the ER lumen to bind nascent target protein and presumably recruit the Hsp70 chaperone system. Despite this arrangement of domains, bar graph 18 of FIG. 22D indicates that the fusion protein did not significantly enhance the level of secretion of the co-expressed IL13Rα2TF-Fc target protein. Similarly, bar graph 19 shows that only moderately positive results were obtained when the IL13Rα2TF-Fc target protein was co-expressed with a fusion protein comprising a portion of a transmembrane region of a Type III protein when expressed in the configuration diagrammed in FIG. 22B. Type III transmembrane proteins comprise more than one transmembrane-spanning region as indicated in the diagram in FIG. 18. For the culture leading to the results illustrated in bar graph 19, a fusion protein was constructed using one of the transmembrane regions of the Type III LIMP2 transmembrane protein that has the N- and C-termini directionality of a Type II transmembrane protein with respect to the ER membrane. (See, domain configuration of the construct in FIG. 22B.) The results illustrated in bar graphs 18 and 19 indicate that despite adopting an order of domains that preserves the location and availability of the CMP and TPB domains in the ER lumen, such fusion proteins were not as effective as fusion proteins having the configuration illustrated in FIG. 22A in significantly enhancing secretion of a co-expressed target protein. The data suggest that one or more factors other than the arrangement of domains with respect to the ER lumen must be taken into consideration if a fusion protein comprising a Type II transmembrane region or a Type III transmembrane region having the same orientation as a Type II transmembrane portion is to be used as a TMR domain of a fusion protein for enhancing secretion of a co-expressed target protein.

Bar graph 21 of FIG. 22D shows that use of a fusion protein comprising N- and C-terminal transmembrane regions from the Type III LIMP2 transmembrane protein (see, the diagram of the "TMR-CMP-TPB(gE)-TMR" construct in FIG. 22C) was also only moderately effective in significantly enhancing the level of secretion of a co-expressed IL13Rα2TF-Fc target protein.

Example 22

Importance of the TMR Domain on the Export of Target Protein from the Endoplasmic Reticulum (ER)

Example 21 shows the importance of selecting a TMR domains that does not interfere with the procession of the fusion protein/target protein complex from the ER to the Golgi apparatus. In this example, the TMR domain of a CMP-TPB(gE)-TMR(VSVG) was engineered to contain a known ER retention sequence (dilysine motif) at its C-terminus to determine the effect of the ER retention of the fusion protein on the level of secreted target protein. The V5-tagged IL13Rα2TF-Fc target protein used in this experiment was the same as described in Example 2 and Table 4 above.

FIGS. 23A and 23B shown diagrams of nucleic acid constructs encoding the two fusion protein constructs used in this experiment. The first fusion protein construct (FIG. 23A) comprised a segment encoding a CMP domain comprising a peptide from the J domain of the Erdj4 protein (IKKAFHKLAMKY; SEQ ID NO:9) linked to a segment encoding the Fc-binding region of the gE protein as a TPB domain, followed by a segment encoding a Flag epitope tag, which in turn was linked to a segment encoding a TMR domain comprising a transmembrane region of the VSV-G protein. This first fusion protein was designated "CMP-TPB (gE)-TMR(VSVG)". See FIG. 23A. The amino acid sequence for the encoded Flag-tagged CMP-TPB(gE)-TMR (VSVG) fusion protein used in this experiment is described in Table 49 of Example 21 above.

The second fusion protein construct shown in FIG. 23B was the same as the construct described for the first fusion protein as shown in FIG. 23A, except that the segment encoding the TMR domain comprised a mutated version of the VSVG transmembrane region in which the C-terminal amino acid sequence was altered to add the sequence K-T-C thereby creating a tandem lysine (dilysine) motif with the lysine residues at positions −3 and −4 from the C-terminus, which is a known ER retention signal for the fusion protein. Compare C-terminal amino acid sequence in FIG. 23A (SEQ ID NO:193) with that in FIG. 23B (SEQ ID NO:194). This fusion protein was designated "CMP-TPB(gE)-TMR (VSVG) with KK motif".

The amino acid sequence of the Flag-tagged CMP-TPB (gE)-TMR(VSVG) with KK motif" fusion protein is shown in Table 58 below.

TABLE 58

Amino Acid Sequence of a "Flag-Tagged CMP-TPB(gE)-TM1 with KK motif" Fusion Protein.

| Encoded Protein or Region (N- to C- terminal) | Sequence Identifier | Amino Acid Sequence 123456789012345678901234567890 |
|---|---|---|
| Flag-tagged CMP-TPB(gE)-TMR(VSVG) with KK motif fusion protein | SEQ ID NO: 174 | MALWMRLLPLLALLALWGPDPAAAGTGSGE<br>FIKKAFHKLAMKYDIGGGGSGGGGSGGGGS<br>AAAGTPKTSWRRVSVGEDVSLLPAPGPTGR<br>GPTQKLLWAVEPLDGCGPLHPSWVSLMPPK<br>QVPETVVDAACMRAPVPLAMAYAPPAPSAT<br>GGLRTDFVWQERAAVVNRSLVIHGVRETDS<br>GLYTLSVGDIKDPARQVASVVLVVQPAPVP<br>TPPPTPADYDEDDNDEGEDESLAGTPASGT<br>PRLPPPPAPPRSWPSAPEVSHVRGVTVRME<br>TPEAILFSPGETFSTNVSIHAIAHDDQTYS<br>MDVVWLRFDVPTSCAEMRIYESCLYHPQLP<br>ECLSPADAPCAASTWTSRLAVRSYAGCSRT<br>NPPPRCSAEAHMEPVPGLAWQAASVNLEFR<br>DASPQHSGLYLCVVYVNDHIHAWGHITIST<br>AAQYRNAVVEQPLPQRGADLAELEGDYKDD<br>DDKGSRDDESLFFGDTGLSKNPIELVEGWF<br>SSWKSSIASFFFIIGLIIGLFLVLRVGIHL<br>CIKLKHTKKRQIYTDIEMNRLGKKTC |
| Human insulin signal sequence | residues 1-24 of SEQ ID NO: 174 | MALWMRLLPLLALLALWGPDPAAA |
| Linker | residues 25-31 of SEQ ID NO: 174 | GTGSGEF |
| CMP Domain (peptide from J domain of Erdj4) | residues 32-43 of SEQ ID NO: 174 | IKKAFHKLAMKY |
| Linker | residues 44-63 of SEQ ID NO: 174 | DIGGGGSGGGGSGGGGSAAA |
| TPB(gE) Domain | residues 64-442 of SEQ ID NO: 174 | GTPKTSWRRVSVGEDVSLLPAPGPTGRGPT<br>QKLLWAVEPLDGCGPLHPSWVSLMPPKQVP<br>ETVVDAACMRAPVPLAMAYAPPAPSATGGL<br>RTDFVWQERAAVVNRSLVIHGVRETDSGLY<br>TLSVGDIKDPARQVASVVLVVQPAPVPTPP<br>PTPADYDEDDNDEGEDESLAGTPASGTPRL<br>PPPPAPPRSWPSAPEVSHVRGVTVRMETPE<br>AILFSPGETFSTNVSIHAIAHDDQTYSMDV<br>VWLRFDVPTSCAEMRIYESCLYHPQLPECL<br>SPADAPCAASTWTSRLAVRSYAGCSRTNPP<br>PRCSAEAHMEPVPGLAWQAASVNLEFRDAS<br>PQHSGLYLCVVYVNDHIHAWGHITISTAAQ<br>YRNAVVEQPLPQRGADLAE |
| Linker | residues 443-445 of SEQ ID NO: 174 | LEG |
| Flag epitope domain | residues 446-453 of SEQ ID NO: 174 | DYKDDDDK |
| Linker | residues 454-456 of SEQ ID NO: 174 | GSR |
| TMR Domain (VSVG) with KK motif | residues 457-536 of SEQ ID NO: 174 | DDESLFFGDTGLSKNPIELVEGWFSSWKSS<br>IASFFFIIGLIIGLFLVLRVGIHLCIKLKH<br>TKKRQIYTDIEMNRLGKKTC |

HEK293 cells were transfected with expression vector plasmids to compare levels of expression in culture media of IL13Rα2TF-Fc target protein expressed alone, IL13Rα2TF-Fc target protein co-expressed with the CMP-TPB(gE)-TMR(VSVG) fusion protein, or target protein co-expressed with the CMP-TPB(gE)-TMR(VSVG) with KK motif fusion protein. Transfected cells were cultured for two days, and samples of cell media were harvested and analyzed by ELISA with Protein A as a binding protein for the target protein and peroxidase conjugated goat anti-Human IgG F(ab')₂ Fragment (Jackson ImmunoResearch Laboratories, 109-036-098) for detection of immobilized target. Wells of a 96-well plate were coated with recombinant Protein A and incubated with culture media of transfected cells expressing IL13Rα2TF-Fc target protein alone, culture media of transfected cells co-expressing the target protein and the CMP-TPB(gE)-TMR(VSVG) fusion protein, or culture media of transfected cells co-expressing the target protein and the CMP-TPB(gE)-TMR(VSVG) with KK motif fusion protein. The captured target protein was then detected using the F(ab')2 fragment reagent.

Figure 23C:
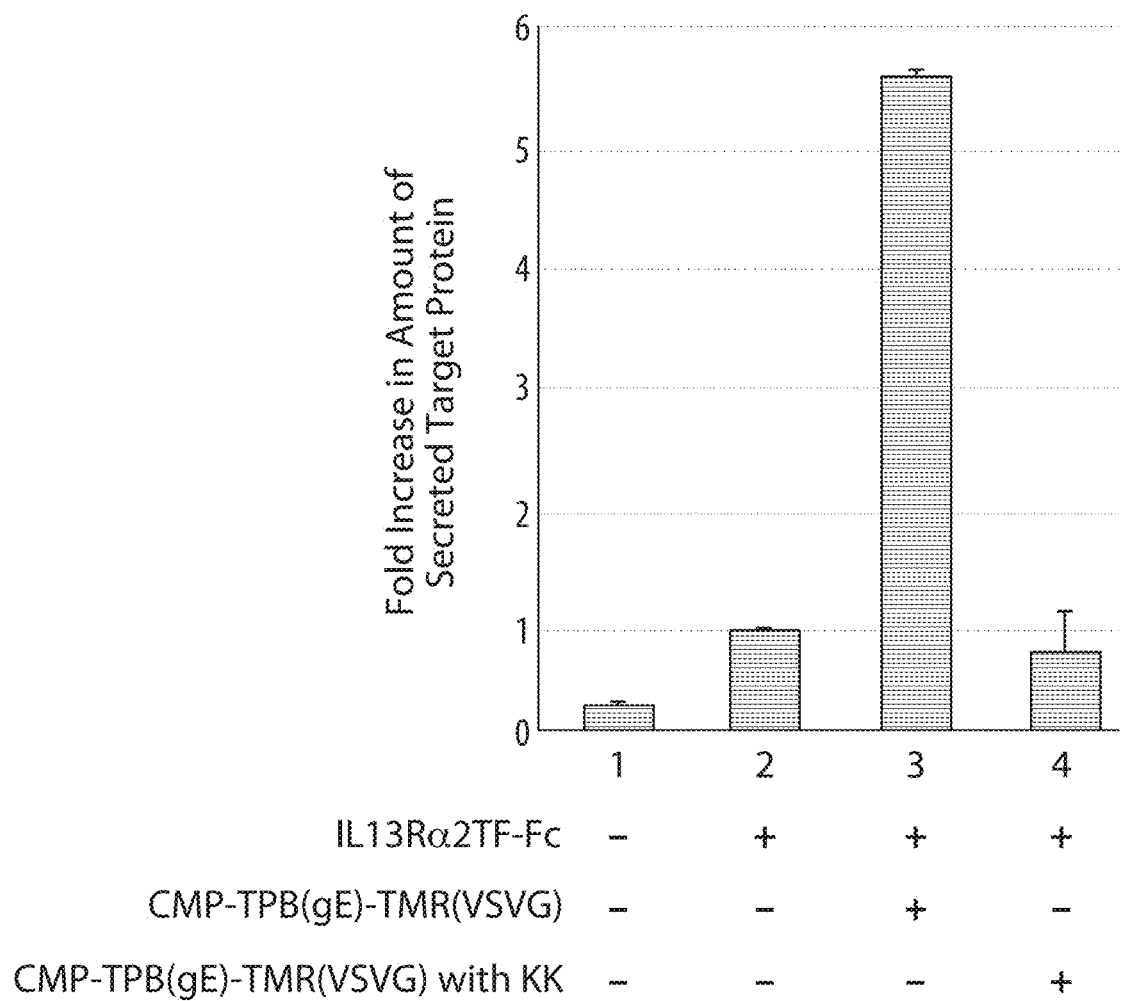
FIG. 23C is a series of bar graphs showing the fold increase in the amount of IL13Rα2TF-Fc target protein detected by ELISA in the media of cultures of transfected HEK293 host cells expressing the target protein alone (bar graph 2), co-expressing the target protein and a CMP-TPB (gE)-TMR(VSVG) fusion protein of diagram FIG. 23A (bar graph 3), or co-expressing the target protein and a "CMP-TPB(gE)-TMR(VSVG) with KK motif" fusion protein of diagram FIG. 23B (bar graph 4). The presence ("+") or absence ("−") of expression vectors encoding target protein or fusion protein in the transfected host cells of each culture is indicated below each bar graph. Mock cultures contained cells transfected with expression vector lacking a structural gene for expressing any protein and were used as a negative control (bar graph 1). The results show that co-expression of the IL13Rα2TF-Fc target protein with the CMP-TPB(gE)-TMR(VSVG) fusion protein (bar graph 3) significantly enhanced the level of target protein secreted into the culture media as compared to the level of target protein secreted into the culture media when the target protein was expressed in the absence of either fusion protein (bar graph 2). In contrast, co-expression of the IL13Rα2TF-Fc target protein with the "CMP-TPB(gE)-TMR(VSVG) with KK motif" did not enhance and in fact reduced the level of target protein secreted into the culture media (bar graph 4) as compared to the level of target protein secreted into the culture media when the target protein was expressed in the absence of either fusion protein (bar graph 2). The result shown in bar graph 4 suggests that localization and retention of the fusion protein (presumably bound to a IL13Rα2TF-Fc target protein) in the ER may inhibit orderly progression of the target protein into the secretory pathway. See Example 22 for additional details.

FIG. 23C shows the results of ELISAs to detect IL13Rα2TF-Fc target protein in the culture media. As shown in bar graph 3 of FIG. 23C, co-expression of the first fusion protein, CMP-TPB(gE)-TMR(VSVG), and the IL13Rα2TF-Fc target protein significantly enhanced the level of target protein secreted from the cells by 5.5-fold (bar graph 3) over the level of target protein secreted from cells expressing the target protein alone (bar graph 2). However, as shown in bar graph 4 of FIG. 23C, co-expression of the second fusion protein, CMP-TPB(gE)-TMR(VSVG) with KK, and the IL13Rα2TF-Fc target protein resulted in no enhancement in the level of target protein secreted from cells compared to that in cells expressing the target protein alone (bar graph 2). In fact, the level of target protein secreted from cells co-expressing the target protein and the CMP-TPB(gE)-TMR(VSVG) with KK (bar graph 4) appeared to be even less than that of cells expressing the target protein alone (bar graph 2).

The results show that the presence of the dilysine ER retention signal abolished the secretion enhancing activity of the fusion protein. The results are consistent with those shown in Example 10 for a CASE fusion protein of the invention comprising the same TPD and TMR domains, but lacking a CMP domain. These results indicate that for a fusion protein of the invention to enhance secretion of a co-expressed target protein, the TMR domain of the fusion protein must be able to function and associate with the membrane of the intracellular secretory pathway without being retained in the ER. Accordingly, as a general principle, a transmembrane region useful as a TMR domain in a cell-associated secretion-enhancing fusion protein of the invention should not comprise a C-terminal dilysine (KK) motif or any other signal or sequence known to localize a transmembrane protein in the ER.

All patents, applications, and publications cited in the above text are incorporated herein by reference.

Other variations and embodiments of the invention described herein will now be apparent to those of skill in the art without departing from the disclosure of the invention or the claims below.

SEQUENCE LISTING

```
<160> NUMBER OF SEQ ID NOS: 232

<210> SEQ ID NO 1
<211> LENGTH: 9
<212> TYPE: PRT
<213> ORGANISM: Artificial Sequence
<220> FEATURE:
<223> OTHER INFORMATION: consensus J domain sequence
<220> FEATURE:
<221> NAME/KEY: MISC_FEATURE
<222> LOCATION: (1)..(1)
<223> OTHER INFORMATION: X1 is isoleucine, leucine, valine, alanine, or
      methionine
<220> FEATURE:
<221> NAME/KEY: MISC_FEATURE
<222> LOCATION: (2)..(3)
<223> OTHER INFORMATION: X2 and X3 are each independently any amino acid
      with the proviso that one or both are lysine or arginine
<220> FEATURE:
<221> NAME/KEY: MISC_FEATURE
<222> LOCATION: (4)..(4)
<223> OTHER INFORMATION: X4 is any amino acid or X4 may be absent when
      X1 through X3 are present and X5 through X9 are present
<220> FEATURE:
<221> NAME/KEY: MISC_FEATURE
<222> LOCATION: (5)..(5)
<223> OTHER INFORMATION: X5 is tyrosine, tryptophan, or phenylalanine
<220> FEATURE:
<221> NAME/KEY: MISC_FEATURE
<222> LOCATION: (6)..(7)
<223> OTHER INFORMATION: X6 and X7 are each independently any amino acid
      with the proviso that one or both are lysine or arginine; or
      either one of X6 and X7 may be absent when the other is lysine or
      arginine and when X1 through X5 are present and X8 and X9 are
      present
<220> FEATURE:
<221> NAME/KEY: MISC_FEATURE
<222> LOCATION: (8)..(9)
<223> OTHER INFORMATION: X8 and X9 are any amino acid with the proviso
      that one or both are leucine or alanine; or one of X8 and X9 may
      be absent when the other is leucine or alanine and when X1 through
      X7 are present

<400> SEQUENCE: 1
```

```
Xaa Xaa Xaa Xaa Xaa Xaa Xaa Xaa Xaa
1               5

<210> SEQ ID NO 2
<211> LENGTH: 10
<212> TYPE: PRT
<213> ORGANISM: Artificial Sequence
<220> FEATURE:
<223> OTHER INFORMATION: J domain peptide

<400> SEQUENCE: 2

Ile Lys Lys Ala Tyr Lys Leu Ala Leu Gln
1               5                   10

<210> SEQ ID NO 3
<211> LENGTH: 10
<212> TYPE: PRT
<213> ORGANISM: Artificial Sequence
<220> FEATURE:
<223> OTHER INFORMATION: J domain peptide

<400> SEQUENCE: 3

Ile Lys Lys Ala Tyr Arg Leu Ala Leu Gln
1               5                   10

<210> SEQ ID NO 4
<211> LENGTH: 10
<212> TYPE: PRT
<213> ORGANISM: Artificial Sequence
<220> FEATURE:
<223> OTHER INFORMATION: J domain peptide

<400> SEQUENCE: 4

Ile Lys Lys Ala Tyr Arg Lys Ala Leu Gln
1               5                   10

<210> SEQ ID NO 5
<211> LENGTH: 10
<212> TYPE: PRT
<213> ORGANISM: Artificial Sequence
<220> FEATURE:
<223> OTHER INFORMATION: J domain decapeptide

<400> SEQUENCE: 5

Ile Lys Lys Ala Tyr Arg Lys Leu Leu Gln
1               5                   10

<210> SEQ ID NO 6
<211> LENGTH: 9
<212> TYPE: PRT
<213> ORGANISM: Artificial Sequence
<220> FEATURE:
<223> OTHER INFORMATION: Protein expression enhancing polypeptide

<400> SEQUENCE: 6

Ile Lys Lys Ala Tyr Arg Lys Leu Ala
1               5

<210> SEQ ID NO 7
<211> LENGTH: 12
<212> TYPE: PRT
<213> ORGANISM: Artificial Sequence
<220> FEATURE:
<223> OTHER INFORMATION: Protein expression-enhancing polypeptide

<400> SEQUENCE: 7

Ile Arg Lys Ala Tyr Arg Lys Leu Ser Leu Thr Leu
```

```
1               5                  10
```

<210> SEQ ID NO 8
<211> LENGTH: 12
<212> TYPE: PRT
<213> ORGANISM: Artificial Sequence
<220> FEATURE:
<223> OTHER INFORMATION: Protein expression-enhancing polypeptide

<400> SEQUENCE: 8

```
Ile Lys Lys Gln Tyr Arg Leu Leu Ser Leu Lys Tyr
1               5                  10
```

<210> SEQ ID NO 9
<211> LENGTH: 12
<212> TYPE: PRT
<213> ORGANISM: Artificial Sequence
<220> FEATURE:
<223> OTHER INFORMATION: Protein expression-enhancing polypeptide

<400> SEQUENCE: 9

```
Ile Lys Lys Ala Phe His Lys Leu Ala Met Lys Tyr
1               5                  10
```

<210> SEQ ID NO 10
<211> LENGTH: 12
<212> TYPE: PRT
<213> ORGANISM: Artificial Sequence
<220> FEATURE:
<223> OTHER INFORMATION: Protein expression-enhancing polypeptide

<400> SEQUENCE: 10

```
Ile Arg Gln Ala Phe Lys Lys Leu Ala Leu Lys Leu
1               5                  10
```

<210> SEQ ID NO 11
<211> LENGTH: 12
<212> TYPE: PRT
<213> ORGANISM: Artificial Sequence
<220> FEATURE:
<223> OTHER INFORMATION: Protein expression-enhancing polypeptide

<400> SEQUENCE: 11

```
Ile Ile Lys Ala Tyr Arg Lys Leu Ala Leu Gln Trp
1               5                  10
```

<210> SEQ ID NO 12
<211> LENGTH: 12
<212> TYPE: PRT
<213> ORGANISM: Artificial Sequence
<220> FEATURE:
<223> OTHER INFORMATION: Protein expression-enhancing polypeptide

<400> SEQUENCE: 12

```
Ile Ala Arg Ala Tyr Arg Gln Leu Ala Arg Arg Tyr
1               5                  10
```

<210> SEQ ID NO 13
<211> LENGTH: 12
<212> TYPE: PRT
<213> ORGANISM: Artificial Sequence
<220> FEATURE:
<223> OTHER INFORMATION: Protein expression-enhancing polypeptide

<400> SEQUENCE: 13

```
Ile Lys Arg Ala Tyr Arg Arg Gln Ala Leu Arg Tyr
1               5                  10
```

```
<210> SEQ ID NO 14
<211> LENGTH: 12
<212> TYPE: PRT
<213> ORGANISM: Artificial Sequence
<220> FEATURE:
<223> OTHER INFORMATION: Protein expression-enhancing polypeptide

<400> SEQUENCE: 14

Ile Lys Lys Ser Tyr Arg Lys Leu Ala Leu Lys Tyr
1               5                   10

<210> SEQ ID NO 15
<211> LENGTH: 12
<212> TYPE: PRT
<213> ORGANISM: Artificial Sequence
<220> FEATURE:
<223> OTHER INFORMATION: Protein expression-enhancing polypeptide

<400> SEQUENCE: 15

Ile Lys Lys Ala Tyr Lys Arg Leu Ala Met Lys Tyr
1               5                   10

<210> SEQ ID NO 16
<211> LENGTH: 58
<212> TYPE: PRT
<213> ORGANISM: Artificial Sequence
<220> FEATURE:
<223> OTHER INFORMATION: Isolated J-domain

<400> SEQUENCE: 16

Lys Asp Tyr Tyr Gln Thr Leu Gly Leu Ala Arg Gly Ala Ser Asp Glu
1               5                   10                  15

Glu Ile Lys Arg Ala Tyr Arg Arg Gln Ala Leu Arg Tyr His Pro Asp
            20                  25                  30

Lys Asn Lys Glu Pro Gly Ala Glu Glu Lys Phe Lys Glu Ile Ala Glu
        35                  40                  45

Ala Tyr Asp Val Leu Ser Asp Pro Arg Lys
    50                  55

<210> SEQ ID NO 17
<211> LENGTH: 58
<212> TYPE: PRT
<213> ORGANISM: Artificial Sequence
<220> FEATURE:
<223> OTHER INFORMATION: Isolated J domain

<400> SEQUENCE: 17

Leu Asn Phe Tyr Gln Phe Leu Gly Val Gln Gln Asp Ala Ser Ser Ala
1               5                   10                  15

Asp Ile Arg Lys Ala Tyr Arg Lys Leu Ser Leu Thr Leu His Pro Asp
            20                  25                  30

Lys Asn Lys Asp Glu Asn Ala Glu Thr Gln Phe Arg Gln Leu Val Ala
        35                  40                  45

Ile Tyr Glu Val Leu Lys Asp Asp Glu Arg
    50                  55

<210> SEQ ID NO 18
<211> LENGTH: 55
<212> TYPE: PRT
<213> ORGANISM: Artificial Sequence
<220> FEATURE:
<223> OTHER INFORMATION: ErdJ2 domain
```

```
<400> SEQUENCE: 18

Tyr Asn Pro Tyr Glu Val Leu Asn Leu Asp Pro Gly Ala Thr Val Ala
1               5                   10                  15

Glu Ile Lys Lys Gln Tyr Arg Leu Leu Ser Leu Lys Tyr His Pro Asp
            20                  25                  30

Lys Gly Gly Asp Glu Val Met Phe Met Arg Ile Ala Lys Ala Tyr Ala
        35                  40                  45

Ala Leu Thr Asp Glu Glu Ser
    50                  55

<210> SEQ ID NO 19
<211> LENGTH: 59
<212> TYPE: PRT
<213> ORGANISM: Artificial Sequence
<220> FEATURE:
<223> OTHER INFORMATION: ErdJ3 domain

<400> SEQUENCE: 19

Arg Asp Phe Tyr Lys Ile Leu Gly Val Pro Arg Ser Ala Ser Ile Lys
1               5                   10                  15

Asp Ile Lys Lys Ala Tyr Arg Lys Leu Ala Leu Gln Leu His Pro Asp
            20                  25                  30

Arg Asn Pro Asp Asp Pro Gln Ala Gln Glu Lys Phe Gln Asp Leu Gly
        35                  40                  45

Ala Ala Tyr Glu Val Leu Ser Asp Ser Glu Lys
    50                  55

<210> SEQ ID NO 20
<211> LENGTH: 58
<212> TYPE: PRT
<213> ORGANISM: Artificial Sequence
<220> FEATURE:
<223> OTHER INFORMATION: ErdJ4 domain

<400> SEQUENCE: 20

Lys Ser Tyr Tyr Asp Ile Leu Gly Val Pro Lys Ser Ala Ser Glu Arg
1               5                   10                  15

Gln Ile Lys Lys Ala Phe His Lys Leu Ala Met Lys Tyr His Pro Asp
            20                  25                  30

Lys Asn Lys Ser Pro Asp Ala Glu Ala Lys Phe Arg Glu Ile Ala Glu
        35                  40                  45

Ala Tyr Glu Thr Leu Ser Asp Ala Asn Arg
    50                  55

<210> SEQ ID NO 21
<211> LENGTH: 59
<212> TYPE: PRT
<213> ORGANISM: Artificial Sequence
<220> FEATURE:
<223> OTHER INFORMATION: ErdJ5 domain

<400> SEQUENCE: 21

Gln Asp Phe Tyr Ser Leu Leu Gly Val Ser Lys Thr Ala Ser Ser Arg
1               5                   10                  15

Glu Ile Arg Gln Ala Phe Lys Lys Leu Ala Leu Lys Leu His Pro Asp
            20                  25                  30

Lys Asn Pro Asn Asn Pro Asn Ala His Gly Asp Phe Leu Lys Ile Asn
        35                  40                  45

Arg Ala Tyr Glu Val Leu Lys Asp Glu Asp Leu
    50                  55
```

<210> SEQ ID NO 22
<211> LENGTH: 62
<212> TYPE: PRT
<213> ORGANISM: Artificial Sequence
<220> FEATURE:
<223> OTHER INFORMATION: ErdJ6 domain

<400> SEQUENCE: 22

Arg Asp Tyr Tyr Lys Ile Leu Gly Val Lys Arg Asn Ala Lys Lys Gln
1               5                   10                  15

Glu Ile Ile Lys Ala Tyr Arg Lys Leu Ala Leu Gln Trp His Pro Asp
            20                  25                  30

Asn Phe Gln Asn Glu Glu Lys Lys Ala Glu Lys Lys Phe Ile
        35                  40                  45

Asp Ile Ala Ala Ala Lys Glu Val Leu Ser Asp Pro Glu Met
    50                  55                  60

<210> SEQ ID NO 23
<211> LENGTH: 59
<212> TYPE: PRT
<213> ORGANISM: Artificial Sequence
<220> FEATURE:
<223> OTHER INFORMATION: hCSP J domain

<400> SEQUENCE: 23

Glu Ser Leu Tyr His Val Leu Gly Leu Asp Lys Asn Ala Thr Ser Asp
1               5                   10                  15

Asp Ile Lys Lys Ser Tyr Arg Lys Leu Ala Leu Lys Tyr His Pro Asp
            20                  25                  30

Lys Asn Pro Asp Asn Pro Glu Ala Ala Asp Lys Phe Lys Glu Ile Asn
        35                  40                  45

Asn Ala His Ala Ile Leu Thr Asp Ala Thr Lys
    50                  55

<210> SEQ ID NO 24
<211> LENGTH: 57
<212> TYPE: PRT
<213> ORGANISM: Artificial Sequence
<220> FEATURE:
<223> OTHER INFORMATION: SV40 large T Ag

<400> SEQUENCE: 24

Leu Gln Leu Met Asp Leu Leu Gly Leu Glu Arg Ser Ala Trp Gly Asn
1               5                   10                  15

Ile Pro Leu Met Arg Lys Ala Tyr Leu Lys Lys Cys Lys Glu Phe His
            20                  25                  30

Pro Asp Lys Gly Gly Asp Glu Glu Lys Met Lys Lys Met Asn Thr Leu
        35                  40                  45

Tyr Lys Lys Met Glu Asp Gly Val Lys
    50                  55

<210> SEQ ID NO 25
<211> LENGTH: 59
<212> TYPE: PRT
<213> ORGANISM: Artificial Sequence
<220> FEATURE:
<223> OTHER INFORMATION: Dna J

<400> SEQUENCE: 25

Gln Asp Tyr Tyr Glu Ile Leu Gly Val Ser Lys Thr Ala Glu Glu Arg
1               5                   10                  15

-continued

```
Glu Ile Lys Lys Ala Tyr Lys Arg Leu Ala Met Lys Tyr His Pro Asp
            20                  25                  30

Arg Asn Gln Gly Asp Lys Glu Ala Glu Ala Lys Phe Lys Glu Ile Lys
        35                  40                  45

Glu Ala Tyr Glu Val Leu Thr Asp Ser Gln Lys
    50                  55

<210> SEQ ID NO 26
<211> LENGTH: 68
<212> TYPE: PRT
<213> ORGANISM: Artificial Sequence
<220> FEATURE:
<223> OTHER INFORMATION: Dna J homolog, member 8

<400> SEQUENCE: 26

Asn Pro Phe Glu Val Leu Gln Ile Asp Pro Glu Val Thr Asp Glu Glu
1               5                   10                  15

Ile Lys Lys Arg Phe Arg Gln Leu Ser Ile Leu Val His Pro Asp Lys
            20                  25                  30

Asn Gln Asp Asp Ala Asp Arg Ala Gln Lys Ala Phe Glu Ala Val Asp
        35                  40                  45

Lys Ala Tyr Lys Leu Leu Leu Asp Gln Glu Gln Lys Lys Arg Ala Leu
    50                  55                  60

Asp Val Ile Gln
65

<210> SEQ ID NO 27
<211> LENGTH: 59
<212> TYPE: PRT
<213> ORGANISM: Artificial Sequence
<220> FEATURE:
<223> OTHER INFORMATION: DnaJ homolog, member 5B

<400> SEQUENCE: 27

Glu Ala Leu Tyr Glu Ile Leu Gly Leu His Lys Gly Ala Ser Asn Glu
1               5                   10                  15

Glu Ile Lys Lys Thr Tyr Arg Lys Leu Ala Leu Lys His His Pro Asp
            20                  25                  30

Lys Asn Pro Asp Asp Pro Ala Ala Thr Glu Lys Phe Lys Glu Ile Asn
        35                  40                  45

Asn Ala His Ala Ile Leu Thr Asp Ile Ser Lys
    50                  55

<210> SEQ ID NO 28
<211> LENGTH: 58
<212> TYPE: PRT
<213> ORGANISM: Artificial Sequence
<220> FEATURE:
<223> OTHER INFORMATION: DnaJ homolog, member 14

<400> SEQUENCE: 28

Leu Asn Pro Phe His Val Leu Gly Val Glu Ala Thr Ala Ser Asp Val
1               5                   10                  15

Glu Leu Lys Lys Ala Tyr Arg Gln Leu Ala Val Met Val His Pro Asp
            20                  25                  30

Lys Asn His His Pro Arg Ala Glu Glu Ala Phe Lys Val Leu Arg Ala
        35                  40                  45

Ala Trp Asp Ile Val Ser Asn Ala Glu Lys
    50                  55
```

<210> SEQ ID NO 29
<211> LENGTH: 69
<212> TYPE: PRT
<213> ORGANISM: Artificial Sequence
<220> FEATURE:
<223> OTHER INFORMATION: DnaJ homolog, member 25 precursor

<400> SEQUENCE: 29

```
Arg Asp Cys Tyr Glu Val Leu Gly Val Ser Arg Ser Ala Gly Lys Ala
1               5                   10                  15

Glu Ile Ala Arg Ala Tyr Arg Gln Leu Ala Arg Arg Tyr His Pro Asp
            20                  25                  30

Arg Tyr Arg Pro Gln Pro Gly Asp Glu Gly Pro Gly Arg Thr Pro Gln
        35                  40                  45

Ser Ala Glu Glu Ala Phe Leu Leu Val Ala Thr Ala Tyr Glu Thr Leu
    50                  55                  60

Lys Asp Glu Glu Thr
65
```

<210> SEQ ID NO 30
<211> LENGTH: 60
<212> TYPE: PRT
<213> ORGANISM: Artificial Sequence
<220> FEATURE:
<223> OTHER INFORMATION: DnaJ homolog, member 2, isoform a

<400> SEQUENCE: 30

```
Ala Ser Tyr Tyr Glu Ile Leu Asp Val Pro Arg Ser Ala Ser Ala Asp
1               5                   10                  15

Asp Ile Lys Lys Ala Tyr Arg Arg Lys Ala Leu Gln Trp His Pro Asp
            20                  25                  30

Lys Asn Pro Asp Asn Lys Glu Phe Ala Glu Lys Phe Lys Glu Val
        35                  40                  45

Ala Glu Ala Tyr Glu Val Leu Ser Asp Lys His Lys
    50                  55                  60
```

<210> SEQ ID NO 31
<211> LENGTH: 60
<212> TYPE: PRT
<213> ORGANISM: Artificial Sequence
<220> FEATURE:
<223> OTHER INFORMATION: DnaJ homolog, member 2, isoform b

<400> SEQUENCE: 31

```
Ala Ser Tyr Tyr Glu Ile Leu Asp Val Pro Arg Ser Ala Ser Ala Asp
1               5                   10                  15

Asp Ile Lys Lys Ala Tyr Arg Arg Lys Ala Leu Gln Trp His Pro Asp
            20                  25                  30

Lys Asn Pro Asp Asn Lys Glu Phe Ala Glu Lys Phe Lys Glu Val
        35                  40                  45

Ala Glu Ala Tyr Glu Val Leu Ser Asp Lys His Lys
    50                  55                  60
```

<210> SEQ ID NO 32
<211> LENGTH: 56
<212> TYPE: PRT
<213> ORGANISM: Artificial Sequence
<220> FEATURE:
<223> OTHER INFORMATION: Chain A, Bc008182 protein

<400> SEQUENCE: 32

```
Thr Thr Tyr Tyr Asp Val Leu Gly Val Lys Pro Asn Ala Thr Gln Glu
1               5                   10                  15

Glu Leu Lys Lys Ala Tyr Arg Lys Leu Ala Leu Lys Tyr His Pro Asp
                20                  25                  30

Lys Asn Pro Asn Glu Gly Glu Lys Phe Lys Gln Ile Ser Gln Ala Tyr
            35                  40                  45

Glu Val Leu Ser Asp Ala Lys Lys
        50                  55
```

<210> SEQ ID NO 33
<211> LENGTH: 60
<212> TYPE: PRT
<213> ORGANISM: Artificial Sequence
<220> FEATURE:
<223> OTHER INFORMATION: Chain A, Hsj1a

<400> SEQUENCE: 33

```
Ala Ser Tyr Tyr Glu Ile Leu Asp Val Pro Arg Ser Ala Ser Ala Asp
1               5                   10                  15

Asp Ile Lys Lys Ala Tyr Arg Arg Lys Ala Leu Gln Trp His Pro Asp
                20                  25                  30

Lys Asn Pro Asp Asn Lys Glu Phe Ala Glu Lys Lys Phe Lys Glu Val
            35                  40                  45

Ala Glu Ala Tyr Glu Val Leu Ser Asp Lys His Lys
        50                  55                  60
```

<210> SEQ ID NO 34
<211> LENGTH: 58
<212> TYPE: PRT
<213> ORGANISM: Artificial Sequence
<220> FEATURE:
<223> OTHER INFORMATION: Chain A, protein Rap1

<400> SEQUENCE: 34

```
Lys Asp Ser Trp Asp Met Leu Gly Val Lys Pro Gly Ala Ser Arg Asp
1               5                   10                  15

Glu Val Asn Lys Ala Tyr Arg Lys Leu Ala Val Leu Leu His Pro Asp
                20                  25                  30

Lys Cys Val Ala Pro Gly Ser Glu Asp Ala Phe Lys Ala Val Val Asn
            35                  40                  45

Ala Arg Thr Ala Leu Leu Lys Asn Ile Lys
        50                  55
```

<210> SEQ ID NO 35
<211> LENGTH: 60
<212> TYPE: PRT
<213> ORGANISM: Artificial Sequence
<220> FEATURE:
<223> OTHER INFORMATION: Chain A, protein Hcg3

<400> SEQUENCE: 35

```
Val Asp Tyr Tyr Glu Val Leu Asp Val Pro Arg Gln Ala Ser Ser Glu
1               5                   10                  15

Ala Ile Lys Lys Ala Tyr Arg Lys Leu Ala Leu Lys Trp His Pro Asp
                20                  25                  30

Lys Asn Pro Glu Asn Lys Glu Glu Ala Glu Arg Arg Phe Lys Gln Val
            35                  40                  45

Ala Glu Ala Tyr Glu Val Leu Ser Asp Ala Lys Lys
        50                  55                  60
```

```
<210> SEQ ID NO 36
<211> LENGTH: 59
<212> TYPE: PRT
<213> ORGANISM: Artificial Sequence
<220> FEATURE:
<223> OTHER INFORMATION: Chain A, Tid1 protein

<400> SEQUENCE: 36

Gly Asp Tyr Tyr Gln Ile Leu Gly Val Pro Arg Asn Ala Ser Gln Lys
1               5                   10                  15

Glu Ile Lys Lys Ala Tyr Tyr Gln Leu Ala Lys Lys Tyr His Pro Asp
            20                  25                  30

Thr Asn Lys Asp Asp Pro Lys Ala Lys Glu Lys Phe Ser Gln Leu Ala
        35                  40                  45

Glu Ala Tyr Glu Val Leu Ser Asp Glu Val Lys
    50                  55

<210> SEQ ID NO 37
<211> LENGTH: 58
<212> TYPE: PRT
<213> ORGANISM: Artificial Sequence
<220> FEATURE:
<223> OTHER INFORMATION: Chain A, DjaJ subfamily B, member 9

<400> SEQUENCE: 37

Gly Ser Tyr Tyr Asp Ile Leu Gly Val Pro Lys Ser Ala Ser Glu Arg
1               5                   10                  15

Gln Ile Lys Lys Ala Phe His Lys Leu Ala Met Lys Tyr His Pro Asp
            20                  25                  30

Lys Asn Lys Ser Pro Asp Ala Glu Ala Lys Phe Arg Glu Ile Ala Glu
        35                  40                  45

Ala Tyr Glu Thr Leu Ser Asp Ala Asn Arg
    50                  55

<210> SEQ ID NO 38
<211> LENGTH: 58
<212> TYPE: PRT
<213> ORGANISM: Artificial Sequence
<220> FEATURE:
<223> OTHER INFORMATION: Chain A, DjaJ subfamily B, member 12

<400> SEQUENCE: 38

Gly Asp Tyr Tyr Glu Ile Leu Gly Val Ser Arg Gly Ala Ser Asp Glu
1               5                   10                  15

Asp Leu Lys Lys Ala Tyr Arg Arg Leu Ala Leu Lys Phe His Pro Asp
            20                  25                  30

Lys Asn His Ala Pro Gly Ala Thr Glu Ala Phe Lys Ala Ile Gly Thr
        35                  40                  45

Ala Tyr Ala Val Leu Ser Asn Pro Glu Lys
    50                  55

<210> SEQ ID NO 39
<211> LENGTH: 58
<212> TYPE: PRT
<213> ORGANISM: Artificial Sequence
<220> FEATURE:
<223> OTHER INFORMATION: Chain A, huHsp40 (HDJ-1)

<400> SEQUENCE: 39

Lys Asp Tyr Tyr Gln Thr Leu Gly Leu Ala Arg Gly Ala Ser Asp Glu
1               5                   10                  15

Glu Ile Lys Arg Ala Tyr Arg Arg Gln Ala Leu Arg Tyr His Pro Asp
```

-continued

```
                20                  25                  30

Lys Asn Lys Glu Pro Gly Ala Glu Glu Lys Phe Lys Glu Ile Ala Glu
            35                  40                  45

Ala Tyr Asp Val Leu Ser Asp Pro Arg Lys
        50                  55

<210> SEQ ID NO 40
<211> LENGTH: 59
<212> TYPE: PRT
<213> ORGANISM: Artificial Sequence
<220> FEATURE:
<223> OTHER INFORMATION: Chain A, DnaJ chrom. region 18 protein

<400> SEQUENCE: 40

Thr Ala Leu Tyr Asp Leu Leu Gly Val Pro Ser Thr Ala Thr Gln Ala
1               5                   10                  15

Gln Ile Lys Ala Ala Tyr Tyr Arg Gln Cys Phe Leu Tyr His Pro Asp
                20                  25                  30

Arg Asn Ser Gly Ser Ala Glu Ala Ala Glu Arg Phe Thr Arg Ile Ser
            35                  40                  45

Gln Ala Tyr Val Val Leu Gly Ser Ala Thr Leu
        50                  55

<210> SEQ ID NO 41
<211> LENGTH: 60
<212> TYPE: PRT
<213> ORGANISM: Artificial Sequence
<220> FEATURE:
<223> OTHER INFORMATION: Chain A, DjaJ subfamily B, member 8

<400> SEQUENCE: 41

Ala Asn Tyr Tyr Glu Val Leu Gly Val Gln Ala Ser Ala Ser Pro Glu
1               5                   10                  15

Asp Ile Lys Lys Ala Tyr Arg Lys Leu Ala Leu Arg Trp His Pro Asp
                20                  25                  30

Lys Asn Pro Asp Asn Lys Glu Glu Ala Glu Lys Lys Phe Lys Leu Val
            35                  40                  45

Ser Glu Ala Tyr Glu Val Leu Ser Asp Ser Lys Lys
        50                  55                  60

<210> SEQ ID NO 42
<211> LENGTH: 59
<212> TYPE: PRT
<213> ORGANISM: Artificial Sequence
<220> FEATURE:
<223> OTHER INFORMATION: Chain A, DjaJ subfamily C, member 12

<400> SEQUENCE: 42

Glu Asp Tyr Tyr Thr Leu Leu Gly Cys Asp Glu Leu Ser Ser Val Glu
1               5                   10                  15

Gln Ile Leu Ala Glu Phe Lys Val Arg Ala Leu Glu Cys His Pro Asp
                20                  25                  30

Lys His Pro Glu Asn Pro Lys Ala Val Glu Thr Phe Gln Lys Leu Gln
            35                  40                  45

Lys Ala Lys Glu Ile Leu Thr Asn Glu Glu Ser
        50                  55

<210> SEQ ID NO 43
<211> LENGTH: 57
<212> TYPE: PRT
<213> ORGANISM: Artificial Sequence
```

```
<220> FEATURE:
<223> OTHER INFORMATION: Chain A, DnaJ domain of Kiaa0730 protein

<400> SEQUENCE: 43

Ser Ile Leu Lys Glu Val Thr Ser Val Val Glu Gln Ala Trp Lys Leu
1               5                   10                  15

Pro Glu Ser Glu Arg Lys Lys Ile Ile Arg Arg Leu Tyr Leu Lys Trp
                20                  25                  30

His Pro Asp Lys Asn Pro Glu Asn His Asp Ile Ala Asn Glu Val Phe
            35                  40                  45

Lys His Leu Gln Asn Glu Ile Asn Arg
        50                  55

<210> SEQ ID NO 44
<211> LENGTH: 60
<212> TYPE: PRT
<213> ORGANISM: Artificial Sequence
<220> FEATURE:
<223> OTHER INFORMATION: DnaJ homolog, subfamily B, member 6, isoform a

<400> SEQUENCE: 44

Val Asp Tyr Tyr Glu Val Leu Gly Val Gln Arg His Ala Ser Pro Glu
1               5                   10                  15

Asp Ile Lys Lys Ala Tyr Arg Lys Leu Ala Leu Lys Trp His Pro Asp
                20                  25                  30

Lys Asn Pro Glu Asn Lys Glu Glu Ala Glu Arg Lys Phe Lys Gln Val
            35                  40                  45

Ala Glu Ala Tyr Glu Val Leu Ser Asp Ala Lys Lys
        50                  55                  60

<210> SEQ ID NO 45
<211> LENGTH: 60
<212> TYPE: PRT
<213> ORGANISM: Artificial Sequence
<220> FEATURE:
<223> OTHER INFORMATION: DnaJ homolog, subfamily B, member 6, isoform b

<400> SEQUENCE: 45

Val Asp Tyr Tyr Glu Val Leu Gly Val Gln Arg His Ala Ser Pro Glu
1               5                   10                  15

Asp Ile Lys Lys Ala Tyr Arg Lys Leu Ala Leu Lys Trp His Pro Asp
                20                  25                  30

Lys Asn Pro Glu Asn Lys Glu Glu Ala Glu Arg Lys Phe Lys Gln Val
            35                  40                  45

Ala Glu Ala Tyr Glu Val Leu Ser Asp Ala Lys Lys
        50                  55                  60

<210> SEQ ID NO 46
<211> LENGTH: 58
<212> TYPE: PRT
<213> ORGANISM: Artificial Sequence
<220> FEATURE:
<223> OTHER INFORMATION: DnaJ homolog, subfamily B, member 9 precursor

<400> SEQUENCE: 46

Lys Ser Tyr Tyr Asp Ile Leu Gly Val Pro Lys Ser Ala Ser Glu Arg
1               5                   10                  15

Gln Ile Lys Lys Ala Phe His Lys Leu Ala Met Lys Tyr His Pro Asp
                20                  25                  30

Lys Asn Lys Ser Pro Asp Ala Glu Ala Lys Phe Arg Glu Ile Ala Glu
            35                  40                  45
```

Ala Tyr Glu Thr Leu Ser Asp Ala Asn Arg
        50                  55

<210> SEQ ID NO 47
<211> LENGTH: 60
<212> TYPE: PRT
<213> ORGANISM: Artificial Sequence
<220> FEATURE:
<223> OTHER INFORMATION: DnaJ (Hsp40) homolog, subfamily C, member 8,
      isoform CRA c

<400> SEQUENCE: 47

Leu Asn Pro Phe Glu Val Leu Gln Ile Asp Pro Glu Val Thr Asp Glu
1               5                   10                  15

Glu Ile Lys Lys Arg Phe Arg Gln Leu Ser Ile Leu Val His Pro Asp
            20                  25                  30

Lys Asn Gln Asp Asp Ala Asp Arg Ala Gln Lys Ala Phe Glu Ala Val
        35                  40                  45

Asp Lys Ala Tyr Lys Leu Leu Leu Asp Gln Glu Gln
    50                  55                  60

<210> SEQ ID NO 48
<211> LENGTH: 59
<212> TYPE: PRT
<213> ORGANISM: Artificial Sequence
<220> FEATURE:
<223> OTHER INFORMATION: DnaJ (Hsp40) homolog, subfamily C, member 13,
      isoform CRA b

<400> SEQUENCE: 48

Asp Asp Ala Tyr Glu Val Leu Asn Leu Pro Gln Gly Gln Gly Pro His
1               5                   10                  15

Asp Glu Ser Lys Ile Arg Lys Ala Tyr Phe Arg Leu Ala Gln Lys Tyr
            20                  25                  30

His Pro Asp Lys Asn Pro Glu Gly Arg Asp Met Phe Glu Lys Val Asn
        35                  40                  45

Lys Ala Tyr Glu Phe Leu Cys Thr Lys Ser Ala
    50                  55

<210> SEQ ID NO 49
<211> LENGTH: 35
<212> TYPE: PRT
<213> ORGANISM: Artificial Sequence
<220> FEATURE:
<223> OTHER INFORMATION: DnaJ (Hsp40) homolog, subfamily C, member 19,
      isoform CRA e

<400> SEQUENCE: 49

Arg Glu Ala Ala Leu Ile Leu Gly Val Ser Pro Thr Ala Asn Lys Gly
1               5                   10                  15

Lys Ile Arg Asp Ala His Arg Arg Ile Met Leu Leu Asn His Pro Asp
            20                  25                  30

Lys Gly Lys
        35

<210> SEQ ID NO 50
<211> LENGTH: 59
<212> TYPE: PRT
<213> ORGANISM: Artificial Sequence
<220> FEATURE:
<223> OTHER INFORMATION: DnaJ (Hsp40) homolog, subfamily C, member 5,
      isoform CRA_b -continued

<400> SEQUENCE: 50

Glu Ser Leu Tyr His Val Leu Gly Leu Asp Lys Asn Ala Thr Ser Asp
1               5                   10                  15

Asp Ile Lys Lys Ser Tyr Arg Lys Leu Ala Leu Lys Tyr His Pro Asp
            20                  25                  30

Lys Asn Pro Asp Asn Pro Glu Ala Ala Asp Lys Phe Lys Glu Ile Asn
        35                  40                  45

Asn Ala His Ala Ile Leu Thr Asp Ala Thr Lys
    50                  55

<210> SEQ ID NO 51
<211> LENGTH: 59
<212> TYPE: PRT
<213> ORGANISM: Artificial Sequence
<220> FEATURE:
<223> OTHER INFORMATION: DnaJ (Hsp40) homolog, subfamily C, member 4,
      isoform CRA_f

<400> SEQUENCE: 51

Ser Thr Tyr Tyr Glu Leu Leu Gly Val His Pro Gly Ala Ser Thr Glu
1               5                   10                  15

Glu Val Lys Arg Ala Phe Phe Ser Lys Ser Lys Glu Leu His Pro Asp
            20                  25                  30

Arg Asp Pro Gly Asn Pro Ser Leu His Ser Arg Phe Val Glu Leu Ser
        35                  40                  45

Glu Ala Tyr Arg Val Leu Ser Arg Glu Gln Ser
    50                  55

<210> SEQ ID NO 52
<211> LENGTH: 65
<212> TYPE: PRT
<213> ORGANISM: Artificial Sequence
<220> FEATURE:
<223> OTHER INFORMATION: human zinc finger, CSL-type containing 3,
      isoform CRA_c

<400> SEQUENCE: 52

Lys Asp Trp Tyr Ser Ile Leu Gly Ala Asp Pro Ser Ala Asn Ile Ser
1               5                   10                  15

Asp Leu Lys Gln Lys Tyr Gln Lys Leu Ile Leu Met Tyr His Pro Asp
            20                  25                  30

Lys Gln Ser Thr Asp Val Pro Ala Gly Thr Val Glu Glu Cys Val Gln
        35                  40                  45

Lys Phe Ile Glu Ile Asp Gln Ala Trp Lys Ile Leu Gly Asn Glu Glu
    50                  55                  60

Thr
65

<210> SEQ ID NO 53
<211> LENGTH: 59
<212> TYPE: PRT
<213> ORGANISM: Artificial Sequence
<220> FEATURE:
<223> OTHER INFORMATION: DnaJ (Hsp40) homolog, subfamily C, member 17,
      isoform CRA_a

<400> SEQUENCE: 53

Met Asp Leu Tyr Ala Leu Leu Gly Ile Glu Glu Lys Ala Ala Asp Lys
1               5                   10                  15

Glu Val Lys Lys Ala Tyr Arg Gln Lys Ala Leu Ser Cys His Pro Asp
            20                  25                  30

-continued

Lys Asn Pro Asp Asn Pro Arg Ala Ala Glu Leu Phe His Gln Leu Ser
            35                  40                  45

Gln Ala Leu Glu Val Leu Thr Asp Ala Ala Ala
    50                  55

<210> SEQ ID NO 54
<211> LENGTH: 58
<212> TYPE: PRT
<213> ORGANISM: Artificial Sequence
<220> FEATURE:
<223> OTHER INFORMATION: DnaJ (Hsp40) homolog, subfamily B, member 9,
      isoform CRA_a

<400> SEQUENCE: 54

Lys Ser Tyr Tyr Asp Ile Leu Gly Val Pro Lys Ser Ala Ser Glu Arg
1               5                   10                  15

Gln Ile Lys Lys Ala Phe His Lys Leu Ala Met Lys Tyr His Pro Asp
            20                  25                  30

Lys Asn Lys Ser Pro Asp Ala Glu Ala Lys Phe Arg Glu Ile Ala Glu
            35                  40                  45

Gly Ala Ser Val Pro Ala Ala Ser Ser Phe
    50                  55

<210> SEQ ID NO 55
<211> LENGTH: 59
<212> TYPE: PRT
<213> ORGANISM: Artificial Sequence
<220> FEATURE:
<223> OTHER INFORMATION: DnaJ (Hsp40) homolog, subfamily C, member 4,
      isoform CRA_g

<400> SEQUENCE: 55

Ser Thr Tyr Tyr Glu Leu Leu Gly Val His Pro Gly Ala Ser Thr Glu
1               5                   10                  15

Glu Val Lys Arg Ala Phe Phe Ser Lys Ser Lys Glu Leu His Pro Asp
            20                  25                  30

Arg Asp Pro Gly Asn Pro Ser Leu His Ser Arg Phe Val Glu Leu Ser
            35                  40                  45

Glu Ala Tyr Arg Val Leu Ser Arg Glu Gln Ser
    50                  55

<210> SEQ ID NO 56
<211> LENGTH: 59
<212> TYPE: PRT
<213> ORGANISM: Artificial Sequence
<220> FEATURE:
<223> OTHER INFORMATION: DnaJ (Hsp40) homolog, subfamily C, member 4,
      isoform CRA_a

<400> SEQUENCE: 56

Ser Thr Tyr Tyr Glu Leu Leu Gly Val His Pro Gly Ala Ser Thr Glu
1               5                   10                  15

Glu Val Lys Arg Ala Phe Phe Ser Lys Ser Lys Glu Leu His Pro Asp
            20                  25                  30

Arg Asp Pro Gly Asn Pro Ser Leu His Ser Arg Phe Val Glu Leu Ser
            35                  40                  45

Glu Ala Tyr Arg Val Leu Ser Arg Glu Gln Ser
    50                  55

<210> SEQ ID NO 57
<211> LENGTH: 62

```
<212> TYPE: PRT
<213> ORGANISM: Artificial Sequence
<220> FEATURE:
<223> OTHER INFORMATION: DnaJ (Hsp40) homolog, subfamily C, member 11,
      isoform CRA_c

<400> SEQUENCE: 57

Glu Asp Tyr Tyr Ser Leu Leu Asn Val Arg Arg Glu Ala Ser Ser Glu
1               5                   10                  15

Glu Leu Lys Ala Ala Tyr Arg Arg Leu Cys Met Leu Tyr His Pro Asp
            20                  25                  30

Lys His Arg Asp Pro Glu Leu Lys Ser Gln Ala Glu Arg Leu Phe Asn
        35                  40                  45

Leu Val His Gln Ala Tyr Glu Val Leu Ser Asp Pro Gln Thr
    50                  55                  60

<210> SEQ ID NO 58
<211> LENGTH: 65
<212> TYPE: PRT
<213> ORGANISM: Artificial Sequence
<220> FEATURE:
<223> OTHER INFORMATION: zinc finger, CSL-type containing 3, isoform
      CRA_b

<400> SEQUENCE: 58

Lys Asp Trp Tyr Ser Ile Leu Gly Ala Asp Pro Ser Ala Asn Ile Ser
1               5                   10                  15

Asp Leu Lys Gln Lys Tyr Gln Lys Leu Ile Leu Met Tyr His Pro Asp
            20                  25                  30

Lys Gln Ser Thr Asp Val Pro Ala Gly Thr Val Glu Cys Val Gln
        35                  40                  45

Lys Phe Ile Glu Ile Asp Gln Ala Trp Lys Ile Leu Gly Asn Glu Glu
    50                  55                  60

Thr
65

<210> SEQ ID NO 59
<211> LENGTH: 66
<212> TYPE: PRT
<213> ORGANISM: Artificial Sequence
<220> FEATURE:
<223> OTHER INFORMATION: J-type co-chaperone HSC20, isoform CRA_c

<400> SEQUENCE: 59

Arg Asp Tyr Phe Ser Leu Met Asp Cys Asn Arg Ser Phe Arg Val Asp
1               5                   10                  15

Thr Ala Lys Leu Gln His Arg Tyr Gln Gln Leu Gln Arg Leu Val His
            20                  25                  30

Pro Asp Phe Phe Ser Gln Arg Ser Gln Thr Glu Lys Asp Phe Ser Glu
        35                  40                  45

Lys His Ser Thr Leu Val Asn Asp Ala Tyr Lys Thr Leu Leu Ala Pro
    50                  55                  60

Leu Ser
65

<210> SEQ ID NO 60
<211> LENGTH: 69
<212> TYPE: PRT
<213> ORGANISM: Artificial Sequence
<220> FEATURE:
<223> OTHER INFORMATION: hCG1994888, isoform CRA_d
```

```
<400> SEQUENCE: 60

Arg Asp Cys Tyr Glu Val Leu Gly Val Ser Arg Ser Ala Gly Lys Ala
1               5                   10                  15

Glu Ile Ala Arg Ala Tyr Arg Gln Leu Ala Arg Arg Tyr His Pro Asp
            20                  25                  30

Arg Tyr Arg Pro Gln Pro Gly Asp Glu Gly Pro Gly Arg Thr Pro Gln
        35                  40                  45

Ser Ala Glu Glu Ala Phe Leu Leu Val Ala Thr Ala Tyr Glu Thr Leu
    50                  55                  60

Lys Asp Glu Glu Thr
65

<210> SEQ ID NO 61
<211> LENGTH: 49
<212> TYPE: PRT
<213> ORGANISM: Artificial Sequence
<220> FEATURE:
<223> OTHER INFORMATION: human DnaJ (Hsp40) homolog, subfamily A, member
      1, isoform CRA_a

<400> SEQUENCE: 61

Thr Thr Tyr Tyr Asp Val Leu Gly Val Lys Pro Asn Ala Thr Gln Glu
1               5                   10                  15

Glu Leu Lys Lys Ala Tyr Arg Lys Leu Ala Leu Lys Tyr His Pro Asp
            20                  25                  30

Lys Asn Pro Asn Glu Gly Glu Lys Val Lys Met Leu Tyr Ile Ser Ser
        35                  40                  45

Gln

<210> SEQ ID NO 62
<211> LENGTH: 77
<212> TYPE: PRT
<213> ORGANISM: Artificial Sequence
<220> FEATURE:
<223> OTHER INFORMATION: VSV-G glycoprotein TMRD

<400> SEQUENCE: 62

Asp Asp Glu Ser Leu Phe Phe Gly Asp Thr Gly Leu Ser Lys Asn Pro
1               5                   10                  15

Ile Glu Leu Val Glu Gly Trp Phe Ser Ser Trp Lys Ser Ser Ile Ala
            20                  25                  30

Ser Phe Phe Phe Ile Ile Gly Leu Ile Ile Gly Leu Phe Leu Val Leu
        35                  40                  45

Arg Val Gly Ile His Leu Cys Ile Lys Leu Lys His Thr Lys Lys Arg
    50                  55                  60

Gln Ile Tyr Thr Asp Ile Glu Met Asn Arg Leu Gly Lys
65                  70                  75

<210> SEQ ID NO 63
<211> LENGTH: 151
<212> TYPE: PRT
<213> ORGANISM: Artificial Sequence
<220> FEATURE:
<223> OTHER INFORMATION: Human herpesvirus 1 Envelope glycoprotein E
      Type I

<400> SEQUENCE: 63

Pro Thr His Pro His Val Gly Ala Pro His Ala Pro Pro Thr His
1               5                   10                  15

Gly Ala Leu Arg Leu Gly Ala Val Met Gly Ala Ala Leu Leu Leu Ser
```

```
            20                  25                  30
Ala Leu Gly Leu Ser Val Trp Ala Cys Met Thr Cys Trp Arg Arg Arg
        35                  40                  45

Ala Trp Arg Ala Val Lys Ser Arg Ala Ser Gly Lys Gly Pro Thr Tyr
    50                  55                  60

Ile Arg Val Ala Asp Ser Glu Leu Tyr Ala Asp Trp Ser Ser Asp Ser
65                  70                  75                  80

Glu Gly Glu Arg Asp Gln Val Pro Trp Leu Ala Pro Pro Glu Arg Pro
                85                  90                  95

Asp Ser Pro Ser Thr Asn Gly Ser Gly Phe Glu Ile Leu Ser Pro Thr
            100                 105                 110

Ala Pro Ser Val Tyr Pro Arg Ser Asp Gly His Gln Ser Arg Arg Gln
        115                 120                 125

Leu Thr Thr Phe Gly Ser Gly Arg Pro Asp Arg Arg Tyr Ser Gln Ala
    130                 135                 140

Ser Asp Ser Ser Val Phe Trp
145                 150

<210> SEQ ID NO 64
<211> LENGTH: 144
<212> TYPE: PRT
<213> ORGANISM: Artificial Sequence
<220> FEATURE:
<223> OTHER INFORMATION: Human herpesvirus 1 Envelope glycoprotein I
      Type I

<400> SEQUENCE: 64

Pro His Gly Val Asn His Glu Pro Pro Ser Asn Ala Thr Arg Ala Thr
1               5                   10                  15

Arg Asp Ser Arg Ser Ala Leu Thr Val Thr Gln Ile Ile Gln Ile Ala
            20                  25                  30

Ile Pro Ala Ser Ile Ile Ala Leu Val Phe Leu Gly Ser Cys Ile Cys
        35                  40                  45

Phe Ile His Arg Cys Gln Arg Arg Tyr Arg Arg Ser Arg Arg Pro Ile
    50                  55                  60

Tyr Asn Pro Gln Ile Pro Thr Gly Ile Ser Cys Ala Val Asn Glu Ala
65                  70                  75                  80

Ala Met Ala Arg Leu Gly Ala Glu Leu Lys Ser His Pro Ser Thr Pro
                85                  90                  95

Pro Lys Ser Arg Arg Arg Ser Ser Arg Thr Pro Met Pro Ser Leu Thr
            100                 105                 110

Ala Ile Ala Glu Glu Ser Glu Pro Ala Gly Ala Ala Gly Leu Pro Thr
        115                 120                 125

Pro Pro Val Asp Pro Thr Thr Ser Thr Pro Thr Pro Pro Leu Leu Val
    130                 135                 140

<210> SEQ ID NO 65
<211> LENGTH: 36
<212> TYPE: PRT
<213> ORGANISM: Artificial Sequence
<220> FEATURE:
<223> OTHER INFORMATION: human p23 Type I

<400> SEQUENCE: 65

Thr Arg Val Leu Tyr Phe Ser Ile Phe Ser Met Phe Cys Leu Ile Gly
1               5                   10                  15

Leu Ala Thr Trp Gln Val Phe Tyr Leu Arg Arg Phe Phe Lys Ala Lys
            20                  25                  30
```

```
Lys Leu Ile Glu
        35

<210> SEQ ID NO 66
<211> LENGTH: 35
<212> TYPE: PRT
<213> ORGANISM: Artificial Sequence
<220> FEATURE:
<223> OTHER INFORMATION: human p24 Type I

<400> SEQUENCE: 66

Ser Arg Val Val Leu Trp Ser Phe Phe Glu Ala Leu Val Leu Val Ala
1               5                   10                  15

Met Thr Leu Gly Gln Ile Tyr Tyr Leu Lys Arg Phe Phe Glu Val Arg
            20                  25                  30

Arg Val Val
        35

<210> SEQ ID NO 67
<211> LENGTH: 64
<212> TYPE: PRT
<213> ORGANISM: Artificial Sequence
<220> FEATURE:
<223> OTHER INFORMATION: human CD4 Type I

<400> SEQUENCE: 67

Gln Pro Met Ala Leu Ile Val Leu Gly Gly Val Ala Gly Leu Leu Leu
1               5                   10                  15

Phe Ile Gly Leu Gly Ile Phe Phe Cys Val Arg Cys Arg His Arg Arg
            20                  25                  30

Arg Gln Ala Glu Arg Met Ser Gln Ile Lys Arg Leu Leu Ser Glu Lys
        35                  40                  45

Lys Thr Cys Gln Cys Pro His Arg Phe Gln Lys Thr Cys Ser Pro Ile
    50                  55                  60

<210> SEQ ID NO 68
<211> LENGTH: 58
<212> TYPE: PRT
<213> ORGANISM: Artificial Sequence
<220> FEATURE:
<223> OTHER INFORMATION: human Integrin alpha V Type I

<400> SEQUENCE: 68

Pro Val Pro Val Trp Val Ile Ile Leu Ala Val Leu Ala Gly Leu Leu
1               5                   10                  15

Leu Leu Ala Val Leu Val Phe Val Met Tyr Arg Met Gly Phe Phe Lys
            20                  25                  30

Arg Val Arg Pro Pro Gln Glu Glu Gln Glu Arg Glu Gln Leu Gln Pro
        35                  40                  45

His Glu Asn Gly Glu Gly Asn Ser Glu Thr
    50                  55

<210> SEQ ID NO 69
<211> LENGTH: 45
<212> TYPE: PRT
<213> ORGANISM: Artificial Sequence
<220> FEATURE:
<223> OTHER INFORMATION: human UGT1 Type I

<400> SEQUENCE: 69

Leu Asp Val Ile Gly Phe Leu Leu Ala Val Val Leu Thr Val Ala Phe
1               5                   10                  15
```

-continued

Ile Thr Phe Lys Cys Cys Ala Tyr Gly Tyr Arg Lys Cys Leu Gly Lys
            20                  25                  30

Lys Gly Arg Val Lys Lys Ala His Lys Ser Lys Thr His
        35                  40                  45

<210> SEQ ID NO 70
<211> LENGTH: 180
<212> TYPE: PRT
<213> ORGANISM: Artificial Sequence
<220> FEATURE:
<223> OTHER INFORMATION: human Calnexin Type I

<400> SEQUENCE: 70

Pro Phe Arg Met Thr Pro Phe Ser Ala Ile Gly Leu Glu Leu Trp Ser
1               5                   10                  15

Met Thr Ser Asp Ile Phe Phe Asp Asn Phe Ile Ile Cys Ala Asp Arg
            20                  25                  30

Arg Ile Val Asp Asp Trp Ala Asn Asp Gly Trp Gly Leu Lys Lys Ala
        35                  40                  45

Ala Asp Gly Ala Ala Glu Pro Gly Val Val Gly Gln Met Ile Glu Ala
    50                  55                  60

Ala Glu Glu Arg Pro Trp Leu Trp Val Val Tyr Ile Leu Thr Val Ala
65                  70                  75                  80

Leu Pro Val Phe Leu Val Ile Leu Phe Cys Cys Ser Gly Lys Lys Gln
                85                  90                  95

Thr Ser Gly Met Glu Tyr Lys Lys Thr Asp Ala Pro Gln Pro Asp Val
            100                 105                 110

Lys Glu Glu Glu Glu Glu Lys Glu Glu Lys Asp Lys Gly Asp Glu
        115                 120                 125

Glu Glu Glu Gly Glu Glu Lys Leu Glu Glu Lys Gln Lys Ser Asp Ala
    130                 135                 140

Glu Glu Asp Gly Gly Thr Val Ser Gln Glu Glu Asp Arg Lys Pro
145                 150                 155                 160

Lys Ala Glu Glu Asp Glu Ile Leu Asn Arg Ser Pro Arg Asn Arg Lys
                165                 170                 175

Pro Arg Arg Glu
            180

<210> SEQ ID NO 71
<211> LENGTH: 211
<212> TYPE: PRT
<213> ORGANISM: Artificial Sequence
<220> FEATURE:
<223> OTHER INFORMATION: human KDEL receptor 1 Type IV

<400> SEQUENCE: 71

Asn Leu Phe Arg Phe Leu Gly Asp Leu Ser His Leu Leu Ala Ile Ile
1               5                   10                  15

Leu Leu Leu Leu Lys Ile Trp Lys Ser Arg Ser Cys Ala Gly Ile Ser
            20                  25                  30

Gly Lys Ser Gln Val Leu Phe Ala Val Val Phe Thr Ala Arg Tyr Leu
        35                  40                  45

Asp Leu Phe Thr Asn Tyr Ile Ser Leu Tyr Asn Thr Cys Met Lys Val
    50                  55                  60

Val Tyr Ile Ala Cys Ser Phe Thr Thr Val Trp Leu Ile Tyr Ser Lys
65                  70                  75                  80

Phe Lys Ala Thr Tyr Asp Gly Asn His Asp Thr Phe Arg Val Glu Phe

```
                  85                  90                  95
Leu Val Val Pro Thr Ala Ile Leu Ala Phe Leu Val Asn His Asp Phe
            100                 105                 110

Thr Pro Leu Glu Ile Leu Trp Thr Phe Ser Ile Tyr Leu Glu Ser Val
            115                 120                 125

Ala Ile Leu Pro Gln Leu Phe Met Val Ser Lys Thr Gly Glu Ala Glu
            130                 135                 140

Thr Ile Thr Ser His Tyr Leu Phe Ala Leu Gly Val Tyr Arg Thr Leu
145                 150                 155                 160

Tyr Leu Phe Asn Trp Ile Trp Arg Tyr His Phe Glu Gly Phe Phe Asp
                165                 170                 175

Leu Ile Ala Ile Val Ala Gly Leu Val Gln Thr Val Leu Tyr Cys Asp
                180                 185                 190

Phe Phe Tyr Leu Tyr Ile Thr Lys Val Leu Lys Gly Lys Lys Leu Ser
                195                 200                 205

Leu Pro Ala
    210

<210> SEQ ID NO 72
<211> LENGTH: 35
<212> TYPE: PRT
<213> ORGANISM: Artificial Sequence
<220> FEATURE:
<223> OTHER INFORMATION: Gp73 Type II

<400> SEQUENCE: 72

Met Met Gly Leu Gly Asn Gly Arg Arg Ser Met Lys Ser Pro Pro Leu
1               5                   10                  15

Val Leu Ala Ala Leu Val Ala Cys Ile Ile Val Leu Gly Phe Asn Tyr
            20                  25                  30

Trp Ile Ala
        35

<210> SEQ ID NO 73
<211> LENGTH: 37
<212> TYPE: PRT
<213> ORGANISM: Artificial Sequence
<220> FEATURE:
<223> OTHER INFORMATION: human LAMP2 Type I

<400> SEQUENCE: 73

Thr Ile Leu Ile Pro Ile Ile Val Gly Ala Gly Leu Ser Gly Leu Ile
1               5                   10                  15

Ile Val Ile Val Ile Ala Tyr Val Ile Gly Arg Arg Lys Ser Tyr Ala
            20                  25                  30

Gly Tyr Gln Thr Leu
        35

<210> SEQ ID NO 74
<211> LENGTH: 29
<212> TYPE: PRT
<213> ORGANISM: Artificial Sequence
<220> FEATURE:
<223> OTHER INFORMATION: human LIMP2 Type IV

<400> SEQUENCE: 74

Met Gly Arg Cys Cys Phe Tyr Thr Ala Gly Thr Leu Ser Leu Leu Leu
1               5                   10                  15

Leu Val Thr Ser Val Thr Leu Leu Val Ala Arg Val Phe
            20                  25
```

<210> SEQ ID NO 75
<211> LENGTH: 47
<212> TYPE: PRT
<213> ORGANISM: Artificial Sequence
<220> FEATURE:
<223> OTHER INFORMATION: human LIMP2 fragment of TM domain Type IV

<400> SEQUENCE: 75

```
Thr Leu Ile Ile Thr Asn Ile Pro Tyr Ile Ile Met Ala Leu Gly Val
1               5                   10                  15

Phe Phe Gly Leu Val Phe Thr Trp Leu Ala Cys Lys Gly Gln Gly Ser
            20                  25                  30

Met Asp Glu Gly Thr Ala Asp Glu Arg Ala Pro Leu Ile Arg Thr
        35                  40                  45
```

<210> SEQ ID NO 76
<211> LENGTH: 94
<212> TYPE: PRT
<213> ORGANISM: Artificial Sequence
<220> FEATURE:
<223> OTHER INFORMATION: human CD Man-6-P receptor Type I

<400> SEQUENCE: 76

```
Ser His Leu Ser Val Gly Ser Ile Leu Leu Val Thr Phe Ala Ser Leu
1               5                   10                  15

Val Ala Val Tyr Val Val Gly Gly Phe Leu Tyr Gln Arg Leu Val Val
            20                  25                  30

Gly Ala Lys Gly Met Glu Gln Phe Pro His Leu Ala Phe Trp Gln Asp
        35                  40                  45

Leu Gly Asn Leu Val Ala Asp Gly Cys Asp Phe Val Cys Arg Ser Lys
    50                  55                  60

Pro Arg Asn Val Pro Ala Ala Tyr Arg Gly Val Gly Asp Asp Gln Leu
65                  70                  75                  80

Gly Glu Glu Ser Glu Arg Asp Asp His Leu Leu Pro Met
                85                  90
```

<210> SEQ ID NO 77
<211> LENGTH: 189
<212> TYPE: PRT
<213> ORGANISM: Artificial Sequence
<220> FEATURE:
<223> OTHER INFORMATION: human CI Man-6-P receptor Type I

<400> SEQUENCE: 77

```
Ser Gln Ala Val Gly Ala Val Leu Ser Leu Leu Leu Val Ala Leu Thr
1               5                   10                  15

Cys Cys Leu Leu Ala Leu Leu Leu Tyr Lys Lys Glu Arg Arg Glu Thr
            20                  25                  30

Val Ile Ser Lys Leu Thr Thr Cys Cys Arg Arg Ser Ser Asn Val Ser
        35                  40                  45

Tyr Lys Tyr Ser Lys Val Asn Lys Glu Glu Glu Thr Asp Glu Asn Glu
    50                  55                  60

Thr Glu Trp Leu Met Glu Glu Ile Gln Leu Pro Pro Pro Arg Gln Gly
65                  70                  75                  80

Lys Glu Gly Gln Glu Asn Gly His Ile Thr Thr Lys Ser Val Lys Ala
                85                  90                  95

Leu Ser Ser Leu His Gly Asp Asp Gln Asp Ser Glu Asp Glu Val Leu
            100                 105                 110
```

```
Thr Ile Pro Glu Val Lys Val His Ser Gly Arg Gly Ala Gly Ala Glu
            115                 120                 125

Ser Ser His Pro Val Arg Asn Ala Gln Ser Asn Ala Leu Gln Glu Arg
    130                 135                 140

Glu Asp Asp Arg Val Gly Leu Val Arg Gly Glu Lys Ala Arg Lys Gly
145                 150                 155                 160

Lys Ser Ser Ser Ala Gln Gln Lys Thr Val Ser Ser Thr Lys Leu Val
                165                 170                 175

Ser Phe His Asp Asp Ser Asp Glu Asp Leu Leu His Ile
                180                 185

<210> SEQ ID NO 78
<211> LENGTH: 53
<212> TYPE: PRT
<213> ORGANISM: Artificial Sequence
<220> FEATURE:
<223> OTHER INFORMATION: VSV-G with dilysine motif Type I

<400> SEQUENCE: 78

Ser Ser Trp Lys Ser Ser Ile Ala Ser Phe Phe Ile Ile Gly Leu
1               5                   10                  15

Ile Ile Gly Leu Phe Leu Val Leu Arg Val Gly Ile His Leu Cys Ile
                20                  25                  30

Lys Leu Lys His Thr Lys Lys Arg Gln Ile Tyr Thr Asp Ile Glu Met
            35                  40                  45

Asn Arg Leu Gly Lys
        50

<210> SEQ ID NO 79
<211> LENGTH: 93
<212> TYPE: PRT
<213> ORGANISM: Artificial Sequence
<220> FEATURE:
<223> OTHER INFORMATION: human Calnexin Truncated TMR Type I

<400> SEQUENCE: 79

Pro Phe Arg Met Thr Pro Phe Ser Ala Ile Gly Leu Glu Leu Trp Ser
1               5                   10                  15

Met Thr Ser Asp Ile Phe Phe Asp Asn Phe Ile Ile Cys Ala Asp Arg
                20                  25                  30

Arg Ile Val Asp Asp Trp Ala Asn Asp Gly Trp Gly Leu Lys Lys Ala
            35                  40                  45

Ala Asp Gly Ala Ala Glu Pro Gly Val Val Gln Met Ile Glu Ala
        50                  55                  60

Ala Glu Glu Arg Pro Trp Leu Trp Val Tyr Ile Leu Thr Val Ala
65                  70                  75                  80

Leu Pro Val Phe Leu Val Ile Leu Phe Cys Cys Ser Gly
                85                  90

<210> SEQ ID NO 80
<211> LENGTH: 36
<212> TYPE: PRT
<213> ORGANISM: Artificial Sequence
<220> FEATURE:
<223> OTHER INFORMATION: human KDEL receptor1 TMR7 Type IV

<400> SEQUENCE: 80

Asp Leu Ile Ala Ile Val Ala Gly Leu Val Gln Thr Val Leu Tyr Cys
1               5                   10                  15

Asp Phe Phe Tyr Leu Tyr Ile Thr Lys Val Leu Lys Gly Lys Lys Leu
```

```
                    20                  25                  30

Ser Leu Pro Ala
        35

<210> SEQ ID NO 81
<211> LENGTH: 35
<212> TYPE: PRT
<213> ORGANISM: Artificial Sequence
<220> FEATURE:
<223> OTHER INFORMATION: Human ERGIC-53 Type I

<400> SEQUENCE: 81

Leu Ser Thr Val His Phe Ile Ile Phe Val Val Gln Thr Val Leu
1               5                  10                  15

Phe Ile Gly Tyr Ile Met Tyr Arg Ser Gln Gln Glu Ala Ala Lys
            20                  25                  30

Lys Phe Phe
        35

<210> SEQ ID NO 82
<211> LENGTH: 29
<212> TYPE: PRT
<213> ORGANISM: Artificial Sequence
<220> FEATURE:
<223> OTHER INFORMATION: Gp83 TMR domain

<400> SEQUENCE: 82

Leu Gly Gly Val Leu Tyr Leu Ile Ser Leu Cys Val Ser Leu Pro Ala
1               5                  10                  15

Ser Phe Ala Arg Arg Arg Arg Leu Gly Arg Trp Gln Glu
            20                  25

<210> SEQ ID NO 83
<211> LENGTH: 5
<212> TYPE: PRT
<213> ORGANISM: Artificial Sequence
<220> FEATURE:
<223> OTHER INFORMATION: Suitable linkers

<400> SEQUENCE: 83

Asp Ile Ala Ala Ala
1               5

<210> SEQ ID NO 84
<211> LENGTH: 7
<212> TYPE: PRT
<213> ORGANISM: Artificial Sequence
<220> FEATURE:
<223> OTHER INFORMATION: Suitable linkers

<400> SEQUENCE: 84

Asp Ile Ala Ala Ala Leu Glu
1               5

<210> SEQ ID NO 85
<211> LENGTH: 6
<212> TYPE: PRT
<213> ORGANISM: Artificial Sequence
<220> FEATURE:
<223> OTHER INFORMATION: Suitable linkers

<400> SEQUENCE: 85

Gly Thr Gly Ser Glu Phe
1               5
```

```
<210> SEQ ID NO 86
<211> LENGTH: 4
<212> TYPE: PRT
<213> ORGANISM: Artificial Sequence
<220> FEATURE:
<223> OTHER INFORMATION: Suitable linkers

<400> SEQUENCE: 86

Ala Ser Thr Lys
1

<210> SEQ ID NO 87
<211> LENGTH: 12
<212> TYPE: PRT
<213> ORGANISM: Artificial Sequence
<220> FEATURE:
<223> OTHER INFORMATION: Suitable linkers

<400> SEQUENCE: 87

Gly Gly Gly Ser Gly Gly Ser Gly Gly Ser Gly Gly
1               5                   10

<210> SEQ ID NO 88
<211> LENGTH: 17
<212> TYPE: PRT
<213> ORGANISM: Artificial Sequence
<220> FEATURE:
<223> OTHER INFORMATION: Suitable linkers

<400> SEQUENCE: 88

Asp Ile Gly Gly Gly Ser Gly Gly Ser Gly Gly Ser Gly Gly Ala Ala
1               5                   10                  15

Ala

<210> SEQ ID NO 89
<211> LENGTH: 16
<212> TYPE: PRT
<213> ORGANISM: Artificial Sequence
<220> FEATURE:
<223> OTHER INFORMATION: Suitable linkers

<400> SEQUENCE: 89

Ala Lys Thr Thr Pro Lys Leu Glu Glu Gly Glu Phe Ser Glu Ala Arg
1               5                   10                  15

<210> SEQ ID NO 90
<211> LENGTH: 17
<212> TYPE: PRT
<213> ORGANISM: Artificial Sequence
<220> FEATURE:
<223> OTHER INFORMATION: Suitable linkers

<400> SEQUENCE: 90

Ala Lys Thr Thr Pro Lys Leu Glu Glu Gly Glu Phe Ser Glu Ala Arg
1               5                   10                  15

Val

<210> SEQ ID NO 91
<211> LENGTH: 9
<212> TYPE: PRT
<213> ORGANISM: Artificial Sequence
<220> FEATURE:
<223> OTHER INFORMATION: Suitable linkers

<400> SEQUENCE: 91
```

```
Ala Lys Thr Thr Pro Lys Leu Gly Gly
1               5
```

<210> SEQ ID NO 92
<211> LENGTH: 10
<212> TYPE: PRT
<213> ORGANISM: Artificial Sequence
<220> FEATURE:
<223> OTHER INFORMATION: Suitable linkers

<400> SEQUENCE: 92

```
Ser Ala Lys Thr Thr Pro Lys Leu Gly Gly
1               5                   10
```

<210> SEQ ID NO 93
<211> LENGTH: 6
<212> TYPE: PRT
<213> ORGANISM: Artificial Sequence
<220> FEATURE:
<223> OTHER INFORMATION: Suitable linkers

<400> SEQUENCE: 93

```
Ser Ala Lys Thr Thr Pro
1               5
```

<210> SEQ ID NO 94
<211> LENGTH: 6
<212> TYPE: PRT
<213> ORGANISM: Artificial Sequence
<220> FEATURE:
<223> OTHER INFORMATION: Suitable linkers

<400> SEQUENCE: 94

```
Arg Ala Asp Ala Ala Pro
1               5
```

<210> SEQ ID NO 95
<211> LENGTH: 9
<212> TYPE: PRT
<213> ORGANISM: Artificial Sequence
<220> FEATURE:
<223> OTHER INFORMATION: Suitable linkers

<400> SEQUENCE: 95

```
Arg Ala Asp Ala Ala Pro Thr Val Ser
1               5
```

<210> SEQ ID NO 96
<211> LENGTH: 12
<212> TYPE: PRT
<213> ORGANISM: Artificial Sequence
<220> FEATURE:
<223> OTHER INFORMATION: Suitable linkers

<400> SEQUENCE: 96

```
Arg Ala Asp Ala Ala Ala Ala Gly Gly Pro Gly Ser
1               5                   10
```

<210> SEQ ID NO 97
<211> LENGTH: 27
<212> TYPE: PRT
<213> ORGANISM: Artificial Sequence
<220> FEATURE:
<223> OTHER INFORMATION: Suitable linkers

<400> SEQUENCE: 97

```
Arg Ala Asp Ala Ala Ala Ala Gly Gly Gly Gly Ser Gly Gly Gly Gly
```

```
            1               5                  10                  15
Ser Gly Gly Gly Gly Ser Gly Gly Gly Ser
            20                  25

<210> SEQ ID NO 98
<211> LENGTH: 18
<212> TYPE: PRT
<213> ORGANISM: Artificial Sequence
<220> FEATURE:
<223> OTHER INFORMATION: Suitable linkers

<400> SEQUENCE: 98

Ser Ala Lys Thr Thr Pro Lys Leu Glu Glu Gly Glu Phe Ser Glu Ala
1               5                  10                  15

Arg Val

<210> SEQ ID NO 99
<211> LENGTH: 5
<212> TYPE: PRT
<213> ORGANISM: Artificial Sequence
<220> FEATURE:
<223> OTHER INFORMATION: Suitable linkers

<400> SEQUENCE: 99

Ala Asp Ala Ala Pro
1               5

<210> SEQ ID NO 100
<211> LENGTH: 12
<212> TYPE: PRT
<213> ORGANISM: Artificial Sequence
<220> FEATURE:
<223> OTHER INFORMATION: Suitable linkers

<400> SEQUENCE: 100

Ala Asp Ala Ala Pro Thr Val Ser Ile Phe Pro Pro
1               5                  10

<210> SEQ ID NO 101
<211> LENGTH: 5
<212> TYPE: PRT
<213> ORGANISM: Artificial Sequence
<220> FEATURE:
<223> OTHER INFORMATION: Suitable linkers

<400> SEQUENCE: 101

Thr Val Ala Ala Pro
1               5

<210> SEQ ID NO 102
<211> LENGTH: 12
<212> TYPE: PRT
<213> ORGANISM: Artificial Sequence
<220> FEATURE:
<223> OTHER INFORMATION: Suitable linkers

<400> SEQUENCE: 102

Thr Val Ala Ala Pro Ser Val Phe Ile Phe Pro Pro
1               5                  10

<210> SEQ ID NO 103
<211> LENGTH: 6
<212> TYPE: PRT
<213> ORGANISM: Artificial Sequence
<220> FEATURE:
<223> OTHER INFORMATION: Suitable linkers
```

<400> SEQUENCE: 103

Gln Pro Lys Ala Ala Pro
1               5

<210> SEQ ID NO 104
<211> LENGTH: 13
<212> TYPE: PRT
<213> ORGANISM: Artificial Sequence
<220> FEATURE:
<223> OTHER INFORMATION: Suitable linkers

<400> SEQUENCE: 104

Gln Pro Lys Ala Ala Pro Ser Val Thr Leu Phe Pro Pro
1               5                   10

<210> SEQ ID NO 105
<211> LENGTH: 6
<212> TYPE: PRT
<213> ORGANISM: Artificial Sequence
<220> FEATURE:
<223> OTHER INFORMATION: Suitable linkers

<400> SEQUENCE: 105

Ala Lys Thr Thr Pro Pro
1               5

<210> SEQ ID NO 106
<211> LENGTH: 13
<212> TYPE: PRT
<213> ORGANISM: Artificial Sequence
<220> FEATURE:
<223> OTHER INFORMATION: Suitable linkers

<400> SEQUENCE: 106

Ala Lys Thr Thr Pro Pro Ser Val Thr Pro Leu Ala Pro
1               5                   10

<210> SEQ ID NO 107
<211> LENGTH: 6
<212> TYPE: PRT
<213> ORGANISM: Artificial Sequence
<220> FEATURE:
<223> OTHER INFORMATION: Suitable linkers

<400> SEQUENCE: 107

Ala Lys Thr Thr Ala Pro
1               5

<210> SEQ ID NO 108
<211> LENGTH: 13
<212> TYPE: PRT
<213> ORGANISM: Artificial Sequence
<220> FEATURE:
<223> OTHER INFORMATION: Suitable linkers

<400> SEQUENCE: 108

Ala Lys Thr Thr Ala Pro Ser Val Tyr Pro Leu Ala Pro
1               5                   10

<210> SEQ ID NO 109
<211> LENGTH: 6
<212> TYPE: PRT
<213> ORGANISM: Artificial Sequence
<220> FEATURE:
<223> OTHER INFORMATION: Suitable linkers

```
<400> SEQUENCE: 109

Ala Ser Thr Lys Gly Pro
1               5

<210> SEQ ID NO 110
<211> LENGTH: 13
<212> TYPE: PRT
<213> ORGANISM: Artificial Sequence
<220> FEATURE:
<223> OTHER INFORMATION: Suitable linkers

<400> SEQUENCE: 110

Ala Ser Thr Lys Gly Pro Ser Val Phe Pro Leu Ala Pro
1               5                   10

<210> SEQ ID NO 111
<211> LENGTH: 15
<212> TYPE: PRT
<213> ORGANISM: Artificial Sequence
<220> FEATURE:
<223> OTHER INFORMATION: Suitable linkers

<400> SEQUENCE: 111

Gly Gly Gly Gly Ser Gly Gly Gly Gly Ser Gly Gly Gly Gly Ser
1               5                   10                  15

<210> SEQ ID NO 112
<211> LENGTH: 15
<212> TYPE: PRT
<213> ORGANISM: Artificial Sequence
<220> FEATURE:
<223> OTHER INFORMATION: Suitable linkers

<400> SEQUENCE: 112

Gly Glu Asn Lys Val Glu Tyr Ala Pro Ala Leu Met Ala Leu Ser
1               5                   10                  15

<210> SEQ ID NO 113
<211> LENGTH: 15
<212> TYPE: PRT
<213> ORGANISM: Artificial Sequence
<220> FEATURE:
<223> OTHER INFORMATION: Suitable linkers

<400> SEQUENCE: 113

Gly Pro Ala Lys Glu Leu Thr Pro Leu Lys Glu Ala Lys Val Ser
1               5                   10                  15

<210> SEQ ID NO 114
<211> LENGTH: 15
<212> TYPE: PRT
<213> ORGANISM: Artificial Sequence
<220> FEATURE:
<223> OTHER INFORMATION: Suitable linkers

<400> SEQUENCE: 114

Gly His Glu Ala Ala Ala Val Met Gln Val Gln Tyr Pro Ala Ser
1               5                   10                  15

<210> SEQ ID NO 115
<211> LENGTH: 8
<212> TYPE: PRT
<213> ORGANISM: Artificial Sequence
<220> FEATURE:
<223> OTHER INFORMATION: Suitable linkers

<400> SEQUENCE: 115
```

```
Gly Gly Gly Gly Gly Gly Gly Pro
1               5

<210> SEQ ID NO 116
<211> LENGTH: 9
<212> TYPE: PRT
<213> ORGANISM: Artificial Sequence
<220> FEATURE:
<223> OTHER INFORMATION: Suitable linkers

<400> SEQUENCE: 116

Gly Gly Gly Gly Gly Gly Gly Gly Pro
1               5

<210> SEQ ID NO 117
<211> LENGTH: 9
<212> TYPE: PRT
<213> ORGANISM: Artificial Sequence
<220> FEATURE:
<223> OTHER INFORMATION: Suitable linkers

<400> SEQUENCE: 117

Pro Ala Pro Asn Leu Leu Gly Gly Pro
1               5

<210> SEQ ID NO 118
<211> LENGTH: 7
<212> TYPE: PRT
<213> ORGANISM: Artificial Sequence
<220> FEATURE:
<223> OTHER INFORMATION: Suitable linkers

<400> SEQUENCE: 118

Pro Asn Leu Leu Gly Gly Pro
1               5

<210> SEQ ID NO 119
<211> LENGTH: 7
<212> TYPE: PRT
<213> ORGANISM: Artificial Sequence
<220> FEATURE:
<223> OTHER INFORMATION: Suitable linkers

<400> SEQUENCE: 119

Gly Gly Gly Gly Gly Gly Pro
1               5

<210> SEQ ID NO 120
<211> LENGTH: 9
<212> TYPE: PRT
<213> ORGANISM: Artificial Sequence
<220> FEATURE:
<223> OTHER INFORMATION: Suitable linkers

<400> SEQUENCE: 120

Pro Ala Pro Glu Leu Leu Gly Gly Pro
1               5

<210> SEQ ID NO 121
<211> LENGTH: 13
<212> TYPE: PRT
<213> ORGANISM: Artificial Sequence
<220> FEATURE:
<223> OTHER INFORMATION: Suitable linkers

<400> SEQUENCE: 121
```

```
Pro Thr Ile Ser Pro Ala Pro Asn Leu Leu Gly Gly Pro
1               5                   10

<210> SEQ ID NO 122
<211> LENGTH: 16
<212> TYPE: PRT
<213> ORGANISM: Artificial Sequence
<220> FEATURE:
<223> OTHER INFORMATION: Suitable linkers

<400> SEQUENCE: 122

Thr Val Ala Ala Asp Asp Asp Lys Ser Val Phe Ile Val Pro Pro
1               5                   10                  15

<210> SEQ ID NO 123
<211> LENGTH: 10
<212> TYPE: PRT
<213> ORGANISM: Artificial Sequence
<220> FEATURE:
<223> OTHER INFORMATION: Suitable linkers

<400> SEQUENCE: 123

Thr Val Asp Asp Asp Asp Lys Ala Ala Pro
1               5                   10

<210> SEQ ID NO 124
<211> LENGTH: 9
<212> TYPE: PRT
<213> ORGANISM: Artificial Sequence
<220> FEATURE:
<223> OTHER INFORMATION: Suitable linkers

<400> SEQUENCE: 124

Leu Val Pro Arg Gly Ser Ala Ala Pro
1               5

<210> SEQ ID NO 125
<211> LENGTH: 8
<212> TYPE: PRT
<213> ORGANISM: Artificial Sequence
<220> FEATURE:
<223> OTHER INFORMATION: Suitable linkers

<400> SEQUENCE: 125

Ala Ser Thr Lys Gly Pro Ser Val
1               5

<210> SEQ ID NO 126
<211> LENGTH: 10
<212> TYPE: PRT
<213> ORGANISM: Artificial Sequence
<220> FEATURE:
<223> OTHER INFORMATION: Suitable linkers

<400> SEQUENCE: 126

Ala Ser Thr Lys Gly Pro Ser Val Phe Pro
1               5                   10

<210> SEQ ID NO 127
<211> LENGTH: 7
<212> TYPE: PRT
<213> ORGANISM: Artificial Sequence
<220> FEATURE:
<223> OTHER INFORMATION: Suitable linkers

<400> SEQUENCE: 127

Thr Val Ala Ala Pro Ser Val
```

```
1               5

<210> SEQ ID NO 128
<211> LENGTH: 9
<212> TYPE: PRT
<213> ORGANISM: Artificial Sequence
<220> FEATURE:
<223> OTHER INFORMATION: Suitable linkers

<400> SEQUENCE: 128

Thr Val Ala Ala Pro Ser Val Phe Ile
1               5

<210> SEQ ID NO 129
<211> LENGTH: 55
<212> TYPE: DNA
<213> ORGANISM: Artificial Sequence
<220> FEATURE:
<223> OTHER INFORMATION: Polylinker coding sequence

<400> SEQUENCE: 129
agcttggtac cggatccgaa ttcgatatcg cggccgctct cgagtctaga gggcc            55

<210> SEQ ID NO 130
<211> LENGTH: 47
<212> TYPE: DNA
<213> ORGANISM: Artificial Sequence
<220> FEATURE:
<223> OTHER INFORMATION: Polylinker coding sequence

<400> SEQUENCE: 130
ctctagactc gagagcggcc gcgatatcga attcggatcc ggtacca                     47

<210> SEQ ID NO 131
<211> LENGTH: 14
<212> TYPE: PRT
<213> ORGANISM: Artificial Sequence
<220> FEATURE:
<223> OTHER INFORMATION: V5 tag aa sequence

<400> SEQUENCE: 131

Gly Lys Pro Ile Pro Asn Pro Leu Leu Gly Leu Asp Ser Thr
1               5                   10

<210> SEQ ID NO 132
<211> LENGTH: 8
<212> TYPE: PRT
<213> ORGANISM: Artificial Sequence
<220> FEATURE:
<223> OTHER INFORMATION: Flag tag aa sequence

<400> SEQUENCE: 132

Asp Tyr Lys Asp Asp Asp Asp Lys
1               5

<210> SEQ ID NO 133
<211> LENGTH: 24
<212> TYPE: DNA
<213> ORGANISM: Artificial Sequence
<220> FEATURE:
<223> OTHER INFORMATION: Coding sequence for Flag

<400> SEQUENCE: 133
gattacaagg atgacgatga caag                                              24

<210> SEQ ID NO 134
```

```
<211> LENGTH: 509
<212> TYPE: PRT
<213> ORGANISM: Artificial Sequence
<220> FEATURE:
<223> OTHER INFORMATION: V5-tagged FVII-Fc Monomer

<400> SEQUENCE: 134
```

| | | | | | | | | | | | | | | | |
|---|---|---|---|---|---|---|---|---|---|---|---|---|---|---|---|
| Met | Ala | Leu | Trp | Met | Arg | Leu | Leu | Pro | Leu | Leu | Ala | Leu | Leu | Ala | Leu |
| 1 | | | | 5 | | | | | 10 | | | | | 15 | |
| Trp | Gly | Pro | Asp | Pro | Ala | Ala | Ala | Gly | Thr | Gly | Ser | Gly | Glu | Phe | Ile |
| | | | 20 | | | | | 25 | | | | | 30 | | |
| Lys | Lys | Ala | Phe | His | Lys | Leu | Ala | Met | Lys | Tyr | Asp | Ile | Gly | Gly | Gly |
| | | | 35 | | | | | 40 | | | | | 45 | | |
| Gly | Ser | Gly | Gly | Gly | Ser | Gly | Gly | Gly | Ser | Ala | Ala | Ala | Gly |
| | | 50 | | | | | 55 | | | | | 60 | | | |
| Thr | Pro | Lys | Thr | Ser | Trp | Arg | Val | Ser | Val | Gly | Glu | Asp | Val | Ser |
| 65 | | | | | 70 | | | | | 75 | | | | | 80 |
| Leu | Leu | Pro | Ala | Pro | Gly | Pro | Thr | Gly | Arg | Gly | Pro | Thr | Gln | Lys | Leu |
| | | | | 85 | | | | | 90 | | | | | 95 | |
| Leu | Trp | Ala | Val | Glu | Pro | Leu | Asp | Gly | Cys | Gly | Pro | Leu | His | Pro | Ser |
| | | | | 100 | | | | | 105 | | | | | 110 | |
| Trp | Val | Ser | Leu | Met | Pro | Pro | Lys | Gln | Val | Pro | Glu | Thr | Val | Val | Asp |
| | | | 115 | | | | | 120 | | | | | 125 | | |
| Ala | Ala | Cys | Met | Arg | Ala | Pro | Val | Pro | Leu | Ala | Met | Ala | Tyr | Ala | Pro |
| | | 130 | | | | | 135 | | | | | 140 | | | |
| Pro | Ala | Pro | Ser | Ala | Thr | Gly | Gly | Leu | Arg | Thr | Asp | Phe | Val | Trp | Gln |
| 145 | | | | | 150 | | | | | 155 | | | | | 160 |
| Glu | Arg | Ala | Ala | Val | Val | Asn | Arg | Ser | Leu | Val | Ile | His | Gly | Val | Arg |
| | | | | 165 | | | | | 170 | | | | | 175 | |
| Glu | Thr | Asp | Ser | Gly | Leu | Tyr | Thr | Leu | Ser | Val | Gly | Asp | Ile | Lys | Asp |
| | | | 180 | | | | | 185 | | | | | 190 | | |
| Pro | Ala | Arg | Gln | Val | Ala | Ser | Val | Val | Leu | Val | Gln | Pro | Ala | Pro |
| | | 195 | | | | | 200 | | | | | 205 | | | |
| Val | Pro | Thr | Pro | Pro | Pro | Thr | Pro | Ala | Asp | Tyr | Asp | Glu | Asp | Asn |
| | 210 | | | | | 215 | | | | | 220 | | | | |
| Asp | Glu | Gly | Glu | Asp | Glu | Ser | Leu | Ala | Gly | Thr | Pro | Ala | Ser | Gly | Thr |
| 225 | | | | | 230 | | | | | 235 | | | | | 240 |
| Pro | Arg | Leu | Pro | Pro | Pro | Ala | Pro | Arg | Ser | Trp | Pro | Ser | Ala |
| | | | | 245 | | | | | 250 | | | | | 255 | |
| Pro | Glu | Val | Ser | His | Val | Arg | Gly | Val | Thr | Val | Arg | Met | Glu | Thr | Pro |
| | | | 260 | | | | | 265 | | | | | 270 | | |
| Glu | Ala | Ile | Leu | Phe | Ser | Pro | Gly | Glu | Thr | Phe | Ser | Thr | Asn | Val | Ser |
| | | | 275 | | | | | 280 | | | | | 285 | | |
| Ile | His | Ala | Ile | Ala | His | Asp | Asp | Gln | Thr | Tyr | Ser | Met | Asp | Val | Val |
| | | 290 | | | | | 295 | | | | | 300 | | | |
| Trp | Leu | Arg | Phe | Asp | Val | Pro | Thr | Ser | Cys | Ala | Glu | Met | Arg | Ile | Tyr |
| 305 | | | | | 310 | | | | | 315 | | | | | 320 |
| Glu | Ser | Cys | Leu | Tyr | His | Pro | Gln | Leu | Pro | Glu | Cys | Leu | Ser | Pro | Ala |
| | | | | 325 | | | | | 330 | | | | | 335 | |
| Asp | Ala | Pro | Cys | Ala | Ala | Ser | Thr | Trp | Thr | Ser | Arg | Leu | Ala | Val | Arg |
| | | | 340 | | | | | 345 | | | | | 350 | | |
| Ser | Tyr | Ala | Gly | Cys | Ser | Arg | Thr | Asn | Pro | Pro | Arg | Cys | Ser | Ala |
| | | 355 | | | | | 360 | | | | | 365 | | | |
| Glu | Ala | His | Met | Glu | Pro | Val | Pro | Gly | Leu | Ala | Trp | Gln | Ala | Ala | Ser |
| | 370 | | | | | 375 | | | | | 380 | | | | |

```
Val Asn Leu Glu Phe Arg Asp Ala Ser Pro Gln His Ser Gly Leu Tyr
385                 390                 395                 400

Leu Cys Val Val Tyr Val Asn Asp His Ile His Ala Trp Gly His Ile
            405                 410                 415

Thr Ile Ser Thr Ala Ala Gln Tyr Arg Asn Ala Val Val Glu Gln Pro
        420                 425                 430

Leu Pro Gln Arg Gly Ala Asp Leu Ala Glu Leu Glu Gly Asp Tyr Lys
            435                 440                 445

Asp Asp Asp Asp Lys Gly Ser Arg Ser Ser Trp Lys Ser Ser Ile Ala
        450                 455                 460

Ser Phe Phe Phe Ile Ile Gly Leu Ile Ile Gly Leu Phe Leu Val Leu
465                 470                 475                 480

Arg Val Gly Ile His Leu Cys Ile Lys Leu Lys His Thr Lys Lys Arg
                485                 490                 495

Gln Ile Tyr Thr Asp Ile Glu Met Asn Arg Leu Gly Lys
            500                 505
```

```
<210> SEQ ID NO 135
<211> LENGTH: 194
<212> TYPE: PRT
<213> ORGANISM: Artificial Sequence
<220> FEATURE:
<223> OTHER INFORMATION: V5-tagged J-Prot G fusion

<400> SEQUENCE: 135

Met Ala Pro Gln Asn Leu Ser Thr Phe Cys Leu Leu Leu Leu Tyr Leu
1               5                   10                  15

Ile Gly Ala Val Ile Ala Gly Arg Asp Phe Tyr Lys Ile Leu Gly Val
                20                  25                  30

Pro Arg Ser Ala Ser Ile Lys Asp Ile Lys Lys Ala Tyr Arg Lys Leu
            35                  40                  45

Ala Leu Gln Leu His Pro Asp Arg Asn Pro Asp Asp Pro Gln Ala Gln
        50                  55                  60

Glu Lys Phe Gln Asp Leu Gly Ala Ala Tyr Glu Val Leu Ser Asp Ser
65                  70                  75                  80

Glu Lys Arg Asp Ile Gly Gly Gly Ser Gly Gly Ser Gly Gly Ser Gly
                85                  90                  95

Gly Ala Ala Thr Tyr Lys Leu Val Ile Asn Gly Lys Thr Leu Lys
                100                 105                 110

Gly Glu Thr Thr Thr Glu Ala Val Asp Ala Ala Thr Ala Glu Lys Val
            115                 120                 125

Phe Lys Gln Tyr Ala Asn Asp Asn Gly Val Asp Gly Glu Trp Thr Tyr
        130                 135                 140

Asp Asp Ala Thr Lys Thr Phe Thr Val Thr Glu Lys Pro Glu Val Ile
145                 150                 155                 160

Asp Ala Ser Glu Leu Thr Pro Ala Val Thr Leu Glu Gly Asp Tyr Lys
                165                 170                 175

Asp Asp Asp Asp Lys Gly Ser Arg Gly Pro Tyr Ser Ile Val Ser Pro
                180                 185                 190

Lys Cys

<210> SEQ ID NO 136
<211> LENGTH: 570
<212> TYPE: PRT
<213> ORGANISM: Artificial Sequence
<220> FEATURE:
```

<223> OTHER INFORMATION: Flag-tagged J-gE-TM1 seq

<400> SEQUENCE: 136

```
Met Ala Pro Gln Asn Leu Ser Thr Phe Cys Leu Leu Leu Leu Tyr Leu
1               5                   10                  15
Ile Gly Ala Val Ile Ala Gly Arg Asp Phe Tyr Lys Ile Leu Gly Val
            20                  25                  30
Pro Arg Ser Ala Ser Ile Lys Asp Ile Lys Lys Ala Tyr Arg Lys Leu
        35                  40                  45
Ala Leu Gln Leu His Pro Asp Arg Asn Pro Asp Pro Gln Ala Gln
    50                  55                  60
Glu Lys Phe Gln Asp Leu Gly Ala Ala Tyr Glu Val Leu Ser Asp Ser
65                  70                  75                  80
Glu Lys Arg Asp Ile Gly Gly Gly Ser Gly Gly Ser Gly Ser Gly
                85                  90                  95
Gly Ala Ala Ala Gly Thr Pro Lys Thr Ser Trp Arg Arg Val Ser Val
            100                 105                 110
Gly Glu Asp Val Ser Leu Leu Pro Ala Pro Gly Pro Thr Gly Arg Gly
            115                 120                 125
Pro Thr Gln Lys Leu Leu Trp Ala Val Glu Pro Leu Asp Gly Cys Gly
    130                 135                 140
Pro Leu His Pro Ser Trp Val Ser Leu Met Pro Pro Lys Gln Val Pro
145                 150                 155                 160
Glu Thr Val Val Asp Ala Ala Cys Met Arg Ala Pro Val Pro Leu Ala
                165                 170                 175
Met Ala Tyr Ala Pro Pro Ala Pro Ser Ala Thr Gly Gly Leu Arg Thr
            180                 185                 190
Asp Phe Val Trp Gln Glu Arg Ala Ala Val Val Asn Arg Ser Leu Val
        195                 200                 205
Ile His Gly Val Arg Glu Thr Asp Ser Gly Leu Tyr Thr Leu Ser Val
    210                 215                 220
Gly Asp Ile Lys Asp Pro Ala Arg Gln Val Ala Ser Val Val Leu Val
225                 230                 235                 240
Val Gln Pro Ala Pro Val Pro Thr Pro Pro Thr Pro Ala Asp Tyr
                245                 250                 255
Asp Glu Asp Asp Asn Asp Glu Gly Glu Asp Glu Ser Leu Ala Gly Thr
            260                 265                 270
Pro Ala Ser Gly Thr Pro Arg Leu Pro Pro Pro Ala Pro Pro Arg
        275                 280                 285
Ser Trp Pro Ser Ala Pro Glu Val Ser His Val Arg Gly Val Thr Val
    290                 295                 300
Arg Met Glu Thr Pro Glu Ala Ile Leu Phe Ser Pro Gly Glu Thr Phe
305                 310                 315                 320
Ser Thr Asn Val Ser Ile His Ala Ile Ala His Asp Asp Gln Thr Tyr
                325                 330                 335
Ser Met Asp Val Val Trp Leu Arg Phe Asp Val Pro Thr Ser Cys Ala
            340                 345                 350
Glu Met Arg Ile Tyr Glu Ser Cys Leu Tyr His Pro Gln Leu Pro Glu
        355                 360                 365
Cys Leu Ser Pro Ala Asp Ala Pro Cys Ala Ala Ser Thr Trp Thr Ser
    370                 375                 380
Arg Leu Ala Val Arg Ser Tyr Ala Gly Cys Ser Arg Thr Asn Pro Pro
385                 390                 395                 400
```

```
Pro Arg Cys Ser Ala Glu Ala His Met Glu Pro Val Pro Gly Leu Ala
                405                 410                 415
Trp Gln Ala Ala Ser Val Asn Leu Glu Phe Arg Asp Ala Ser Pro Gln
        420                 425                 430
His Ser Gly Leu Tyr Leu Cys Val Val Tyr Val Asn Asp His Ile His
    435                 440                 445
Ala Trp Gly His Ile Thr Ile Ser Thr Ala Ala Gln Tyr Arg Asn Ala
450                 455                 460
Val Val Glu Gln Pro Leu Pro Gln Arg Gly Ala Asp Leu Ala Glu Leu
465                 470                 475                 480
Glu Gly Asp Tyr Lys Asp Asp Asp Lys Gly Ser Arg Asp Asp Glu
                485                 490                 495
Ser Leu Phe Phe Gly Asp Thr Gly Leu Ser Lys Asn Pro Ile Glu Leu
                500                 505                 510
Val Glu Gly Trp Phe Ser Ser Trp Lys Ser Ser Ile Ala Ser Phe Phe
            515                 520                 525
Phe Ile Ile Gly Leu Ile Ile Gly Leu Phe Leu Val Leu Arg Val Gly
    530                 535                 540
Ile His Leu Cys Ile Lys Leu Lys His Thr Lys Lys Arg Gln Ile Tyr
545                 550                 555                 560
Thr Asp Ile Glu Met Asn Arg Leu Gly Lys
                565                 570

<210> SEQ ID NO 137
<211> LENGTH: 599
<212> TYPE: PRT
<213> ORGANISM: Artificial Sequence
<220> FEATURE:
<223> OTHER INFORMATION: V5-tagged IL13R alpha 2TF-Fc monomer

<400> SEQUENCE: 137

Met Ala Phe Val Cys Leu Ala Ile Gly Cys Leu Tyr Thr Phe Leu Ile
1               5                   10                  15
Ser Thr Thr Phe Gly Cys Thr Ser Ser Ser Asp Thr Glu Ile Lys Val
                20                  25                  30
Asn Pro Pro Gln Asp Phe Glu Ile Val Asp Pro Gly Tyr Leu Gly Tyr
            35                  40                  45
Leu Tyr Leu Gln Trp Gln Pro Pro Leu Ser Leu Asp His Phe Lys Glu
    50                  55                  60
Cys Thr Val Glu Tyr Glu Leu Lys Tyr Arg Asn Ile Gly Ser Glu Thr
65                  70                  75                  80
Trp Lys Thr Ile Ile Thr Lys Asn Leu His Tyr Lys Asp Gly Phe Asp
                85                  90                  95
Leu Asn Lys Gly Ile Glu Ala Lys Ile His Thr Leu Leu Pro Trp Gln
                100                 105                 110
Cys Thr Asn Gly Ser Glu Val Gln Ser Ser Trp Ala Glu Thr Thr Tyr
            115                 120                 125
Trp Ile Ser Pro Gln Gly Ile Pro Glu Thr Lys Val Gln Asp Met Asp
    130                 135                 140
Cys Val Tyr Tyr Asn Trp Gln Tyr Leu Leu Cys Ser Trp Lys Pro Gly
145                 150                 155                 160
Ile Gly Val Leu Leu Asp Thr Asn Tyr Asn Leu Phe Tyr Trp Tyr Glu
                165                 170                 175
Gly Leu Asp His Ala Leu Gln Cys Val Asp Tyr Ile Lys Ala Asp Gly
                180                 185                 190
```

```
Gln Asn Ile Gly Cys Arg Phe Pro Tyr Leu Glu Ala Ser Asp Tyr Lys
    195                 200                 205

Asp Phe Tyr Ile Cys Val Asn Gly Ser Ser Glu Asn Lys Pro Ile Arg
210                 215                 220

Ser Ser Tyr Phe Thr Phe Gln Leu Gln Asn Ile Val Lys Pro Leu Pro
225                 230                 235                 240

Pro Val Tyr Leu Thr Phe Thr Arg Glu Ser Ser Cys Glu Ile Lys Leu
                245                 250                 255

Lys Trp Ser Ile Pro Leu Gly Pro Ile Pro Ala Arg Cys Phe Asp Tyr
                260                 265                 270

Glu Ile Glu Ile Arg Glu Asp Asp Thr Thr Leu Val Thr Ala Thr Val
            275                 280                 285

Glu Asn Glu Thr Tyr Thr Leu Lys Thr Thr Asn Glu Thr Arg Gln Leu
        290                 295                 300

Cys Phe Val Val Arg Ser Lys Val Asn Ile Tyr Cys Ser Asp Asp Gly
305                 310                 315                 320

Ile Trp Ser Glu Trp Ser Asp Lys Gln Cys Trp Glu Gly Glu Asp Leu
                325                 330                 335

Ser Lys Lys Gly Thr Gly Ser Glu Phe Asp Ile Ala Ala Ala Leu Glu
            340                 345                 350

Gly Lys Pro Ile Pro Asn Pro Leu Leu Gly Leu Asp Ser Thr Ser Arg
        355                 360                 365

Pro Lys Ser Cys Asp Lys Thr His Thr Cys Pro Pro Cys Pro Ala Pro
    370                 375                 380

Glu Leu Leu Gly Gly Pro Ser Val Phe Leu Phe Pro Pro Lys Pro Lys
385                 390                 395                 400

Asp Thr Leu Met Ile Ser Arg Thr Pro Glu Val Thr Cys Val Val Val
                405                 410                 415

Asp Val Ser His Glu Asp Pro Glu Val Lys Phe Asn Trp Tyr Val Asp
            420                 425                 430

Gly Val Glu Val His Asn Ala Lys Thr Lys Pro Arg Glu Glu Gln Tyr
        435                 440                 445

Asn Ser Thr Tyr Arg Val Val Ser Val Leu Thr Val Leu His Gln Asp
    450                 455                 460

Trp Leu Asn Gly Lys Glu Tyr Lys Cys Lys Val Ser Asn Lys Ala Leu
465                 470                 475                 480

Pro Ala Pro Ile Glu Lys Thr Ile Ser Lys Ala Lys Gly Gln Pro Arg
                485                 490                 495

Glu Pro Gln Val Tyr Thr Leu Pro Pro Ser Arg Asp Glu Leu Thr Lys
            500                 505                 510

Asn Gln Val Ser Leu Thr Cys Leu Val Lys Gly Phe Tyr Pro Ser Asp
        515                 520                 525

Ile Ala Val Glu Trp Glu Ser Asn Gly Gln Pro Glu Asn Asn Tyr Lys
    530                 535                 540

Thr Thr Pro Pro Val Leu Asp Ser Asp Gly Ser Phe Phe Leu Tyr Ser
545                 550                 555                 560

Lys Leu Thr Val Asp Lys Ser Arg Trp Gln Gln Gly Asn Val Phe Ser
                565                 570                 575

Cys Ser Val Met His Glu Ala Leu His Asn His Tyr Thr Gln Lys Ser
            580                 585                 590

Leu Ser Leu Ser Pro Gly Lys
                595
```

```
<210> SEQ ID NO 138
<211> LENGTH: 233
<212> TYPE: PRT
<213> ORGANISM: Artificial Sequence
<220> FEATURE:
<223> OTHER INFORMATION: Flag-tagged J-IL13 fusion

<400> SEQUENCE: 138

Met Ala Pro Gln Asn Leu Ser Thr Phe Cys Leu Leu Leu Leu Tyr Leu
1               5                   10                  15

Ile Gly Ala Val Ile Ala Gly Arg Asp Phe Tyr Lys Ile Leu Gly Val
            20                  25                  30

Pro Arg Ser Ala Ser Ile Lys Asp Ile Lys Lys Ala Tyr Arg Lys Leu
        35                  40                  45

Ala Leu Gln Leu His Pro Asp Arg Asn Pro Asp Asp Pro Gln Ala Gln
    50                  55                  60

Glu Lys Phe Gln Asp Leu Gly Ala Ala Tyr Glu Val Leu Ser Asp Ser
65                  70                  75                  80

Glu Lys Arg Asp Ile Gly Gly Gly Ser Gly Gly Ser Gly Gly Ser Gly
                85                  90                  95

Gly Ala Ala Ala Leu Thr Cys Leu Gly Gly Phe Ala Ser Pro Gly Pro
            100                 105                 110

Val Pro Pro Ser Thr Ala Leu Arg Glu Leu Ile Glu Glu Leu Val Asn
        115                 120                 125

Ile Thr Gln Asn Gln Lys Ala Pro Leu Cys Asn Gly Ser Met Val Trp
    130                 135                 140

Ser Ile Asn Leu Thr Ala Gly Met Tyr Cys Ala Ala Leu Glu Ser Leu
145                 150                 155                 160

Ile Asn Val Ser Gly Cys Ser Ala Ile Glu Lys Thr Gln Arg Met Leu
                165                 170                 175

Ser Gly Phe Cys Pro His Lys Val Ser Ala Gly Gln Phe Ser Ser Leu
            180                 185                 190

His Val Arg Asp Thr Lys Ile Glu Val Ala Gln Phe Val Lys Asp Leu
        195                 200                 205

Leu Leu His Leu Lys Lys Leu Phe Arg Glu Gly Gln Phe Asn Leu Glu
    210                 215                 220

Gly Asp Tyr Lys Asp Asp Asp Lys
225                 230

<210> SEQ ID NO 139
<211> LENGTH: 313
<212> TYPE: PRT
<213> ORGANISM: Artificial Sequence
<220> FEATURE:
<223> OTHER INFORMATION: Flag-tagged J-IL13-TM1

<400> SEQUENCE: 139

Met Ala Pro Gln Asn Leu Ser Thr Phe Cys Leu Leu Leu Leu Tyr Leu
1               5                   10                  15

Ile Gly Ala Val Ile Ala Gly Arg Asp Phe Tyr Lys Ile Leu Gly Val
            20                  25                  30

Pro Arg Ser Ala Ser Ile Lys Asp Ile Lys Lys Ala Tyr Arg Lys Leu
        35                  40                  45

Ala Leu Gln Leu His Pro Asp Arg Asn Pro Asp Asp Pro Gln Ala Gln
    50                  55                  60

Glu Lys Phe Gln Asp Leu Gly Ala Ala Tyr Glu Val Leu Ser Asp Ser
65                  70                  75                  80
```

Glu Lys Arg Asp Ile Gly Gly Ser Gly Ser Gly Ser Gly
            85              90              95

Gly Ala Ala Leu Thr Cys Leu Gly Phe Ala Ser Pro Gly Pro
            100             105             110

Val Pro Pro Ser Thr Ala Leu Arg Glu Leu Ile Glu Glu Leu Val Asn
            115             120             125

Ile Thr Gln Asn Gln Lys Ala Pro Leu Cys Asn Gly Ser Met Val Trp
            130             135             140

Ser Ile Asn Leu Thr Ala Gly Met Tyr Cys Ala Ala Leu Glu Ser Leu
145             150             155             160

Ile Asn Val Ser Gly Cys Ser Ala Ile Glu Lys Thr Gln Arg Met Leu
                165             170             175

Ser Gly Phe Cys Pro His Lys Val Ser Ala Gly Gln Phe Ser Ser Leu
                180             185             190

His Val Arg Asp Thr Lys Ile Glu Val Ala Gln Phe Val Lys Asp Leu
                195             200             205

Leu Leu His Leu Lys Lys Leu Phe Arg Glu Gly Gln Phe Asn Leu Glu
            210             215             220

Gly Asp Tyr Lys Asp Asp Asp Lys Gly Ser Arg Asp Asp Glu Ser
225             230             235             240

Leu Phe Phe Gly Asp Thr Gly Leu Ser Lys Asn Pro Ile Glu Leu Val
                245             250             255

Glu Gly Trp Phe Ser Ser Trp Lys Ser Ser Ile Ala Ser Phe Phe
                260             265             270

Ile Ile Gly Leu Ile Ile Gly Leu Phe Leu Val Leu Arg Val Gly Ile
                275             280             285

His Leu Cys Ile Lys Leu Lys His Thr Lys Lys Arg Gln Ile Tyr Thr
                290             295             300

Asp Ile Glu Met Asn Arg Leu Gly Lys
305                 310

<210> SEQ ID NO 140
<211> LENGTH: 2600
<212> TYPE: PRT
<213> ORGANISM: Artificial Sequence
<220> FEATURE:
<223> OTHER INFORMATION: V5-tagged F8-Fc monomer

<400> SEQUENCE: 140

Met Gln Ile Glu Leu Ser Thr Cys Phe Phe Leu Cys Leu Leu Arg Phe
1               5               10              15

Cys Phe Ser Ala Thr Arg Arg Tyr Tyr Leu Gly Ala Val Glu Leu Ser
                20              25              30

Trp Asp Tyr Met Gln Ser Asp Leu Gly Glu Leu Pro Val Asp Ala Arg
            35              40              45

Phe Pro Pro Arg Val Pro Lys Ser Phe Pro Phe Asn Thr Ser Val Val
50              55              60

Tyr Lys Lys Thr Leu Phe Val Glu Phe Thr Asp His Leu Phe Asn Ile
65              70              75              80

Ala Lys Pro Arg Pro Pro Trp Met Gly Leu Leu Gly Pro Thr Ile Gln
                85              90              95

Ala Glu Val Tyr Asp Thr Val Val Ile Thr Leu Lys Asn Met Ala Ser
                100             105             110

His Pro Val Ser Leu His Ala Val Gly Val Ser Tyr Trp Lys Ala Ser
            115             120             125

```
Glu Gly Ala Glu Tyr Asp Asp Gln Thr Ser Gln Arg Glu Lys Glu Asp
        130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asp Asn Ser
    370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
        435                 440                 445

Ala Tyr Thr Asp Glu Thr Phe Lys Thr Arg Glu Ala Ile Gln His Glu
    450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
        515                 520                 525

Lys Tyr Lys Trp Thr Val Thr Val Glu Asp Gly Pro Thr Lys Ser Asp
    530                 535                 540

Pro Arg Cys Leu Thr Arg Tyr Tyr Ser Ser Phe Val Asn Met Glu Arg
```

```
            545                 550                 555                 560

Asp Leu Ala Ser Gly Leu Ile Gly Pro Leu Ile Cys Tyr Lys Glu
                565                 570                 575

Ser Val Asp Gln Arg Gly Asn Gln Ile Met Ser Asp Lys Arg Asn Val
                580                 585                 590

Ile Leu Phe Ser Val Phe Asp Glu Asn Arg Ser Trp Tyr Leu Thr Glu
                595                 600                 605

Asn Ile Gln Arg Phe Leu Pro Asn Pro Ala Gly Val Gln Leu Glu Asp
                610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
                660                 665                 670

Ser Gly Tyr Thr Phe Lys His Lys Met Val Tyr Glu Asp Thr Leu Thr
                675                 680                 685

Leu Phe Pro Phe Ser Gly Glu Thr Val Phe Met Ser Met Glu Asn Pro
                690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
                740                 745                 750

Asn Asn Ala Ile Glu Pro Arg Ser Phe Ser Gln Asn Ser Arg His Pro
                755                 760                 765

Ser Thr Arg Gln Lys Gln Phe Asn Ala Thr Thr Ile Pro Glu Asn Asp
                770                 775                 780

Ile Glu Lys Thr Asp Pro Trp Phe Ala His Arg Thr Pro Met Pro Lys
785                 790                 795                 800

Ile Gln Asn Val Ser Ser Ser Asp Leu Leu Met Leu Leu Arg Gln Ser
                805                 810                 815

Pro Thr Pro His Gly Leu Ser Leu Ser Asp Leu Gln Glu Ala Lys Tyr
                820                 825                 830

Glu Thr Phe Ser Asp Asp Pro Ser Pro Gly Ala Ile Asp Ser Asn Asn
                835                 840                 845

Ser Leu Ser Glu Met Thr His Phe Arg Pro Gln Leu His His Ser Gly
                850                 855                 860

Asp Met Val Phe Thr Pro Glu Ser Gly Leu Gln Leu Arg Leu Asn Glu
865                 870                 875                 880

Lys Leu Gly Thr Thr Ala Ala Thr Glu Leu Lys Lys Leu Asp Phe Lys
                885                 890                 895

Val Ser Ser Thr Ser Asn Asn Leu Ile Ser Thr Ile Pro Ser Asp Asn
                900                 905                 910

Leu Ala Ala Gly Thr Asp Asn Thr Ser Ser Leu Gly Pro Pro Ser Met
                915                 920                 925

Pro Val His Tyr Asp Ser Gln Leu Asp Thr Thr Leu Phe Gly Lys Lys
                930                 935                 940

Ser Ser Pro Leu Thr Glu Ser Gly Gly Pro Leu Ser Leu Ser Glu Glu
945                 950                 955                 960

Asn Asn Asp Ser Lys Leu Leu Glu Ser Gly Leu Met Asn Ser Gln Glu
                965                 970                 975
```

```
Ser Ser Trp Gly Lys Asn Val Ser Ser Thr Glu Ser Gly Arg Leu Phe
        980                 985                 990

Lys Gly Lys Arg Ala His Gly Pro Ala Leu Leu Thr Lys Asp Asn Ala
        995                 1000                1005

Leu Phe Lys Val Ser Ile Ser Leu Leu Lys Thr Asn Lys Thr Ser
        1010                1015                1020

Asn Asn Ser Ala Thr Asn Arg Lys Thr His Ile Asp Gly Pro Ser
        1025                1030                1035

Leu Leu Ile Glu Asn Ser Pro Ser Val Trp Gln Asn Ile Leu Glu
        1040                1045                1050

Ser Asp Thr Glu Phe Lys Lys Val Thr Pro Leu Ile His Asp Arg
        1055                1060                1065

Met Leu Met Asp Lys Asn Ala Thr Ala Leu Arg Leu Asn His Met
        1070                1075                1080

Ser Asn Lys Thr Thr Ser Ser Lys Asn Met Glu Met Val Gln Gln
        1085                1090                1095

Lys Lys Glu Gly Pro Ile Pro Pro Asp Ala Gln Asn Pro Asp Met
        1100                1105                1110

Ser Phe Phe Lys Met Leu Phe Leu Pro Glu Ser Ala Arg Trp Ile
        1115                1120                1125

Gln Arg Thr His Gly Lys Asn Ser Leu Asn Ser Gly Gln Gly Pro
        1130                1135                1140

Ser Pro Lys Gln Leu Val Ser Leu Gly Pro Glu Lys Ser Val Glu
        1145                1150                1155

Gly Gln Asn Phe Leu Ser Glu Lys Asn Lys Val Val Val Gly Lys
        1160                1165                1170

Gly Glu Phe Thr Lys Asp Val Gly Leu Lys Glu Met Val Phe Pro
        1175                1180                1185

Ser Ser Arg Asn Leu Phe Leu Thr Asn Leu Asp Asn Leu His Glu
        1190                1195                1200

Asn Asn Thr His Asn Gln Glu Lys Lys Ile Gln Glu Glu Ile Glu
        1205                1210                1215

Lys Lys Glu Thr Leu Ile Gln Glu Asn Val Val Leu Pro Gln Ile
        1220                1225                1230

His Thr Val Thr Gly Thr Lys Asn Phe Met Lys Asn Leu Phe Leu
        1235                1240                1245

Leu Ser Thr Arg Gln Asn Val Glu Gly Ser Tyr Asp Gly Ala Tyr
        1250                1255                1260

Ala Pro Val Leu Gln Asp Phe Arg Ser Leu Asn Asp Ser Thr Asn
        1265                1270                1275

Arg Thr Lys Lys His Thr Ala His Phe Ser Lys Lys Gly Glu Glu
        1280                1285                1290

Glu Asn Leu Glu Gly Leu Gly Asn Gln Thr Lys Gln Ile Val Glu
        1295                1300                1305

Lys Tyr Ala Cys Thr Thr Arg Ile Ser Pro Asn Thr Ser Gln Gln
        1310                1315                1320

Asn Phe Val Thr Gln Arg Ser Lys Arg Ala Leu Lys Gln Phe Arg
        1325                1330                1335

Leu Pro Leu Glu Glu Thr Glu Leu Glu Lys Arg Ile Ile Val Asp
        1340                1345                1350

Asp Thr Ser Thr Gln Trp Ser Lys Asn Met Lys His Leu Thr Pro
        1355                1360                1365
```

-continued

| | | | | | | | | | | | | |
|---|---|---|---|---|---|---|---|---|---|---|---|---|
|Ser|Thr 1370|Leu|Thr|Gln|Ile 1375|Asp|Tyr|Asn|Glu 1380|Lys|Glu|Lys Gly Ala|
|Ile|Thr 1385|Gln|Ser|Pro|Leu 1390|Ser|Asp|Cys|Leu 1395|Thr|Arg|Ser His Ser|
|Ile|Pro 1400|Gln|Ala|Asn|Arg 1405|Ser|Pro|Leu|Pro 1410|Ile|Ala|Lys Val Ser|
|Ser|Phe 1415|Pro|Ser|Ile|Arg 1420|Pro|Ile|Tyr|Leu 1425|Thr|Arg|Val Leu Phe|
|Gln|Asp 1430|Asn|Ser|Ser|His 1435|Leu|Pro|Ala|Ala 1440|Ser|Tyr|Arg Lys Lys|
|Asp|Ser 1445|Gly|Val|Gln|Glu 1450|Ser|Ser|His|Phe 1455|Leu|Gln|Gly Ala Lys|
|Lys|Asn 1460|Asn|Leu|Ser|Leu 1465|Ala|Ile|Leu|Thr 1470|Leu|Glu|Met Thr Gly|
|Asp|Gln 1475|Arg|Glu|Val|Gly 1480|Ser|Leu|Gly|Thr 1485|Ser|Ala|Thr Asn Ser|
|Val|Thr 1490|Tyr|Lys|Lys|Val 1495|Glu|Asn|Thr|Val 1500|Leu|Pro|Lys Pro Asp|
|Leu|Pro 1505|Lys|Thr|Ser|Gly 1510|Lys|Val|Glu|Leu 1515|Leu|Pro|Lys Val His|
|Ile|Tyr 1520|Gln|Lys|Asp|Leu 1525|Phe|Pro|Thr|Glu 1530|Thr|Ser|Asn Gly Ser|
|Pro|Gly 1535|His|Leu|Asp|Leu 1540|Val|Glu|Gly|Ser 1545|Leu|Leu|Gln Gly Thr|
|Glu|Gly 1550|Ala|Ile|Lys|Trp 1555|Asn|Glu|Ala|Asn 1560|Arg|Pro|Gly Lys Val|
|Pro|Phe 1565|Leu|Arg|Val|Ala 1570|Thr|Glu|Ser|Ser 1575|Ala|Lys|Thr Pro Ser|
|Lys|Leu 1580|Leu|Asp|Pro|Leu 1585|Ala|Trp|Asp|Asn 1590|His|Tyr|Gly Thr Gln|
|Ile|Pro 1595|Lys|Glu|Glu|Trp 1600|Lys|Ser|Gln|Glu 1605|Lys|Ser|Pro Glu Lys|
|Thr|Ala 1610|Phe|Lys|Lys|Lys 1615|Asp|Thr|Ile|Leu 1620|Ser|Leu|Asn Ala Cys|
|Glu|Ser 1625|Asn|His|Ala|Ile 1630|Ala|Ala|Ile|Asn 1635|Glu|Gly|Gln Asn Lys|
|Pro|Glu 1640|Ile|Glu|Val|Thr 1645|Trp|Ala|Lys|Gln 1650|Gly|Arg|Thr Glu Arg|
|Leu|Cys 1655|Ser|Gln|Asn|Pro 1660|Pro|Val|Leu|Lys 1665|Arg|His|Gln Arg Glu|
|Ile|Thr 1670|Arg|Thr|Thr|Leu 1675|Gln|Ser|Asp|Gln 1680|Glu|Glu|Ile Asp Tyr|
|Asp|Asp 1685|Thr|Ile|Ser|Val 1690|Glu|Met|Lys|Lys 1695|Glu|Asp|Phe Asp Ile|
|Tyr|Asp 1700|Glu|Asp|Glu|Asn 1705|Gln|Ser|Pro|Arg 1710|Ser|Phe|Gln Lys Lys|
|Thr|Arg 1715|His|Tyr|Phe|Ile 1720|Ala|Ala|Val|Glu 1725|Arg|Leu|Trp Asp Tyr|
|Gly|Met 1730|Ser|Ser|Ser|Pro 1735|His|Val|Leu|Arg 1740|Asn|Arg|Ala Gln Ser|
|Gly|Ser 1745|Val|Pro|Gln|Phe 1750|Lys|Lys|Val|Val 1755|Phe|Gln|Glu Phe Thr|
|Asp|Gly|Ser|Phe|Thr|Gln|Pro|Leu|Tyr|Arg|Gly|Glu|Leu Asn Glu|

-continued

```
            1760                1765                1770
His Leu Gly Leu Leu Gly Pro Tyr Ile Arg Ala Glu Val Glu Asp
            1775                1780                1785
Asn Ile Met Val Thr Phe Arg Asn Gln Ala Ser Arg Pro Tyr Ser
            1790                1795                1800
Phe Tyr Ser Ser Leu Ile Ser Tyr Glu Glu Asp Gln Arg Gln Gly
            1805                1810                1815
Ala Glu Pro Arg Lys Asn Phe Val Lys Pro Asn Glu Thr Lys Thr
            1820                1825                1830
Tyr Phe Trp Lys Val Gln His His Met Ala Pro Thr Lys Asp Glu
            1835                1840                1845
Phe Asp Cys Lys Ala Trp Ala Tyr Phe Ser Asp Val Asp Leu Glu
            1850                1855                1860
Lys Asp Val His Ser Gly Leu Ile Gly Pro Leu Leu Val Cys His
            1865                1870                1875
Thr Asn Thr Leu Asn Pro Ala His Gly Arg Gln Val Thr Val Gln
            1880                1885                1890
Glu Phe Ala Leu Phe Phe Thr Ile Phe Asp Glu Thr Lys Ser Trp
            1895                1900                1905
Tyr Phe Thr Glu Asn Met Glu Arg Asn Cys Arg Ala Pro Cys Asn
            1910                1915                1920
Ile Gln Met Glu Asp Pro Thr Phe Lys Glu Asn Tyr Arg Phe His
            1925                1930                1935
Ala Ile Asn Gly Tyr Ile Met Asp Thr Leu Pro Gly Leu Val Met
            1940                1945                1950
Ala Gln Asp Gln Arg Ile Arg Trp Tyr Leu Leu Ser Met Gly Ser
            1955                1960                1965
Asn Glu Asn Ile His Ser Ile His Phe Ser Gly His Val Phe Thr
            1970                1975                1980
Val Arg Lys Lys Glu Glu Tyr Lys Met Ala Leu Tyr Asn Leu Tyr
            1985                1990                1995
Pro Gly Val Phe Glu Thr Val Glu Met Leu Pro Ser Lys Ala Gly
            2000                2005                2010
Ile Trp Arg Val Glu Cys Leu Ile Gly Glu His Leu His Ala Gly
            2015                2020                2025
Met Ser Thr Leu Phe Leu Val Tyr Ser Asn Lys Cys Gln Thr Pro
            2030                2035                2040
Leu Gly Met Ala Ser Gly His Ile Arg Asp Phe Gln Ile Thr Ala
            2045                2050                2055
Ser Gly Gln Tyr Gly Gln Trp Ala Pro Lys Leu Ala Arg Leu His
            2060                2065                2070
Tyr Ser Gly Ser Ile Asn Ala Trp Ser Thr Lys Glu Pro Phe Ser
            2075                2080                2085
Trp Ile Lys Val Asp Leu Leu Ala Pro Met Ile Ile His Gly Ile
            2090                2095                2100
Lys Thr Gln Gly Ala Arg Gln Lys Phe Ser Ser Leu Tyr Ile Ser
            2105                2110                2115
Gln Phe Ile Ile Met Tyr Ser Leu Asp Gly Lys Lys Trp Gln Thr
            2120                2125                2130
Tyr Arg Gly Asn Ser Thr Gly Thr Leu Met Val Phe Phe Gly Asn
            2135                2140                2145
Val Asp Ser Ser Gly Ile Lys His Asn Ile Phe Asn Pro Pro Ile
            2150                2155                2160
```

```
Ile Ala Arg Tyr Ile Arg Leu His Pro Thr His Tyr Ser Ile Arg
2165                2170                2175

Ser Thr Leu Arg Met Glu Leu Met Gly Cys Asp Leu Asn Ser Cys
2180                2185                2190

Ser Met Pro Leu Gly Met Glu Ser Lys Ala Ile Ser Asp Ala Gln
2195                2200                2205

Ile Thr Ala Ser Ser Tyr Phe Thr Asn Met Phe Ala Thr Trp Ser
2210                2215                2220

Pro Ser Lys Ala Arg Leu His Leu Gln Gly Arg Ser Asn Ala Trp
2225                2230                2235

Arg Pro Gln Val Asn Asn Pro Lys Glu Trp Leu Gln Val Asp Phe
2240                2245                2250

Gln Lys Thr Met Lys Val Thr Gly Val Thr Thr Gln Gly Val Lys
2255                2260                2265

Ser Leu Leu Thr Ser Met Tyr Val Lys Glu Phe Leu Ile Ser Ser
2270                2275                2280

Ser Gln Asp Gly His Gln Trp Thr Leu Phe Phe Gln Asn Gly Lys
2285                2290                2295

Val Lys Val Phe Gln Gly Asn Gln Asp Ser Phe Thr Pro Val Val
2300                2305                2310

Asn Ser Leu Asp Pro Pro Leu Leu Thr Arg Tyr Leu Arg Ile His
2315                2320                2325

Pro Gln Ser Trp Val His Gln Ile Ala Leu Arg Met Glu Val Leu
2330                2335                2340

Gly Cys Glu Ala Gln Asp Leu Tyr Leu Glu Gly Lys Pro Ile Pro
2345                2350                2355

Asn Pro Leu Leu Gly Leu Asp Ser Thr Ser Arg Pro Lys Ser Cys
2360                2365                2370

Asp Lys Thr His Thr Cys Pro Pro Cys Pro Ala Pro Glu Leu Leu
2375                2380                2385

Gly Gly Pro Ser Val Phe Leu Phe Pro Pro Lys Pro Lys Asp Thr
2390                2395                2400

Leu Met Ile Ser Arg Thr Pro Glu Val Thr Cys Val Val Val Asp
2405                2410                2415

Val Ser His Glu Asp Pro Glu Val Lys Phe Asn Trp Tyr Val Asp
2420                2425                2430

Gly Val Glu Val His Asn Ala Lys Thr Lys Pro Arg Glu Glu Gln
2435                2440                2445

Tyr Asn Ser Thr Tyr Arg Val Val Ser Val Leu Thr Val Leu His
2450                2455                2460

Gln Asp Trp Leu Asn Gly Lys Glu Tyr Lys Cys Lys Val Ser Asn
2465                2470                2475

Lys Ala Leu Pro Ala Pro Ile Glu Lys Thr Ile Ser Lys Ala Lys
2480                2485                2490

Gly Gln Pro Arg Glu Pro Gln Val Tyr Thr Leu Pro Pro Ser Arg
2495                2500                2505

Asp Glu Leu Thr Lys Asn Gln Val Ser Leu Thr Cys Leu Val Lys
2510                2515                2520

Gly Phe Tyr Pro Ser Asp Ile Ala Val Glu Trp Glu Ser Asn Gly
2525                2530                2535

Gln Pro Glu Asn Asn Tyr Lys Thr Thr Pro Pro Val Leu Asp Ser
2540                2545                2550
```

Asp Gly Ser Phe Phe Leu Tyr Ser Lys Leu Thr Val Asp Lys Ser
    2555                2560                2565

Arg Trp Gln Gln Gly Asn Val Phe Ser Cys Ser Val Met His Glu
2570                2575                2580

Ala Leu His Asn His Tyr Thr Gln Lys Ser Leu Ser Leu Ser Pro
    2585                2590                2595

Gly Lys
    2600

<210> SEQ ID NO 141
<211> LENGTH: 529
<212> TYPE: PRT
<213> ORGANISM: Artificial Sequence
<220> FEATURE:
<223> OTHER INFORMATION: Flag-tagged J-gE-TM2

<400> SEQUENCE: 141

Met Ala Pro Gln Asn Leu Ser Thr Phe Cys Leu Leu Leu Tyr Leu
1               5                   10                  15

Ile Gly Ala Val Ile Ala Gly Arg Asp Phe Tyr Lys Ile Leu Gly Val
            20                  25                  30

Pro Arg Ser Ala Ser Ile Lys Asp Ile Lys Lys Ala Tyr Arg Lys Leu
        35                  40                  45

Ala Leu Gln Leu His Pro Asp Arg Asn Pro Asp Asp Pro Gln Ala Gln
50                  55                  60

Glu Lys Phe Gln Asp Leu Gly Ala Ala Tyr Glu Val Leu Ser Asp Ser
65              70                  75                  80

Glu Lys Arg Asp Ile Gly Gly Gly Ser Gly Ser Gly Gly Ser Gly
                85                  90                  95

Gly Ala Ala Ala Gly Thr Pro Lys Thr Ser Trp Arg Arg Val Ser Val
            100                 105                 110

Gly Glu Asp Val Ser Leu Leu Pro Ala Pro Gly Pro Thr Gly Arg Gly
        115                 120                 125

Pro Thr Gln Lys Leu Leu Trp Ala Val Glu Pro Leu Asp Gly Cys Gly
130                 135                 140

Pro Leu His Pro Ser Trp Val Ser Leu Met Pro Pro Lys Gln Val Pro
145                 150                 155                 160

Glu Thr Val Val Asp Ala Ala Cys Met Arg Ala Pro Val Pro Leu Ala
                165                 170                 175

Met Ala Tyr Ala Pro Pro Ala Pro Ser Ala Thr Gly Gly Leu Arg Thr
            180                 185                 190

Asp Phe Val Trp Gln Glu Arg Ala Ala Val Val Asn Arg Ser Leu Val
        195                 200                 205

Ile His Gly Val Arg Glu Thr Asp Ser Gly Leu Tyr Thr Leu Ser Val
    210                 215                 220

Gly Asp Ile Lys Asp Pro Ala Arg Gln Val Ala Ser Val Val Leu Val
225                 230                 235                 240

Val Gln Pro Ala Pro Val Pro Thr Pro Pro Thr Pro Ala Asp Tyr
                245                 250                 255

Asp Glu Asp Asp Asn Asp Glu Gly Glu Asp Glu Ser Leu Ala Gly Thr
            260                 265                 270

Pro Ala Ser Gly Thr Pro Arg Leu Pro Pro Pro Ala Pro Pro Arg
        275                 280                 285

Ser Trp Pro Ser Ala Pro Glu Val Ser His Val Arg Gly Val Thr Val
    290                 295                 300

```
Arg Met Glu Thr Pro Glu Ala Ile Leu Phe Ser Pro Gly Glu Thr Phe
305                 310                 315                 320

Ser Thr Asn Val Ser Ile His Ala Ile Ala His Asp Asp Gln Thr Tyr
            325                 330                 335

Ser Met Asp Val Val Trp Leu Arg Phe Asp Val Pro Thr Ser Cys Ala
            340                 345                 350

Glu Met Arg Ile Tyr Glu Ser Cys Leu Tyr His Pro Gln Leu Pro Glu
            355                 360                 365

Cys Leu Ser Pro Ala Asp Ala Pro Cys Ala Ala Ser Thr Trp Thr Ser
370                 375                 380

Arg Leu Ala Val Arg Ser Tyr Ala Gly Cys Ser Arg Thr Asn Pro Pro
385                 390                 395                 400

Pro Arg Cys Ser Ala Glu Ala His Met Glu Pro Val Pro Gly Leu Ala
                405                 410                 415

Trp Gln Ala Ala Ser Val Asn Leu Glu Phe Arg Asp Ala Ser Pro Gln
                420                 425                 430

His Ser Gly Leu Tyr Leu Cys Val Val Tyr Val Asn Asp His Ile His
                435                 440                 445

Ala Trp Gly His Ile Thr Ile Ser Thr Ala Ala Gln Tyr Arg Asn Ala
450                 455                 460

Val Val Glu Gln Pro Leu Pro Gln Arg Gly Ala Asp Leu Ala Glu Leu
465                 470                 475                 480

Glu Gly Asp Tyr Lys Asp Asp Asp Lys Gly Ser Arg Thr Arg Val
                485                 490                 495

Leu Tyr Phe Ser Ile Phe Ser Met Phe Cys Leu Ile Gly Leu Ala Thr
            500                 505                 510

Trp Gln Val Phe Tyr Leu Arg Arg Phe Phe Lys Ala Lys Lys Leu Ile
            515                 520                 525

Glu

<210> SEQ ID NO 142
<211> LENGTH: 233
<212> TYPE: PRT
<213> ORGANISM: Artificial Sequence
<220> FEATURE:
<223> OTHER INFORMATION: Light chain of bevacizumab

<400> SEQUENCE: 142

Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Ser Ala Ser Gln Asp Ile
            35                  40                  45

Ser Asn Tyr Leu Asn Trp Tyr Gln Gln Lys Pro Gly Lys Ala Pro Lys
50                  55                  60

Val Leu Ile Tyr Phe Thr Ser Ser Leu His Ser Gly Val Pro Ser Arg
65                  70                  75                  80

Phe Ser Gly Ser Gly Ser Gly Thr Asp Phe Thr Leu Thr Ile Ser Ser
                85                  90                  95

Leu Gln Pro Glu Asp Phe Ala Thr Tyr Tyr Cys Gln Gln Tyr Ser Thr
            100                 105                 110

Val Pro Trp Thr Phe Gly Gln Gly Thr Lys Val Glu Ile Lys Arg Thr
            115                 120                 125

Val Ala Ala Pro Ser Val Phe Ile Phe Pro Pro Ser Asp Glu Gln Leu
```

```
            130                 135                 140
Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
                180                 185                 190

Ser Leu Ser Ser Thr Leu Thr Leu Ser Lys Ala Asp Tyr Glu Lys His
                195                 200                 205

Lys Val Tyr Ala Cys Glu Val Thr His Gln Gly Leu Ser Ser Pro Val
                210                 215                 220

Thr Lys Ser Phe Asn Arg Gly Glu Cys
225                 230

<210> SEQ ID NO 143
<211> LENGTH: 472
<212> TYPE: PRT
<213> ORGANISM: Artificial Sequence
<220> FEATURE:
<223> OTHER INFORMATION: Heavy chain of bevacizumab

<400> SEQUENCE: 143

Met Gly Trp Ser Leu Ile Ile Leu Phe Leu Val Ala Thr Ala Thr Gly
1               5                   10                  15

Val His Ser Glu Val Gln Leu Val Glu Ser Gly Gly Gly Leu Val Gln
                20                  25                  30

Pro Gly Gly Ser Leu Arg Leu Ser Cys Ala Ala Ser Gly Tyr Thr Phe
                35                  40                  45

Thr Asn Tyr Gly Met Asn Trp Val Arg Gln Ala Pro Gly Lys Gly Leu
        50                  55                  60

Glu Trp Val Gly Trp Ile Asn Thr Tyr Thr Gly Glu Pro Thr Tyr Ala
65                  70                  75                  80

Ala Asp Phe Lys Arg Arg Phe Thr Phe Ser Leu Asp Thr Ser Lys Ser
                85                  90                  95

Thr Ala Tyr Leu Gln Met Asn Ser Leu Arg Ala Glu Asp Thr Ala Val
                100                 105                 110

Tyr Tyr Cys Ala Lys Tyr Pro His Tyr Tyr Gly Ser Ser His Trp Tyr
                115                 120                 125

Phe Asp Val Trp Gly Gln Gly Thr Leu Val Thr Val Ser Ser Ala Ser
                130                 135                 140

Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
                180                 185                 190

His Thr Phe Pro Ala Val Leu Gln Ser Ser Gly Leu Tyr Ser Leu Ser
                195                 200                 205

Ser Val Val Thr Val Pro Ser Ser Ser Leu Gly Thr Gln Thr Tyr Ile
                210                 215                 220

Cys Asn Val Asn His Lys Pro Ser Asn Thr Lys Val Asp Lys Lys Val
225                 230                 235                 240

Glu Pro Lys Ser Cys Asp Lys Thr His Thr Cys Pro Pro Cys Pro Ala
                245                 250                 255

Pro Glu Leu Leu Gly Gly Pro Ser Val Phe Leu Phe Pro Pro Lys Pro
```

```
                260                 265                 270
Lys Asp Thr Leu Met Ile Ser Arg Thr Pro Glu Val Thr Cys Val Val
            275                 280                 285

Val Asp Val Ser His Glu Asp Pro Glu Val Lys Phe Asn Trp Tyr Val
        290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
            340                 345                 350

Leu Pro Ala Pro Ile Glu Lys Thr Ile Ser Lys Ala Lys Gly Gln Pro
        355                 360                 365

Arg Glu Pro Gln Val Tyr Thr Leu Pro Pro Ser Arg Asp Glu Leu Thr
    370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Tyr
            420                 425                 430

Ser Lys Leu Thr Val Asp Lys Ser Arg Trp Gln Gln Gly Asn Val Phe
        435                 440                 445

Ser Cys Ser Val Met His Glu Ala Leu His Asn His Tyr Thr Gln Lys
    450                 455                 460

Ser Leu Ser Leu Ser Pro Gly Lys
465                 470

<210> SEQ ID NO 144
<211> LENGTH: 233
<212> TYPE: PRT
<213> ORGANISM: Artificial Sequence
<220> FEATURE:
<223> OTHER INFORMATION: Light chain of adalimumab

<400> SEQUENCE: 144

Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Arg Ser Ser Gln Gly Ile
        35                  40                  45

Arg Asn Tyr Leu His Trp Tyr Gln Gln Lys Pro Gly Lys Ala Pro Lys
    50                  55                  60

Leu Leu Ile Tyr Ala Ala Ser Thr Leu Gln Ser Gly Val Pro Ser Arg
65                  70                  75                  80

Phe Ser Gly Ser Gly Ser Gly Thr Asp Phe Thr Leu Thr Ile Ser Ser
                85                  90                  95

Leu Gln Pro Glu Asp Val Ala Thr Tyr Tyr Cys Gln Arg Tyr Asn Arg
            100                 105                 110

Ala Pro Tyr Thr Phe Gly Gln Gly Thr Lys Val Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
```

```
                145                 150                 155                 160
Arg Glu Ala Lys Val Gln Trp Lys Val Asp Asn Ala Leu Gln Ser Gly
                    165                 170                 175

Asn Ser Gln Glu Ser Val Thr Glu Gln Asp Ser Lys Asp Ser Thr Tyr
                    180                 185                 190

Ser Leu Ser Ser Thr Leu Thr Leu Ser Lys Ala Asp Tyr Glu Lys His
                    195                 200                 205

Lys Val Tyr Ala Cys Glu Val Thr His Gln Gly Leu Ser Ser Pro Val
                    210                 215                 220

Thr Lys Ser Phe Asn Arg Gly Glu Cys
225                 230

<210> SEQ ID NO 145
<211> LENGTH: 470
<212> TYPE: PRT
<213> ORGANISM: Artificial Sequence
<220> FEATURE:
<223> OTHER INFORMATION: Heavy chain of adalimumab

<400> SEQUENCE: 145

Met Gly Trp Ser Leu Ile Ile Leu Phe Leu Val Ala Thr Ala Thr Gly
1               5                   10                  15

Val His Ser Glu Val Gln Leu Val Glu Ser Gly Gly Gly Leu Val Gln
                    20                  25                  30

Pro Gly Arg Ser Leu Arg Leu Ser Cys Ala Ala Ser Gly Phe Thr Phe
                    35                  40                  45

Asp Asp Tyr Ala Met His Trp Val Arg Gln Ala Pro Gly Lys Gly Leu
        50                  55                  60

Glu Trp Val Ser Ala Ile Thr Trp Asn Ser Gly His Ile Asp Tyr Ala
65                  70                  75                  80

Asp Ser Val Glu Gly Arg Phe Thr Ile Ser Arg Asp Asn Ala Lys Asn
                    85                  90                  95

Ser Leu Tyr Leu Gln Met Asn Ser Leu Arg Ala Glu Asp Thr Ala Val
                    100                 105                 110

Tyr Tyr Cys Ala Lys Val Ser Tyr Leu Ser Thr Ala Ser Ser Leu Asp
                    115                 120                 125

Val Trp Gly Gln Gly Thr Leu Val Thr Val Ser Ser Ala Ser Thr Lys
                    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                    165                 170                 175

Val Thr Val Ser Trp Asn Ser Gly Ala Leu Thr Ser Gly Val His Thr
                    180                 185                 190

Phe Pro Ala Val Leu Gln Ser Ser Gly Leu Tyr Ser Leu Ser Ser Val
                    195                 200                 205

Val Thr Val Pro Ser Ser Ser Leu Gly Thr Gln Thr Tyr Ile Cys Asn
                    210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                    245                 250                 255

Leu Leu Gly Gly Pro Ser Val Phe Leu Phe Pro Pro Lys Pro Lys Asp
                    260                 265                 270

Thr Leu Met Ile Ser Arg Thr Pro Glu Val Thr Cys Val Val Val Asp
```

```
                275                 280                 285
Val Ser His Glu Asp Pro Glu Val Lys Phe Asn Trp Tyr Val Asp Gly
290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Asp Glu Leu Thr Lys Asn
370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

Ser Leu Ser Pro Gly Lys
465                 470

<210> SEQ ID NO 146
<211> LENGTH: 169
<212> TYPE: PRT
<213> ORGANISM: Artificial Sequence
<220> FEATURE:
<223> OTHER INFORMATION: Flag-tagged J-Prot A fusion

<400> SEQUENCE: 146

Met Ala Pro Gln Asn Leu Ser Thr Phe Cys Leu Leu Leu Leu Tyr Leu
1               5                   10                  15

Ile Gly Ala Val Ile Ala Gly Arg Asp Phe Tyr Lys Ile Leu Gly Val
                20                  25                  30

Pro Arg Ser Ala Ser Ile Lys Asp Ile Lys Lys Ala Tyr Arg Lys Leu
            35                  40                  45

Ala Leu Gln Leu His Pro Asp Arg Asn Pro Asp Pro Gln Ala Gln
50                  55                  60

Glu Lys Phe Gln Asp Leu Gly Ala Ala Tyr Glu Val Leu Ser Asp Ser
65                  70                  75                  80

Glu Lys Arg Asp Ile Gly Gly Ser Gly Gly Ser Gly Gly Ser Gly
                85                  90                  95

Gly Ala Ala Ala Asp Asn Lys Phe Asn Lys Glu Gln Gln Asn Ala
            100                 105                 110

Phe Tyr Glu Ile Leu Asn Met Pro Asn Leu Asn Glu Glu Gln Arg Asn
                115                 120                 125

Gly Phe Ile Gln Ser Leu Lys Asp Asp Pro Ser Gln Ser Ala Asn Val
            130                 135                 140

Leu Gly Glu Ala Lys Lys Leu Asn Asp Ser Gln Ala Pro Lys Leu Glu
145                 150                 155                 160

Gly Asp Tyr Lys Asp Asp Asp Asp Lys
```

<210> SEQ ID NO 147
<211> LENGTH: 249
<212> TYPE: PRT
<213> ORGANISM: Artificial Sequence
<220> FEATURE:
<223> OTHER INFORMATION: Flag-tagged J-Prot A-TM1

<400> SEQUENCE: 147

Met Ala Pro Gln Asn Leu Ser Thr Phe Cys Leu Leu Leu Tyr Leu
1               5                   10                  15

Ile Gly Ala Val Ile Ala Gly Arg Asp Phe Tyr Lys Ile Leu Gly Val
            20                  25                  30

Pro Arg Ser Ala Ser Ile Lys Asp Ile Lys Lys Ala Tyr Arg Lys Leu
        35                  40                  45

Ala Leu Gln Leu His Pro Asp Arg Asn Pro Asp Pro Gln Ala Gln
50                  55                  60

Glu Lys Phe Gln Asp Leu Gly Ala Ala Tyr Glu Val Leu Ser Asp Ser
65                  70                  75                  80

Glu Lys Arg Asp Ile Gly Gly Ser Gly Gly Ser Gly Gly Ser Gly
                85                  90                  95

Gly Ala Ala Ala Ala Asp Asn Lys Phe Asn Lys Glu Gln Gln Asn Ala
            100                 105                 110

Phe Tyr Glu Ile Leu Asn Met Pro Asn Leu Asn Glu Glu Gln Arg Asn
            115                 120                 125

Gly Phe Ile Gln Ser Leu Lys Asp Asp Pro Ser Gln Ser Ala Asn Val
130                 135                 140

Leu Gly Glu Ala Lys Lys Leu Asn Asp Ser Gln Ala Pro Lys Leu Glu
145                 150                 155                 160

Gly Asp Tyr Lys Asp Asp Asp Asp Lys Gly Ser Arg Asp Asp Glu Ser
                165                 170                 175

Leu Phe Phe Gly Asp Thr Gly Leu Ser Lys Asn Pro Ile Glu Leu Val
            180                 185                 190

Glu Gly Trp Phe Ser Ser Trp Lys Ser Ser Ile Ala Ser Phe Phe Phe
            195                 200                 205

Ile Ile Gly Leu Ile Ile Gly Leu Phe Leu Val Leu Arg Val Gly Ile
            210                 215                 220

His Leu Cys Ile Lys Leu Lys His Thr Lys Lys Arg Gln Ile Tyr Thr
225                 230                 235                 240

Asp Ile Glu Met Asn Arg Leu Gly Lys
                245

<210> SEQ ID NO 148
<211> LENGTH: 261
<212> TYPE: PRT
<213> ORGANISM: Artificial Sequence
<220> FEATURE:
<223> OTHER INFORMATION: Flag-tagged J-Prot G-TM1

<400> SEQUENCE: 148

Met Ala Pro Gln Asn Leu Ser Thr Phe Cys Leu Leu Leu Tyr Leu
1               5                   10                  15

Ile Gly Ala Val Ile Ala Gly Arg Asp Phe Tyr Lys Ile Leu Gly Val
            20                  25                  30

Pro Arg Ser Ala Ser Ile Lys Asp Ile Lys Lys Ala Tyr Arg Lys Leu
        35                  40                  45

Ala Leu Gln Leu His Pro Asp Arg Asn Pro Asp Pro Gln Ala Gln
    50                  55                  60

Glu Lys Phe Gln Asp Leu Gly Ala Ala Tyr Glu Val Leu Ser Asp Ser
65                  70                  75                  80

Glu Lys Arg Asp Ile Gly Gly Gly Ser Gly Gly Ser Gly Gly Ser Gly
                85                  90                  95

Gly Ala Ala Ala Thr Tyr Lys Leu Val Ile Asn Gly Lys Thr Leu Lys
                100                 105                 110

Gly Glu Thr Thr Thr Glu Ala Val Asp Ala Ala Thr Ala Glu Lys Val
                115                 120                 125

Phe Lys Gln Tyr Ala Asn Asp Asn Gly Val Asp Gly Glu Trp Thr Tyr
130                 135                 140

Asp Asp Ala Thr Lys Thr Phe Thr Val Thr Glu Lys Pro Glu Val Ile
145                 150                 155                 160

Asp Ala Ser Glu Leu Thr Pro Ala Val Thr Leu Glu Gly Asp Tyr Lys
                165                 170                 175

Asp Asp Asp Asp Lys Gly Ser Arg Asp Asp Glu Ser Leu Phe Phe Gly
                180                 185                 190

Asp Thr Gly Leu Ser Lys Asn Pro Ile Glu Leu Val Glu Gly Trp Phe
                195                 200                 205

Ser Ser Trp Lys Ser Ser Ile Ala Ser Phe Phe Ile Ile Gly Leu
        210                 215                 220

Ile Ile Gly Leu Phe Leu Val Leu Arg Val Gly Ile His Leu Cys Ile
225                 230                 235                 240

Lys Leu Lys His Thr Lys Lys Arg Gln Ile Tyr Thr Asp Ile Glu Met
                245                 250                 255

Asn Arg Leu Gly Lys
            260

<210> SEQ ID NO 149
<211> LENGTH: 417
<212> TYPE: PRT
<213> ORGANISM: Artificial Sequence
<220> FEATURE:
<223> OTHER INFORMATION: Flag-tagged J-g1-TM1

<400> SEQUENCE: 149

Met Ala Pro Gln Asn Leu Ser Thr Phe Cys Leu Leu Leu Tyr Leu
1               5                   10                  15

Ile Gly Ala Val Ile Ala Gly Arg Asp Phe Tyr Lys Ile Leu Gly Val
                20                  25                  30

Pro Arg Ser Ala Ser Ile Lys Asp Ile Lys Lys Ala Tyr Arg Lys Leu
            35                  40                  45

Ala Leu Gln Leu His Pro Asp Arg Asn Pro Asp Pro Gln Ala Gln
    50                  55                  60

Glu Lys Phe Gln Asp Leu Gly Ala Ala Tyr Glu Val Leu Ser Asp Ser
65                  70                  75                  80

Glu Lys Arg Asp Ile Gly Gly Gly Ser Gly Gly Ser Gly Gly Ser Gly
                85                  90                  95

Gly Ala Ala Ala Leu Val Val Arg Gly Pro Thr Val Ser Leu Val Ser
                100                 105                 110

Asn Ser Phe Val Asp Ala Gly Ala Leu Gly Pro Asp Gly Val Val Glu
            115                 120                 125

Glu Asp Leu Leu Ile Leu Gly Glu Leu Arg Phe Val Gly Asp Gln Val
130                 135                 140

```
Pro His Thr Thr Tyr Tyr Asp Gly Val Val Glu Leu Trp His Tyr Pro
145                 150                 155                 160

Met Gly His Lys Cys Pro Arg Val Val His Val Val Thr Val Thr Ala
                165                 170                 175

Cys Pro Arg Arg Pro Ala Val Ala Phe Ala Leu Cys Arg Ala Thr Asp
            180                 185                 190

Ser Thr His Ser Pro Ala Tyr Pro Thr Leu Glu Leu Asn Leu Ala Gln
        195                 200                 205

Gln Pro Leu Leu Arg Val Arg Arg Ala Thr Arg Asp Tyr Ala Gly Val
    210                 215                 220

Tyr Val Leu Arg Val Trp Val Gly Asp Ala Pro Asn Ala Ser Leu Phe
225                 230                 235                 240

Val Leu Gly Met Ala Ile Ala Ala Glu Gly Thr Leu Ala Tyr Asn Gly
                245                 250                 255

Ser Ala His Gly Ser Cys Asp Pro Lys Leu Leu Pro Tyr Ser Ala Pro
            260                 265                 270

Arg Leu Ala Pro Ala Ser Val Tyr Gln Pro Ala Pro Asn Pro Ala Ser
        275                 280                 285

Thr Pro Ser Thr Thr Thr Ser Thr Pro Ser Thr Thr Thr Ser Thr Pro
    290                 295                 300

Ser Thr Thr Ile Pro Ala Pro Gln Ala Ser Thr Thr Pro Phe Pro Thr
305                 310                 315                 320

Gly Asp Pro Lys Pro Gln Leu Glu Gly Asp Tyr Lys Asp Asp Asp Asp
                325                 330                 335

Lys Gly Ser Arg Asp Asp Glu Ser Leu Phe Phe Gly Asp Thr Gly Leu
            340                 345                 350

Ser Lys Asn Pro Ile Glu Leu Val Glu Gly Trp Phe Ser Ser Trp Lys
        355                 360                 365

Ser Ser Ile Ala Ser Phe Phe Phe Ile Ile Gly Leu Ile Ile Gly Leu
    370                 375                 380

Phe Leu Val Leu Arg Val Gly Ile His Leu Cys Ile Lys Leu Lys His
385                 390                 395                 400

Thr Lys Lys Arg Gln Ile Tyr Thr Asp Ile Glu Met Asn Arg Leu Gly
                405                 410                 415

Lys
```

<210> SEQ ID NO 150
<211> LENGTH: 341
<212> TYPE: PRT
<213> ORGANISM: Artificial Sequence
<220> FEATURE:
<223> OTHER INFORMATION: Flag-tagged J-hFcR-TM1

<400> SEQUENCE: 150

```
Met Ala Pro Gln Asn Leu Ser Thr Phe Cys Leu Leu Leu Leu Tyr Leu
1                   5                   10                  15

Ile Gly Ala Val Ile Ala Gly Arg Asp Phe Tyr Lys Ile Leu Gly Val
                20                  25                  30

Pro Arg Ser Ala Ser Ile Lys Asp Ile Lys Lys Ala Tyr Arg Lys Leu
            35                  40                  45

Ala Leu Gln Leu His Pro Asp Arg Asn Pro Asp Asp Pro Gln Ala Gln
        50                  55                  60

Glu Lys Phe Gln Asp Leu Gly Ala Ala Tyr Glu Val Leu Ser Asp Ser
65                  70                  75                  80

Glu Lys Arg Asp Ile Gly Gly Gly Ser Gly Gly Ser Gly Gly Ser Gly
```

```
                    85                  90                  95
Gly Ala Ala Ala Val Ile Thr Leu Gln Pro Pro Trp Val Ser Val
            100                 105                 110

Phe Gln Glu Glu Thr Val Thr Leu His Cys Glu Val Leu His Leu Pro
            115                 120                 125

Gly Ser Ser Thr Gln Trp Phe Leu Asn Gly Thr Ala Thr Gln Thr
        130                 135                 140

Ser Thr Pro Ser Tyr Arg Ile Thr Ser Ala Ser Val Asn Asp Ser Gly
145                 150                 155                 160

Glu Tyr Arg Cys Gln Arg Gly Leu Ser Gly Arg Ser Asp Pro Ile Gln
                165                 170                 175

Leu Glu Ile His Arg Gly Trp Leu Leu Leu Gln Val Ser Ser Arg Val
                180                 185                 190

Phe Thr Glu Gly Glu Pro Leu Ala Leu Arg Cys His Ala Trp Lys Asp
                195                 200                 205

Lys Leu Val Tyr Asn Val Leu Tyr Tyr Arg Asn Gly Lys Ala Phe Lys
            210                 215                 220

Phe Phe His Trp Asn Ser Asn Leu Thr Ile Leu Lys Thr Asn Ile Ser
225                 230                 235                 240

His Asn Gly Thr Tyr His Cys Ser Gly Met Leu Glu Gly Asp Tyr Lys
                245                 250                 255

Asp Asp Asp Asp Lys Gly Ser Arg Asp Asp Glu Ser Leu Phe Phe Gly
                260                 265                 270

Asp Thr Gly Leu Ser Lys Asn Pro Ile Glu Leu Val Glu Gly Trp Phe
            275                 280                 285

Ser Ser Trp Lys Ser Ser Ile Ala Ser Phe Phe Ile Ile Gly Leu
        290                 295                 300

Ile Ile Gly Leu Phe Leu Val Leu Arg Val Gly Ile His Leu Cys Ile
305                 310                 315                 320

Lys Leu Lys His Thr Lys Lys Arg Gln Ile Tyr Thr Asp Ile Glu Met
                325                 330                 335

Asn Arg Leu Gly Lys
            340

<210> SEQ ID NO 151
<211> LENGTH: 667
<212> TYPE: PRT
<213> ORGANISM: Artificial Sequence
<220> FEATURE:
<223> OTHER INFORMATION: Flag-tagged J-gE-KDELR

<400> SEQUENCE: 151

Met Ala Leu Trp Met Arg Leu Leu Pro Leu Leu Ala Leu Leu Ala Leu
1               5                   10                  15

Trp Gly Pro Asp Pro Ala Ala Ala Gly Thr Gly Ser Gly Glu Phe Ile
            20                  25                  30

Lys Lys Ala Phe His Lys Leu Ala Met Lys Tyr Asp Ile Gly Gly Gly
        35                  40                  45

Gly Ser Gly Gly Gly Gly Ser Gly Gly Gly Gly Ser Ala Ala Ala Gly
    50                  55                  60

Thr Pro Lys Thr Ser Trp Arg Arg Val Ser Val Gly Glu Asp Val Ser
65                  70                  75                  80

Leu Leu Pro Ala Pro Gly Pro Thr Gly Arg Gly Pro Thr Gln Lys Leu
                85                  90                  95

Leu Trp Ala Val Glu Pro Leu Asp Gly Cys Gly Pro Leu His Pro Ser
```

```
                100             105             110
Trp Val Ser Leu Met Pro Pro Lys Gln Val Pro Glu Thr Val Val Asp
            115                 120                 125

Ala Ala Cys Met Arg Ala Pro Val Pro Leu Ala Met Ala Tyr Ala Pro
        130                 135                 140

Pro Ala Pro Ser Ala Thr Gly Gly Leu Arg Thr Asp Phe Val Trp Gln
145                 150                 155                 160

Glu Arg Ala Ala Val Val Asn Arg Ser Leu Val Ile His Gly Val Arg
                165                 170                 175

Glu Thr Asp Ser Gly Leu Tyr Thr Leu Ser Val Gly Asp Ile Lys Asp
            180                 185                 190

Pro Ala Arg Gln Val Ala Ser Val Leu Val Val Gln Pro Ala Pro
        195                 200                 205

Val Pro Thr Pro Pro Thr Pro Ala Asp Tyr Asp Glu Asp Asp Asn
    210                 215                 220

Asp Glu Gly Glu Asp Glu Ser Leu Ala Gly Thr Pro Ala Ser Gly Thr
225                 230                 235                 240

Pro Arg Leu Pro Pro Pro Ala Pro Pro Arg Ser Trp Pro Ser Ala
                245                 250                 255

Pro Glu Val Ser His Val Arg Gly Val Thr Val Arg Met Glu Thr Pro
            260                 265                 270

Glu Ala Ile Leu Phe Ser Pro Gly Glu Thr Phe Ser Thr Asn Val Ser
                275                 280                 285

Ile His Ala Ile Ala His Asp Asp Gln Thr Tyr Ser Met Asp Val Val
        290                 295                 300

Trp Leu Arg Phe Asp Val Pro Thr Ser Cys Ala Glu Met Arg Ile Tyr
305                 310                 315                 320

Glu Ser Cys Leu Tyr His Pro Gln Leu Pro Glu Cys Leu Ser Pro Ala
                325                 330                 335

Asp Ala Pro Cys Ala Ala Ser Thr Trp Thr Ser Arg Leu Ala Val Arg
            340                 345                 350

Ser Tyr Ala Gly Cys Ser Arg Thr Asn Pro Pro Arg Cys Ser Ala
        355                 360                 365

Glu Ala His Met Glu Pro Val Pro Gly Leu Ala Trp Gln Ala Ala Ser
370                 375                 380

Val Asn Leu Glu Phe Arg Asp Ala Ser Pro Gln His Ser Gly Leu Tyr
385                 390                 395                 400

Leu Cys Val Val Tyr Val Asn Asp His Ile His Ala Trp Gly His Ile
                405                 410                 415

Thr Ile Ser Thr Ala Ala Gln Tyr Arg Asn Ala Val Val Glu Gln Pro
            420                 425                 430

Leu Pro Gln Arg Gly Ala Asp Leu Ala Glu Leu Gly Asp Tyr Lys
        435                 440                 445

Asp Asp Asp Asp Lys Gly Ser Arg Asn Leu Phe Arg Phe Leu Gly Asp
450                 455                 460

Leu Ser His Leu Leu Ala Ile Ile Leu Leu Leu Lys Ile Trp Lys
465                 470                 475                 480

Ser Arg Ser Cys Ala Gly Ile Ser Gly Lys Ser Gln Val Leu Phe Ala
                485                 490                 495

Val Val Phe Thr Ala Arg Tyr Leu Asp Leu Phe Thr Asn Tyr Ile Ser
            500                 505                 510

Leu Tyr Asn Thr Cys Met Lys Val Val Tyr Ile Ala Cys Ser Phe Thr
        515                 520                 525
```

-continued

```
Thr Val Trp Leu Ile Tyr Ser Lys Phe Lys Ala Thr Tyr Asp Gly Asn
        530                 535                 540

His Asp Thr Phe Arg Val Glu Phe Leu Val Val Pro Thr Ala Ile Leu
545                 550                 555                 560

Ala Phe Leu Val Asn His Asp Phe Thr Pro Leu Glu Ile Leu Trp Thr
                565                 570                 575

Phe Ser Ile Tyr Leu Glu Ser Val Ala Ile Leu Pro Gln Leu Phe Met
            580                 585                 590

Val Ser Lys Thr Gly Glu Ala Glu Thr Ile Thr Ser His Tyr Leu Phe
        595                 600                 605

Ala Leu Gly Val Tyr Arg Thr Leu Tyr Leu Phe Asn Trp Ile Trp Arg
    610                 615                 620

Tyr His Phe Glu Gly Phe Phe Asp Leu Ile Ala Ile Val Ala Gly Leu
625                 630                 635                 640

Val Gln Thr Val Leu Tyr Cys Asp Phe Phe Tyr Leu Tyr Ile Thr Lys
                645                 650                 655

Val Leu Lys Gly Lys Lys Leu Ser Leu Pro Ala
            660                 665

<210> SEQ ID NO 152
<211> LENGTH: 4
<212> TYPE: PRT
<213> ORGANISM: Artificial Sequence
<220> FEATURE:
<223> OTHER INFORMATION: KDEL

<400> SEQUENCE: 152

Lys Asp Glu Leu
1

<210> SEQ ID NO 153
<211> LENGTH: 466
<212> TYPE: PRT
<213> ORGANISM: Artificial Sequence
<220> FEATURE:
<223> OTHER INFORMATION: Flag-tagged J-gE'-KDELR

<400> SEQUENCE: 153

Met Ala Leu Trp Met Arg Leu Leu Pro Leu Leu Ala Leu Leu Ala Leu
1               5                   10                  15

Trp Gly Pro Asp Pro Ala Ala Ala Gly Thr Gly Ser Gly Glu Phe Ile
                20                  25                  30

Lys Lys Ala Phe His Lys Leu Ala Met Lys Tyr Asp Ile Gly Gly Gly
            35                  40                  45

Gly Ser Gly Gly Gly Gly Ser Gly Gly Gly Gly Ser Ala Ala Ala Ala
        50                  55                  60

Pro Glu Val Ser His Val Arg Gly Val Thr Val Arg Met Glu Thr Pro
65                  70                  75                  80

Glu Ala Ile Leu Phe Ser Pro Gly Glu Thr Phe Ser Thr Asn Val Ser
                85                  90                  95

Ile His Ala Ile Ala His Asp Asp Gln Thr Tyr Ser Met Asp Val Val
            100                 105                 110

Trp Leu Arg Phe Asp Val Pro Thr Ser Cys Ala Glu Met Arg Ile Tyr
        115                 120                 125

Glu Ser Cys Leu Tyr His Pro Gln Leu Pro Glu Cys Leu Ser Pro Ala
    130                 135                 140

Asp Ala Pro Cys Ala Ala Ser Thr Trp Thr Ser Arg Leu Ala Val Arg
```

| | | | 145 | | | | 150 | | | | 155 | | | | 160 |
|---|---|---|---|---|---|---|---|---|---|---|---|---|---|---|---|
| Ser | Tyr | Ala | Gly | Cys | Ser | Arg | Thr | Asn | Pro | Pro | Arg | Cys | Ser | Ala | |

Ser Tyr Ala Gly Cys Ser Arg Thr Asn Pro Pro Arg Cys Ser Ala
              165                 170                 175

Glu Ala His Met Glu Pro Val Pro Gly Leu Ala Trp Gln Ala Ala Ser
              180                 185                 190

Val Asn Leu Glu Phe Arg Asp Ala Ser Pro Gln His Ser Gly Leu Tyr
              195                 200                 205

Leu Cys Val Val Tyr Val Asn Asp His Ile His Ala Trp Gly His Ile
210                 215                 220

Thr Ile Ser Thr Ala Ala Gln Tyr Arg Asn Ala Val Val Glu Gln Pro
225                 230                 235                 240

Leu Leu Glu Gly Asp Tyr Lys Asp Asp Asp Lys Gly Ser Arg Asn
              245                 250                 255

Leu Phe Arg Phe Leu Gly Asp Leu Ser His Leu Leu Ala Ile Ile Leu
              260                 265                 270

Leu Leu Leu Lys Ile Trp Lys Ser Arg Ser Cys Ala Gly Ile Ser Gly
              275                 280                 285

Lys Ser Gln Val Leu Phe Ala Val Val Phe Thr Ala Arg Tyr Leu Asp
290                 295                 300

Leu Phe Thr Asn Tyr Ile Ser Leu Tyr Asn Thr Cys Met Lys Val Val
305                 310                 315                 320

Tyr Ile Ala Cys Ser Phe Thr Thr Val Trp Leu Ile Tyr Ser Lys Phe
              325                 330                 335

Lys Ala Thr Tyr Asp Gly Asn His Asp Thr Phe Arg Val Glu Phe Leu
              340                 345                 350

Val Val Pro Thr Ala Ile Leu Ala Phe Leu Val Asn His Asp Phe Thr
              355                 360                 365

Pro Leu Glu Ile Leu Trp Thr Phe Ser Ile Tyr Leu Glu Ser Val Ala
              370                 375                 380

Ile Leu Pro Gln Leu Phe Met Val Ser Lys Thr Gly Glu Ala Glu Thr
385                 390                 395                 400

Ile Thr Ser His Tyr Leu Phe Ala Leu Gly Val Tyr Arg Thr Leu Tyr
              405                 410                 415

Leu Phe Asn Trp Ile Trp Arg Tyr His Phe Glu Gly Phe Phe Asp Leu
              420                 425                 430

Ile Ala Ile Val Ala Gly Leu Val Gln Thr Val Leu Tyr Cys Asp Phe
              435                 440                 445

Phe Tyr Leu Tyr Ile Thr Lys Val Leu Lys Gly Lys Lys Leu Ser Leu
              450                 455                 460

Pro Ala
465

<210> SEQ ID NO 154
<211> LENGTH: 468
<212> TYPE: PRT
<213> ORGANISM: Artificial Sequence
<220> FEATURE:
<223> OTHER INFORMATION: PEEP-FcB6.1-KDELR

<400> SEQUENCE: 154

Met Ala Leu Trp Met Arg Leu Leu Pro Leu Leu Ala Leu Leu Ala Leu
1               5                   10                  15

Trp Gly Pro Asp Pro Ala Ala Ala Gly Thr Gly Ser Gly Glu Phe Ile
              20                  25                  30

Lys Lys Ala Phe His Lys Leu Ala Met Lys Tyr Asp Ile Gly Gly Gly

```
                35                  40                  45
Gly Ser Gly Gly Gly Ser Gly Gly Gly Ser Ala Ala Ala Ala
             50                  55                  60
Pro Glu Glu Ala Leu Ile Val Val Asp Met Gln Arg Asp Phe Met Pro
 65                  70                  75                  80
Gly Gly Ala Leu Pro Val Pro Glu Gly Asp Lys Ile Ile Pro Lys Val
                 85                  90                  95
Asn Glu Tyr Ile Arg Lys Phe Lys Glu Lys Gly Ala Leu Ile Val Ala
                100                 105                 110
Thr Arg Asp Trp His Pro Glu Asn His Ile Ser Phe Arg Glu Arg Gly
                115                 120                 125
Gly Pro Trp Pro Arg His Cys Val Gln Asn Thr Pro Gly Ala Glu Phe
            130                 135                 140
Val Val Asp Leu Pro Glu Asp Ala Val Ile Ile Ser Lys Ala Thr Glu
145                 150                 155                 160
Pro Asp Lys Glu Ala Tyr Ser Gly Phe Glu Gly Thr Asp Leu Ala Lys
                165                 170                 175
Ile Leu Arg Gly Asn Gly Val Lys Arg Val Tyr Ile Cys Gly Val Ala
            180                 185                 190
Thr Glu Tyr Cys Val Ser Arg Thr Ala Val Asp Ala Leu Lys His Gly
        195                 200                 205
Phe Glu Val Tyr Leu Leu Arg Asp Ala Val Lys Gly Ile Lys Pro Thr
210                 215                 220
Phe Glu Gln Gln Ser Phe Phe Tyr Met Ser Leu Lys Gly Ile Lys Ile
225                 230                 235                 240
Val Gln Phe Leu Glu Gly Asp Tyr Lys Asp Asp Asp Lys Gly Ser
            245                 250                 255
Arg Asn Leu Phe Arg Phe Leu Gly Asp Leu Ser His Leu Leu Ala Ile
            260                 265                 270
Ile Leu Leu Leu Leu Lys Ile Trp Lys Ser Arg Ser Cys Ala Gly Ile
        275                 280                 285
Ser Gly Lys Ser Gln Val Leu Phe Ala Val Val Phe Thr Ala Arg Tyr
    290                 295                 300
Leu Asp Leu Phe Thr Asn Tyr Ile Ser Leu Tyr Asn Thr Cys Met Lys
305                 310                 315                 320
Val Val Tyr Ile Ala Cys Ser Phe Thr Thr Val Trp Leu Ile Tyr Ser
            325                 330                 335
Lys Phe Lys Ala Thr Tyr Asp Gly Asn His Asp Thr Phe Arg Val Glu
            340                 345                 350
Phe Leu Val Val Pro Thr Ala Ile Leu Ala Phe Leu Val Asn His Asp
        355                 360                 365
Phe Thr Pro Leu Glu Ile Leu Trp Thr Phe Ser Ile Tyr Leu Glu Ser
    370                 375                 380
Val Ala Ile Leu Pro Gln Leu Phe Met Val Ser Lys Thr Gly Glu Ala
385                 390                 395                 400
Glu Thr Ile Thr Ser His Tyr Leu Phe Ala Leu Gly Val Tyr Arg Thr
            405                 410                 415
Leu Tyr Leu Phe Asn Trp Ile Trp Arg Tyr His Phe Glu Gly Phe Phe
        420                 425                 430
Asp Leu Ile Ala Ile Val Ala Gly Leu Val Gln Thr Val Leu Tyr Cys
    435                 440                 445
Asp Phe Phe Tyr Leu Tyr Ile Thr Lys Val Leu Lys Gly Lys Lys Leu
450                 455                 460
```

Ser Leu Pro Ala
465

<210> SEQ ID NO 155
<211> LENGTH: 345
<212> TYPE: PRT
<213> ORGANISM: Artificial Sequence
<220> FEATURE:
<223> OTHER INFORMATION: PEEP-GB919-KDELR

<400> SEQUENCE: 155

Met Ala Leu Trp Met Arg Leu Leu Pro Leu Leu Ala Leu Leu Ala Leu
1               5                   10                  15

Trp Gly Pro Asp Pro Ala Ala Ala Gly Thr Gly Ser Gly Glu Phe Ile
            20                  25                  30

Lys Lys Ala Phe His Lys Leu Ala Met Lys Tyr Asp Ile Gly Gly Gly
        35                  40                  45

Gly Ser Gly Gly Gly Ser Gly Gly Gly Ser Ala Ala Ala
    50                  55                  60

Asp Thr Tyr Lys Leu Ile Leu Asn Gly Lys Thr Leu Lys Gly Glu Thr
65                  70                  75                  80

Thr Thr Glu Ala Val Asp Ala Ala Thr Ala Glu Lys Val Phe Lys His
                85                  90                  95

Tyr Ala Asn Glu His Gly Val His Gly His Trp Thr Tyr Asp Pro Glu
            100                 105                 110

Thr Lys Thr Phe Thr Val Thr Glu Leu Glu Gly Asp Tyr Lys Asp Asp
        115                 120                 125

Asp Asp Lys Gly Ser Arg Asn Leu Phe Arg Phe Leu Gly Asp Leu Ser
    130                 135                 140

His Leu Leu Ala Ile Ile Leu Leu Leu Leu Lys Ile Trp Lys Ser Arg
145                 150                 155                 160

Ser Cys Ala Gly Ile Ser Gly Lys Ser Gln Val Leu Phe Ala Val Val
                165                 170                 175

Phe Thr Ala Arg Tyr Leu Asp Leu Phe Thr Asn Tyr Ile Ser Leu Tyr
            180                 185                 190

Asn Thr Cys Met Lys Val Val Tyr Ile Ala Cys Ser Phe Thr Thr Val
        195                 200                 205

Trp Leu Ile Tyr Ser Lys Phe Lys Ala Thr Tyr Asp Gly Asn His Asp
    210                 215                 220

Thr Phe Arg Val Glu Phe Leu Val Val Pro Thr Ala Ile Leu Ala Phe
225                 230                 235                 240

Leu Val Asn His Asp Phe Thr Pro Leu Glu Ile Leu Trp Thr Phe Ser
                245                 250                 255

Ile Tyr Leu Glu Ser Val Ala Ile Leu Pro Gln Leu Phe Met Val Ser
            260                 265                 270

Lys Thr Gly Glu Ala Glu Thr Ile Thr Ser His Tyr Leu Phe Ala Leu
        275                 280                 285

Gly Val Tyr Arg Thr Leu Tyr Leu Phe Asn Trp Ile Trp Arg Tyr His
    290                 295                 300

Phe Glu Gly Phe Phe Asp Leu Ile Ala Ile Val Ala Gly Leu Val Gln
305                 310                 315                 320

Thr Val Leu Tyr Cys Asp Phe Phe Tyr Leu Tyr Ile Thr Lys Val Leu
                325                 330                 335

Lys Gly Lys Lys Leu Ser Leu Pro Ala
            340                 345

```
<210> SEQ ID NO 156
<211> LENGTH: 520
<212> TYPE: PRT
<213> ORGANISM: Artificial Sequence
<220> FEATURE:
<223> OTHER INFORMATION: PEEP-gE-TMR(CD4)

<400> SEQUENCE: 156
```

| | | | | | | | | | | | | | | | |
|---|---|---|---|---|---|---|---|---|---|---|---|---|---|---|---|
| Met | Ala | Leu | Trp | Met | Arg | Leu | Leu | Pro | Leu | Leu | Ala | Leu | Leu | Ala | Leu |
| 1 | | | | 5 | | | | | 10 | | | | | 15 | |
| Trp | Gly | Pro | Asp | Pro | Ala | Ala | Ala | Gly | Thr | Gly | Ser | Gly | Glu | Phe | Ile |
| | | | 20 | | | | | 25 | | | | | 30 | | |
| Lys | Lys | Ala | Phe | His | Lys | Leu | Ala | Met | Lys | Tyr | Asp | Ile | Gly | Gly | Gly |
| | | 35 | | | | | 40 | | | | | 45 | | | |
| Gly | Ser | Gly | Gly | Gly | Ser | Gly | Gly | Gly | Ser | Ala | Ala | Ala | Gly |
| | 50 | | | | | 55 | | | | | 60 | | |
| Thr | Pro | Lys | Thr | Ser | Trp | Arg | Arg | Val | Ser | Val | Gly | Glu | Asp | Val | Ser |
| 65 | | | | | 70 | | | | | 75 | | | | | 80 |
| Leu | Leu | Pro | Ala | Pro | Gly | Pro | Thr | Gly | Arg | Gly | Pro | Thr | Gln | Lys | Leu |
| | | | | 85 | | | | | 90 | | | | | 95 | |
| Leu | Trp | Ala | Val | Glu | Pro | Leu | Asp | Gly | Cys | Gly | Pro | Leu | His | Pro | Ser |
| | | | 100 | | | | | 105 | | | | | 110 | | |
| Trp | Val | Ser | Leu | Met | Pro | Pro | Lys | Gln | Val | Pro | Glu | Thr | Val | Val | Asp |
| | | 115 | | | | | 120 | | | | | 125 | | | |
| Ala | Ala | Cys | Met | Arg | Ala | Pro | Val | Pro | Leu | Ala | Met | Ala | Tyr | Ala | Pro |
| | 130 | | | | | 135 | | | | | 140 | | | | |
| Pro | Ala | Pro | Ser | Ala | Thr | Gly | Gly | Leu | Arg | Thr | Asp | Phe | Val | Trp | Gln |
| 145 | | | | | 150 | | | | | 155 | | | | | 160 |
| Glu | Arg | Ala | Ala | Val | Val | Asn | Arg | Ser | Leu | Val | Ile | His | Gly | Val | Arg |
| | | | | 165 | | | | | 170 | | | | | 175 | |
| Glu | Thr | Asp | Ser | Gly | Leu | Tyr | Thr | Leu | Ser | Val | Gly | Asp | Ile | Lys | Asp |
| | | | 180 | | | | | 185 | | | | | 190 | | |
| Pro | Ala | Arg | Gln | Val | Ala | Ser | Val | Val | Leu | Val | Val | Gln | Pro | Ala | Pro |
| | | 195 | | | | | 200 | | | | | 205 | | | |
| Val | Pro | Thr | Pro | Pro | Pro | Thr | Pro | Ala | Asp | Tyr | Asp | Glu | Asp | Asp | Asn |
| | 210 | | | | | 215 | | | | | 220 | | | | |
| Asp | Glu | Gly | Glu | Asp | Glu | Ser | Leu | Ala | Gly | Thr | Pro | Ala | Ser | Gly | Thr |
| 225 | | | | | 230 | | | | | 235 | | | | | 240 |
| Pro | Arg | Leu | Pro | Pro | Pro | Pro | Ala | Pro | Pro | Arg | Ser | Trp | Pro | Ser | Ala |
| | | | | 245 | | | | | 250 | | | | | 255 | |
| Pro | Glu | Val | Ser | His | Val | Arg | Gly | Val | Thr | Val | Arg | Met | Glu | Thr | Pro |
| | | | 260 | | | | | 265 | | | | | 270 | | |
| Glu | Ala | Ile | Leu | Phe | Ser | Pro | Gly | Glu | Thr | Phe | Ser | Thr | Asn | Val | Ser |
| | | 275 | | | | | 280 | | | | | 285 | | | |
| Ile | His | Ala | Ile | Ala | His | Asp | Asp | Gln | Thr | Tyr | Ser | Met | Asp | Val | Val |
| | 290 | | | | | 295 | | | | | 300 | | | | |
| Trp | Leu | Arg | Phe | Asp | Val | Pro | Thr | Ser | Cys | Ala | Glu | Met | Arg | Ile | Tyr |
| 305 | | | | | 310 | | | | | 315 | | | | | 320 |
| Glu | Ser | Cys | Leu | Tyr | His | Pro | Gln | Leu | Pro | Glu | Cys | Leu | Ser | Pro | Ala |
| | | | | 325 | | | | | 330 | | | | | 335 | |
| Asp | Ala | Pro | Cys | Ala | Ala | Ser | Thr | Trp | Thr | Ser | Arg | Leu | Ala | Val | Arg |
| | | | 340 | | | | | 345 | | | | | 350 | | |
| Ser | Tyr | Ala | Gly | Cys | Ser | Arg | Thr | Asn | Pro | Pro | Arg | Cys | Ser | Ala |
| | | 355 | | | | | 360 | | | | | 365 | | |

Glu Ala His Met Glu Pro Val Pro Gly Leu Ala Trp Gln Ala Ser
370 375 380

Val Asn Leu Glu Phe Arg Asp Ala Ser Pro Gln His Ser Gly Leu Tyr
385 390 395 400

Leu Cys Val Val Tyr Val Asn Asp His Ile His Ala Trp Gly His Ile
405 410 415

Thr Ile Ser Thr Ala Ala Gln Tyr Arg Asn Ala Val Val Glu Gln Pro
420 425 430

Leu Pro Gln Arg Gly Ala Asp Leu Ala Glu Leu Glu Gly Asp Tyr Lys
435 440 445

Asp Asp Asp Asp Lys Gly Ser Arg Gln Pro Met Ala Leu Ile Val Leu
450 455 460

Gly Gly Val Ala Gly Leu Leu Leu Phe Ile Gly Leu Gly Ile Phe Phe
465 470 475 480

Cys Val Arg Cys Arg His Arg Arg Gln Ala Glu Arg Met Ser Gln
485 490 495

Ile Lys Arg Leu Leu Ser Glu Lys Lys Thr Cys Gln Cys Pro His Arg
500 505 510

Phe Gln Lys Thr Cys Ser Pro Ile
515 520

<210> SEQ ID NO 157
<211> LENGTH: 514
<212> TYPE: PRT
<213> ORGANISM: Artificial Sequence
<220> FEATURE:
<223> OTHER INFORMATION: PEEP-gE-TMR(integrin)

<400> SEQUENCE: 157

Met Ala Leu Trp Met Arg Leu Leu Pro Leu Leu Ala Leu Leu Ala Leu
1 5 10 15

Trp Gly Pro Asp Pro Ala Ala Ala Gly Thr Gly Ser Gly Glu Phe Ile
20 25 30

Lys Lys Ala Phe His Lys Leu Ala Met Lys Tyr Asp Ile Gly Gly Gly
35 40 45

Gly Ser Gly Gly Gly Gly Ser Gly Gly Gly Gly Ser Ala Ala Ala Gly
50 55 60

Thr Pro Lys Thr Ser Trp Arg Arg Val Ser Val Gly Glu Asp Val Ser
65 70 75 80

Leu Leu Pro Ala Pro Gly Pro Thr Gly Arg Gly Pro Thr Gln Lys Leu
85 90 95

Leu Trp Ala Val Glu Pro Leu Asp Gly Cys Gly Pro Leu His Pro Ser
100 105 110

Trp Val Ser Leu Met Pro Pro Lys Gln Val Pro Glu Thr Val Val Asp
115 120 125

Ala Ala Cys Met Arg Ala Pro Val Pro Leu Ala Met Ala Tyr Ala Pro
130 135 140

Pro Ala Pro Ser Ala Thr Gly Gly Leu Arg Thr Asp Phe Val Trp Gln
145 150 155 160

Glu Arg Ala Ala Val Val Asn Arg Ser Leu Val Ile His Gly Val Arg
165 170 175

Glu Thr Asp Ser Gly Leu Tyr Thr Leu Ser Val Gly Asp Ile Lys Asp
180 185 190

Pro Ala Arg Gln Val Ala Ser Val Val Leu Val Val Gln Pro Ala Pro
195 200 205

Val Pro Thr Pro Pro Thr Pro Ala Asp Tyr Asp Glu Asp Asn
    210                 215                 220

Asp Glu Gly Glu Asp Glu Ser Leu Ala Gly Thr Pro Ala Ser Gly Thr
225                 230                 235                 240

Pro Arg Leu Pro Pro Pro Ala Pro Pro Arg Ser Trp Pro Ser Ala
                245                 250                 255

Pro Glu Val Ser His Val Arg Gly Val Thr Val Arg Met Glu Thr Pro
                260                 265                 270

Glu Ala Ile Leu Phe Ser Pro Gly Glu Thr Phe Ser Thr Asn Val Ser
            275                 280                 285

Ile His Ala Ile Ala His Asp Asp Gln Thr Tyr Ser Met Asp Val Val
    290                 295                 300

Trp Leu Arg Phe Asp Val Pro Thr Ser Cys Ala Glu Met Arg Ile Tyr
305                 310                 315                 320

Glu Ser Cys Leu Tyr His Pro Gln Leu Pro Glu Cys Leu Ser Pro Ala
                325                 330                 335

Asp Ala Pro Cys Ala Ala Ser Thr Trp Thr Ser Arg Leu Ala Val Arg
                340                 345                 350

Ser Tyr Ala Gly Cys Ser Arg Thr Asn Pro Pro Arg Cys Ser Ala
                355                 360                 365

Glu Ala His Met Glu Pro Val Pro Gly Leu Ala Trp Gln Ala Ala Ser
    370                 375                 380

Val Asn Leu Glu Phe Arg Asp Ala Ser Pro Gln His Ser Gly Leu Tyr
385                 390                 395                 400

Leu Cys Val Val Tyr Val Asn Asp His Ile His Ala Trp Gly His Ile
                405                 410                 415

Thr Ile Ser Thr Ala Ala Gln Tyr Arg Asn Ala Val Val Glu Gln Pro
                420                 425                 430

Leu Pro Gln Arg Gly Ala Asp Leu Ala Glu Leu Glu Gly Asp Tyr Lys
            435                 440                 445

Asp Asp Asp Asp Lys Gly Ser Arg Pro Val Pro Val Trp Val Ile Ile
    450                 455                 460

Leu Ala Val Leu Ala Gly Leu Leu Leu Ala Val Leu Val Phe Val
465                 470                 475                 480

Met Tyr Arg Met Gly Phe Phe Lys Arg Val Arg Pro Pro Gln Glu Glu
                485                 490                 495

Gln Glu Arg Glu Gln Leu Gln Pro His Glu Asn Gly Glu Gly Asn Ser
                500                 505                 510

Glu Thr

<210> SEQ ID NO 158
<211> LENGTH: 501
<212> TYPE: PRT
<213> ORGANISM: Artificial Sequence
<220> FEATURE:
<223> OTHER INFORMATION: PEEP-gE-TMR(UGT1)

<400> SEQUENCE: 158

Met Ala Leu Trp Met Arg Leu Leu Pro Leu Leu Ala Leu Leu Ala Leu
1               5                   10                  15

Trp Gly Pro Asp Pro Ala Ala Ala Gly Thr Gly Ser Gly Glu Phe Ile
                20                  25                  30

Lys Lys Ala Phe His Lys Leu Ala Met Lys Tyr Asp Ile Gly Gly Gly
            35                  40                  45

```
Gly Ser Gly Gly Gly Ser Gly Gly Gly Ser Ala Ala Ala Gly
 50              55              60

Thr Pro Lys Thr Ser Trp Arg Val Ser Val Gly Glu Asp Val Ser
 65              70              75              80

Leu Leu Pro Ala Pro Gly Pro Thr Gly Arg Gly Pro Thr Gln Lys Leu
                 85              90              95

Leu Trp Ala Val Glu Pro Leu Asp Gly Cys Gly Pro Leu His Pro Ser
                100             105             110

Trp Val Ser Leu Met Pro Pro Lys Gln Val Pro Glu Thr Val Val Asp
            115             120             125

Ala Ala Cys Met Arg Ala Pro Val Pro Leu Ala Met Ala Tyr Ala Pro
130             135             140

Pro Ala Pro Ser Ala Thr Gly Gly Leu Arg Thr Asp Phe Val Trp Gln
145             150             155             160

Glu Arg Ala Ala Val Val Asn Arg Ser Leu Val Ile His Gly Val Arg
                165             170             175

Glu Thr Asp Ser Gly Leu Tyr Thr Leu Ser Val Gly Asp Ile Lys Asp
            180             185             190

Pro Ala Arg Gln Val Ala Ser Val Val Leu Val Val Gln Pro Ala Pro
        195             200             205

Val Pro Thr Pro Pro Thr Pro Ala Asp Tyr Asp Glu Asp Asp Asn
210             215             220

Asp Glu Gly Glu Asp Glu Ser Leu Ala Gly Thr Pro Ala Ser Gly Thr
225             230             235             240

Pro Arg Leu Pro Pro Pro Ala Pro Pro Arg Ser Trp Pro Ser Ala
                245             250             255

Pro Glu Val Ser His Val Arg Gly Val Thr Val Arg Met Glu Thr Pro
            260             265             270

Glu Ala Ile Leu Phe Ser Pro Gly Glu Thr Phe Ser Thr Asn Val Ser
        275             280             285

Ile His Ala Ile Ala His Asp Asp Gln Thr Tyr Ser Met Asp Val Val
290             295             300

Trp Leu Arg Phe Asp Val Pro Thr Ser Cys Ala Glu Met Arg Ile Tyr
305             310             315             320

Glu Ser Cys Leu Tyr His Pro Gln Leu Pro Glu Cys Leu Ser Pro Ala
                325             330             335

Asp Ala Pro Cys Ala Ala Ser Thr Trp Thr Ser Arg Leu Ala Val Arg
            340             345             350

Ser Tyr Ala Gly Cys Ser Arg Thr Asn Pro Pro Arg Cys Ser Ala
        355             360             365

Glu Ala His Met Glu Pro Val Pro Gly Leu Ala Trp Gln Ala Ala Ser
370             375             380

Val Asn Leu Glu Phe Arg Asp Ala Ser Pro Gln His Ser Gly Leu Tyr
385             390             395             400

Leu Cys Val Val Tyr Val Asn Asp His Ile His Ala Trp Gly His Ile
                405             410             415

Thr Ile Ser Thr Ala Ala Gln Tyr Arg Asn Ala Val Val Glu Gln Pro
            420             425             430

Leu Pro Gln Arg Gly Ala Asp Leu Ala Glu Leu Gly Asp Tyr Lys
        435             440             445

Asp Asp Asp Asp Lys Gly Ser Arg Leu Asp Val Ile Gly Phe Leu Leu
450             455             460

Ala Val Val Leu Thr Val Ala Phe Ile Thr Phe Lys Cys Cys Ala Tyr
```

```
            465                 470                 475                 480

Gly Tyr Arg Lys Cys Leu Gly Lys Lys Gly Arg Val Lys Lys Ala His
                485                 490                 495

Lys Ser Lys Thr His
            500

<210> SEQ ID NO 159
<211> LENGTH: 492
<212> TYPE: PRT
<213> ORGANISM: Artificial Sequence
<220> FEATURE:
<223> OTHER INFORMATION: PEEP-gE-TMR(KDELR')

<400> SEQUENCE: 159

Met Ala Leu Trp Met Arg Leu Leu Pro Leu Leu Ala Leu Leu Ala Leu
1               5                   10                  15

Trp Gly Pro Asp Pro Ala Ala Ala Gly Thr Gly Ser Gly Glu Phe Ile
            20                  25                  30

Lys Lys Ala Phe His Lys Leu Ala Met Lys Tyr Asp Ile Gly Gly Gly
        35                  40                  45

Gly Ser Gly Gly Gly Ser Gly Gly Gly Ser Ala Ala Ala Gly
    50                  55                  60

Thr Pro Lys Thr Ser Trp Arg Arg Val Ser Val Gly Glu Asp Val Ser
65                  70                  75                  80

Leu Leu Pro Ala Pro Gly Pro Thr Gly Arg Gly Pro Thr Gln Lys Leu
                85                  90                  95

Leu Trp Ala Val Glu Pro Leu Asp Gly Cys Gly Pro Leu His Pro Ser
            100                 105                 110

Trp Val Ser Leu Met Pro Pro Lys Gln Val Pro Glu Thr Val Val Asp
        115                 120                 125

Ala Ala Cys Met Arg Ala Pro Val Pro Leu Ala Met Ala Tyr Ala Pro
    130                 135                 140

Pro Ala Pro Ser Ala Thr Gly Gly Leu Arg Thr Asp Phe Val Trp Gln
145                 150                 155                 160

Glu Arg Ala Ala Val Val Asn Arg Ser Leu Val Ile His Gly Val Arg
                165                 170                 175

Glu Thr Asp Ser Gly Leu Tyr Thr Leu Ser Val Gly Asp Ile Lys Asp
            180                 185                 190

Pro Ala Arg Gln Val Ala Ser Val Val Leu Val Val Gln Pro Ala Pro
        195                 200                 205

Val Pro Thr Pro Pro Pro Thr Pro Ala Asp Tyr Asp Glu Asp Asp Asn
    210                 215                 220

Asp Glu Gly Glu Asp Glu Ser Leu Ala Gly Thr Pro Ala Ser Gly Thr
225                 230                 235                 240

Pro Arg Leu Pro Pro Pro Pro Ala Pro Pro Arg Ser Trp Pro Ser Ala
                245                 250                 255

Pro Glu Val Ser His Val Arg Gly Val Thr Val Arg Met Glu Thr Pro
            260                 265                 270

Glu Ala Ile Leu Phe Ser Pro Gly Glu Thr Phe Ser Thr Asn Val Ser
        275                 280                 285

Ile His Ala Ile Ala His Asp Asp Gln Thr Tyr Ser Met Asp Val Val
    290                 295                 300

Trp Leu Arg Phe Asp Val Pro Thr Ser Cys Ala Glu Met Arg Ile Tyr
305                 310                 315                 320

Glu Ser Cys Leu Tyr His Pro Gln Leu Pro Glu Cys Leu Ser Pro Ala
```

```
            325                 330                 335
Asp Ala Pro Cys Ala Ala Ser Thr Trp Thr Ser Arg Leu Ala Val Arg
            340                 345                 350

Ser Tyr Ala Gly Cys Ser Arg Thr Asn Pro Pro Arg Cys Ser Ala
            355                 360                 365

Glu Ala His Met Glu Pro Val Pro Gly Leu Ala Trp Gln Ala Ser
    370                 375                 380

Val Asn Leu Glu Phe Arg Asp Ala Ser Pro Gln His Ser Gly Leu Tyr
385                 390                 395                 400

Leu Cys Val Val Tyr Val Asn Asp His Ile His Ala Trp Gly His Ile
            405                 410                 415

Thr Ile Ser Thr Ala Ala Gln Tyr Arg Asn Ala Val Val Glu Gln Pro
            420                 425                 430

Leu Pro Gln Arg Gly Ala Asp Leu Ala Glu Leu Glu Gly Asp Tyr Lys
            435                 440                 445

Asp Asp Asp Asp Lys Gly Ser Arg Asp Leu Ile Ala Ile Val Ala Gly
            450                 455                 460

Leu Val Gln Thr Val Leu Tyr Cys Asp Phe Phe Tyr Leu Tyr Ile Thr
465                 470                 475                 480

Lys Val Leu Lys Gly Lys Lys Leu Ser Leu Pro Ala
            485                 490

<210> SEQ ID NO 160
<211> LENGTH: 492
<212> TYPE: PRT
<213> ORGANISM: Artificial Sequence
<220> FEATURE:
<223> OTHER INFORMATION: PEEP-gE-TMR(p23)

<400> SEQUENCE: 160

Met Ala Leu Trp Met Arg Leu Leu Pro Leu Leu Ala Leu Leu Ala Leu
1               5                   10                  15

Trp Gly Pro Asp Pro Ala Ala Ala Gly Thr Gly Ser Gly Glu Phe Ile
            20                  25                  30

Lys Lys Ala Phe His Lys Leu Ala Met Lys Tyr Asp Ile Gly Gly Gly
        35                  40                  45

Gly Ser Gly Gly Gly Gly Ser Gly Gly Gly Gly Ser Ala Ala Ala Gly
    50                  55                  60

Thr Pro Lys Thr Ser Trp Arg Arg Val Ser Val Gly Glu Asp Val Ser
65                  70                  75                  80

Leu Leu Pro Ala Pro Gly Pro Thr Gly Arg Gly Pro Thr Gln Lys Leu
                85                  90                  95

Leu Trp Ala Val Glu Pro Leu Asp Gly Cys Gly Pro Leu His Pro Ser
            100                 105                 110

Trp Val Ser Leu Met Pro Pro Lys Gln Val Pro Glu Thr Val Val Asp
        115                 120                 125

Ala Ala Cys Met Arg Ala Pro Val Pro Leu Ala Met Ala Tyr Ala Pro
    130                 135                 140

Pro Ala Pro Ser Ala Thr Gly Gly Leu Arg Thr Asp Phe Val Trp Gln
145                 150                 155                 160

Glu Arg Ala Ala Val Val Asn Arg Ser Leu Val Ile His Gly Val Arg
                165                 170                 175

Glu Thr Asp Ser Gly Leu Tyr Thr Leu Ser Val Gly Asp Ile Lys Asp
            180                 185                 190

Pro Ala Arg Gln Val Ala Ser Val Val Leu Val Val Gln Pro Ala Pro
```

```
                195                 200                 205
Val Pro Thr Pro Pro Thr Pro Ala Asp Tyr Asp Glu Asp Asn
210                 215                 220

Asp Glu Gly Glu Asp Glu Ser Leu Ala Gly Thr Pro Ala Ser Gly Thr
225                 230                 235                 240

Pro Arg Leu Pro Pro Pro Ala Pro Arg Ser Trp Pro Ser Ala
                245                 250                 255

Pro Glu Val Ser His Val Arg Gly Val Thr Val Arg Met Glu Thr Pro
                260                 265                 270

Glu Ala Ile Leu Phe Ser Pro Gly Glu Thr Phe Ser Thr Asn Val Ser
                275                 280                 285

Ile His Ala Ile Ala His Asp Asp Gln Thr Tyr Ser Met Asp Val Val
290                 295                 300

Trp Leu Arg Phe Asp Val Pro Thr Ser Cys Ala Glu Met Arg Ile Tyr
305                 310                 315                 320

Glu Ser Cys Leu Tyr His Pro Gln Leu Pro Glu Cys Leu Ser Pro Ala
                325                 330                 335

Asp Ala Pro Cys Ala Ala Ser Thr Trp Thr Ser Arg Leu Ala Val Arg
                340                 345                 350

Ser Tyr Ala Gly Cys Ser Arg Thr Asn Pro Pro Arg Cys Ser Ala
                355                 360                 365

Glu Ala His Met Glu Pro Val Pro Gly Leu Ala Trp Gln Ala Ala Ser
370                 375                 380

Val Asn Leu Glu Phe Arg Asp Ala Ser Pro Gln His Ser Gly Leu Tyr
385                 390                 395                 400

Leu Cys Val Val Tyr Val Asn Asp His Ile His Ala Trp Gly His Ile
                405                 410                 415

Thr Ile Ser Thr Ala Ala Gln Tyr Arg Asn Ala Val Val Glu Gln Pro
                420                 425                 430

Leu Pro Gln Arg Gly Ala Asp Leu Ala Glu Leu Glu Gly Asp Tyr Lys
                435                 440                 445

Asp Asp Asp Asp Lys Gly Ser Arg Thr Arg Val Leu Tyr Phe Ser Ile
450                 455                 460

Phe Ser Met Phe Cys Leu Ile Gly Leu Ala Thr Trp Gln Val Phe Tyr
465                 470                 475                 480

Leu Arg Arg Phe Phe Lys Ala Lys Lys Leu Ile Glu
                485                 490

<210> SEQ ID NO 161
<211> LENGTH: 491
<212> TYPE: PRT
<213> ORGANISM: Artificial Sequence
<220> FEATURE:
<223> OTHER INFORMATION: PEEP-gE-TMR(p24)

<400> SEQUENCE: 161

Met Ala Leu Trp Met Arg Leu Leu Pro Leu Leu Ala Leu Leu Ala Leu
1               5                   10                  15

Trp Gly Pro Asp Pro Ala Ala Ala Gly Thr Gly Ser Gly Glu Phe Ile
                20                  25                  30

Lys Lys Ala Phe His Lys Leu Ala Met Lys Tyr Asp Ile Gly Gly Gly
                35                  40                  45

Gly Ser Gly Gly Gly Gly Ser Gly Gly Gly Gly Ser Ala Ala Ala Gly
                50                  55                  60

Thr Pro Lys Thr Ser Trp Arg Arg Val Ser Val Gly Glu Asp Val Ser
```

```
             65                  70                  75                  80
Leu Leu Pro Ala Pro Gly Pro Thr Gly Arg Gly Pro Thr Gln Lys Leu
                     85                  90                  95
Leu Trp Ala Val Glu Pro Leu Asp Gly Cys Gly Pro Leu His Pro Ser
                    100                 105                 110
Trp Val Ser Leu Met Pro Pro Lys Gln Val Pro Glu Thr Val Val Asp
                    115                 120                 125
Ala Ala Cys Met Arg Ala Pro Val Pro Leu Ala Met Ala Tyr Ala Pro
                    130                 135                 140
Pro Ala Pro Ser Ala Thr Gly Gly Leu Arg Thr Asp Phe Val Trp Gln
145                 150                 155                 160
Glu Arg Ala Ala Val Val Asn Arg Ser Leu Val Ile His Gly Val Arg
                    165                 170                 175
Glu Thr Asp Ser Gly Leu Tyr Thr Leu Ser Val Gly Asp Ile Lys Asp
                    180                 185                 190
Pro Ala Arg Gln Val Ala Ser Val Val Leu Val Val Gln Pro Ala Pro
                    195                 200                 205
Val Pro Thr Pro Pro Thr Pro Ala Asp Tyr Asp Glu Asp Asp Asn
210                 215                 220
Asp Glu Gly Glu Asp Glu Ser Leu Ala Gly Thr Pro Ala Ser Gly Thr
225                 230                 235                 240
Pro Arg Leu Pro Pro Pro Ala Pro Arg Ser Trp Pro Ser Ala
                    245                 250                 255
Pro Glu Val Ser His Val Arg Gly Val Thr Val Arg Met Glu Thr Pro
                    260                 265                 270
Glu Ala Ile Leu Phe Ser Pro Gly Glu Thr Phe Ser Thr Asn Val Ser
                    275                 280                 285
Ile His Ala Ile Ala His Asp Asp Gln Thr Tyr Ser Met Asp Val Val
                    290                 295                 300
Trp Leu Arg Phe Asp Val Pro Thr Ser Cys Ala Glu Met Arg Ile Tyr
305                 310                 315                 320
Glu Ser Cys Leu Tyr His Pro Gln Leu Pro Glu Cys Leu Ser Pro Ala
                    325                 330                 335
Asp Ala Pro Cys Ala Ala Ser Thr Trp Thr Ser Arg Leu Ala Val Arg
                    340                 345                 350
Ser Tyr Ala Gly Cys Ser Arg Thr Asn Pro Pro Arg Cys Ser Ala
                    355                 360                 365
Glu Ala His Met Glu Pro Val Pro Gly Leu Ala Trp Gln Ala Ala Ser
                    370                 375                 380
Val Asn Leu Glu Phe Arg Asp Ala Ser Pro Gln His Ser Gly Leu Tyr
385                 390                 395                 400
Leu Cys Val Val Tyr Val Asn Asp His Ile His Ala Trp Gly His Ile
                    405                 410                 415
Thr Ile Ser Thr Ala Ala Gln Tyr Arg Asn Ala Val Val Glu Gln Pro
                    420                 425                 430
Leu Pro Gln Arg Gly Ala Asp Leu Ala Glu Leu Glu Gly Asp Tyr Lys
                    435                 440                 445
Asp Asp Asp Asp Lys Gly Ser Arg Ser Arg Val Val Leu Trp Ser Phe
450                 455                 460
Phe Glu Ala Leu Val Leu Val Ala Met Thr Leu Gly Gln Ile Tyr Tyr
465                 470                 475                 480
Leu Lys Arg Phe Phe Glu Val Arg Arg Val Val
                    485                 490
```

<210> SEQ ID NO 162
<211> LENGTH: 493
<212> TYPE: PRT
<213> ORGANISM: Artificial Sequence
<220> FEATURE:
<223> OTHER INFORMATION: PEEP-gE-TMR(LAMP2)

<400> SEQUENCE: 162

Met Ala Leu Trp Met Arg Leu Leu Pro Leu Leu Ala Leu Leu Ala Leu
1               5                   10                  15

Trp Gly Pro Asp Pro Ala Ala Ala Gly Thr Gly Ser Gly Glu Phe Ile
            20                  25                  30

Lys Lys Ala Phe His Lys Leu Ala Met Lys Tyr Asp Ile Gly Gly Gly
        35                  40                  45

Gly Ser Gly Gly Gly Gly Ser Gly Gly Gly Gly Ser Ala Ala Ala Gly
    50                  55                  60

Thr Pro Lys Thr Ser Trp Arg Arg Val Ser Val Gly Glu Asp Val Ser
65                  70                  75                  80

Leu Leu Pro Ala Pro Gly Pro Thr Gly Arg Gly Pro Thr Gln Lys Leu
                85                  90                  95

Leu Trp Ala Val Glu Pro Leu Asp Gly Cys Gly Pro Leu His Pro Ser
            100                 105                 110

Trp Val Ser Leu Met Pro Pro Lys Gln Val Pro Glu Thr Val Val Asp
        115                 120                 125

Ala Ala Cys Met Arg Ala Pro Val Pro Leu Ala Met Ala Tyr Ala Pro
    130                 135                 140

Pro Ala Pro Ser Ala Thr Gly Gly Leu Arg Thr Asp Phe Val Trp Gln
145                 150                 155                 160

Glu Arg Ala Ala Val Val Asn Arg Ser Leu Val Ile His Gly Val Arg
                165                 170                 175

Glu Thr Asp Ser Gly Leu Tyr Thr Leu Ser Val Gly Asp Ile Lys Asp
            180                 185                 190

Pro Ala Arg Gln Val Ala Ser Val Val Leu Val Val Gln Pro Ala Pro
        195                 200                 205

Val Pro Thr Pro Pro Thr Pro Ala Asp Tyr Asp Glu Asp Asp Asn
    210                 215                 220

Asp Glu Gly Glu Asp Glu Ser Leu Ala Gly Thr Pro Ala Ser Gly Thr
225                 230                 235                 240

Pro Arg Leu Pro Pro Pro Pro Ala Pro Pro Arg Ser Trp Pro Ser Ala
                245                 250                 255

Pro Glu Val Ser His Val Arg Gly Val Thr Val Arg Met Glu Thr Pro
            260                 265                 270

Glu Ala Ile Leu Phe Ser Pro Gly Glu Thr Phe Ser Thr Asn Val Ser
        275                 280                 285

Ile His Ala Ile Ala His Asp Asp Gln Thr Tyr Ser Met Asp Val Val
    290                 295                 300

Trp Leu Arg Phe Asp Val Pro Thr Ser Cys Ala Glu Met Arg Ile Tyr
305                 310                 315                 320

Glu Ser Cys Leu Tyr His Pro Gln Leu Pro Glu Cys Leu Ser Pro Ala
                325                 330                 335

Asp Ala Pro Cys Ala Ala Ser Thr Trp Thr Ser Arg Leu Ala Val Arg
            340                 345                 350

Ser Tyr Ala Gly Cys Ser Arg Thr Asn Pro Pro Arg Cys Ser Ala
        355                 360                 365

```
Glu Ala His Met Glu Pro Val Pro Gly Leu Ala Trp Gln Ala Ser
    370                 375                 380

Val Asn Leu Glu Phe Arg Asp Ala Ser Pro Gln His Ser Gly Leu Tyr
385                 390                 395                 400

Leu Cys Val Val Tyr Val Asn Asp His Ile His Ala Trp Gly His Ile
                405                 410                 415

Thr Ile Ser Thr Ala Ala Gln Tyr Arg Asn Ala Val Val Glu Gln Pro
            420                 425                 430

Leu Pro Gln Arg Gly Ala Asp Leu Ala Glu Leu Glu Gly Asp Tyr Lys
        435                 440                 445

Asp Asp Asp Asp Lys Gly Ser Arg Thr Ile Leu Ile Pro Ile Ile Val
450                 455                 460

Gly Ala Gly Leu Ser Gly Leu Ile Ile Val Ile Val Ile Ala Tyr Val
465                 470                 475                 480

Ile Gly Arg Arg Lys Ser Tyr Ala Gly Tyr Gln Thr Leu
                485                 490
```

<210> SEQ ID NO 163
<211> LENGTH: 503
<212> TYPE: PRT
<213> ORGANISM: Artificial Sequence
<220> FEATURE:
<223> OTHER INFORMATION: PEEP-gE-TMR(LIMP2')

<400> SEQUENCE: 163

```
Met Ala Leu Trp Met Arg Leu Leu Pro Leu Leu Ala Leu Leu Ala Leu
1               5                   10                  15

Trp Gly Pro Asp Pro Ala Ala Ala Gly Thr Gly Ser Gly Glu Phe Ile
                20                  25                  30

Lys Lys Ala Phe His Lys Leu Ala Met Lys Tyr Asp Ile Gly Gly Gly
                35                  40                  45

Gly Ser Gly Gly Gly Gly Ser Gly Gly Gly Gly Ser Ala Ala Ala Gly
        50                  55                  60

Thr Pro Lys Thr Ser Trp Arg Arg Val Ser Val Gly Glu Asp Val Ser
65                  70                  75                  80

Leu Leu Pro Ala Pro Gly Pro Thr Gly Arg Gly Pro Thr Gln Lys Leu
                85                  90                  95

Leu Trp Ala Val Glu Pro Leu Asp Gly Cys Gly Pro Leu His Pro Ser
            100                 105                 110

Trp Val Ser Leu Met Pro Pro Lys Gln Val Pro Glu Thr Val Val Asp
        115                 120                 125

Ala Ala Cys Met Arg Ala Pro Val Pro Leu Ala Met Ala Tyr Ala Pro
    130                 135                 140

Pro Ala Pro Ser Ala Thr Gly Gly Leu Arg Thr Asp Phe Val Trp Gln
145                 150                 155                 160

Glu Arg Ala Ala Val Val Asn Arg Ser Leu Val Ile His Gly Val Arg
                165                 170                 175

Glu Thr Asp Ser Gly Leu Tyr Thr Leu Ser Val Gly Asp Ile Lys Asp
            180                 185                 190

Pro Ala Arg Gln Val Ala Ser Val Val Leu Val Val Gln Pro Ala Pro
        195                 200                 205

Val Pro Thr Pro Pro Pro Thr Pro Ala Asp Tyr Asp Glu Asp Asp Asn
    210                 215                 220

Asp Glu Gly Glu Asp Glu Ser Leu Ala Gly Thr Pro Ala Ser Gly Thr
225                 230                 235                 240
```

```
Pro Arg Leu Pro Pro Pro Ala Pro Pro Arg Ser Trp Pro Ser Ala
            245                 250                 255

Pro Glu Val Ser His Val Arg Gly Val Thr Val Arg Met Glu Thr Pro
        260                 265                 270

Glu Ala Ile Leu Phe Ser Pro Gly Thr Phe Ser Thr Asn Val Ser
            275                 280                 285

Ile His Ala Ile Ala His Asp Asp Gln Thr Tyr Ser Met Asp Val Val
        290                 295                 300

Trp Leu Arg Phe Asp Val Pro Thr Ser Cys Ala Glu Met Arg Ile Tyr
305                 310                 315                 320

Glu Ser Cys Leu Tyr His Pro Gln Leu Pro Glu Cys Leu Ser Pro Ala
            325                 330                 335

Asp Ala Pro Cys Ala Ala Ser Thr Trp Thr Ser Arg Leu Ala Val Arg
            340                 345                 350

Ser Tyr Ala Gly Cys Ser Arg Thr Asn Pro Pro Arg Cys Ser Ala
            355                 360                 365

Glu Ala His Met Glu Pro Val Pro Gly Leu Ala Trp Gln Ala Ala Ser
            370                 375                 380

Val Asn Leu Glu Phe Arg Asp Ala Ser Pro Gln His Ser Gly Leu Tyr
385                 390                 395                 400

Leu Cys Val Val Tyr Val Asn Asp His Ile His Ala Trp Gly His Ile
                405                 410                 415

Thr Ile Ser Thr Ala Ala Gln Tyr Arg Asn Ala Val Val Glu Gln Pro
            420                 425                 430

Leu Pro Gln Arg Gly Ala Asp Leu Ala Glu Leu Gly Asp Tyr Lys
            435                 440                 445

Asp Asp Asp Asp Lys Gly Ser Arg Thr Leu Ile Ile Thr Asn Ile Pro
450                 455                 460

Tyr Ile Ile Met Ala Leu Gly Val Phe Phe Gly Leu Val Phe Thr Trp
465                 470                 475                 480

Leu Ala Cys Lys Gly Gln Gly Ser Met Asp Glu Gly Thr Ala Asp Glu
            485                 490                 495

Arg Ala Pro Leu Ile Arg Thr
            500
```

<210> SEQ ID NO 164
<211> LENGTH: 550
<212> TYPE: PRT
<213> ORGANISM: Artificial Sequence
<220> FEATURE:
<223> OTHER INFORMATION: PEEP-gE-TMR(CDM6PR)

<400> SEQUENCE: 164

```
Met Ala Leu Trp Met Arg Leu Leu Pro Leu Leu Ala Leu Leu Ala Leu
1               5                   10                  15

Trp Gly Pro Asp Pro Ala Ala Ala Gly Thr Gly Ser Gly Glu Phe Ile
            20                  25                  30

Lys Lys Ala Phe His Lys Leu Ala Met Lys Tyr Asp Ile Gly Gly Gly
        35                  40                  45

Gly Ser Gly Gly Gly Gly Ser Gly Gly Gly Gly Ser Ala Ala Ala Gly
    50                  55                  60

Thr Pro Lys Thr Ser Trp Arg Arg Val Ser Val Gly Glu Asp Val Ser
65                  70                  75                  80

Leu Leu Pro Ala Pro Gly Pro Thr Gly Arg Gly Pro Thr Gln Lys Leu
                85                  90                  95
```

```
Leu Trp Ala Val Glu Pro Leu Asp Gly Cys Gly Pro Leu His Pro Ser
            100                 105                 110

Trp Val Ser Leu Met Pro Pro Lys Gln Val Pro Glu Thr Val Val Asp
            115                 120                 125

Ala Ala Cys Met Arg Ala Pro Val Pro Leu Ala Met Ala Tyr Ala Pro
            130                 135                 140

Pro Ala Pro Ser Ala Thr Gly Gly Leu Arg Thr Asp Phe Val Trp Gln
145                 150                 155                 160

Glu Arg Ala Ala Val Val Asn Arg Ser Leu Val Ile His Gly Val Arg
                165                 170                 175

Glu Thr Asp Ser Gly Leu Tyr Thr Leu Ser Val Gly Asp Ile Lys Asp
            180                 185                 190

Pro Ala Arg Gln Val Ala Ser Val Val Leu Val Val Gln Pro Ala Pro
        195                 200                 205

Val Pro Thr Pro Pro Thr Pro Ala Asp Tyr Asp Glu Asp Asp Asn
    210                 215                 220

Asp Glu Gly Glu Asp Glu Ser Leu Ala Gly Thr Pro Ala Ser Gly Thr
225                 230                 235                 240

Pro Arg Leu Pro Pro Pro Ala Pro Arg Ser Trp Pro Ser Ala
                245                 250                 255

Pro Glu Val Ser His Val Arg Gly Val Thr Val Arg Met Glu Thr Pro
                260                 265                 270

Glu Ala Ile Leu Phe Ser Pro Gly Thr Phe Ser Thr Asn Val Ser
            275                 280                 285

Ile His Ala Ile Ala His Asp Asp Gln Thr Tyr Ser Met Asp Val Val
        290                 295                 300

Trp Leu Arg Phe Asp Val Pro Thr Ser Cys Ala Glu Met Arg Ile Tyr
305                 310                 315                 320

Glu Ser Cys Leu Tyr His Pro Gln Leu Pro Glu Cys Leu Ser Pro Ala
                325                 330                 335

Asp Ala Pro Cys Ala Ala Ser Thr Trp Thr Ser Arg Leu Ala Val Arg
            340                 345                 350

Ser Tyr Ala Gly Cys Ser Arg Thr Asn Pro Pro Arg Cys Ser Ala
        355                 360                 365

Glu Ala His Met Glu Pro Val Pro Gly Leu Ala Trp Gln Ala Ala Ser
    370                 375                 380

Val Asn Leu Glu Phe Arg Asp Ala Ser Pro Gln His Ser Gly Leu Tyr
385                 390                 395                 400

Leu Cys Val Val Tyr Val Asn Asp His Ile His Ala Trp Gly His Ile
                405                 410                 415

Thr Ile Ser Thr Ala Ala Gln Tyr Arg Asn Ala Val Glu Gln Pro
            420                 425                 430

Leu Pro Gln Arg Gly Ala Asp Leu Ala Glu Leu Glu Gly Asp Tyr Lys
        435                 440                 445

Asp Asp Asp Asp Lys Gly Ser Arg Ser His Leu Ser Val Gly Ser Ile
450                 455                 460

Leu Leu Val Thr Phe Ala Ser Leu Val Ala Val Tyr Val Val Gly Gly
465                 470                 475                 480

Phe Leu Tyr Gln Arg Leu Val Val Gly Ala Lys Gly Met Glu Gln Phe
                485                 490                 495

Pro His Leu Ala Phe Trp Gln Asp Leu Gly Asn Leu Val Ala Asp Gly
            500                 505                 510
```

```
Cys Asp Phe Val Cys Arg Ser Lys Pro Arg Asn Val Pro Ala Ala Tyr
            515                 520                 525

Arg Gly Val Gly Asp Gln Leu Gly Glu Glu Ser Glu Glu Arg Asp
        530                 535                 540

Asp His Leu Leu Pro Met
545                 550

<210> SEQ ID NO 165
<211> LENGTH: 533
<212> TYPE: PRT
<213> ORGANISM: Artificial Sequence
<220> FEATURE:
<223> OTHER INFORMATION: PEEP-gE-TMR(VSVG)

<400> SEQUENCE: 165

Met Ala Leu Trp Met Arg Leu Leu Pro Leu Leu Ala Leu Leu Ala Leu
1               5                   10                  15

Trp Gly Pro Asp Pro Ala Ala Ala Gly Thr Gly Ser Gly Glu Phe Ile
            20                  25                  30

Lys Lys Ala Phe His Lys Leu Ala Met Lys Tyr Asp Ile Gly Gly Gly
            35                  40                  45

Gly Ser Gly Gly Gly Gly Ser Gly Gly Gly Gly Ser Ala Ala Ala Gly
        50                  55                  60

Thr Pro Lys Thr Ser Trp Arg Arg Val Ser Val Gly Glu Asp Val Ser
65              70                  75                  80

Leu Leu Pro Ala Pro Gly Pro Thr Arg Gly Pro Thr Gln Lys Leu
            85                  90                  95

Leu Trp Ala Val Glu Pro Leu Asp Gly Cys Gly Pro Leu His Pro Ser
            100                 105                 110

Trp Val Ser Leu Met Pro Pro Lys Gln Val Pro Glu Thr Val Val Asp
            115                 120                 125

Ala Ala Cys Met Arg Ala Pro Val Pro Leu Ala Met Ala Tyr Ala Pro
        130                 135                 140

Pro Ala Pro Ser Ala Thr Gly Gly Leu Arg Thr Asp Phe Val Trp Gln
145             150                 155                 160

Glu Arg Ala Ala Val Val Asn Arg Ser Leu Val Ile His Gly Val Arg
                165                 170                 175

Glu Thr Asp Ser Gly Leu Tyr Thr Leu Ser Val Gly Asp Ile Lys Asp
            180                 185                 190

Pro Ala Arg Gln Val Ala Ser Val Val Leu Val Val Gln Pro Ala Pro
            195                 200                 205

Val Pro Thr Pro Pro Thr Pro Ala Asp Tyr Asp Glu Asp Asp Asn
        210                 215                 220

Asp Glu Gly Glu Asp Glu Ser Leu Ala Gly Thr Pro Ala Ser Gly Thr
225             230                 235                 240

Pro Arg Leu Pro Pro Pro Ala Pro Arg Ser Trp Pro Ser Ala
            245                 250                 255

Pro Glu Val Ser His Val Arg Gly Val Thr Val Arg Met Glu Thr Pro
            260                 265                 270

Glu Ala Ile Leu Phe Ser Pro Gly Glu Thr Phe Ser Thr Asn Val Ser
            275                 280                 285

Ile His Ala Ile Ala His Asp Asp Gln Thr Tyr Ser Met Asp Val Val
        290                 295                 300

Trp Leu Arg Phe Asp Val Pro Thr Ser Cys Ala Glu Met Arg Ile Tyr
305             310                 315                 320
```

```
Glu Ser Cys Leu Tyr His Pro Gln Leu Pro Glu Cys Leu Ser Pro Ala
                325                 330                 335

Asp Ala Pro Cys Ala Ala Ser Thr Trp Thr Ser Arg Leu Ala Val Arg
            340                 345                 350

Ser Tyr Ala Gly Cys Ser Arg Thr Asn Pro Pro Arg Cys Ser Ala
            355                 360                 365

Glu Ala His Met Glu Pro Val Pro Gly Leu Ala Trp Gln Ala Ala Ser
370                 375                 380

Val Asn Leu Glu Phe Arg Asp Ala Ser Pro Gln His Ser Gly Leu Tyr
385                 390                 395                 400

Leu Cys Val Val Tyr Val Asn Asp His Ile His Ala Trp Gly His Ile
                405                 410                 415

Thr Ile Ser Thr Ala Ala Gln Tyr Arg Asn Ala Val Val Glu Gln Pro
                420                 425                 430

Leu Pro Gln Arg Gly Ala Asp Leu Ala Glu Leu Glu Gly Asp Tyr Lys
            435                 440                 445

Asp Asp Asp Asp Lys Gly Ser Arg Asp Asp Glu Ser Leu Phe Phe Gly
450                 455                 460

Asp Thr Gly Leu Ser Lys Asn Pro Ile Glu Leu Val Glu Gly Trp Phe
465                 470                 475                 480

Ser Ser Trp Lys Ser Ser Ile Ala Ser Phe Phe Ile Ile Gly Leu
                485                 490                 495

Ile Ile Gly Leu Phe Leu Val Leu Arg Val Gly Ile His Leu Cys Ile
                500                 505                 510

Lys Leu Lys His Thr Lys Lys Arg Gln Ile Tyr Thr Asp Ile Glu Met
                515                 520                 525

Asn Arg Leu Gly Lys
        530

<210> SEQ ID NO 166
<211> LENGTH: 636
<212> TYPE: PRT
<213> ORGANISM: Artificial Sequence
<220> FEATURE:
<223> OTHER INFORMATION: PEEP-gE-TMR(CNX)

<400> SEQUENCE: 166

Met Ala Leu Trp Met Arg Leu Leu Pro Leu Leu Ala Leu Leu Ala Leu
1               5                   10                  15

Trp Gly Pro Asp Pro Ala Ala Ala Gly Thr Gly Ser Gly Glu Phe Ile
                20                  25                  30

Lys Lys Ala Phe His Lys Leu Ala Met Lys Tyr Asp Ile Gly Gly Gly
            35                  40                  45

Gly Ser Gly Gly Gly Gly Ser Gly Gly Gly Gly Ser Ala Ala Ala Gly
        50                  55                  60

Thr Pro Lys Thr Ser Trp Arg Arg Val Ser Val Gly Glu Asp Val Ser
65                  70                  75                  80

Leu Leu Pro Ala Pro Gly Pro Thr Gly Arg Gly Pro Thr Gln Lys Leu
                85                  90                  95

Leu Trp Ala Val Glu Pro Leu Asp Gly Cys Gly Pro Leu His Pro Ser
            100                 105                 110

Trp Val Ser Leu Met Pro Pro Lys Gln Val Pro Glu Thr Val Val Asp
        115                 120                 125

Ala Ala Cys Met Arg Ala Pro Val Pro Leu Ala Met Ala Tyr Ala Pro
    130                 135                 140
```

```
Pro Ala Pro Ser Ala Thr Gly Gly Leu Arg Thr Asp Phe Val Trp Gln
145                 150                 155                 160

Glu Arg Ala Ala Val Val Asn Arg Ser Leu Val Ile His Gly Val Arg
            165                 170                 175

Glu Thr Asp Ser Gly Leu Tyr Thr Leu Ser Val Gly Asp Ile Lys Asp
            180                 185                 190

Pro Ala Arg Gln Val Ala Ser Val Leu Val Val Gln Pro Ala Pro
            195                 200                 205

Val Pro Thr Pro Pro Thr Pro Ala Asp Tyr Asp Glu Asp Asn
    210                 215                 220

Asp Glu Gly Glu Asp Glu Ser Leu Ala Gly Thr Pro Ala Ser Gly Thr
225                 230                 235                 240

Pro Arg Leu Pro Pro Pro Ala Pro Pro Arg Ser Trp Pro Ser Ala
            245                 250                 255

Pro Glu Val Ser His Val Arg Gly Val Thr Val Arg Met Glu Thr Pro
            260                 265                 270

Glu Ala Ile Leu Phe Ser Pro Gly Glu Thr Phe Ser Thr Asn Val Ser
            275                 280                 285

Ile His Ala Ile Ala His Asp Asp Gln Thr Tyr Ser Met Asp Val Val
    290                 295                 300

Trp Leu Arg Phe Asp Val Pro Thr Ser Cys Ala Glu Met Arg Ile Tyr
305                 310                 315                 320

Glu Ser Cys Leu Tyr His Pro Gln Leu Pro Glu Cys Leu Ser Pro Ala
            325                 330                 335

Asp Ala Pro Cys Ala Ala Ser Thr Trp Thr Ser Arg Leu Ala Val Arg
            340                 345                 350

Ser Tyr Ala Gly Cys Ser Arg Thr Asn Pro Pro Arg Cys Ser Ala
            355                 360                 365

Glu Ala His Met Glu Pro Val Pro Gly Leu Ala Trp Gln Ala Ala Ser
            370                 375                 380

Val Asn Leu Glu Phe Arg Asp Ala Ser Pro Gln His Ser Gly Leu Tyr
385                 390                 395                 400

Leu Cys Val Val Tyr Val Asn Asp His Ile His Ala Trp Gly His Ile
            405                 410                 415

Thr Ile Ser Thr Ala Ala Gln Tyr Arg Asn Ala Val Val Glu Gln Pro
            420                 425                 430

Leu Pro Gln Arg Gly Ala Asp Leu Ala Glu Leu Glu Gly Asp Tyr Lys
            435                 440                 445

Asp Asp Asp Asp Lys Gly Ser Arg Pro Phe Arg Met Thr Pro Phe Ser
450                 455                 460

Ala Ile Gly Leu Glu Leu Trp Ser Met Thr Ser Asp Ile Phe Phe Asp
465                 470                 475                 480

Asn Phe Ile Ile Cys Ala Asp Arg Arg Ile Val Asp Asp Trp Ala Asn
            485                 490                 495

Asp Gly Trp Gly Leu Lys Lys Ala Ala Asp Gly Ala Ala Glu Pro Gly
            500                 505                 510

Val Val Gly Gln Met Ile Glu Ala Ala Glu Arg Pro Trp Leu Trp
            515                 520                 525

Val Val Tyr Ile Leu Thr Val Ala Leu Pro Val Phe Leu Val Ile Leu
            530                 535                 540

Phe Cys Cys Ser Gly Lys Lys Gln Thr Ser Gly Met Glu Tyr Lys Lys
545                 550                 555                 560

Thr Asp Ala Pro Gln Pro Asp Val Lys Glu Glu Glu Glu Glu Lys Glu
```

565                 570                 575
Glu Glu Lys Asp Lys Gly Asp Glu Glu Glu Gly Glu Glu Lys Leu
            580                 585                 590

Glu Glu Lys Gln Lys Ser Asp Ala Glu Glu Asp Gly Gly Thr Val Ser
            595                 600                 605

Gln Glu Glu Glu Asp Arg Lys Pro Lys Ala Glu Asp Glu Ile Leu
610                 615                 620

Asn Arg Ser Pro Arg Asn Arg Lys Pro Arg Arg Glu
625                 630                 635

<210> SEQ ID NO 167
<211> LENGTH: 549
<212> TYPE: PRT
<213> ORGANISM: Artificial Sequence
<220> FEATURE:
<223> OTHER INFORMATION: PEEP-gE-TMR(CNX')

<400> SEQUENCE: 167

Met Ala Leu Trp Met Arg Leu Leu Pro Leu Leu Ala Leu Leu Ala Leu
1               5                   10                  15

Trp Gly Pro Asp Pro Ala Ala Ala Gly Thr Gly Ser Gly Glu Phe Ile
            20                  25                  30

Lys Lys Ala Phe His Lys Leu Ala Met Lys Tyr Asp Ile Gly Gly Gly
        35                  40                  45

Gly Ser Gly Gly Gly Gly Ser Gly Gly Gly Gly Ser Ala Ala Ala Gly
    50                  55                  60

Thr Pro Lys Thr Ser Trp Arg Arg Val Ser Val Gly Glu Asp Val Ser
65                  70                  75                  80

Leu Leu Pro Ala Pro Gly Pro Thr Gly Arg Gly Pro Thr Gln Lys Leu
                85                  90                  95

Leu Trp Ala Val Glu Pro Leu Asp Gly Cys Gly Pro Leu His Pro Ser
            100                 105                 110

Trp Val Ser Leu Met Pro Pro Lys Gln Val Pro Glu Thr Val Val Asp
        115                 120                 125

Ala Ala Cys Met Arg Ala Pro Val Pro Leu Ala Met Ala Tyr Ala Pro
    130                 135                 140

Pro Ala Pro Ser Ala Thr Gly Gly Leu Arg Thr Asp Phe Val Trp Gln
145                 150                 155                 160

Glu Arg Ala Ala Val Val Asn Arg Ser Leu Val Ile His Gly Val Arg
                165                 170                 175

Glu Thr Asp Ser Gly Leu Tyr Thr Leu Ser Val Gly Asp Ile Lys Asp
            180                 185                 190

Pro Ala Arg Gln Val Ala Ser Val Val Leu Val Val Gln Pro Ala Pro
        195                 200                 205

Val Pro Thr Pro Pro Pro Thr Pro Ala Asp Tyr Asp Glu Asp Asp Asn
    210                 215                 220

Asp Glu Gly Glu Asp Glu Ser Leu Ala Gly Thr Pro Ala Ser Gly Thr
225                 230                 235                 240

Pro Arg Leu Pro Pro Pro Pro Ala Pro Pro Arg Ser Trp Pro Ser Ala
                245                 250                 255

Pro Glu Val Ser His Val Arg Gly Val Thr Val Arg Met Glu Thr Pro
            260                 265                 270

Glu Ala Ile Leu Phe Ser Pro Gly Glu Thr Phe Ser Thr Asn Val Ser
        275                 280                 285

Ile His Ala Ile Ala His Asp Asp Gln Thr Tyr Ser Met Asp Val Val

```
                     290                 295                 300

Trp Leu Arg Phe Asp Val Pro Thr Ser Cys Ala Glu Met Arg Ile Tyr
305                 310                 315                 320

Glu Ser Cys Leu Tyr His Pro Gln Leu Pro Glu Cys Leu Ser Pro Ala
                325                 330                 335

Asp Ala Pro Cys Ala Ala Ser Thr Trp Thr Ser Arg Leu Ala Val Arg
                340                 345                 350

Ser Tyr Ala Gly Cys Ser Arg Thr Asn Pro Pro Arg Cys Ser Ala
                355                 360                 365

Glu Ala His Met Glu Pro Val Pro Gly Leu Ala Trp Gln Ala Ala Ser
            370                 375                 380

Val Asn Leu Glu Phe Arg Asp Ala Ser Pro Gln His Ser Gly Leu Tyr
385                 390                 395                 400

Leu Cys Val Val Tyr Val Asn Asp His Ile His Ala Trp Gly His Ile
                405                 410                 415

Thr Ile Ser Thr Ala Ala Gln Tyr Arg Asn Ala Val Val Glu Gln Pro
                420                 425                 430

Leu Pro Gln Arg Gly Ala Asp Leu Ala Glu Leu Glu Gly Asp Tyr Lys
            435                 440                 445

Asp Asp Asp Asp Lys Gly Ser Arg Pro Phe Arg Met Thr Pro Phe Ser
450                 455                 460

Ala Ile Gly Leu Glu Leu Trp Ser Met Thr Ser Asp Ile Phe Phe Asp
465                 470                 475                 480

Asn Phe Ile Ile Cys Ala Asp Arg Arg Ile Val Asp Asp Trp Ala Asn
                485                 490                 495

Asp Gly Trp Gly Leu Lys Lys Ala Ala Asp Gly Ala Ala Glu Pro Gly
            500                 505                 510

Val Val Gly Gln Met Ile Glu Ala Glu Glu Arg Pro Trp Leu Trp
            515                 520                 525

Val Val Tyr Ile Leu Thr Val Ala Leu Pro Val Phe Leu Val Ile Leu
            530                 535                 540

Phe Cys Cys Ser Gly
545

<210> SEQ ID NO 168
<211> LENGTH: 607
<212> TYPE: PRT
<213> ORGANISM: Artificial Sequence
<220> FEATURE:
<223> OTHER INFORMATION: PEEP-gE-TMR(gE)

<400> SEQUENCE: 168

Met Ala Leu Trp Met Arg Leu Leu Pro Leu Leu Ala Leu Leu Ala Leu
1               5                   10                  15

Trp Gly Pro Asp Pro Ala Ala Ala Gly Thr Gly Ser Gly Glu Phe Ile
                20                  25                  30

Lys Lys Ala Phe His Lys Leu Ala Met Lys Tyr Asp Ile Gly Gly Gly
            35                  40                  45

Gly Ser Gly Gly Gly Gly Ser Gly Gly Gly Gly Ser Ala Ala Ala Gly
        50                  55                  60

Thr Pro Lys Thr Ser Trp Arg Arg Val Ser Gly Glu Asp Val Ser
65                  70                  75                  80

Leu Leu Pro Ala Pro Gly Pro Thr Gly Arg Gly Pro Thr Gln Lys Leu
                85                  90                  95

Leu Trp Ala Val Glu Pro Leu Asp Gly Cys Gly Pro Leu His Pro Ser
```

```
                100                 105                 110
Trp Val Ser Leu Met Pro Pro Lys Gln Val Pro Glu Thr Val Val Asp
            115                 120                 125

Ala Ala Cys Met Arg Ala Pro Val Pro Leu Ala Met Ala Tyr Ala Pro
            130                 135                 140

Pro Ala Pro Ser Ala Thr Gly Gly Leu Arg Thr Asp Phe Val Trp Gln
145                 150                 155                 160

Glu Arg Ala Ala Val Val Asn Arg Ser Leu Val Ile His Gly Val Arg
                165                 170                 175

Glu Thr Asp Ser Gly Leu Tyr Thr Leu Ser Val Gly Asp Ile Lys Asp
                180                 185                 190

Pro Ala Arg Gln Val Ala Ser Val Leu Val Val Gln Pro Ala Pro
            195                 200                 205

Val Pro Thr Pro Pro Thr Pro Ala Asp Tyr Asp Glu Asp Asn
210                 215                 220

Asp Glu Gly Glu Asp Glu Ser Leu Ala Gly Thr Pro Ala Ser Gly Thr
225                 230                 235                 240

Pro Arg Leu Pro Pro Pro Ala Pro Pro Arg Ser Trp Pro Ser Ala
            245                 250                 255

Pro Glu Val Ser His Val Arg Gly Val Thr Val Arg Met Glu Thr Pro
                260                 265                 270

Glu Ala Ile Leu Phe Ser Pro Gly Glu Thr Phe Ser Thr Asn Val Ser
            275                 280                 285

Ile His Ala Ile Ala His Asp Asp Gln Thr Tyr Ser Met Asp Val Val
            290                 295                 300

Trp Leu Arg Phe Asp Val Pro Thr Ser Cys Ala Glu Met Arg Ile Tyr
305                 310                 315                 320

Glu Ser Cys Leu Tyr His Pro Gln Leu Pro Glu Cys Leu Ser Pro Ala
            325                 330                 335

Asp Ala Pro Cys Ala Ala Ser Thr Trp Thr Ser Arg Leu Ala Val Arg
            340                 345                 350

Ser Tyr Ala Gly Cys Ser Arg Thr Asn Pro Pro Arg Cys Ser Ala
            355                 360                 365

Glu Ala His Met Glu Pro Val Pro Gly Leu Ala Trp Gln Ala Ala Ser
            370                 375                 380

Val Asn Leu Glu Phe Arg Asp Ala Ser Pro Gln His Ser Gly Leu Tyr
385                 390                 395                 400

Leu Cys Val Val Tyr Val Asn Asp His Ile His Ala Trp Gly His Ile
                405                 410                 415

Thr Ile Ser Thr Ala Ala Gln Tyr Arg Asn Ala Val Val Glu Gln Pro
                420                 425                 430

Leu Pro Gln Arg Gly Ala Asp Leu Ala Glu Leu Glu Gly Asp Tyr Lys
            435                 440                 445

Asp Asp Asp Asp Lys Gly Ser Arg Pro Thr His Pro His Val Gly Ala
            450                 455                 460

Pro Pro His Ala Pro Pro Thr His Gly Ala Leu Arg Leu Gly Ala Val
465                 470                 475                 480

Met Gly Ala Ala Leu Leu Leu Ser Ala Leu Gly Leu Ser Val Trp Ala
                485                 490                 495

Cys Met Thr Cys Trp Arg Arg Arg Ala Trp Arg Ala Val Lys Ser Arg
                500                 505                 510

Ala Ser Gly Lys Gly Pro Thr Tyr Ile Arg Val Ala Asp Ser Glu Leu
            515                 520                 525
```

```
Tyr Ala Asp Trp Ser Ser Asp Ser Glu Gly Glu Arg Asp Gln Val Pro
            530                 535                 540

Trp Leu Ala Pro Pro Glu Arg Pro Asp Ser Pro Ser Thr Asn Gly Ser
545                 550                 555                 560

Gly Phe Glu Ile Leu Ser Pro Thr Ala Pro Ser Val Tyr Pro Arg Ser
            565                 570                 575

Asp Gly His Gln Ser Arg Arg Gln Leu Thr Thr Phe Gly Ser Gly Arg
            580                 585                 590

Pro Asp Arg Arg Tyr Ser Gln Ala Ser Asp Ser Ser Val Phe Trp
            595                 600                 605

<210> SEQ ID NO 169
<211> LENGTH: 491
<212> TYPE: PRT
<213> ORGANISM: Artificial Sequence
<220> FEATURE:
<223> OTHER INFORMATION: PEEP-gE-TMR(ERGIC53)

<400> SEQUENCE: 169

Met Ala Leu Trp Met Arg Leu Leu Pro Leu Leu Ala Leu Leu Ala Leu
1               5                   10                  15

Trp Gly Pro Asp Pro Ala Ala Ala Gly Thr Gly Ser Gly Glu Phe Ile
            20                  25                  30

Lys Lys Ala Phe His Lys Leu Ala Met Lys Tyr Asp Ile Gly Gly Gly
            35                  40                  45

Gly Ser Gly Gly Gly Ser Gly Gly Gly Ser Ala Ala Ala Gly
        50                  55                  60

Thr Pro Lys Thr Ser Trp Arg Arg Val Ser Val Gly Glu Asp Val Ser
65                  70                  75                  80

Leu Leu Pro Ala Pro Gly Pro Thr Gly Arg Gly Pro Thr Gln Lys Leu
                85                  90                  95

Leu Trp Ala Val Glu Pro Leu Asp Gly Cys Gly Pro Leu His Pro Ser
            100                 105                 110

Trp Val Ser Leu Met Pro Pro Lys Gln Val Pro Glu Thr Val Val Asp
            115                 120                 125

Ala Ala Cys Met Arg Ala Pro Val Pro Leu Ala Met Ala Tyr Ala Pro
            130                 135                 140

Pro Ala Pro Ser Ala Thr Gly Gly Leu Arg Thr Asp Phe Val Trp Gln
145                 150                 155                 160

Glu Arg Ala Ala Val Val Asn Arg Ser Leu Val Ile His Gly Val Arg
                165                 170                 175

Glu Thr Asp Ser Gly Leu Tyr Thr Leu Ser Val Gly Asp Ile Lys Asp
            180                 185                 190

Pro Ala Arg Gln Val Ala Ser Val Val Leu Val Val Gln Pro Ala Pro
            195                 200                 205

Val Pro Thr Pro Pro Pro Thr Pro Ala Asp Tyr Asp Glu Asp Asp Asn
            210                 215                 220

Asp Glu Gly Glu Asp Glu Ser Leu Ala Gly Thr Pro Ala Ser Gly Thr
225                 230                 235                 240

Pro Arg Leu Pro Pro Pro Ala Pro Arg Ser Trp Pro Ser Ala
                245                 250                 255

Pro Glu Val Ser His Val Arg Gly Val Thr Val Arg Met Glu Thr Pro
            260                 265                 270

Glu Ala Ile Leu Phe Ser Pro Gly Glu Thr Phe Ser Thr Asn Val Ser
            275                 280                 285
```

```
Ile His Ala Ile Ala His Asp Gln Thr Tyr Ser Met Asp Val Val
    290                 295                 300

Trp Leu Arg Phe Asp Val Pro Thr Ser Cys Ala Glu Met Arg Ile Tyr
305                 310                 315                 320

Glu Ser Cys Leu Tyr His Pro Gln Leu Pro Glu Cys Leu Ser Pro Ala
                325                 330                 335

Asp Ala Pro Cys Ala Ala Ser Thr Trp Thr Ser Arg Leu Ala Val Arg
            340                 345                 350

Ser Tyr Ala Gly Cys Ser Arg Thr Asn Pro Pro Arg Cys Ser Ala
        355                 360                 365

Glu Ala His Met Glu Pro Val Pro Gly Leu Ala Trp Gln Ala Ala Ser
370                 375                 380

Val Asn Leu Glu Phe Arg Asp Ala Ser Pro Gln His Ser Gly Leu Tyr
385                 390                 395                 400

Leu Cys Val Val Tyr Val Asn Asp His Ile His Ala Trp Gly His Ile
                405                 410                 415

Thr Ile Ser Thr Ala Ala Gln Tyr Arg Asn Ala Val Val Glu Gln Pro
            420                 425                 430

Leu Pro Gln Arg Gly Ala Asp Leu Ala Glu Leu Glu Gly Asp Tyr Lys
        435                 440                 445

Asp Asp Asp Asp Lys Gly Ser Arg Leu Ser Thr Val His Phe Ile Ile
450                 455                 460

Phe Val Val Val Gln Thr Val Leu Phe Ile Gly Tyr Ile Met Tyr Arg
465                 470                 475                 480

Ser Gln Gln Glu Ala Ala Ala Lys Lys Phe Phe
                485                 490

<210> SEQ ID NO 170
<211> LENGTH: 485
<212> TYPE: PRT
<213> ORGANISM: Artificial Sequence
<220> FEATURE:
<223> OTHER INFORMATION: PEEP-gE-TRM(gp84)

<400> SEQUENCE: 170

Met Ala Leu Trp Met Arg Leu Leu Pro Leu Leu Ala Leu Leu Ala Leu
1               5                   10                  15

Trp Gly Pro Asp Pro Ala Ala Ala Gly Thr Gly Ser Gly Glu Phe Ile
                20                  25                  30

Lys Lys Ala Phe His Lys Leu Ala Met Lys Tyr Asp Ile Gly Gly Gly
            35                  40                  45

Gly Ser Gly Gly Gly Gly Ser Gly Gly Gly Gly Ser Ala Ala Ala Gly
    50                  55                  60

Thr Pro Lys Thr Ser Trp Arg Arg Val Ser Val Gly Glu Asp Val Ser
65                  70                  75                  80

Leu Leu Pro Ala Pro Gly Pro Thr Gly Arg Gly Pro Thr Gln Lys Leu
                85                  90                  95

Leu Trp Ala Val Glu Pro Leu Asp Gly Cys Gly Pro Leu His Pro Ser
            100                 105                 110

Trp Val Ser Leu Met Pro Pro Lys Gln Val Pro Glu Thr Val Val Asp
        115                 120                 125

Ala Ala Cys Met Arg Ala Pro Val Pro Leu Ala Met Ala Tyr Ala Pro
    130                 135                 140

Pro Ala Pro Ser Ala Thr Gly Gly Leu Arg Thr Asp Phe Val Trp Gln
145                 150                 155                 160
```

Glu Arg Ala Ala Val Val Asn Arg Ser Leu Val Ile His Gly Val Arg
                165                 170                 175

Glu Thr Asp Ser Gly Leu Tyr Thr Leu Ser Val Gly Asp Ile Lys Asp
            180                 185                 190

Pro Ala Arg Gln Val Ala Ser Val Val Leu Val Val Gln Pro Ala Pro
        195                 200                 205

Val Pro Thr Pro Pro Pro Thr Pro Ala Asp Tyr Asp Glu Asp Asp Asn
210                 215                 220

Asp Glu Gly Glu Asp Glu Ser Leu Ala Gly Thr Pro Ala Ser Gly Thr
225                 230                 235                 240

Pro Arg Leu Pro Pro Pro Ala Pro Arg Ser Trp Pro Ser Ala
                245                 250                 255

Pro Glu Val Ser His Val Arg Gly Val Thr Val Arg Met Glu Thr Pro
            260                 265                 270

Glu Ala Ile Leu Phe Ser Pro Gly Glu Thr Phe Ser Thr Asn Val Ser
        275                 280                 285

Ile His Ala Ile Ala His Asp Asp Gln Thr Tyr Ser Met Asp Val Val
    290                 295                 300

Trp Leu Arg Phe Asp Val Pro Thr Ser Cys Ala Glu Met Arg Ile Tyr
305                 310                 315                 320

Glu Ser Cys Leu Tyr His Pro Gln Leu Pro Glu Cys Leu Ser Pro Ala
                325                 330                 335

Asp Ala Pro Cys Ala Ala Ser Thr Trp Thr Ser Arg Leu Ala Val Arg
            340                 345                 350

Ser Tyr Ala Gly Cys Ser Arg Thr Asn Pro Pro Pro Arg Cys Ser Ala
        355                 360                 365

Glu Ala His Met Glu Pro Val Pro Gly Leu Ala Trp Gln Ala Ala Ser
    370                 375                 380

Val Asn Leu Glu Phe Arg Asp Ala Ser Pro Gln His Ser Gly Leu Tyr
385                 390                 395                 400

Leu Cys Val Val Tyr Val Asn Asp His Ile His Ala Trp Gly His Ile
                405                 410                 415

Thr Ile Ser Thr Ala Ala Gln Tyr Arg Asn Ala Val Val Glu Gln Pro
            420                 425                 430

Leu Pro Gln Arg Gly Ala Asp Leu Ala Glu Leu Glu Gly Asp Tyr Lys
        435                 440                 445

Asp Asp Asp Asp Lys Gly Ser Arg Leu Gly Gly Val Leu Tyr Leu Ile
    450                 455                 460

Ser Leu Cys Val Ser Leu Pro Ala Ser Phe Ala Arg Arg Arg Arg Leu
465                 470                 475                 480

Gly Arg Trp Gln Glu
                485

<210> SEQ ID NO 171
<211> LENGTH: 464
<212> TYPE: PRT
<213> ORGANISM: Artificial Sequence
<220> FEATURE:
<223> OTHER INFORMATION: PEEP-gE-TMR(gp73)

<400> SEQUENCE: 171

Met Met Gly Leu Gly Asn Gly Arg Arg Ser Met Lys Ser Pro Pro Leu
1               5                   10                  15

Val Leu Ala Ala Leu Val Ala Cys Ile Ile Val Leu Gly Phe Asn Tyr
            20                  25                  30

```
Trp Ile Ala Gly Thr Gly Ser Gly Glu Phe Ile Lys Lys Ala Phe His
         35                  40                  45

Lys Leu Ala Met Lys Tyr Asp Ile Gly Gly Gly Ser Gly Gly Gly
     50                  55                  60

Gly Ser Gly Gly Gly Ser Ala Ala Ala Gly Thr Pro Lys Thr Ser
 65              70                  75                  80

Trp Arg Arg Val Ser Val Gly Glu Asp Val Ser Leu Leu Pro Ala Pro
                 85                  90                  95

Gly Pro Thr Gly Arg Gly Pro Thr Gln Lys Leu Leu Trp Ala Val Glu
             100                 105                 110

Pro Leu Asp Gly Cys Gly Pro Leu His Pro Ser Trp Val Ser Leu Met
         115                 120                 125

Pro Pro Lys Gln Val Pro Glu Thr Val Val Asp Ala Ala Cys Met Arg
     130                 135                 140

Ala Pro Val Pro Leu Ala Met Ala Tyr Ala Pro Pro Ala Pro Ser Ala
145                 150                 155                 160

Thr Gly Gly Leu Arg Thr Asp Phe Val Trp Gln Glu Arg Ala Ala Val
                 165                 170                 175

Val Asn Arg Ser Leu Val Ile His Gly Val Arg Glu Thr Asp Ser Gly
             180                 185                 190

Leu Tyr Thr Leu Ser Val Gly Asp Ile Lys Asp Pro Ala Arg Gln Val
         195                 200                 205

Ala Ser Val Val Leu Val Val Gln Pro Ala Pro Val Pro Thr Pro Pro
210                 215                 220

Pro Thr Pro Ala Asp Tyr Asp Glu Asp Asp Asn Asp Glu Gly Glu Asp
225                 230                 235                 240

Glu Ser Leu Ala Gly Thr Pro Ala Ser Gly Thr Pro Arg Leu Pro Pro
                 245                 250                 255

Pro Pro Ala Pro Pro Arg Ser Trp Pro Ser Ala Pro Glu Val Ser His
             260                 265                 270

Val Arg Gly Val Thr Val Arg Met Glu Thr Pro Glu Ala Ile Leu Phe
         275                 280                 285

Ser Pro Gly Glu Thr Phe Ser Thr Asn Val Ser Ile His Ala Ile Ala
     290                 295                 300

His Asp Asp Gln Thr Tyr Ser Met Asp Val Val Trp Leu Arg Phe Asp
305                 310                 315                 320

Val Pro Thr Ser Cys Ala Glu Met Arg Ile Tyr Glu Ser Cys Leu Tyr
                 325                 330                 335

His Pro Gln Leu Pro Glu Cys Leu Ser Pro Ala Asp Ala Pro Cys Ala
             340                 345                 350

Ala Ser Thr Trp Thr Ser Arg Leu Ala Val Arg Ser Tyr Ala Gly Cys
         355                 360                 365

Ser Arg Thr Asn Pro Pro Arg Cys Ser Ala Glu Ala His Met Glu
     370                 375                 380

Pro Val Pro Gly Leu Ala Trp Gln Ala Ala Ser Val Asn Leu Glu Phe
385                 390                 395                 400

Arg Asp Ala Ser Pro Gln His Ser Gly Leu Tyr Leu Cys Val Val Tyr
                 405                 410                 415

Val Asn Asp His Ile His Ala Trp Gly His Ile Thr Ile Ser Thr Ala
             420                 425                 430

Ala Gln Tyr Arg Asn Ala Val Val Glu Gln Pro Leu Pro Gln Arg Gly
         435                 440                 445
```

```
            Ala Asp Leu Ala Glu Leu Glu Gly Asp Tyr Lys Asp Asp Asp Lys
                450                 455                 460

<210> SEQ ID NO 172
<211> LENGTH: 458
<212> TYPE: PRT
<213> ORGANISM: Artificial Sequence
<220> FEATURE:
<223> OTHER INFORMATION: TMR(LIMP2')-PEEP-gE

<400> SEQUENCE: 172

Met Gly Arg Cys Cys Phe Tyr Thr Ala Gly Thr Leu Ser Leu Leu
1               5                   10                  15

Leu Val Thr Ser Val Thr Leu Leu Val Ala Arg Val Phe Gly Thr Gly
                20                  25                  30

Ser Gly Glu Phe Ile Lys Lys Ala Phe His Lys Leu Ala Met Lys Tyr
                35                  40                  45

Asp Ile Gly Gly Gly Ser Gly Gly Gly Ser Gly Gly Gly
    50                  55                  60

Ser Ala Ala Ala Gly Thr Pro Lys Thr Ser Trp Arg Arg Val Ser Val
65                  70                  75                  80

Gly Glu Asp Val Ser Leu Leu Pro Ala Pro Gly Pro Thr Gly Arg Gly
                    85                  90                  95

Pro Thr Gln Lys Leu Leu Trp Ala Val Glu Pro Leu Asp Gly Cys Gly
                100                 105                 110

Pro Leu His Pro Ser Trp Val Ser Leu Met Pro Pro Lys Gln Val Pro
            115                 120                 125

Glu Thr Val Val Asp Ala Ala Cys Met Arg Ala Pro Val Pro Leu Ala
            130                 135                 140

Met Ala Tyr Ala Pro Pro Ala Pro Ser Ala Thr Gly Gly Leu Arg Thr
145                 150                 155                 160

Asp Phe Val Trp Gln Glu Arg Ala Ala Val Val Asn Arg Ser Leu Val
                    165                 170                 175

Ile His Gly Val Arg Glu Thr Asp Ser Gly Leu Tyr Thr Leu Ser Val
                180                 185                 190

Gly Asp Ile Lys Asp Pro Ala Arg Gln Val Ala Ser Val Val Leu Val
            195                 200                 205

Val Gln Pro Ala Pro Val Pro Thr Pro Pro Pro Thr Pro Ala Asp Tyr
210                 215                 220

Asp Glu Asp Asp Asn Asp Glu Gly Glu Asp Glu Ser Leu Ala Gly Thr
225                 230                 235                 240

Pro Ala Ser Gly Thr Pro Arg Leu Pro Pro Pro Ala Pro Pro Arg
                    245                 250                 255

Ser Trp Pro Ser Ala Pro Glu Val Ser His Val Arg Gly Val Thr Val
                260                 265                 270

Arg Met Glu Thr Pro Glu Ala Ile Leu Phe Ser Pro Gly Glu Thr Phe
            275                 280                 285

Ser Thr Asn Val Ser Ile His Ala Ile Ala His Asp Asp Gln Thr Tyr
            290                 295                 300

Ser Met Asp Val Val Trp Leu Arg Phe Asp Val Pro Thr Ser Cys Ala
305                 310                 315                 320

Glu Met Arg Ile Tyr Glu Ser Cys Leu Tyr His Pro Gln Leu Pro Glu
                325                 330                 335

Cys Leu Ser Pro Ala Asp Ala Pro Cys Ala Ala Ser Thr Trp Thr Ser
            340                 345                 350
```

```
Arg Leu Ala Val Arg Ser Tyr Ala Gly Cys Ser Arg Thr Asn Pro Pro
            355                 360                 365

Pro Arg Cys Ser Ala Glu Ala His Met Glu Pro Val Pro Gly Leu Ala
    370                 375                 380

Trp Gln Ala Ala Ser Val Asn Leu Glu Phe Arg Asp Ala Ser Pro Gln
385                 390                 395                 400

His Ser Gly Leu Tyr Leu Cys Val Val Tyr Val Asn Asp His Ile His
                405                 410                 415

Ala Trp Gly His Ile Thr Ile Ser Thr Ala Ala Gln Tyr Arg Asn Ala
            420                 425                 430

Val Val Glu Gln Pro Leu Pro Gln Arg Gly Ala Asp Leu Ala Glu Leu
            435                 440                 445

Glu Gly Asp Tyr Lys Asp Asp Asp Lys
            450                 455

<210> SEQ ID NO 173
<211> LENGTH: 508
<212> TYPE: PRT
<213> ORGANISM: Artificial Sequence
<220> FEATURE:
<223> OTHER INFORMATION: TMR(LIMP')-PEEP-gE-TMR(LIMP')

<400> SEQUENCE: 173

Met Gly Arg Cys Cys Phe Tyr Thr Ala Gly Thr Leu Ser Leu Leu Leu
1               5                   10                  15

Leu Val Thr Ser Val Thr Leu Leu Val Ala Arg Val Phe Gly Thr Gly
            20                  25                  30

Ser Gly Glu Phe Ile Lys Lys Ala Phe His Lys Leu Ala Met Lys Tyr
        35                  40                  45

Asp Ile Gly Gly Gly Ser Gly Gly Gly Ser Gly Gly Gly Gly
    50                  55                  60

Ser Ala Ala Gly Thr Pro Lys Thr Ser Trp Arg Arg Val Ser Val
65                  70                  75                  80

Gly Glu Asp Val Ser Leu Leu Pro Ala Pro Gly Pro Thr Arg Gly
                85                  90                  95

Pro Thr Gln Lys Leu Leu Trp Ala Val Glu Pro Leu Asp Gly Cys Gly
            100                 105                 110

Pro Leu His Pro Ser Trp Val Ser Leu Met Pro Pro Lys Gln Val Pro
        115                 120                 125

Glu Thr Val Val Asp Ala Ala Cys Met Arg Ala Pro Val Pro Leu Ala
    130                 135                 140

Met Ala Tyr Ala Pro Pro Ala Pro Ser Ala Thr Gly Gly Leu Arg Thr
145                 150                 155                 160

Asp Phe Val Trp Gln Glu Arg Ala Ala Val Val Asn Arg Ser Leu Val
                165                 170                 175

Ile His Gly Val Arg Glu Thr Asp Ser Gly Leu Tyr Thr Leu Ser Val
            180                 185                 190

Gly Asp Ile Lys Asp Pro Ala Arg Gln Val Ala Ser Val Val Leu Val
        195                 200                 205

Val Gln Pro Ala Pro Val Pro Thr Pro Pro Thr Pro Ala Asp Tyr
    210                 215                 220

Asp Glu Asp Asp Asn Asp Glu Gly Glu Asp Glu Ser Leu Ala Gly Thr
225                 230                 235                 240

Pro Ala Ser Gly Thr Pro Arg Leu Pro Pro Pro Pro Ala Pro Pro Arg
                245                 250                 255
```

Ser Trp Pro Ser Ala Pro Glu Val Ser His Val Arg Gly Val Thr Val
            260                 265                 270

Arg Met Glu Thr Pro Glu Ala Ile Leu Phe Ser Pro Gly Glu Thr Phe
        275                 280                 285

Ser Thr Asn Val Ser Ile His Ala Ile Ala His Asp Asp Gln Thr Tyr
    290                 295                 300

Ser Met Asp Val Val Trp Leu Arg Phe Asp Val Pro Thr Ser Cys Ala
305                 310                 315                 320

Glu Met Arg Ile Tyr Glu Ser Cys Leu Tyr His Pro Gln Leu Pro Glu
                325                 330                 335

Cys Leu Ser Pro Ala Asp Ala Pro Cys Ala Ala Ser Thr Trp Thr Ser
            340                 345                 350

Arg Leu Ala Val Arg Ser Tyr Ala Gly Cys Ser Arg Thr Asn Pro Pro
        355                 360                 365

Pro Arg Cys Ser Ala Glu Ala His Met Glu Pro Val Pro Gly Leu Ala
    370                 375                 380

Trp Gln Ala Ala Ser Val Asn Leu Glu Phe Arg Asp Ala Ser Pro Gln
385                 390                 395                 400

His Ser Gly Leu Tyr Leu Cys Val Val Tyr Val Asn Asp His Ile His
                405                 410                 415

Ala Trp Gly His Ile Thr Ile Ser Thr Ala Ala Gln Tyr Arg Asn Ala
            420                 425                 430

Val Val Glu Gln Pro Leu Pro Gln Arg Gly Ala Asp Leu Ala Glu Leu
        435                 440                 445

Glu Gly Asp Tyr Lys Asp Asp Asp Lys Gly Ser Arg Thr Leu Ile
    450                 455                 460

Ile Thr Asn Ile Pro Tyr Ile Ile Met Ala Leu Gly Val Phe Phe Gly
465                 470                 475                 480

Leu Val Phe Thr Trp Leu Ala Cys Lys Gly Gln Gly Ser Met Asp Glu
                485                 490                 495

Gly Thr Ala Asp Glu Arg Ala Pro Leu Ile Arg Thr
            500                 505

<210> SEQ ID NO 174
<211> LENGTH: 536
<212> TYPE: PRT
<213> ORGANISM: Artificial Sequence
<220> FEATURE:
<223> OTHER INFORMATION: PEEP-gE-TMR(KK motif)

<400> SEQUENCE: 174

Met Ala Leu Trp Met Arg Leu Leu Pro Leu Leu Ala Leu Leu Ala Leu
1               5                   10                  15

Trp Gly Pro Asp Pro Ala Ala Ala Gly Thr Gly Ser Gly Glu Phe Ile
            20                  25                  30

Lys Lys Ala Phe His Lys Leu Ala Met Lys Tyr Asp Ile Gly Gly Gly
        35                  40                  45

Gly Ser Gly Gly Gly Gly Ser Gly Gly Gly Gly Ser Ala Ala Ala Gly
    50                  55                  60

Thr Pro Lys Thr Ser Trp Arg Arg Val Ser Val Gly Glu Asp Val Ser
65                  70                  75                  80

Leu Leu Pro Ala Pro Gly Pro Thr Gly Arg Gly Pro Thr Gln Lys Leu
                85                  90                  95

Leu Trp Ala Val Glu Pro Leu Asp Gly Cys Gly Pro Leu His Pro Ser
            100                 105                 110

```
Trp Val Ser Leu Met Pro Pro Lys Gln Val Pro Glu Thr Val Val Asp
            115                 120                 125

Ala Ala Cys Met Arg Ala Pro Val Pro Leu Ala Met Ala Tyr Ala Pro
    130                 135                 140

Pro Ala Pro Ser Ala Thr Gly Gly Leu Arg Thr Asp Phe Val Trp Gln
145                 150                 155                 160

Glu Arg Ala Ala Val Val Asn Arg Ser Leu Val Ile His Gly Val Arg
                165                 170                 175

Glu Thr Asp Ser Gly Leu Tyr Thr Leu Ser Val Gly Asp Ile Lys Asp
            180                 185                 190

Pro Ala Arg Gln Val Ala Ser Val Val Leu Val Val Gln Pro Ala Pro
    195                 200                 205

Val Pro Thr Pro Pro Thr Pro Ala Asp Tyr Asp Glu Asp Asp Asn
210                 215                 220

Asp Glu Gly Glu Asp Glu Ser Leu Ala Gly Thr Pro Ala Ser Gly Thr
225                 230                 235                 240

Pro Arg Leu Pro Pro Pro Ala Pro Arg Ser Trp Pro Ser Ala
                245                 250                 255

Pro Glu Val Ser His Val Arg Gly Val Thr Val Arg Met Glu Thr Pro
                260                 265                 270

Glu Ala Ile Leu Phe Ser Pro Gly Glu Thr Phe Ser Thr Asn Val Ser
        275                 280                 285

Ile His Ala Ile Ala His Asp Gln Thr Tyr Ser Met Asp Val Val
    290                 295                 300

Trp Leu Arg Phe Asp Val Pro Thr Ser Cys Ala Glu Met Arg Ile Tyr
305                 310                 315                 320

Glu Ser Cys Leu Tyr His Pro Gln Leu Pro Glu Cys Leu Ser Pro Ala
                325                 330                 335

Asp Ala Pro Cys Ala Ala Ser Thr Trp Thr Ser Arg Leu Ala Val Arg
                340                 345                 350

Ser Tyr Ala Gly Cys Ser Arg Thr Asn Pro Pro Arg Cys Ser Ala
    355                 360                 365

Glu Ala His Met Glu Pro Val Pro Gly Leu Ala Trp Gln Ala Ala Ser
    370                 375                 380

Val Asn Leu Glu Phe Arg Asp Ala Ser Pro Gln His Ser Gly Leu Tyr
385                 390                 395                 400

Leu Cys Val Val Tyr Val Asn Asp His Ile His Ala Trp Gly His Ile
                405                 410                 415

Thr Ile Ser Thr Ala Ala Gln Tyr Arg Asn Ala Val Val Glu Gln Pro
            420                 425                 430

Leu Pro Gln Arg Gly Ala Asp Leu Ala Glu Leu Glu Gly Asp Tyr Lys
        435                 440                 445

Asp Asp Asp Asp Lys Gly Ser Arg Asp Asp Glu Ser Leu Phe Phe Gly
450                 455                 460

Asp Thr Gly Leu Ser Lys Asn Pro Ile Glu Leu Val Glu Gly Trp Phe
465                 470                 475                 480

Ser Ser Trp Lys Ser Ser Ile Ala Ser Phe Phe Ile Ile Gly Leu
                485                 490                 495

Ile Ile Gly Leu Phe Leu Val Leu Arg Val Gly Ile His Leu Cys Ile
            500                 505                 510

Lys Leu Lys His Thr Lys Lys Arg Gln Ile Tyr Thr Asp Ile Glu Met
        515                 520                 525

Asn Arg Leu Gly Lys Lys Thr Cys
```

```
                530                 535

<210> SEQ ID NO 175
<211> LENGTH: 13
<212> TYPE: PRT
<213> ORGANISM: Artificial Sequence
<220> FEATURE:
<223> OTHER INFORMATION: Linker (Table 7)

<400> SEQUENCE: 175

Gly Thr Gly Ser Glu Phe Asp Ile Ala Ala Ala Leu Glu
1               5                   10

<210> SEQ ID NO 176
<211> LENGTH: 7
<212> TYPE: PRT
<213> ORGANISM: Artificial Sequence
<220> FEATURE:
<223> OTHER INFORMATION: Linker (Table 18)

<400> SEQUENCE: 176

Gly Thr Gly Ser Gly Glu Phe
1               5

<210> SEQ ID NO 177
<211> LENGTH: 6
<212> TYPE: PRT
<213> ORGANISM: Artificial Sequence
<220> FEATURE:
<223> OTHER INFORMATION: hexaHis tag

<400> SEQUENCE: 177

His His His His His His
1               5

<210> SEQ ID NO 178
<211> LENGTH: 20
<212> TYPE: PRT
<213> ORGANISM: Artificial Sequence
<220> FEATURE:
<223> OTHER INFORMATION: linker

<400> SEQUENCE: 178

Asp Ile Gly Gly Gly Gly Ser Gly Gly Gly Gly Ser Gly Gly Gly Gly
1               5                   10                  15

Ser Ala Ala Ala
            20

<210> SEQ ID NO 179
<211> LENGTH: 20
<212> TYPE: PRT
<213> ORGANISM: Artificial Sequence
<220> FEATURE:
<223> OTHER INFORMATION: (G4S)4 linker

<400> SEQUENCE: 179

Gly Gly Gly Gly Ser Gly Gly Gly Gly Ser Gly Gly Gly Gly Ser Gly
1               5                   10                  15

Gly Gly Gly Ser
            20

<210> SEQ ID NO 180
<211> LENGTH: 10
<212> TYPE: PRT
<213> ORGANISM: Artificial Sequence
<220> FEATURE:
```

```
<223> OTHER INFORMATION: Suitable linkers

<400> SEQUENCE: 180

Gly Gly Gly Gly Ser Gly Gly Gly Gly Ser
1               5                   10

<210> SEQ ID NO 181
<211> LENGTH: 5
<212> TYPE: PRT
<213> ORGANISM: Artificial Sequence
<220> FEATURE:
<223> OTHER INFORMATION: Suitable linkers

<400> SEQUENCE: 181

Gly Gly Gly Gly Ser
1               5

<210> SEQ ID NO 182
<211> LENGTH: 482
<212> TYPE: PRT
<213> ORGANISM: Artificial Sequence
<220> FEATURE:
<223> OTHER INFORMATION: Flag-tagged TPB(gE)-TMR(VSGV) fusion protein

<400> SEQUENCE: 182

Met Ala Leu Trp Met Arg Leu Leu Pro Leu Ala Leu Leu Ala Leu
1               5                   10                  15

```
                260             265             270
Ser Met Asp Val Val Trp Leu Arg Phe Asp Val Pro Thr Ser Cys Ala
        275             280             285
Glu Met Arg Ile Tyr Glu Ser Cys Leu Tyr His Pro Gln Leu Pro Glu
        290             295             300
Cys Leu Ser Pro Ala Asp Ala Pro Cys Ala Ala Ser Thr Trp Thr Ser
305             310             315             320
Arg Leu Ala Val Arg Ser Tyr Ala Gly Cys Ser Arg Thr Asn Pro Pro
                325             330             335
Pro Arg Cys Ser Ala Glu Ala His Met Glu Pro Val Pro Gly Leu Ala
                340             345             350
Trp Gln Ala Ala Ser Val Asn Leu Glu Phe Arg Asp Ala Ser Pro Gln
            355             360             365
His Ser Gly Leu Tyr Leu Cys Val Val Tyr Val Asn Asp His Ile His
        370             375             380
Ala Trp Gly His Ile Thr Ile Ser Thr Ala Ala Gln Tyr Arg Asn Ala
385             390             395             400
Val Val Glu Gln Pro Leu Pro Gln Arg Gly Ala Asp Leu Ala Glu Leu
                405             410             415
Glu Gly Asp Tyr Lys Asp Asp Asp Lys Gly Ser Arg Ser Ser Trp
                420             425             430
Lys Ser Ser Ile Ala Ser Phe Phe Ile Ile Gly Leu Ile Ile Gly
            435             440             445
Leu Phe Leu Val Leu Arg Val Gly Ile His Leu Cys Ile Lys Leu Lys
        450             455             460
His Thr Lys Lys Arg Gln Ile Tyr Thr Asp Ile Glu Met Asn Arg Leu
465             470             475             480
Gly Lys

<210> SEQ ID NO 183
<211> LENGTH: 103
<212> TYPE: PRT
<213> ORGANISM: Artificial Sequence
<220> FEATURE:
<223> OTHER INFORMATION: Flag-Tagged TMR(VSVG) Polypeptide

<400> SEQUENCE: 183

Met Ala Leu Trp Met Arg Leu Leu Pro Leu Leu Ala Leu Leu Ala Leu
1               5                   10                  15
Trp Gly Pro Asp Pro Ala Ala Ala Gly Thr Gly Ser Gly Glu Phe Asp
                20                  25                  30
Ile Ala Ala Ala Leu Glu Gly Asp Tyr Lys Asp Asp Asp Asp Lys Gly
            35                  40                  45
Ser Arg Ser Ser Trp Lys Ser Ser Ile Ala Ser Phe Phe Ile Ile
        50                  55                  60
Gly Leu Ile Ile Gly Leu Phe Leu Val Leu Arg Val Gly Ile His Leu
65                  70                  75                  80
Cys Ile Lys Leu Lys His Thr Lys Lys Arg Gln Ile Tyr Thr Asp Ile
                85                  90                  95
Glu Met Asn Arg Leu Gly Lys
            100

<210> SEQ ID NO 184
<211> LENGTH: 261
<212> TYPE: PRT
<213> ORGANISM: Artificial Sequence
```

<220> FEATURE:
<223> OTHER INFORMATION: Flag-Tagged TMR(KDELR) Polypeptide

<400> SEQUENCE: 184

```
Met Ala Leu Trp Met Arg Leu Leu Pro Leu Ala Leu Leu Ala Leu
1               5                   10                  15

Trp Gly Pro Asp Pro Ala Ala Ala Gly Thr Gly Ser Gly Glu Phe Asp
                20                  25                  30

Ile Ala Ala Ala Leu Glu Gly Asp Tyr Lys Asp Asp Asp Lys Gly
            35                  40                  45

Ser Arg Asn Leu Phe Arg Phe Leu Gly Asp Leu Ser His Leu Leu Ala
    50                  55                  60

Ile Ile Leu Leu Leu Leu Lys Ile Trp Lys Ser Arg Ser Cys Ala Gly
65                  70                  75                  80

Ile Ser Gly Lys Ser Gln Val Leu Phe Ala Val Val Phe Thr Ala Arg
                85                  90                  95

Tyr Leu Asp Leu Phe Thr Asn Tyr Ile Ser Leu Tyr Asn Thr Cys Met
                100                 105                 110

Lys Val Val Tyr Ile Ala Cys Ser Phe Thr Thr Val Trp Leu Ile Tyr
            115                 120                 125

Ser Lys Phe Lys Ala Thr Tyr Asp Gly Asn His Asp Thr Phe Arg Val
    130                 135                 140

Glu Phe Leu Val Val Pro Thr Ala Ile Leu Ala Phe Leu Val Asn His
145                 150                 155                 160

Asp Phe Thr Pro Leu Glu Ile Leu Trp Thr Phe Ser Ile Tyr Leu Glu
                165                 170                 175

Ser Val Ala Ile Leu Pro Gln Leu Phe Met Val Ser Lys Thr Gly Glu
            180                 185                 190

Ala Glu Thr Ile Thr Ser His Tyr Leu Phe Ala Leu Gly Val Tyr Arg
        195                 200                 205

Thr Leu Tyr Leu Phe Asn Trp Ile Trp Arg Tyr His Phe Glu Gly Phe
    210                 215                 220

Phe Asp Leu Ile Ala Ile Val Ala Gly Leu Val Gln Thr Val Leu Tyr
225                 230                 235                 240

Cys Asp Phe Phe Tyr Leu Tyr Ile Thr Lys Val Leu Lys Gly Lys Lys
                245                 250                 255

Leu Ser Leu Pro Ala
            260
```

<210> SEQ ID NO 185
<211> LENGTH: 640
<212> TYPE: PRT
<213> ORGANISM: Artificial Sequence
<220> FEATURE:
<223> OTHER INFORMATION: Flag-Tagged TPB(gE)-TMR(KDELR)

<400> SEQUENCE: 185

```
Met Ala Leu Trp Met Arg Leu Leu Pro Leu Ala Leu Leu Ala Leu
1               5                   10                  15

Trp Gly Pro Asp Pro Ala Ala Ala Gly Thr Gly Ser Gly Glu Phe Asp
                20                  25                  30

Ile Ala Ala Ala Gly Thr Pro Lys Thr Ser Trp Arg Arg Val Ser Val
            35                  40                  45

Gly Glu Asp Val Ser Leu Leu Pro Ala Pro Gly Pro Thr Gly Arg Gly
    50                  55                  60

Pro Thr Gln Lys Leu Leu Trp Ala Val Glu Pro Leu Asp Gly Cys Gly
```

```
             65                  70                  75                  80
Pro Leu His Pro Ser Trp Val Ser Leu Met Pro Pro Lys Gln Val Pro
                    85                  90                  95
Glu Thr Val Val Asp Ala Ala Cys Met Arg Ala Pro Val Pro Leu Ala
                100                 105                 110
Met Ala Tyr Ala Pro Pro Ala Pro Ser Ala Thr Gly Gly Leu Arg Thr
            115                 120                 125
Asp Phe Val Trp Gln Glu Arg Ala Ala Val Asn Arg Ser Leu Val
        130                 135                 140
Ile His Gly Val Arg Glu Thr Asp Ser Gly Leu Tyr Thr Leu Ser Val
145                 150                 155                 160
Gly Asp Ile Lys Asp Pro Ala Arg Gln Val Ala Ser Val Leu Val
                165                 170                 175
Val Gln Pro Ala Pro Val Pro Thr Pro Pro Thr Pro Ala Asp Tyr
                180                 185                 190
Asp Glu Asp Asp Asn Asp Glu Gly Glu Asp Glu Ser Leu Ala Gly Thr
                195                 200                 205
Pro Ala Ser Gly Thr Pro Arg Leu Pro Pro Pro Ala Pro Pro Arg
            210                 215                 220
Ser Trp Pro Ser Ala Pro Glu Val Ser His Val Arg Gly Val Thr Val
225                 230                 235                 240
Arg Met Glu Thr Pro Glu Ala Ile Leu Phe Ser Pro Gly Glu Thr Phe
                245                 250                 255
Ser Thr Asn Val Ser Ile His Ala Ile Ala His Asp Asp Gln Thr Tyr
                260                 265                 270
Ser Met Asp Val Val Trp Leu Arg Phe Asp Val Pro Thr Ser Cys Ala
            275                 280                 285
Glu Met Arg Ile Tyr Glu Ser Cys Leu Tyr His Pro Gln Leu Pro Glu
            290                 295                 300
Cys Leu Ser Pro Ala Asp Ala Pro Cys Ala Ala Ser Thr Trp Thr Ser
305                 310                 315                 320
Arg Leu Ala Val Arg Ser Tyr Ala Gly Cys Ser Arg Thr Asn Pro Pro
                325                 330                 335
Pro Arg Cys Ser Ala Glu Ala His Met Glu Pro Val Pro Gly Leu Ala
                340                 345                 350
Trp Gln Ala Ala Ser Val Asn Leu Glu Phe Arg Asp Ala Ser Pro Gln
            355                 360                 365
His Ser Gly Leu Tyr Leu Cys Val Val Tyr Val Asn Asp His Ile His
        370                 375                 380
Ala Trp Gly His Ile Thr Ile Ser Thr Ala Ala Gln Tyr Arg Asn Ala
385                 390                 395                 400
Val Val Glu Gln Pro Leu Pro Gln Arg Gly Ala Asp Leu Ala Glu Leu
                405                 410                 415
Glu Gly Asp Tyr Lys Asp Asp Asp Lys Gly Ser Arg Asn Leu Phe
            420                 425                 430
Arg Phe Leu Gly Asp Leu Ser His Leu Leu Ala Ile Ile Leu Leu Leu
        435                 440                 445
Leu Lys Ile Trp Lys Ser Arg Ser Cys Ala Gly Ile Ser Gly Lys Ser
        450                 455                 460
Gln Val Leu Phe Ala Val Val Phe Thr Ala Arg Tyr Leu Asp Leu Phe
465                 470                 475                 480
Thr Asn Tyr Ile Ser Leu Tyr Asn Thr Cys Met Lys Val Val Tyr Ile
                485                 490                 495
```

```
Ala Cys Ser Phe Thr Thr Val Trp Leu Ile Tyr Ser Lys Phe Lys Ala
            500                 505                 510

Thr Tyr Asp Gly Asn His Asp Thr Phe Arg Val Glu Phe Leu Val Val
            515                 520                 525

Pro Thr Ala Ile Leu Ala Phe Leu Val Asn His Asp Phe Thr Pro Leu
            530                 535                 540

Glu Ile Leu Trp Thr Phe Ser Ile Tyr Leu Glu Ser Val Ala Ile Leu
545                 550                 555                 560

Pro Gln Leu Phe Met Val Ser Lys Thr Gly Glu Ala Glu Thr Ile Thr
            565                 570                 575

Ser His Tyr Leu Phe Ala Leu Gly Val Tyr Arg Thr Leu Tyr Leu Phe
            580                 585                 590

Asn Trp Ile Trp Arg Tyr His Phe Glu Gly Phe Phe Asp Leu Ile Ala
            595                 600                 605

Ile Val Ala Gly Leu Val Gln Thr Val Leu Tyr Cys Asp Phe Phe Tyr
            610                 615                 620

Leu Tyr Ile Thr Lys Val Leu Lys Gly Lys Lys Leu Ser Leu Pro Ala
625                 630                 635                 640

<210> SEQ ID NO 186
<211> LENGTH: 471
<212> TYPE: PRT
<213> ORGANISM: Artificial Sequence
<220> FEATURE:
<223> OTHER INFORMATION: V5-tagged TNFR1TF-Fc Target Protein Monomer

<400> SEQUENCE: 186

Met Gly Leu Ser Thr Val Pro Asp Leu Leu Leu Pro Leu Val Leu Leu
1               5                   10                  15

Glu Leu Leu Val Gly Ile Tyr Pro Ser Gly Val Ile Gly Leu Val Pro
            20                  25                  30

His Leu Gly Asp Arg Glu Lys Arg Asp Ser Val Cys Pro Gln Gly Lys
        35                  40                  45

Tyr Ile His Pro Gln Asn Asn Ser Ile Cys Cys Thr Lys Cys His Lys
    50                  55                  60

Gly Thr Tyr Leu Tyr Asn Asp Cys Pro Gly Pro Gly Gln Asp Thr Asp
65                  70                  75                  80

Cys Arg Glu Cys Glu Ser Gly Ser Phe Thr Ala Ser Glu Asn His Leu
                85                  90                  95

Arg His Cys Leu Ser Cys Ser Lys Cys Arg Lys Glu Met Gly Gln Val
            100                 105                 110

Glu Ile Ser Ser Cys Thr Val Asp Arg Asp Thr Val Cys Gly Cys Arg
        115                 120                 125

Lys Asn Gln Tyr Arg His Tyr Trp Ser Glu Asn Leu Phe Gln Cys Phe
    130                 135                 140

Asn Cys Ser Leu Cys Leu Asn Gly Thr Val His Leu Ser Cys Gln Glu
145                 150                 155                 160

Lys Gln Asn Thr Val Cys Thr Cys His Ala Gly Phe Phe Leu Arg Glu
                165                 170                 175

Asn Glu Cys Val Ser Cys Ser Asn Cys Lys Lys Ser Leu Glu Cys Thr
            180                 185                 190

Lys Leu Cys Leu Pro Gln Ile Glu Asn Val Lys Gly Thr Glu Asp Ser
        195                 200                 205

Gly Thr Thr Gly Thr Gly Ser Glu Phe Asp Ile Ala Ala Ala Leu Glu
    210                 215                 220
```

Gly Lys Pro Ile Pro Asn Pro Leu Leu Gly Leu Asp Ser Thr Ser Arg
225                 230                 235                 240

Pro Lys Ser Cys Asp Lys Thr His Thr Cys Pro Pro Cys Pro Ala Pro
            245                 250                 255

Glu Leu Leu Gly Gly Pro Ser Val Phe Leu Phe Pro Pro Lys Pro Lys
        260                 265                 270

Asp Thr Leu Met Ile Ser Arg Thr Pro Glu Val Thr Cys Val Val Val
    275                 280                 285

Asp Val Ser His Glu Asp Pro Glu Val Lys Phe Asn Trp Tyr Val Asp
290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Asp Glu Leu Thr Lys
370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
    450                 455                 460

Leu Ser Leu Ser Pro Gly Lys
465                 470

<210> SEQ ID NO 187
<211> LENGTH: 715
<212> TYPE: PRT
<213> ORGANISM: Artificial Sequence
<220> FEATURE:
<223> OTHER INFORMATION: V5-tagged FVII-Fc target protein monomer

<400> SEQUENCE: 187

Met Val Ser Gln Ala Leu Arg Leu Leu Cys Leu Leu Leu Gly Leu Gln
1               5                   10                  15

Gly Cys Leu Ala Ala Gly Gly Val Ala Lys Ala Ser Gly Gly Glu Thr
            20                  25                  30

Arg Asp Met Pro Trp Lys Pro Gly Pro His Arg Val Phe Val Thr Gln
        35                  40                  45

Glu Glu Ala His Gly Val Leu His Arg Arg Arg Arg Ala Asn Ala Phe
    50                  55                  60

Leu Glu Glu Leu Arg Pro Gly Ser Leu Glu Arg Glu Cys Lys Glu Glu
65                  70                  75                  80

Gln Cys Ser Phe Glu Glu Ala Arg Glu Ile Phe Lys Asp Ala Glu Arg
                85                  90                  95

Thr Lys Leu Phe Trp Ile Ser Tyr Ser Asp Gly Asp Gln Cys Ala Ser
            100                 105                 110

-continued

```
Ser Pro Cys Gln Asn Gly Gly Ser Cys Lys Asp Gln Leu Gln Ser Tyr
        115                 120                 125
Ile Cys Phe Cys Leu Pro Ala Phe Glu Gly Arg Asn Cys Glu Thr His
    130                 135                 140
Lys Asp Asp Gln Leu Ile Cys Val Asn Glu Asn Gly Gly Cys Glu Gln
145                 150                 155                 160
Tyr Cys Ser Asp His Thr Gly Thr Lys Arg Ser Cys Arg Cys His Glu
            165                 170                 175
Gly Tyr Ser Leu Leu Ala Asp Gly Val Ser Cys Thr Pro Thr Val Glu
        180                 185                 190
Tyr Pro Cys Gly Lys Ile Pro Ile Leu Glu Lys Arg Asn Ala Ser Lys
        195                 200                 205
Pro Gln Gly Arg Ile Val Gly Gly Lys Val Cys Pro Lys Gly Glu Cys
    210                 215                 220
Pro Trp Gln Val Leu Leu Leu Val Asn Gly Ala Gln Leu Cys Gly Gly
225                 230                 235                 240
Thr Leu Ile Asn Thr Ile Trp Val Val Ser Ala Ala His Cys Phe Asp
            245                 250                 255
Lys Ile Lys Asn Trp Arg Asn Leu Ile Ala Val Leu Gly Glu His Asp
        260                 265                 270
Leu Ser Glu His Asp Gly Asp Glu Gln Ser Arg Arg Val Ala Gln Val
    275                 280                 285
Ile Ile Pro Ser Thr Tyr Val Pro Gly Thr Thr Asn His Asp Ile Ala
        290                 295                 300
Leu Leu Arg Leu His Gln Pro Val Val Leu Thr Asp His Val Val Pro
305                 310                 315                 320
Leu Cys Leu Pro Glu Arg Thr Phe Ser Glu Arg Thr Leu Ala Phe Val
            325                 330                 335
Arg Phe Ser Leu Val Ser Gly Trp Gly Gln Leu Leu Asp Arg Gly Ala
        340                 345                 350
Thr Ala Leu Glu Leu Met Val Leu Asn Val Pro Arg Leu Met Thr Gln
    355                 360                 365
Asp Cys Leu Gln Gln Ser Arg Lys Val Gly Asp Ser Pro Asn Ile Thr
370                 375                 380
Glu Tyr Met Phe Cys Ala Gly Tyr Ser Asp Gly Ser Lys Asp Ser Cys
385                 390                 395                 400
Lys Gly Asp Ser Gly Gly Pro His Ala Thr His Tyr Arg Gly Thr Trp
            405                 410                 415
Tyr Leu Thr Gly Ile Val Ser Trp Gly Gln Gly Cys Ala Thr Val Gly
        420                 425                 430
His Phe Gly Val Tyr Thr Arg Val Ser Gln Tyr Ile Glu Trp Leu Gln
    435                 440                 445
Lys Leu Met Arg Ser Glu Pro Arg Pro Gly Val Leu Leu Arg Ala Pro
    450                 455                 460
Phe Pro Leu Glu Gly Lys Pro Ile Pro Asn Pro Leu Leu Gly Leu Asp
465                 470                 475                 480
Ser Thr Ser Arg Pro Lys Ser Cys Asp Lys Thr His Thr Cys Pro Pro
            485                 490                 495
Cys Pro Ala Pro Glu Leu Leu Gly Gly Pro Ser Val Phe Leu Phe Pro
        500                 505                 510
Pro Lys Pro Lys Asp Thr Leu Met Ile Ser Arg Thr Pro Glu Val Thr
    515                 520                 525
```

```
Cys Val Val Asp Val Ser His Glu Asp Pro Glu Val Lys Phe Asn
    530                 535                 540

Trp Tyr Val Asp Gly Val Glu Val His Asn Ala Lys Thr Lys Pro Arg
545                 550                 555                 560

Glu Glu Gln Tyr Asn Ser Thr Tyr Arg Val Val Ser Val Leu Thr Val
                565                 570                 575

Leu His Gln Asp Trp Leu Asn Gly Lys Glu Tyr Lys Cys Lys Val Ser
            580                 585                 590

Asn Lys Ala Leu Pro Ala Pro Ile Glu Lys Thr Ile Ser Lys Ala Lys
        595                 600                 605

Gly Gln Pro Arg Glu Pro Gln Val Tyr Thr Leu Pro Pro Ser Arg Asp
610                 615                 620

Glu Leu Thr Lys Asn Gln Val Ser Leu Thr Cys Leu Val Lys Gly Phe
625                 630                 635                 640

Tyr Pro Ser Asp Ile Ala Val Glu Trp Glu Ser Asn Gly Gln Pro Glu
                645                 650                 655

Asn Asn Tyr Lys Thr Thr Pro Pro Val Leu Asp Ser Asp Gly Ser Phe
            660                 665                 670

Phe Leu Tyr Ser Lys Leu Thr Val Asp Lys Ser Arg Trp Gln Gln Gly
        675                 680                 685

Asn Val Phe Ser Cys Ser Val Met His Glu Ala Leu His Asn His Tyr
690                 695                 700

Thr Gln Lys Ser Leu Ser Leu Ser Pro Gly Lys
705                 710                 715

<210> SEQ ID NO 188
<211> LENGTH: 710
<212> TYPE: PRT
<213> ORGANISM: Artificial Sequence
<220> FEATURE:
<223> OTHER INFORMATION: V5-tagged FIX-Fc target protein monomer

<400> SEQUENCE: 188

Met Gln Arg Val Asn Met Ile Met Ala Glu Ser Pro Gly Leu Ile Thr
1               5                   10                  15

Ile Cys Leu Leu Gly Tyr Leu Leu Ser Ala Glu Cys Thr Val Phe Leu
            20                  25                  30

Asp His Glu Asn Ala Asn Lys Ile Leu Asn Arg Pro Lys Arg Tyr Asn
        35                  40                  45

Ser Gly Lys Leu Glu Glu Phe Val Gln Gly Asn Leu Glu Arg Glu Cys
    50                  55                  60

Met Glu Glu Lys Cys Ser Phe Glu Glu Ala Arg Glu Val Phe Glu Asn
65                  70                  75                  80

Thr Glu Arg Thr Thr Glu Phe Trp Lys Gln Tyr Val Asp Gly Asp Gln
                85                  90                  95

Cys Glu Ser Asn Pro Cys Leu Asn Gly Gly Ser Cys Lys Asp Asp Ile
            100                 105                 110

Asn Ser Tyr Glu Cys Trp Cys Pro Phe Gly Phe Glu Gly Lys Asn Cys
        115                 120                 125

Glu Leu Asp Val Thr Cys Asn Ile Lys Asn Gly Arg Cys Glu Gln Phe
    130                 135                 140

Cys Lys Asn Ser Ala Asp Asn Lys Val Val Cys Ser Cys Thr Glu Gly
145                 150                 155                 160

Tyr Arg Leu Ala Glu Asn Gln Lys Ser Cys Glu Pro Ala Val Pro Phe
                165                 170                 175
```

-continued

Pro Cys Gly Arg Val Ser Val Ser Gln Thr Ser Lys Leu Thr Arg Ala
                180                 185                 190

Glu Thr Val Phe Pro Asp Val Asp Tyr Val Asn Ser Thr Glu Ala Glu
            195                 200                 205

Thr Ile Leu Asp Asn Ile Thr Gln Ser Thr Gln Ser Phe Asn Asp Phe
        210                 215                 220

Thr Arg Val Val Gly Gly Glu Asp Ala Lys Pro Gly Gln Phe Pro Trp
225                 230                 235                 240

Gln Val Val Leu Asn Gly Lys Val Asp Ala Phe Cys Gly Gly Ser Ile
                245                 250                 255

Val Asn Glu Lys Trp Ile Val Thr Ala Ala His Cys Val Glu Thr Gly
            260                 265                 270

Val Lys Ile Thr Val Val Ala Gly Glu His Asn Ile Glu Glu Thr Glu
        275                 280                 285

His Thr Glu Gln Lys Arg Asn Val Ile Arg Ile Ile Pro His His Asn
    290                 295                 300

Tyr Asn Ala Ala Ile Asn Lys Tyr Asn His Asp Ile Ala Leu Leu Glu
305                 310                 315                 320

Leu Asp Glu Pro Leu Val Leu Asn Ser Tyr Val Thr Pro Ile Cys Ile
                325                 330                 335

Ala Asp Lys Glu Tyr Thr Asn Ile Phe Leu Lys Phe Gly Ser Gly Tyr
            340                 345                 350

Val Ser Gly Trp Gly Arg Val Phe His Lys Gly Arg Ser Ala Leu Val
        355                 360                 365

Leu Gln Tyr Leu Arg Val Pro Leu Val Asp Arg Ala Thr Cys Leu Arg
    370                 375                 380

Ser Thr Lys Phe Thr Ile Tyr Asn Asn Met Phe Cys Ala Gly Phe His
385                 390                 395                 400

Glu Gly Gly Arg Asp Ser Cys Gln Gly Asp Ser Gly Gly Pro His Val
                405                 410                 415

Thr Glu Val Glu Gly Thr Ser Phe Leu Thr Gly Ile Ile Ser Trp Gly
            420                 425                 430

Glu Glu Cys Ala Met Lys Gly Lys Tyr Gly Ile Tyr Thr Lys Val Ser
        435                 440                 445

Arg Tyr Val Asn Trp Ile Lys Glu Lys Thr Lys Leu Thr Leu Glu Gly
    450                 455                 460

Lys Pro Ile Pro Asn Pro Leu Leu Gly Leu Asp Ser Thr Ser Arg Pro
465                 470                 475                 480

Lys Ser Cys Asp Lys Thr His Thr Cys Pro Pro Cys Pro Ala Pro Glu
                485                 490                 495

Leu Leu Gly Gly Pro Ser Val Phe Leu Phe Pro Pro Lys Pro Lys Asp
            500                 505                 510

Thr Leu Met Ile Ser Arg Thr Pro Glu Val Thr Cys Val Val Val Asp
        515                 520                 525

Val Ser His Glu Asp Pro Glu Val Lys Phe Asn Trp Tyr Val Asp Gly
    530                 535                 540

Val Glu Val His Asn Ala Lys Thr Lys Pro Arg Glu Glu Gln Tyr Asn
545                 550                 555                 560

Ser Thr Tyr Arg Val Val Ser Val Leu Thr Val Leu His Gln Asp Trp
                565                 570                 575

Leu Asn Gly Lys Glu Tyr Lys Cys Lys Val Ser Asn Lys Ala Leu Pro
            580                 585                 590

Ala Pro Ile Glu Lys Thr Ile Ser Lys Ala Lys Gly Gln Pro Arg Glu

```
                595                 600                 605
Pro Gln Val Tyr Thr Leu Pro Pro Ser Arg Asp Glu Leu Thr Lys Asn
610                 615                 620

Gln Val Ser Leu Thr Cys Leu Val Lys Gly Phe Tyr Pro Ser Asp Ile
625                 630                 635                 640

Ala Val Glu Trp Glu Ser Asn Gly Gln Pro Glu Asn Asn Tyr Lys Thr
                645                 650                 655

Thr Pro Pro Val Leu Asp Ser Asp Gly Ser Phe Phe Leu Tyr Ser Lys
                660                 665                 670

Leu Thr Val Asp Lys Ser Arg Trp Gln Gln Gly Asn Val Phe Ser Cys
                675                 680                 685

Ser Val Met His Glu Ala Leu His Asn His Tyr Thr Gln Lys Ser Leu
690                 695                 700

Ser Leu Ser Pro Gly Lys
705                 710

<210> SEQ ID NO 189
<211> LENGTH: 2600
<212> TYPE: PRT
<213> ORGANISM: Artificial Sequence
<220> FEATURE:
<223> OTHER INFORMATION: V5-Tagged FVIII-Fc Target Protein Monomer

<400> SEQUENCE: 189

Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
                20                  25                  30

Trp Asp Tyr Met Gln Ser Asp Leu Gly Glu Leu Pro Val Asp Ala Arg
            35                  40                  45

Phe Pro Pro Arg Val Pro Lys Ser Phe Pro Phe Asn Thr Ser Val Val
50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
                100                 105                 110

His Pro Val Ser Leu His Ala Val Gly Val Ser Tyr Trp Lys Ala Ser
            115                 120                 125

Glu Gly Ala Glu Tyr Asp Asp Gln Thr Ser Gln Arg Glu Lys Glu Asp
        130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
```

```
                    245                 250                 255
        Val Asn Arg Ser Leu Pro Gly Leu Ile Gly Cys His Arg Lys Ser Val
                        260                 265                 270

Tyr Trp His Val Ile Gly Met Gly Thr Thr Pro Glu Val His Ser Ile
                        275                 280                 285

Phe Leu Glu Gly His Thr Phe Leu Val Arg Asn His Arg Gln Ala Ser
                        290                 295                 300

Leu Glu Ile Ser Pro Ile Thr Phe Leu Thr Ala Gln Thr Leu Leu Met
        305                 310                 315                 320

Asp Leu Gly Gln Phe Leu Leu Phe Cys His Ile Ser Ser His Gln His
                        325                 330                 335

Asp Gly Met Glu Ala Tyr Val Lys Val Asp Ser Cys Pro Glu Glu Pro
                        340                 345                 350

Gln Leu Arg Met Lys Asn Asn Glu Glu Ala Glu Asp Tyr Asp Asp Asp
                        355                 360                 365

Leu Thr Asp Ser Glu Met Asp Val Val Arg Phe Asp Asp Asn Ser
        370                 375                 380

Pro Ser Phe Ile Gln Ile Arg Ser Val Ala Lys Lys His Pro Lys Thr
        385                 390                 395                 400

Trp Val His Tyr Ile Ala Ala Glu Glu Glu Asp Trp Asp Tyr Ala Pro
                        405                 410                 415

Leu Val Leu Ala Pro Asp Asp Arg Ser Tyr Lys Ser Gln Tyr Leu Asn
                        420                 425                 430

Asn Gly Pro Gln Arg Ile Gly Arg Lys Tyr Lys Lys Val Arg Phe Met
                        435                 440                 445

Ala Tyr Thr Asp Glu Thr Phe Lys Thr Arg Glu Ala Ile Gln His Glu
                        450                 455                 460

Ser Gly Ile Leu Gly Pro Leu Leu Tyr Gly Glu Val Gly Asp Thr Leu
        465                 470                 475                 480

Leu Ile Ile Phe Lys Asn Gln Ala Ser Arg Pro Tyr Asn Ile Tyr Pro
                        485                 490                 495

His Gly Ile Thr Asp Val Arg Pro Leu Tyr Ser Arg Arg Leu Pro Lys
                        500                 505                 510

Gly Val Lys His Leu Lys Asp Phe Pro Ile Leu Pro Gly Glu Ile Phe
                        515                 520                 525

Lys Tyr Lys Trp Thr Val Thr Val Glu Asp Gly Pro Thr Lys Ser Asp
                        530                 535                 540

Pro Arg Cys Leu Thr Arg Tyr Tyr Ser Ser Phe Val Asn Met Glu Arg
        545                 550                 555                 560

Asp Leu Ala Ser Gly Leu Ile Gly Pro Leu Leu Ile Cys Tyr Lys Glu
                        565                 570                 575

Ser Val Asp Gln Arg Gly Asn Gln Ile Met Ser Asp Lys Arg Asn Val
                        580                 585                 590

Ile Leu Phe Ser Val Phe Asp Glu Asn Arg Ser Trp Tyr Leu Thr Glu
                        595                 600                 605

Asn Ile Gln Arg Phe Leu Pro Asn Pro Ala Gly Val Gln Leu Glu Asp
                        610                 615                 620

Pro Glu Phe Gln Ala Ser Asn Ile Met His Ser Ile Asn Gly Tyr Val
        625                 630                 635                 640

Phe Asp Ser Leu Gln Leu Ser Val Cys Leu His Glu Val Ala Tyr Trp
                        645                 650                 655

Tyr Ile Leu Ser Ile Gly Ala Gln Thr Asp Phe Leu Ser Val Phe Phe
                        660                 665                 670
```

-continued

Ser Gly Tyr Thr Phe Lys His Lys Met Val Tyr Glu Asp Thr Leu Thr
        675                 680                 685

Leu Phe Pro Phe Ser Gly Glu Thr Val Phe Met Ser Met Glu Asn Pro
690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
                740                 745                 750

Asn Asn Ala Ile Glu Pro Arg Ser Phe Ser Gln Asn Ser Arg His Pro
                755                 760                 765

Ser Thr Arg Gln Lys Gln Phe Asn Ala Thr Thr Ile Pro Glu Asn Asp
770                 775                 780

Ile Glu Lys Thr Asp Pro Trp Phe Ala His Arg Thr Pro Met Pro Lys
785                 790                 795                 800

Ile Gln Asn Val Ser Ser Ser Asp Leu Leu Met Leu Arg Gln Ser
                805                 810                 815

Pro Thr Pro His Gly Leu Ser Leu Ser Asp Leu Gln Glu Ala Lys Tyr
                820                 825                 830

Glu Thr Phe Ser Asp Asp Pro Ser Pro Gly Ala Ile Asp Ser Asn Asn
                835                 840                 845

Ser Leu Ser Glu Met Thr His Phe Arg Pro Gln Leu His His Ser Gly
                850                 855                 860

Asp Met Val Phe Thr Pro Glu Ser Gly Leu Gln Leu Arg Leu Asn Glu
865                 870                 875                 880

Lys Leu Gly Thr Thr Ala Ala Thr Glu Leu Lys Lys Leu Asp Phe Lys
                885                 890                 895

Val Ser Ser Thr Ser Asn Asn Leu Ile Ser Thr Ile Pro Ser Asp Asn
                900                 905                 910

Leu Ala Ala Gly Thr Asp Asn Thr Ser Ser Leu Gly Pro Pro Ser Met
                915                 920                 925

Pro Val His Tyr Asp Ser Gln Leu Asp Thr Thr Leu Phe Gly Lys Lys
                930                 935                 940

Ser Ser Pro Leu Thr Glu Ser Gly Gly Pro Leu Ser Leu Ser Glu Glu
945                 950                 955                 960

Asn Asn Asp Ser Lys Leu Leu Glu Ser Gly Leu Met Asn Ser Gln Glu
                965                 970                 975

Ser Ser Trp Gly Lys Asn Val Ser Ser Thr Glu Ser Gly Arg Leu Phe
                980                 985                 990

Lys Gly Lys Arg Ala His Gly Pro Ala Leu Leu Thr Lys Asp Asn Ala
                995                 1000                1005

Leu Phe Lys Val Ser Ile Ser Leu Leu Lys Thr Asn Lys Thr Ser
        1010                1015                1020

Asn Asn Ser Ala Thr Asn Arg Lys Thr His Ile Asp Gly Pro Ser
        1025                1030                1035

Leu Leu Ile Glu Asn Ser Pro Ser Val Trp Gln Asn Ile Leu Glu
        1040                1045                1050

Ser Asp Thr Glu Phe Lys Lys Val Thr Pro Leu Ile His Asp Arg
        1055                1060                1065

Met Leu Met Asp Lys Asn Ala Thr Ala Leu Arg Leu Asn His Met
        1070                1075                1080

-continued

```
Ser Asn Lys Thr Thr Ser Ser Lys Asn Met Glu Met Val Gln Gln
1085                1090                1095

Lys Lys Glu Gly Pro Ile Pro Pro Asp Ala Gln Asn Pro Asp Met
1100                1105                1110

Ser Phe Phe Lys Met Leu Phe Leu Pro Glu Ser Ala Arg Trp Ile
1115                1120                1125

Gln Arg Thr His Gly Lys Asn Ser Leu Asn Ser Gly Gln Gly Pro
1130                1135                1140

Ser Pro Lys Gln Leu Val Ser Leu Gly Pro Glu Lys Ser Val Glu
1145                1150                1155

Gly Gln Asn Phe Leu Ser Glu Lys Asn Lys Val Val Val Gly Lys
1160                1165                1170

Gly Glu Phe Thr Lys Asp Val Gly Leu Lys Glu Met Val Phe Pro
1175                1180                1185

Ser Ser Arg Asn Leu Phe Leu Thr Asn Leu Asp Asn Leu His Glu
1190                1195                1200

Asn Asn Thr His Asn Gln Glu Lys Lys Ile Gln Glu Glu Ile Glu
1205                1210                1215

Lys Lys Glu Thr Leu Ile Gln Glu Asn Val Val Leu Pro Gln Ile
1220                1225                1230

His Thr Val Thr Gly Thr Lys Asn Phe Met Lys Asn Leu Phe Leu
1235                1240                1245

Leu Ser Thr Arg Gln Asn Val Glu Gly Ser Tyr Asp Gly Ala Tyr
1250                1255                1260

Ala Pro Val Leu Gln Asp Phe Arg Ser Leu Asn Asp Ser Thr Asn
1265                1270                1275

Arg Thr Lys Lys His Thr Ala His Phe Ser Lys Lys Gly Glu Glu
1280                1285                1290

Glu Asn Leu Glu Gly Leu Gly Asn Gln Thr Lys Gln Ile Val Glu
1295                1300                1305

Lys Tyr Ala Cys Thr Thr Arg Ile Ser Pro Asn Thr Ser Gln Gln
1310                1315                1320

Asn Phe Val Thr Gln Arg Ser Lys Arg Ala Leu Lys Gln Phe Arg
1325                1330                1335

Leu Pro Leu Glu Glu Thr Glu Leu Glu Lys Arg Ile Ile Val Asp
1340                1345                1350

Asp Thr Ser Thr Gln Trp Ser Lys Asn Met Lys His Leu Thr Pro
1355                1360                1365

Ser Thr Leu Thr Gln Ile Asp Tyr Asn Glu Lys Glu Lys Gly Ala
1370                1375                1380

Ile Thr Gln Ser Pro Leu Ser Asp Cys Leu Thr Arg Ser His Ser
1385                1390                1395

Ile Pro Gln Ala Asn Arg Ser Pro Leu Pro Ile Ala Lys Val Ser
1400                1405                1410

Ser Phe Pro Ser Ile Arg Pro Ile Tyr Leu Thr Arg Val Leu Phe
1415                1420                1425

Gln Asp Asn Ser Ser His Leu Pro Ala Ala Ser Tyr Arg Lys Lys
1430                1435                1440

Asp Ser Gly Val Gln Glu Ser Ser His Phe Leu Gln Gly Ala Lys
1445                1450                1455

Lys Asn Asn Leu Ser Leu Ala Ile Leu Thr Leu Glu Met Thr Gly
1460                1465                1470

Asp Gln Arg Glu Val Gly Ser Leu Gly Thr Ser Ala Thr Asn Ser
```

-continued

|  | 1475 |  |  | 1480 |  |  | 1485 |  |  |
| Val | Thr | Tyr | Lys | Lys | Val | Glu | Asn | Thr | Val | Leu | Pro | Lys | Pro | Asp |
|  | 1490 |  |  | 1495 |  |  | 1500 |  |  |
| Leu | Pro | Lys | Thr | Ser | Gly | Lys | Val | Glu | Leu | Leu | Pro | Lys | Val | His |
|  | 1505 |  |  | 1510 |  |  | 1515 |  |  |
| Ile | Tyr | Gln | Lys | Asp | Leu | Phe | Pro | Thr | Glu | Thr | Ser | Asn | Gly | Ser |
|  | 1520 |  |  | 1525 |  |  | 1530 |  |  |
| Pro | Gly | His | Leu | Asp | Leu | Val | Glu | Gly | Ser | Leu | Leu | Gln | Gly | Thr |
|  | 1535 |  |  | 1540 |  |  | 1545 |  |  |
| Glu | Gly | Ala | Ile | Lys | Trp | Asn | Glu | Ala | Asn | Arg | Pro | Gly | Lys | Val |
|  | 1550 |  |  | 1555 |  |  | 1560 |  |  |
| Pro | Phe | Leu | Arg | Val | Ala | Thr | Glu | Ser | Ser | Ala | Lys | Thr | Pro | Ser |
|  | 1565 |  |  | 1570 |  |  | 1575 |  |  |
| Lys | Leu | Leu | Asp | Pro | Leu | Ala | Trp | Asp | Asn | His | Tyr | Gly | Thr | Gln |
|  | 1580 |  |  | 1585 |  |  | 1590 |  |  |
| Ile | Pro | Lys | Glu | Glu | Trp | Lys | Ser | Gln | Glu | Lys | Ser | Pro | Glu | Lys |
|  | 1595 |  |  | 1600 |  |  | 1605 |  |  |
| Thr | Ala | Phe | Lys | Lys | Lys | Asp | Thr | Ile | Leu | Ser | Leu | Asn | Ala | Cys |
|  | 1610 |  |  | 1615 |  |  | 1620 |  |  |
| Glu | Ser | Asn | His | Ala | Ile | Ala | Ala | Ile | Asn | Glu | Gly | Gln | Asn | Lys |
|  | 1625 |  |  | 1630 |  |  | 1635 |  |  |
| Pro | Glu | Ile | Glu | Val | Thr | Trp | Ala | Lys | Gln | Gly | Arg | Thr | Glu | Arg |
|  | 1640 |  |  | 1645 |  |  | 1650 |  |  |
| Leu | Cys | Ser | Gln | Asn | Pro | Pro | Val | Leu | Lys | Arg | His | Gln | Arg | Glu |
|  | 1655 |  |  | 1660 |  |  | 1665 |  |  |
| Ile | Thr | Arg | Thr | Thr | Leu | Gln | Ser | Asp | Gln | Glu | Glu | Ile | Asp | Tyr |
|  | 1670 |  |  | 1675 |  |  | 1680 |  |  |
| Asp | Asp | Thr | Ile | Ser | Val | Glu | Met | Lys | Lys | Glu | Asp | Phe | Asp | Ile |
|  | 1685 |  |  | 1690 |  |  | 1695 |  |  |
| Tyr | Asp | Glu | Asp | Glu | Asn | Gln | Ser | Pro | Arg | Ser | Phe | Gln | Lys | Lys |
|  | 1700 |  |  | 1705 |  |  | 1710 |  |  |
| Thr | Arg | His | Tyr | Phe | Ile | Ala | Ala | Val | Glu | Arg | Leu | Trp | Asp | Tyr |
|  | 1715 |  |  | 1720 |  |  | 1725 |  |  |
| Gly | Met | Ser | Ser | Ser | Pro | His | Val | Leu | Arg | Asn | Arg | Ala | Gln | Ser |
|  | 1730 |  |  | 1735 |  |  | 1740 |  |  |
| Gly | Ser | Val | Pro | Gln | Phe | Lys | Lys | Val | Val | Phe | Gln | Glu | Phe | Thr |
|  | 1745 |  |  | 1750 |  |  | 1755 |  |  |
| Asp | Gly | Ser | Phe | Thr | Gln | Pro | Leu | Tyr | Arg | Gly | Glu | Leu | Asn | Glu |
|  | 1760 |  |  | 1765 |  |  | 1770 |  |  |
| His | Leu | Gly | Leu | Leu | Gly | Pro | Tyr | Ile | Arg | Ala | Glu | Val | Glu | Asp |
|  | 1775 |  |  | 1780 |  |  | 1785 |  |  |
| Asn | Ile | Met | Val | Thr | Phe | Arg | Asn | Gln | Ala | Ser | Arg | Pro | Tyr | Ser |
|  | 1790 |  |  | 1795 |  |  | 1800 |  |  |
| Phe | Tyr | Ser | Ser | Leu | Ile | Ser | Tyr | Glu | Glu | Asp | Gln | Arg | Gln | Gly |
|  | 1805 |  |  | 1810 |  |  | 1815 |  |  |
| Ala | Glu | Pro | Arg | Lys | Asn | Phe | Val | Lys | Pro | Asn | Glu | Thr | Lys | Thr |
|  | 1820 |  |  | 1825 |  |  | 1830 |  |  |
| Tyr | Phe | Trp | Lys | Val | Gln | His | His | Met | Ala | Pro | Thr | Lys | Asp | Glu |
|  | 1835 |  |  | 1840 |  |  | 1845 |  |  |
| Phe | Asp | Cys | Lys | Ala | Trp | Ala | Tyr | Phe | Ser | Asp | Val | Asp | Leu | Glu |
|  | 1850 |  |  | 1855 |  |  | 1860 |  |  |
| Lys | Asp | Val | His | Ser | Gly | Leu | Ile | Gly | Pro | Leu | Leu | Val | Cys | His |
|  | 1865 |  |  | 1870 |  |  | 1875 |  |  |

```
Thr Asn Thr Leu Asn Pro Ala His Gly Arg Gln Val Thr Val Gln
    1880            1885                1890

Glu Phe Ala Leu Phe Phe Thr Ile Phe Asp Glu Thr Lys Ser Trp
    1895            1900                1905

Tyr Phe Thr Glu Asn Met Glu Arg Asn Cys Arg Ala Pro Cys Asn
    1910            1915                1920

Ile Gln Met Glu Asp Pro Thr Phe Lys Glu Asn Tyr Arg Phe His
    1925            1930                1935

Ala Ile Asn Gly Tyr Ile Met Asp Thr Leu Pro Gly Leu Val Met
    1940            1945                1950

Ala Gln Asp Gln Arg Ile Arg Trp Tyr Leu Leu Ser Met Gly Ser
    1955            1960                1965

Asn Glu Asn Ile His Ser Ile His Phe Ser Gly His Val Phe Thr
    1970            1975                1980

Val Arg Lys Lys Glu Glu Tyr Lys Met Ala Leu Tyr Asn Leu Tyr
    1985            1990                1995

Pro Gly Val Phe Glu Thr Val Glu Met Leu Pro Ser Lys Ala Gly
    2000            2005                2010

Ile Trp Arg Val Glu Cys Leu Ile Gly Glu His Leu His Ala Gly
    2015            2020                2025

Met Ser Thr Leu Phe Leu Val Tyr Ser Asn Lys Cys Gln Thr Pro
    2030            2035                2040

Leu Gly Met Ala Ser Gly His Ile Arg Asp Phe Gln Ile Thr Ala
    2045            2050                2055

Ser Gly Gln Tyr Gly Gln Trp Ala Pro Lys Leu Ala Arg Leu His
    2060            2065                2070

Tyr Ser Gly Ser Ile Asn Ala Trp Ser Thr Lys Glu Pro Phe Ser
    2075            2080                2085

Trp Ile Lys Val Asp Leu Leu Ala Pro Met Ile Ile His Gly Ile
    2090            2095                2100

Lys Thr Gln Gly Ala Arg Gln Lys Phe Ser Ser Leu Tyr Ile Ser
    2105            2110                2115

Gln Phe Ile Ile Met Tyr Ser Leu Asp Gly Lys Lys Trp Gln Thr
    2120            2125                2130

Tyr Arg Gly Asn Ser Thr Gly Thr Leu Met Val Phe Phe Gly Asn
    2135            2140                2145

Val Asp Ser Ser Gly Ile Lys His Asn Ile Phe Asn Pro Pro Ile
    2150            2155                2160

Ile Ala Arg Tyr Ile Arg Leu His Pro Thr His Tyr Ser Ile Arg
    2165            2170                2175

Ser Thr Leu Arg Met Glu Leu Met Gly Cys Asp Leu Asn Ser Cys
    2180            2185                2190

Ser Met Pro Leu Gly Met Glu Ser Lys Ala Ile Ser Asp Ala Gln
    2195            2200                2205

Ile Thr Ala Ser Ser Tyr Phe Thr Asn Met Phe Ala Thr Trp Ser
    2210            2215                2220

Pro Ser Lys Ala Arg Leu His Leu Gln Gly Arg Ser Asn Ala Trp
    2225            2230                2235

Arg Pro Gln Val Asn Asn Pro Lys Glu Trp Leu Gln Val Asp Phe
    2240            2245                2250

Gln Lys Thr Met Lys Val Thr Gly Val Thr Thr Gln Gly Val Lys
    2255            2260                2265
```

| | | | | | | | | | | | |
|---|---|---|---|---|---|---|---|---|---|---|---|
|Ser|Leu|Leu|Thr|Ser|Met|Tyr|Val|Lys|Glu|Phe|Leu|Ile|Ser|Ser|
|2270| | | | |2275| | | |2280| | | | | |

Ser Leu Leu Thr Ser Met Tyr Val Lys Glu Phe Leu Ile Ser Ser
2270                2275               2280

Ser Gln Asp Gly His Gln Trp Thr Leu Phe Phe Gln Asn Gly Lys
    2285                2290               2295

Val Lys Val Phe Gln Gly Asn Gln Asp Ser Phe Thr Pro Val Val
2300                2305               2310

Asn Ser Leu Asp Pro Pro Leu Leu Thr Arg Tyr Leu Arg Ile His
    2315                2320               2325

Pro Gln Ser Trp Val His Gln Ile Ala Leu Arg Met Glu Val Leu
    2330                2335               2340

Gly Cys Glu Ala Gln Asp Leu Tyr Leu Glu Gly Lys Pro Ile Pro
    2345                2350               2355

Asn Pro Leu Leu Gly Leu Asp Ser Thr Ser Arg Pro Lys Ser Cys
    2360                2365               2370

Asp Lys Thr His Thr Cys Pro Pro Cys Pro Ala Pro Glu Leu Leu
    2375                2380               2385

Gly Gly Pro Ser Val Phe Leu Phe Pro Pro Lys Pro Lys Asp Thr
    2390                2395               2400

Leu Met Ile Ser Arg Thr Pro Glu Val Thr Cys Val Val Val Asp
    2405                2410               2415

Val Ser His Glu Asp Pro Glu Val Lys Phe Asn Trp Tyr Val Asp
    2420                2425               2430

Gly Val Glu Val His Asn Ala Lys Thr Lys Pro Arg Glu Glu Gln
    2435                2440               2445

Tyr Asn Ser Thr Tyr Arg Val Val Ser Val Leu Thr Val Leu His
    2450                2455               2460

Gln Asp Trp Leu Asn Gly Lys Glu Tyr Lys Cys Lys Val Ser Asn
    2465                2470               2475

Lys Ala Leu Pro Ala Pro Ile Glu Lys Thr Ile Ser Lys Ala Lys
    2480                2485               2490

Gly Gln Pro Arg Glu Pro Gln Val Tyr Thr Leu Pro Pro Ser Arg
    2495                2500               2505

Asp Glu Leu Thr Lys Asn Gln Val Ser Leu Thr Cys Leu Val Lys
    2510                2515               2520

Gly Phe Tyr Pro Ser Asp Ile Ala Val Glu Trp Glu Ser Asn Gly
    2525                2530               2535

Gln Pro Glu Asn Asn Tyr Lys Thr Thr Pro Pro Val Leu Asp Ser
    2540                2545               2550

Asp Gly Ser Phe Phe Leu Tyr Ser Lys Leu Thr Val Asp Lys Ser
    2555                2560               2565

Arg Trp Gln Gln Gly Asn Val Phe Ser Cys Ser Val Met His Glu
    2570                2575               2580

Ala Leu His Asn His Tyr Thr Gln Lys Ser Leu Ser Leu Ser Pro
    2585                2590               2595

Gly Lys
    2600

<210> SEQ ID NO 190
<211> LENGTH: 506
<212> TYPE: PRT
<213> ORGANISM: Artificial Sequence
<220> FEATURE:
<223> OTHER INFORMATION: flag-tagged TPB(gE)-TMR(VSVG) fusion protein

<400> SEQUENCE: 190

```
Met Ala Leu Trp Met Arg Leu Leu Pro Leu Ala Leu Leu Ala Leu
1               5                   10                  15

Trp Gly Pro Asp Pro Ala Ala Gly Thr Gly Ser Gly Glu Phe Asp
            20                  25                  30

Ile Ala Ala Ala Gly Thr Pro Lys Thr Ser Trp Arg Arg Val Ser Val
                35                  40                  45

Gly Glu Asp Val Ser Leu Leu Pro Ala Pro Gly Pro Thr Gly Arg Gly
    50                  55                  60

Pro Thr Gln Lys Leu Leu Trp Ala Val Glu Pro Leu Asp Gly Cys Gly
65                  70                  75                  80

Pro Leu His Pro Ser Trp Val Ser Leu Met Pro Pro Lys Gln Val Pro
                85                  90                  95

Glu Thr Val Val Asp Ala Ala Cys Met Arg Ala Pro Val Pro Leu Ala
            100                 105                 110

Met Ala Tyr Ala Pro Pro Ala Pro Ser Ala Thr Gly Gly Leu Arg Thr
            115                 120                 125

Asp Phe Val Trp Gln Glu Arg Ala Ala Val Val Asn Arg Ser Leu Val
            130                 135                 140

Ile His Gly Val Arg Glu Thr Asp Ser Gly Leu Tyr Thr Leu Ser Val
145                 150                 155                 160

Gly Asp Ile Lys Asp Pro Ala Arg Gln Val Ala Ser Val Val Leu Val
                165                 170                 175

Val Gln Pro Ala Pro Val Pro Thr Pro Pro Thr Pro Ala Asp Tyr
            180                 185                 190

Asp Glu Asp Asp Asn Asp Glu Gly Glu Asp Glu Ser Leu Ala Gly Thr
            195                 200                 205

Pro Ala Ser Gly Thr Pro Arg Leu Pro Pro Pro Ala Pro Pro Arg
210                 215                 220

Ser Trp Pro Ser Ala Pro Glu Val Ser His Val Arg Gly Val Thr Val
225                 230                 235                 240

Arg Met Glu Thr Pro Glu Ala Ile Leu Phe Ser Pro Gly Glu Thr Phe
                245                 250                 255

Ser Thr Asn Val Ser Ile His Ala Ile Ala His Asp Gln Thr Tyr
            260                 265                 270

Ser Met Asp Val Val Trp Leu Arg Phe Asp Val Pro Thr Ser Cys Ala
            275                 280                 285

Glu Met Arg Ile Tyr Glu Ser Cys Leu Tyr His Pro Gln Leu Pro Glu
            290                 295                 300

Cys Leu Ser Pro Ala Asp Ala Pro Cys Ala Ala Ser Thr Trp Thr Ser
305                 310                 315                 320

Arg Leu Ala Val Arg Ser Tyr Ala Gly Cys Ser Arg Thr Asn Pro Pro
                325                 330                 335

Pro Arg Cys Ser Ala Glu Ala His Met Glu Pro Val Pro Gly Leu Ala
            340                 345                 350

Trp Gln Ala Ala Ser Val Asn Leu Glu Phe Arg Asp Ala Ser Pro Gln
            355                 360                 365

His Ser Gly Leu Tyr Leu Cys Val Val Tyr Val Asn Asp His Ile His
            370                 375                 380

Ala Trp Gly His Ile Thr Ile Ser Thr Ala Ala Gln Tyr Arg Asn Ala
385                 390                 395                 400

Val Val Glu Gln Pro Leu Pro Gln Arg Gly Ala Asp Leu Ala Glu Leu
                405                 410                 415

Glu Gly Asp Tyr Lys Asp Asp Asp Asp Lys Gly Ser Arg Asp Asp Glu
```

```
                  420                 425                 430
Ser Leu Phe Phe Gly Asp Thr Gly Leu Ser Lys Asn Pro Ile Glu Leu
            435                 440                 445

Val Glu Gly Trp Phe Ser Ser Trp Lys Ser Ser Ile Ala Ser Phe Phe
        450                 455                 460

Phe Ile Ile Gly Leu Ile Gly Leu Phe Val Leu Arg Val Gly
465                 470                 475                 480

Ile His Leu Cys Ile Lys Leu Lys His Thr Lys Lys Arg Gln Ile Tyr
                485                 490                 495

Thr Asp Ile Glu Met Asn Arg Leu Gly Lys
            500                 505

<210> SEQ ID NO 191
<211> LENGTH: 509
<212> TYPE: PRT
<213> ORGANISM: Artificial Sequence
<220> FEATURE:
<223> OTHER INFORMATION: flag-tagged TPB(gE)-TMR(VSVG) with KK motif

<400> SEQUENCE: 191

Met Ala Leu Trp Met Arg Leu Leu Pro Leu Leu Ala Leu Leu Ala Leu
1               5                   10                  15

Trp Gly Pro Asp Pro Ala Ala Ala Gly Thr Gly Ser Gly Glu Phe Asp
            20                  25                  30

Ile Ala Ala Ala Gly Thr Pro Lys Thr Ser Trp Arg Arg Val Ser Val
        35                  40                  45

Gly Glu Asp Val Ser Leu Leu Pro Ala Pro Gly Pro Thr Gly Arg Gly
    50                  55                  60

Pro Thr Gln Lys Leu Leu Trp Ala Val Glu Pro Leu Asp Gly Cys Gly
65              70                  75                  80

Pro Leu His Pro Ser Trp Val Ser Leu Met Pro Pro Lys Gln Val Pro
                85                  90                  95

Glu Thr Val Val Asp Ala Ala Cys Met Arg Ala Pro Val Pro Leu Ala
            100                 105                 110

Met Ala Tyr Ala Pro Pro Ala Pro Ser Ala Thr Gly Gly Leu Arg Thr
        115                 120                 125

Asp Phe Val Trp Gln Glu Arg Ala Ala Val Val Asn Arg Ser Leu Val
    130                 135                 140

Ile His Gly Val Arg Glu Thr Asp Ser Gly Leu Tyr Thr Leu Ser Val
145                 150                 155                 160

Gly Asp Ile Lys Asp Pro Ala Arg Gln Val Ala Ser Val Val Leu Val
                165                 170                 175

Val Gln Pro Ala Pro Val Pro Thr Pro Pro Thr Pro Ala Asp Tyr
            180                 185                 190

Asp Glu Asp Asp Asn Asp Glu Gly Glu Asp Glu Ser Leu Ala Gly Thr
        195                 200                 205

Pro Ala Ser Gly Thr Pro Arg Leu Pro Pro Pro Ala Pro Pro Arg
    210                 215                 220

Ser Trp Pro Ser Ala Pro Glu Val Ser His Val Arg Gly Val Thr Val
225                 230                 235                 240

Arg Met Glu Thr Pro Glu Ala Ile Leu Phe Ser Pro Gly Glu Thr Phe
                245                 250                 255

Ser Thr Asn Val Ser Ile His Ala Ile Ala His Asp Asp Gln Thr Tyr
            260                 265                 270

Ser Met Asp Val Val Trp Leu Arg Phe Asp Val Pro Thr Ser Cys Ala
```

```
                275                 280                 285
Glu Met Arg Ile Tyr Glu Ser Cys Leu Tyr His Pro Gln Leu Pro Glu
    290                 295                 300

Cys Leu Ser Pro Ala Asp Ala Pro Cys Ala Ala Ser Thr Trp Thr Ser
305                 310                 315                 320

Arg Leu Ala Val Arg Ser Tyr Ala Gly Cys Ser Arg Thr Asn Pro Pro
                325                 330                 335

Pro Arg Cys Ser Ala Glu Ala His Met Glu Pro Val Pro Gly Leu Ala
            340                 345                 350

Trp Gln Ala Ala Ser Val Asn Leu Glu Phe Arg Asp Ala Ser Pro Gln
        355                 360                 365

His Ser Gly Leu Tyr Leu Cys Val Val Tyr Val Asn Asp His Ile His
    370                 375                 380

Ala Trp Gly His Ile Thr Ile Ser Thr Ala Ala Gln Tyr Arg Asn Ala
385                 390                 395                 400

Val Val Glu Gln Pro Leu Pro Gln Arg Gly Ala Asp Leu Ala Glu Leu
                405                 410                 415

Glu Gly Asp Tyr Lys Asp Asp Asp Lys Gly Ser Arg Asp Glu
            420                 425                 430

Ser Leu Phe Phe Gly Asp Thr Gly Leu Ser Lys Asn Pro Ile Glu Leu
        435                 440                 445

Val Glu Gly Trp Phe Ser Ser Trp Lys Ser Ser Ile Ala Ser Phe Phe
    450                 455                 460

Phe Ile Ile Gly Leu Ile Ile Gly Leu Phe Leu Val Leu Arg Val Gly
465                 470                 475                 480

Ile His Leu Cys Ile Lys Leu Lys His Thr Lys Lys Arg Gln Ile Tyr
                485                 490                 495

Thr Asp Ile Glu Met Asn Arg Leu Gly Lys Lys Thr Cys
            500                 505

<210> SEQ ID NO 192
<211> LENGTH: 120
<212> TYPE: PRT
<213> ORGANISM: Artificial Sequence
<220> FEATURE:
<223> OTHER INFORMATION: flag-tagged CMP-TPB(Prot A) fusion protein

<400> SEQUENCE: 192

Met Ala Leu Trp Met Arg Leu Leu Pro Leu Leu Ala Leu Leu Ala Leu
1               5                   10                  15

Trp Gly Pro Asp Pro Ala Ala Ala Gly Thr Gly Ser Gly Glu Phe Ile
                20                  25                  30

Lys Lys Ala Phe His Lys Leu Ala Met Lys Tyr Asp Ile Gly Gly Gly
            35                  40                  45

Gly Ser Gly Gly Gly Gly Ser Gly Gly Gly Gly Ser Ala Ala Ala Gln
        50                  55                  60

Gln Asn Ala Phe Tyr Glu Ile Leu Asn Met Pro Asn Leu Asn Glu Glu
65                  70                  75                  80

Gln Arg Asn Gly Phe Ile Gln Ser Leu Lys Asp Asp Pro Ser Gln Ser
                85                  90                  95

Ala Asn Val Leu Gly Glu Ala Lys Lys Leu Asn Asp Ser Leu Glu Gly
            100                 105                 110

Asp Tyr Lys Asp Asp Asp Asp Lys
        115                 120
```

```
<210> SEQ ID NO 193
<211> LENGTH: 77
<212> TYPE: PRT
<213> ORGANISM: Artificial Sequence
<220> FEATURE:
<223> OTHER INFORMATION: transmembrane retention domain

<400> SEQUENCE: 193

Asp Asp Glu Ser Leu Phe Phe Gly Asp Thr Gly Leu Ser Lys Asn Pro
1               5                   10                  15

Ile Glu Leu Val Glu Gly Trp Phe Ser Ser Trp Lys Ser Ser Ile Ala
            20                  25                  30

Ser Phe Phe Phe Ile Ile Gly Leu Ile Ile Gly Leu Phe Leu Val Leu
        35                  40                  45

Arg Val Gly Ile His Leu Cys Ile Lys Leu Lys His Thr Lys Lys Arg
    50                  55                  60

Gln Ile Tyr Thr Asp Ile Glu Met Asn Arg Leu Gly Lys
65                  70                  75

<210> SEQ ID NO 194
<211> LENGTH: 80
<212> TYPE: PRT
<213> ORGANISM: Artificial Sequence
<220> FEATURE:
<223> OTHER INFORMATION: transmembran retention domain

<400> SEQUENCE: 194

Asp Asp Glu Ser Leu Phe Phe Gly Asp Thr Gly Leu Ser Lys Asn Pro
1               5                   10                  15

Ile Glu Leu Val Glu Gly Trp Phe Ser Ser Trp Lys Ser Ser Ile Ala
            20                  25                  30

Ser Phe Phe Phe Ile Ile Gly Leu Ile Ile Gly Leu Phe Leu Val Leu
        35                  40                  45

Arg Val Gly Ile His Leu Cys Ile Lys Leu Lys His Thr Lys Lys Arg
    50                  55                  60

Gln Ile Tyr Thr Asp Ile Glu Met Asn Arg Leu Gly Lys Lys Thr Cys
65                  70                  75                  80

<210> SEQ ID NO 195
<211> LENGTH: 185
<212> TYPE: PRT
<213> ORGANISM: Artificial Sequence
<220> FEATURE:
<223> OTHER INFORMATION: Flag-Tagged TPB(Prot A)-TMR(VSVG) Fusion
      Protein

<400> SEQUENCE: 195

Met Ala Leu Trp Met Arg Leu Leu Pro Leu Leu Ala Leu Leu Ala Leu
1               5                   10                  15

Trp Gly Pro Asp Pro Ala Ala Ala Gly Thr Gly Ser Gly Glu Phe Asp
            20                  25                  30

Ile Ala Ala Ala Ala Asp Asn Lys Phe Asn Lys Glu Gln Gln Asn Ala
        35                  40                  45

Phe Tyr Glu Ile Leu Asn Met Pro Asn Leu Asn Glu Glu Gln Arg Asn
    50                  55                  60

Gly Phe Ile Gln Ser Leu Lys Asp Asp Pro Ser Gln Ser Ala Asn Val
65                  70                  75                  80

Leu Gly Glu Ala Lys Lys Leu Asn Asp Ser Gln Ala Pro Lys Leu Glu
            85                  90                  95

Gly Asp Tyr Lys Asp Asp Asp Asp Lys Gly Ser Arg Asp Asp Glu Ser
```

```
                    100               105                110

Leu Phe Phe Gly Asp Thr Gly Leu Ser Lys Asn Pro Ile Glu Leu Val
            115                 120                 125

Glu Gly Trp Phe Ser Ser Trp Lys Ser Ser Ile Ala Ser Phe Phe Phe
            130                 135                 140

Ile Ile Gly Leu Ile Ile Gly Leu Phe Leu Val Leu Arg Val Gly Ile
145                 150                 155                 160

His Leu Cys Ile Lys Leu Lys His Thr Lys Lys Arg Gln Ile Tyr Thr
                165                 170                 175

Asp Ile Glu Met Asn Arg Leu Gly Lys
                180                 185

<210> SEQ ID NO 196
<211> LENGTH: 197
<212> TYPE: PRT
<213> ORGANISM: Artificial Sequence
<220> FEATURE:
<223> OTHER INFORMATION: Flag-Tagged TPB(Prot G)-TMR(VSVG) Fusion
      Protein

<400> SEQUENCE: 196

Met Ala Leu Trp Met Arg Leu Leu Pro Leu Ala Leu Leu Ala Leu
1               5                   10                  15

Trp Gly Pro Asp Pro Ala Ala Ala Gly Thr Gly Ser Gly Glu Phe Asp
            20                  25                  30

Ile Ala Ala Ala Thr Tyr Lys Leu Val Ile Asn Gly Lys Thr Leu Lys
                35                  40                  45

Gly Glu Thr Thr Thr Glu Ala Val Asp Ala Ala Thr Ala Glu Lys Val
50                  55                  60

Phe Lys Gln Tyr Ala Asn Asp Asn Gly Val Asp Gly Glu Trp Thr Tyr
65                  70                  75                  80

Asp Asp Ala Thr Lys Thr Phe Thr Val Thr Glu Lys Pro Glu Val Ile
                85                  90                  95

Asp Ala Ser Glu Leu Thr Pro Ala Val Thr Leu Glu Gly Asp Tyr Lys
                100                 105                 110

Asp Asp Asp Asp Lys Gly Ser Arg Asp Asp Glu Ser Leu Phe Phe Gly
                115                 120                 125

Asp Thr Gly Leu Ser Lys Asn Pro Ile Glu Leu Val Glu Gly Trp Phe
            130                 135                 140

Ser Ser Trp Lys Ser Ser Ile Ala Ser Phe Phe Phe Ile Ile Gly Leu
145                 150                 155                 160

Ile Ile Gly Leu Phe Leu Val Leu Arg Val Gly Ile His Leu Cys Ile
                165                 170                 175

Lys Leu Lys His Thr Lys Lys Arg Gln Ile Tyr Thr Asp Ile Glu Met
                180                 185                 190

Asn Arg Leu Gly Lys
            195

<210> SEQ ID NO 197
<211> LENGTH: 183
<212> TYPE: PRT
<213> ORGANISM: Artificial Sequence
<220> FEATURE:
<223> OTHER INFORMATION: Flag-tagged TPB(GB919)-TMR(VSVG) Fusion Protein

<400> SEQUENCE: 197

Met Ala Leu Trp Met Arg Leu Leu Pro Leu Ala Leu Leu Ala Leu
1               5                   10                  15
```

```
Trp Gly Pro Asp Pro Ala Ala Ala Gly Thr Gly Ser Gly Glu Phe Asp
            20                  25                  30

Ile Ala Ala Ala Asp Thr Tyr Lys Leu Ile Leu Asn Gly Lys Thr Leu
            35                  40                  45

Lys Gly Glu Thr Thr Thr Glu Ala Val Asp Ala Ala Thr Ala Glu Lys
 50                  55                  60

Val Phe Lys His Tyr Ala Asn Glu His Gly Val His Gly His Trp Thr
 65                  70                  75                  80

Tyr Asp Pro Glu Thr Lys Thr Phe Thr Val Thr Glu Leu Glu Gly Asp
                85                  90                  95

Tyr Lys Asp Asp Asp Asp Lys Gly Ser Arg Asp Glu Ser Leu Phe
                100                 105                 110

Phe Gly Asp Thr Gly Leu Ser Lys Asn Pro Ile Glu Leu Val Glu Gly
                115                 120                 125

Trp Phe Ser Ser Trp Lys Ser Ser Ile Ala Ser Phe Phe Ile Ile
130                 135                 140

Gly Leu Ile Ile Gly Leu Phe Leu Val Leu Arg Val Gly Ile His Leu
145                 150                 155                 160

Cys Ile Lys Leu Lys His Thr Lys Arg Gln Ile Tyr Thr Asp Ile
                165                 170                 175

Glu Met Asn Arg Leu Gly Lys
                180
```

<210> SEQ ID NO 198
<211> LENGTH: 319
<212> TYPE: PRT
<213> ORGANISM: Artificial Sequence
<220> FEATURE:
<223> OTHER INFORMATION: Flag-Tagged TPB(Prot A)-TMR(KDELR) Fusion
      Protein

<400> SEQUENCE: 198

```
Met Ala Leu Trp Met Arg Leu Leu Pro Leu Leu Ala Leu Leu Ala Leu
 1               5                  10                  15

Trp Gly Pro Asp Pro Ala Ala Ala Gly Thr Gly Ser Gly Glu Phe Asp
            20                  25                  30

Ile Ala Ala Ala Asp Asn Lys Phe Asn Lys Glu Gln Gln Asn Ala
            35                  40                  45

Phe Tyr Glu Ile Leu Asn Met Pro Asn Leu Asn Glu Glu Gln Arg Asn
 50                  55                  60

Gly Phe Ile Gln Ser Leu Lys Asp Asp Pro Ser Gln Ser Ala Asn Val
 65                  70                  75                  80

Leu Gly Glu Ala Lys Lys Leu Asn Asp Ser Gln Ala Pro Lys Leu Glu
                85                  90                  95

Gly Asp Tyr Lys Asp Asp Asp Lys Gly Ser Arg Asn Leu Phe Arg
                100                 105                 110

Phe Leu Gly Asp Leu Ser His Leu Leu Ala Ile Leu Leu Leu Leu
                115                 120                 125

Lys Ile Trp Lys Ser Arg Ser Cys Ala Gly Ile Ser Gly Lys Ser Gln
130                 135                 140

Val Leu Phe Ala Val Val Phe Thr Ala Arg Tyr Leu Asp Leu Phe Thr
145                 150                 155                 160

Asn Tyr Ile Ser Leu Tyr Asn Thr Cys Met Lys Val Val Tyr Ile Ala
                165                 170                 175

Cys Ser Phe Thr Thr Val Trp Leu Ile Tyr Ser Lys Phe Lys Ala Thr
```

```
            180                 185                 190
Tyr Asp Gly Asn His Asp Thr Phe Arg Val Glu Phe Leu Val Val Pro
            195                 200                 205
Thr Ala Ile Leu Ala Phe Leu Val Asn His Asp Phe Thr Pro Leu Glu
            210                 215                 220
Ile Leu Trp Thr Phe Ser Ile Tyr Leu Glu Ser Val Ala Ile Leu Pro
225                 230                 235                 240
Gln Leu Phe Met Val Ser Lys Thr Gly Glu Ala Glu Thr Ile Thr Ser
                245                 250                 255
His Tyr Leu Phe Ala Leu Gly Val Tyr Arg Thr Leu Tyr Leu Phe Asn
            260                 265                 270
Trp Ile Trp Arg Tyr His Phe Glu Gly Phe Phe Asp Leu Ile Ala Ile
            275                 280                 285
Val Ala Gly Leu Val Gln Thr Val Leu Tyr Cys Asp Phe Phe Tyr Leu
            290                 295                 300
Tyr Ile Thr Lys Val Leu Lys Gly Lys Lys Leu Ser Leu Pro Ala
305                 310                 315

<210> SEQ ID NO 199
<211> LENGTH: 332
<212> TYPE: PRT
<213> ORGANISM: Artificial Sequence
<220> FEATURE:
<223> OTHER INFORMATION: Flag-Tagged TPB(Prot G)-TMR(KDELR) Fusion
      Protein

<400> SEQUENCE: 199

Met Ala Leu Trp Met Arg Leu Leu Pro Leu Leu Ala Leu Leu Ala Leu
1               5                   10                  15
Trp Gly Pro Asp Pro Ala Ala Ala Gly Thr Gly Ser Gly Glu Phe Asp
            20                  25                  30
Ile Ala Ala Ala Thr Tyr Lys Leu Val Ile Asn Gly Lys Thr Leu
            35                  40                  45
Lys Gly Glu Thr Thr Thr Glu Ala Val Asp Ala Ala Thr Ala Glu Lys
50                  55                  60
Val Phe Lys Gln Tyr Ala Asn Asp Asn Gly Val Asp Gly Glu Trp Thr
65                  70                  75                  80
Tyr Asp Asp Ala Thr Lys Thr Phe Thr Val Thr Glu Lys Pro Glu Val
                85                  90                  95
Ile Asp Ala Ser Glu Leu Thr Pro Ala Val Thr Leu Glu Gly Asp Tyr
            100                 105                 110
Lys Asp Asp Asp Lys Gly Ser Arg Asn Leu Phe Arg Phe Leu Gly
            115                 120                 125
Asp Leu Ser His Leu Leu Ala Ile Ile Leu Leu Leu Lys Ile Trp
            130                 135                 140
Lys Ser Arg Ser Cys Ala Gly Ile Ser Gly Lys Ser Gln Val Leu Phe
145                 150                 155                 160
Ala Val Val Phe Thr Ala Arg Tyr Leu Asp Leu Phe Thr Asn Tyr Ile
                165                 170                 175
Ser Leu Tyr Asn Thr Cys Met Lys Val Val Tyr Ile Ala Cys Ser Phe
            180                 185                 190
Thr Thr Val Trp Leu Ile Tyr Ser Lys Phe Lys Ala Thr Tyr Asp Gly
            195                 200                 205
Asn His Asp Thr Phe Arg Val Glu Phe Leu Val Val Pro Thr Ala Ile
            210                 215                 220
```

```
Leu Ala Phe Leu Val Asn His Asp Phe Thr Pro Leu Glu Ile Leu Trp
225                 230                 235                 240

Thr Phe Ser Ile Tyr Leu Glu Ser Val Ala Ile Leu Pro Gln Leu Phe
                245                 250                 255

Met Val Ser Lys Thr Gly Glu Ala Glu Thr Ile Thr Ser His Tyr Leu
            260                 265                 270

Phe Ala Leu Gly Val Tyr Arg Thr Leu Tyr Leu Phe Asn Trp Ile Trp
        275                 280                 285

Arg Tyr His Phe Glu Gly Phe Phe Asp Leu Ile Ala Ile Val Ala Gly
    290                 295                 300

Leu Val Gln Thr Val Leu Tyr Cys Asp Phe Phe Tyr Leu Tyr Ile Thr
305                 310                 315                 320

Lys Val Leu Lys Gly Lys Lys Leu Ser Leu Pro Ala
                325                 330

<210> SEQ ID NO 200
<211> LENGTH: 317
<212> TYPE: PRT
<213> ORGANISM: Artificial Sequence
<220> FEATURE:
<223> OTHER INFORMATION: Flag-Tagged TPB(GB919)-TMR(KDELR) Fusion
      Protein

<400> SEQUENCE: 200

Met Ala Leu Trp Met Arg Leu Leu Pro Leu Leu Ala Leu Leu Ala Leu
1               5                   10                  15

Trp Gly Pro Asp Pro Ala Ala Ala Gly Thr Gly Ser Gly Glu Phe Asp
            20                  25                  30

Ile Ala Ala Asp Thr Tyr Lys Leu Ile Leu Asn Gly Lys Thr Leu
        35                  40                  45

Lys Gly Glu Thr Thr Thr Glu Ala Val Asp Ala Ala Thr Ala Glu Lys
50                  55                  60

Val Phe Lys His Tyr Ala Asn Glu His Gly Val His Gly His Trp Thr
65                  70                  75                  80

Tyr Asp Pro Glu Thr Lys Thr Phe Thr Val Thr Glu Leu Glu Gly Asp
                85                  90                  95

Tyr Lys Asp Asp Asp Asp Lys Gly Ser Arg Asn Leu Phe Arg Phe Leu
            100                 105                 110

Gly Asp Leu Ser His Leu Leu Ala Ile Ile Leu Leu Leu Leu Lys Ile
        115                 120                 125

Trp Lys Ser Arg Ser Cys Ala Gly Ile Ser Gly Lys Ser Gln Val Leu
    130                 135                 140

Phe Ala Val Val Phe Thr Ala Arg Tyr Leu Asp Leu Phe Thr Asn Tyr
145                 150                 155                 160

Ile Ser Leu Tyr Asn Thr Cys Met Lys Val Val Tyr Ile Ala Cys Ser
                165                 170                 175

Phe Thr Thr Val Trp Leu Ile Tyr Ser Lys Phe Lys Ala Thr Tyr Asp
            180                 185                 190

Gly Asn His Asp Thr Phe Arg Val Glu Phe Leu Val Val Pro Thr Ala
        195                 200                 205

Ile Leu Ala Phe Leu Val Asn His Asp Phe Thr Pro Leu Glu Ile Leu
    210                 215                 220

Trp Thr Phe Ser Ile Tyr Leu Glu Ser Val Ala Ile Leu Pro Gln Leu
225                 230                 235                 240

Phe Met Val Ser Lys Thr Gly Glu Ala Glu Thr Ile Thr Ser His Tyr
                245                 250                 255
```

-continued

Leu Phe Ala Leu Gly Val Tyr Arg Thr Leu Tyr Leu Phe Asn Trp Ile
              260                 265                 270

Trp Arg Tyr His Phe Glu Gly Phe Asp Leu Ile Ala Ile Val Ala
        275                 280                 285

Gly Leu Val Gln Thr Val Leu Tyr Cys Asp Phe Phe Tyr Leu Tyr Ile
    290                 295                 300

Thr Lys Val Leu Lys Gly Lys Lys Leu Ser Leu Pro Ala
305                 310                 315

<210> SEQ ID NO 201
<211> LENGTH: 188
<212> TYPE: PRT
<213> ORGANISM: Artificial Sequence
<220> FEATURE:
<223> OTHER INFORMATION: Flag-Tagged TPB(Prot A)-TMR(VSVG) with KK Motif
      Fusion Protein

<400> SEQUENCE: 201

Met Ala Leu Trp Met Arg Leu Leu Pro Leu Leu Ala Leu Leu Ala Leu
1               5                   10                  15

Trp Gly Pro Asp Pro Ala Ala Ala Gly Thr Gly Ser Gly Glu Phe Asp
            20                  25                  30

Ile Ala Ala Ala Asp Asn Lys Phe Asn Lys Glu Gln Gln Asn Ala
        35                  40                  45

Phe Tyr Glu Ile Leu Asn Met Pro Asn Leu Asn Glu Glu Gln Arg Asn
    50                  55                  60

Gly Phe Ile Gln Ser Leu Lys Asp Asp Pro Ser Gln Ser Ala Asn Val
65                  70                  75                  80

Leu Gly Glu Ala Lys Lys Leu Asn Asp Ser Gln Ala Pro Lys Leu Glu
                85                  90                  95

Gly Asp Tyr Lys Asp Asp Asp Lys Gly Ser Arg Asp Asp Glu Ser
            100                 105                 110

Leu Phe Phe Gly Asp Thr Gly Leu Ser Lys Asn Pro Ile Glu Leu Val
        115                 120                 125

Glu Gly Trp Phe Ser Ser Trp Lys Ser Ser Ile Ala Ser Phe Phe Phe
    130                 135                 140

Ile Ile Gly Leu Ile Ile Gly Leu Phe Leu Val Leu Arg Val Gly Ile
145                 150                 155                 160

His Leu Cys Ile Lys Leu Lys His Thr Lys Lys Arg Gln Ile Tyr Thr
                165                 170                 175

Asp Ile Glu Met Asn Arg Leu Gly Lys Lys Thr Cys
            180                 185

<210> SEQ ID NO 202
<211> LENGTH: 186
<212> TYPE: PRT
<213> ORGANISM: Artificial Sequence
<220> FEATURE:
<223> OTHER INFORMATION: Flag-Tagged TPB(Prot GB919)-TMR(VSVG) with KK
      Motif Fusion Protein

<400> SEQUENCE: 202

Met Ala Leu Trp Met Arg Leu Leu Pro Leu Leu Ala Leu Leu Ala Leu
1               5                   10                  15

Trp Gly Pro Asp Pro Ala Ala Ala Gly Thr Gly Ser Gly Glu Phe Asp
            20                  25                  30

Ile Ala Ala Ala Asp Thr Tyr Lys Leu Ile Leu Asn Gly Lys Thr Leu
        35                  40                  45

```
Lys Gly Glu Thr Thr Thr Glu Ala Val Asp Ala Ala Thr Ala Glu Lys
        50                  55                  60

Val Phe Lys His Tyr Ala Asn Glu His Gly Val His Gly His Trp Thr
 65              70                  75                  80

Tyr Asp Pro Glu Thr Lys Thr Phe Thr Val Thr Glu Leu Glu Gly Asp
                 85                  90                  95

Tyr Lys Asp Asp Asp Asp Lys Gly Ser Arg Asp Asp Glu Ser Leu Phe
                100                 105                 110

Phe Gly Asp Thr Gly Leu Ser Lys Asn Pro Ile Glu Leu Val Glu Gly
            115                 120                 125

Trp Phe Ser Ser Trp Lys Ser Ser Ile Ala Ser Phe Phe Phe Ile Ile
        130                 135                 140

Gly Leu Ile Ile Gly Leu Phe Leu Val Leu Arg Val Gly Ile His Leu
145                 150                 155                 160

Cys Ile Lys Leu Lys His Thr Lys Lys Arg Gln Ile Tyr Thr Asp Ile
                165                 170                 175

Glu Met Asn Arg Leu Gly Lys Lys Thr Cys
                180                 185

<210> SEQ ID NO 203
<211> LENGTH: 8
<212> TYPE: PRT
<213> ORGANISM: Artificial Sequence
<220> FEATURE:
<223> OTHER INFORMATION: J domain polypeptide

<400> SEQUENCE: 203

Ile Lys Lys Tyr Arg Lys Leu Ala
1               5

<210> SEQ ID NO 204
<211> LENGTH: 8
<212> TYPE: PRT
<213> ORGANISM: Artificial Sequence
<220> FEATURE:
<223> OTHER INFORMATION: J domain polypeptide

<400> SEQUENCE: 204

Ile Lys Lys Ala Tyr Lys Leu Ala
1               5

<210> SEQ ID NO 205
<211> LENGTH: 8
<212> TYPE: PRT
<213> ORGANISM: Artificial Sequence
<220> FEATURE:
<223> OTHER INFORMATION: J domain polypeptide

<400> SEQUENCE: 205

Ile Lys Lys Ala Tyr Arg Leu Ala
1               5

<210> SEQ ID NO 206
<211> LENGTH: 8
<212> TYPE: PRT
<213> ORGANISM: Artificial Sequence
<220> FEATURE:
<223> OTHER INFORMATION: J domain polypeptide

<400> SEQUENCE: 206

Ile Lys Lys Ala Tyr Arg Lys Ala
1               5
```

```
<210> SEQ ID NO 207
<211> LENGTH: 9
<212> TYPE: PRT
<213> ORGANISM: Artificial Sequence
<220> FEATURE:
<223> OTHER INFORMATION: J domain polypeptide

<400> SEQUENCE: 207

Leu Lys Lys Ala Tyr Arg Lys Leu Ala
1               5

<210> SEQ ID NO 208
<211> LENGTH: 9
<212> TYPE: PRT
<213> ORGANISM: Artificial Sequence
<220> FEATURE:
<223> OTHER INFORMATION: J domain polypeptide

<400> SEQUENCE: 208

Val Lys Lys Ala Tyr Arg Lys Leu Ala
1               5

<210> SEQ ID NO 209
<211> LENGTH: 9
<212> TYPE: PRT
<213> ORGANISM: Artificial Sequence
<220> FEATURE:
<223> OTHER INFORMATION: J domain polypeptide

<400> SEQUENCE: 209

Met Lys Lys Ala Tyr Arg Lys Leu Ala
1               5

<210> SEQ ID NO 210
<211> LENGTH: 9
<212> TYPE: PRT
<213> ORGANISM: Artificial Sequence
<220> FEATURE:
<223> OTHER INFORMATION: J domain polypeptide

<400> SEQUENCE: 210

Ala Lys Lys Ala Tyr Arg Lys Leu Ala
1               5

<210> SEQ ID NO 211
<211> LENGTH: 9
<212> TYPE: PRT
<213> ORGANISM: Artificial Sequence
<220> FEATURE:
<223> OTHER INFORMATION: J domain polypeptide

<400> SEQUENCE: 211

Ile Ala Lys Ala Tyr Arg Lys Leu Ala
1               5

<210> SEQ ID NO 212
<211> LENGTH: 9
<212> TYPE: PRT
<213> ORGANISM: Artificial Sequence
<220> FEATURE:
<223> OTHER INFORMATION: J domain polypeptide

<400> SEQUENCE: 212

Ile Lys Ala Ala Tyr Arg Lys Leu Ala
1               5
```

<210> SEQ ID NO 213
<211> LENGTH: 9
<212> TYPE: PRT
<213> ORGANISM: Artificial Sequence
<220> FEATURE:
<223> OTHER INFORMATION: J domain polypeptide

<400> SEQUENCE: 213

Ile Lys Lys Arg Tyr Arg Lys Leu Ala
1               5

<210> SEQ ID NO 214
<211> LENGTH: 9
<212> TYPE: PRT
<213> ORGANISM: Artificial Sequence
<220> FEATURE:
<223> OTHER INFORMATION: J domain polypeptide

<400> SEQUENCE: 214

Ile Lys Lys Ser Tyr Arg Lys Leu Ala
1               5

<210> SEQ ID NO 215
<211> LENGTH: 9
<212> TYPE: PRT
<213> ORGANISM: Artificial Sequence
<220> FEATURE:
<223> OTHER INFORMATION: J domain polypeptide

<400> SEQUENCE: 215

Ile Lys Lys Gln Tyr Arg Lys Leu Ala
1               5

<210> SEQ ID NO 216
<211> LENGTH: 9
<212> TYPE: PRT
<213> ORGANISM: Artificial Sequence
<220> FEATURE:
<223> OTHER INFORMATION: J domain polypeptide

<400> SEQUENCE: 216

Ile Lys Lys Glu Tyr Arg Lys Leu Ala
1               5

<210> SEQ ID NO 217
<211> LENGTH: 9
<212> TYPE: PRT
<213> ORGANISM: Artificial Sequence
<220> FEATURE:
<223> OTHER INFORMATION: J domain polypeptide

<400> SEQUENCE: 217

Ile Lys Lys Phe Tyr Arg Lys Leu Ala
1               5

<210> SEQ ID NO 218
<211> LENGTH: 9
<212> TYPE: PRT
<213> ORGANISM: Artificial Sequence
<220> FEATURE:
<223> OTHER INFORMATION: J domain polypeptide

<400> SEQUENCE: 218

Ile Lys Lys Cys Tyr Arg Lys Leu Ala
1               5

```
<210> SEQ ID NO 219
<211> LENGTH: 9
<212> TYPE: PRT
<213> ORGANISM: Artificial Sequence
<220> FEATURE:
<223> OTHER INFORMATION: J domain polypeptide

<400> SEQUENCE: 219

Ile Lys Lys Ala Phe Arg Lys Leu Ala
1               5

<210> SEQ ID NO 220
<211> LENGTH: 9
<212> TYPE: PRT
<213> ORGANISM: Artificial Sequence
<220> FEATURE:
<223> OTHER INFORMATION: J domain polypeptide

<400> SEQUENCE: 220

Ile Lys Lys Ala Trp Arg Lys Leu Ala
1               5

<210> SEQ ID NO 221
<211> LENGTH: 9
<212> TYPE: PRT
<213> ORGANISM: Artificial Sequence
<220> FEATURE:
<223> OTHER INFORMATION: J domain polypeptide

<400> SEQUENCE: 221

Ile Lys Lys Ala Tyr Arg Lys Gln Ala
1               5

<210> SEQ ID NO 222
<211> LENGTH: 9
<212> TYPE: PRT
<213> ORGANISM: Artificial Sequence
<220> FEATURE:
<223> OTHER INFORMATION: J domain polypeptide

<400> SEQUENCE: 222

Ile Lys Lys Ala Tyr Arg Lys Met Ala
1               5

<210> SEQ ID NO 223
<211> LENGTH: 9
<212> TYPE: PRT
<213> ORGANISM: Artificial Sequence
<220> FEATURE:
<223> OTHER INFORMATION: J domain polypeptide

<400> SEQUENCE: 223

Ile Lys Lys Ala Tyr Arg Lys Ile Ala
1               5

<210> SEQ ID NO 224
<211> LENGTH: 9
<212> TYPE: PRT
<213> ORGANISM: Artificial Sequence
<220> FEATURE:
<223> OTHER INFORMATION: J domain polypeptide

<400> SEQUENCE: 224

Ile Lys Lys Ala Tyr Arg Lys Ala Ala
1               5

<210> SEQ ID NO 225
```

```
<211> LENGTH: 9
<212> TYPE: PRT
<213> ORGANISM: Artificial Sequence
<220> FEATURE:
<223> OTHER INFORMATION: J domain polypeptide

<400> SEQUENCE: 225

Ile Lys Lys Ala Tyr Arg Lys Val Ala
1               5

<210> SEQ ID NO 226
<211> LENGTH: 9
<212> TYPE: PRT
<213> ORGANISM: Artificial Sequence
<220> FEATURE:
<223> OTHER INFORMATION: J domain polypeptide

<400> SEQUENCE: 226

Ile Lys Lys Ala Tyr Arg Lys Arg Ala
1               5

<210> SEQ ID NO 227
<211> LENGTH: 9
<212> TYPE: PRT
<213> ORGANISM: Artificial Sequence
<220> FEATURE:
<223> OTHER INFORMATION: J domain polypeptide

<400> SEQUENCE: 227

Ile Lys Lys Ala Tyr Arg Lys Leu Met
1               5

<210> SEQ ID NO 228
<211> LENGTH: 9
<212> TYPE: PRT
<213> ORGANISM: Artificial Sequence
<220> FEATURE:
<223> OTHER INFORMATION: J domain polypeptide

<400> SEQUENCE: 228

Ile Lys Lys Ala Tyr Arg Lys Leu Ile
1               5

<210> SEQ ID NO 229
<211> LENGTH: 9
<212> TYPE: PRT
<213> ORGANISM: Artificial Sequence
<220> FEATURE:
<223> OTHER INFORMATION: J domain polypeptide

<400> SEQUENCE: 229

Ile Lys Lys Ala Tyr Arg Lys Leu Val
1               5

<210> SEQ ID NO 230
<211> LENGTH: 9
<212> TYPE: PRT
<213> ORGANISM: Artificial Sequence
<220> FEATURE:
<223> OTHER INFORMATION: J domain polypeptide

<400> SEQUENCE: 230

Ile Lys Lys Ala Tyr Arg Lys Leu Cys
1               5

<210> SEQ ID NO 231
<211> LENGTH: 9
```

```
<212> TYPE: PRT
<213> ORGANISM: Artificial Sequence
<220> FEATURE:
<223> OTHER INFORMATION: J domain polypeptide

<400> SEQUENCE: 231

Ile Lys Lys Ala Tyr Arg Lys Leu Ser
1               5

<210> SEQ ID NO 232
<211> LENGTH: 9
<212> TYPE: PRT
<213> ORGANISM: Artificial Sequence
<220> FEATURE:
<223> OTHER INFORMATION: J domain polypeptide

<400> SEQUENCE: 232

Ile Lys Lys Ala Tyr Arg Lys Leu Tyr
1               5
```

What is claimed is:

1. A cell-associated, secretion-enhancing (CASE) fusion protein comprising:

(a) a target protein binding (TPB) domain, (b) a transmembrane retention (TMR) domain, and (c) optionally, a chaperone machinery peptide (CMP) domain;

wherein co-expression in a host cell in culture of the CASE fusion protein and a target protein enhances the level of target protein secreted from the host cell in the culture media as compared to the level of target protein secreted from a host cell expressing the target protein in the absence of the CASE fusion protein.

2. The CASE fusion protein of claim 1, wherein the TPB domain comprises a polypeptide that binds a target protein of interest, wherein the polypeptide is selected from the group consisting of: an antibody, an antigen-binding fragment of an antibody, an antibody binding region of an antibody-binding protein, a polypeptide ligand of a receptor protein, a ligand-binding domain of a receptor protein, a polypeptide antigen, a polypeptide epitope, and a PDZ domain.

3. The CASE fusion protein of claim 1, wherein the TPB domain is an antigen-binding fragment of an antibody.

4. The CASE fusion protein of claim 1, wherein the TPB domain is a polypeptide that binds to an antibody.

5. The CASE fusion protein of claim 4, wherein the polypeptide comprises an antibody binding region of Protein L.

6. The CASE fusion protein of claim 1, wherein the TPB domain comprises a polypeptide that binds to an Fc region.

7. The CASE fusion protein of claim 6, wherein the polypeptide is an Fc-binding portion of a protein selected from the group consisting of: Protein A, Protein G, glycoprotein E, FcB6, GB919, and hFcR.

8. The CASE fusion protein of claim 1, wherein the TPB domain comprises a polypeptide ligand of a receptor protein.

9. The CASE fusion protein of claim 8, wherein the polypeptide ligand of a receptor protein is a cytokine.

10. The CASE fusion protein of claim 1, wherein the TPB domain comprises a ligand-binding domain of a receptor protein.

11. The CASE fusion protein of claim 10, wherein the ligand-binding domain of a receptor is a cytokine binding domain of a cytokine receptor.

12. The CASE fusion protein of claim 1, wherein the TPB domain comprises a single chain Fv.

13. The CASE fusion protein of claim 1, wherein the TPB domain comprises the antigen-binding site of a single domain antibody.

14. The CASE fusion protein of claim 1, wherein the TMR domain comprises a polypeptide that comprises at least a membrane-spanning region of a transmembrane protein.

15. The CASE fusion protein of claim 14, wherein the transmembrane protein is selected from the group consisting of: human CD4, human p23, human p24, human LAMP2, human LIMP2, cation dependent mannose-6-phosphate receptor, vesicular stomatitis virus glycoprotein (VSV-G), herpesvirus 1 envelope glycoprotein I, Borna disease virus gp84, and human KDEL receptor 1 protein.

16. The CASE fusion protein of claim 14, wherein the transmembrane protein is vesicular stomatitis virus glycoprotein (VSV-G), human p23, or human KDEL receptor 1 protein.

17. The CASE fusion protein of any one of claims 14-16, wherein the polypeptide comprising at least a membrane-spanning region of a transmembrane protein also comprises one or more amino acids flanking the membrane-spanning region.

18. The CASE fusion protein of claim 17, wherein the one or more amino acids flanking the transmembrane region are upstream and/or downstream from the membrane-spanning region.

19. The CASE fusion protein of claim 14, wherein the transmembrane protein is selected from the group consisting of: a Type I transmembrane protein, a Type II transmembrane protein, a Type III transmembrane protein, and a Type IV transmembrane protein.

20. The CASE fusion protein of claim 14, wherein the TMR domain comprises a polypeptide of any of SEQ ID NOS:62-82 or a portion thereof comprising at least a membrane-spanning region.

21. The CASE fusion protein of claim 19 or claim 20, wherein the polypeptide comprising at least a membrane-spanning region of a transmembrane protein also comprises one or more amino acids flanking the membrane-spanning region.

22. The CASE fusion protein of claim 21, wherein the one or more amino acids flanking the membrane-spanning region are upstream and/or downstream from the membrane-spanning region.

23. The CASE fusion protein according to claim 22, wherein the TMR domain is selected from the group of polypeptides consisting of: residues 459-522 of SEQ ID NO:156, residues 459-494 of SEQ ID NO:160, residues 459-495 of SEQ ID NO:162, residues 459-535 of SEQ ID NO:165, SEQ ID NO:193 and truncations of such polypeptides that retain the property of retaining the CASE fusion protein expressed by a host cell within the intracellular compartment.

24. The CASE fusion protein of claim 23, wherein the TMR domain comprises a C-terminal portion of p23, KDEL receptor 1, or VSV-G, which C-terminal portion includes the membrane-spanning region.

25. The CASE fusion protein of claim 1 comprising a CMP domain, wherein the CMP domain is selected from the group consisting of:
(a) an isolated J domain of a J protein, or an active fragment of a J domain; or
(b) an isolated polypeptide analog of a J domain, wherein said J domain analog polypeptide comprises the amino acid sequence of formula I:

```
              (I)
                        (SEQ ID NO: 1)
X1-X2-X3-X4-X5-X6-X7-X8-X9,
``` wherein:
X1 is isoleucine (I), leucine (L), valine (V), alanine (A), or methionine (M);
X2 and X3 are each independently any amino acid with the proviso that one or both are K or R;
X4 is any amino acid or X4 may be absent when X1 through X3 are present and X5 through X9 are present;
X5 is tyrosine (Y), tryptophan (W), or phenylalanine (F);
X6 and X7 are each independently any amino acid with the proviso that one or both are lysine (K) or arginine (R); or either one of X6 and X7 may be absent when the other is K or R and when X1 through X5 are present and X8 and X9 are present; and
X8 and X9 are any amino acid with the proviso that one or both are leucine (L) or alanine (A); or one of X8 and X9 may be absent when the other is L or A and when X1 through X7 are present.

26. The CASE fusion protein according to claim 25, wherein said CMP domain comprises an amino acid sequence selected from the group consisting of:

```
                        (SEQ ID NO: 2)
IKKAYKLALQ, (SEQ ID NO: 3)
IKKAYRLALQ, (SEQ ID NO: 4)
IKKAYRKALQ, (SEQ ID NO: 5)
IKKAYRKLLQ, (SEQ ID NO: 6)
IKKAYRKLA, (SEQ ID NO: 7)
IRKAYRKLSLTL, (SEQ ID NO: 8)
IKKQYRLLSLKY, (SEQ ID NO: 9)
IKKAFHKLAMKY, (SEQ ID NO: 10)
IRQAFKKLALKL, (SEQ ID NO: 11)
IIKAYRKLALQW, (SEQ ID NO: 12)
IARAYRQLARRY, (SEQ ID NO: 13)
IKRAYRRQALRY, (SEQ ID NO: 14)
IKKSYRKLALKY,
and
                        (SEQ ID NO: 15)
IKKAYKRLAMKY.
```

27. The CASE fusion protein according to claim 25, wherein said CMP domain comprises the amino acid sequence: IKKAFHKLAMKY (SEQ ID NO:9) or IKKAYRKLA (SEQ ID NO:6).

28. The fusion protein of claim 1 comprising a CMP domain, wherein the CMP domain comprises an amino acid sequence selected from the group consisting of:

| | | |
|---|---|---|
| SEQ ID NO: 2 | SEQ ID NO: 3 | SEQ ID NO: 4 |
| SEQ ID NO: 5 | SEQ ID NO: 6 | SEQ ID NO: 7 |
| SEQ ID NO: 8 | SEQ ID NO: 9 | SEQ ID NO: 10 |
| SEQ ID NO: 11 | SEQ ID NO: 12 | SEQ ID NO: 13 |
| SEQ ID NO: 14 | SEQ ID NO: 15 | SEQ ID NO: 16 |
| SEQ ID NO: 17 | SEQ ID NO: 18 | SEQ ID NO: 19 |
| SEQ ID NO: 20 | SEQ ID NO: 21 | SEQ ID NO: 22 |
| SEQ ID NO: 23 | SEQ ID NO: 24 | SEQ ID NO: 25 |
| SEQ ID NO: 26 | SEQ ID NO: 27 | SEQ ID NO: 28 |
| SEQ ID NO: 29 | SEQ ID NO: 30 | SEQ ID NO: 31 |
| SEQ ID NO: 32 | SEQ ID NO: 33 | SEQ ID NO: 34 |
| SEQ ID NO: 35 | SEQ ID NO: 36 | SEQ ID NO: 37 |
| SEQ ID NO: 38 | SEQ ID NO: 39 | SEQ ID NO: 40 |
| SEQ ID NO: 41 | SEQ ID NO: 42 | SEQ ID NO: 43 |
| SEQ ID NO: 44 | SEQ ID NO: 45 | SEQ ID NO: 46 |
| SEQ ID NO: 47 | SEQ ID NO: 48 | SEQ ID NO: 49 |
| SEQ ID NO: 50 | SEQ ID NO: 51 | SEQ ID NO: 52 |
| SEQ ID NO: 53 | SEQ ID NO: 54 | SEQ ID NO: 55 |
| SEQ ID NO: 56 | SEQ ID NO: 57 | SEQ ID NO: 58 |
| SEQ ID NO: 59 | SEQ ID NO: 60 and | SEQ ID NO: 61. |

29. The CASE fusion protein of claim 1 comprising a CMP domain, wherein the CMP domain comprises a fragment of a J protein or a fragment of a Hsp70 protein; wherein co-expression of the CASE fusion protein comprising the CMP domain and a target protein bound by the CASE fusion protein in a host cell enhances the level of target protein secreted from the host cell compared to the level of target protein secreted from a host cell co-expressing the target protein and a CASE fusion protein without the CMP domain.

30. The CASE fusion protein of claim 1, comprising a domain structure, N-terminal to C-terminal, selected from the group consisting of:
(TPB domain)-L-(TMR domain),
(CMP domain)-L-(TPB domain)-L-(TMR domain), and
(TPB domain)-L-(CMP domain)-L-(TMR domain),
wherein each L is, independently, a direct peptide bond or a linker of one or more amino acids.

31. The CASE fusion protein of claim 30, wherein said TMR domain comprises a membrane-spanning region of a Type I, a Type III, or a Type IV protein.

32. The CASE fusion protein of claim 30, wherein said TMR domain comprises a membrane-spanning region of a Type I transmembrane protein.

33. The CASE fusion protein of claim 30, wherein the TMR domain comprising an amino acid sequence selected from the group consisting of:

| | | |
|---|---|---|
| SEQ ID NO: 62 | SEQ ID NO: 63 | SEQ ID NO: 64 |
| SEQ ID NO: 65 | SEQ ID NO: 66 | SEQ ID NO: 67 |
| SEQ ID NO: 71 | SEQ ID NO: 73 | SEQ ID NO: 74 |
| SEQ ID NO: 75 | SEQ ID NO: 76 | SEQ ID NO: 77 |
| SEQ ID NO: 80 and | SEQ ID NO: 82. | |

34. The CASE fusion protein of claim 1, comprising a domain structure, N-terminal to C-terminal, selected from the group consisting of:
(TMR domain)-L-(TPB domain),
(TMR domain)-L-(CMP domain)-L-(TPB domain), or
(TMR domain)-L-(TPB domain)-L-(CMP domain),
wherein each L is, independently, a direct peptide bond or a linker of one or more amino acids.

35. The CASE fusion protein of claim 34, wherein said TMR domain comprises a membrane-spanning region of a Type II or a Type III transmembrane protein.

36. The CASE fusion protein of claim 1, comprising a domain structure, N-terminal to C-terminal, selected from the group consisting of:
(TMR domain)-L-(TPB domain)-L-(TMR domain), or
(TMR domain)-L-(CMP domain)-L-(TPB domain)-L-(TMR domain),
wherein said TMR domains are the same or different, and wherein each L is, independently, a direct peptide bond or a linker of one or more amino acids.

37. The CASE fusion protein of claim 36, wherein said N-terminal TMR domain comprises a membrane-spanning region of a Type II or a Type III protein, and wherein said C-terminal TMR domain comprises a membrane-spanning region of a Type I, a Type III, or a Type IV protein.

38. The CASE fusion protein of claim 36, wherein said TMR domains may be the same or different and each comprises a membrane-spanning region of a Type III protein.

39. The CASE fusion protein of claim 38, wherein each of said TMR domains comprises one or more membrane-spanning regions of KDEL receptor 1 or LIMP2.

40. The CASE fusion protein of claim 38, wherein said TMR domains may be the same or different and each comprises a membrane-spanning region taken from the KDEL receptor 1 C-terminal fragment SEQ ID NO:71.

41. The CASE fusion protein of any one of claims 30-40, wherein each linker, L, if present, is independently an amino acid or is selected from the group consisting of: LE, SR, LEG, GSR, GTGSEFDIAAALE (SEQ ID NO:175); GTGSGEF (SEQ ID NO:176); DIAAA (SEQ ID NO:83); DIAAALE (SEQ ID NO:84); GTGSEF (SEQ ID NO:85); AS; TVA; ASTK (SEQ ID NO:86); GGGSGGSGGSGG (SEQ ID NO:87); DIGGGSGGSGGSGGAAA (SEQ ID NO:88); DIGGGGSGGGGSGGGGSAAA (SEQ ID NO:178); AKTTPKLEEGEFSEAR (SEQ ID NO:89); AKTTPKLEEGEFSEARV (SEQ ID NO:90); AKTTPKLGG (SEQ ID NO:91); SAKTTPKLGG (SEQ ID NO:92); SAKTTP (SEQ ID NO:93); RADAAP (SEQ ID NO:94); RADAAPTVS (SEQ ID NO:95); RADAAAAGGPGS (SEQ ID NO:96); RADAAAA(G$_4$S)$_4$ (SEQ ID NO:97); SAKTTPKLEEGEFSEARV (SEQ ID NO:98); ADAAP (SEQ ID NO:99); ADAAPTVSIFPP (SEQ ID NO:100); TVAAP (SEQ ID NO:101); TVAAPSVFIFPP (SEQ ID NO:102); QPKAAP (SEQ ID NO:103); QPKAAPSVTLFPP (SEQ ID NO:104); AKTTPP (SEQ ID NO:105); AKTTPPSVTPLAP (SEQ ID NO:106); AKTTAP (SEQ ID NO:107); AKTTAPSVYPLAP (SEQ ID NO:108); ASTKGP (SEQ ID NO:109); ASTKGPSVFPLAP (SEQ ID NO:110); GGGGS (SEQ ID NO:181); GGGGSGGGGS (SEQ ID NO:180); GGGGSGGGGSGGGGS (SEQ ID NO:111); GGGGSGGGGSGGGGSGGGGS (SEQ ID NO:179); GENKVEYAPALMALS (SEQ ID NO:112); GPAKELTPLKEAKVS (SEQ ID NO:113); GHEAAAVMQVQYPAS (SEQ ID NO:114); GGGGGGGP (SEQ ID NO:115); GGGGGGGGP (SEQ ID NO:116); PAPNLLGGP (SEQ ID NO:117); PNLLGGP (SEQ ID NO:118); GGGGGGP (SEQ ID NO:119); PAPELLGGP (SEQ ID NO:120); PTISPAPNLLGGP (SEQ ID NO:121); TVAADDDDKSVFIVPP (SEQ ID NO:122); TVDDDD-KAAP (SEQ ID NO:123); LVPRGSAAP (SEQ ID NO:124); ASTKGPSV (SEQ ID NO:125); ASTKGPSVFP (SEQ ID NO:126); TVAAPSV (SEQ ID NO:127); TVAAPSVFI (SEQ ID NO:128).

42. The fusion protein of claim 1, further comprising:
(d) an epitope tag.

43. The fusion protein of claim 42, wherein said epitope tag is selected from the group consisting of: a polyhistidine tag, V5 tag, Myc tag, Flag tag, and an influenza hemagglutinin tag.

44. The fusion protein of claim 43, wherein said epitope tag is selected from the group consisting of: GKPIPN-PLLGLDST (SEQ ID NO:131), DYKDDDDK (SEQ ID NO:132), and HHHHHH (SEQ ID NO:177).

45. An isolated polynucleotide comprising a nucleic acid sequence encoding a CASE fusion protein according to any one of claims 1-44.

46. The isolated polynucleotide of claim 45, further comprising a nucleotide sequence encoding a signal sequence located in frame at the 5' end of said polynucleotide.

47. The isolated polynucleotide of claim 46, wherein said signal sequence is a signal sequence that is native to the protein from which the N-terminal domain of the encoded fusion protein is derived.

48. The isolated polynucleotide of claim 46, wherein the signal sequence is the signal sequence of a J protein.

49. The isolated polynucleotide of claim 46, wherein the signal sequence is the signal sequence for human insulin.

50. A nucleic acid vector comprising the isolated nucleic acid molecule according to any one of claims 45-49.

51. The nucleic acid vector of claim 50 comprising a plasmid selected from the group consisting of: pcDNA, pcDNA3.3 TOPO, pTT3, and pEF-BOS.

52. A host cell comprising the nucleic acid vector molecule according to claim 50 or claim 51.

53. A method of expressing a fusion protein comprising culturing a host cell according to claim 52 under conditions sufficient to produce the encoded CASE fusion protein.

54. A method of enhancing the level of secretion of a target protein of interest that is expressed in a host cell comprising: (1) transfecting the host cell with an expression vector comprising a structural gene encoding a CASE fusion protein according to any one of claims 1-44 that exhibits a TPB domain capable of binding to said target protein of interest, and (2) culturing said transfected host cell under conditions for co-expression in said host cell of said CASE fusion protein and said target protein of interest.

55. The method of claim 54, wherein said CASE fusion protein dissociates from said target protein of interest under conditions found within the Golgi apparatus of said host cell.

56. The method of claim 54, wherein said CASE fusion protein dissociates from said target protein of interest under conditions of pH from pH 5.5 to pH 7.

57. The method of claim 54, wherein said CASE fusion protein dissociates from said target protein of interest under conditions of pH from pH 5.5 to pH 6.3.

58. The method of claim 54, wherein said CASE fusion protein dissociates from said target protein of interest under conditions of pH from pH 5.5 to pH 6.

59. A method of enhancing the level of a target protein of interest secreted from a host cell expressing said target protein, the method comprising the steps of:
  1) constructing a recombinant gene encoding a CASE fusion protein according to any one of claims 1-44 having a target protein binding (TPB) domain capable of binding said target protein expressed by said host cell;
  2) inserting the recombinant gene into an expression vector to form a recombinant expression vector wherein said recombinant gene sequence is operably linked to a transcriptional promoter sequence;
  3) transfecting said recombinant expression vector into host cells that are compatible with said promoter sequence; and
  4) culturing said transfected host cells under conditions that permit co-expression of said CASE fusion protein encoded by said recombinant gene and of said target protein of interest.

60. A method of restoring a secreted protein function in cells of a mammalian subject that are deficient in the secretion of a native secreted protein that provides said secreted protein function comprising: inserting into cells of the subject an exogenous nucleic acid molecule encoding a CASE fusion protein according to any one of claims 1-44, wherein the target protein binding domain of the CASE fusion protein binds the native secreted protein, and wherein co-expression of the CASE fusion protein and the native secreted protein in the cells enhances the level of native secreted protein to provide said secreted protein function to the subject.

61. The method according to claim 60, wherein the subject has a disease associated with the deficient secretion of the native protein in the subject.

62. The method according to claim 61, wherein said disease is selected from the group consisting of a prion-associated disease, Alzheimer's disease, Parkinson's disease, Huntington's disease, cystic fibrosis (CF), and α1-antitrypsin (AAT) deficiency.

63. The method according to claim 62, wherein the subject is a human subject deficient in the secretion of cystic fibrosis transmembrane conductance regulator protein and the disease is cystic fibrosis, and wherein expression of said CASE fusion protein in cells of said subject increases the level of circulating cystic fibrosis transmembrane conductance regulator protein in said subject.

64. The method according to claim 62, wherein the subject is a human subject deficient in secretion of AAT and the disease is AAT deficiency, and wherein expression of said CASE fusion protein in cells of said subject increases the level of circulating AAT in said subject.

\* \* \* \* \*